United States Patent
Bonner et al.

(10) Patent No.: US 12,178,875 B2
(45) Date of Patent: *Dec. 31, 2024

(54) LYMPHATIC SYSTEM-DIRECTING LIPID PRODRUGS

(71) Applicants: Seaport Therapeutics, Inc., Boston, MA (US); Monash University, Clayton (AU)

(72) Inventors: Daniel Kenneth Bonner, Sharon, MA (US); Ketki Karanam, Newton, MA (US); James Tendai Mutamba, Newton, MA (US); Rishab R. Shyam, Arlington, MA (US); Jamie Simpson, Chestnut Hill, MA (US); Sifei Han, Bundoora (AU); Luojuan Hu, Bundoora (AU); Christopher John Hamilton Porter, South Melbourne (AU); Tim Quach, Boston, MA (US); Natalie Trevaskis, Newington (AU)

(73) Assignees: Seaport Therapeutics, Inc., Boston, MA (US); Monash University, Clayton (AU)

( * ) Notice: Subject to any disclaimer, the term of this patent is extended or adjusted under 35 U.S.C. 154(b) by 0 days.

This patent is subject to a terminal disclaimer.

(21) Appl. No.: 18/425,761

(22) Filed: Jan. 29, 2024

(65) Prior Publication Data

US 2024/0207411 A1  Jun. 27, 2024

Related U.S. Application Data

(63) Continuation of application No. 16/642,794, filed as application No. PCT/US2018/048642 on Aug. 29, 2018, now Pat. No. 11,883,497.

(60) Provisional application No. 62/551,627, filed on Aug. 29, 2017, provisional application No. 62/607,700, filed on Dec. 19, 2017, provisional application No. 62/607,749, filed on Dec. 19, 2017, provisional application No. 62/714,029, filed on Aug. 2, 2018, provisional application No. 62/724,274, filed on Aug. 29, 2018, provisional application No. 62/724,440, filed on Aug. 29, 2018.

(51) Int. Cl.
*A61K 47/06* (2006.01)
*A61K 45/06* (2006.01)
*A61K 47/54* (2017.01)

(52) U.S. Cl.
CPC ............ *A61K 47/543* (2017.08); *A61K 45/06* (2013.01)

(58) Field of Classification Search
CPC ................. A61K 47/43; A61K 45/06
USPC ..................................... 424/181.1
See application file for complete search history.

(56) References Cited

U.S. PATENT DOCUMENTS

| | | | |
|---|---|---|---|
| 4,587,262 A | 5/1986 | Arnould et al. | |
| 4,958,046 A | 9/1990 | Rosenberg et al. | |
| 5,962,440 A | 10/1999 | Sulsky | |
| 6,013,665 A | 1/2000 | DeMichele et al. | |
| 6,054,591 A | 4/2000 | Aono et al. | |
| 6,417,191 B1 | 7/2002 | Barry et al. | |
| 6,552,065 B2 | 4/2003 | Remiszewski et al. | |
| 7,390,799 B2 | 6/2008 | Bruncko et al. | |
| 7,557,210 B2 | 7/2009 | Singh et al. | |
| 7,635,690 B2 | 12/2009 | Schinazi et al. | |
| 8,138,347 B2 | 3/2012 | Knight et al. | |
| 8,338,439 B2 | 12/2012 | Singh et al. | |
| 8,455,510 B2 | 6/2013 | Nan et al. | |
| 11,311,512 B2 | 4/2022 | Porter et al. | |
| 11,883,497 B2 * | 1/2024 | Bonner | C07D 209/08 |
| 2004/0204472 A1 | 10/2004 | Briggs et al. | |
| 2007/0191415 A1 | 8/2007 | Kumar et al. | |
| 2009/0023805 A1 | 1/2009 | Marrast et al. | |
| 2009/0297533 A1 | 12/2009 | Lichter et al. | |
| 2010/0298560 A1 | 11/2010 | Choi et al. | |
| 2011/0213028 A1 | 9/2011 | Milne et al. | |
| 2011/0243884 A1 | 10/2011 | O'Shea et al. | |
| 2013/0030007 A1 | 1/2013 | Penninger et al. | |
| 2014/0081016 A1 | 3/2014 | Felzmann et al. | |
| 2014/0234418 A1 | 8/2014 | Coulter et al. | |
| 2014/0328793 A1 | 11/2014 | Gavegnano et al. | |

(Continued)

FOREIGN PATENT DOCUMENTS

| | | |
|---|---|---|
| JP | 200312691 A | 1/2003 |
| WO | 1994009010 A1 | 4/1994 |

(Continued)

OTHER PUBLICATIONS

Lalanne et al., "Metabolism evaluation of biomimetic prodrugs by in vitro models and mass spectrometry," Int. J. Pharm> 2009;379(2):235-43.
Lalanne et al., "Synthesis and biological evaluation of two glycerolipidic prodrugs of didanosine for direct lymphatic delivery against HIV," Bioorg. Med. Chem. Lett. 2007;17(8):2237-40.
Levine and Raines, "Trimethyl lock: a trigger for molecular release in chemistry, biology, and pharmacology," Chem. Sci. 2012; 3(8):2412-2420.
Li et al., "Mycophenolate mofetil or tacrolimus compared with intravenous cyclophosphamide in the induction treatment for active lupus nephritis," Nephrol. Dial. Transplant 2012; 27(4): 1467-72.

(Continued)

*Primary Examiner* — Yevgeny Valenrod
(74) *Attorney, Agent, or Firm* — WOMBLE BOND DICKINSON (US) LLP; Danielle L. Herritt; Matthew J. Powers

(57) ABSTRACT

The present invention provides lymphatic system-directing lipid prodrugs, pharmaceutical compositions thereof, methods of producing such prodrugs and compositions, as well as methods of improving the bioavailability or other properties of a therapeutic agent that comprises part of the lipid prodrug. The present invention also provides methods of treating a disease, disorder, or condition such as those disclosed herein, comprising administering to a patient in need thereof a provided lipid prodrug or a pharmaceutical composition thereof.

11 Claims, 21 Drawing Sheets

(56) References Cited

U.S. PATENT DOCUMENTS

| | | | |
|---|---|---|---|
| 2017/0326103 | A1 | 11/2017 | Porter et al. |
| 2018/0243425 | A1 | 8/2018 | Porter et al. |
| 2018/0258094 | A1 | 9/2018 | Long et al. |
| 2018/0318318 | A1 | 11/2018 | Wang et al. |
| 2019/0105299 | A1 | 4/2019 | Porter et al. |
| 2022/0211664 | A1 | 7/2022 | Porter et al. |

FOREIGN PATENT DOCUMENTS

| | | | |
|---|---|---|---|
| WO | 199735843 | A1 | 10/1997 |
| WO | 2001042246 | A2 | 6/2001 |
| WO | 2002088112 | A1 | 11/2002 |
| WO | 2003063794 | A2 | 8/2003 |
| WO | 2004019973 | A1 | 3/2004 |
| WO | 2004089925 | A1 | 10/2004 |
| WO | 2004106328 | A1 | 12/2004 |
| WO | 2005007623 | A2 | 1/2005 |
| WO | 2005112919 | A2 | 12/2005 |
| WO | 2005113554 | A2 | 12/2005 |
| WO | 2006078846 | A1 | 7/2006 |
| WO | 2006122806 | A2 | 11/2006 |
| WO | 2007016176 | A2 | 2/2007 |
| WO | 2007044729 | A2 | 4/2007 |
| WO | 2007053452 | A1 | 5/2007 |
| WO | 2007070514 | A1 | 6/2007 |
| WO | 2007084786 | A1 | 7/2007 |
| WO | 2007129161 | A2 | 11/2007 |
| WO | 2008039218 | A2 | 4/2008 |
| WO | 2008048611 | A1 | 4/2008 |
| WO | 2008109943 | A1 | 9/2008 |
| WO | 2008118802 | A1 | 10/2008 |
| WO | 2009018389 | A1 | 2/2009 |
| WO | 2009114512 | A1 | 9/2009 |
| WO | 2009143295 | A1 | 11/2009 |
| WO | 2011051967 | A2 | 5/2011 |
| WO | 2011090760 | A1 | 7/2011 |
| WO | 2011120044 | A1 | 9/2011 |
| WO | 2015116904 | A1 | 8/2015 |
| WO | 2016023082 | A1 | 2/2016 |
| WO | 2017041139 | A1 | 3/2017 |
| WO | 2017049245 | A2 | 3/2017 |
| WO | 2018237282 | A1 | 12/2018 |
| WO | 2019046478 | A1 | 3/2019 |
| WO | 2019046491 | A1 | 3/2019 |
| WO | 2019126378 | A1 | 6/2019 |
| WO | 2020028787 | A1 | 2/2020 |

OTHER PUBLICATIONS

Ling and Luster, "Allergen-Specific CD4+ T Cells in Human Asthma," Ann. Am. Thorac. Soc. 2016; 13(Suppl 1): S25-S30.
Ling et al., C1q restrains autoimmunity and viral infection by regulating CD8+ T Cell metabolism; Science. May 4, 2018;360(6388):558-563.
Liénard et al., "Structural basis for the broad-spectrum inhibition of metallo-beta-lactamases by thiols," Org. Biomol. Chem. 2008;6(13):2282-94.
Loiseau et al., "Lymphotropic antifilarial agents derived from closantel and chlorambucil," Int. J. Parasitol. 1997; 27(4):443-7.
Lonshakov et al., "Synthesis and properties of 3'-azido-3'-deoxythymidine derivatives of glycerolipids," Pharm. Chem. J. 2011;44(10):557-563.
Lui et al., "Effect of mycophenolate mofetil on severity of nephritis and nitric oxide production in lupus-prone MRL/lpr mice," Lupus. 2002;11(7):411-8.
Lv et al., "Mycophenolate Mofetil Modulates Differentiation of Th1/Th2 and the Secretion of Cytokines in an Active Crohn's Disease Mouse Model," Int. J. Mol. Sci. 2015; 16(11):26654-66.
Maria and Davidson, "Emerging areas for therapeutic discovery in SLE," Curr. Opin. Immunol. 2018;55:1-8.
Mattarei et al., "Novel lipid-mimetic prodrugs delivering active compounds to adipose tissue," Eur. J. Med. Chem. 2017;135:77-88.

Meliambro et al., "Therapy for Proliferative Lupus Nephritis," Rheum. Dis. Clin. North Am. 2018;44(4):545-560.
Mergen et al., "Antiepileptic activity of 1,3-dihexadecanoylamino-2-valproyl-propan-2-ol, a prodrug of valproic acid endowed with a tropism for the central nervous system," J. Pharm. Pharmacol. 1991; 43(11):815-6.
Michel et al., "Mycophenolate mofetil in multiple sclerosis: a multicentre retrospective study on 344 patients," J. Neurol. Neurosurg. Psychiatry. 2014;85(3):279-83.
Miller and Karpus, "Experimental autoimmune encephalomyelitis in the mouse," Curr. Protoc. Immunol. 2007; Chapter 15: Unit 15.1.
Minard-Colin et al., "Lymphoma depletion during CD20 immunotherapy in mice is mediated by macrophage Fc?RI, Fc?RIII, and Fc?RIV," Blood. 2008;112(4):1205-1213.
Miyamoto et al., "A novel prodrug strategy for extremely hydrophobic agents: conjugation to symmetrically branched glycerol trimer improves pharmacological and pharmacokinetic properties of fenofibrate," Mol. Pharm. 2013;10(7):2723-9.
Mok, "Mycophenolate mofetil for lupus nephritis: an update," Expert Rev. Clin. Immunol. 2015;11(12):1353-64.
Nakajima, et al., "Effectiveness of tacrolimus in comparison with methotrexate or biologics in propensity score-matched patients with rheumatoid arthritis," Mod. Rheumatol. 2016; 26(6):836-843.
Nash et al., "Phase 3 study comparing methotrexate and tacrolimus with methotrexate and cyclosporine for prophylaxis of acute graft-versus-host disease after marrow transplantation from unrelated donors," Blood. 2000;96:2062-2068.
Negi and Das, "CNS: Not an immunoprivilaged site anymore but a virtual secondary lymphoid organ," Int. Rev. Immunol. 2018;37(1):57-68.
Nieschlag et al., "Testosterone replacement therapy: current trends and future directions," Hum. Reprod. Update. 2004; 10(5):409-19.
Ning et al., "Visualizing metabolically labeled glycoconjugates of living cells by copper-free and fast huisgen cycloadditions," Angew. Chem. Int. Ed. Engl. 2008; 47(12): 2253-5.
Okayama et al., "Mast cells are involved in the pathogenesis of indomethacin-induced rat enteritis," J. Gastroenterol. 2009; 44(Suppl 19):35-9.
Osborne et al., "Lower allopregnanolone during pregnancy predicts postpartum depression: An exploratory study," Psychoneuroendocrinology. 2017;79:116-121.
Pallet et al., "Impact of Immunosuppressive Drugs on the Metabolism of T Cells," Int. Rev. Cell. Mol. Biol. 2018; 341:169-200.
Paris et al., "Glycerides as prodrugs. 1. Synthesis and antiinflammatory activity of 1,3-bis(alkanoyl)-2-(O-acetylsalicyloyl)glycerides (aspirin triglycerides).," J. Med. Chem. 1979; 22(6):683-7.
Paris et al., "Glycerides as prodrugs. 2. 1,3-Dialkanoyl-2-(2-methyl-4-oxo-1,3-benzodioxan-2-yl)glycerides (cyclic aspirin triglycerides) as antiinflammatory agents," J. Med. Chem. 1980;23(1):79-82.
Paris et al., "Glycerides as prodrugs. 3. Synthesis and antiinflammatory activity of [1-(p-chlorobenzoyl)-5-methoxy-2-methylindole-3-acetyl]glycerides (indomethacin glycerides)," J. Med. Chem. 1980;23(1):9-13.
PCT International Search Report and Written Opinion from PCT/AU2015/050460 dated Oct. 15, 2015.
PCT International Search Report and Written Opinion from PCT/AU2016/050845 dated Oct. 27, 2016.
PCT International Search Report and Written Opinion from PCT/AU2020/050997 dated Dec. 1, 2020.
PCT International Search Report and Written Opinion from PCT/US2018/048642 dated Dec. 11, 2018.
PCT International Search Report and Written Opinion from PCT/US2018/066580 dated Apr. 24, 2019.
PCT International Search Report and Written Opinion from PCT/US2018/066585 dated Apr. 30, 2019.
PCT International Search Report and Written Opinion from PCT/US2019/044877 dated Oct. 24, 2019.
PCT International Search Report and Written Opinion from PCT/US2020/020387 dated Jun. 24, 2020.
PCT International Search Report and Written Opinion from PCT/US2020/020398 dated Jul. 20, 2020.
PCT International Search Report and Written Opinion from PCT/US2020/020433 dated Jun. 26, 2020.

(56) References Cited

OTHER PUBLICATIONS

Perché et al., "Prenatal testosterone treatment potentiates the aggression-inhibiting effect of the neurosteroid dehydroepiandrosterone in female mice," Agress. Behav. 2001;27(2):130-8.
Pesu et al., "Jak3, severe combined immunodeficiency, and a new class of immunosuppressive drugs," Immunol. Rev. 2005; 203:127-42.
Ple et al., "Natural killer cells accumulate in lung-draining lymph nodes and regulate airway eosinophilia in a murine model of asthma," Scand. J. Immunol. 2010;72(2):118-27.
Pond and Tozer, "First-pass elimination. Basic concepts and clinical consequences," Clin. Pharmacokinet. 1984;9(1):1-25.
Pouton "Formulation of poorly water-soluble drugs for oral administration: Physicochemical and physiological issues and the lipid formulation classification system," Eur. J. Pharm. Sci. 2006; 29(3-4):278-87.
Pouton, "Lipid formulations for oral administration of drugs: non-emulsifying, self-emulsifying and 'self-microemulsifying' drug delivery systems," Eur. J. Pharm. Sci. 2000; 11(Suppl 2):S93-8.
Powell et al., "The immunomodulatory drugs cyclosporin A, mycophenolate mofetil, and sirolimus (rapamycin) inhibit allergen-induced proliferation and IL-5 production by PBMCs from atopic asthmatic patients," 2001;108(6):915-7.
Pubmed Compound Summary for CID 132121512, '1-O-[3R,5S,8S,9S,10S,13S,14S,17S)-17-Acetyl-10,13-dimethyl-11-oxo-1,2,3,4,5,6,7,8,9,12,14,15,16,17-; tetradecahydrocyclopenta[a]phenanthren-3-yl] 3-O-[1,3-di (hexadecanoyloxy)propan-2-yl]propanedioate', U.S. National Library of Medicine, Jan. 29, 2018 https://pubchem.ncbi.nlm.nih.gov/compound/132131512).
Renna et al., "Optimization of the treatment with immunosuppressants and biologics in inflammatory bowel disease," World J. Gastroenterol. 2014;20(29):9675-9690.
Rodriguez-Lago et al., "Previous exposure to biologics and C-reactive protein are associated with the response to tacrolimus in inflammatory bowel disease," Rev. Esp. Enferm. Dig. 2016;108(9):550-7.
Rogawski et al., "Neuroactive steroids for the treatment of status epilepticus," Epilepsia. 2013;54(Suppl 6):93-8.
Rupprecht, "Neuroactive steroids: mechanisms of action and neuropsychopharmacological properties," Psychoneuroendocrinology. 2003;20(2):139-68.
Sagiv-Barfi et al., "Ibrutinib enhances the antitumor immune response induced by intratumoral injection of a TLR9 ligand in mouse lymphoma," Blood. 2015; 125(13):2079-86.
Schüle et al., "The role of allopregnanolone in depression and anxiety," Prog. Neurobiol. 2014;113:79-87.
Scriba et al., "Bioavailability of Phenytoin Following Oral Administration of Phenytoin-lipid Conjugates to Rats," J. Pharm. Pharmacol. 1995; 47(11):945-948.
Scriba, "Synthesis and in vitro degradation of testosterone-lipid conjugates," Arch. Pharm. (Weinheim), 1995; 328(3):271-6.
Shastina et al., "Synthesis, properties, and Anti-HIV activity of new lipophilic 3'-azido-3'-deoxythymidine conjugates containing functional phosphoric linkages," Russian Journal of Bioorganic Chemistry. 2013;39:161-169.
Siebert et al., "New Analogues of Mycophenolic Acid," Mini Rev. Med. Chem. 2017;17(9):734-745.
Silverman, "Chapter 8—Prodrugsand Drug Delivery Systems," in The Organic Chemistry of Drug Design and Drug Action (Second Edition), 2004 (pp. 497-557, 520-525).
Silverman, "Chapter 9—Prodrugs and Drug Delivery Systems," in The Organic Chemistry of Drug Design and Drug Action (Third Edition), 2014 (pp. 423-486).
Skanji et al., "A new nanomedicine based on didanosine glycerolipidic prodrug enhances the long term accumulation of drug in a HIV sanctuary," Int. J. Pharm. 2011;414(1-2):285-97.
Smith and Cooper, "Mycophenolate mofetil therapy in the management of inflammatory bowel disease—a retrospective case series and review," J. Crohns Colitis. 2014;8(8):890-7.
Smith et al., "Modular assembly of macrocyclic organo-peptide hybrids using synthetic and genetically encoded precursors," Angew. Chem. Int. Ed. Engl. 2011;50(22):5075-80.
Sobczak, "Synthesis and characterization of polyester conjugates of ciprofloxacin," Eur. J. Med. Chem. 2010;45(9):3844-9.
Stadnyk et al., "Neutrophil migration into indomethacin induced rat small intestinal injury is CD11a/CD18 and CD11b/CD18 co-dependent," Gut. 2002;50(5):629-635.
Stump et al., "Lymphatic Changes in Respiratory Diseases: More than Just Remodeling of the Lung?" AM. J. Respir. Cell Mol. Biol. 2017;57(3):272-279.
Subba Reddy et al., "A Concise and Convergent Total Synthesis of Two Novel Cytotoxic Hydroquinones, Lanneaquinol and (R)-2'-Hydroxylanneaquinol," Helv. Chim. Acta. 2013; 96(10):1983-1990.
Sugihara et al., "Studies on intestinal lymphatic absorption of drugs. I. Lymphatic absorption of alkyl ester derivatives and alpha-monoglyceride derivatives of drugs," J. Pharmacobiodyn. 1988; 11(5):369-76.
Sugihara et al., "Studies on intestinal lymphatic absorption of drugs. II. Glyceride prodrugs for improving lymphatic absorption of naproxen and nicotinic acid," J. Pharmacobiodyn. 1988;11(8):555-62.
Takada et al., "Conversion of a novel 5-fluorouracil (5-FU) derivative to 5-FU in rats," Res. Commun. Chem. Pathol. Pharmacol. 1983;40(1):99-108.
Takagi et al., "The synthesis of enantiomerically pure novel liquid crystal compounds containing the bis(trifluoromethyl) alkanediol moiety," Tetrahedron Asymmetry. 2004;15(17):2591-2594.
Tan and Lawrence, "Use of mycophenolate mofetil in inflammatory bowel disease," World J. Gastroenterol. 2009;15(13):1594-1599.
Tanaka et al., "Structure of FK506, a novel immunosuppressant isolated from Streptomyces," J. Am. Chem. Soc. 1987;109(16):5031-5033.
Taniguchi et al., "A Case of Severe Bronchial Asthma Controlled with Tacrolimus," J. Allergy (Cairo). 2011;201:479129.
Taylor and Ryan, "Understanding mechanisms of hypertension in systemic lupus erythematosus," Ther. Adv. Cardiovasc. Dis. 2017;11(1):20-32.
Tohda et al., "Establishment of a novel B-cell lymphoma cell line with suppressed growth by gamma-secretase inhibitors," Leuk. Res. 2006;30(11):1385-90.
Tranoy-Opalinski et al., "Design of self-immolative linkers for tumour-activated prodrug therapy," Anticancer Agents Med. Chem. 2008;8(6):618-37.
Trevaskis et al., "Bile increases intestinal lymphatic drug transport in the fasted rat," Pharm. Res. 2005;22(11):1863-1870.
Trevaskis et al., "From sewer to saviour—targeting the lymphatic system to promote drug exposure and activity," Nature Review Drug Discovery. 2015;14:781-803.
Van Bruggen et al., "Attenuation of murine lupus nephritis by mycophenolate mofetil," J. Am. Soc. Nephrol. 1998;9(8):1407-15.
Van Dieren et al., "Local application of tacrolimus in distal colitis: feasible and safe," Inflamm. Bowel Dis. 2009; 15(2):193-8.
Wagner et al., "Selective epimerization and skeletal resection in the ascomycin framework: A study of the biological consequences of lactam rotamer selection," Tetrahedron. 1996;52(29):9643-9654.
Warren et al., "Evaluation of the Structural Determinants of Polymeric Precipitation Inhibitors Using Solvent Shift Methods and Principle Component Analysis," Mol. Pharmaceutics. 2013;10(8):2823-2848.
Weyand and Goronzy, "Immunometabolism in early and late stages of rheumatoid arthritis," Nat. Rev. Rheumatol. 2017;13(5):291-301.
Wiebe and Kavaliers, "Analgesic effects of the putative FSH-suppressing gonadal steroid, 3 alpha-hydroxy-4-pregnen-20-one: possible modes of action," Brain Res. 1988;461(1):150-7.
Wirtz et al., "Chemically induced mouse models of acute and chronic intestinal inflammation," Nat. Protoc. 2017;12(7):1295-1309.
Wittman et al.,. "Synthesis and antitumor activity of novel paclitaxel-chlorambucil hybrids," Bioorg. Med. Chem. Lett. 2001;11(6):811-814.
Wolbers et al., "Viability study of HL60 cells in contact with commonly used microchip materials," Electrophoresis. 2006;27(24):5073-80.

(56) References Cited

OTHER PUBLICATIONS

Young and Kerr, "Total Synthesis of (+)-Nakadomarin A," J. Am. Chem. Soc. 2007; 129(5):1465-1469.
Zgair et al., "Oral administration of cannabis with lipids leads to high levels of cannabinoids in the intestinal lymphatic system and prominent immunomodulation," Scientific Report. 2017;7(14542):1-2.
Cammack et al., "substituent." Oxford Dictionary Biochemistry and Molecular Biology Revised Edition (2000). Oxford University Press.
Daintith, "substituent." Oxford Dictionary of Chemistry 6th Edition (2008). Oxford University Press.
IUPAC, Commission on Nomenclature of Organic Chemistry. A Guide to IUPAC Nomenclature of Organic Compounds (Recommendations 1993), 1993, Blackwell Scientific publications, Copyright 1993 IUPAC; Downloaded May 6, 2020 fromhttps://www.acdlabs.com/iupac/nomenclature/93/r93_125.htm.
IUPAC, Compendium of Chemical Terminology, 2nd ed. (the "Gold Book"). Compiled by A. D. McNaught and A. Wilkinson. Blackwell Scientific Publications, Oxford (1997). Online version (2019) created by S. J. Chalk. ISBN 0-9678550-9-8.https://doi.org/10.1351/goldbook; Downloaded May 5, 2020.
Wikipedia contributors. (Feb. 11, 2015). Substitution reaction. In Wikipedia, The Free Encyclopedia. Archived May 9, 2015, 8:42:39, at https://web.archive.org/web/20150509084239/https://en.wikipedia.org/wiki/- Substitution_reaction.
Codelli et al., "Second-Generation Difluorinated Cyclooctynes for Copper-Free Click Chemistry," J. Am. Chem. Soc. 2008; 130(34):11486-11493.
Dommerholt et al., "Readily Accessible Bicyclononynes for Bioorthogonal Labeling and Three-Dimensional Imaging of Living Cells," Angewandte Chemie International Edition, vol. 49, 2010 (pp. 9422-9425).
Jewett et al., "Rapid Cu-Free Click Chemistry with Readily Synthesized Biarylazacyclooctynones," Journal of the American Chemical Society, vol. 132, No. 11, 2010 (pp. 3688-3690).
Han, Sifei, et al., "Constitutive Triglyceride Turnover into the Mesenteric Lymph Is Unable to Support Efficient Lymphatic Transport of a Biomimetic Triglyceride Prodrug," Journal of Pharmaceutical Sciences, vol. 105, pp. 786-796 (2016).
Extended European Search Report and Opinion issued in European Application No. 18851922.7 on Apr. 13, 2021, 8 pages.
Alouane et al., "Self-immolative spacers: kinetic aspects, structure-property relationships, and applications," Angew. Chem. Int. Ed. Engl. 2015;54(26):7492-509.
Alouane et al., "Self-immolative spacers: kinetic aspects, structure-property relationships, and applications," Supporting Information, Angew. Chem. Int. Ed. Engl. 2015;(10 pages).
Amory et al., "Oral testosterone-triglyceride conjugate in rabbits: single-dose pharmacokinetics and comparison with oral testosterone undecanoate," J. Androl. 2003; 24 (5): 716-20.
Amsberry et al., "Amine prodrugs which utilize hydroxy amide lactonization. II. A potential esterase-sensitive amide prodrug," Pharm. Res. 1991; 8(4):455-61.
Andréen et al., "Sex steroid induced negative mood may be explained by the paradoxical effect mediated by GABAA modulators," Psychoneuroendocrinology. 2009;34(8):1121-32.
Belin de Chantemèle et al., "Cyclooxygenase-2 preserves flow-mediated remodelling in old obese Zucker rat Mesenteric arteries," Cardiovas. Res. 2010;86(3):516-25.
Benenato K F: "Preparation of compounds and lipid nanoparticle compositions for intracellular delivery of therapeutic agents," WO2017049245 A2, vol. 166, Mar. 23, 2017, pp. 1-2, XP055786021.
Bitran et al., "Anxiolytic effect of progesterone is mediated by the neurosteroid allopregnanolone at brain GABAA receptors," J. Neuroendocrinol. 1995;7(3): 171-7.
Blencowe et al., "Self-immolative linkers in polymeric delivery systems," Polym. Chem. 2011, 2:773-790.
Bourgeois et al., "Application of thermal analysis to the study of lipidic prodrug incorporation into nanocarriers," J. Therm. Anal. Calorim. 2009; 98: 65-71.
Braile-Fabris et al., "Controlled clinical trial of IV cyclophosphamide versus IV methylprednisolone in severe neurological manifestations in systemic lupus erythematosus," Ann. Rheum. Dis. 2005; 64(4): 620-25.
Brand et al., "Collagen-induced arthritis," Nat. Protoc. 2007; 2(5): 1269-75.
Charette et al., "Practical and Highly Regio- and Stereoselective Synthesis of 2-Substituted Dihydropyridines and Piperidines: Application to the Synthesis of (−)-Coniine," J. Am. Chem. Soc. 2001; 123(47):11829-11830.
Chowdhury and Ghosh, "Highly Regio- and Enantioselective Organocatalytic Conjugate Addition of Alkyl Methyl Ketones to a β-Silylmethylene Malonate," Org. Lett. 2009; 11(15):3270-3273.
Coutinho and Chapman, "The anti-inflamatory and immunosuppressive effects of glucocorticoids, recent developments and mechanistic insights," Mol. Cell. Endrocrinol. 2011;335(1):2-13.
Cyr et al., "Recent progress on nuclear receptor RORγ modulators," Bioorg. Med. Chem. Lett. 2016; 26(18):4387-4393.
D'yakova et al., "lymphotropic prodrugs based on 2', 3'-didehydro-3'-deoxythymidine. Synthesis and sensitivity to hydrolysis," Russian Journal of Bioorganic Chemistry. 2011; 47(10): 1588-1593.
Deverre et al., "In-vitro evaluation of filaricidal activity of GABA and 1,3-dipalmitoyl-2-(4-aminobutyryl)glycerol HCI: a diglyceride prodrug," J. Pharm. Pharmacol. 1989; 41(3):191-3.
DeWolf and Sykes "Alloimmune T Cells in transplantation," J. Clin. Invest. 2017;127(7):2473-2481.
Edwards et al., "Animal models for the study of intestinal lymphatic drug transport," Adv. Drug. Deliv. Rev. 2011; 50(1-2):45-60.
Freitag et al., "Gliadin-primed CD4+CD45RBlowCD25-T cells drive gluten-dependent small intestinal damage after adoptive transfer into lymphopenic mice," Gut. 2009;58(12):1597-605.
Frye and Duncan, "Progesterone metabolites, effective at the GABAA receptor complex, attenuate pain sensitivity in rats," Brain Res. 1994:643(1-2):194-203.
Frye and Walf, "Changes in progesterone metabolites in the hippocampus can modulate open field and forced swim test behavior of proestrous rats," Horm. Behav. 2002;41(3):306-15.
Garzon-Aburbeh et al., "1,3-Dipalmitoylglycerol ester of chlorambucil as a lymphotropic, orally administrable antineoplastic agent," J. Med. Chem. 1983; 26(8):1200-1203.
Garzon-Aburbeh et al., "A lymphotropic prodrug of L-dopa: synthesis, pharmacological properties and pharmacokinetic behavior of 1,3-dihexadecanoyl-2-[(S)-2-amino-3-(3,4-dihydroxyphenyl)propanoyl]propane-1,2,3-triol," J. Med. Chem. 1986; 29(5):687-691.
Goodin, "Glucocorticoid treatment of multiple sclerosis," Handb. Clin. Neurol. 2014;122:455-64.
Gossauer and Kühne, "Synthesen von Gallenfarbstoffen, V. Stereospezifische Totalsynthesen diastereomerer Mesobilirhodine und Isomesobilirhodine," Justus Liebigs Annalender Chemie. 1977;4:664-686.
Grainge et al., "Case series reporting the effectiveness of mycophenolate mofetil in treatment-resistant asthma," Eur. Respir. J. 2013; 42(4):1134-7.
Griffin et al., "Niemann-Pick type C disease involves disrupted neurosteroidogenesis and responds to allopregnanolone," Nat. Med. 2004;10(7):704-11.
Guo et al., "Rheumatoid arthritis: Pathological mechanisms and modern pharmacologic therapies," Bone Res. 2018;6:15.
Gupta et al., "Dexamethasone cyclophosphamide pulse therapy in systemic lupus erythematosus: a case report," J. Dermatolg. Treat. 2009;20(1):55-8.
Han et al., "Lymphatic Transport and Lymphocyte Targeting of a Triglyceride Mimetic Prodrug is Enhanced in a Large Animal Model: Studies in Greyhound Dogs," Mol. Pharm. 2016; 13(10):3351-3361.
Han et al., "Targeted delivery of a model immunomodulator to the lymphatic system: comparison of alkyl ester versus triglyceride mimetic lipid prodrug strategies," J. Control Release. 2014; 177:1-10.

(56) References Cited

OTHER PUBLICATIONS

Hsieh et al., "Selective COX2 inhibition improves whole body and muscular insulin resistance in fructose-fed rats," Eur. J. Clin. Invest. 2008;38(11):812-9.

Hu et al., "Glyceride-Mimetic Prodrugs Incorporating Self-Immolative Spacers Promote Lymphatic Transport, Avoid First-Pass Metabolism, and Enhance Oral Bioavailability," Angew. Chem. Int. Ed. Engl. 2016;55(44):13700-13705.

Huvelle et al., "Syntheses and kinetic studies of cyclisation-based self-immolative spacers," Org. Biomol. Chem. 2017;15(16):3435-3443.

Irwin and Diaz Brinton, "Allopregnanolone as regenerative therapeutic for Alzheimer's disease: translational development and clinical promise," Prog. Neurobiol. 2014;113:40-55.

Irwin et al., "Frontiers in therapeutic development of allopregnanolone for Alzheimer's disease and other neurological disorders," Front. Cell. Neurosci. 2014;8:203.

Iwaszkiewicz-Grzes et al., "Synthesis and biological activity of mycophenolic acid-amino acid derivatives," Eur. J. Med. Chem. 2013;69:863-71.

Janossy and Greaves, "Lymphocyte activation: I. Response of T and B lymphocytes to phytomitogens," Clin. Exp. Immunol. 1971;9(4):483-498.

Jeong et al., "Dose optimization of tacrolimus for improving survival time of PEGylated islets in a rat-to-mouse xenograft model," Macromolecular Research. 2016;24(12):1047-1054.

Jew et al., "Asymmetric synthesis of (R)-(+)-etomoxir," Tetrahedron: Asymmetry. 1997; 8(8):1187-1192.

Kai et al., "Structure-activity relationship study of flowering-inducer FN against Lemna paucicostata," Tetrahedron. 2008; 64(28):6760-6769.

Kanes et al., "Brexanolone (SAGE-547 injection) in post-partum depression: a randomised controlled trial," Lancet. 2017;390(10093):480-489.

Kihel et al., "Synthesis and evaluation of the anti-inflammatory effects of niflumic acid lipophilic prodrugs in brain edema," Arzneimittelforschung. 1996;46(11):1040-4.

Kim et al., "Convenient Synthesis of Electron Deficient Dienes via Pd(0) Catalyzed Coupling," Synlett. 1998; 1998(10):1059-1060.

Kim et al., "The Anti-Inflammatory Effects of Oral-Formulated Tacrolimus in Mice with Experimental Autoimmune Encephalomyelitis," J. Korean Med. Sci. 2017;32(9):1502-1507.

Koboziev et al., "Gut-associated lymphoid tissue, T cell trafficking, and chronic intestinal inflammation," Ann. NY. Acad. Sci. 2010;1207(Suppl 1):E86-E93.

Kratz et al., "Prodrug strategies in anticancer chemotherapy," ChemMedChem. 2008; 3(1):20-53.

Han, Sifei, et al., "Profiling the Role of Deacylation-Reacylation in the Lymphatic Transport of a Triglyceride-Mimetic Prodrug," Pharm. Res., vol. 32, pp. 1830-1844 (2015).

Han, Sifei, "Triglyceride-mimetic approaches for targeted drug delivery to the lymphatic system: A mechanistic study," A thesis submitted for the degree of Doctor of Philosophy, Monash University (published Oct. 31, 2017).

* cited by examiner

LYMPHATIC SYSTEM-DIRECTING LIPID PRODRUGS

CROSS-REFERENCE TO RELATED APPLICATIONS

This application is a continuation application of U.S. patent application Ser. No. 16/642,794 filed on Feb. 27, 2020, which is a national stage application filed under 35 U.S.C. § 371 of International Patent Application No. PCT/US2018/048642, filed on Aug. 29, 2018, which claims the benefit of U.S. Provisional Patent Application Nos. 62/551,627, filed on Aug. 29, 2017; 62/607,700, filed on Dec. 19, 2017; 62/607,749, filed on Dec. 19, 2017; 62/714,029, filed on Aug. 2, 2018; 62/724,274, filed on Aug. 29, 2018; and 62/724,440, filed on Aug. 29, 2018; the entirety of each of which is hereby incorporated by reference.

TECHNICAL FIELD

The present invention relates to compounds in the form of prodrugs, in particular, compounds that promote transport of a pharmaceutical agent to the lymphatic system and subsequently enhance release of the parent drug. The present invention also relates to compositions and methods of using such prodrugs.

BACKGROUND OF THE INVENTION

The lymphatic system consists of a specialized network of vessels, nodes and lymphoid tissues that are distributed throughout the body in close proximity to the vascular system. The lymphatic system plays a number of key roles in immune response, fluid balance, nutrient absorption, lipid homeostasis, and tumor metastasis. Due to the unique anatomical and physiological characteristics of the lymphatic system, targeted drug delivery to and through the lymphatic system has been suggested as a means to improve both pharmacokinetic and pharmacodynamic profiles.

Lymphatic drug transport has the potential to enhance oral bioavailability through avoidance of first pass metabolism, to alter systemic drug disposition, and to enhance efficacy against lymph or lymphocyte mediated pathologies such as lymphoma, leukemia, lymphatic tumor metastasis, autoimmune disease, lymph resident infections and transplant rejection. In order for drugs to access the intestinal lymph, they must first associate with intestinal lymph lipoproteins that are assembled in intestinal absorptive cells (enterocytes) in response to lipid absorption. Association with these lipoproteins subsequently promotes drug transport into the lymph since their size precludes ready diffusion across the vascular endothelium lining the blood capillaries that drain the small intestine. Instead, these large colloidal structures enter the lymphatic capillaries since the lymphatic endothelium is considerably more permeable than that of the vascular endothelium.

Historically, drugs with high lymphatic transport have been highly lipophilic in order to promote physical association with lipoproteins (usually, but not exclusively, log D>5 and solubility in long chain triglyceride of >50 mg/g). Therefore, highly lipophilic analogues of drugs have been envisaged as one way to promote lymphatic drug transport. However, chemical modification of a parent drug can result in a reduction in potency and in many cases, significant increases in lipophilicity have been correlated with increases in toxicity.

Compounds in the form of lipophilic prodrugs provide a means to temporarily increase lipophilicity and lipoprotein affinity of a pharmaceutical compound, thereby increasing lymphatic targeting. Having been transported via the lymphatic system, the prodrug is cleaved, thereby releasing the parent drug in order to be active at its target site.

Lipophilic esters of drugs have been explored as more bioavailable versions of existing drugs. For example, testosterone undecanoate is a marketed drug for hypogonadism and other conditions. Oral administration of testosterone itself is problematic because of its extensive first pass metabolism in the liver and resulting very low bioavailability. The undecanoate ester of testosterone redirects a small proportion of the absorbed dose into the lymphatic system, thereby avoiding hepatic first pass metabolism and increasing the oral bioavailability of testosterone. However, this process is still very inefficient, and the bioavailability of testosterone after oral administration of the undecanoate ester is thought to be <5%.

Accordingly, there exists a need to develop novel lipid-pharmaceutical agent conjugates that facilitate stable transport of the pharmaceutical agent to the intestinal lymph and that readily revert to the parent active agent in order to be active.

SUMMARY OF THE INVENTION

In one aspect, the present invention provides a compound of Formula VI:

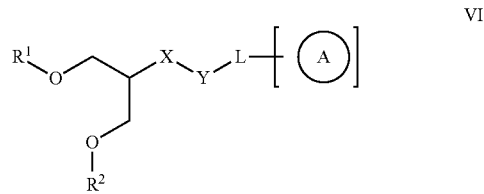

or a pharmaceutically acceptable salt thereof, wherein each variable is as defined herein.

In another aspect, the present invention provides a method of treating a disease, disorder, or condition such as one of those disclosed herein, comprising administering to a patient in need thereof an effective amount of a disclosed compound, such as a compound of Formula VI, or a pharmaceutically acceptable salt thereof.

DETAILED DESCRIPTION OF THE INVENTION

Figure 1:
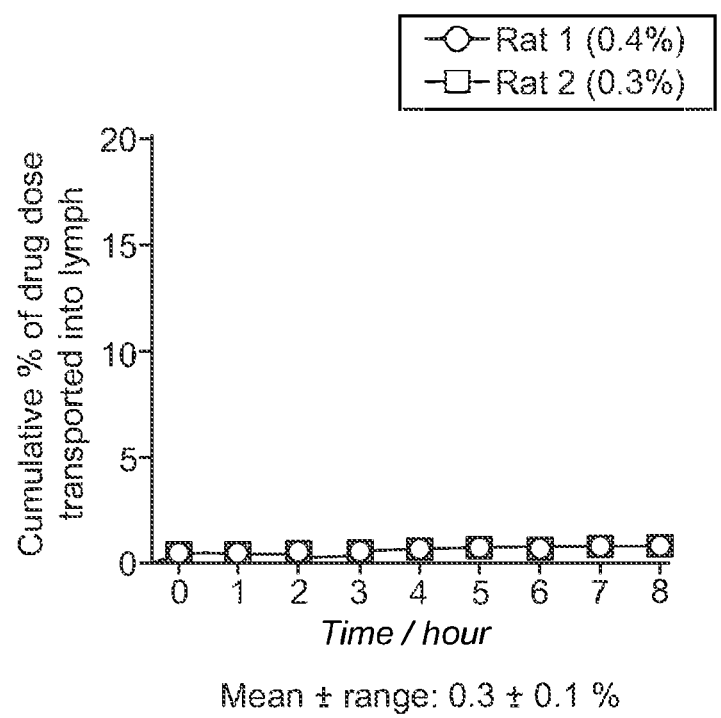
FIG. 1 shows lymphatic transport data for mycophenolic acid prodrug MPA-I-17 in rats.

1. General Description of Certain Aspects of the Invention

Lymphatic System-Directing Prodrugs

Compounds of the present invention, and compositions thereof, are useful in promoting transport of a therapeutic agent to the lymphatic system and in subsequently enhancing release of the parent drug, i.e. the therapeutic agent.

In one aspect, the present invention provides a compound of Formula I:

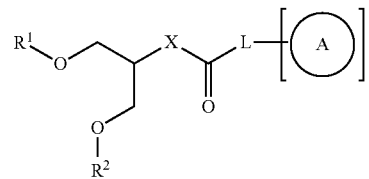

or a pharmaceutically acceptable salt thereof, wherein:
$R^1$ and $R^2$ are each independently hydrogen, a lipid, or —C(O)$R^3$;
each $R^3$ is independently a saturated or unsaturated, straight or branched $C_{2-37}$ hydrocarbon chain;
X is —O—, —NR—, or —S—;
each R is independently hydrogen or an optionally substituted $C_{1-4}$ aliphatic;
L is a covalent bond or a bivalent, saturated or unsaturated, straight or branched $C_{1-20}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

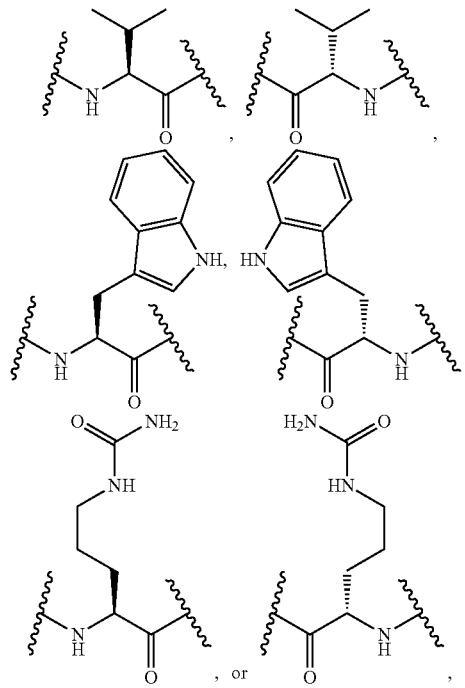

wherein:
each -Cy- is independently an optionally substituted 5-6 membered bivalent aryl ring having 0-4 heteroatoms independently selected from nitrogen, oxygen, or sulfur; or

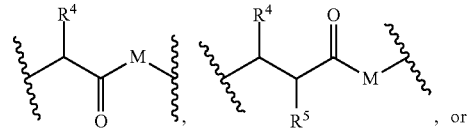

-continued

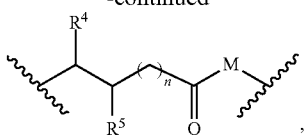

wherein:
R⁴ and R⁵ are each independently hydrogen or $C_{1-4}$ aliphatic;
M is a self-immolative group;
n is 0-18;
R⁶ is hydrogen or $C_{1-4}$ aliphatic; and
A is a therapeutic agent.

In one aspect, the present invention provides a compound of Formula VI:

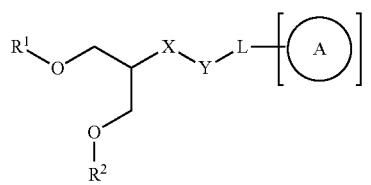

or a pharmaceutically acceptable salt thereof, wherein:
R¹ and R² are each independently hydrogen, an acid-labile group, a lipid, or —C(O)R³;
each R³ is independently a saturated or unsaturated, straight or branched, optionally substituted $C_{1-37}$ hydrocarbon chain;
X is —O—, —NR—, —S—, —O($C_{1-6}$ aliphatic)-O—, —O($C_{1-6}$ aliphatic)-S—, —O($C_{1-6}$ aliphatic)-NR—, —S($C_{1-6}$ aliphatic)-O—, —S($C_{1-6}$ aliphatic)-S—, —S($C_{1-6}$ aliphatic)-NR—, —NR($C_{1-6}$ aliphatic)-O—, —NR($C_{1-6}$ aliphatic)-S—, or —NR($C_{1-6}$ aliphatic)-NR—, wherein 0-2 methylene units of the $C_{1-6}$ aliphatic group are independently and optionally replaced with —O—, —NR—, or —S— and the $C_{1-6}$ aliphatic group is independently and optionally substituted with 1, 2, or 3 deuterium or halogen atoms;
each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;
Y is absent or is —C(O)—, —C(NR)—, or —C(S)—;
L is a covalent bond or a bivalent, saturated or unsaturated, straight or branched, optionally substituted bivalent $C_{1-30}$ hydrocarbon chain, wherein 0-8 methylene units of L are independently replaced by -Cy-, —O—, —NR—, —S—, —OC(O)—, —C(O)O—, —C(O)—, —S(O)—, —S(O)₂—, —C(S)—, —NRS(O)₂—, —S(O)₂NR—, —NRC(O)—, —C(O)NR—, —OC(O)NR—, —NRC(O)O—, or an amino acid; and wherein 1 methylene unit of L is optionally replaced with -M-; or
L is

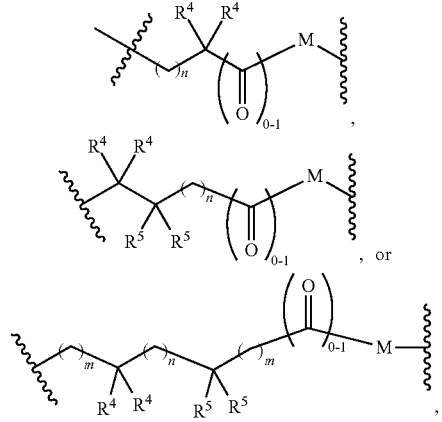

wherein either the right-hand side or left-hand side of L is attached to A;
each -Cy- is independently an optionally substituted 3-6 membered bivalent saturated, partially unsaturated, or aromatic ring having 0-4 heteroatoms independently selected from nitrogen, oxygen, or sulfur;
each R⁴ and R⁵ is independently hydrogen, deuterium, halogen, —CN, —OR, —NR₂, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or a $C_{1-6}$ aliphatic group optionally substituted with —CN, —OR, —NR₂, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or the $C_{1-6}$ aliphatic is optionally substituted with 1, 2, 3, 4, 5, or 6 deuterium or halogen atoms; or
two instances of R⁴ or R⁵ attached to the same carbon atom, taken together with the carbon atom to which they are attached, form a 3-6 membered saturated monocyclic carbocyclic ring or 3-6 membered saturated heterocyclic ring having 1-2 heteroatoms independently selected from nitrogen, oxygen, or sulfur;
-M- is a self-immolative group;
n is 0-18;
each m is independently 0-6; and
A is a therapeutic agent.

In one aspect, the present invention provides a method of treating a disease, disorder, or condition in a patient in need thereof, comprising administering to the patient a disclosed lipid prodrug, such as a compound of Formula I or VI, or a pharmaceutically acceptable salt thereof.

It is understood that a disclosed lipid prodrug may exist in the form of a pharmaceutically acceptable salt. Thus, a reference to a "lipid prodrug" is also a disclosure of "lipid prodrug or a pharmaceutically acceptable salt thereof." It follows that such a lipid prodrug or pharmaceutically acceptable salt thereof may be used in a pharmaceutical composition and a method of use, such as those disclosed herein.

One approach to directing drugs into the lymphatic transport system is to employ prodrugs that participate in endogenous pathways that control the absorption, transport (including passive transport), and metabolism of dietary lipids. In one aspect, the present invention provides a lipid prodrug comprising a therapeutic agent conjugated to a glycerol-based moiety comprising up to two fatty acids or other lipids. Without wishing to be bound by theory, it is believed that such a prodrug mimics a dietary triglyceride, such that it participates in triglyceride processing and metabolism in the GI tract. Where appropriate, certain lipid prodrug scaffolds may be modified from the literature for use in accordance with the present disclosure. For example, certain drug-lipid conjugates and lipid prodrug scaffolds are disclosed in WO 2017/041139 and WO 2016/023082, each of which is hereby incorporated by reference in its entirety. Further examples of drug-lipid conjugates where the parent drug contains an available carboxylic acid group and has been directly conjugated to a glyceride backbone are described in Paris, G. Y. et al., J. Med. Chem. 1979, 22, (6), 683-687; Garzon Aburbeh, A. et al., J. Med. Chem. 1983, 26, (8), 1200-1203; Deverre, J. R.; et al., J. Pharm. Pharmacol. 1989, 41, (3), 191-193; Mergen, F. et al, J. Pharm. Pharmacol. 1991, 43, (11), 815-816; Garzon Aburbeh, A. et al, J. Med. Chem. 1986, 29, (5), 687-69; and Han, S. et al. J. Control. Release 2014, 177, 1-10.

Further examples have used a short linker where the drug does not contain an available carboxylic acid (Scriba, G. K. E., Arch. Pharm. (Weinheim) 1995, 328, (3), 271-276; and Scriba, G. K. E. et al, J. Pharm. Pharmacol. 1995, 47, (11), 945-948). Other examples have utilized an ester linkage to the drug and an ether linkage to the glyceride (Sugihara, J. et al., J. Pharmacobiodyn. 1988, 11, (5), 369-376; and Sugihara, J. et al., J. Pharmacobiodyn. 1988, 11, (8), 555-562).

Typical use of prodrug strategies to improve a therapeutic agent's (active pharmaceutical agent's) pharmacokinetic properties relies on cleavage in vivo to the parent agent via non-specific degradation or enzymatic cleavage, thus allowing the agent to exert its biological activity. The present invention, in one aspect, provides modified glyceride-based compounds (lipid prodrugs) that direct lymphatic transport of a therapeutic agent and improve cleavage of the lipid prodrug to the therapeutic agent.

Dietary lipids, including triglycerides, follow a particular metabolic pathway to gain access to the lymph (and ultimately the systemic circulation) that is entirely distinct from that of other nutrients such as proteins and carbohydrates. After ingestion, dietary triglycerides are hydrolyzed by lipases in the lumen to release one monoglyceride and two fatty acids for each molecule of triglyceride. The monoglyceride and two fatty acids are subsequently absorbed into enterocytes and re-esterified to triglycerides.

Resynthesised triglycerides are assembled into intestinal lipoproteins, primarily chylomicrons. After formation, chylomicrons are exocytosed from enterocytes and subsequently gain preferential access to the intestinal lymphatics. Once within the lymphatic system, chylomicrons containing packaged triglycerides drain through a series of capillaries, nodes and ducts to join the systemic circulation at the junction of the left subclavian vein and internal jugular vein. Following entry into blood circulation, triglycerides in chylomicrons are preferentially and efficiently taken up by tissues with high expression levels of lipoprotein lipases, such as adipose tissue, the liver, and potentially certain types of tumor tissues.

Lipid prodrugs are expected to behave similarly to natural triglycerides and to be transported to and through the lymphatic system to reach the systemic circulation without interacting with the liver. In some embodiments, the lipid prodrugs are cleaved, releasing the therapeutic agent, after the prodrugs have reached the systemic circulation, or after reaching a target tissue. In some embodiments, the lipid prodrugs release the therapeutic agent by destruction of a self-immolative linker that attaches the therapeutic agent to the glyercol-derived group, or by enzymatic cleavage of a linker. In this way, the pharmacokinetic and pharmacodynamic profiles of the parent therapeutic agent may be manipulated to enhance access to the lymph and lymphoid tissues, thereby promoting oral bioavailability via avoidance of first-pass metabolism (and potentially intestinal efflux). Accordingly, in some embodiments, the disclosed lipid prodrug has improved oral bioavailability, reduced first-pass metabolism, reduced liver toxicity, or improved other pharmacokinetic properties as compared with the parent therapeutic agent. In some embodiments, the disclosed lipid prodrug has increased drug targeting (as compared with the parent therapeutic agent) to sites within the lymph, lymph nodes and lymphoid tissues, and to sites of high lipid utilization and lipoprotein lipase expression such as adipose tissue, liver and some tumours.

In certain aspects, the present invention provides methods of modulating the delivery, distribution, or other properties of a therapeutic agent. In one aspect, the present invention provides a method of delivering a therapeutic agent to the systemic circulation of a patient in need thereof, wherein the therapeutic agent partially, substantially, or completely bypasses first-pass liver metabolism in the patient, comprising the step of administering to the patient a disclosed lipid prodrug of the therapeutic agent. In another aspect, the present invention provides a method of modifying a therapeutic agent to partially, substantially, or completely bypass first-pass liver metabolism in a patient after administration of the therapeutic agent, comprising the step of preparing a disclosed lipid prodrug of the therapeutic agent. In some embodiments, the lipid prodrug is administered orally. In some embodiments, preparing the lipid prodrug comprises the step of conjugating a therapeutic agent to a glycerol-based scaffold comprising two fatty acids or other lipids, thereby providing the lipid prodrug.

In another aspect, the present invention provides a method of improving oral bioavailability of a therapeutic agent, enhancing gut absorption of a therapeutic agent, or decreasing metabolism, decomposition, or efflux in the gut of a therapeutic agent, comprising the step of preparing a disclosed lipid prodrug of the therapeutic agent.

In another aspect, the present invention provides a method of modifying, e.g., improving, delivery of a therapeutic agent to a target tissue, comprising the step of preparing a disclosed lipid prodrug of the therapeutic agent. In some embodiments, the target tissue is the lymph, a lymph node (such as a mesenteric lymph node), adipose tissue, liver, or a tumor, such as a lymph node site of metastasis.

Lipid prodrugs that readily convert to parent therapeutic agent after transport via the systemic circulation have reduced free drug concentrations in the gastrointestinal (GI) tract, which may provide benefits in reducing gastrointestinal irritation or toxicity, and/or in increased drug solubility in intestinal bile salt micelles (due to similarities to endogenous monoglycerides). Disclosed lipid prodrugs may also in certain embodiments have increased passive membrane permeability (due to greater lipophilicity compared with the parent therapeutic agent). In some embodiments, the lipid prodrug has greater solubility in lipid formulations or vehicles comprising either lipids alone or mixtures of lipids with surfactants and/or cosolvents, allowing for the use of lipophilic formulations for otherwise highly hydrophilic therapeutic agents.

In one aspect, the present invention provides a compound of Formula I:

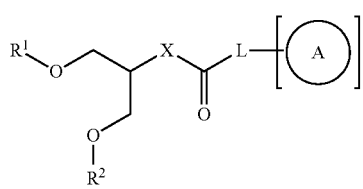

I or a pharmaceutically acceptable salt thereof, wherein:
  $R^1$ and $R^2$ are each independently hydrogen, a lipid, or —C(O)R$^3$;
  each $R^3$ is independently a saturated or unsaturated, straight or branched $C_{2-37}$ hydrocarbon chain;
  X is —O—, —NR—, or —S—;
  each R is independently hydrogen or an optionally substituted $C_{1-4}$ aliphatic;
  L is a covalent bond or a bivalent, saturated or unsaturated, straight or branched $C_{1-20}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

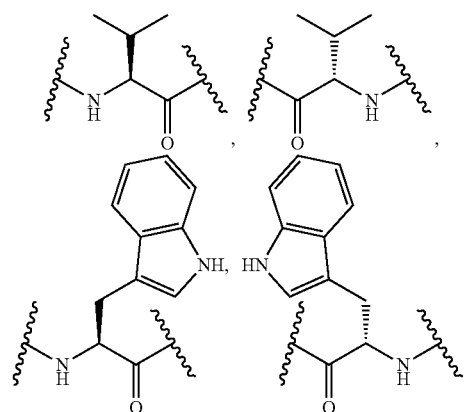

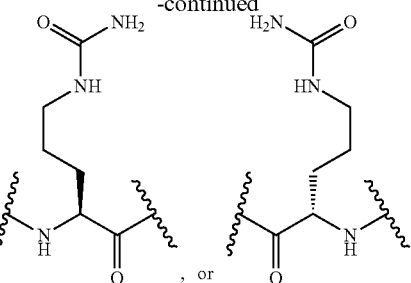

, or

, wherein:
  each -Cy- is independently an optionally substituted 5-6 membered bivalent aryl ring having 0-4 heteroatoms independently selected from nitrogen, oxygen, or sulfur; or
  L is

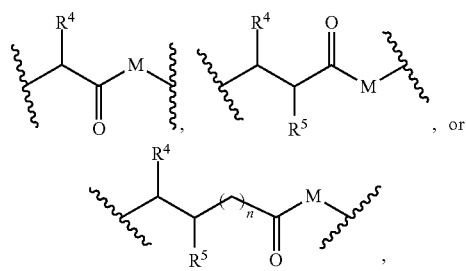

, wherein:
  $R^4$ and $R^5$ are each independently hydrogen or $C_{1-4}$ aliphatic;
  M is a self-immolative group;
  n is 0-18;
  $R^6$ is hydrogen or $C_{1-4}$ aliphatic; and
  A is a therapeutic agent.

As defined above and described herein, $R^1$ and $R^2$ are each independently hydrogen, a lipid such as a fatty acid, or —C(O)R$_3$.

In some embodiments, $R^1$ is hydrogen. In some embodiments, $R^1$ is a lipid. In some embodiments, $R^1$ is a fatty acid. In some embodiments, $R^1$ is —C(O)R$^3$.

In some embodiments, $R^1$ is selected from those depicted in Table A, below.

In some embodiments, $R^2$ is hydrogen. In some embodiments, $R^2$ is a lipid. In some embodiments, $R^2$ is a fatty acid. In some embodiments, $R^2$ is —C(O)R$^3$.

In some embodiments, $R^2$ is selected from those depicted in Table A, below.

As defined above and described herein, each $R^3$ is independently a saturated or unsaturated, straight or branched $C_{2-37}$ hydrocarbon chain.

In some embodiments, $R^3$ is a saturated, straight $C_{2-37}$ hydrocarbon chain. In some embodiments, $R^3$ is an unsaturated, straight $C_{2-37}$ hydrocarbon chain. In some embodiments, $R^3$ is a saturated, branched $C_{2-37}$ hydrocarbon chain. In some embodiments, $R^3$ is an unsaturated, branched $C_{2-37}$ hydrocarbon chain.

In some embodiments, $R^3$ is selected from those depicted in Table A, below.

As defined above and described herein, X is —O—, —NR—, or —S—.

In some embodiments, X is —O—. In some embodiments, X is —NR—. In some embodiments, X is —S—.

In some embodiments, X is selected from those depicted in Table A, below.

As defined above and described herein, each R is independently hydrogen or an optionally substituted $C_{1-4}$ aliphatic.

In some embodiments, R is hydrogen. In some embodiments, R is an optionally substituted $C_{1-4}$ aliphatic.

In some embodiments, R is selected from those depicted in Table A, below.

As defined above and described herein, L is a covalent bond or a bivalent, saturated or unsaturated, straight or branched $C_{1-20}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

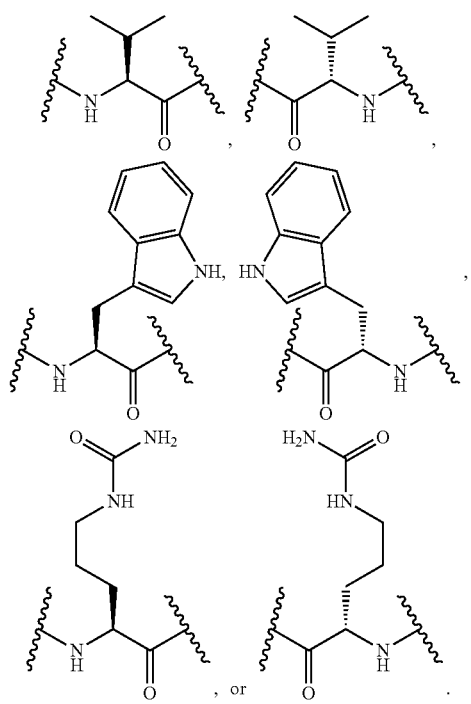

In some embodiments, L is a covalent bond. In some embodiments, L is a bivalent, saturated, straight $C_{1-20}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

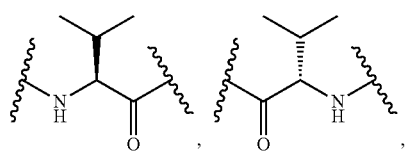

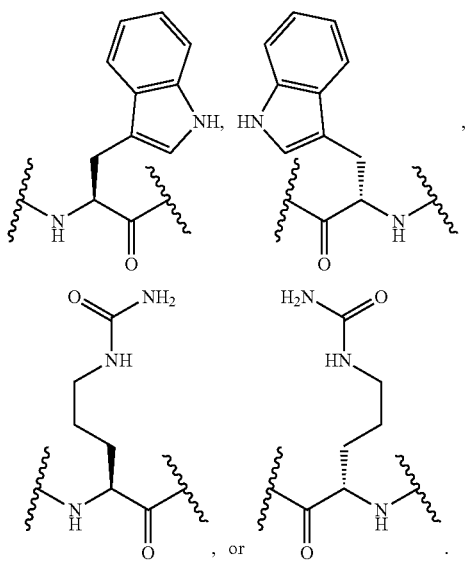

In some embodiments, L is a bivalent, saturated, branched $C_{1-20}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

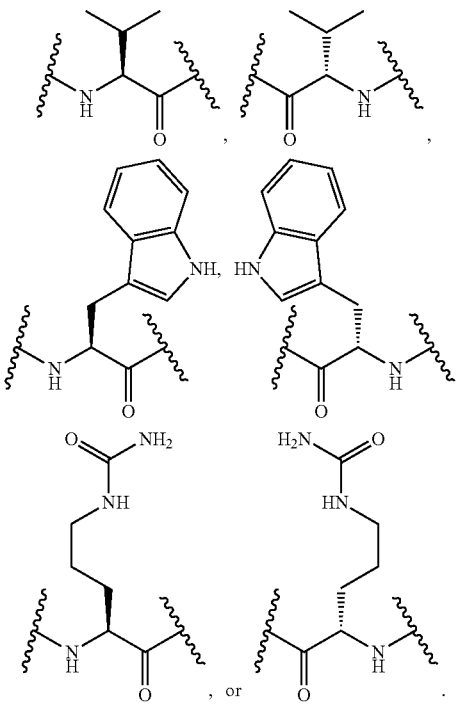

In some embodiments, L is a bivalent, unsaturated, straight $C_{1-20}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

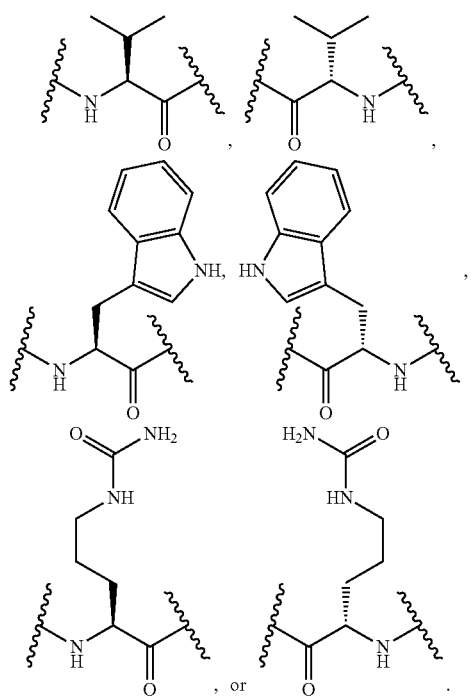

, or

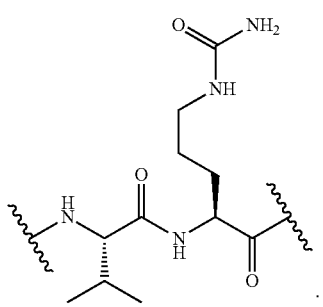 [SMILES: *N[C@H](C(=O)N[C@@H](CCCNC(N)=O)C(*)=O)C(C)C]

In some embodiments, L is a bivalent, unsaturated, branched $C_{1-20}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, or —NRC(O)O—.

In some embodiments, L comprises

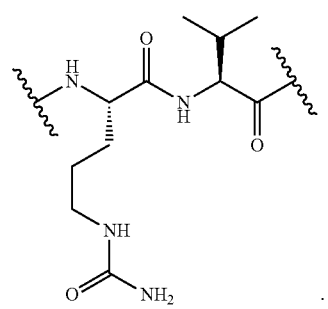 [SMILES: *N[C@@H](CCCNC(N)=O)C(=O)N[C@H](C(*)=O)C(C)C]

In some embodiments, L comprises

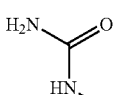

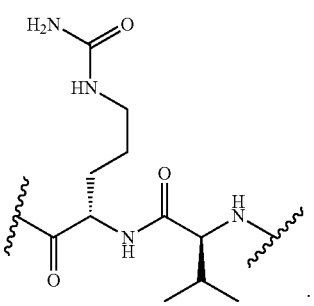 [SMILES: *N[C@H](C(=O)N[C@@H](CCCNC(N)=O)C(*)=O)C(C)C]

In some embodiments, L comprises

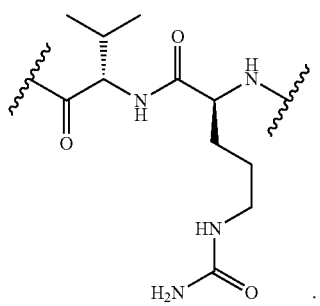 [SMILES: *N[C@@H](CCCNC(N)=O)C(=O)N[C@H](C(*)=O)C(C)C]

In some embodiments, L comprises

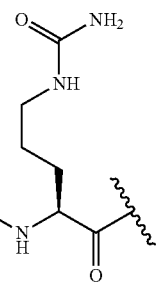

In some embodiments, L comprises

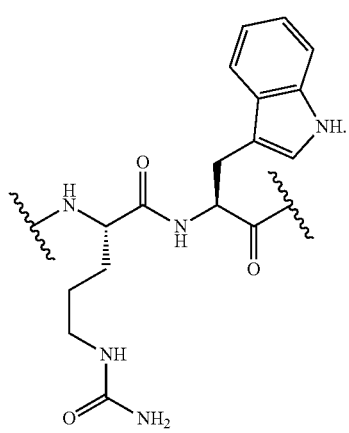 [SMILES: *N[C@@H](CCCNC(N)=O)C(=O)N[C@@H](Cc1c[nH]c2ccccc12)C(*)=O]

In some embodiments, L comprises

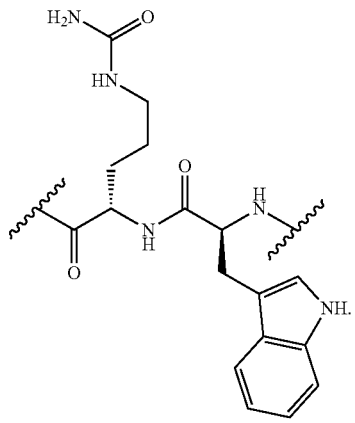 [SMILES: *N[C@@H](Cc1c[nH]c2ccccc12)C(=O)N[C@@H](CCCNC(N)=O)C(*)=O]

In some embodiments, L comprises

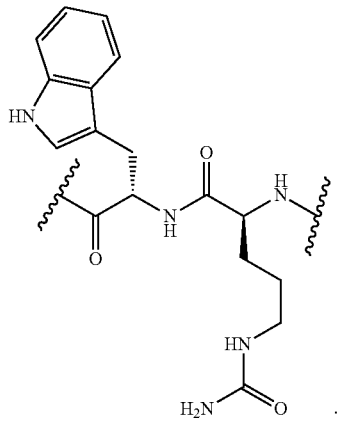 [SMILES: *N[C@@H](CCCNC(N)=O)C(=O)N[C@@H](Cc1c[nH]c2ccccc12)C(*)=O]

In some embodiments, L is selected from those depicted in Table A, below.

As defined above and described herein, each -Cy- is independently an optionally substituted 5-6 membered bivalent aryl ring having 0-4 heteroatoms independently selected from nitrogen, oxygen, or sulfur.

In some embodiments, -Cy- is an optionally substituted 5-6 membered bivalent aryl ring having 0-4 heteroatoms independently selected from nitrogen, oxygen, or sulfur. In some embodiments, -Cy- is an optionally substituted 5 membered bivalent aryl ring having 0-4 heteroatoms independently selected from nitrogen, oxygen, or sulfur. In some embodiments, -Cy- is an optionally substituted 6 membered bivalent aryl ring having 0-4 heteroatoms independently selected from nitrogen, oxygen, or sulfur.

In some embodiments, -Cy- is selected from those depicted in Table A, below.

As defined above and described herein, L is

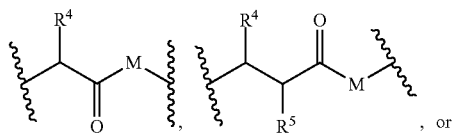

In some embodiments, L is

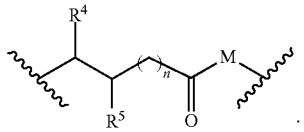

In some embodiments, L is

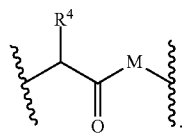

In some embodiments, L is

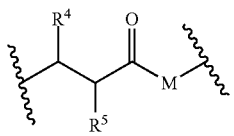

In some embodiments, L is

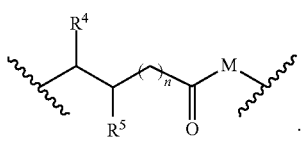

In some embodiments, L is selected from those depicted in Table A, below.

As defined above and described herein, $R^4$ and $R^5$ are each independently hydrogen or $C_{1-4}$ aliphatic.

In some embodiments, $R^4$ is hydrogen. In some embodiments, $R^4$ is $C_{1-4}$ aliphatic. In some embodiments, $R^4$ is methyl. In some embodiments, $R^4$ is ethyl. In some embodiments, $R^4$ is n-propyl. In some embodiments, $R^4$ is isopropyl. In some embodiments, $R^4$ is cyclopropyl or cyclobutyl. In some embodiments, $R^4$ is n-butyl. In some embodiments, $R^4$ is sec-butyl. In some embodiments, $R^4$ is isobutyl. In some embodiments, $R^4$ is tert-butyl. In some embodiments, $R^4$ is selected from those depicted in Table A, below.

In some embodiments, $R^5$ is hydrogen. In some embodiments, $R^5$ is $C_{1-4}$ aliphatic. In some embodiments, $R^5$ is methyl. In some embodiments, $R^5$ is ethyl. In some embodiments, $R^5$ is n-propyl. In some embodiments, $R^5$ is isopropyl. In some embodiments, $R^5$ is cyclopropyl or cyclobutyl. In some embodiments, $R^5$ is n-butyl. In some embodiments, $R^5$ is sec-butyl. In some embodiments, $R^5$ is isobutyl. In some embodiments, $R^5$ is tert-butyl. In some embodiments, $R^4$ is selected from those depicted in Table 1, below. In some embodiments, $R^5$ is selected from those depicted in Table A, below.

As defined above and described herein, M is a self-immolative group.

In some embodiments, M is a self-immolative group.
In some embodiments, M is

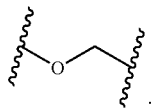

In some embodiments, M is

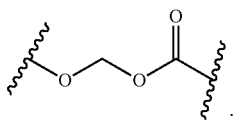

In some embodiments, M is

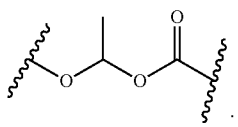 [SMILES: *OC(C)OC(*)=O]

In some embodiments, M is

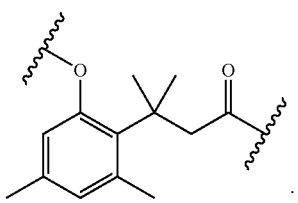 [SMILES: *Oc1cc(C)cc(C)c1C(C)(C)CC(*)=O]

In some embodiments, M is

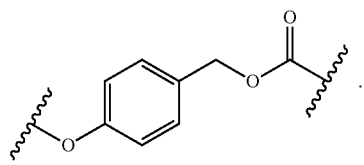 [SMILES: *Oc1ccc(COC(*)=O)cc1 ; "."]

In some embodiments, M is

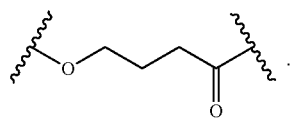 [SMILES: *OCCCC(*)=O ; "."]

In some embodiments, M is selected from those depicted in Table A, below.

As defined above and described herein, n is 0-18.

In some embodiments, n is 0. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10. In some embodiments, n is 11. In some embodiments, n is 12. In some embodiments, n is 13. In some embodiments, n is 14. In some embodiments, n is 15. In some embodiments, n is 16. In some embodiments, n is 17. In some embodiments, n is 18.

In some embodiments, n is selected from those depicted in Table A, below.

As defined above and described herein, $R^6$ is hydrogen or $C_{1-4}$ aliphatic.

In some embodiments, $R^6$ is hydrogen. In some embodiments, $R^6$ is $C_{1-4}$ aliphatic. In some embodiments, $R^6$ is methyl. In some embodiments, $R^6$ is ethyl. In some embodiments, $R^6$ is n-propyl. In some embodiments, $R^6$ is isopropyl. In some embodiments, $R^6$ is n-butyl. In some embodiments, $R^6$ is isobutyl. In some embodiments, $R^6$ is tert-butyl.

In some embodiments, $R^6$ is selected from those depicted in Table A, below.

As defined above and described herein, A is a therapeutic agent.

In some embodiments, A is a therapeutic agent.

In some embodiments, A is a therapeutic agent selected from any of those set forth in Tables 1-7, or a derivative thereof, below.

One of ordinary skill in the art will appreciate that certain therapeutic agents listed in Tables 1-7 are in the form of prodrugs. For example, mycophenolate mofetil is a prodrug of a mycophenolic acid. Thus, it will be appreciated that a lipid prodrug moiety of the present invention is attached to the therapeutic agent or the active form thereof. For the purpose of clarity, and by way of example, it will be understood that a provided lipid prodrug moiety is attached at any modifiable oxygen, sulfur, or nitrogen atom of the therapeutic agent, e.g. either mycophenolate mofetil or mycophenolic acid.

In some embodiments, A is selected from those depicted in Table A, below.

In one aspect, the present invention provides a compound of Formula VI:

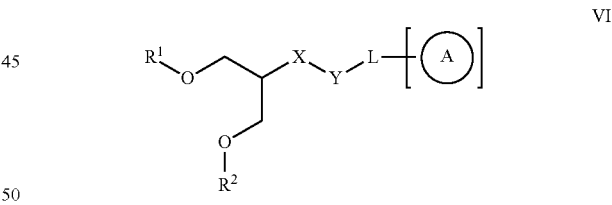

or a pharmaceutically acceptable salt thereof, wherein:
$R^1$ and $R^2$ are each independently hydrogen, an acid-labile group, a lipid, or —C(O)$R^3$;
each $R^3$ is independently a saturated or unsaturated, straight or branched, optionally substituted $C_{1-37}$ hydrocarbon chain;
X is —O—, —NR—, —S—, —O($C_{1-6}$ aliphatic)-O—, —O($C_{1-6}$ aliphatic)-S—, —O($C_{1-6}$ aliphatic)-NR—, —S($C_{1-6}$ aliphatic)-O—, —S($C_{1-6}$ aliphatic)-S—, —S($C_{1-6}$ aliphatic)-NR—, —NR($C_{1-6}$ aliphatic)-O—, —NR($C_{1-6}$ aliphatic)-S—, or —NR($C_{1-6}$ aliphatic)-NR—, wherein 0-2 methylene units of the $C_{1-6}$ aliphatic group are independently and optionally replaced with —O—, —NR—, or —S— and the $C_{1-6}$ aliphatic group is independently and optionally substituted with 1, 2, or 3 deuterium or halogen atoms;

each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

Y is absent or is —C(O)—, —C(NR)—, or —C(S)—;

L is a covalent bond or a bivalent, saturated or unsaturated, straight or branched, optionally substituted bivalent $C_{1-30}$ hydrocarbon chain, wherein 0-8 methylene units of L are independently replaced by -Cy-, —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or an amino acid; and wherein 1 methylene unit of L is optionally replaced with -M-; or L is

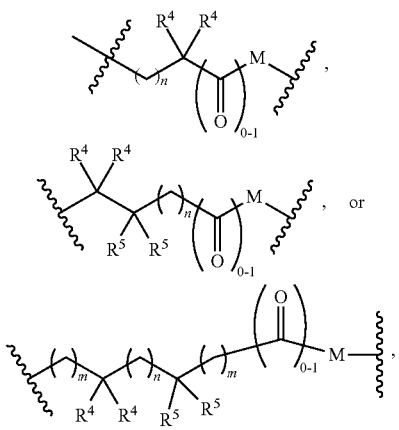

wherein either the right-hand side or left-hand side of L is attached to A;

each -Cy- is independently an optionally substituted 3-6 membered bivalent saturated, partially unsaturated, or aromatic ring having 0-4 heteroatoms independently selected from nitrogen, oxygen, or sulfur;

each $R^4$ and $R^5$ is independently hydrogen, deuterium, halogen, —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or a $C_{1-6}$ aliphatic group optionally substituted with —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or the $C_{1-6}$ aliphatic is optionally substituted with 1, 2, 3, 4, 5, or 6 deuterium or halogen atoms; or two instances of $R^4$ or $R^5$ attached to the same carbon atom, taken together with the carbon atom to which they are attached, form a 3-6 membered saturated monocyclic carbocyclic ring or 3-6 membered saturated heterocyclic ring having 1-2 heteroatoms independently selected from nitrogen, oxygen, or sulfur;

-M- is a self-immolative group;

n is 0-18;

each m is independently 0-6; and

A is a therapeutic agent.

As defined above and described herein, $R^1$ and $R^2$ are each independently hydrogen, an acid-labile group, a lipid such as a fatty acid, or —C(O)R$^3$.

In some embodiments, $R^1$ is hydrogen. In some embodiments, $R^1$ is an acid-labile group. In some embodiments, $R^1$ is a lipid. In some embodiments, $R^1$ is a fatty acid. In some embodiments, $R^1$ is —C(O)R$^3$. In some embodiments, $R^1$ is selected from those depicted in Table A, below.

In some embodiments, $R^2$ is hydrogen. In some embodiments, $R^2$ is an acid-labile group. In some embodiments, $R^2$ is a lipid. In some embodiments, $R^2$ is a fatty acid. In some embodiments, $R^2$ is —C(O)R$^3$. In some embodiments, $R^2$ is selected from those depicted in Table A, below.

In some embodiments, each of $R^1$ and $R^2$ is independently a fatty acid, phosphatide, phospholipid, or analogue thereof, such as those described in detail below. In some embodiments, each fatty acid is independently a saturated or unsaturated medium-chain or long-chain fatty acid. In some embodiments, each fatty acid independently has a $C_2$-$C_{40}$ chain. In some embodiments, each fatty acid independently has a $C_6$-$C_{20}$, $C_8$-$C_{20}$, $C_{10}$-$C_{20}$, $C_{10}$-$C_{18}$, $C_{12}$-$C_{18}$, $C_{14}$-$C_{18}$, $C_{16}$-$C_{18}$, or $C_{10}$-$C_{16}$ chain. In some embodiments, each fatty acid is independently selected from oleic acid, palmitic acid, EPA, or DHA.

In some embodiments, $R^1$ and $R^2$ are each independently selected from an acid labile group such as tert-butoxycarbonyl (Boc), an amino acid, PEG group, —C(O)OR, —C(O)NR$_2$, —CH$_2$OR, —C(NR)R, or —P(O)$_2$OR.

As defined above and described herein, each $R^3$ is independently a saturated or unsaturated, straight or branched, optionally substituted $C_{1-37}$ hydrocarbon chain.

In some embodiments, $R^3$ is a saturated, straight, optionally substituted $C_{1-37}$ hydrocarbon chain. In some embodiments, $R^3$ is an unsaturated, straight, optionally substituted $C_{1-37}$ hydrocarbon chain. In some embodiments, $R^3$ is a saturated, branched, optionally substituted $C_{1-37}$ hydrocarbon chain. In some embodiments, $R^3$ is an unsaturated, branched, optionally substituted $C_{1-37}$ hydrocarbon chain. In some embodiments, $R^3$ is selected from those depicted in Table A, below.

As defined above and described herein, X is —O—, —NR—, —S—, —O($C_{1-6}$ aliphatic)-O—, —O($C_{1-6}$ aliphatic)-S—, —O($C_{1-6}$ aliphatic)-NR—, —S($C_{1-6}$ aliphatic)-O—, —S($C_{1-6}$ aliphatic)-S—, —S($C_{1-6}$ aliphatic)-NR—, —NR($C_{1-6}$ aliphatic)-O—, —NR($C_{1-6}$ aliphatic)-S—, or —NR($C_{1-6}$ aliphatic)-NR—, wherein 0-2 methylene units of the $C_{1-6}$ aliphatic group are independently and optionally replaced with —O—, —NR—, or —S— and the $C_{1-6}$ aliphatic group is independently and optionally substituted with 1, 2, or 3 deuterium or halogen atoms.

In some embodiments, X is —O—. In some embodiments, X is —NR—. In some embodiments, X is —S—. In some embodiments, X is —O($C_{1-6}$ aliphatic)-O—. In some embodiments, X is —O($C_{1-6}$ aliphatic)-S—. In some embodiments, X is —O($C_{1-6}$ aliphatic)-NR—. In some embodiments, X is —S($C_{1-6}$ aliphatic)-O—. In some embodiments, X is —S($C_{1-6}$ aliphatic)-S—. In some embodiments, X is —S($C_{1-6}$ aliphatic)-NR—. In some embodiments, X is —NR($C_{1-6}$ aliphatic)-O—. In some embodiments, X is —NR($C_{1-6}$ aliphatic)-S—. In some embodiments, X is —NR($C_{1-6}$ aliphatic)-NR—. In any of the foregoing embodiments, 0-2 methylene units of the bivalent $C_{1-6}$ aliphatic group are independently and optionally replaced with —O—, —NR—, or —S— and the bivalent $C_{1-6}$ aliphatic group is independently and optionally substituted with 1, 2, or 3 deuterium or halogen atoms. In some embodiments, X is selected from those depicted in Table A, below.

As defined above and described herein, Y is absent or is —C(O)—, —C(NR)—, or —C(S)—.

In some embodiments, Y is absent. In some embodiments, Y is —C(O)—. In some embodiments, Y is —C(NR)—. In some embodiments, Y is —C(S)—. In some embodiments, Y is selected from those depicted in Table A, below.

As defined above and described herein, L is a covalent bond or a bivalent, saturated or unsaturated, straight or branched, optionally substituted bivalent $C_{1-30}$ hydrocarbon chain, wherein 0-8 methylene units of L are independently replaced by -Cy-, —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or an amino acid; and wherein 1 methylene unit of L is optionally replaced with -M-; or L is

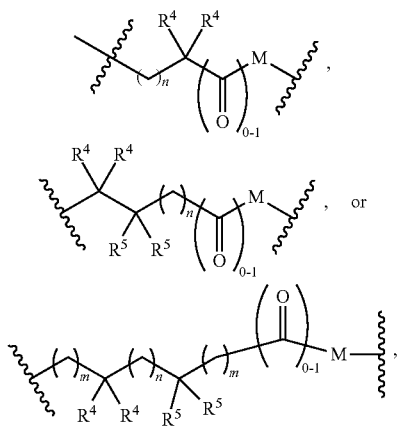

wherein either the right-hand side or left-hand side of L is attached to A.

In some embodiments, L is a covalent bond. In some embodiments, L is a bivalent, saturated or unsaturated, straight or branched, optionally substituted bivalent $C_{1-30}$ (e.g., $C_{3-30}$, $C_{5-30}$, $C_{7-30}$, $C_{3-25}$, $C_{5-25}$, $C_{7-25}$, $C_{3-20}$, $C_{5-20}$, $C_{7-20}$, $C_{6-18}$, $C_{6-18}$, $C_{7-17}$, $C_{8-16}$, $C_{8-15}$, $C_{8-14}$, $C_{7-13}$, $C_{6-12}$, etc.) hydrocarbon chain, wherein 0-8 (i.e., 0, 1, 2, 3, 4, 5, 6, 7, or 8) methylene units of L are independently replaced by -Cy-, —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or an amino acid; and wherein 1 methylene unit of L is optionally replaced with -M-. In some embodiments, L is

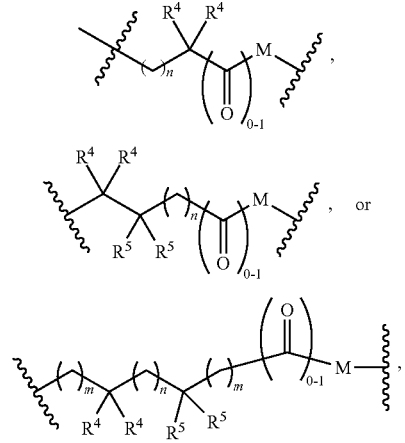

wherein either the right-hand side or left-hand side of L is attached to A.

In some embodiments, L is a covalent bond or a bivalent, saturated or unsaturated, straight or branched, optionally substituted bivalent $C_{1-30}$ (e.g., $C_{3-30}$, $C_{5-30}$, $C_{7-30}$, $C_{3-25}$, $C_{5-25}$, $C_{7-25}$, $C_{3-20}$, $C_{5-20}$, $C_{7-20}$, $C_{8-18}$, $C_{6-18}$, $C_{7-17}$, $C_{8-16}$, $C_{8-15}$, $C_{8-14}$, $C_{7-13}$, $C_{6-12}$, etc.) hydrocarbon chain, wherein 0-8 (i.e., 0, 1, 2, 3, 4, 5, 6, 7, or 8) methylene units of L are independently replaced by -Cy-, —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or an amino acid selected from

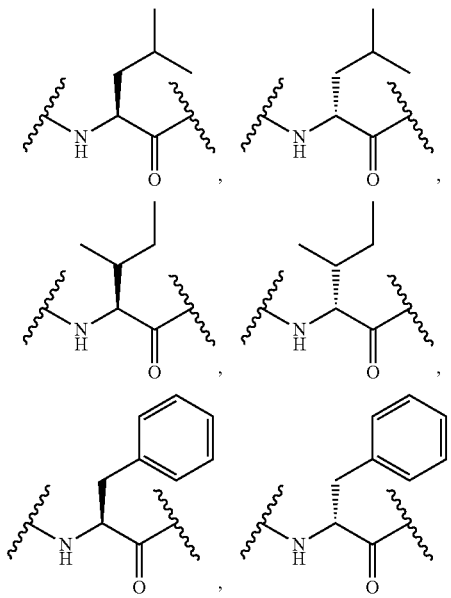

-continued

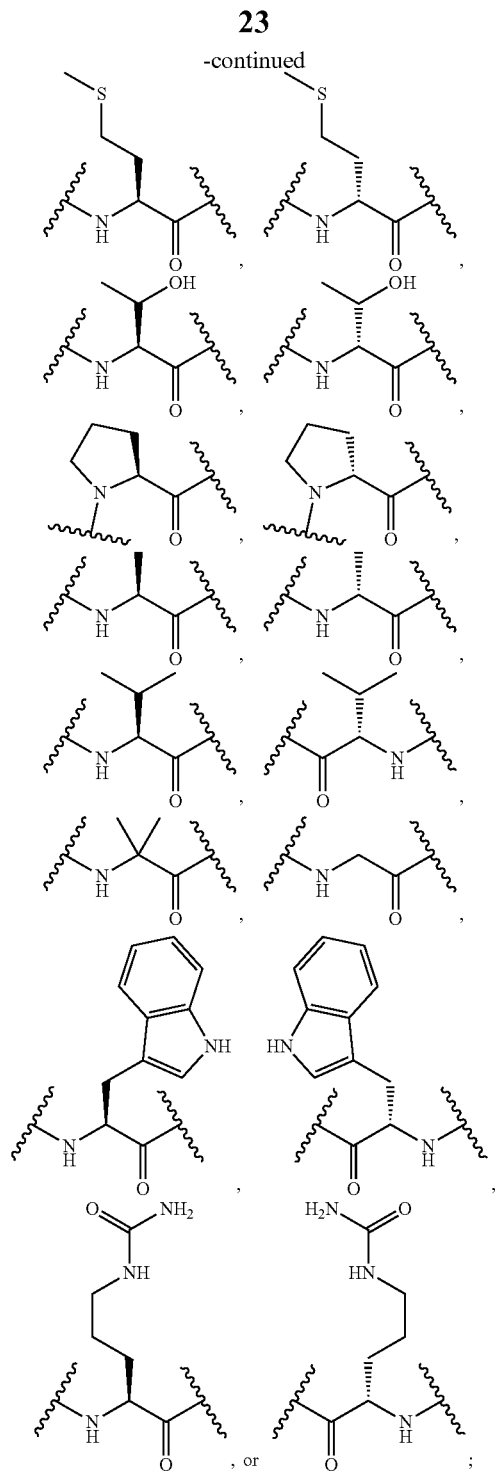

and wherein 1 methylene unit of L is optionally replaced with -M-; or

L is

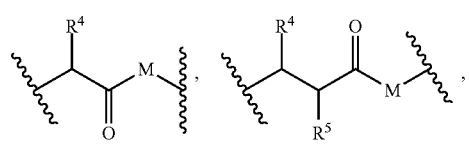

-continued

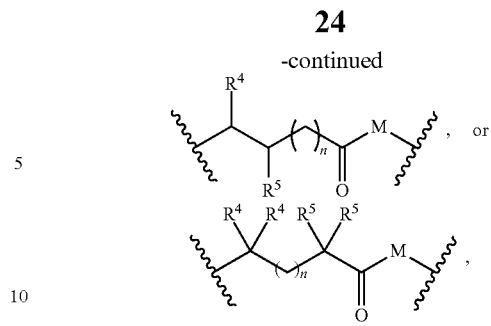

wherein either the right-hand side or left-hand side of L is attached to A.

In some embodiments, L is a bivalent, saturated or unsaturated, straight or branched, optionally substituted bivalent $C_{1-20}$ (e.g., $C_{3-20}$, $C_{5-20}$, $C_{7-20}$, $C_{8-18}$, $C_{6-18}$, $C_{7-17}$, $C_{8-16}$, $C_{8-15}$, $C_{8-14}$, $C_{7-13}$, $C_{6-12}$, etc.) hydrocarbon chain, wherein 0-8 (i.e., 0, 1, 2, 3, 4, 5, 6, 7, or 8) methylene units of L are independently replaced by -Cy-, —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or a naturally-occurring amino acid such as

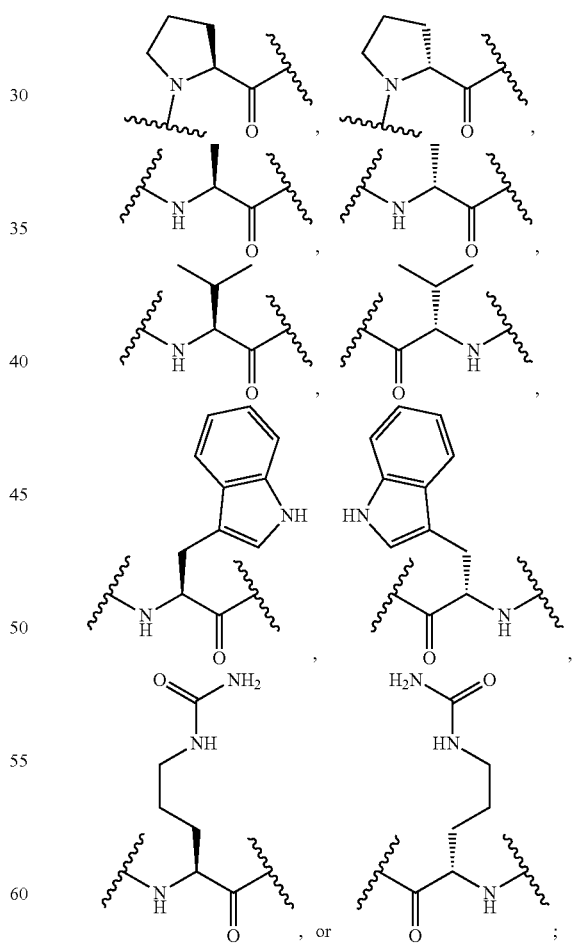

and wherein 1 methylene unit of L is optionally replaced with -M-. In some embodiments, L is a covalent bond or a bivalent, saturated or unsaturated, straight or branched $C_{3-16}$, $C_{5-12}$, $C_{8-16}$ or $C_{6-16}$ hydrocarbon chain, wherein 0-6, 0-4, 0-3, or 0-1 methylene units of L are independently replaced by -Cy-, —O—, —NR—, —S—, —OC(O)—, —C(O)O—, —C(O)—, —S(O)—, —S(O)₂—, —C(S)—, —NRS(O)₂—, —S(O)₂NR—, —NRC(O)—, —C(O)NR—, —OC(O)NR—, —NRC(O)O—,

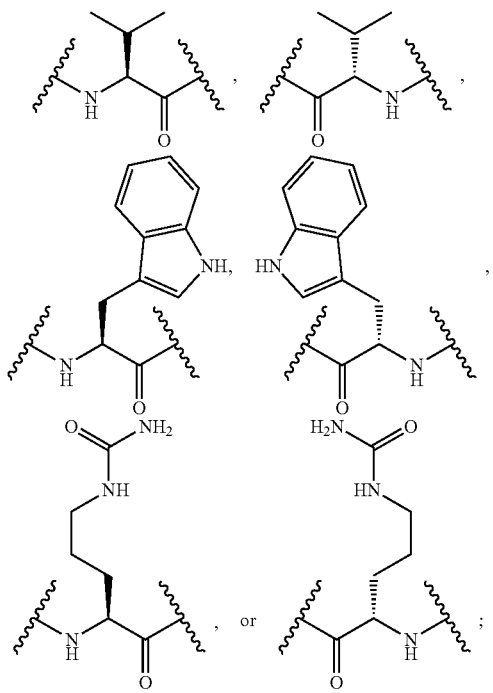

and 1 methylene unit of L is optionally replaced with -M-. In some embodiments, L is a bivalent, saturated, straight $C_{3-20}$, $C_{5-16}$, $C_{6-12}$, $C_{7-20}$, $C_{5-20}$, $C_{8-18}$, $C_{6-18}$, $C_{7-17}$, $C_{8-16}$, $C_{8-15}$, $C_{8-14}$, $C_{7-13}$, or $C_{6-12}$ hydrocarbon chain, wherein 0-6, 0-4, 0-3, or 0-1 methylene units of L are independently replaced by -Cy-, —O—, —NR—, —S—, —OC(O)—, —C(O)O—, —C(O)—, —S(O)—, —S(O)₂—, —NRS(O)₂—, —S(O)₂NR—, —NRC(O)—, —C(O)NR—, —OC(O)NR—, or —NRC(O)O—; and 1 methylene unit of L is optionally replaced with -M-. In some embodiments, L is a bivalent, saturated, straight $C_{3-20}$, $C_{5-16}$, $C_{6-12}$, $C_{5-20}$, $C_{7-20}$, $C_{8-18}$, $C_{6-18}$, $C_{7-17}$, $C_{8-16}$, $C_{8-15}$, $C_{8-14}$, $C_{7-13}$, or $C_{6-12}$ hydrocarbon chain, wherein 0-6, 0-4, 0-3, or 0-1 methylene units of L are independently replaced by —O—, —NR—, —S—, —OC(O)—, —C(O)O—, —C(O)—, —S(O)—, —S(O)₂—, or —C(S)—; and 1 methylene unit of L is optionally replaced with -M-.

In some embodiments, L is a bivalent, saturated $C_{3-30}$, $C_{5-25}$, $C_{6-20}$, $C_{8-20}$, $C_{10-18}$, $C_{5-20}$, $C_{7-20}$, $C_{8-18}$, $C_{6-18}$, $C_{7-17}$, $C_{8-16}$, $C_{8-15}$, $C_{8-14}$, $C_{7-13}$, or $C_{6-12}$ hydrocarbon chain optionally substituted with 1, 2, 3, or 4 $R^4$ groups, wherein 0-4 methylene units of L are independently replaced by —O—, —OC(O)—, —C(O)O—, or —C(O)—; and 1 methylene unit of L is optionally replaced with -M-.

In some embodiments, L is a bivalent, saturated $C_{1-25}$, $C_{5-25}$, $C_{5-20}$, $C_{7-20}$, $C_{8-18}$, $C_{6-18}$, $C_7$-17, $C_{8-16}$, $C_{8-15}$, $C_{8-14}$, $C_{7-13}$, or $C_{6-12}$ hydrocarbon chain optionally substituted with 1, 2, 3, or 4 groups selected from deuterium, halogen, —CN, a 3-6 membered saturated or partially unsaturated monocyclic carbocyclic ring, phenyl, a 4-6 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or a $C_{1-6}$ aliphatic group optionally substituted with 1, 2, 3, 4, 5, or 6 deuterium or halogen atoms; wherein 0-4 methylene units of L are independently replaced by —O—, —OC(O)—, —C(O)O—, or —C(O)—; and 1 methylene unit of L is optionally replaced with -M-.

In some embodiments, L comprises (—OCH₂CH₂—)₁₋₈ (i.e., 1-8 polyethylene glycol (PEG) units). In some embodiments, L comprises 1, 2, 3, 4, 5, 6, 7, or 8 PEG units.

In some embodiments, 0-6 units of L are independently replaced by —O—, —S—, —OC(O)—, —C(O)O—, —C(O)—, or —C(S)—; and 1 methylene unit of L is optionally replaced with -M-.

In some embodiments, L comprises

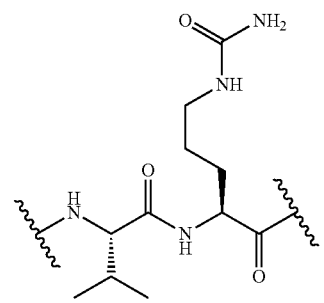

In some embodiments, L comprises

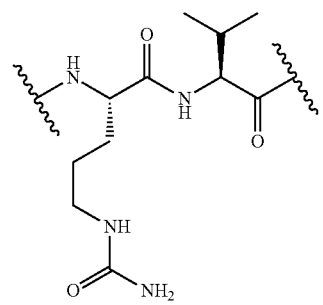

In some embodiments, L comprises

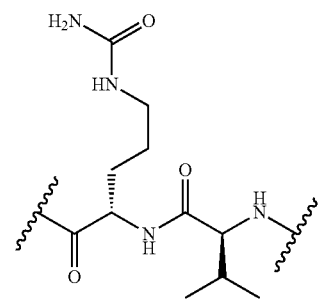

In some embodiments, L comprises

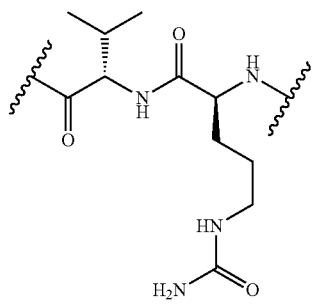

In some embodiments, L comprises

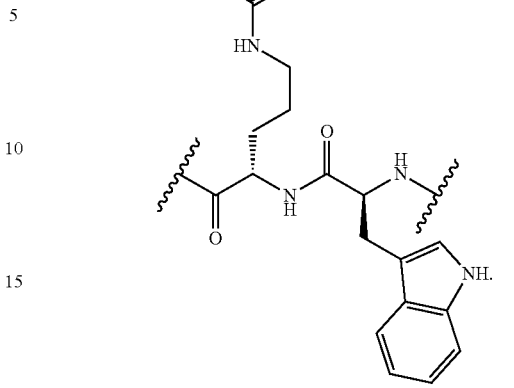

In some embodiments, L comprises

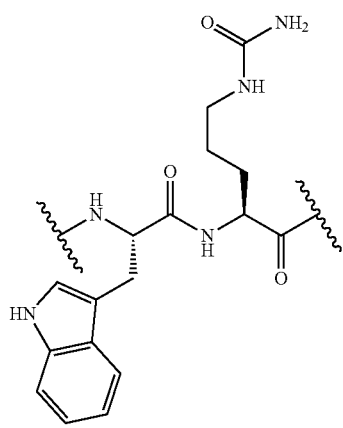

In some embodiments, L comprises

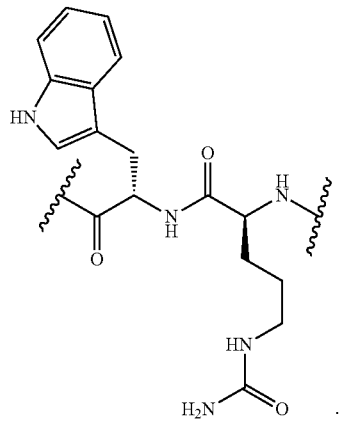

In some embodiments, L comprises

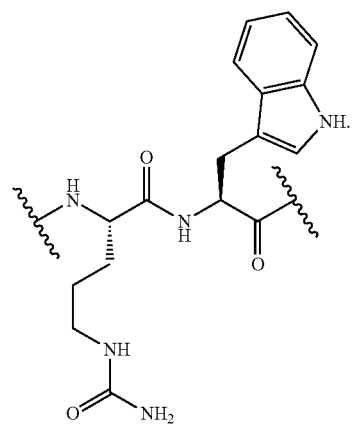 [SMILES: *N[C@@H](CCCNC(N)=O)C(=O)N[C@@H](Cc1c[nH]c2ccccc12)C(*)=O]

In some embodiments, 1 methylene unit of L is replaced with -M-.

In some embodiments, 1, 2, 3, or 4 available hydrogen atoms of L are replaced with an $R^4$ group, i.e., L is optionally substituted with 1, 2, 3, or 4 $R^4$ groups.

In some embodiments, a methylene unit of L is replaced with an amino acid. The amino acid may be naturally-occurring or non-naturally occurring. In some embodiments, the amino acid is selected from a non-polar or branched chain amino acid (BCAA). In some embodiments, the amino acid is selected from valine, isoleucine, leucine, methionine, alanine, proline, glycine, phenylalanine, tyrosine, tryptophan, histidine, asparagine, glutamine, serine threonine, lysine, arginine, histidine, aspartic acid, glutamic acid, cysteine, selenocysteine, or tyrosine. In some embodiments, the amino acid is an L-amino acid. In some embodiments, the amino acid is a D-amino acid.

In some embodiments, L is selected from those depicted in Table A, below.

As defined above and described herein, each -Cy- is independently an optionally substituted 3-6 membered bivalent saturated, partially unsaturated, or aromatic ring having 0-4 heteroatoms independently selected from nitrogen, oxygen, or sulfur.

In some embodiments, -Cy- is an optionally substituted 3-6 membered bivalent saturated ring having 0-4 heteroatoms independently selected from nitrogen, oxygen, or sulfur. In some embodiments, -Cy- is an optionally substituted 5-membered bivalent saturated, partially unsaturated, or aromatic ring having 0-4 heteroatoms independently selected from nitrogen, oxygen, or sulfur. In some embodiments, -Cy- is an optionally substituted 6-membered bivalent saturated, partially unsaturated, or aromatic ring having 0-4 heteroatoms independently selected from nitrogen, oxygen, or sulfur. In some embodiments, -Cy- is selected from those depicted in Table A, below.

As defined above and described herein, each $R^4$ and $R^5$ is independently hydrogen, deuterium, halogen, —CN, —OR, —$NR_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or a $C_{1-6}$ aliphatic group optionally substituted with —CN, —OR, —$NR_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or the $C_{1-6}$ aliphatic is optionally substituted with 1, 2, 3, 4, 5, or 6 deuterium or halogen atoms; or two instances of $R^4$ or $R^5$ attached to the same carbon atom, taken together with the carbon atom to which they are attached, form a 3-6 membered saturated monocyclic carbocyclic ring or 3-6 membered saturated heterocyclic ring having 1-2 heteroatoms independently selected from nitrogen, oxygen, or sulfur.

In some embodiments, $R^4$ is hydrogen. In some embodiments, $R^4$ is deuterium. In some embodiments, $R^4$ is halogen. In some embodiments, $R^4$ is —CN. In some embodiments, $R^4$ is —OR. In some embodiments, $R^4$ is —$NR_2$. In some embodiments, $R^4$ is —SR. In some embodiments, $R^4$ is a 3-8 membered saturated or partially unsaturated monocyclic carbocyclic ring. In some embodiments, $R^4$ is phenyl. In some embodiments, $R^4$ is an 8-10 membered bicyclic aromatic carbocyclic ring. In some embodiments, $R^4$ is a 4-8 membered saturated or partially unsaturated monocyclic heterocyclic ring having 1-2 heteroatoms independently selected from nitrogen, oxygen, or sulfur. In some embodiments, $R^4$ is a 5-6 membered monocyclic heteroaromatic ring having 1-4 heteroatoms independently selected from nitrogen, oxygen, or sulfur. In some embodiments, $R^4$ is an 8-10 membered bicyclic heteroaromatic ring having 1-5 heteroatoms independently selected from nitrogen, oxygen, or sulfur. In some embodiments, $R^4$ is a $C_{1-6}$ aliphatic group optionally substituted with —CN, —OR, —$NR_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur. In some embodiments, $R^4$ is a $C_{1-6}$ aliphatic group optionally substituted with 1, 2, 3, 4, 5, or 6 deuterium or halogen atoms. In some embodiments, two instances of $R^4$ attached to the same carbon atom, taken together with the carbon atom to which they are attached, form a 3-6 membered saturated monocyclic carbocyclic ring or 3-6 membered saturated heterocyclic ring having 1-2 heteroatoms independently selected from nitrogen, oxygen, or sulfur.

In some embodiments, each $R^4$ is independently hydrogen, deuterium, halogen, —CN, or $C_{1-4}$ aliphatic optionally substituted with 1, 2, 3, 4, 5, or 6 deuterium or halogen atoms; or two instances of $R^4$ attached to the same carbon atom, taken together with the carbon atom to which they are attached, form a 3-6 membered saturated monocyclic carbocyclic ring or 3-6 membered saturated heterocyclic ring having 1-2 heteroatoms independently selected from nitrogen, oxygen, or sulfur.

In some embodiments, at least one instance of $R^4$ is not hydrogen.

In some embodiments, $R^4$ is $C_{1-4}$ aliphatic optionally substituted with 1, 2, 3, 4, 5, or 6 deuterium or halogen atoms. In some embodiments, $R^4$ is $C_{1-4}$ alkyl optionally substituted with 1, 2, or 3 deuterium or halogen atoms. In some embodiments, $R^4$ is methyl optionally substituted with 1, 2, or 3 deuterium or halogen atoms. In some embodiments, $R^4$ is ethyl. In some embodiments, $R^4$ is n-propyl. In some embodiments, $R^4$ is isopropyl. In some embodiments, $R^4$ is n-butyl. In some embodiments, $R^4$ is isobutyl. In some embodiments, $R^4$ is tert-butyl. In some embodiments, $R^4$ is selected from those depicted in Table A, below.

In some embodiments, $R^5$ is hydrogen. In some embodiments, $R^5$ is deuterium. In some embodiments, $R^5$ is halogen. In some embodiments, $R^5$ is —CN. In some embodiments, $R^5$ is —OR. In some embodiments, $R^5$ is —$NR_2$. In some embodiments, $R^5$ is —SR. In some embodiments, $R^5$ is a 3-8 membered saturated or partially unsaturated monocyclic carbocyclic ring. In some embodiments, $R^5$ is phenyl. In some embodiments, $R^5$ is an 8-10 membered bicyclic aromatic carbocyclic ring. In some embodiments, $R^5$ is a 4-8 membered saturated or partially unsaturated monocyclic heterocyclic ring having 1-2 heteroatoms independently selected from nitrogen, oxygen, or sulfur. In some embodiments, $R^5$ is a 5-6 membered monocyclic heteroaromatic ring having 1-4 heteroatoms independently selected from nitrogen, oxygen, or sulfur. In some embodiments, $R^5$ is an 8-10 membered bicyclic heteroaromatic ring having 1-5 heteroatoms independently selected from nitrogen, oxygen, or sulfur. In some embodiments, $R^5$ is a $C_{1-6}$ aliphatic group optionally substituted with —CN, —OR, —$NR_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur. In some embodiments, $R^5$ is a $C_{1-6}$ aliphatic group optionally substituted with 1, 2, 3, 4, 5, or 6 deuterium or halogen atoms. In some embodiments, two instances of $R^5$ attached to the same carbon atom, taken together with the carbon atom to which they are attached, form a 3-6 membered saturated monocyclic carbocyclic ring or 3-6 membered saturated heterocyclic ring having 1-2 heteroatoms independently selected from nitrogen, oxygen, or sulfur.

In some embodiments, each $R^5$ is independently hydrogen, deuterium, halogen, —CN, or $C_{1-4}$ aliphatic optionally substituted with 1, 2, 3, 4, 5, or 6 deuterium or halogen atoms; or two instances of $R^5$ attached to the same carbon atom, taken together with the carbon atom to which they are attached, form a 3-6 membered saturated monocyclic carbocyclic ring or 3-6 membered saturated heterocyclic ring having 1-2 heteroatoms independently selected from nitrogen, oxygen, or sulfur.

In some embodiments, at least one instance of $R^5$ is not hydrogen.

In some embodiments, $R^5$ is $C_{1-4}$ aliphatic optionally substituted with 1, 2, 3, 4, 5, or 6 deuterium or halogen atoms. In some embodiments, $R^5$ is methyl optionally substituted with 1, 2, or 3 deuterium or halogen atoms. In some embodiments, $R^5$ is ethyl. In some embodiments, $R^5$ is n-propyl. In some embodiments, $R^5$ is isopropyl. In some embodiments, $R^5$ is n-butyl. In some embodiments, $R^5$ is isobutyl. In some embodiments, $R^5$ is tert-butyl. In some embodiments, $R^5$ is selected from those depicted in Table A, below.

As defined above and described herein, -M- is a self-immolative group.

In some embodiments, -M- is an acetal, an o-benzylalcohol, a p-benzylalcohol, a styryl group, a coumarin, or a group that self-immolates via a cyclization reaction. In some embodiments, -M- is selected from a disulfide, hydrazone, acetal self-immolative group, carboxyacetal self-immolative group, carboxy(methylacetal) self-immolative group, para-hydroxybenzyl self-immolative group, para-hydroxybenzyl carbonyl self-immolative group, flipped ester self-immolative group, trimethyl lock self-immolative group, or 2-hydroxyphenyl carbamate (2-HPC) self-immolative group.

In some embodiments, -M- is selected from one of the following:

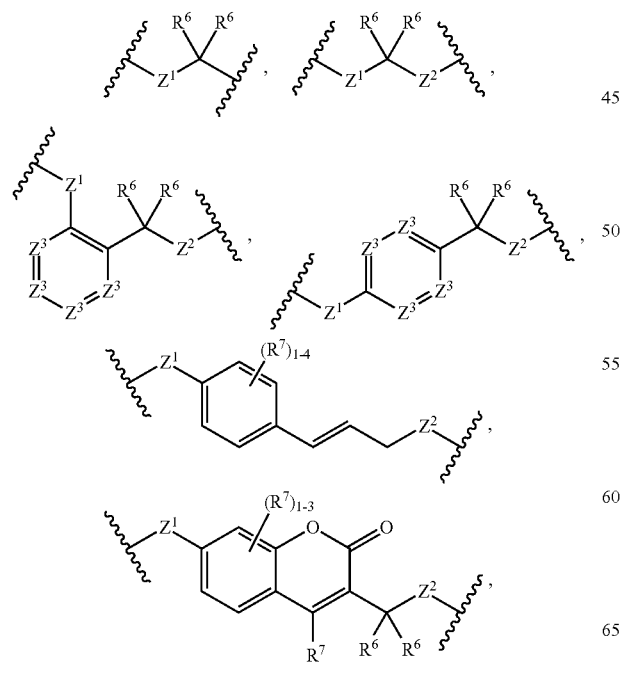

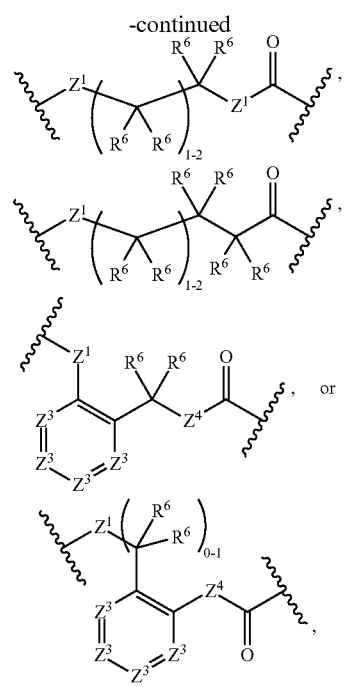

wherein each $R^6$ is independently selected from hydrogen, deuterium, $C_{1-10}$ aliphatic, halogen, or —CN;

each $R^7$ is independently selected from hydrogen, deuterium, halogen, —CN, —OR, —NR$_2$, —NO$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or a $C_{1-6}$ aliphatic group optionally substituted with —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or the $C_{1-6}$ aliphatic is optionally substituted with 1, 2, 3, 4, 5, or 6 deuterium or halogen atoms;

each $Z^1$ is independently selected from —O—, —NR—, or —S—;

each $Z^2$ is independently selected from —O—, —NR—, —S—, —OC(O)—, —NRC(O)O—, or —OC(O)NR—;

each $Z^3$ is independently selected from =N— or =C(R$^7$)—; and each $Z^4$ is independently selected from —O—, —NR—, —S—, —C(R$^6$)$_2$—, or a covalent bond.

As defined generally above and described herein, each $R^6$ is independently selected from hydrogen, deuterium, $C_{1-10}$ aliphatic, halogen, or —CN. In some embodiments, $R^6$ is hydrogen. In some embodiments, $R^6$ is deuterium. In some embodiments, $R^6$ is $C_{1-10}$ aliphatic. In some embodiments, $R^6$ is halogen. In some embodiments, $R^6$ is —CN.

In some embodiments, $R^6$ is hydrogen, $C_{1-5}$ alkyl, halogen, or —CN. In some embodiments, $R^6$ is hydrogen or $C_{1-3}$ alkyl. In some embodiments, $R^6$ is hydrogen or methyl.

In some embodiments, each instance of $R^6$ in the above formulae is the same. In some embodiments, each $R^6$ is different. In some embodiments, one $R^6$ is hydrogen. In some embodiments, one $R^6$ is $C_{1-5}$ aliphatic. In some embodiments, each $R^6$ is hydrogen. In some embodiments, each $R^6$ is $C_{1-5}$ aliphatic. In some embodiments, $R^6$ is selected from those depicted in Table A, below.

As defined generally above and described herein, each $R^7$ is independently selected from hydrogen, deuterium, halogen, —CN, —OR, —NR$_2$, —NO$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or a $C_{1-6}$ aliphatic group optionally substituted with —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or the $C_{1-6}$ aliphatic group is optionally substituted with 1, 2, 3, 4, 5, or 6 deuterium or halogen atoms.

In some embodiments, $R^7$ is hydrogen. In some embodiments, $R^7$ is deuterium. In some embodiments, $R^7$ is halogen. In some embodiments, $R^7$ is —CN. In some embodiments, $R^7$ is —OR. In some embodiments, $R^7$ is —NR$_2$. In some embodiments, $R^7$ is —NO$_2$. In some embodiments, $R^7$ is —SR. In some embodiments, $R^7$ is a 3-8 membered saturated or partially unsaturated monocyclic carbocyclic ring. In some embodiments, $R^7$ is phenyl. In some embodiments, $R^7$ is an 8-10 membered bicyclic aromatic carbocyclic ring. In some embodiments, $R^7$ is a 4-8 membered saturated or partially unsaturated monocyclic heterocyclic ring having 1-2 heteroatoms independently selected from nitrogen, oxygen, or sulfur. In some embodiments, $R^7$ is a 5-6 membered monocyclic heteroaromatic ring having 1-4 heteroatoms independently selected from nitrogen, oxygen, or sulfur. In some embodiments, $R^7$ is or an 8-10 membered bicyclic heteroaromatic ring having 1-5 heteroatoms independently selected from nitrogen, oxygen, or sulfur. In some embodiments, $R^7$ is or a $C_{1-6}$ aliphatic group optionally substituted with —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur. In some embodiments, $R^7$ is a $C_{1-6}$ aliphatic group optionally substituted with 1, 2, 3, 4, 5, or 6 deuterium or halogen atoms.

In some embodiments, $R^7$ is hydrogen, deuterium, halogen, —CN, —OR, —NR$_2$, —NO$_2$, —SR, a 3-6 membered saturated or partially unsaturated monocyclic carbocyclic ring, phenyl, a 4-6 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or a $C_{1-6}$ aliphatic group optionally substituted with —CN, —OR, —NR$_2$, —SR, a 3-6 membered saturated or partially unsaturated monocyclic carbocyclic ring, phenyl, or a 5-6 membered monocyclic heteroaromatic ring having 1-4 heteroatoms independently selected from nitrogen, oxygen, or sulfur, or the $C_{1-6}$ aliphatic group is optionally substituted with 1, 2, 3, 4, 5, or 6 deuterium or halogen atoms. In some embodiments, $R^7$ is hydrogen, deuterium, halogen, —CN, a 3-6 membered saturated or partially unsaturated monocyclic carbocyclic ring, phenyl, a 5-6 membered monocyclic heteroaromatic ring having 1-4 heteroatoms independently selected from nitrogen, oxygen, or sulfur, or a $C_{1-4}$ alkyl group optionally substituted with —CN, a 3-6 membered saturated or partially unsaturated monocyclic carbocyclic ring, phenyl, or a 5-6 membered monocyclic heteroaromatic ring having 1-4 heteroatoms independently selected from nitrogen, oxygen, or sulfur, or the $C_{1-4}$ alkyl group is optionally substituted with 1, 2, 3, 4, 5, or 6 deuterium or halogen atoms. In some embodiments, $R^7$ is hydrogen, halogen, —CN, —OR, or $C_{1-4}$ alkyl.

In some embodiments, R is hydrogen or $C_{1-4}$ alkyl.

In some embodiments, $R^7$ is selected from those depicted in Table A, below.

As defined generally above and described herein, each $Z^1$ is independently selected from —O—, —NR—, or —S—. In some embodiments, $Z^1$ is —O—. In some embodiments, $Z^1$ is —NR—. In some embodiments, $Z^1$ is —S. In some embodiments, $Z^1$ is —NH— or —NMe-.

In some embodiments, $Z^1$ is selected from those depicted in Table A, below.

As defined generally above and described herein, each $Z^2$ is independently selected from —O—, —NR—, —S—, —OC(O)—, —NRC(O)O—, or —OC(O)NR—.

In some embodiments, $Z^2$ is —O—. In some embodiments, $Z^2$ is —NR—. In some embodiments, $Z^2$ is —S—. In some embodiments, $Z^2$ is —OC(O)—. In some embodiments, $Z^2$ is —NRC(O)O—. In some embodiments, $Z^2$ is —OC(O)NR—.

In some embodiments, each $Z^2$ is independently selected from —O—, —NH—, —NMe-, —S—, —OC(O)—, —NHC(O)O—, —NMeC(O)O—, —OC(O)NH—, or —OC(O)NMe-.

In some embodiments, $Z^2$ is covalently bound to A. In some embodiments, $Z^2$ is —O— or —OC(O)O—.

In some embodiments, $Z^2$ is selected from those depicted in Table A, below.

In some embodiments, $Z^1$ is —O— and $Z^2$ is —O— or —OC(O)O—.

As defined generally above and described herein, each $Z^3$ is independently selected from =N— or =C(R$^7$)—. In some embodiments, $Z^3$ is =N—. In some embodiments, $Z^3$ is =C(R$^7$)—.

In some embodiments, $Z^3$ is selected from those depicted in Table A, below.

As defined generally above and described herein, each $Z^4$ is independently selected from —O—, —NR—, —S—, —C(R$^6$)$_2$—, or a covalent bond. In some embodiments, $Z^4$ is —O—. In some embodiments, $Z^4$ is —NR—. In some embodiments, $Z^4$ is —S—. In some embodiments, $Z^4$ is —C(R$^6$)$_2$—. In some embodiments, $Z^4$ is a covalent bond.

In some embodiments, $Z^4$ is selected from those depicted in Table A, below.

In some embodiments, -M- is selected from one of the following

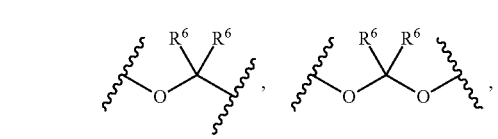

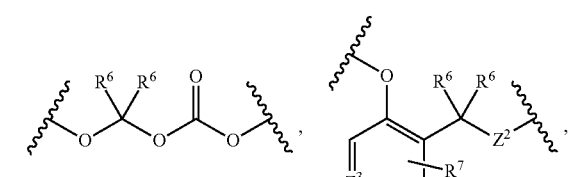

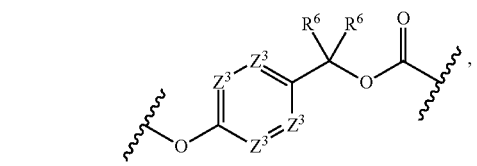

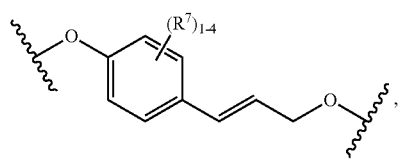

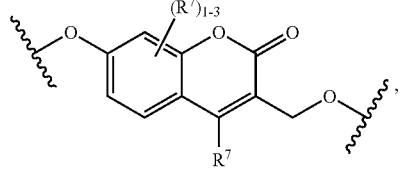

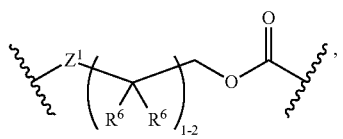

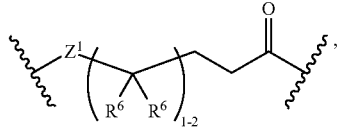

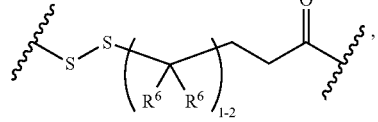

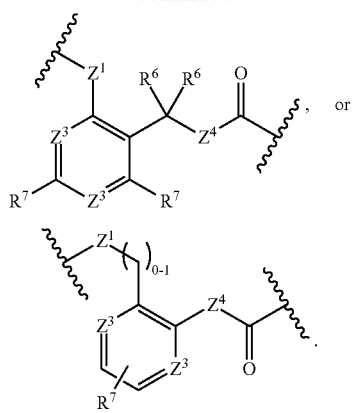

In some embodiments, -M- is selected from

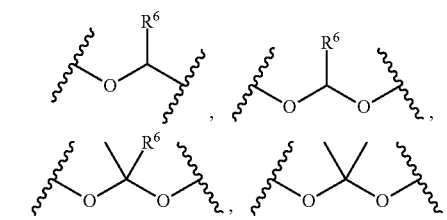

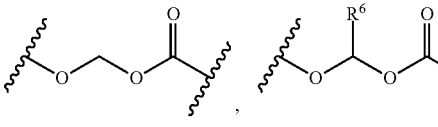

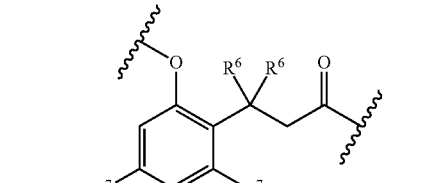

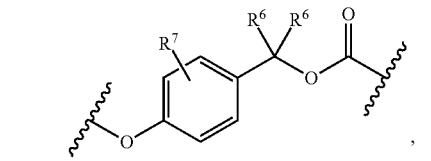

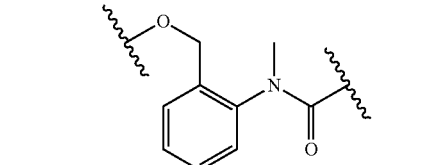

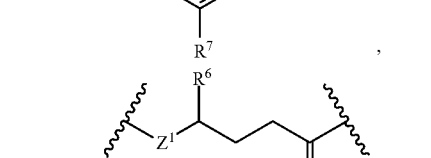

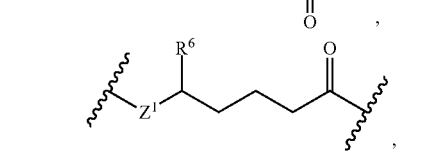

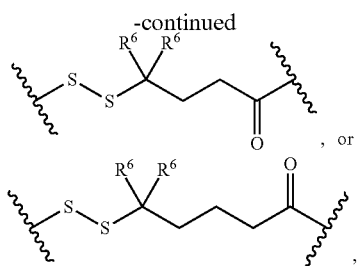

In some embodiments, -M- is selected from

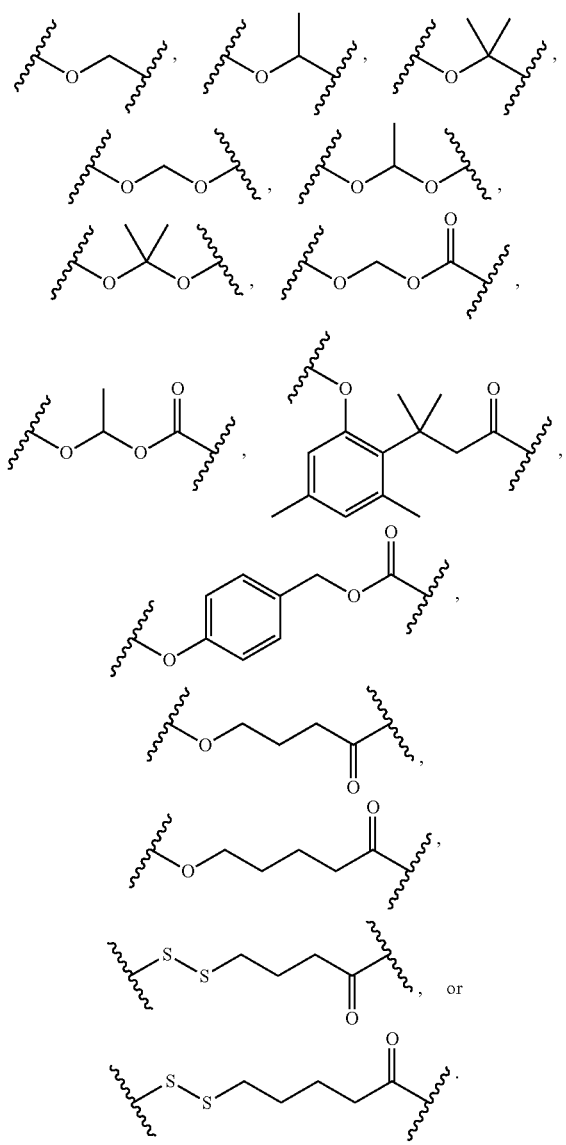

In some embodiments, -M- is selected from those depicted in Table A, below.

As defined above and described herein, n is 0-18.

In some embodiments, n is 0. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10. In some embodiments, n is 11. In some embodiments, n is 12. In some embodiments, n is 13. In some embodiments, n is 14. In some embodiments, n is 15. In some embodiments, n is 16. In some embodiments, n is 17. In some embodiments, n is 18. In some embodiments, n is 1-16, 1-14, 1-12, 1-10, 1-8, 1-6, 1-3, 2-16, 2-14, 2-12, 2-10, 2-8, 2-6, 3-12, 3-8, 3-6, 4-10, 4-8, 4-6, 5-10, 5-8, 5-6, 6-18, 6-10, 6-8, 8-12, 5-18, 5-13, 8-18, 8-17, 8-16, 8-15, 8-16, or 6-16.

As defined above and described herein, each m is independently 0-6. In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, each m is independently 0, 1, or 2. In some embodiments, each m is independently 1, 2, 3, or 4.

As defined above and described herein, A is a therapeutic agent.

In some embodiments, A is a therapeutic agent selected from any of those set forth in Tables 1-7, or a derivative thereof, below.

One of ordinary skill in the art will appreciate that certain therapeutic agents listed in Tables 1-7 are in the form of prodrugs. For example, mycophenolate mofetil is a prodrug of a mycophenolic acid. Thus, it will be appreciated that a lipid prodrug moiety of the present invention is attached to the prodrug of the therapeutic agent or the active form of the prodrug. For the purpose of clarity, and by way of example, it will be understood that a provided lipid prodrug moiety is attached at any modifiable oxygen, sulfur, or nitrogen atom of the therapeutic agent, e.g. either mycophenolate mofetil or mycophenolic acid.

In some embodiments, a disclosed lipid prodrug comprises one or two lipids covalently bound to one or two of the hydroxyl groups of the glyceride-based group shown in, e.g. Formula I or VI.

In some embodiments, a disclosed lipid prodrug further comprises a lipid covalently bound to the therapeutic agent. In some embodiments, such a lipid increases the lipophilicity or other desirable property of the lipid prodrug, e.g. to increase lymphatic uptake and transport. In some embodiments, the lipid is conjugated to the therapeutic agent at an available at an available nitrogen, sulfur, or oxygen atom, such as a carboxylic acid, amine, hydroxyl, or amide. In some embodiments, the lipid is selected from those described below. In some embodiments, the lipid forms an ester of the therapeutic agent.

As used herein, depiction of brackets around a therapeutic agent, A,

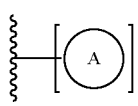

means that the

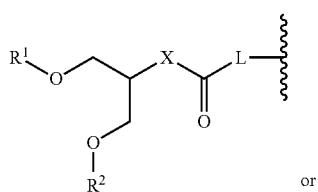

or

-continued

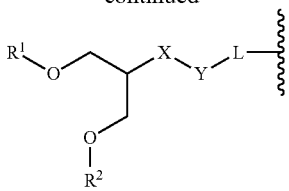

moiety is covalently attached to A at any available modifiable nitrogen, oxygen, or sulfur atom. For purposes of clarity and by way of example, such available modifiable nitrogen, oxygen, or sulfur atoms in the following therapeutic agent compound structure are depicted below, wherein each wavy bond defines the point of attachment to said

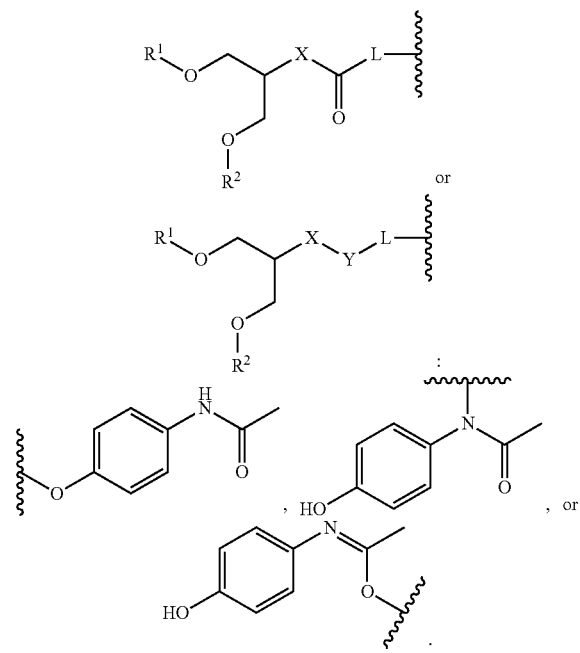

In certain embodiments, the present invention provides a compound of formula I, wherein L is

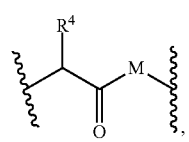

thereby forming a compound of formula II:

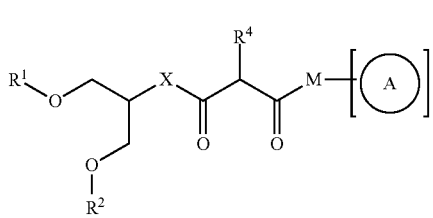

or a pharmaceutically acceptable salt thereof, wherein each of $R^1$, $R^2$, $R^4$, X, M and A is as defined above and described in embodiments herein, both singly and in combination.

In certain embodiments, the present invention provides a compound of formula I, wherein L is

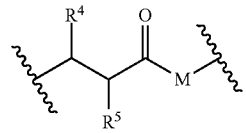

thereby forming a compound of formula III:

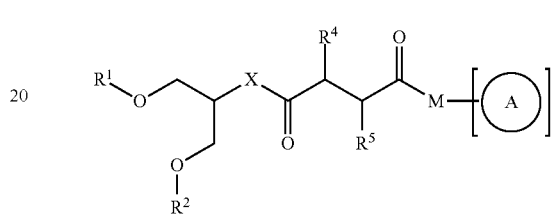

or a pharmaceutically acceptable salt thereof, wherein each of $R^1$, $R^2$, $R^4$, $R^5$, X, M and A is as defined above and described in embodiments herein, both singly and in combination.

In certain embodiments, the present invention provides a compound of formula I, wherein L is

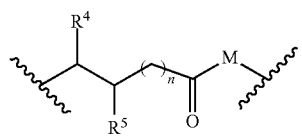

and M is

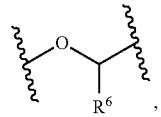

thereby forming a compound of formula IV:

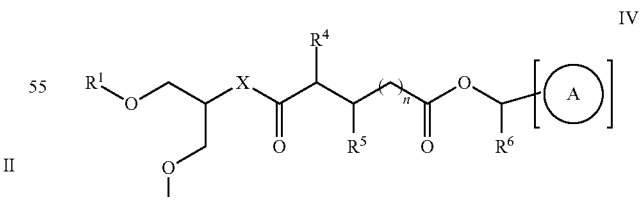

or a pharmaceutically acceptable salt thereof, wherein each of $R^1$, $R^2$, $R^4$, $R^5$, $R^6$, X, and A is as defined above and described in embodiments herein, both singly and in combination.

In some embodiments, the present invention provides a compound of Formula VI-a:

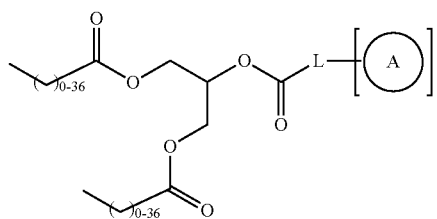

VI-a or a pharmaceutically acceptable salt thereof, wherein each of L, $R^1$, $R^2$, R, X, and A is as defined above and described in embodiments herein, both singly and in combination.

In some embodiments, the present invention provides a compound of Formula VII-a or VII-b:

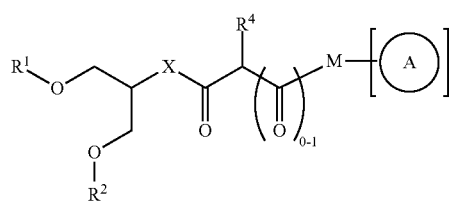

VII-a

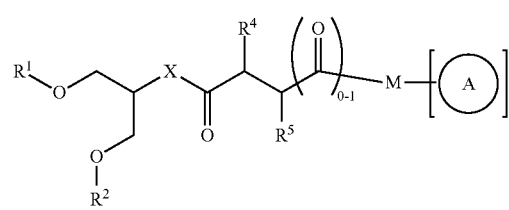

VII-b or a pharmaceutically acceptable salt thereof, wherein each of $R^1$, $R^2$, $R^4$, $R^5$, X, M, and A is as defined above and described in embodiments herein, both singly and in combination.

In some embodiments, the present invention provides a compound of Formula VIII-a or VIII-b:

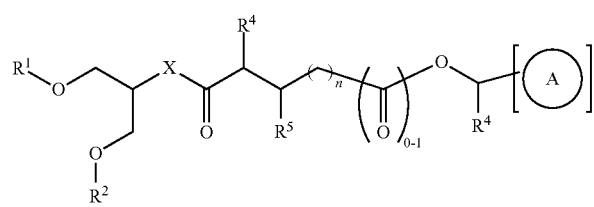

VIII-a or a pharmaceutically acceptable salt thereof, wherein each of $R^1$, $R^2$, $R^4$, $R^5$, X, n, and A is as defined above and described in embodiments herein, both singly and in combination.

In some embodiments, the present invention provides a compound of Formula IX-a, IX-b, IX-c, or IX-d:

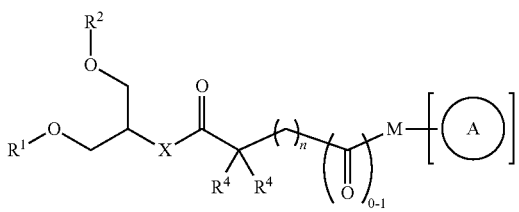

IX-a

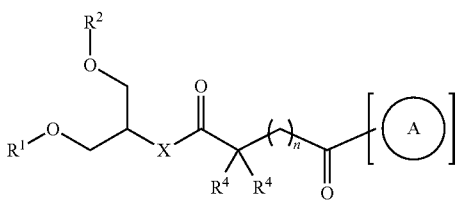

IX-b

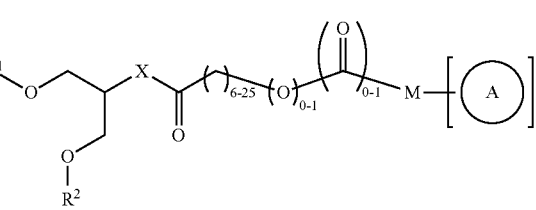

IX-c

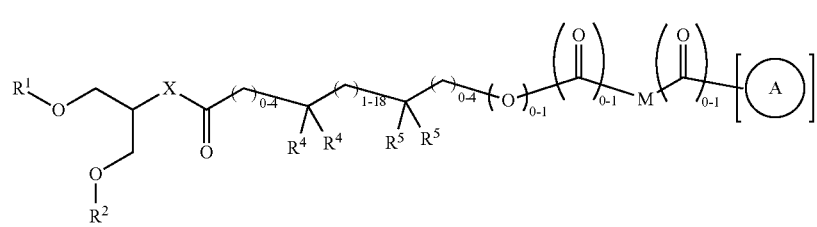

VIII-b

-continued
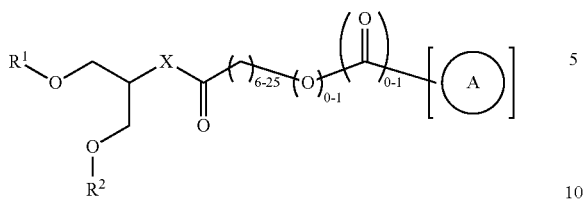
IX-d
or a pharmaceutically acceptable salt thereof, wherein each variable is as defined above and described in embodiments herein, both singly and in combination.
In some embodiments, the present invention provides a compound of Formula X-a, X-b, X-c, X-d, X-e, X-f, X-g, or X-h:
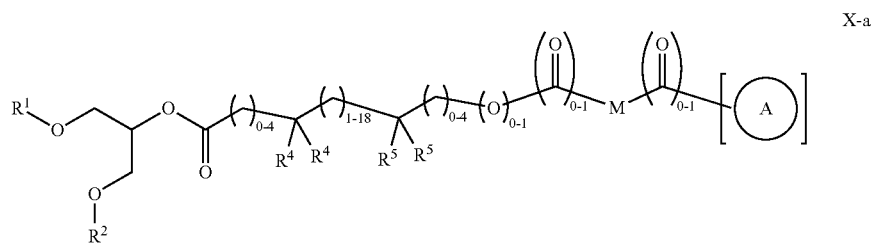
X-a
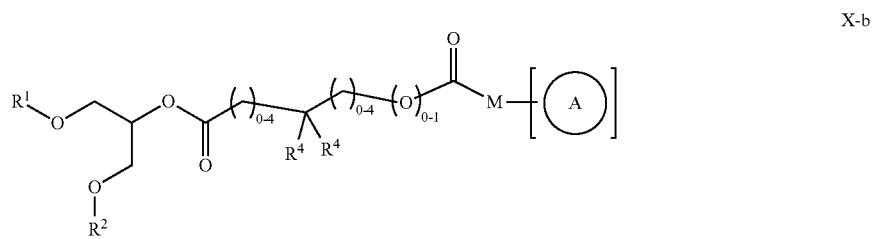
X-b
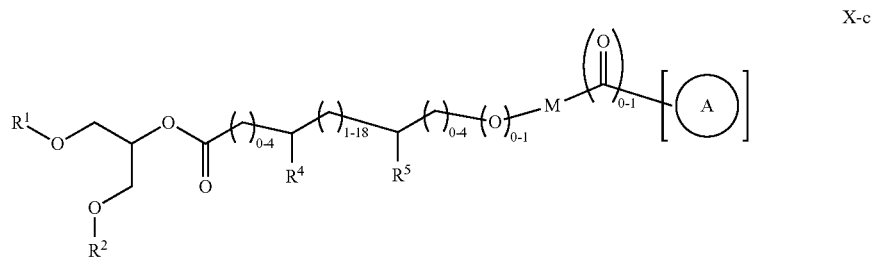
X-c
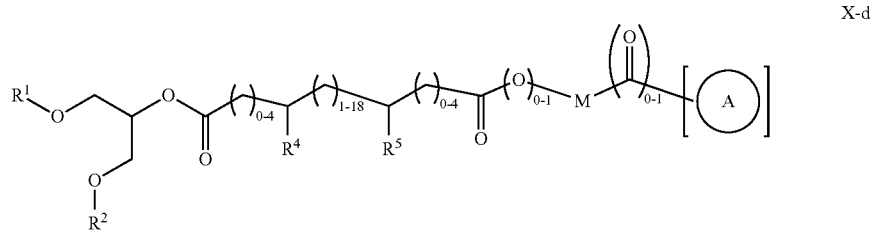
X-d
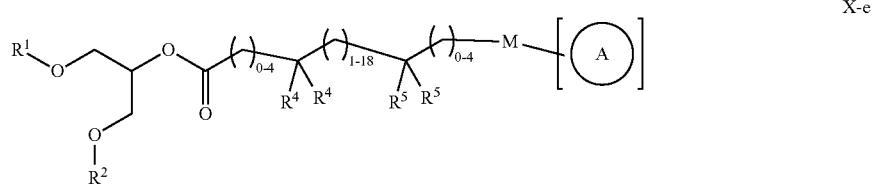
X-e -continued X-f

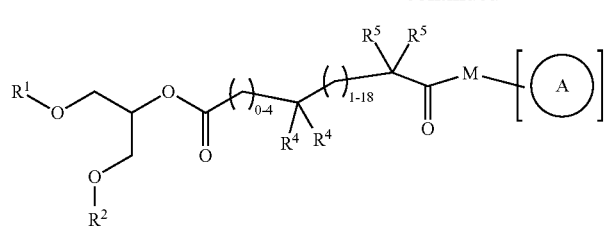

X-g

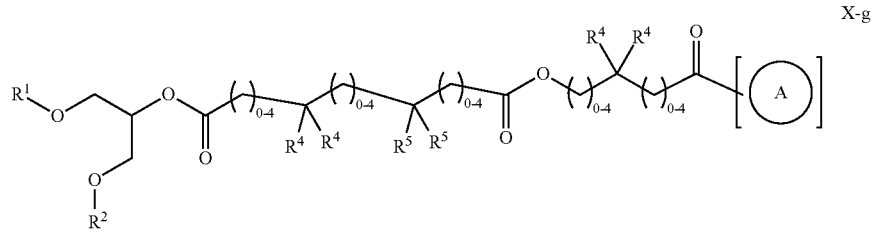

X-h

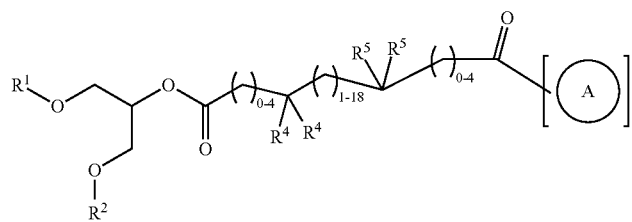

or a pharmaceutically acceptable salt thereof, wherein each variable is as defined above and described in embodiments herein, both singly and in combination.

In some embodiments, the present invention provides a compound of Formula XI-a or XI-b:

XI-a

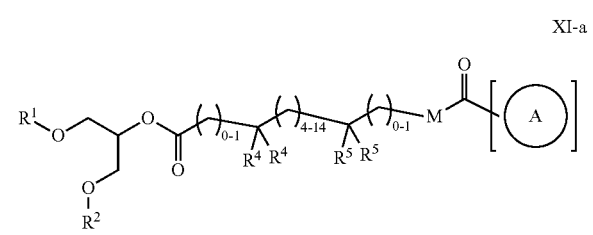

XI-b

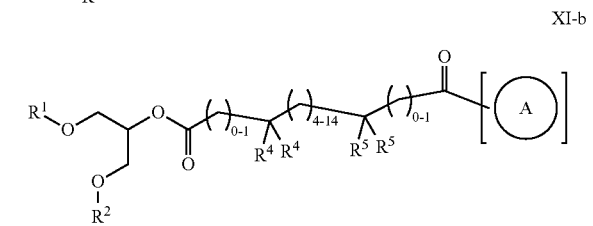

or a pharmaceutically acceptable salt thereof, wherein each variable is as defined above and described in embodiments herein, both singly and in combination.

In the above formulae, when a range of numbers, such as 0-4 or 1-18, is disclosed, individual integers within the range are also specifically disclosed. Thus, the above range of 0-4 includes 0, 1, 2, 3, and 4. The range 1-18 includes 1, 2, 3, 4, 5, 6, 7, 8, 9, 10, 11, 12, 13, 14, 15, 16, 17, and 18 as well as ranges in between such as 6-18 and 8-18. The range 0-1 includes 0 and 1, i.e. the group is optionally present. Where more than one range is disclosed in a formula, each range is independently and optionally selected from the disclosed range. For example, in Formula X-c above, each 0-4 and 0-1 range is varied independently of the others.

In some embodiments, the lipid prodrug is one of those described in U.S. Ser. No. 62/724,274, filed on Aug. 29, 2018, the entirety of which is hereby incorporated by reference.

In some embodiments, the lipid prodrug is one of those described in U.S. Ser. No. 62/724,440, filed on Aug. 29, 2018, the entirety of which is hereby incorporated by reference.

In other embodiments, the present invention provides a compound of Formula V:

V

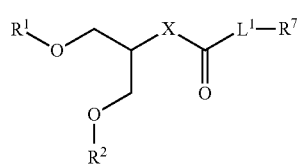

or a pharmaceutically acceptable salt thereof, wherein:
$R^1$ and $R^2$ are each independently hydrogen or —C(O)$R^3$;
each $R^3$ is independently a saturated or unsaturated, straight or branched $C_{2-37}$ hydrocarbon chain;
X is —O—, —NR—, or —S—;
each R is independently hydrogen or an optionally substituted $C_{1-4}$ aliphatic;
$L^1$ is a covalent bond or a bivalent, saturated or unsaturated, straight or branched $C_{1-20}$ hydrocarbon chain, wherein 0-6 methylene units of $L^1$ are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, or —NRC(O)O—, wherein:

each -Cy- is independently an optionally substituted 5-6 membered bivalent aryl ring having 0-4 heteroatoms independently selected from nitrogen, oxygen, or sulfur; and $R^7$ is a moiety suitable for click chemistry or metal-free click chemistry.

$R^1$, $R^2$, $R^3$, X, R, and -Cy- are as defined above and described herein. Embodiments of $R^1$, $R^2$, $R^3$, X, R, and -Cy- are as defined above and described herein.

As defined above and described herein, $L^1$ is a covalent bond or a bivalent, saturated or unsaturated, straight or branched $C_{1-20}$ hydrocarbon chain, wherein 0-6 methylene units of $L^1$ are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, or —NRC(O)O—.

In some embodiments, $L^1$ is a covalent bond. In some embodiments, $L^1$ is a bivalent, saturated, straight $C_{1-20}$ hydrocarbon chain, wherein 0-6 methylene units of $L^1$ are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, or —NRC(O)O—. In some embodiments, $L^1$ is a bivalent, saturated, branched $C_{1-20}$ hydrocarbon chain, wherein 0-6 methylene units of $L^1$ are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, or —NRC(O)O—. In some embodiments, $L^1$ is a bivalent, unsaturated, straight $C_{1-20}$ hydrocarbon chain, wherein 0-6 methylene units of $L^1$ are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, or —NRC(O)O—. In some embodiments, $L^1$ is a bivalent, unsaturated, branched $C_{1-20}$ hydrocarbon chain, wherein 0-6 methylene units of $L^1$ are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, or —NRC(O)O—.

In some embodiments, $L^1$ is selected from those depicted in Table A, below.

As defined above and described herein, $R^7$ is a moiety suitable for click chemistry or metal-free click chemistry.

In some embodiments, $R^7$ is a moiety suitable for click chemistry. In some embodiments, $R^7$ is a moiety suitable for metal-free click chemistry.

In some embodiments, $R^7$ is —N$_3$. In some embodiments, $R^7$ is

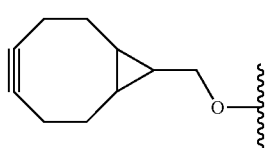

In some embodiments, $R^7$ is

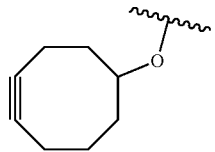

In some embodiments, $R^7$ is

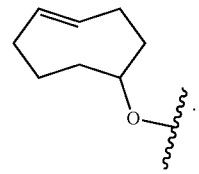

In some embodiments, $R^7$ is

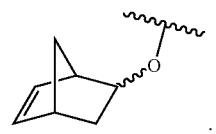 [SMILES: *OC1CC2C=CC1C2]

In some embodiments, $R^7$ is

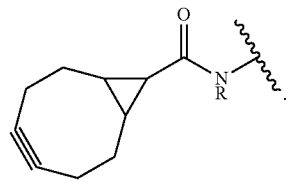

In some embodiments, $R^7$ is

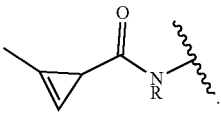

In some embodiments, $R^7$ is

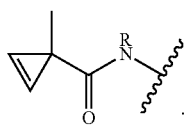

In some embodiments, $R^7$ is
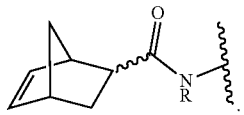
In some embodiments, $R^7$ is
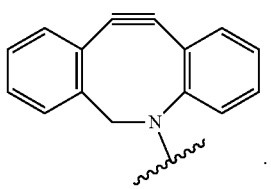 [SMILES: *N1Cc2ccccc2C#Cc2ccccc21]
In some embodiments, $R^7$ is
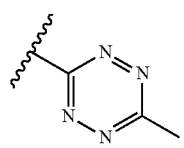
In some embodiments, $R^7$ is
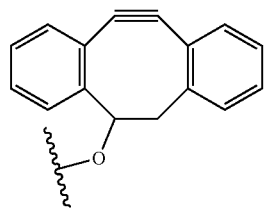
In some embodiments, $R^7$ is
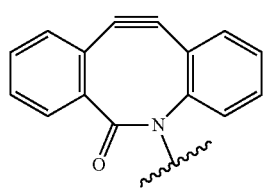
In some embodiments, $R^7$ is
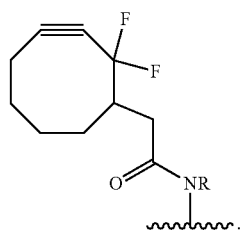
In one aspect, the present invention provides a lipid prodrug compound, or pharmaceutically acceptable salt thereof, shown in Table A:
TABLE A
Exemplary Compounds
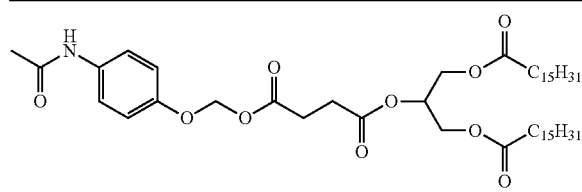
I-1
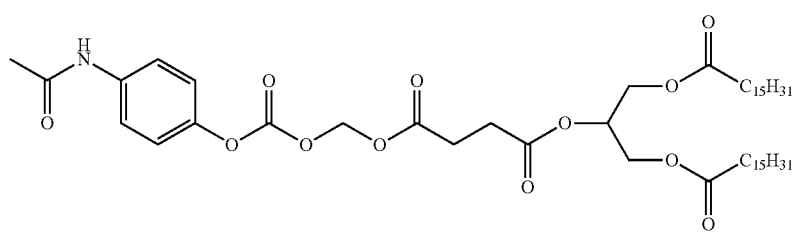
I-2

TABLE A-continued
Exemplary Compounds
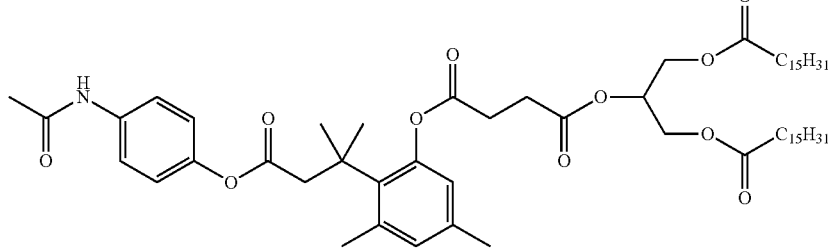
I-3
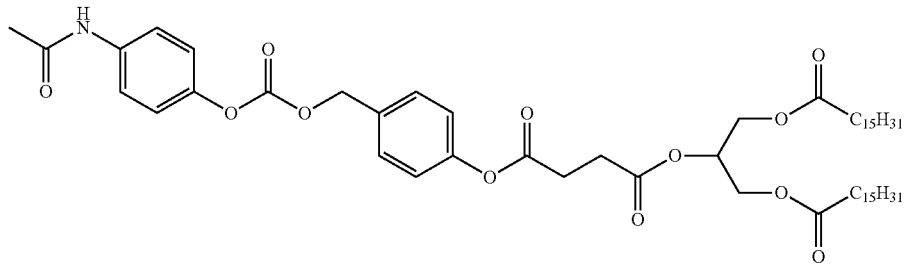
I-4
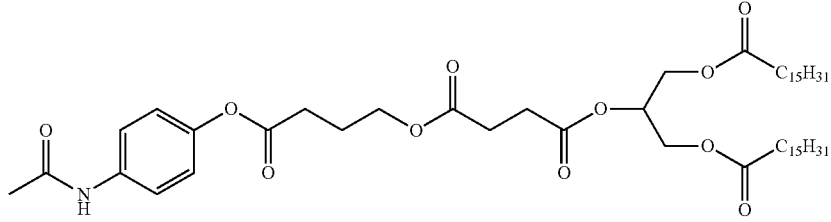
I-5
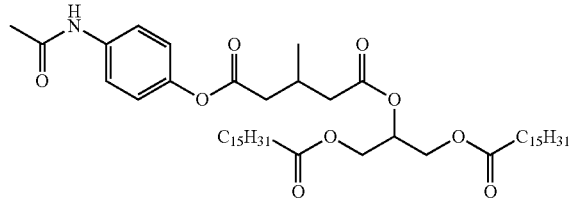
I-6
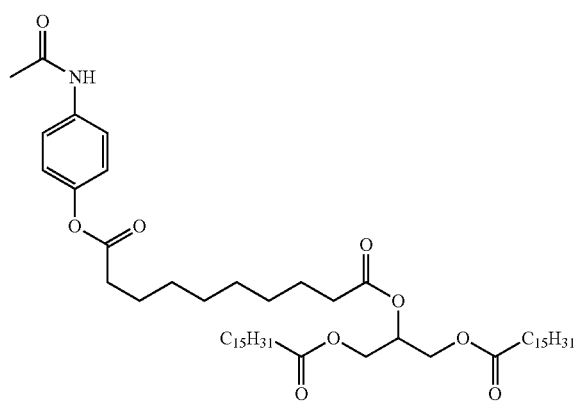
I-7

TABLE A-continued

Exemplary Compounds

I-8

I-9

I-10

I-11

I-12

TABLE A-continued
Exemplary Compounds
I-13
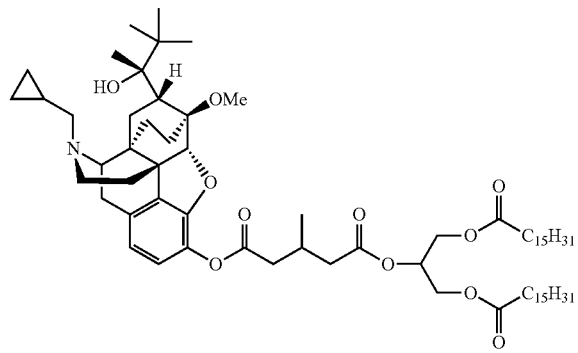
I-14
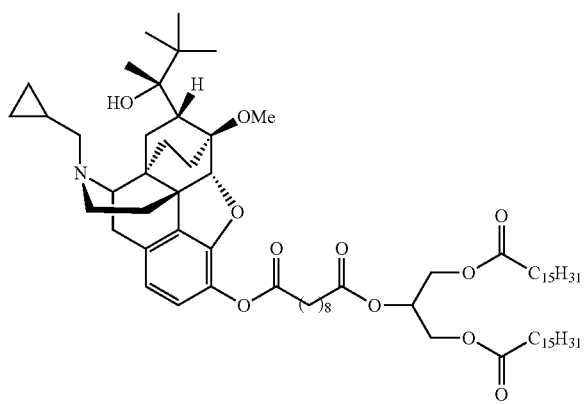
I-15
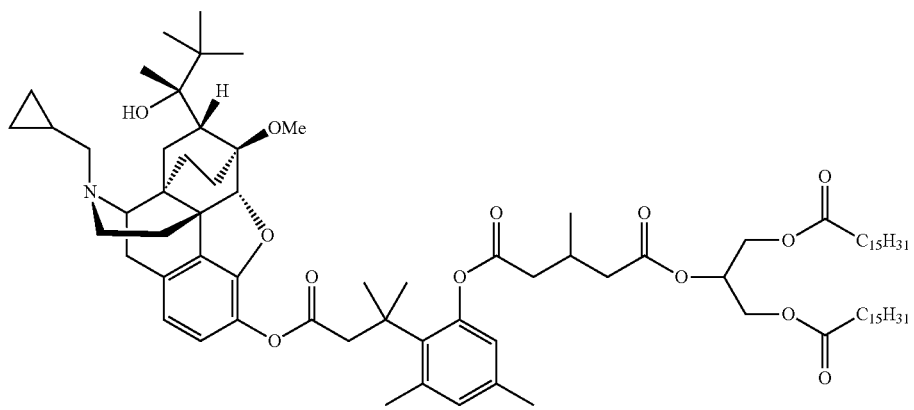
I-16
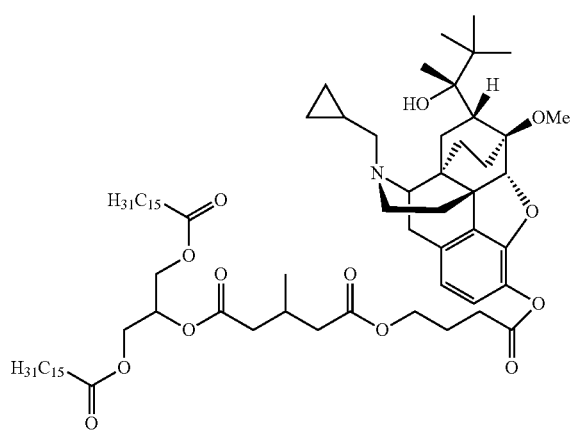

TABLE A-continued

Exemplary Compounds

I-17

I-18

I-19

I-20

TABLE A-continued
Exemplary Compounds
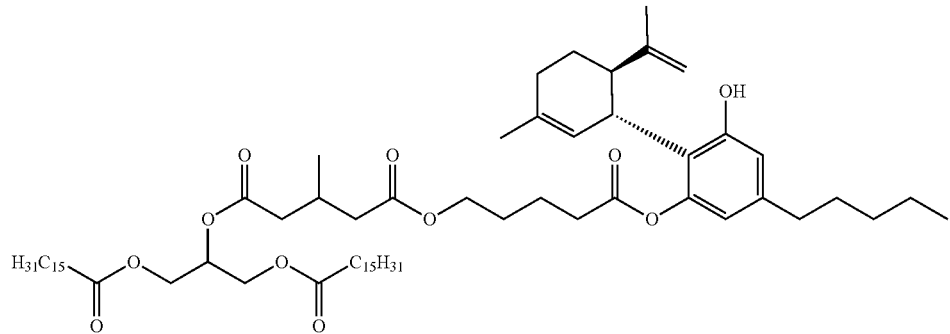
I-21
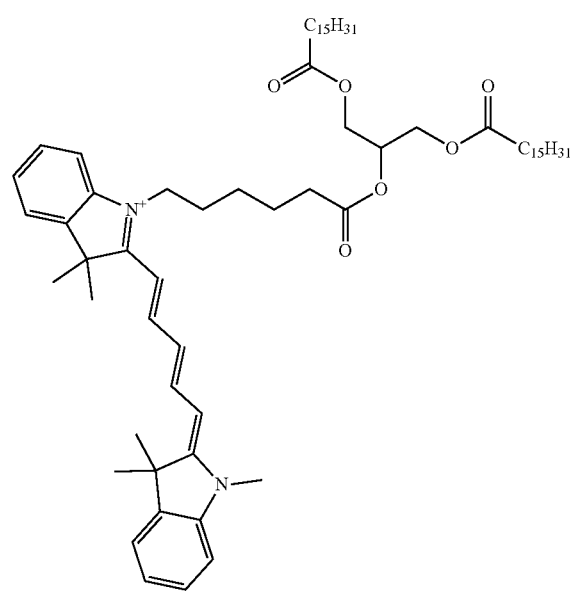
I-22
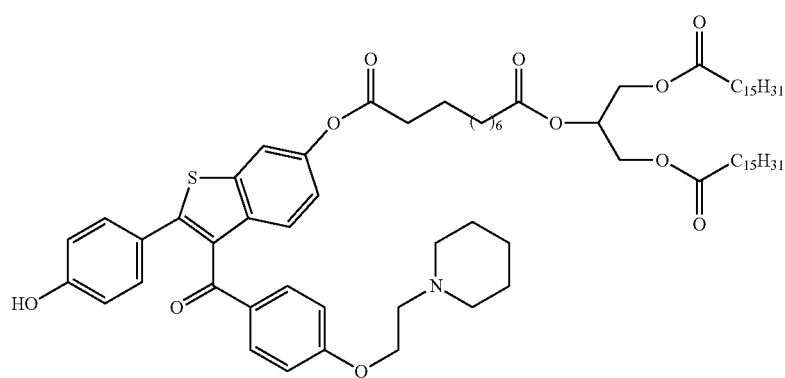
I-23
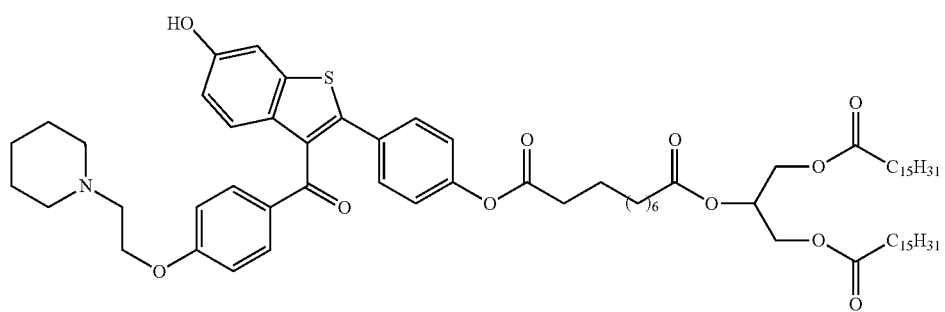
I-24

TABLE A-continued
Exemplary Compounds
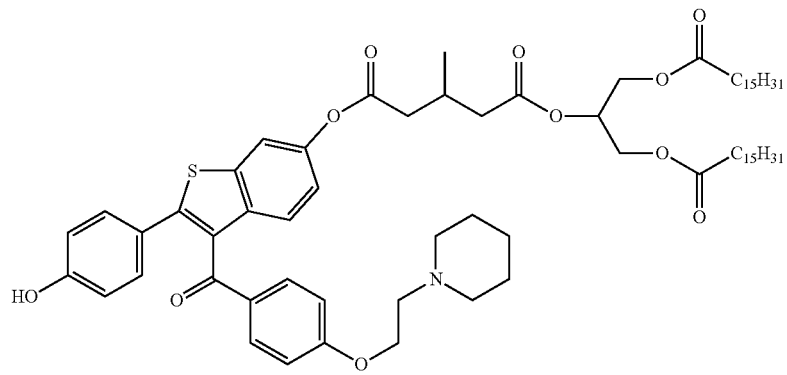
I-25
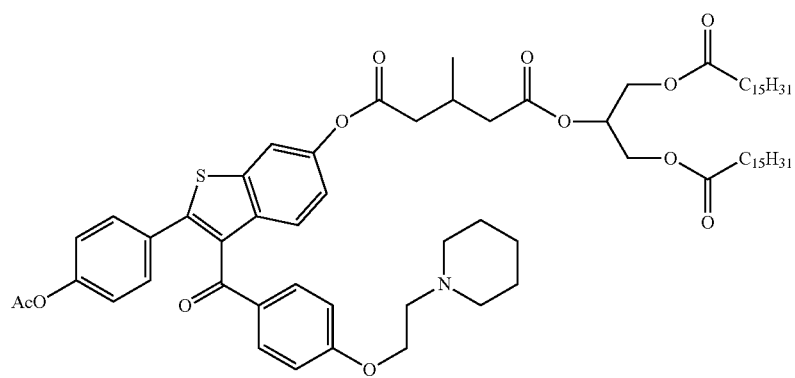
I-26
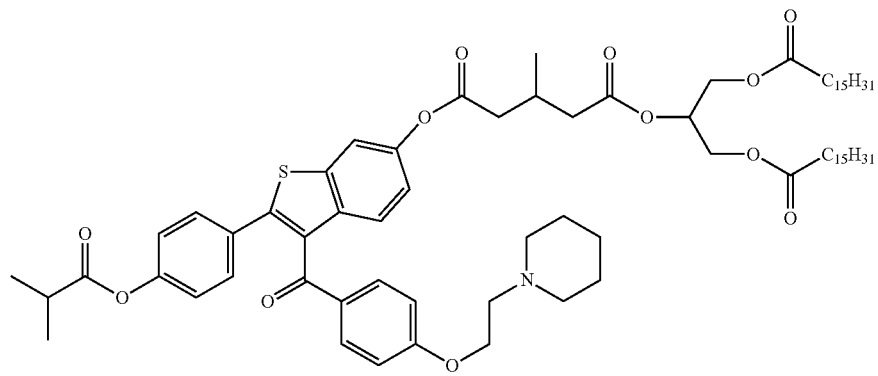
I-27
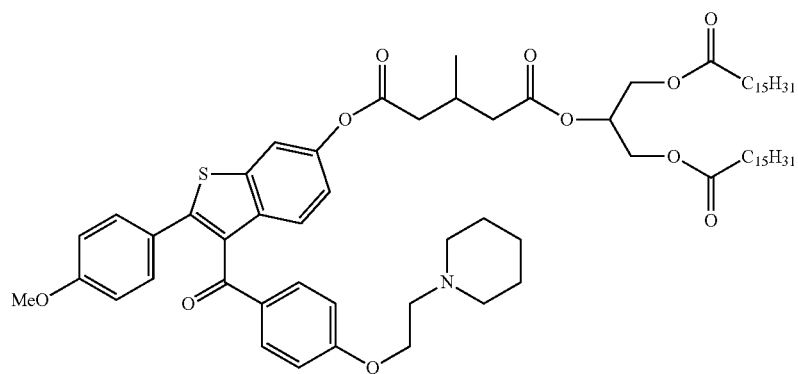
I-28

TABLE A-continued
Exemplary Compounds
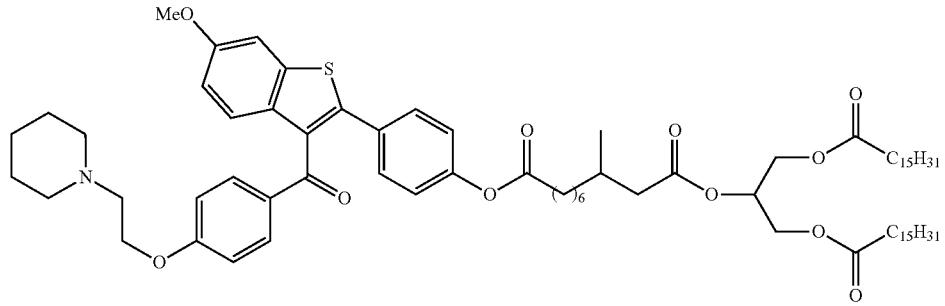
I-29
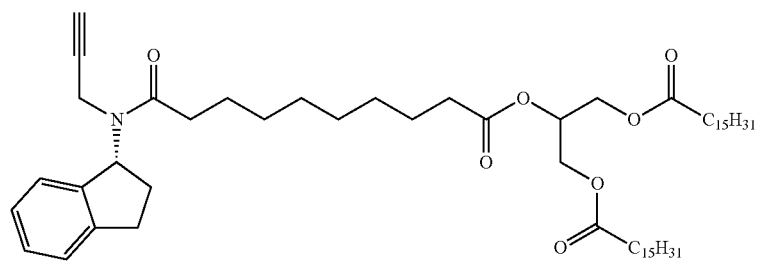
I-30
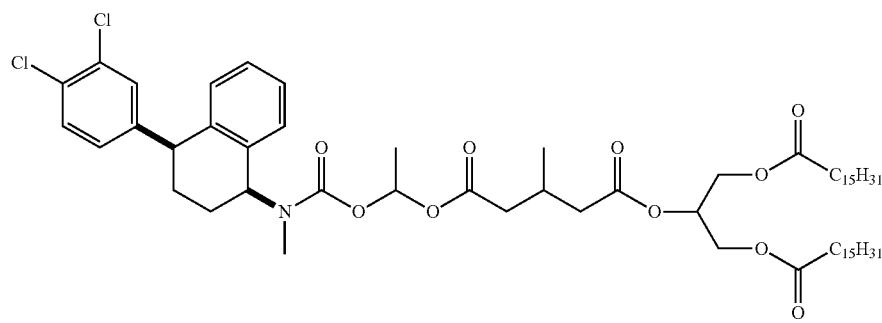
I-31
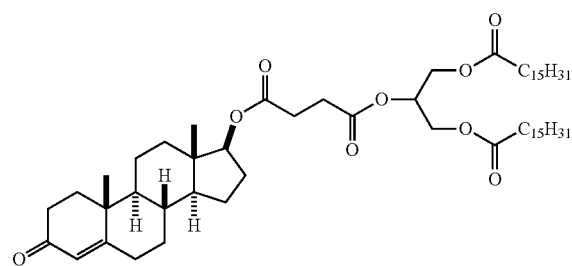
I-32
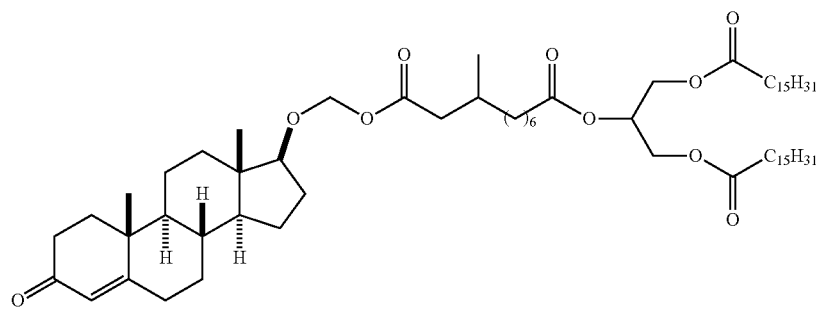
I-33

TABLE A-continued
Exemplary Compounds
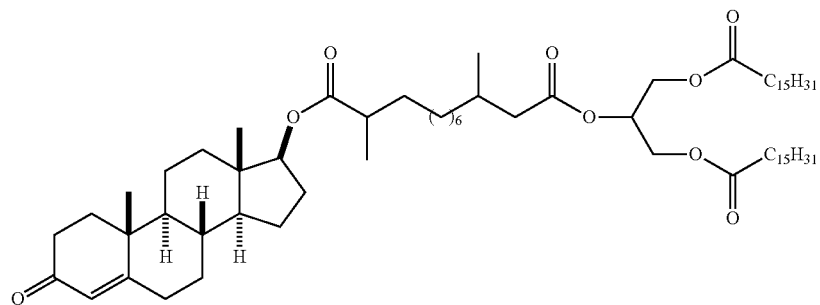
I-34
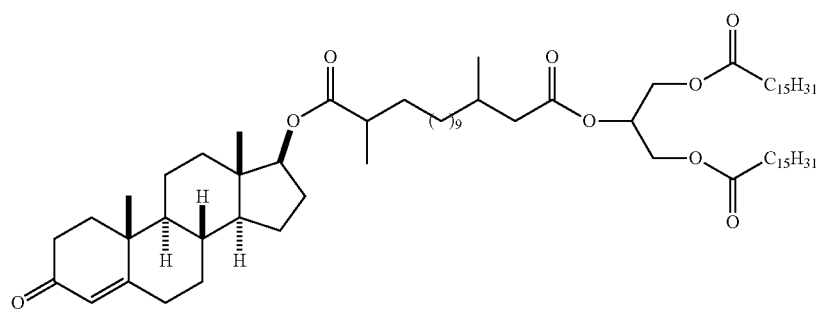
I-35
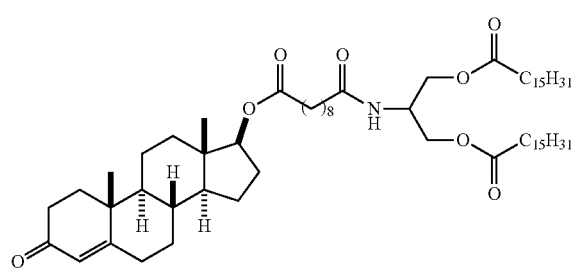
I-36
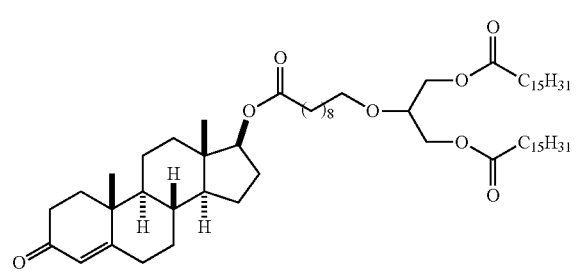
I-37
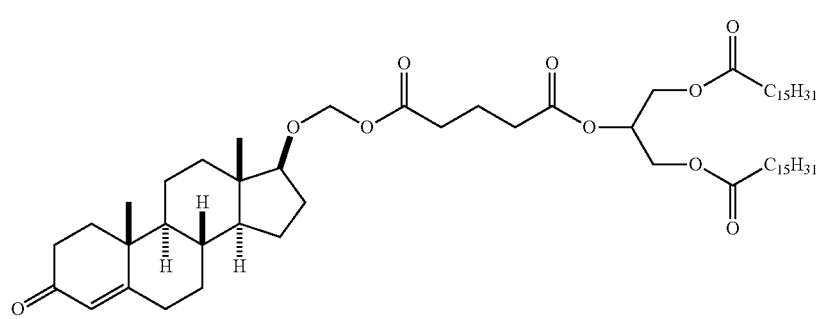
I-38

TABLE A-continued
Exemplary Compounds
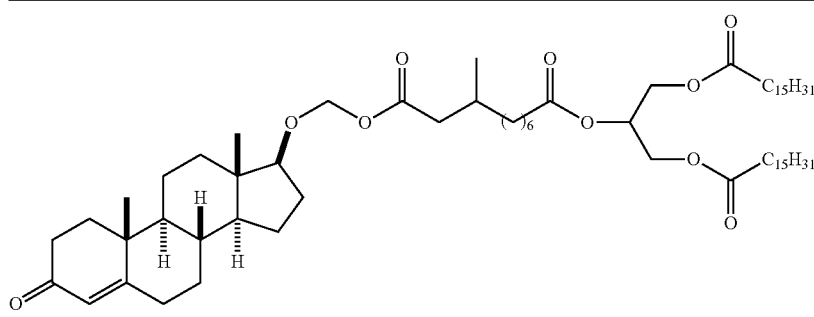
I-39
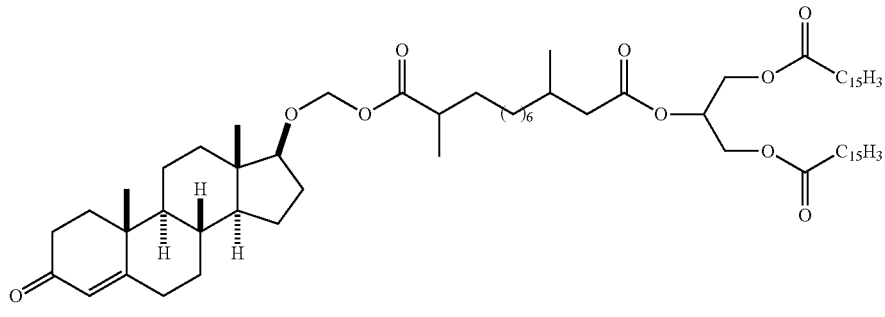
I-40
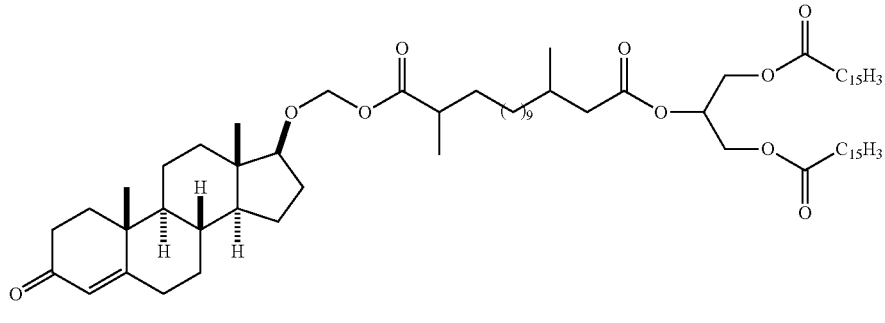
I-41
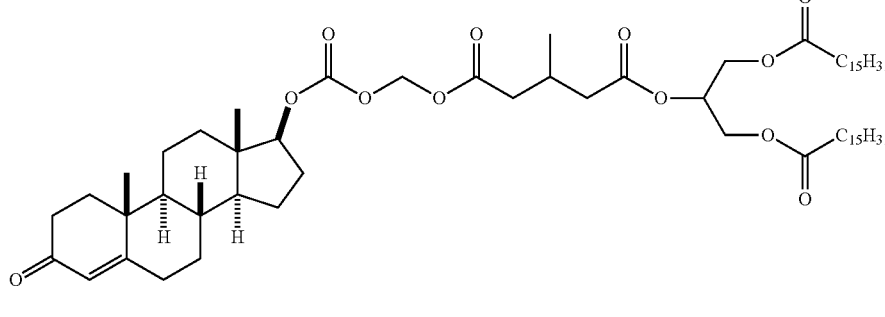
I-42
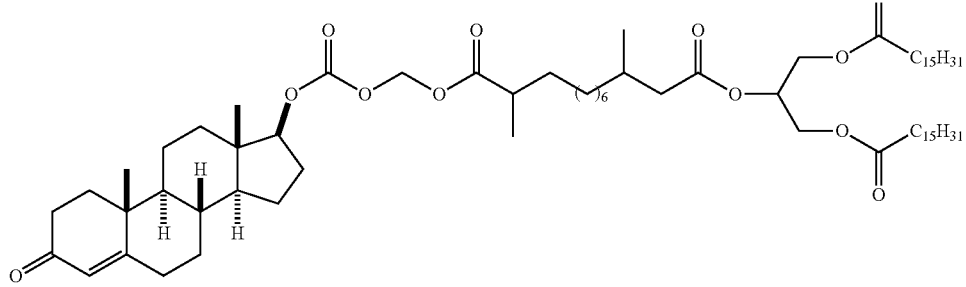
I-43

TABLE A-continued
Exemplary Compounds
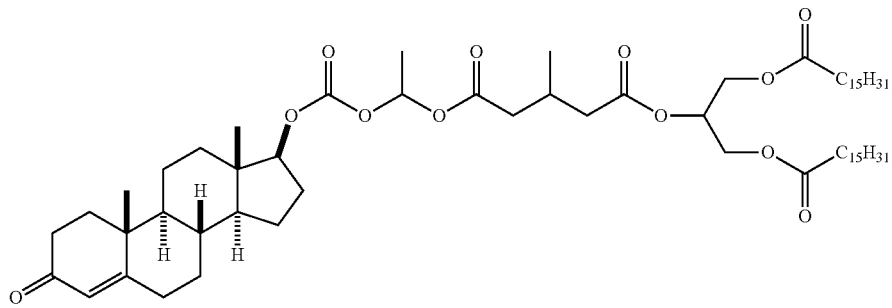
I-44
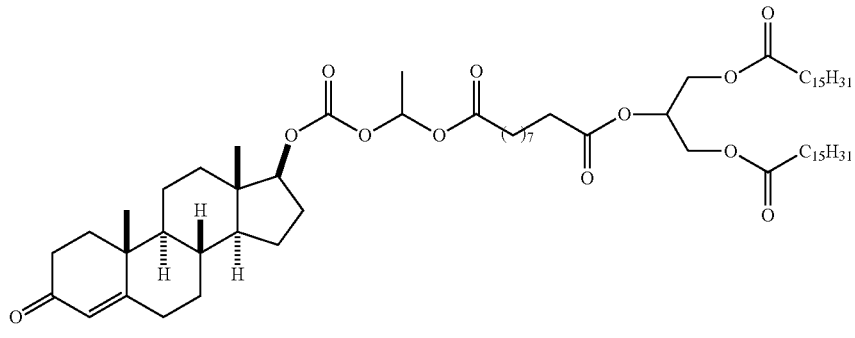
I-45
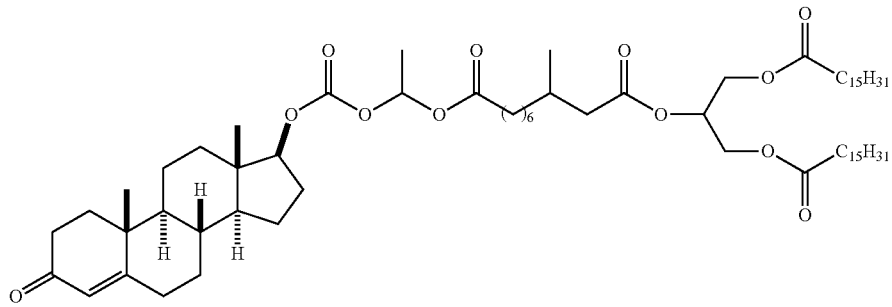
I-46
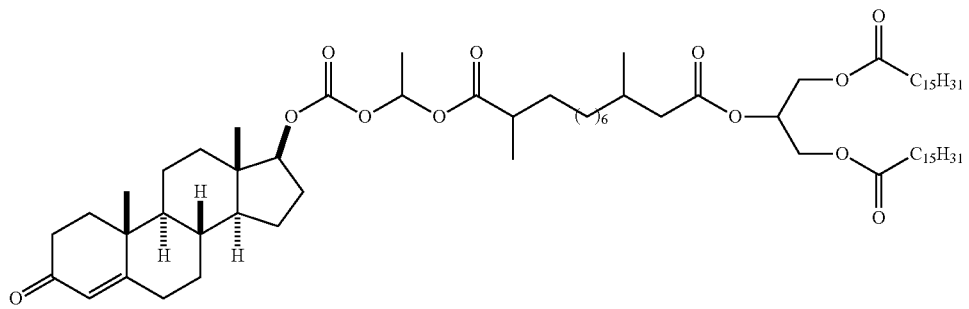
I-47

TABLE A-continued

Exemplary Compounds

I-48

I-49

I-50

I-51

I-52

TABLE A-continued
Exemplary Compounds
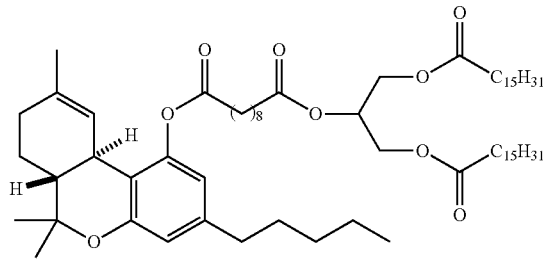
I-53
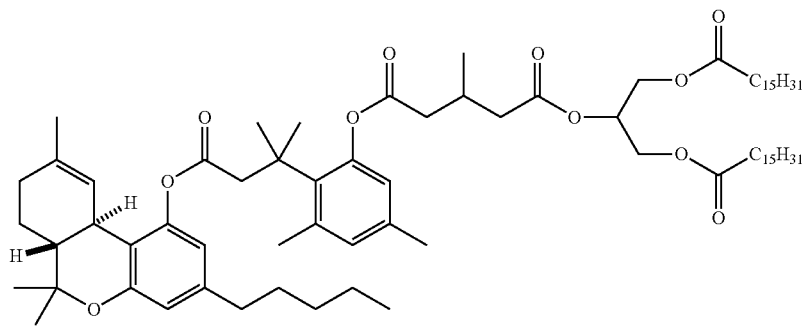
I-54
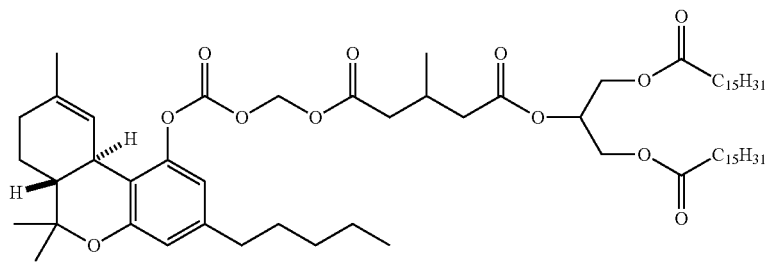
I-55
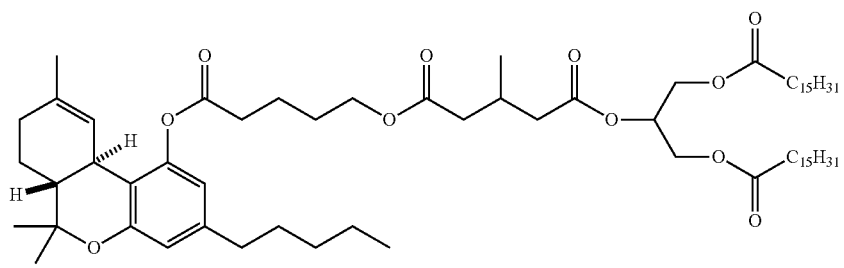
I-56
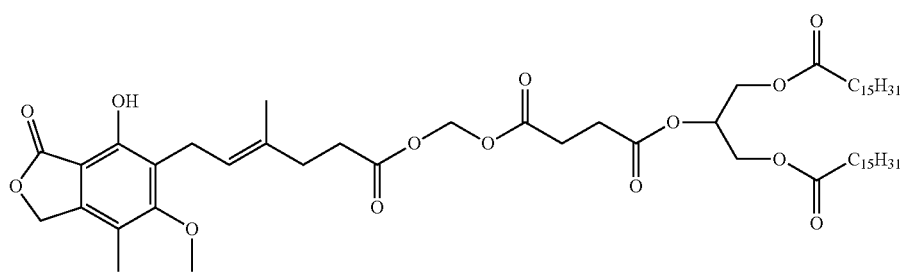
MPA-
MPA-
I-1

TABLE A-continued
Exemplary Compounds
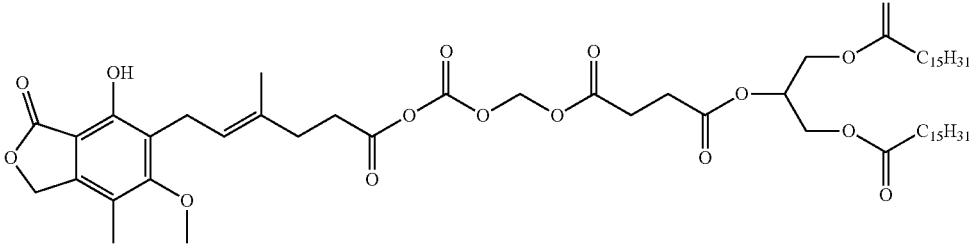 MPA-MPA-I-2
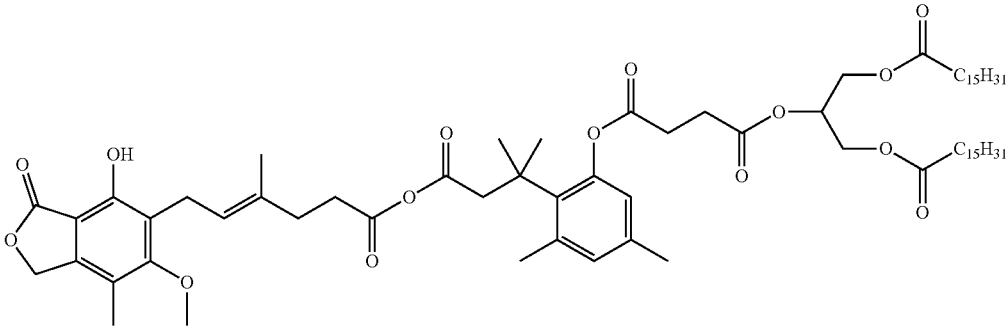 MPA-MPA-I-3
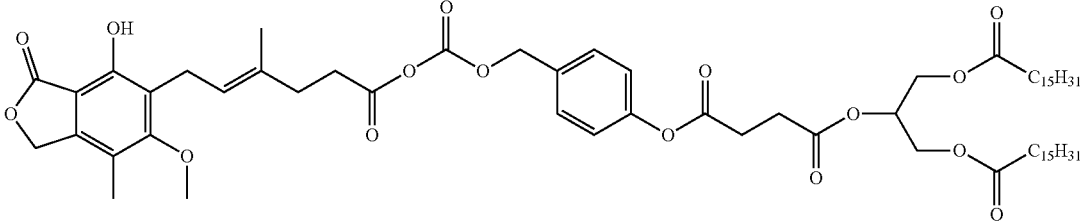 MPA-MPA-I-4
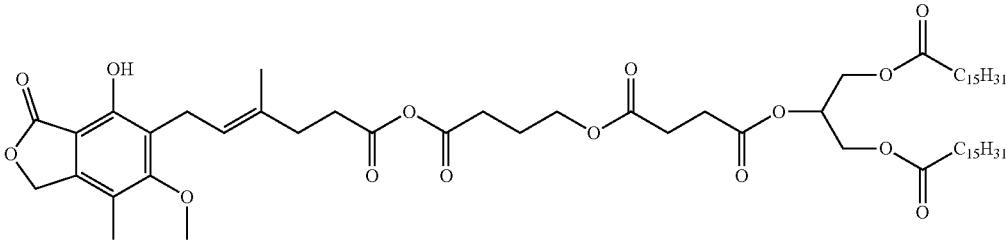 MPA-MPA-I-5
MPA-MPA-I-6
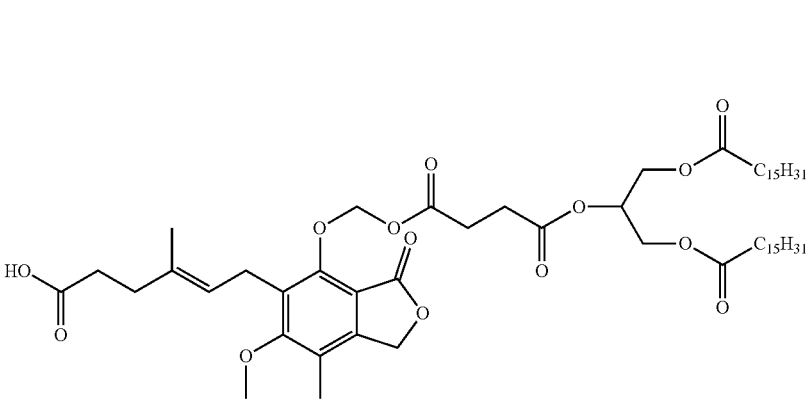

TABLE A-continued

Exemplary Compounds

| Structure | ID |
|---|---|
| (structure) | MPA-MPA-I-7 |
| (structure) | MPA-MPA-I-8 |
| (structure) | MPA-MPA-I-8' |
| (structure) | MPA-MPA-I-9 |

TABLE A-continued

Exemplary Compounds

MPA-MPA-I-10

MPA-MPA-I-11

MPA-MPA-I-12

MPA-MPA-I-13

MPA-MPA-I-14

TABLE A-continued

Exemplary Compounds

| Compound ID |
|---|
| MPA-MPA-I-15 |
| MPA-MPA-I-16 |
| MPA-MPA-I-17 |
| MPA-MPA-I-18 |

TABLE A-continued

Exemplary Compounds

MPA-MPA-I-19

MPA-MPA-I-20

MPA-MPA-I-21

TABLE A-continued
Exemplary Compounds
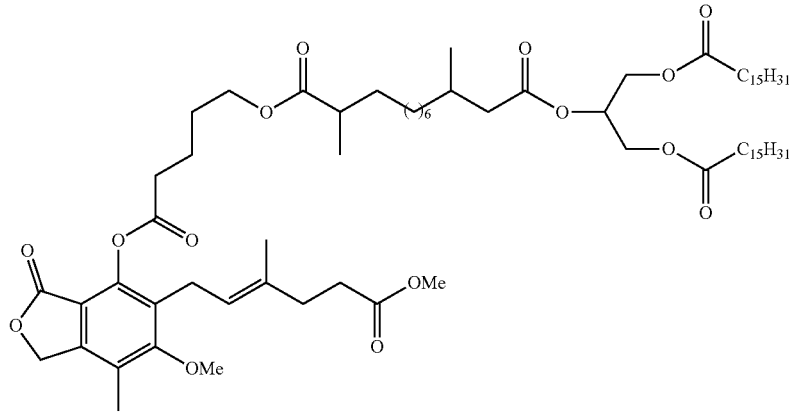
MPA-MPA-I-22
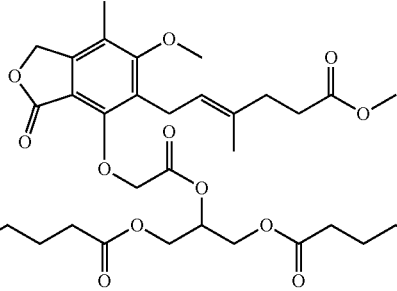
MPA-MPA-I-23
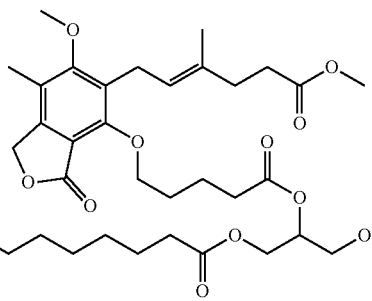
MPA-MPA-I-24
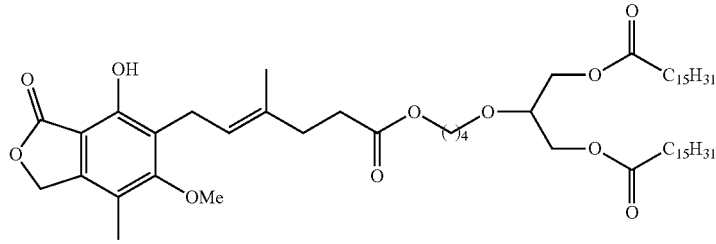
MPA-MPA-I-25
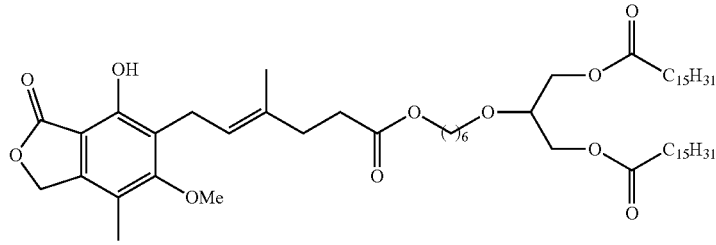
MPA-MPA-I-26

TABLE A-continued
Exemplary Compounds
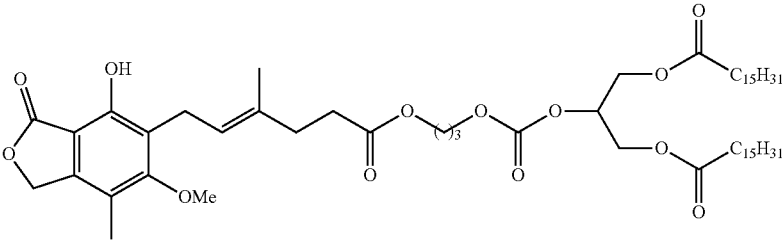   MPA-MPA-I-27
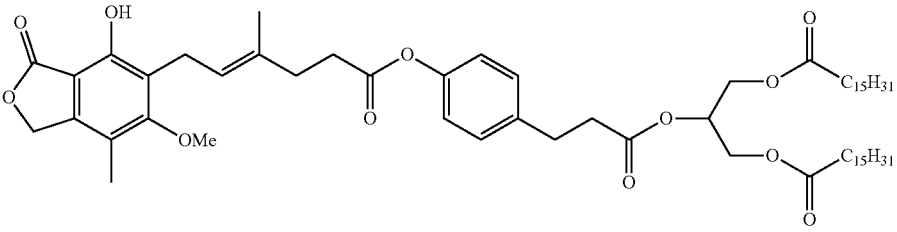   MPA-MPA-I-28
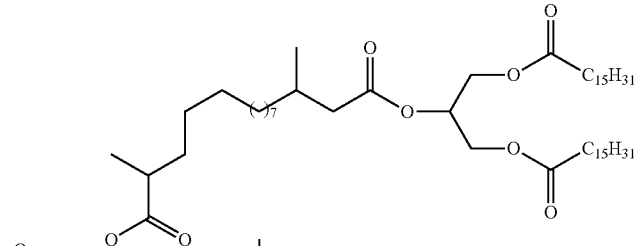   MPA-MPA-I-29
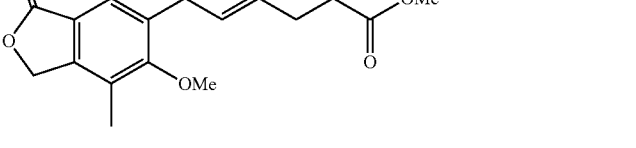   MPA-I-30
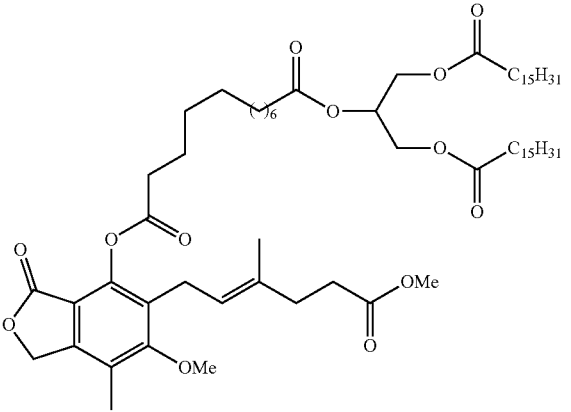

TABLE A-continued

Exemplary Compounds

MPA-I-31

MPA-I-32

MPA-I-33

MPA-I-34

TABLE A-continued

Exemplary Compounds

| Compound ID |
|---|
| MPA-I-35 |
| MPA-I-36 |
| MPA-I-37 |
| MPA-I-38 |
| MPA-I-39 |
| MPA-I-40 |

TABLE A-continued

Exemplary Compounds

| | |
|---|---|
| (structure) | MPA-I-41 |
| (structure) | MPA-I-42 |
| (structure) | MPA-I-43 |
| (structure) | MPA-I-44 |
| (structure) | MPA-I-45 |

TABLE A-continued
Exemplary Compounds
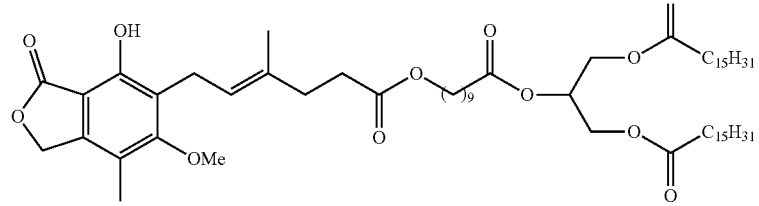
MPA-I-46
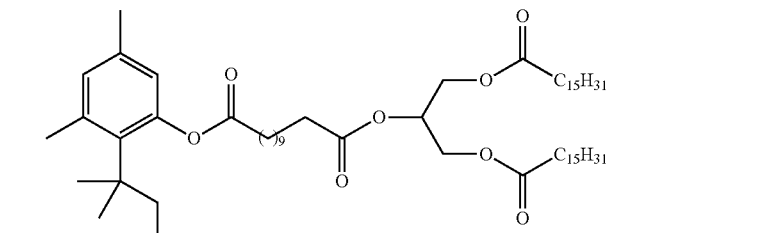
MPA-I-47
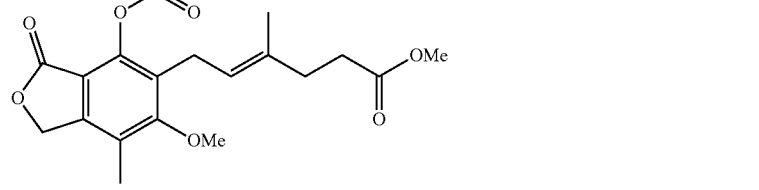
MPA-I-48
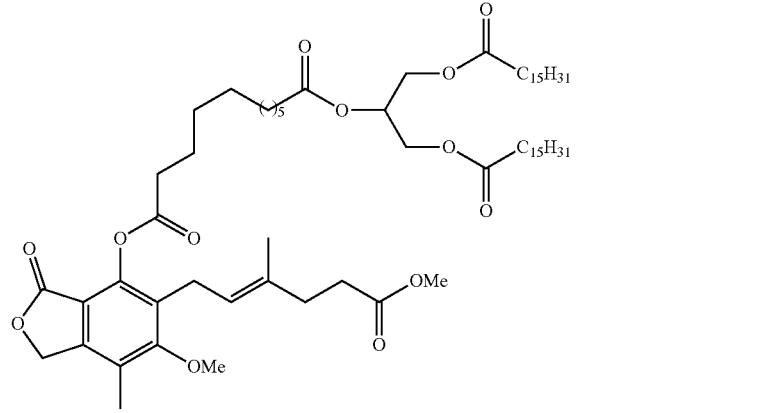
MPA-I-49
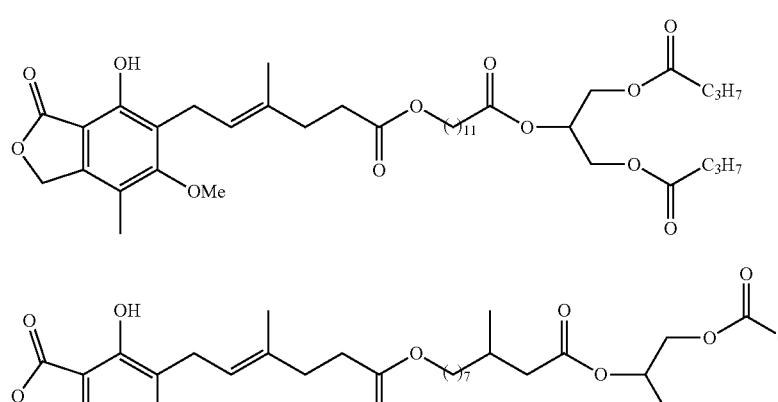
MPA-I-50

TABLE A-continued

Exemplary Compounds

| | |
|---|---|
| (structure) | MPA-I-51 |
| (structure) | MPA-I-52 |
| (structure) | MPA-I-53 |

TABLE A-continued
Exemplary Compounds
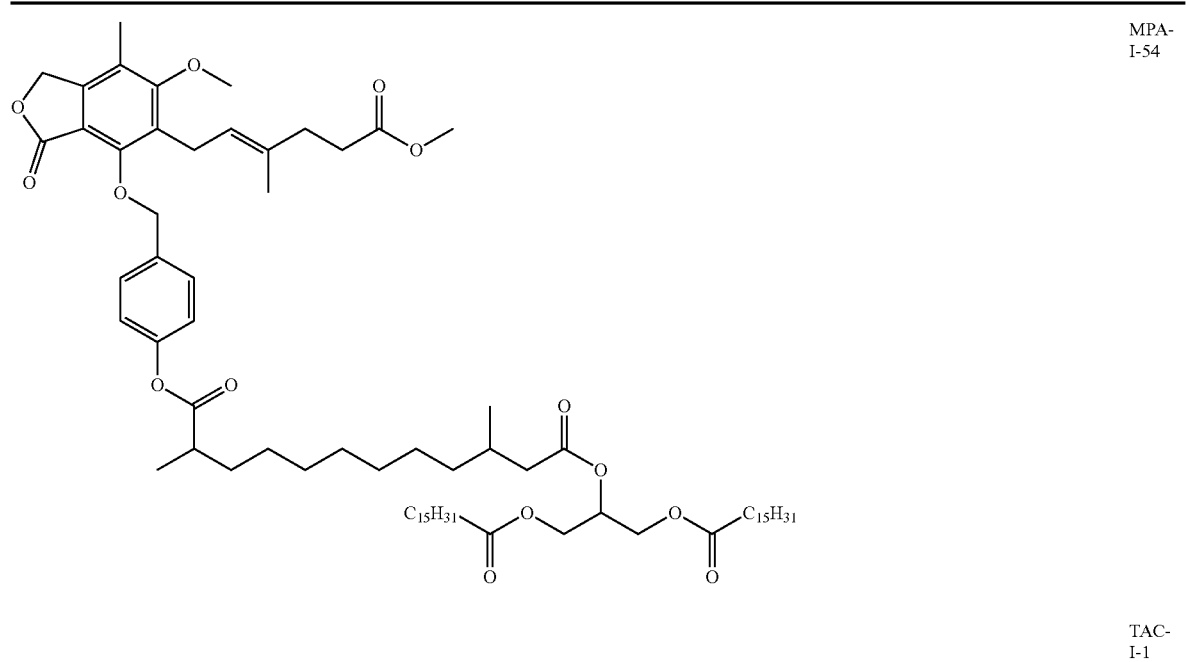
MPA-I-54
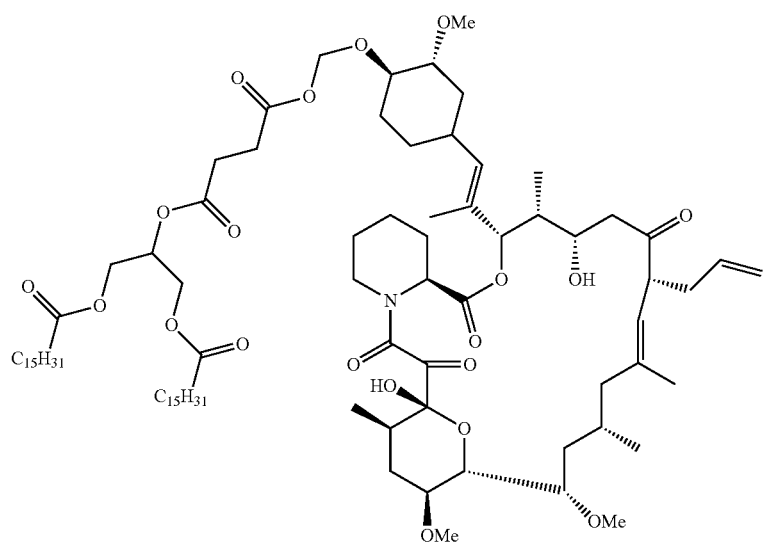
TAC-I-1

TABLE A-continued
Exemplary Compounds
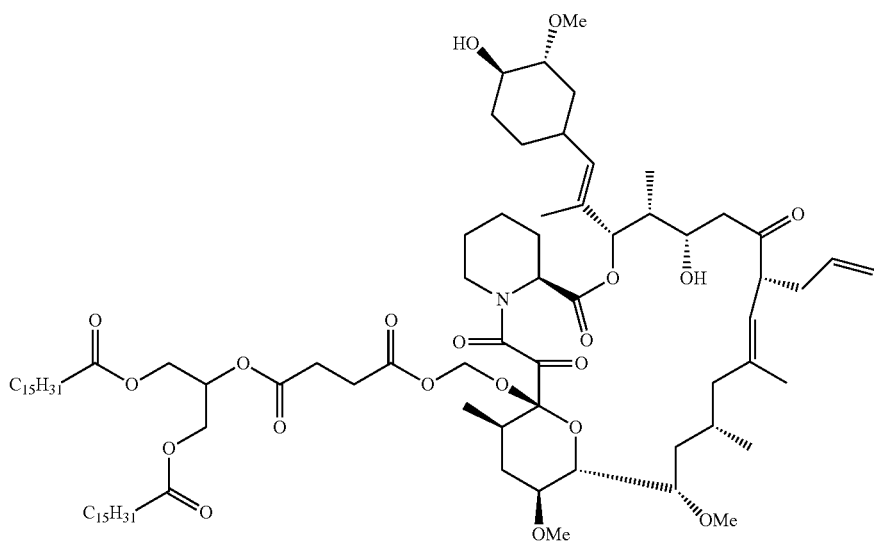
TAC-I-2
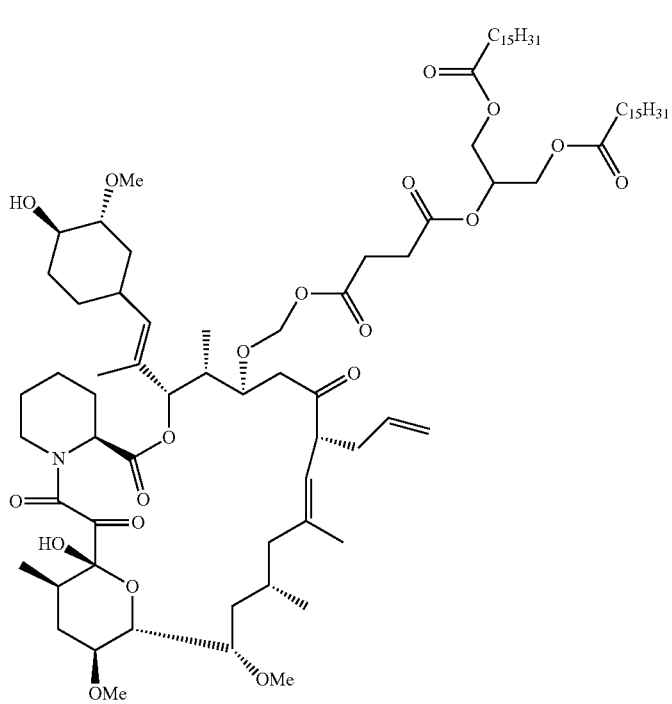
TAC-I-3

TABLE A-continued
Exemplary Compounds
TAC-I-4
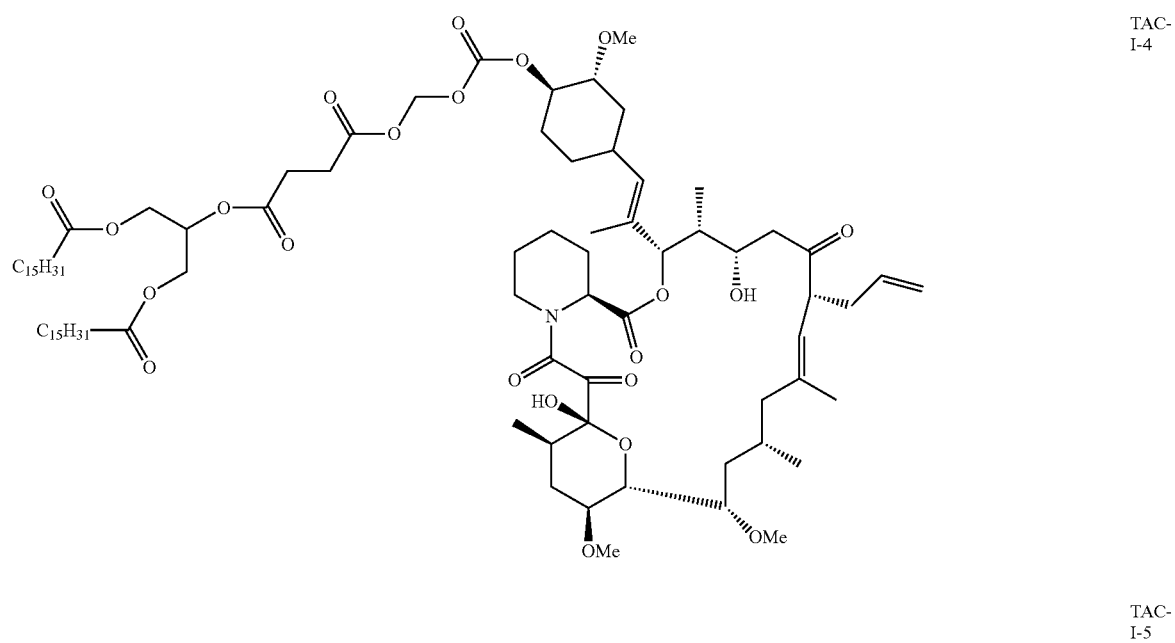
TAC-I-5
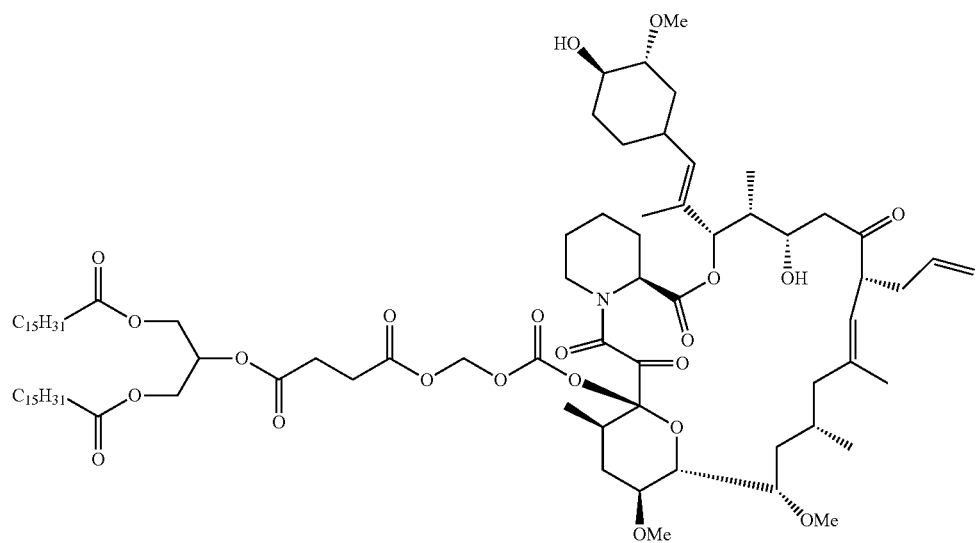

TABLE A-continued
Exemplary Compounds
TAC-I-6
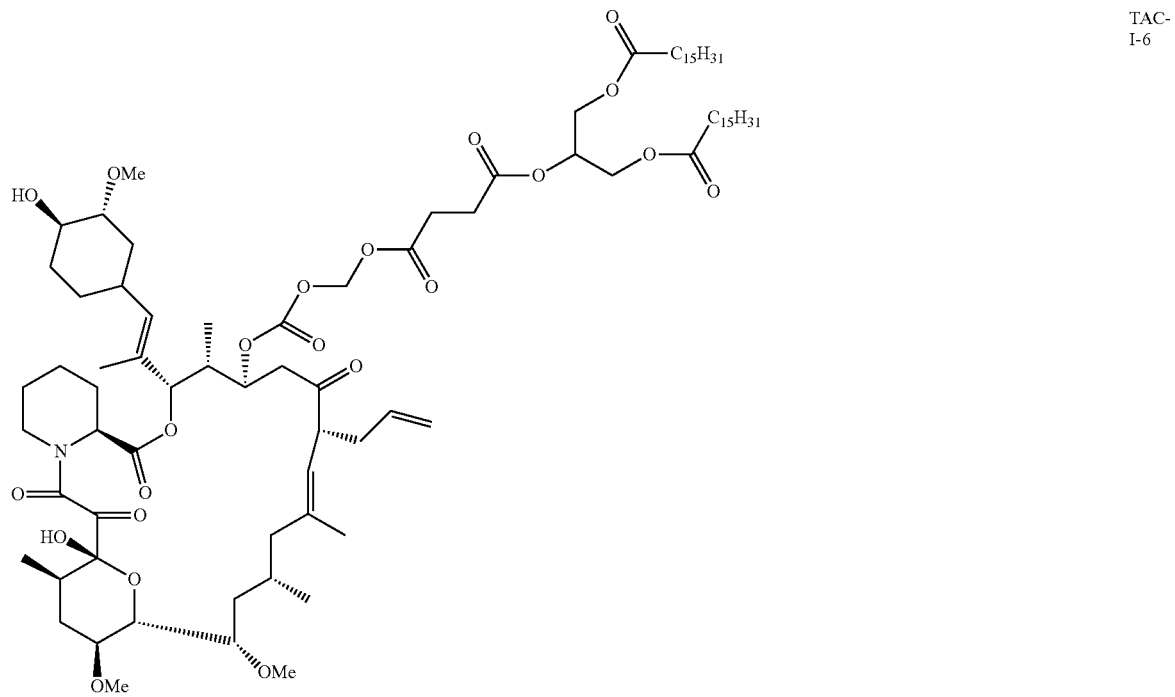
TAC-I-7
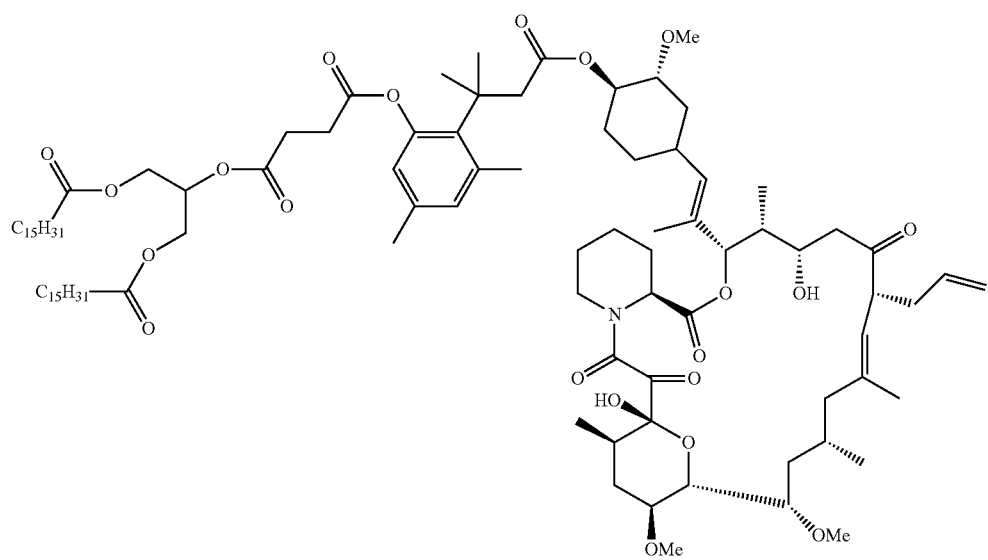

TABLE A-continued
Exemplary Compounds
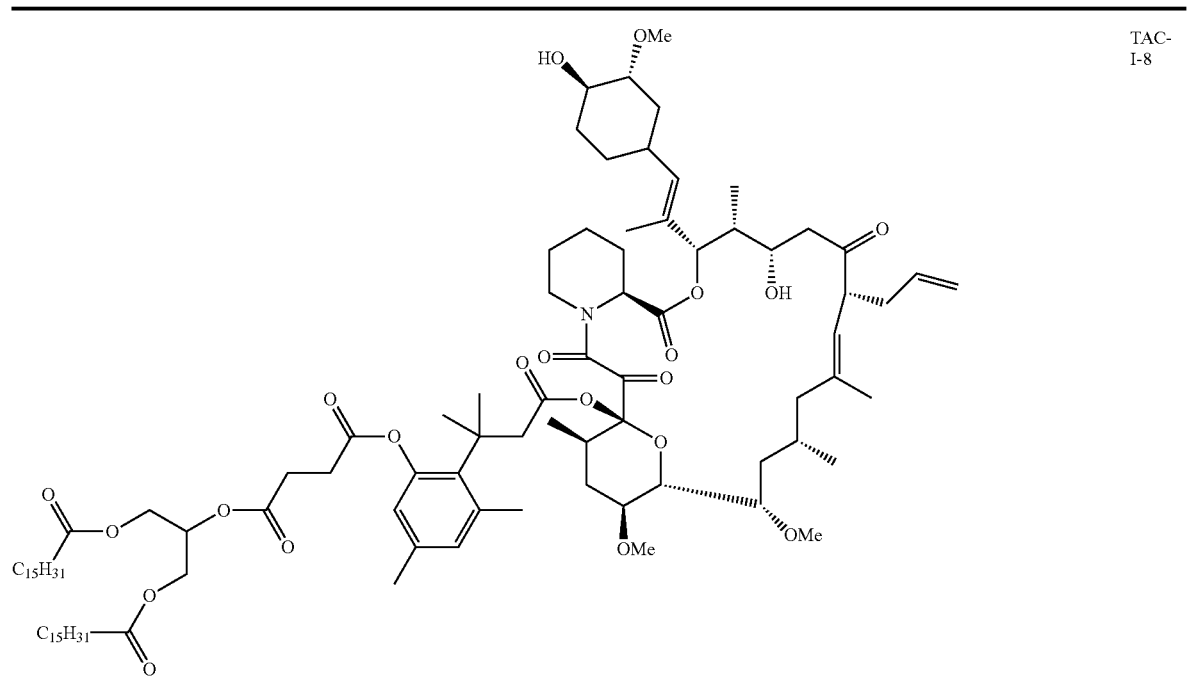
TAC-I-8
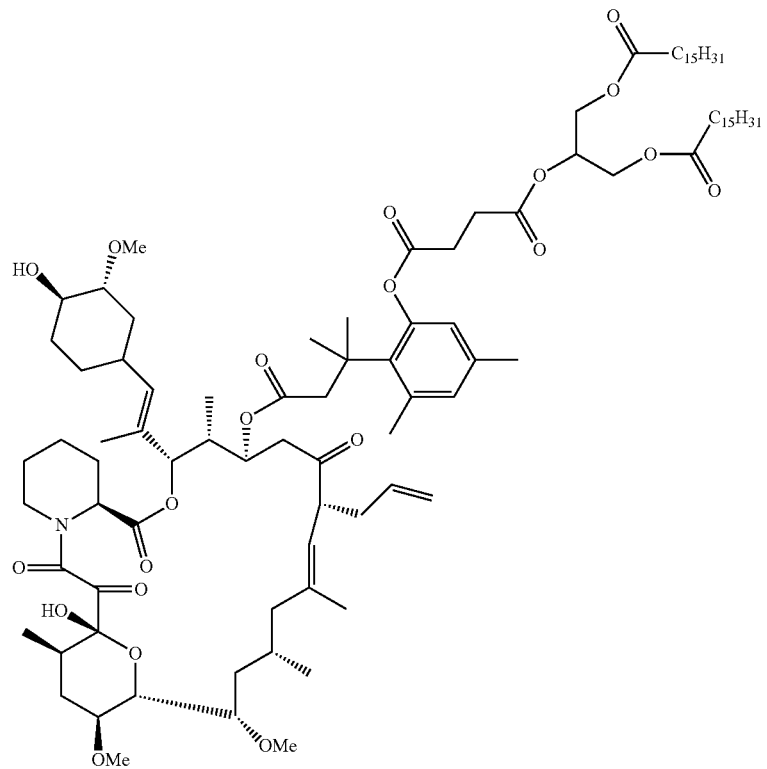
TAC-I-9

TABLE A-continued
Exemplary Compounds
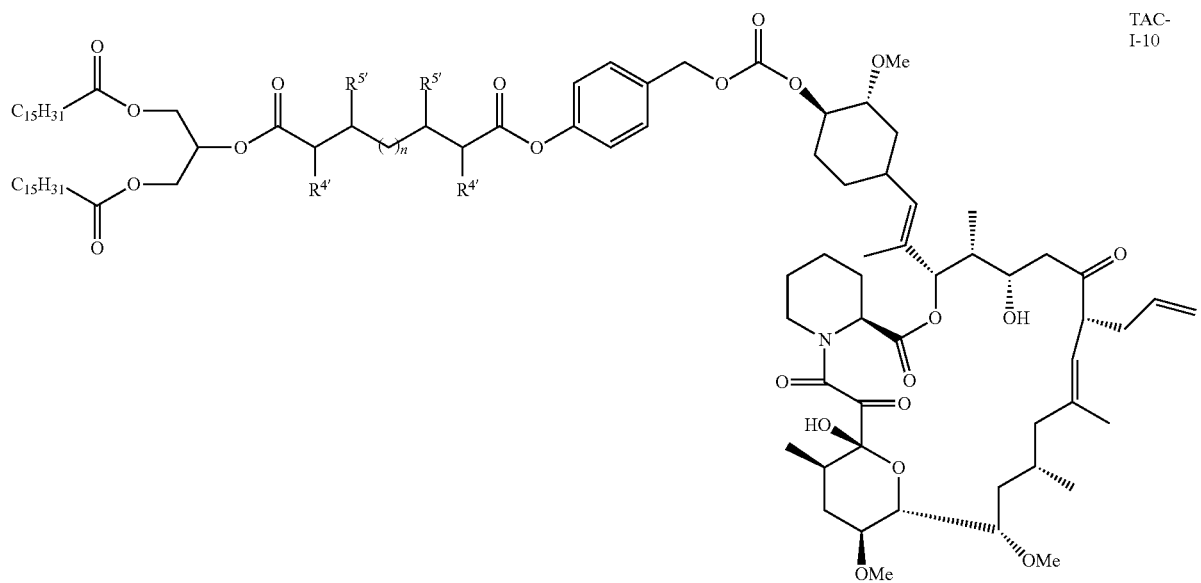
TAC-I-10
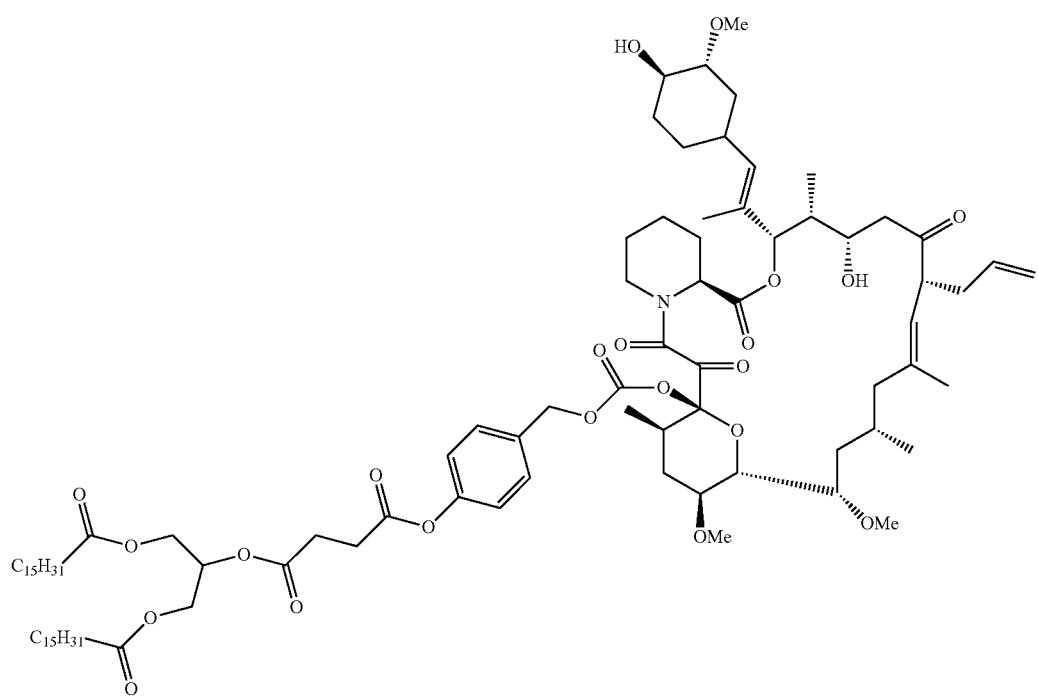
TAC-I-11

TABLE A-continued
Exemplary Compounds
TAC-I-12
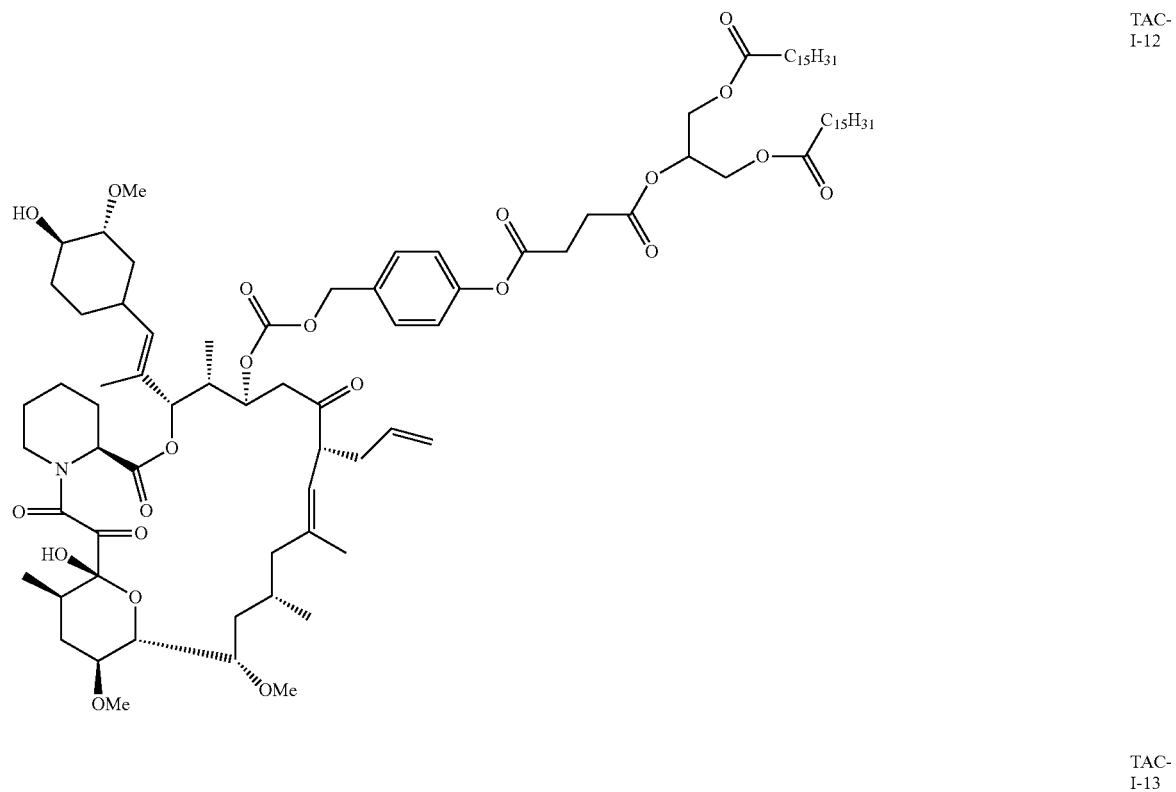
TAC-I-13
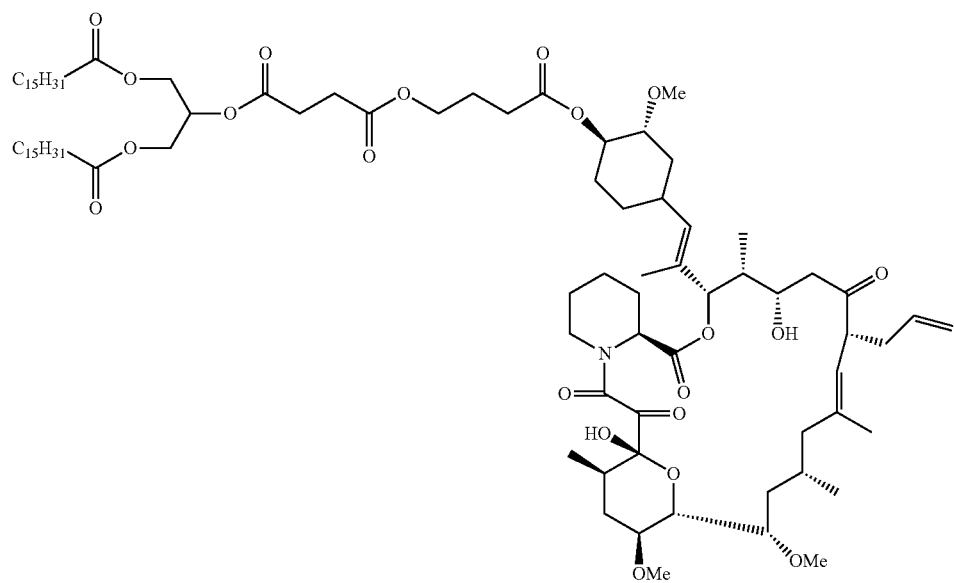

TABLE A-continued
Exemplary Compounds
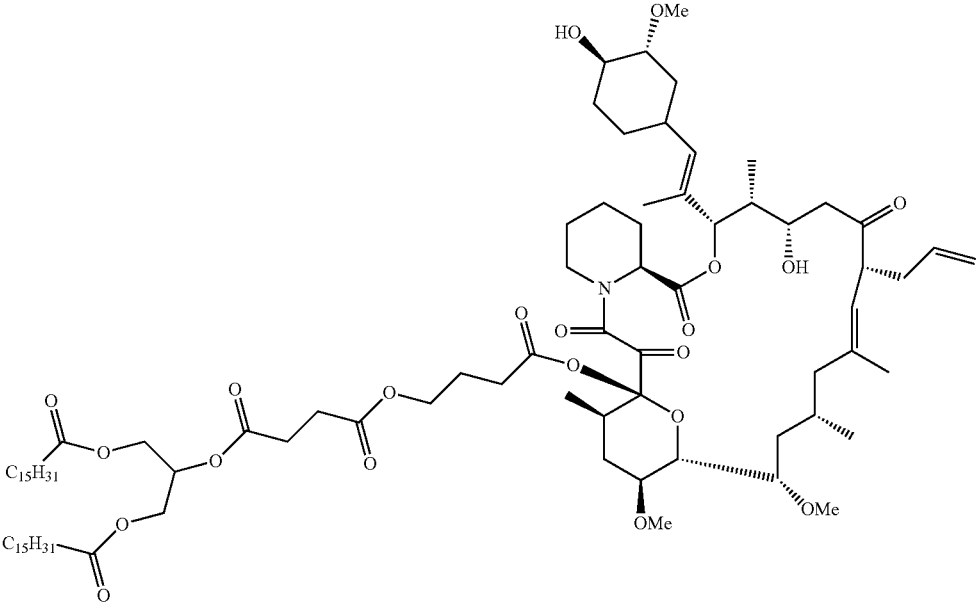
TAC-I-14
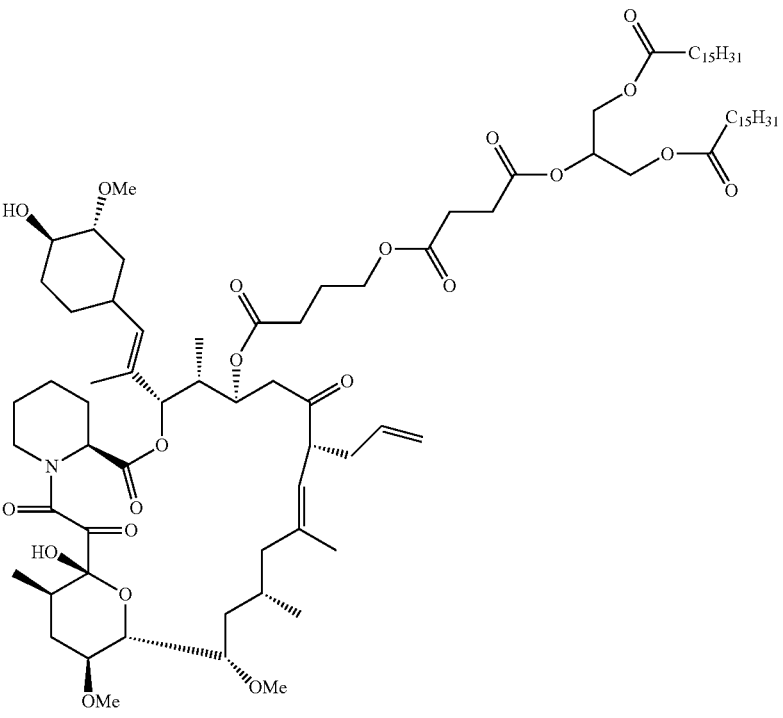
TAC-I-15

TABLE A-continued
Exemplary Compounds
TAC-I-16
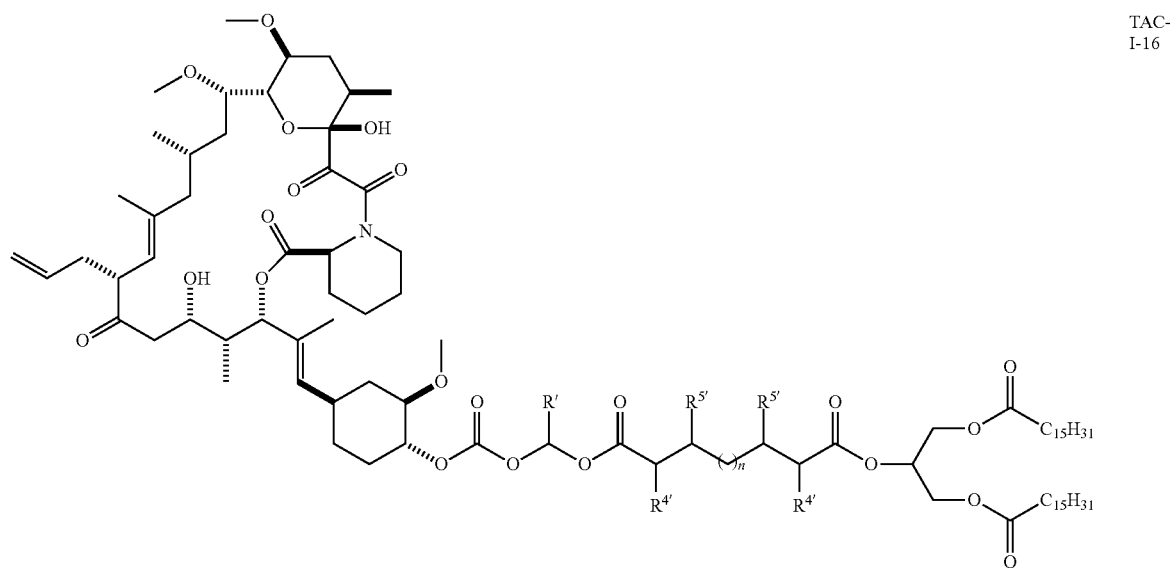
TAC-I-17
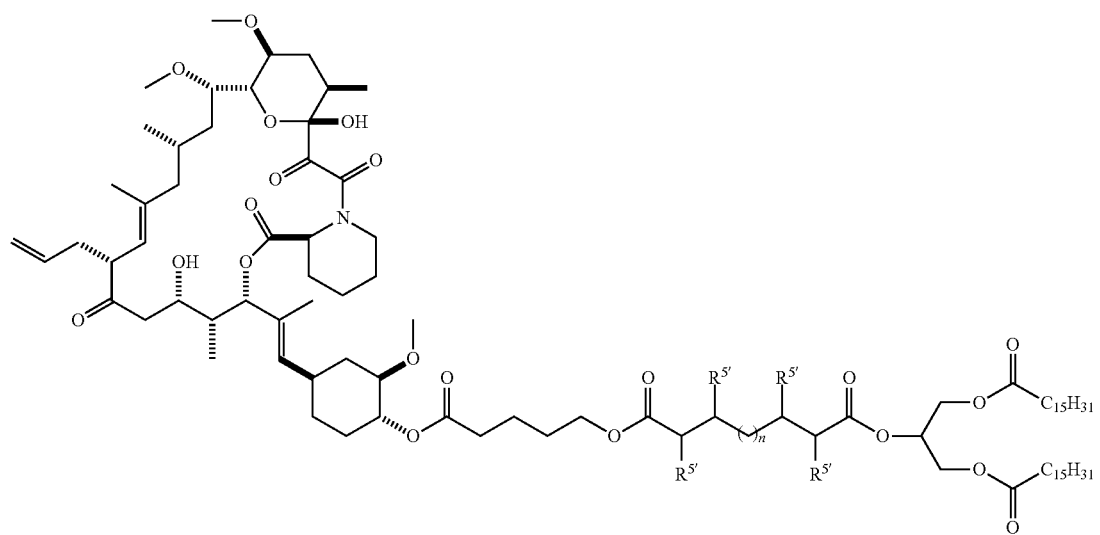

TABLE A-continued
Exemplary Compounds
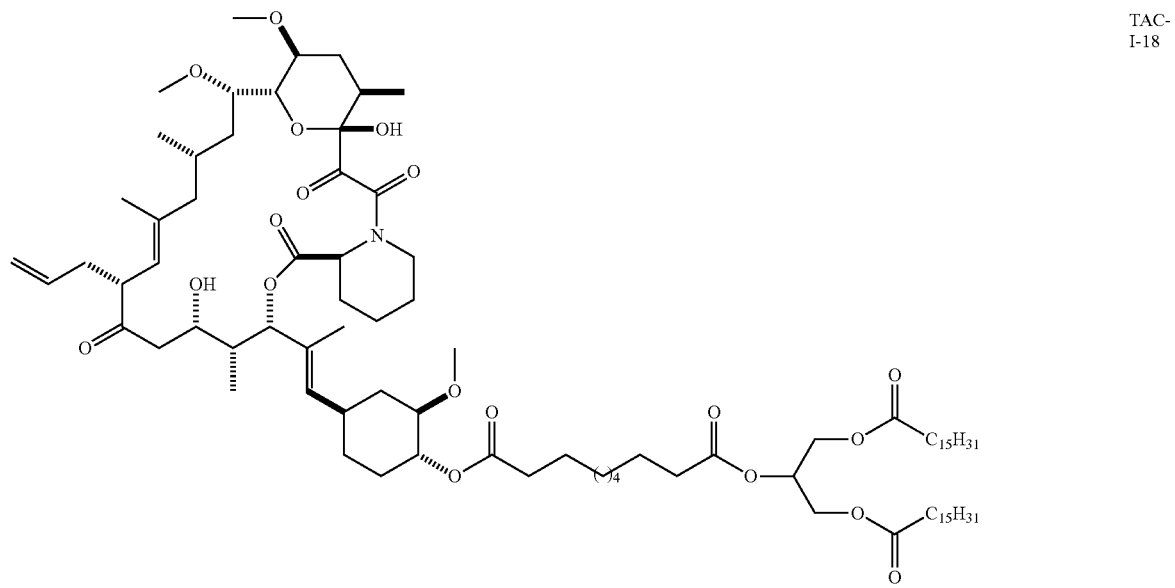
TAC-I-18
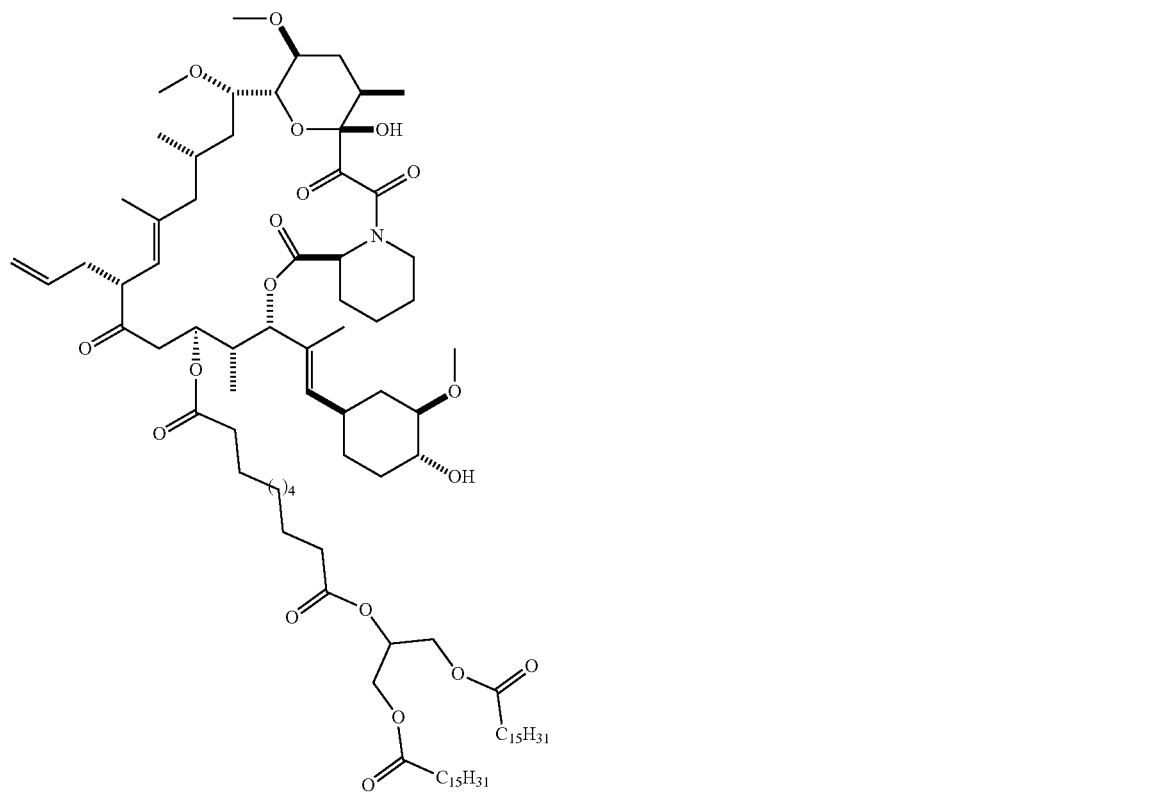
TAC-I-19

TABLE A-continued
Exemplary Compounds
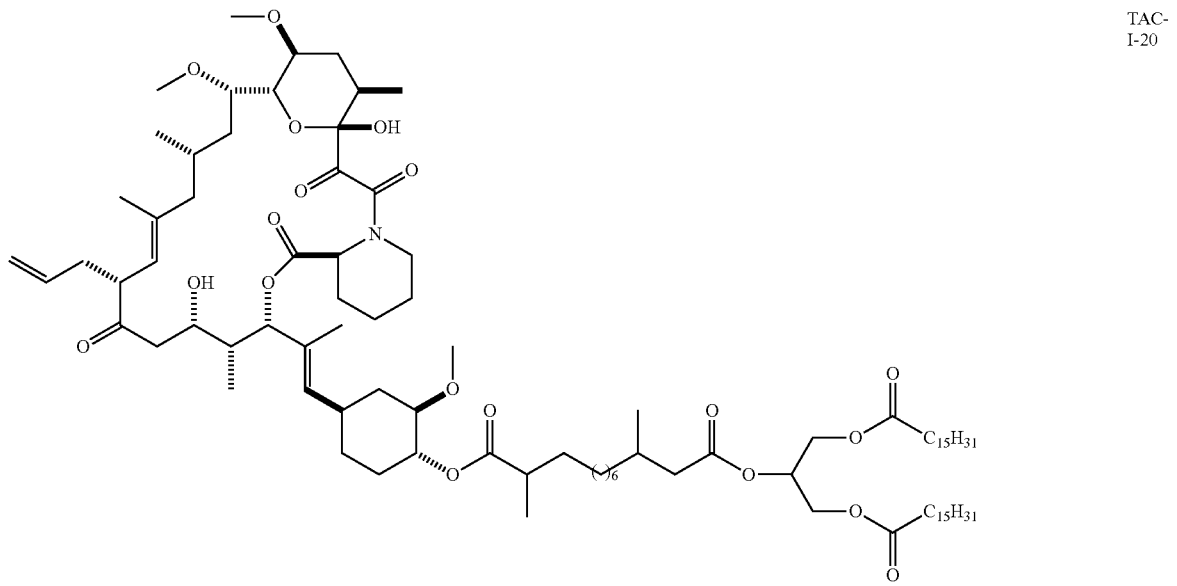
TAC-I-20
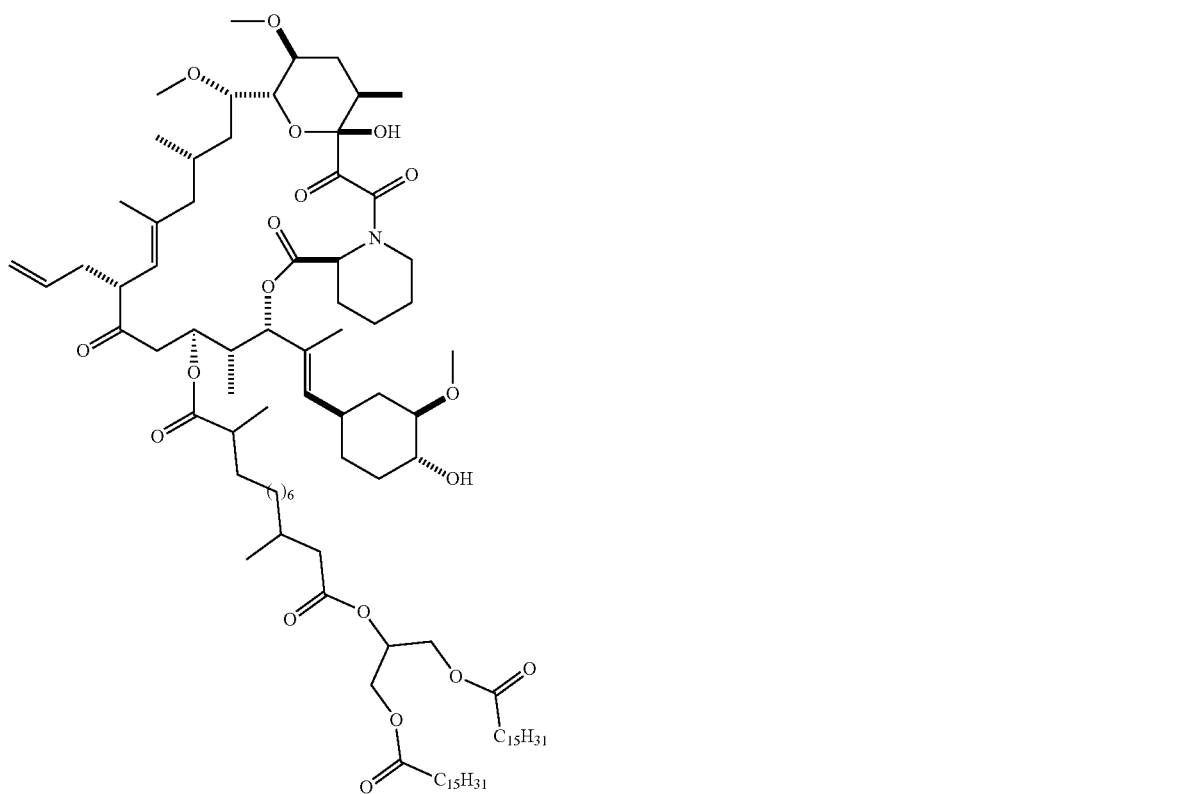
TAC-I-21

TABLE A-continued
Exemplary Compounds
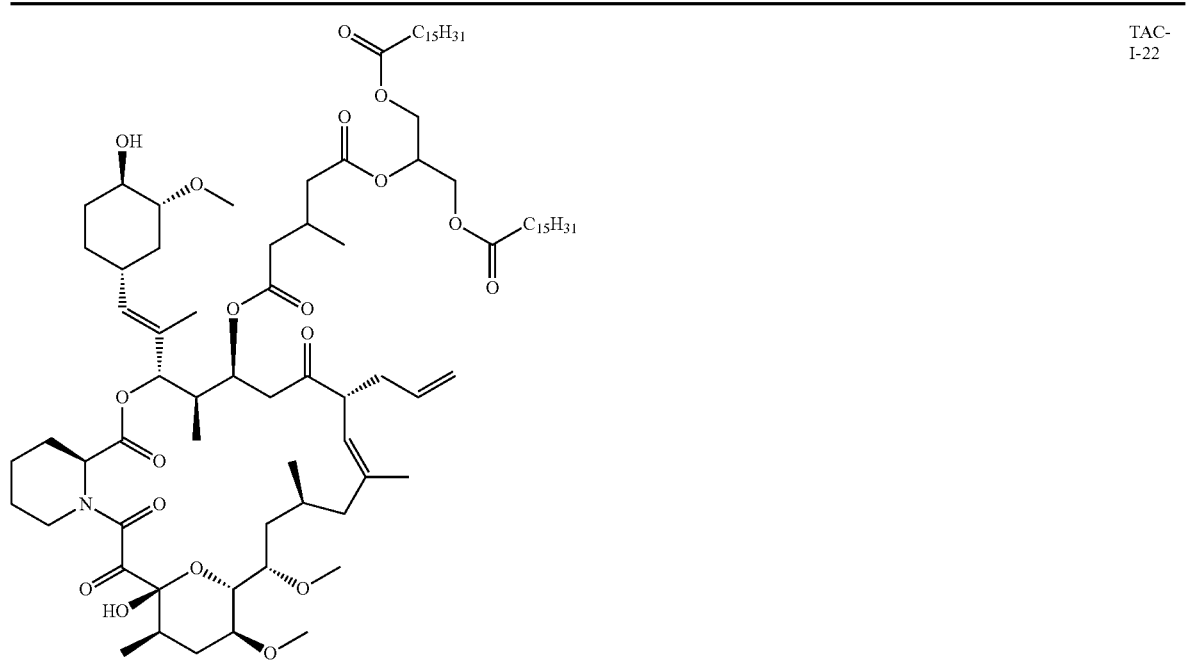
TAC-I-22
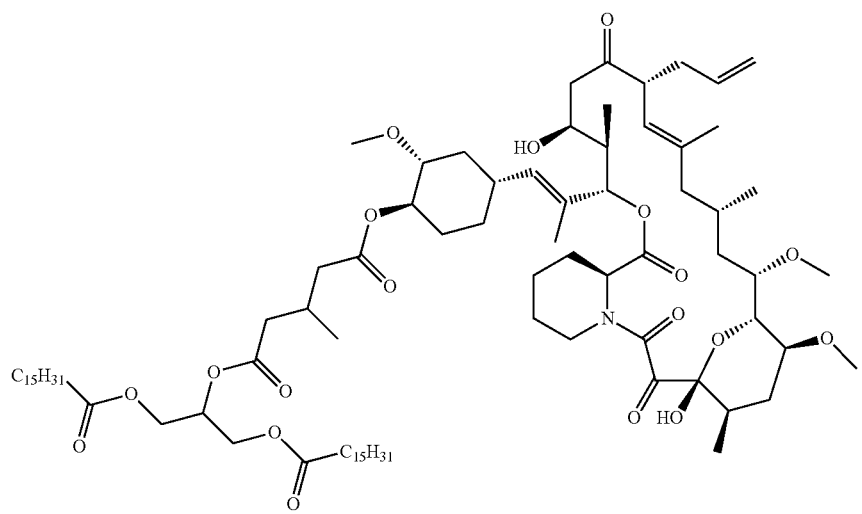
TAC-I-23

TABLE A-continued
Exemplary Compounds
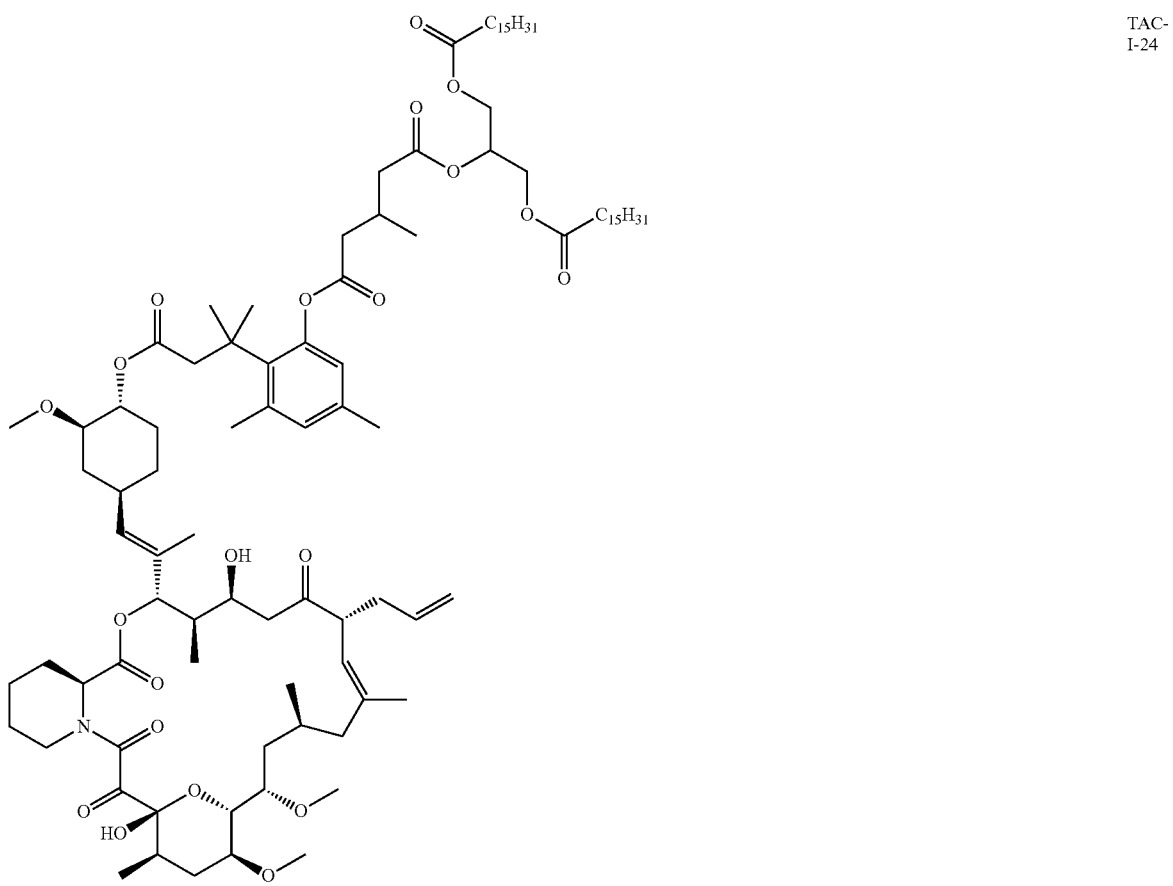
TAC-I-24
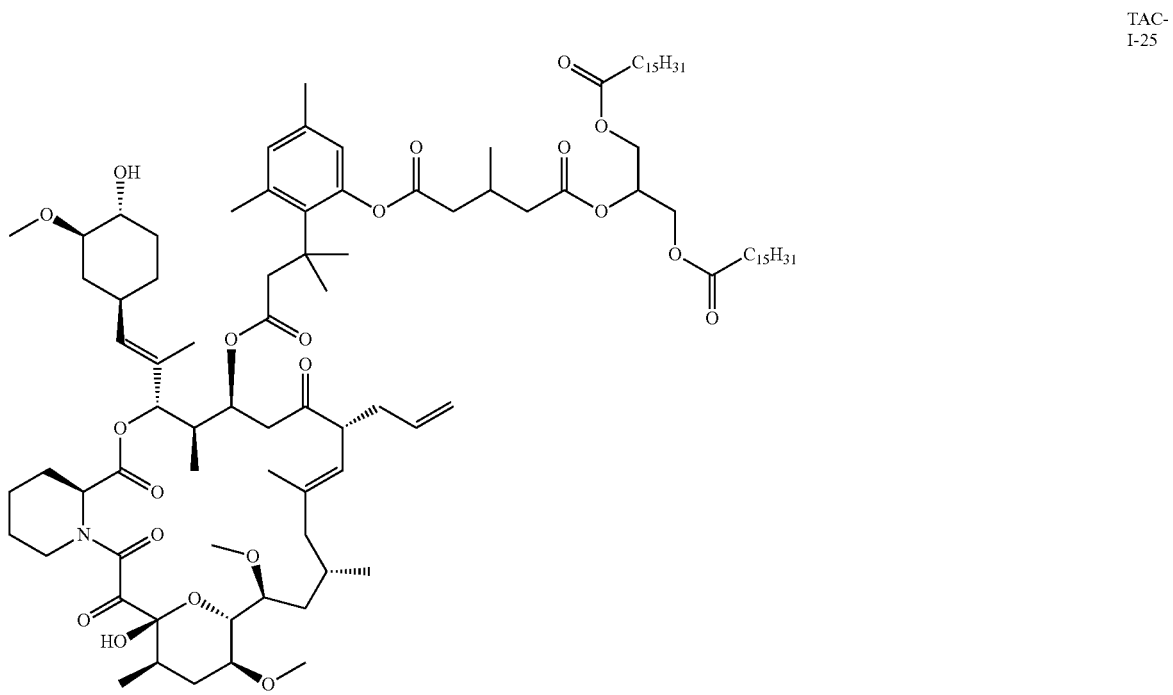
TAC-I-25

TABLE A-continued
Exemplary Compounds
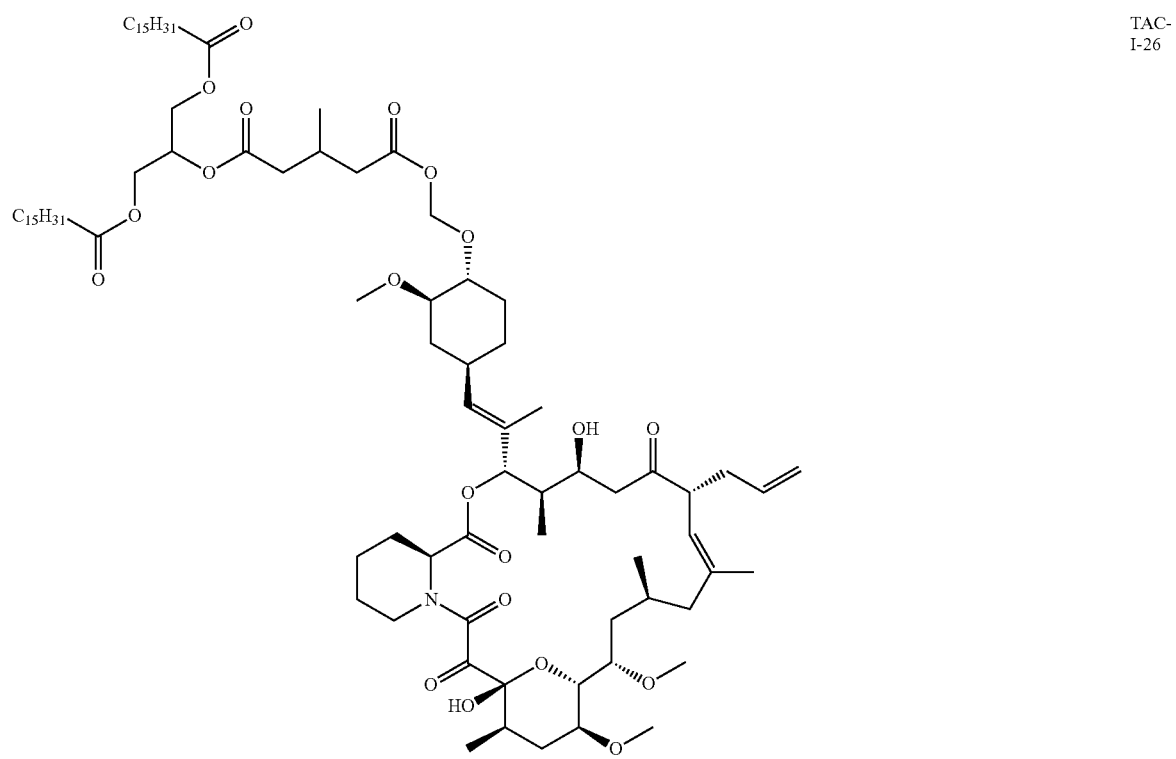
TAC-I-26
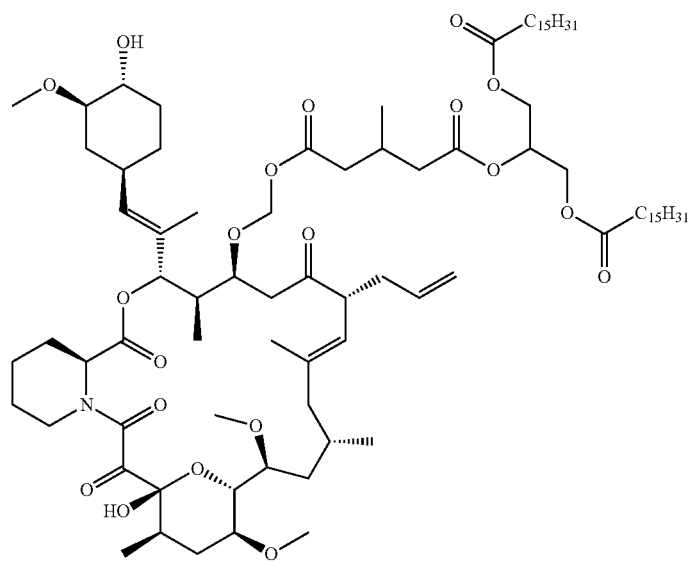
TAC-I-27

TABLE A-continued

Exemplary Compounds

TAC-I-28

TAC-I-29

Lipids, Including Fatty Acids, Phospholipids, Lipid-Processing Mimetics, and Mixtures Thereof for Use in Disclosed Lipid Prodrugs Lipid prodrugs according to the present disclosure mimic the lipid processing that takes place in the human body. In some embodiments, a disclosed lipid prodrug comprises one or two lipids covalently bound to one or two of the hydroxyl groups of the glyceride-based group shown in, e.g. Formula I or VI.

In some embodiments, a disclosed lipid prodrug further comprises a lipid covalently bound to the therapeutic agent.

In some embodiments, such a lipid increases the lipophilicity or other desirable property of the lipid prodrug, e.g. to increase lymphatic uptake and transport. In some embodiments, the lipid is conjugated to the therapeutic agent at an available nitrogen, sulfur, or oxygen atom, such as a carboxylic acid, amine, hydroxyl, or amide. In some embodiments, the lipid is selected from those described below. In some embodiments, the lipid forms an ester of the therapeutic agent.

A variety of lipids are suitable for use in lipid prodrugs of the present disclosure. In some embodiments, the lipid prodrug comprises a fatty acid, phosphatide, phospholipid, or analogue thereof (e.g. phophatidylcholine, lecithin, phosphatidylethanolamine, cephalin, or phosphatidylserine or analogue or portion thereof, such as a partially hydrolyzed portion thereof), or other lipid-processing mimetic (e.g., a group cleaved by lipases, other digestive enzymes, or other mechanisms in the GI tract that enables the lipid prodrug to mimic dietary lipid processing). In some embodiments, the fatty acid is a short-chain, medium-chain, or long-chain fatty acid. In some embodiments, the fatty acid is a saturated fatty acid. In some embodiments, the fatty acid is an unsaturated fatty acid. In some embodiments, the fatty acid is a monounsaturated fatty acid. In some embodiments, the fatty acid is a polyunsaturated fatty acid, such as an ω-3 (omega-3) or ω-6 (omega-6) fatty acid. In some embodiments, the lipid, e.g., fatty acid, has a $C_2$-$C_{60}$ chain. In some embodiments, the lipid, e.g., fatty acid, has a $C_2$-$C_{28}$ chain. In some embodiments, the lipid, e.g., fatty acid, has a $C_2$-$C_{40}$ chain. In some embodiments, the lipid, e.g., fatty acid, has a $C_2$-$C_{12}$ or $C_4$-$C_{12}$ chain. In some embodiments, the lipid, e.g., fatty acid, has a $C_4$-$C_{40}$ chain. In some embodiments, the lipid, e.g., fatty acid, has a $C_4$-$C_{40}$, $C_2$-$C_{38}$, $C_2$-$C_{36}$, $C_2$-$C_{34}$, $C_2$-$C_{32}$, $C_2$-$C_{30}$, $C_4$-$C_{30}$, $C_2$-$C_{28}$, $C_4$-$C_{28}$, $C_2$-$C_{26}$, $C_4$-$C_{26}$, $C_2$-$C_{24}$, $C_4$-$C_{24}$, $C_6$-$C_{24}$, $C_8$-$C_{24}$, $C_{10}$-$C_{24}$, $C_2$-$C_{22}$, $C_4$-$C_{22}$, $C_6$-$C_{22}$, $C_8$-$C_{22}$, $C_{10}$-$C_{22}$, $C_2$-$C_{20}$, $C_4$-$C_{20}$, $C_6$-$C_{20}$, $C_8$-$C_{20}$, $C_{10}$-$C_{20}$, $C_2$-$C_{18}$, $C_4$-$C_{18}$, $C_6$-$C_{18}$, $C_8$-$C_{18}$, $C_{10}$-$C_{18}$, $C_{12}$-$C_{18}$, $C_{14}$-$C_{18}$, $C_{16}$-$C_{18}$, $C_2$-$C_{16}$, $C_4$-$C_{16}$, $C_6$-$C_{16}$, $C_8$-$C_{16}$, $C_{10}$-$C_{16}$, $C_{12}$-$C_{16}$, $C_{14}$-$C_{16}$, $C_2$-$C_{15}$, $C_4$-$C_{15}$, $C_6$-$C_{15}$, $C_8$-$C_{15}$, $C_9$-$C_{15}$, $C_{10}$-$C_{15}$, $C_{11}$-$C_{15}$, $C_{12}$-$C_{15}$, $C_{13}$-$C_{15}$, $C_2$-$C_{14}$, $C_4$-$C_{14}$, $C_6$-$C_{14}$, $C_8$-$C_{14}$, $C_9$-$C_{14}$, $C_{10}$-$C_{14}$, $C_{11}$-$C_{14}$, $C_{12}$-$C_{14}$, $C_2$-$C_{13}$, $C_4$-$C_{13}$, $C_6$-$C_{13}$, $C_7$-$C_{13}$, $C_8$-$C_{13}$, $C_9$-$C_{13}$, $C_{10}$-$C_{13}$, $C_{10}$-$C_{13}$, $C_1$-$C_{13}$, $C_2$-$C_{12}$, $C_4$-$C_{12}$, $C_6$-$C_{12}$, $C_7$-$C_{12}$, $C_8$-$C_{12}$, $C_9$-$C_{12}$, $C_{10}$-$C_{12}$, $C_2$-$C_{11}$, $C_4$-$C_{11}$, $C_6$-$C_{11}$, $C_7$-$C_{11}$, $C_8$-$C_{11}$, $C_9$-$C_{11}$, $C_2$-$C_{10}$, $C_4$-$C_{10}$, $C_2$-$C_9$, $C_4$-$C_9$, $C_2$-$C_8$, $C_4$-$C_8$, $C_2$-$C_7$, $C_4$-$C_7$, $C_2$-$C_6$, or $C_4$-$C_6$, chain. In some embodiments, the lipid, e.g., fatty acid, has a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, $C_{50}$, $C_{51}$, $C_{52}$, $C_{53}$, $C_{54}$, $C_{55}$, $C_{56}$, $C_{57}$, $C_{58}$, $C_{59}$, or $C_{60}$ chain. In some embodiments, the lipid prodrug comprises two fatty acids, each of which is independently selected from a fatty acid having a chain with any one of the foregoing ranges or numbers of carbon atoms. In some embodiments, one of the fatty acids is independently a fatty acid with a $C_6$-$C_{21}$ chain and one is independently a fatty acid with a $C_{12}$-$C_{36}$ chain. In some embodiments, each fatty acid independently has a chain of 11, 12, 13, 14, 15, 16, or 17 carbon atoms.

In some embodiments, the lipid prodrug comprises two lipids. In some embodiments, the two lipids, e.g. fatty acids, taken together have 6-80 carbon atoms (an equivalent carbon number (ECN) of 6-80). In some embodiments, the lipids, e.g., fatty acids, have an ECN of 6-80, 8-80, 10-80, 12-80, 14-80, 16-80, 18-80, 20-80, 22-80, 24-80, 26-80, 28-80, 30-80, 4-76, 6-76, 8-76, 10-76, 12-76, 14-76, 16-76, 18-76, 20-76, 22-76, 24-76, 26-76, 28-76, 30-76, 6-72, 8-72, 10-72, 12-72, 14-72, 16-72, 18-72, 20-72, 22-72, 24-72, 26-72, 28-72, 30-72, 6-68, 8-68, 10-68, 12-68, 14-68, 16-68, 18-68, 20-68, 22-68, 24-68, 26-68, 28-68, 30-68, 6-64, 8-64, 10-64, 12-64, 14-64, 16-64, 18-64, 20-64, 22-64, 24-64, 26-64, 28-64, 30-64, 6-60, 8-60, 10-60, 12-56, 14-56, 16-56, 18-56, 20-56, 22-56, 24-56, 26-56, 28-56, 30-56, 6-52, 8-52, 10-52, 12-52, 14-52, 16-52, 18-52, 20-52, 22-52, 24-52, 26-52, 28-52, 30-52, 6-48, 8-48, 10-48, 12-48, 14-48, 16-48, 18-48, 20-48, 22-48, 24-48, 26-48, 28-48, 30-48, 6-44, 8-44, 10-44, 12-44, 14-44, 16-44, 18-44, 20-44, 22-44, 24-44, 26-44, 28-44, 30-44, 6-40, 8-40, 10-40, 12-40, 14-40, 16-40, 18-40, 20-40, 22-40, 24-40, 26-40, 28-40, 30-40, 6-36, 8-36, 10-36, 12-36, 14-36, 16-36, 18-36, 20-36, 22-36, 24-36, 26-36, 28-36, 30-36, 6-32, 8-32, 10-32, 12-32, 14-32, 16-32, 18-32, 20-32, 22-32, 24-32, 26-32, 28-32, or 30-32.

Suitable fatty acids include saturated straight-chain fatty acids, saturated branched fatty acids, unsaturated fatty acids, hydroxy fatty acids, and polycarboxylic acids. In some embodiments, such fatty acids have up to 32 carbon atoms.

Examples of useful saturated straight-chain fatty acids include those having an even number of carbon atoms, such as butyric acid, caproic acid, caprylic acid, capric acid, lauric acid, myristic acid, palmitic acid, stearic acid, arachic acid, behenic acid, lignoceric acid, hexacosanoic acid, octacosanoic acid, triacontanoic acid and n-dotriacontanoic acid, and those having an odd number of carbon atoms, such as propionic acid, n-valeric acid, enanthic acid, pelargonic acid, hendecanoic acid, tridecanoic acid, pentadecanoic acid, heptadecanoic acid, nonadecanoic acid, heneicosanoic acid, tricosanoic acid, pentacosanoic acid, and heptacosanoic acid.

Examples of suitable saturated branched fatty acids include isobutyric acid, isocaproic acid, isocaprylic acid, isocapric acid, isolauric acid, 11-methyldodecanoic acid, isomyristic acid, 13-methyl-tetradecanoic acid, isopalmitic acid, 15-methyl-hexadecanoic acid, isostearic acid, 17-methyloctadecanoic acid, isoarachic acid, 19-methyl-eicosanoic acid, α-ethyl-hexanoic acid, α-hexyldecanoic acid, α-heptylundecanoic acid, 2-decyltetradecanoic acid, 2-undecyltetradecanoic acid, 2-decylpentadecanoic acid, 2-undecylpentadecanoic acid, and Fine oxocol 1800 acid (product of Nissan Chemical Industries, Ltd.). Suitable saturated odd-carbon branched fatty acids include anteiso fatty acids terminating with an isobutyl group, such as 6-methyl-octanoic acid, 8-methyl-decanoic acid, 10-methyl-dodecanoic acid, 12-methyl-tetradecanoic acid, 14-methyl-hexadecanoic acid, 16-methyl-octadecanoic acid, 18-methyl-eicosanoic acid, 20-methyl-docosanoic acid, 22-methyl-tetracosanoic acid, 24-methyl-hexacosanoic acid, and 26-methyloctacosanoic acid.

Examples of suitable unsaturated fatty acids include 4-decenoic acid, caproleic acid, 4-dodecenoic acid, 5-dodecenoic acid, lauroleic acid, 4-tetradecenoic acid, 5-tetradecenoic acid, 9-tetradecenoic acid, palmitoleic acid, 6-octadecenoic acid, oleic acid, 9-octadecenoic acid, 11-octadecenoic acid, 9-eicosenoic acid, cis-11-eicosenoic acid, cetoleic acid, 13-docosenoic acid, 15-tetracosenoic acid, 17-hexacosenoic acid, 6,9,12,15-hexadecatetraenoic acid, linoleic acid, linolenic acid, α-eleostearic acid, β-eleostearic acid, punicic acid, 6,9,12,15-octadecatetraenoic acid, parinaric acid, 5,8, 11,14-eicosatetraenoic acid, 5,8,11,14,17-eicosapentaenoic acid, 7,10,13,16,19-docosapentaenoic acid, 4,7,10,13,16,19-docosahexaenoic acid, and the like.

Examples of suitable hydroxy fatty acids include α-hydroxylauric acid, α-hydroxymyristic acid, α-hydroxypalmitic acid, α-hydroxystearic acid, ω-hydroxylauric acid, α-hydroxyarachic acid, 9-hydroxy-12-octadecenoic acid, ricinoleic acid, α-hydroxybehenic acid, 9-hydroxy-trans-10, 12-octadecadienic acid, kamolenic acid, ipurolic acid, 9,10-dihydroxystearic acid, 12-hydroxystearic acid and the like.

Examples of suitable polycarboxylic acids include oxalic acid, malonic acid, succinic acid, glutaric acid, adipic acid, pimelic acid, suberic acid, azelaic acid, sebacic acid, D,L-malic acid, and the like.

In some embodiments, each fatty acid is independently selected from Propionic acid, Butyric acid, Valeric acid, Caproic acid, Enanthic acid, Caprylic acid, Pelargonic acid, Capric acid, Undecylic acid, Lauric acid, Tridecylic acid, Myristic acid, Pentadecylic acid, Palmitic acid, Margaric acid, Stearic acid, Nonadecylic acid, arachidic acid, Heneicosylic acid, Behenic acid, Tricosylic acid, Lignoceric acid, Pentacosylic acid, Cerotic acid, Heptacosylic acid, Montanic acid, Nonacosylic acid, Melissic acid, Henatriacontylic acid, Lacceroic acid, Psyllic acid, geddic acid, ceroplastic acid, hexatriacontylic acid, heptatriacontanoic acid, or octatriacontanoic acid.

In some embodiments, each fatty acid is independently selected from α-linolenic acid, stearidonic acid, eicosapentaenoic acid, docosahexaenoic acid, linoleic acid, gamma-linoleic acid, dihomo-gamma-linoleic acid, arachidonic acid, docosatetraenoic acid, palmitoleic acid, vaccenic acid, paullinic acid, oleic acid, elaidic acid, gondoic acid, eurcic acid, nervonic acid, mead acid, adrenic acid, bosseopentaenoic acid, ozubondo acid, sardine acid, herring acid, docosahexaenoic acid, or tetracosanolpentaenoic acid, or another monounsaturated or polyunsaturated fatty acid.

In some embodiments, one or both of the fatty acids is an essential fatty acid. In view of the beneficial health effects of certain essential fatty acids, the therapeutic benefits of disclosed lipid prodrugs may be increased by including such fatty acids in the lipid prodrug. In some embodiments, the essential fatty acid is an n-6 or n-3 essential fatty acid selected from the group consisting of linolenic acid, gamma-linolenic acid, dihomo-gamma-linolenic acid, arachidonic acid, adrenic acid, docosapentaenoic n-6 acid, alpha-linolenic acid, stearidonic acid, the 20:4n-3 acid, eicosapentaenoic acid, docosapentaenoic n-3, or docosahexaenoic acid.

In some embodiments, each fatty acid is independently selected from all-cis-7,10,13-hexadecatrienoic acid, α-linolenic acid, stearidonic acid, eicosatrienoic acid, eicosatetraenoic acid, eicosapentaenoic acid (EPA), docosapentaenoic acid, docosahexaenoic acid (DHA), tetracosapentaenoic acid, tetracosahexaenoic acid, or lipoic acid. In other embodiments, the fatty acid is selected from eicosapentaenoic acid, docosahexaenoic acid, or lipoic acid. Other examples of fatty acids include all-cis-7,10,13-hexadecatrienoic acid, α-linolenic acid (ALA or all-cis-9,12,15-octadecatrienoic acid), stearidonic acid (STD or all-cis-6,9,12,15-octadecatetraenoic acid), eicosatrienoic acid (ETE or all-cis-11,14,17-eicosatrienoic acid), eicosatetraenoic acid (ETA or all-cis-8,11,14,17-eicosatetraenoic acid), eicosapentaenoic acid (EPA), docosapentaenoic acid (DPA, clupanodonic acid or all-cis-7,10,13,16,19-docosapentaenoic acid), docosahexaenoic acid (DHA or all-cis-4,7,10,13,16,19-docosahexaenoic acid), tetracosapentaenoic acid (all-cis-9,12,15,18,21-docosahexaenoic acid), or tetracosahexaenoic acid (nisinic acid or all-cis-6,9,12,15,18,21-tetracosenoic acid). In some embodiments, the fatty acid is a medium-chain fatty acid such as lipoic acid.

Fatty acid chains differ greatly in the length of their chains and may be categorized aaccording to chain length, e.g. as short to very long.

Short-chain fatty acids (SCFA) are fatty acids with chains of about five or less carbons (e.g. butyric acid). In some embodiments, each of the fatty acids is independently a SCFA. In some embodiments, one of the fatty acids is independently a SCFA.

Medium-chain fatty acids (MCFA) include fatty acids with chains of about 6-12 carbons, which can form medium-chain triglycerides. In some embodiments, each of the fatty acids is independently a MCFA. In some embodiments, one of the fatty acids is independently a MCFA.

Long-chain fatty acids (LCFA) include fatty acids with chains of 13-21 carbons. In some embodiments, each of the fatty acids is independently a LCFA. In some embodiments, one of the fatty acids is independently a LCFA.

Very long chain fatty acids (VLCFA) include fatty acids with chains of 22 or more carbons, such as 22-60, 22-50, or 22-40 carbons. In some embodiments, each of the fatty acids is independently a VLCFA. In some embodiments, one of the fatty acids is independently a VLCFA.

In some embodiments, one of the fatty acids is independently a MCFA and one is independently a LCFA.

Use of Click Chemistry to Attach Therapeutic Agent to the Lymphatic Drug-Release Moiety In some embodiments, the therapeutic agent is covalently attached to the lymphatic drug-release moiety (i.e., the remaining portion of the lipid prodrug besides the therapeutic agent) by the use of "click" chemistry. The term "click-ready group" refers to a chemical moiety capable of undergoing a click reaction, such as an azide or alkyne.

Click reactions tend to involve high-energy ("spring-loaded") reagents with well-defined reaction coordinates that give rise to selective bond-forming events of wide scope. Examples include nucleophilic trapping of strained-ring electrophiles (epoxide, aziridines, aziridinium ions, episulfonium ions), certain carbonyl reactivity (e.g., the reaction between aldehydes and hydrazines or hydroxylamines), and several cycloaddition reactions. The azide-alkyne 1,3-dipolar cycloaddition and the Diels-Alder cycloaddition are two such reactions.

Such click reactions (i.e., dipolar cycloadditions) are associated with a high activation energy and therefore require heat or a catalyst. Indeed, use of a copper catalyst is routinely employed in click reactions. However, in certain instances where click chemistry is particularly useful (e.g., in bioconjugation reactions), the presence of copper can be detrimental (See Wolbers, F. et al.; Electrophoresis 2006, 27, 5073). Accordingly, methods of performing dipolar cycloaddition reactions were developed without the use of metal catalysis. Such "metal free" click reactions utilize activated moieties in order to facilitate cycloaddition. Therefore, the present invention provides click-ready groups suitable for metal-free click chemistry.

Certain metal-free click moieties are known in the literature. Examples include 4-dibenzocyclooctynol (DIBO)

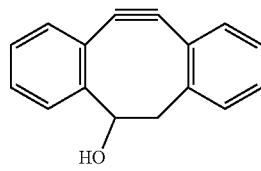

(from Ning et al; Angew Chem Int Ed, 2008, 47, 2253); gem-difluorinated cyclooctynes (DIFO or DFO)

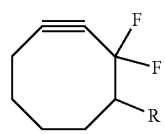

(from Codelli, et al.; *J. Am. Chem. Soc.* 2008, 130, 11486-11493.); biarylazacyclooctynone (BARAC)

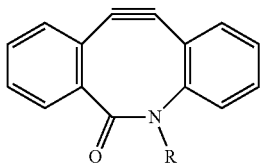

(from Jewett et al.; *J. Am. Chem. Soc.* 2010, 132, 3688.); or bicyclononyne (BCN) (From Dommerholt, et al.; *Angew Chem Int Ed,* 2010, 49, 9422-9425).

As used herein, the phrase "a moiety suitable for metal-free click chemistry" refers to a functional group capable of dipolar cycloaddition without use of a metal catalyst. Such moieties include an activated alkyne (such as a strained cyclooctyne), an oxime (such as a nitrile oxide precursor), or oxanorbornadiene, for coupling to an azide to form a cycloaddition product (e.g., triazole or isoxazole).

Therapeutic Agents and Exemplary Associated Diseases

In accordance with the present invention, a variety of therapeutic agents may be covalently conjugated to the lymphatic system-directing lipids, e.g. triglyceride scaffolds, described herein. In some embodiments, by conjugating a therapeutic agent to a lymphatic system-directing lipid, the present invention enhances desirable properties of the therapeutic agent such as improving oral bioavailability, minimizing destruction of the agent in the gut, avoiding liver first-pass effect, improving therapeutic agent delivery to a target tissue, or increasing the solubility and stability of the therapeutic agents, including the solubility and stability of the agents in vivo.

The present invention provides a method of treating a disease, disorder, or condition in a patient in need thereof comprising administering to said patient a disclosed lipid prodrug. In some embodiments, a disclosed lipid prodrug is useful in treating a disease, disorder, or condition for which the parent therapeutic agent is known to be used. Furthermore, because of the improved delivery and other properties of the disclosed lipid prodrugs, in some embodiments, a disclosed lipid prodrug is useful also for treating or preventing a disease, disorder, or condition for which the parent therapeutic agent is not suitable because of insufficient lymphatic transport, undesired metabolism, off-target toxicity, or the like.

In one aspect, the present invention provides a lipid prodrug of an immunomodulatory therapeutic agent.

In some embodiments, the present invention provides a method of treating an autoimmune disease, disorder, or condition in a patient in need thereof comprising administering to the patient a disclosed lipid prodrug. In some embodiments, the autoimmune disease, disorder, or condition is selected from Behçet's disease, pemphigus vulgaris, refractory incomplete systemic lupus erythematosus, immunoglobulin A nephropathy, small vessel vasculitis, or psoriasis.

In some embodiments, the present invention provides a method of preventing organ transplant rejection in a patient in need thereof, comprising administering a disclosed lipid prodrug to a patient in need thereof.

In some embodiments, a disclosed lipid prodrug modulates the immune system of a patient after administration by increased exposure of the active agent to the lymphatic system of the patient. In some embodiments, a disclosed lipid prodrug is taken up selectively into the lymphatic system of the patient after oral administration. In some embodiments, once in the lymphatic system, the lipid prodrug interacts with immune cells in the lymphatic system. In some embodiments, a disclosed lipid prodrug is delivered selectively to B or T lymphocytes. In some embodiments, a disclosed lipid prodrug modulates the activity of B or T lymphocytes. In some embodiments, a disclosed lipid prodrug modulates the activity of one or more of B cells, dendritic cells, granulocytes, innate lymphoid cells (ILCs), megakaryocytes, monocytes/macrophages, myeloid-derived suppressor cells (MDSC), natural killer (NK) cells, platelets, red blood cells (RBCs), T cells, or thymocytes. In some embodiments, a disclosed lipid prodrug exhibits increased delivery at a given dose or more selective delivery at a given dose to B or T lymphocytes as compared with a corresponding dose of a non-lipid prodrug form of the active agent. In some embodiments, a given dose of a disclosed lipid prodrug more effectively modulates the activity of one or more of B cells, dendritic cells, granulocytes, innate lymphoid cells (ILCs), megakaryocytes, monocytes/macrophages, myeloid-derived suppressor cells (MDSC), natural killer (NK) cells, platelets, red blood cells (RBCs), T cells, or thymocytes, as compared with a corresponding dose of a non-lipid prodrug form of the parent therapeutic agent.

In some embodiments, the present invention provides a method of treating a disease, disorder, or condition in a patient in need thereof, comprising administering to the patient a disclosed lipid prodrug, or a pharmaceutically acceptable salt thereof, wherein the disease, disorder, or condition is selected from Inflammatory disease, Abdominal cavity inflammation, Peritonitis, Mesenteritis, Perihepatitis, Salpingoperitonitis, Autoinflammatory disease, Cryopyrin associated periodic syndrome, CINCA syndrome, Familial cold autoinflammatory syndrome, Muckle Wells syndrome, Cardiovascular inflammation, Carditis, Endocarditis, Bacterial endocarditis, Infectious endocarditis, Non infectious endocarditis, Thromboendocarditis, Pericarditis, Chyloperi-carditis, Dressler syndrome, Pleuropericarditis, Vasculitis, Arteritis, Aortitis, Takayasus arteritis, Endarteritis, HIV associated arteritis, Kawasaki disease, Periarteritis, Polyarteritis nodosa, Temporal arteritis, Extracranial temporal arteritis, Intracranial temporal arteritis, Churg-Strauss syndrome, Cutaneous vasculitis, Perivasculitis, Phlebitis, Lymphangiophlebitis, Thrombophlebitis, Mondor disease, Thromboangiitis, Thromboangiitis obliterans, Thrombophlebitis, Mondor disease, Dermatitis, Acrodermatitis, Angiodermatitis, Drug eruption, Erythema multiforme, Serum sickness, Stevens Johnson syndrome, Toxic epidermal necrolysis, Intertrigo, Skin allergy, Atopic dermatitis, Contact dermatitis, Eczema, Fibrosis, Cicatrix, Tissue adhesions, Pulmonary fibrosis, Idiopathic pulmonary fibrosis, Renal fibrosis, Gastrointestinal inflammation, Anusitis, Biliary tract inflammation, Hepatocholangitis, Cholecystitis, Esophagitis, Eosinophilic esophagitis, Gastritis, Gastroduo-denitis, Gastroenteritis, Hypertrophic gastritis, Hepatitis, Enterohepatitis, Hepatitis virus infection, Hepatitis A virus infection, Hepatitis B virus infection, Hepatitis C virus infection, Hepatitis D virus infection, Hepatitis E virus infection, Hepatitis F virus infection, Hepatitis G virus infection, Hepatocholangitis, Non-viral hepatitis, Alcoholic hepatitis, Autoimmune hepatitis, Perihepatitis, Steatohepatitis, Non-alcoholic steatohepatitis, Inflammatory bowel disease, Colitis, Diverticulitis, Meckel's diverticulitis, Enterocolitis, Acute enterocolitis, Necrotizing enterocolitis, Ileocecitis, Pseudomembranous colitis, Sigmoiditis, Rectosigmoiditis, Ulcerative colitis, Crohns disease, Enteritis, Enterocolitis, Acute enterocolitis, Necrotizing enterocolitis, Enterohepatitis, Hemorrhagic enteritis, Ileitis, Ileocecitis, Pouchitis, Jejunitis, Mucositis, Pancreatitis, Balser necrosis, Necrotizing acute pancreatitis, Peritonitis, Mesenteritis, Perihepatitis, Salpingoperitonitis, Proctitis, Rectosigmoiditis, Ulcerative proctitis, Genitourinary tract inflammation, Genital tract inflammation, Female genital tract inflammation, Endometriosis, Parametritis, Pelvic inflammatory disease, Salpingitis, Vaginitis, Atrophic vaginitis, Bartholinitis, Vulvovaginitis, Vulvitis, Vulvovaginitis, Male genital tract inflammation, Balanitis, Epididymitis, Epididymo-orchitis, Orchitis, Epididymo-orchitis, Periorchitis, Prostatitis, Urinary tract inflammation, Nephritis, Alport syndrome, Glomerulonephritis, Focal segmental glomerulosclerosis, IgA nephropathy, Membranoproliferative glomerulonephritis, Membranous glomerulonephritis, Wegener granulomatosis, Lupus nephritis, Pyelitis, Pyelocystitis, Pyelonephritis, Granulomatosis, Allergic granulomatosis, Sarcoidosis, Wegener granulomatosis, Mastitis, Mouth inflammation, Gingivitis, Pericoronitis, Pharyngitis, Rhinopharyngitis, Sialadenitis, Musculoskeletal system inflammation, Arthritis, Behcets disease, Chondrocalcinosis, Gout, Infectious arthritis, Osteoarthritis, Periarthritis, Psoriatic arthritis, Reiter syndrome, Rheumatoid arthritis, Adult onset Stills disease, Felty syndrome, Juvenile rheumatoid arthritis, Bursitis, Dactylitis, Myositis, Dermatomyositis, Inclusion body myositis, Hereditary inclusion body myositis, Sporadic inclusion body myositis, Polymyositis, Pyomyositis, Nervous system inflammation, Meningitis, Arachnoiditis, Aseptic meningitis, Infectious meningitis, Bacterial meningitis, *Neisseria meningitidis* meningitis, Fungal meningitis, *Cryptococcus neoformans* meningitis, Parasitic meningitis, Viral meningitis, Neoplastic meningitis, Pachymeningitis, Neuritis, Neuromyelitis optica, Poliovirus infection, Postpoliomyelitis syndrome, Ocular and orbital inflammation, Ocular inflammation, Chorioretinitis, Conjunctivitis, Allergic conjunctivitis, Blepharoconjunctivitis, Keratoconjunctivitis, Infectious keratoconjunctivitis, Ophthalmia neonatorum, Trachoma, Uveitis, Intermediate uveitis, Pars planitis, Orbital inflammatory disease, Idiopathic orbital inflammation, Respiratory tract inflammation, Lower respiratory tract inflammation, Bronchitis, Lung inflammation, Asthma, Asthma attack, Exercise induced asthma, Nocturnal asthma, Occupational asthma, Status asthmaticus, Pleurisy, Upper respiratory tract inflammation, Pharyngitis, Rhinopharyngitis, Rhinitis, Allergic rhinitis, Perennial allergic rhinitis, Seasonal allergic rhinitis, Rhinopharyngitis, Sinusitis, Acute sinusitis, Chronic sinusitis, Ethmoiditis, Kartagener syndrome, Pansinusitis, Serositis, Familial mediterranean fever, Systemic inflammatory response syndrome, Immune disorder, Allergy, Delayed hypersensitivity, Contact dermatitis, Hypersensitivity, Immediate hypersensitivity, Food hypersensitivity, Egg hypersensitivity, Milk hypersensitivity, Oral allergy syndrome, Peanut hypersensitivity, Wheat hypersensitivity, Fungal allergy, Immune complex disease, Arthus reaction, Immediate type hypersensitivity, Atopic dermatitis, Respiratory tract allergy, Allergic rhinitis, Perennial allergic rhinitis, Seasonal allergic rhinitis, Asthma, Asthma attack, Exercise induced asthma, Nocturnal asthma, Occupational asthma, Status asthmaticus, Skin allergy, Atopic dermatitis, Contact dermatitis, Eczema, Autoimmune disease, Antiphospholipid syndrome, Autoimmune hemolytic anemia, Cold agglutinin disease, Autoimmune hepatitis, Autoimmune nervous system disease, Autoimmune demyelinating nervous system disease, Stiff person syndrome, Lambert-Eaton syndrome, Behcets disease, Crohns disease, Cutaneous lupus erythematosus, Discoid lupus erythematosus, Evans syndrome, Goodpasture syndrome, Graves disease, Guillain Barre syndrome, Hashimotos disease, Henoch Schonlein purpura, Lupus nephritis, Multiple sclerosis, Myasthenia gravis, Paroxysmal nocturnal hemoglobinuria, Primary biliary cirrhosis, Psoriasis, Parapsoriasis, Psoriatic arthritis, Rheumatoid arthritis, Adult onset Stills disease, Felty syndrome, Juvenile rheumatoid arthritis, Sjoegrens syndrome, Systemic lupus erythematosus, Temporal arteritis, Extracranial temporal arteritis, Intracranial temporal arteritis, Ulcerative colitis, Vitiligo, Non segmental vitiligo, Segmental vitiligo, Wegener granulomatosis, Graft versus host disease, Transplant rejection, Bone marrow transplant rejection, Cell transplant rejection, Corneal transplant rejection, Heart transplant rejection, Kidney transplant rejection, Liver transplant rejection, Lung transplant rejection, Organ transplant rejection, Intestine transplantation, Large intestine transplantation, Small intestine transplantation, Pancreas transplant rejection, Islet cell transplant rejection, Skin transplant rejection, Tissue transplant rejection, Immune deficiency, Agammaglobulinemia, Brutons disease, Combined immunodeficiency, Acquired immune deficiency syndrome, AIDS related complex, Nezelof syndrome, Severe combined immunodeficiency syndrome, Adenosine deaminase deficiency, Common variable immunodeficiency, DiGeorge syndrome, Dysgammaglobulinemia, Immunoglobulin A deficiency, Immunoglobulin G deficiency, Phagocyte bactericidal disorder, Chediak Higashi syndrome, Chronic granulomatous disease, Job syndrome, Wiskott-Aldrich syndrome, Immunoadsorption, Lymphatic system disease, Adenoid disease, Adenoid hypertrophy, Adenoid tumor, Adenoiditis, Lymphadenopathy, Kawasaki disease, Lymphadenitis, Lymphangiophlebitis, Lymphangitis, Lymphatic system tumor, Adenoid tumor, Castleman's disease, Lymphangioma, Cystic hygroma, or Lymphangiomyoma.

In some embodiments, the autoimmune disease, disorder, or condition is selected from Behçet's disease, pemphigus vulgaris, refractory incomplete systemic lupus erythematosus, retroperitoneal fibrosis, idiopathic thrombocytopenic purpura (ITP), scleroderma (systemic sclerosis or SSc), pemphigus vulgaris, granulomatosis with polyangiitis, immunoglobulin A nephropathy, small vessel vasculitis, retroperitoneal fibrosis, and psoriasis.

In some embodiments, the present invention provides a method of treating or preventing organ transplant rejection, graft-versus-host disease, or implant rejection, comprising administering to a patient in need thereof an effective amount of a disclosed lipid prodrug. In some embodiments, the organ transplant is selected from a skin, liver, heart, kidney, pancreas, thymus, small intestine, large intestine, uterus, a vascularized composite allograft (VCA) such as face or hand, bone marrow, allogenic blood and marrow transplant (BMT), cornea, and lung transplant. In some embodiments, the organ transplant rejection is acute or chronic transplant rejection.

In some embodiments, the present invention provides a lipid prodrug for use in the treatment or prevention of a disease or disorder in which increased testosterone levels are beneficial, or a disease or disorder caused by a testosterone deficiency. Such diseases and disorders include, but are not limited to, hypogonadism, anemia due to bone marrow failure, anemia due to renal failure, chronic respiratory failure, chronic cardiac failure, steroid-dependent autoimmune disorders, AIDS wasting, hereditary angioedema or urticaria, terminal breast cancer, or menopause.

In some embodiments, the present invention provides a method of modulating an immune response, comprising administering to a patient in need thereof an effective amount of a disclosed lipid prodrug that comprises an immunomodulatory therapeutic agent. In some embodiments, the immune response includes one or more immune responses mediated by the lymphatic system, or mediated by immune cells in the lymphatic system. In some embodiments, the patient is suffering from a hyperproliferative disease, disorder, or condition such as cancer. In some embodiments, the patient is suffering from an autoimmune disease, disorder, or condition.

Various therapeutic agents are suitable for use in the present invention. Examples of suitable therapeutic agents include, but are not limited to, testosterone, mycophenolic acid (MPA), buprenorphine, oestrogens (estrogen), opiates such as morphine, tetrahydrocannabinol (THC), cannabidiol, metoprolol, raloxifene, alphaxolone, statins such as atorvastatin, pentazocine, propranolol, L-DOPA, lidocaine, chlorpromazine, sertraline, amitriptyline, nortriptyline, pentazocine, glyceryl trinitrate, oxprenolol, labetalol, salbutamol, epitiostanol, melphalan, lovastatin, non-steroidal anti-inflammatory medications (NSAIDS, such as aspirin, ibuprofen, and naproxen), COX-2 inhibitors (such as celecoxib), corticosteroid anti-inflammatory medications (such as prednisolone, prednisone, or dexamethasone), anti-malarial medications (such as hydroxychloroquine), nitrosoureas, methotrexate, dactinomycin, anthracyclines (such as daunorubicin), mitomycin C, bleomycin, mithramycin, drugs acting on immunophilins (such as cyclosporin, tacrolimus, sirolimus), sulfasalazine, leflunomide, mycophenolate, opioids, fingolimod, myriocin, chlorambucil, doxorubicin, nelarabine, cortisone, dexamethasone, prednisone, pralatrexate, vinblastine, bortezomib, nelarabine, daunorubicin hydrochloride, clofarabine, cytarabine, dasatinib, imatinibmesylate, ponatinib hydrochloride, vincristine sulfate, bendamustine hydrochloride, fludarabine phosphate, bosutinib, nilotinib, omacetaxine mepesuccinate, capecitabine, paclitaxel, gemcitabine, fulvestrant, tamoxifen, lapatinib, toremifene, ixabepilone, eribulin, albendazole, ivermectin, diethylcarbamazine, albendazole, doxycycline, closantel, maraviroc, enfuvirtide, deoxythymidine, zidovudine, stavudine, didanosine, zalcitabine, abacavir, lamivudine, emtricitabine, tenofovir, delavirdine, rilpivirine, raltegravir, elvitegravir, lopinavir, indinavir, nelfinavir, amprenavir, ritonavir, or acyclovir, or a pharmaceutically acceptable salt thereof.

In some embodiments, the therapeutic agent is an NSAID or pharmaceutically acceptable salt thereof. Exemplary NSAIDs fall into a number of categories, including: 1) salicylates and various derivatives thereof, including acetyl salicylic acid, salicylic acid, methyl salicylate, diflunisal, and salsalate; 2) the pyrazolone derivatives, including phenylbutazone, oxyphenbutazone, antipyrine, aminopyrine, dipyrone, and apazone; 3) the para-aminophenol derivatives, including acetaminophen (paracetamol), phenacetin and related compounds; 4) indomethacin, sulindac and related compounds; 5) the fenamates, including; mefenamic, meclofenamic, flufenamic, tolfenamic, and etofenamic acids, and related compounds; 6) the proprionic acid derivatives including ibuprofen, naproxen, fenoprofen, ketoprofen, flurbiprofen and related compounds; 7) the oxicam derivatives such as piroxicam and related compounds; 8) the phenylacetic acid derivatives such as diclofenac and related compounds; and 9) other NSAIDs such as tolmetin, etodolac and nabumetone.

In some embodiments, the NSAID is selected from acetyl salicylic acid, salicylic acid, methyl salicylate, diflunisal, salsalate, phenylbutazone, oxyphenbutazone, antipyrine, aminopyrine, dipyrone, apazone, acetaminophen, phenacetin, indomethacin, sulindac, mefenamic, meclofenamic, flufenamic, tolfenamic, etofenamic acid, ibuprofen, naproxen, fenoprofen, ketoprofen, flurbiprofen, prioxicam, diclofenac, tolmetin, etodolac, or nabumetone.

In some embodiments, the therapeutic agent is a 5-amino salicylate (5-ASA) compound, sulfasalazine, balsalazide, or olsalazine.

Examples of suitable imaging agents include, but are not limited to, fluorophores such as the Alexa Fluor series of optical imaging probes for fluorescence microscopy or where the fluorophore has emission spectra in the infra-red range, for in vivo imaging; gamma emitters that can be used for positron emission tomography (PET), such as fluorodeoxyglucose, or chelating agents in order to chelate magnetic resonance imaging probes such as gadolinium or iron.

In some embodiments, the therapeutic agent is selected from non-steroidal anti-inflammatory medications (NSAIDS, such as aspirin, ibuprofen, or naproxen), COX-2 inhibitors (such as celecoxib), corticosteroid anti-inflammatory medications (such as prednisolone, or dexamethasone), anti-malarial medications (such as hydroxychloroquine), cyclophosphamide, PPAR agonists (such as the fibrates), nitrosoureas, platinum, methotrexate, azathioprine, mercaptopurine, fluorouracil, dactinomycin, anthracyclines, mitomycin C, bleomycin, mithramycin, drugs acting on immunophilins (such as ciclosporin, tacrolimus, or sirolimus), sulfasalazine, leflunomide, mycophenolate, opioids, fingolimod, myriocin, chlorambucil, doxorubicin, nelarabine, cortisone, pralatrexate, vinblastine, bortezomib, thiotepa, nelarabine, daunorubicin hydrochloride, clofarabine, cytarabine, dasatinib, imatinibmesylate, ponatinib hydrochloride, vincristine sulfate, bendamustine hydrochloride, fludarabine phosphate, bosutinib, nilotinib, omacetaxine, mepesuccinate, anastrozole, capecitabine, letrozole, paclitaxel, gemcitabine, fulvestrant, tamoxifen, lapatinib, toremifene, ixabepilone, eribulin, albendazole, ivermectin, diethylcarbamazine, doxycycline, closantel, maraviroc, enfuvirtide, deoxythymidine, zidovudine, stavudine, didanosine, zalcitabine, abacavir, lamivudine, emtricitabine, tenofovir, nevirapine, delavirdine, efavirenz, rilpivirine, raltegravir, elvitegravir, lopinavir, indinavir, nelfinavir, amprenavir, ritonavir, acyclovir and immunosuppressants such as mycophenolic acid, cyclosporine, tacrolimus, or sirolimus.

In some embodiments, the therapeutic agent is selected from acetaminophen, buprenorphine, rivastigmine, allopregnanolone (for use in treating, e.g., post-partum depression, Niemann-Pick disease, or Status Epilecticus), brivarectam, tegretol, levetiracetam or brivaracetam or other anticonvulsant (for use in treating, e.g., epilepsy and/or as an anticonvulsant), fosphenytoin, propranolol, tenofivir, a small-molecule chemotherapeutic agent for treating lymphoma, an analgesic such as an NSAID, an oral contraceptive, a therapeutic agent for treating a parasitic disease, a mercaptopurine such as azathioprine or 6-mercaptopurine (for treating inflammatory bowel disease), a corticosteroid, silymarin, paclitaxel, oxaliplatin, docetaxel, gemcitabine, irinotecan, zoledronic acid or other bisphosphonate anticancer agent, cladribine, pralatrexate, romidepsin, bexarotene, bortezomib, bendamustine, chlormethine, nelarabine, belinostat, prednisolone, cyclophosphamide, guperimus, dexanabinol, mitoxantrone, verteporfin, methotrexate, fosbretabulin, pentostatin, or dexamethasone.

In one embodiment, the therapeutic agent is testosterone or a derivative or analogue thereof. Testosterone replacement therapy (TRT) is commonly used for patients with hypogonadism (a disorder characterised by abnormally low serum testosterone levels) to restore their serum testosterone levels to the normal range and thus relieve many of the symptoms of hypogonadism such as mood disturbance and sexual dysfunction.

In some embodiments, the therapeutic agent is a proteasome inhibitor such as bortezomib, carfilzomib, KZR-616, delanzomib, marizomib, ixazomib, LC-530110, TP-110, FV-214, FV-162, or the like.

In some embodiments, the therapeutic agent is a BTK inhibitor such as ibrutinib, ONO-WG-307, ML-319, ZYBT-1, X-022, spebrutinib, or the like.

In some embodiments, the therapeutic agent is a ROR-γt inhibitor or modulator. Exemplary ROR-γt inhibitors and modulators include LYC-55716, digoxin, ursolic acid, SR2211, ML 209, TMP778, TMP920, GSK805, ARN-6039, GNE-3500, MRL-299, JTE-151, VTP-43742, and compounds disclosed in WO2015116904, which is hereby incorporated by reference; see, e.g. Bioorganic & Medicinal Chemistry Letters, Volume 26, Issue 18, 15 Sep. 2016, Pages 4387-4393, hereby incorporated by reference.

In some embodiments, the therapeutic agent is selected from an immunomodulatory imide drug (IMiD) such as thalidomide, lenalidomide, pomalidomide, or apremilast.

In some embodiments, the therapeutic agent is selected from purine synthesis inhibitors (e.g. Azathioprine, Mycophenolic acid), pyrimidine synthesis inhibitors (Leflunomide, Teriflunomide), antifolate (Methotrexate), Macrolides/other IL-2 inhibitors, FKBP/Cyclophilin/Calcineurin (Tacrolimus, Ciclosporin, Pimecrolimus) Abetimus, or Gusperimus.

In some embodiments, the immunomodulatory therapeutic agent is selected from thalidomide, lenalidomide, pomalidomide, apremilast, azathioprine, mycophenolic acid, leflunomide, teriflunomide, methotrexate, a macrolide TL-2 inhibitor, tacrolimus, sirolimus (Rapamune®), everolimus (Certican™), CC-779, ABT578, temsirolimus, TAFA-93, vistusertib, ciclosporin, pimecrolimus, abetimus, or gusperimus.

In some embodiments, the therapeutic agent is one of those in Table 1, below; or a pharmaceutically acceptable salt thereof.

TABLE 1

Exemplary Therapeutic Agents and Associated Diseases and Disorders

| Abbreviated Drug Name | Drug Name | Indication | Mechanism Of Action |
| --- | --- | --- | --- |
| abacavir | abacavir | HIV-1 Infection, HIV-2 Infection | |
| Acetylcysteine | Acetylcysteine injection - | | Antioxidants, Free radical inhibitors |
| Acitretin | Acitretin | Psoriasis, Dermatitis, Cancer | Retinoic acid receptor agonists |
| acyclovir | acyclovir | Herpes Labialis (Oral Herpes), Genital Herpes, Herpes Simplex Virus (HSV) Infections, Varicella Zoster (HHV-3) Infections, Herpes Zoster (Shingles), Fever Blisters, Chicken Pox | |
| Adefovir | Adefovir | HIV infections, Cancer, Hepatitis B, Rheumatic disorders, Graft-versus-host disease | DNA-directed DNA polymerase inhibitors, Cell differentiation stimulants, Immunomodulators, Immunosuppressants |
| Adefovir dipivoxil | Adefovir dipivoxil | Hepatitis B, HIV infections, Rheumatic disorders | DNA-directed DNA polymerase inhibitors, Hepatitis B virus replication inhibitors, Nucleotide reverse transcriptase inhibitors |
| Alatrofloxacin | Alatrofloxacin | | |
| Albendazole | Albendazole | Helminthic Infestations, Cysticercosis (Taeniasis), Giardiasis, Nematodal (Round Worm) Infections, Tape Worm Infections, Ascariasis, Alveolar Echinococcosis (Alveolar Hydatid Disease), Ancylostomiasis (Hookworm Infections), Cystic Echinococcosis (Alveolar Hydatid Disease), Echinococcosis (Hydatid Disease), Neurocysticercosis, Strongyloidiasis, Trichuriasis | Tubulin inhibitors, Vascular endothelial growth factors inhibitors |
| albuterol sulfate | albuterol sulfate | Asthma, Bronchospasm, Obstructive Pulmonary Disease, Chronic Obstructive Pulmonary Disease (COPD), Chronic Bronchitis, Emphysema, Exercise-Induced Bronchoconstriction (EBI), Premature Labor (Tocolysis), Pulmonary Tuberculosis, Status Asthmaticus | Beta 2 Adrenergic Receptor (Beta 2 Adrenoreceptor or ADRB2) Agonist |
| Alendronic acid | Alendronic acid | Postmenopausal osteoporosis, Male osteoporosis, Fracture, Osteitis deformans, Osteoporosis, Corticosteroid-induced osteoporosis, Malignant hypercalcaemia, Bone resorption | Osteoclast inhibitors |

TABLE 1-continued

Exemplary Therapeutic Agents and Associated Diseases and Disorders

| Abbreviated Drug Name | Drug Name | Indication | Mechanism Of Action |
|---|---|---|---|
| Alitretinoin | Alitretinoin | | |
| Alitretinoin | Alitretinoin oral | Acute promyelocytic leukaemia, Multiple myeloma, Ovarian cancer, Psoriasis, Non-Hodgkin's lymphoma, Lung cancer, Preleukaemia, Renal cancer, Cancer, Retinal disorders, Prostate cancer, Kaposi's sarcoma, Head and neck cancer | Retinoic acid receptor agonists, Retinoid X receptor agonists, Protein synthesis inhibitors, Retinoic acid receptor antagonists |
| Alovudine | Alovudine | HIV infections | Nucleoside reverse transcriptase inhibitors |
| Ambrisentan | Ambrisentan | | |
| Amifloxacin | Amifloxacin | Gram-negative infections, Septic shock, Urinary tract infections | Type II DNA topoisomerase inhibitors |
| Amifostine | Amifostine | | |
| Aminolevulinic acid | Aminolevulinic acid | Actinic keratosis, Brain cancer, Warts, Barrett's oesophagus, Photodamage, Skin cancer, Acne vulgaris, Oesophageal cancer, Leucoplakia, Psoriasis | Photosensitisers |
| Aminopterin | Aminopterin | Leukaemia, Endometrial cancer | Antimetabolites, Tetrahydrofolate dehydrogenase inhibitors |
| Aminosalicylic acid | Aminosalicylic acid | | |
| Amiodarone | Amiodarone Cosolvent-free | | |
| Amisulpride | Amisulpride | | Dopamine D2 receptor antagonists, Dopamine D3 receptor antagonists |
| amitriptyline | amitriptyline | Anxiety Disorders, Depression | |
| amprenavir | amprenavir | HIV-1 Infection | |
| Anagrelide | Anagrelide | | |
| anastrozole | anastrozole | Breast Cancer, Metastatic Breast Cancer, Hormone Sensitive Breast Cancer | |
| Aphidicolin | Aphidicolin | Cancer, Herpesvirus infections | DNA-directed DNA polymerase inhibitors |
| Apomorphine | Apomorphine | | Dopamine D2 receptor agonists |
| apremilast | apremilast | Psoriatic Arthritis, Plaque Psoriasis (Psoriasis Vulgaris) | Phosphodiesterase 4 (PDE4 or EC 3.1.4.53) Inhibitor |
| Arbutamine | Arbutamine | | |
| Argatroban | Argatroban | | |
| aripiprazole | aripiprazole | | |
| aspirin | aspirin | Cardiovascular Disease, Angina (Angina Pectoris), Myocardial Infarction, Migraine, Pain, Post-Operative Pain, Osteoarthritis Pain, Dysmenorrhea, Stroke, Cerebral Infarction (Brain Infarction), Back Pain, Pharyngitis, Gouty Arthritis (Gout), Nasopharyngitis (Common Cold), Unstable Angina, Ankylosing Spondylitis (Bekhterev's Disease), Ischemic Cerebral Stroke, Ischemic Stroke, Ischemia, Bronchitis, Arthritis Pain, Cardiovascular Risk Factors, Cerebrovascular Disease, Chronic Stable Angina, Dental Pain, Infectious Fever, Joint Pain, Low Back Pain, Mild Pain, Moderate Pain, Musculoskeletal Pain, Neuralgia, Rheumatoid Arthritis Pain, Sciatic Pain, Stable Angina, Tension -Type Headache, Thromboembolism | |
| Atazanavir/ cobicistat | Atazanavir/ cobicistat | HIV-1 infections | Cytochrome P 450 enzyme system inhibitors, HIV protease inhibitors |

TABLE 1-continued

Exemplary Therapeutic Agents and Associated Diseases and Disorders

| Abbreviated Drug Name | Drug Name | Indication | Mechanism Of Action |
|---|---|---|---|
| Atorvastatin | Atorvastatin | Hyperlipoproteinaemia type IIa, Hypercholesterolaemia, Low HDL cholesterol, Hypertriglyceridaemia, Cardiovascular disorders, Heart failure, Hyperlipoproteinaemia type III, Alzheimer's disease, Neurological disorders | HMG-CoA reductase inhibitors |
| Atovaquone | Atovaquone | | |
| Avibactam/ceftazidime | Avibactam/ceftazidime | | |
| Azacitidine | Azacitidine | | Antimetabolites, DNA methylation inhibitors |
| azathioprine | azathioprine | Liver Transplantation, Heart Transplantation, Polymyositis, Idiopathic Thrombocytopenic Purpura (Immune Thrombocytopenic Purpura), Dermatomyositis, Ulcerative Colitis, Transplantation, Rheumatoid Arthritis, Crohn's Disease (Regional Enteritis), Systemic Lupus Erythematosus, Kidney Transplantation, Acquired (Autoimmune) Hemolytic Anemia, Arteritis, Autoimmune Hepatitis, Pemphigus Vulgaris | |
| Azithromycin | Azithromycin | antibiotic | Protein synthesis inhibitor |
| Aztreonam | Aztreonam | | |
| Baclofen | Baclofen | | |
| Balsalazide | Balsalazide disodium | | |
| Bedaquiline | Bedaquiline | | |
| Belinostat | Belinostat | | |
| bendamustine | bendamustine hydrochloride | Anaplastic Astrocytoma, Glioblastoma Multiforme (GBM), Non-Hodgkin Lymphoma, Diffuse Large B-Cell Lymphoma, High Grade Non-Hodgkin Lymphoma, High-Grade Glioma, Indolent Lymphoma, Intermidiate Non-Hodgkin Lymphoma, Mantle Cell Lymphoma, Refractory Multiple Myeloma, Relapsed Multiple Myeloma | |
| Benzoate and phenylacetate | Benzoate and phenylacetate | | |
| Betaine | Betaine | | |
| Bexarotene | Bexarotene oral | Cutaneous T cell lymphoma, Non-small cell lung cancer, Thyroid cancer | Peroxisome proliferator-activated receptor agonists, Protein synthesis inhibitors, Retinoid X receptor agonists |
| Biapenem | Biapenem | Bacterial infections | Cell wall inhibitors |
| Bicalutamide | Bicalutamide | Prostate cancer | Testosterone congener inhibitors |
| Bortezomib | Bortezomib | Mantle-cell lymphoma; Multiple myeloma | Apoptosis stimulants, Proteasome inhibitors, Immunomodulators |
| Bosentan | Bosentan | Skin ulcer, Pulmonary arterial hypertension, Diabetic foot ulcer, Pulmonary fibrosis, Heart failure, Malignant melanoma, Asthma, Ischaemic heart disorders, Transplant rejection, Inflammatory bowel diseases, Kidney disorders, Myocardial infarction, Reperfusion injury | Endothelin A receptor antagonists, Endothelin B receptor antagonists |
| bosutinib | Bosutinib | Bile Duct Cancer (Cholangiocarcinoma), Colorectal Cancer, Polycystic Kidney Disease, Acute Lymphocytic Leukemia (ALL, Acute Lymphoblastic Leukemia), Chronic Myelocytic Leukemia (CML, Chronic Myeloid Leukemia), Pancreatic Cancer, Metastatic Breast Cancer, Recurrent Glioblastoma Multiforme (GBM) | |

TABLE 1-continued

Exemplary Therapeutic Agents and Associated Diseases and Disorders

| Abbreviated Drug Name | Drug Name | Indication | Mechanism Of Action |
|---|---|---|---|
| Bromfenac | Bromfenac | Ocular inflammation, Ocular pain, Age-related macular degeneration, Postoperative pain, Osteoarthritis, Dry eyes, Dysmenorrhoea | Cyclooxygenase inhibitors |
| Bropirimine | Bropirimine | Bladder cancer, Lymphoma, Herpes simplex virus infections | Interferon alpha stimulants |
| Broxuridine | Broxuridine | Breast cancer, Brain cancer | Antimetabolites, DNA modulators |
| Buprenorphine | Buprenorphine transdermal | Neuropathic Pain, Pain, Cancer Pain, Chronic Pain, Post-Operative Pain, Osteoarthritis Pain, Back Pain, Fibromyalgia, Diabetic Neuropathic Pain, Low Back Pain, Moderate Pain, Musculoskeletal Pain, Rheumatoid Arthritis Pain, Opium addiction | Nociceptin receptor agonists, Opioid delta receptor antagonists, Opioid kappa receptor antagonists, Opioid mu receptor agonists |
| Bupropion | Bupropion | Seasonal affective disorder, Major depressive disorder, Smoking withdrawal, Obesity, Social phobia, Post-traumatic stress disorders | Adrenergic receptor antagonists, Dopamine uptake inhibitors |
| Cabazitaxel | Cabazitaxel | | |
| Cabozantinib | Cabozantinib | | |
| Calcitonin | Calcitonin human for injection | | |
| Calcium levofolinate | Calcium levofolinate | | |
| Cangrelor | Cangrelor | | |
| capecitabine | capecitabine | Breast Cancer, Esophageal Cancer, Colorectal Cancer, Gastric Cancer, Metastatic Breast Cancer, Colon Cancer, Metastatic Colorectal Cancer | |
| Capsaicin | Capsaicin dermal patch | | TRPV1 receptor agonists, Substance P inhibitors |
| Carfilzomib | Carfilzomib | Refractory Multiple Myeloma, Relapsed Multiple Myeloma | Proteasome inhibitors |
| Carvedilol | Carvedilol | Hypertension, Heart failure, Angina pectoris, Atrial fibrillation, Myocardial infarction, Post-traumatic stress disorders, Reperfusion injury, Arrhythmias, Ischaemic heart disorders | Alpha 1 adrenergic receptor antagonists, Beta-adrenergic receptor antagonists, Calcium channel antagonists, Antioxidants |
| Cefepime | Cefepime | | |
| Ceftaroline fosamil | Ceftaroline fosamil | | |
| Ceftazidime | Ceftazidime | | Cell wall inhibitors |
| Ceftibuten | Ceftibuten | Otorhinolaryngological infections, Bacterial infections, Respiratory tract infections | Cell wall inhibitors |
| Ceftolozane/ tazobactam | Ceftolozane/ tazobactam | | |
| celecoxib | celecoxib | Acute Pain, Post-Operative Pain, Osteoarthritis Pain, Juvenile Rheumatoid Arthritis, Back Pain, Ankylosing Spondylitis (Bekhterev's Disease), Dental Pain, Familial Adenomatous Polyposis, Joint Pain, Low Back Pain, Musculoskeletal Pain, Primary Dysmenorrhea, Rheumatoid Arthritis Pain, Tenosynovitis | |
| Celgosivir | Celgosivir | Dengue, HIV infections, Hepatitis C | Alpha-glucosidase inhibitors |
| Ceramide | Ceramide trihexosidase/ alpha-galactosidase A | | |
| ceritinib | ceritinib | | |
| chlorambucil | chlorambucil | Breast Cancer, Ovarian Cancer, Follicular Lymphoma, Waldenstrom Macroglobulinemia, Lymphoma, Non-Hodgkin Lymphoma, Chronic Lymphocytic Leukemia (CLL), Hodgkin Lymphoma, Indolent Lymphoma, | |

TABLE 1-continued

Exemplary Therapeutic Agents and Associated Diseases and Disorders

| Abbreviated Drug Name | Drug Name | Indication | Mechanism Of Action |
|---|---|---|---|
| cholic acid | cholic acid | Mantle Cell Lymphoma, Metastatic Ovarian Cancer, Pediatric Cancer | |
| ciclosporin | ciclosporin | Keratoconjunctivitis sicca (Dry Eye), Corneal Graft Rejection, Vernal Keratoconjunctivitis, Breast Cancer, Lung Cancer, Uveitis, Liver Transplantation, Heart Transplantation, Bone Marrow Transplantation, Lung Transplantation, Psoriasis, Transplantation, Rheumatoid Arthritis, Graft Versus Host Disease (GVHD), Kidney Transplantation, Atopic Dermatitis, Intermediate Uveitis, Posterior Uveitis | |
| Cidofovir | Cidofovir | | |
| Cinacalcet | Cinacalcet | | |
| Ciprofloxacin | Ciprofloxacin | Anthrax, Nosocomial pneumonia, Respiratory tract infections, Intestinal infections, Acute sinusitis, Typhoid, Intra-abdominal infections, Urinary tract infections, Skin and soft tissue infections, Gonorrhoea | DNA gyrase inhibitors, DNA topoisomerase inhibitors |
| Cladribine | Cladribine | | |
| Clazosentan | Clazosentan | | Endothelin A receptor antagonists |
| Clevidipine | Clevidipine | | |
| Clofarabine | Clofarabine | Acute lymphoblastic leukaemia, Histiocytosis, Haematological malignancies, Acute myeloid leukaemia, Myelodysplastic syndromes, Chronic lymphocytic leukaemia, Non-Hodgkin's lymphoma, Psoriasis, Solid tumours, B cell lymphoma | Apoptosis stimulants, DNA synthesis inhibitors |
| Clofazimine | Clofazimine | | |
| closantel | closantel | | |
| Colchicine | Colchicine | | |
| Colfosceril | Colfosceril palmitate, cetyl alcohol, tyloxapol | | |
| Conivaptan | Conivaptan | | |
| cortisone | cortisone | Arthritis, Osteoarthritis, Asthma, Seborrhea, Proteinuria, Juvenile Rheumatoid Arthritis, Retinitis Pigmentosa (Retinitis), Serum Sickness, Polymyositis, Tuberculous Meningitis, Keratitis, Ankylosing Spondylitis (Bekhterev's Disease), Idiopathic Thrombocytopenic Purpura (Immune Thrombocytopenic Purpura), Psoriatic Arthritis, Humoral Hypercalcemia of Malignancy, Psoriasis, Ulcerative Colitis, Rheumatoid Arthritis, Crohn's Disease (Regional Enteritis), Systemic Lupus Erythematosus, Lymphoma, Acute Lymphocytic Leukemia (ALL, Acute Lymphoblastic Leukemia), Allergic Conjunctivitis, Leukemias, Dermatitis, Eczema, Thrombocytopenia, Acquired (Autoimmune) Hemolytic Anemia, Acute and Sub-Acute Bursitis, Acute Nonspecific Tenosynovitis, Acute Rheumatic Heart Disease, Allergic Corneal Marginal Ulcers, Anterior Segment Inflammation, Aspiration Pneumonitis, Atopic Dermatitis, Bacterial Infections, Berylliosis (Chronic Beryllium Disease), Bullous Pemphigoid, Chorioretinitis, Choroiditis, Congenital Adrenal Hyperplasia (Adrenogenital Syndrome), Congenital Hypoplastic | |

TABLE 1-continued

Exemplary Therapeutic Agents and Associated Diseases and Disorders

| Abbreviated Drug Name | Drug Name | Indication | Mechanism Of Action |
|---|---|---|---|
| | | Anemia, Contact Dermatitis, Dermatitis Herpetiformis (Duhring's Disease), Diffuse Posterior Uveitis, Drug Hypersensitivity Reactions, Edema, Epicondylitis, Erythema Multiforme, Erythroblastopenia (RBC Anemia), Herpes Zoster Ophthalmicus, Iritis, Juvenile Arthritis, Loeffler Syndrome (Pulmonary Eosinophilia), Mycosis Fungoides, Nonsuppurative Thyroiditis, Optic Neuritis, Pemphigus, Perennial Allergic Rhinitis, Pulmonary Tuberculosis, Seasonal Allergic Rhinitis, Sympathetic Ophthalmia, Symptomatic Sarcoidosis, Trichomonas Vaginitis | |
| Crizotinib | Crizotinib | | |
| Cromolyn | Cromolyn sodium | | |
| cyclophosphamide | cyclophosphamide | Breast Cancer, Lung Cancer, Ovarian Cancer, Burkitt Lymphoma, Testicular Cancer, Throat Cancer, Retinoblastoma, Follicular Lymphoma, Rhabdomyosarcoma, Hematopoietic Stem Cell Transplantation, Vasculitis, Polymyositis, Lupus Erythematosus, Rheumatoid Arthritis, Systemic Lupus Erythematosus, Cervical Cancer, Lymphoma, Melanoma, Multiple Myeloma (Kahler Disease), Non-Hodgkin Lymphoma, Acute Lymphocytic Leukemia (ALL, Acute Lymphoblastic Leukemia), Acute Myelocytic Leukemia (AML, Acute Myeloblastic Leukemia), Chronic Lymphocytic Leukemia (CLL), Chronic Myelocytic Leukemia (CML, Chronic Myeloid Leukemia), Hodgkin Lymphoma, Liver Cancer, Pancreatic Cancer, Gastric Cancer, Bladder Cancer, Leukemias, Systemic Sclerosis (Scleroderma), Metastatic Breast Cancer, Small-Cell Lung Cancer, Sarcomas, Solid Tumor, Polycythemia Vera, Endometrial Cancer, Acute Lymphoblastic Lymphoma, Adenocarcinoma, Bone Tumor, Choriocarcinoma (Gestational Trophoblastic Neoplasia), Colon Cancer, Hydatidiform Mole, Kidney Disease, Lymphoblastic Lymphoma, Malignant Neoplasms, Metastatic Melanoma, Mycosis Fungoides, Nephrotic Syndrome, Neuroblastoma, Pediatric Cancer, Pheochromocytoma, Wegener Polyangiitis | |
| Cysteamine | Cysteamine | | |
| cytarabine | cytarabine | Leptomeningeal Disease (Neoplastic Meningitis, Leptomeningeal Carcinomatosis), Non-Hodgkin Lymphoma, Acute Lymphocytic Leukemia (ALL, Acute Lymphoblastic Leukemia), Acute Myelocytic Leukemia (AML, Acute Myeloblastic Leukemia), Chronic Myelocytic Leukemia (CML, Chronic Myeloid Leukemia), Meningeal Leukemia, Pediatric Cancer, Refractory Leukemia | |
| Dabrafenib | Dabrafenib | | |
| dactinomycin | dactinomycin | Ewing Sarcoma, Testicular Cancer, Uterine Cancer, Rhabdomyosarcoma, Childhood Rhabdomyosarcoma, Melanoma, Solid Tumor, Endometrial Cancer, Choriocarcinoma (Gestational Trophoblastic Neoplasia), Gestational | |

TABLE 1-continued

Exemplary Therapeutic Agents and Associated Diseases and Disorders

| Abbreviated Drug Name | Drug Name | Indication | Mechanism Of Action |
|---|---|---|---|
| | | Trophoblastic Disease, Hydatidiform Mole, Kaposi Sarcoma, Locally Recurrent Or Locoregional Solid Malignancies, Metastatic Melanoma, Metastatic Nonseminomatous Testicular Cancer, Metastatic Renal Cell Carcinoma, Pediatric Cancer, Wilms' Tumor (Nephroblastoma) | |
| Dalbavancin | Dalbavancin | | |
| Dalfampridine | Dalfampridine | | |
| danazol | danazol | Endometriosis, Hereditary Angioedema (HAE) (C1 Esterase Inhibitor [C1-INH] Deficiency), Fibrocystic Breast Disease | Follicle Stimulating Hormone Receptor (Follitropin Receptor or FSHR) Antagonist; Lutropin Choriogonadotropic Hormone Receptor (Luteinizing Hormone Receptor or LHCGR) Antagonist |
| Dantrolene | Dantrolene low-volume | | |
| Daptomycin | Daptomycin intravenous | Bacteraemia, Bacterial endocarditis, Gram-positive infections, Skin and soft tissue infections, Staphylococcal infections, Osteomyelitis, Urinary tract infections, Community-acquired pneumonia, Burns, Gram-Positive Bacterial Infections, Sepsis, Methicillin-Resistant Staphylococcus aureus (MRSA) Infections, Bacteremia, Bacterial Endocarditis, Complicated Skin And Skin Structure Infections (cSSSI), Hospital Acquired Methicillin-Resistant Staphylococcus aureus (HA-MRSA) Infections, Skin And Soft Tissue Infections, Skin Infections, Surgical Wound Infections | Cell wall inhibitors |
| Darunavir | Darunavir | HIV-1 infections | HIV protease inhibitors |
| dasatinib | dasatinib | Bile Duct Cancer (Cholangiocarcinoma), Oligodendroglioma, Non-Small Cell Lung Cancer, Myelofibrosis, Gliosarcoma, Acute Myelocytic Leukemia (AML, Acute Myeloblastic Leukemia), Pancreatic Cancer, Myelodysplastic Syndrome, Systemic Sclerosis (Scleroderma), Metastatic Breast Cancer, Diffuse Large B-Cell Lymphoma, Polycythemia Vera, Hypereosinophilic Syndrome, Interstitial Lung Fibrosis, Metastatic Hormone Refractory (Castration Resistant, Androgen-Independent) Prostate Cancer, Myeloid Metaplasia, Recurrent Glioblastoma Multiforme (GBM), Refractory Multiple Myeloma, Relapsed Multiple Myeloma, Systemic Mastocytosis | |
| Daunorubicin | Daunorubicin citrate liposome injection | | |
| Decitabine | Decitabine | | |
| Deferiprone | Deferiprone | Iron overload, Pantothenate kinase-associated neurodegeneration, Parkinson's disease, HIV infections, Friedreich's ataxia, Kidney disorders | Chelating agents |
| Defibrotide | Defibrotide | | |
| delavirdine | delavirdine | HIV-1 Infection | |
| Deoxycholic acid | Deoxycholic acid | | Cell membrane modulators, Membrane lipid modulators |

TABLE 1-continued

Exemplary Therapeutic Agents and Associated Diseases and Disorders

| Abbreviated Drug Name | Drug Name | Indication | Mechanism Of Action |
|---|---|---|---|
| deoxythymidine | deoxythymidine | | |
| Desmopressin | Desmopressin acetate | | |
| Dexamethasone | Dexamethasone Intravitreal Implant | Bacterial Conjunctivitis, Uveitis, Keratitis, Blepharitis, Conjunctivitis, Allergic Conjunctivitis, Anterior Segment Inflammation, Anterior Uveitis, Blepharoconjunctivitis, Corneal Ulcers, Herpes Zoster Ophthalmicus, Iritis, Keratoconjunctivitis, Ocular Inflammation, Scleritis | |
| Dexmedetomidine | Dexmedetomidine | | |
| Dexrazoxane | Dexrazoxane | | |
| Dextran sulfate | Dextran sulfate | Ovarian cancer, Cancer metastases, HIV infections | Platelet-derived growth factor inhibitors |
| DHAC | DHAC | Mesothelioma, Prostate cancer, Cancer | RNA methylation inhibitors, RNA synthesis inhibitors |
| Dichlorphenamide | Dichlorphenamide | | |
| Diclofenac | Diclofenac transdermal second generation | | Cyclooxygenase inhibitors |
| Didanosine | Didanosine | HIV infections, Toxoplasmosis | Nucleoside reverse transcriptase inhibitors |
| Didox | Didox | Cancer, Psoriasis, Cytomegalovirus infections, HIV infections | Ribonucleoside triphosphate reductase inhibitors, Ribonucleotide reductase inhibitors |
| Difluprednate | Difluprednate | | |
| Docetaxel | Docetaxel | Breast Cancer, Lung Cancer, Ovarian Cancer, Prostate Cancer, Non-Small Cell Lung Cancer, Esophageal Cancer, Head And Neck Cancer, Gastric Cancer, Metastatic Breast Cancer, Endometrial Cancer, Adenocarcinoma Of The Gastroesophageal Junction, Adenocarcinoma, Head And Neck Cancer Squamous Cell Carcinoma, Hormone Refractory (Castration Resistant, Androgen-Independent) Prostate Cancer, Hormone-Sensitive Prostate Cancer, Metastatic Ovarian Cancer, Metastatic Prostate Cancer, Recurrent Head And Neck Cancer Squamous Cell Carcinoma | Tubulin Inhibitor |
| Dolasetron | Dolasetron | Nausea and vomiting, Psychotic disorders | Serotonin 3 receptor antagonists |
| Doripenem | Doripenem | | Cell wall inhibitors |
| Doxercalciferol | Doxercalciferol | | Calcitriol receptor agonists |
| Doxorubicin | Doxorubicin liposomal | Breast Cancer, Lung Cancer, Ovarian Cancer, Thyroid Cancer, Soft Tissue Sarcoma, Lymphoma, Acute Lymphocytic Leukemia (ALL, Acute Lymphoblastic Leukemia), Acute Myelocytic Leukemia (AML, Acute Myeloblastic Leukemia), Hodgkin Lymphoma, Gastric Cancer, Bladder Cancer, Metastatic Breast Cancer, Sarcomas, Kaposi Sarcoma, Neuroblastoma, Wilms' Tumor (Nephroblastoma) | DNA intercalators, Type II DNA topoisomerase inhibitors |
| doxycycline | doxycycline | Urinary Tract Infections, Malaria, Bacterial Conjunctivitis, Gonorrhea, Rocky Mountain Spotted Fever, Syphilis, Cholera, Upper Respiratory Tract Infections, Lower Respiratory Tract Infections, Acne Vulgaris, Actinomycosis, Anthrax, Bartonellosis, Brucellosis, Chancroid, Extraintestinal Amebiasis, Granuloma Inguinale, Listeriosis, Nongonococcal Urethritis, Plague, Q Fever, Tick-Borne | |

TABLE 1-continued

Exemplary Therapeutic Agents and Associated Diseases and Disorders

| Abbreviated Drug Name | Drug Name | Indication | Mechanism Of Action |
|---|---|---|---|
| droxidopa | droxidopa | Relapsing Fever, Typhus Fever, Uncomplicated Urethral, Endocervical, or Rectal Infections in Adults, Yaws | |
| Edatrexate | Edatrexate | Cancer, Rheumatoid arthritis | Tetrahydrofolate dehydrogenase inhibitors |
| Efavirenz | Efavirenz | HIV-1 infections | Non-nucleoside reverse transcriptase inhibitors |
| Eflapegrastim | Eflapegrastim | | Granulocyte colony stimulating factor stimulants |
| Eflornithine HCl | Eflornithine HCl | | |
| elvitegravir | elvitegravir | HIV-1 Infection | |
| emtricitabine | emtricitabine | HIV-1 Infection | |
| Enalapril maleate | Enalapril maleate (powder for oral solution) | | |
| Entacapone | Entacapone | Parkinson's disease, Restless legs syndrome | Catechol-O-methyltransferase inhibitors |
| Epacadostat | Epacadostat | Malignant melanoma, Ovarian cancer, Fallopian tube cancer, Peritoneal cancer, Solid tumours, Non-small cell lung cancer | Indoleamine-pyrrole 2,3-dioxygenase inhibitors |
| Epinephrine | Epinephrine injection | Asthma, Anaphylaxis, Type I Hypersensitivity, Anaphylactic Shock | Adrenergic receptor agonists |
| epitiostanol | epitiostanol | | |
| Epoprostenol | Epoprostenol intravenous | | |
| ergotamine | ergotamine | Migraine | 5-Hydroxytryptamine Receptor 1A (5 HT1A or G 21 or Serotonin Receptor 1A or HTR1A) Agonist; 5-Hydroxytryptamine Receptor 1B (5 HT1B or S12 or Serotonin 1D Beta Receptor or Serotonin Receptor 1B or HTR1B) Agonist; 5-Hydroxytryptamine Receptor 1D (5 HT1D or Serotonin 1D Alpha Receptor or Serotonin Receptor 1D or HTR1D) Agonist; Alpha 1 Adrenergic Receptor (ADRA1) Antagonist |
| Eribulin | Eribulin | Breast Cancer, Prostate Cancer, Non-Small Cell Lung Cancer, Soft Tissue Sarcoma, Lymphoma, Bladder Cancer, Metastatic Breast Cancer, Solid Tumor, Metastatic Hormone Refractory (Castration Resistant, Androgen-Independent) Prostate Cancer, Transitional Cell Cancer (Urothelial Cell Cancer), Ureter Cancer, Urethral Cancer | |
| Esomeprazole | Esomeprazole | Bleeding ulcer; Gastro-oesophageal reflux; Heartburn; Helicobacter infections; NSAID-induced ulcer; Peptic ulcer; Reflux oesophagitis; Zollinger-Ellison syndrome | Proton pump inhibitors |
| Esperamicin | Esperamicin-A1 | Cancer | DNA inhibitors |
| Estradiol | Estradiol transdermal | | Estrogen receptor agonists |
| estrogen | estrogen (ethinylestradiol + norethindrone) | Hormonal Contraception | Estrogen Receptor (ESR) Agonist; Progesterone Receptor (Nuclear Receptor Subfamily 3 |

TABLE 1-continued

Exemplary Therapeutic Agents and Associated Diseases and Disorders

| Abbreviated Drug Name | Drug Name | Indication | Mechanism Of Action |
|---|---|---|---|
| | | | Group C Member 3 or NR3C3 or PGR) Agonist |
| Ethanolamine oleate | Ethanolamine oleate | | |
| Ethinylestradiol/ norelgestromin | Ethinylestradiol/ norelgestromin transdermal | | Estrogen receptor agonists, Progesterone receptor agonists |
| ethiodized oil | ethiodized oil injection | | |
| etonogestrel | etonogestrel | Hormonal Contraception | Progesterone Receptor (Nuclear Receptor Subfamily 3 Group C Member 3 or NR3C3 or PGR) Agonist |
| everolimus | everolimus | | |
| Exisulind | Exisulind | Familial adenomatous polyposis, Non-small cell lung cancer, Prostate cancer, Breast cancer, Small cell lung cancer | Apoptosis stimulants, Cyclic GMP phosphodiesterase inhibitors, Angiogenesis inhibitors |
| Ezetimibe | Ezetimibe | Sitosterolaemia, Hypercholesterolaemia, Hyperlipoproteinaemia type II, Acute coronary syndromes | Cholesterol absorption inhibitors |
| Ezetimibe/ simvastatin | Ezetimibe/ simvastatin | Hypercholesterolaemia, Acute coronary syndromes, Hyperlipidaemia, Aortic valve stenosis | Cholesterol absorption inhibitors, HMG-CoA reductase inhibitors |
| Faldaprevir | Faldaprevir | Hepatitis C | Hepatitis C virus NS3 protein inhibitors |
| Fasudil | Fasudil | Cerebral vasospasm, Cerebral ischaemia, Pulmonary arterial hypertension, Intracranial thrombosis, Angina pectoris, Atherosclerosis, HIV-1 infections | Calcium channel antagonists, Protein kinase C inhibitors, Rho-associated kinase inhibitors |
| Felbamate | Felbamate | | |
| Fenoldopam | Fenoldopam | | |
| Fenretinide | Fenretinide | Breast cancer, Dry age-related macular degeneration, Glioma, Prostate cancer, Neuroblastoma, Rheumatoid arthritis, Basal cell cancer, Bladder cancer | Plasma retinol-binding protein inhibitors |
| Ferric carboxymaltose | Ferric carboxymaltose | | Iron replacements |
| Ferumoxytol | Ferumoxytol | | Iron replacements |
| Fialuridine | Fialuridine | Hepatitis B | DNA-directed DNA polymerase inhibitors |
| Finasteride | Finasteride | Benign prostatic hyperplasia, Alopecia, Prostate cancer | Cholestenone 5-alpha reductase inhibitors |
| Fingolimod | Fingolimod | Multiple sclerosis, Chronic inflammatory demyelinating polyradiculoneuropathy, Amyotrophic lateral sclerosis, Renal transplant rejection, Optic neuritis, Type 1 diabetes mellitus, Rheumatoid arthritis, Graft-versus-host disease, Myocarditis | Apoptosis stimulants, Immunosuppressants, Sphingosine 1 phosphate receptor modulators |
| Florbenazine F18 | Florbenazine F18 | | Vesicular monoamine transporter 2 inhibitors |
| Florbetaben F18 | Florbetaben F18 | | Positron-emission tomography enhancers |
| Florbetapir F 18 | Florbetapir F 18 | | Emission-computed tomography enhancers |
| Fludarabine | Fludarabine | Follicular Lymphoma, B-Cell Chronic Lymphocytic Leukemia, Refractory Chronic Lymphocytic Leukemia (CLL), Chronic Lymphocytic Leukemia (CLL), B-Cell Non-Hodgkin Lymphoma, Mantle Cell Lymphoma | DNA synthesis inhibitors, Immunosuppressants |

TABLE 1-continued

Exemplary Therapeutic Agents and Associated Diseases and Disorders

| Abbreviated Drug Name | Drug Name | Indication | Mechanism Of Action |
|---|---|---|---|
| Fluorine 18 AV 1451 | Fluorine 18 AV 1451 | | Positron-emission tomography enhancers |
| fluorouracil | fluorouracil | Breast Cancer, Ovarian Cancer, Prostate Cancer, Colorectal Cancer, Cervical Cancer, Liver Cancer, Head And Neck Cancer, Pancreatic Cancer, Gastric Cancer, Actinic (Solar) Keratosis, Endometrial Cancer, Basal Cell Carcinoma (Basal Cell Epithelioma), Paget Disease of Bone, Human Papillomavirus Infections, Kidney Cancer (Renal Cell Cancer), Squamous Cell Carcinoma, Esophageal Cancer, Colorectal Cancer, Cervical Cancer, Liver Cancer, Head And Neck Cancer, Pancreatic Cancer, Gastric Cancer, Adenocarcinoma, Colon Cancer, Gastrointestinal Tract Cancer, Genital Warts (Condylomata Acuminata), Keratoacanthoma, Pediatric Cancer, Rectal Cancer | |
| Fluoxymesterone | Fluoxymesterone | Breast cancer, Delayed puberty, Hypogonadism | Testosterone agonists |
| Flutafuranol F 18 | Flutafuranol F 18 | | Positron-emission tomography enhancers |
| Flutemetamol F 18 | Flutemetamol F 18 | | Positron-emission tomography enhancers |
| Fomepizole | Fomepizole | | |
| Fosaprepitant | Fosaprepitant | | |
| Fosphenytoin | Fosphenytoin | | Sodium channel antagonists |
| Fospropofol | Fospropofol | | Undefined mechanism |
| fulvestrant | fulvestrant | Breast Cancer, Metastatic Breast Cancer, Hormone Sensitive Breast Cancer | |
| Furosemide | Furosemide controlled release | | Loop diuretics |
| Gadobenic acid | Gadobenic acid | | Magnetic resonance imaging enhancers |
| Gadobutrol | Gadobutrol | | |
| Gadoversetamide | Gadoversetamide | | Undefined mechanism |
| Gadoxetate disodium | Gadoxetate disodium | | Magnetic resonance imaging enhancers |
| Ganciclovir | Ganciclovir intravitreal implant | | |
| gemcitabine | Gemcitabine | Breast Cancer, Lung Cancer, Ovarian Cancer, Bile Duct Cancer (Cholangiocarcinoma), Non-Small Cell Lung Cancer, Epithelial Ovarian Cancer, Cervical Cancer, Non-Hodgkin Lymphoma, Hodgkin Lymphoma, Pancreatic Cancer, Bladder Cancer, Metastatic Breast Cancer, Small-Cell Lung Cancer, Metastatic Pancreatic Cancer, Biliary Tumor, Metastatic Adenocarcinoma of The Pancreas, Metastatic Ovarian Cancer, Non-Small Cell Lung Carcinoma, Renal Cell Carcinoma, Transitional Cell Cancer (Urothelial Cell Cancer), Ureter Cancer, Urethral Cancer | DNA synthesis inhibitors |
| Glimepiride | Glimepiride | Type 2 diabetes mellitus | Potassium channel agonists |
| Glycerol | Glycerol phenylbutyrate | | |
| Gonadorelin acetate | Gonadorelin acetate | | |

TABLE 1-continued

Exemplary Therapeutic Agents and Associated Diseases and Disorders

| Abbreviated Drug Name | Drug Name | Indication | Mechanism Of Action |
|---|---|---|---|
| Granisetron | Granisetron transdermal | | Serotonin 3 receptor antagonists |
| Guadecitabine | Guadecitabine | | Antimetabolites, DNA cytosine 5 methyltransferase 1 inhibitors |
| Halofantrine | Halofantrine | | |
| Heparin | Heparin | Disseminated intravascular coagulation; Peripheral arterial occlusive disorders; Pulmonary embolism; Thromboembolism; Venous thrombosis | Thrombin inhibitors |
| hydroxychloroquine | hydroxychloroquine | Malaria, Rheumatoid Arthritis, Systemic Lupus Erythematosus | |
| Hydroxyurea | Hydroxyurea | | |
| Ibandronic acid | Ibandronic acid | | Dimethylallyltranstransferase inhibitors |
| ibrutinib | ibrutinib | | |
| ibuprofen | ibuprofen | Osteoarthritis Pain, Gastric Ulcers, Duodenal Ulcer, Ankylosing Spondylitis (Bekhterev's Disease), Musculoskeletal Inflammation, Myalgia, Rheumatoid Arthritis Pain | Cyclooxygenase inhibitors |
| Idarubicin | Idarubicin | | |
| idelalisib | idelalisib | | |
| Idoxuridine | Idoxuridine | Colorectal cancer, Glioma | DNA synthesis inhibitors |
| Ifosfamide | Ifosfamide | | |
| Iloprost | Iloprost solution for infusion | | |
| imatinib | imatinib mesylate | Soft Tissue Sarcoma, Acute Lymphocytic Leukemia (ALL, Acute Lymphoblastic Leukemia), Chronic Myelocytic Leukemia (CML, Chronic Myeloid Leukemia), Myelodysplastic Syndrome, Gastrointestinal Stromal Tumor (GIST), Myeloproliferative Disorders, Hypereosinophilic Syndrome, Pediatric Cancer, Systemic Mastocytosis | |
| Imiquimod | Imiquimod | Actinic keratosis, Basal cell cancer, Genital warts, Herpes simplex virus infections, Cervical intraepithelial neoplasia, Warts, Molluscum contagiosum, Tinea pedis, Vulvar intraepithelial neoplasia, Photodamage, Hepatitis C, Hepatitis B, HIV infections | Immunostimulants, Toll-like receptor 7 agonists |
| Indinavir | Indinavir | HIV-1 Infection, HIV-2 Infection | HIV protease inhibitors |
| Intoplicine | Intoplicine | Cancer, Solid tumours, Cancer metastases | DNA topoisomerase I inhibitors, Type II DNA topoisomerase inhibitors |
| Iobenguane I-123 | Iobenguane I-123 | | Enzyme inhibitors, Diagnostic imaging enhancers |
| Iobenguane sulfate 131 | Iobenguane sulfate I 131 | | |
| Ioxilan | Ioxilan | | Radiography enhancers |
| Irinotecan | Irinotecan | | |
| Iron isomaltoside 1000 | Iron isomaltoside 1000 | | Iron replacements |
| Iron sucrose | Iron sucrose | | Iron replacements |
| Isavuconazonium | Isavuconazonium | | |
| Ivacaftor | Lumacaftor/ ivacaftor | | |
| ivermectin | ivermectin | Scabies, Elephantiasis (Lymphatic Filariasis), Onchocerciasis (River Blindness), Strongyloidiasis, Rosecea, Head Lice | |

TABLE 1-continued

Exemplary Therapeutic Agents and Associated Diseases and Disorders

| Abbreviated Drug Name | Drug Name | Indication | Mechanism Of Action |
|---|---|---|---|
| ixabepilone | ixabepilone | Prostate Cancer, Non-Small Cell Lung Cancer, Esophageal Cancer, Gastric Cancer, Metastatic Breast Cancer, Metastatic Pancreatic Cancer, Solid Tumor, Endometrial Cancer, Adenocarcinoma | |
| Ixazomib citrate | Ixazomib citrate | | |
| labelalol | labelalol | Hypertension | |
| Lacosamide | Lacosamide | Male osteoporosis; Osteoporosis; Postmenopausal osteoporosis | |
| lamivudine | lamivudine | HIV/AIDS, HIV-1 Infection, Hepatitis B | |
| Lamotrigine | Lamotrigine | Bipolar disorders, Lennox-Gastaut syndrome, Partial epilepsies, Tonic-clonic epilepsy, Absence epilepsy, Epilepsy, Neuropathic pain, Diabetic neuropathies, Schizophrenia | Sodium channel antagonists |
| Lansoprazole | Lansoprazole | | |
| Lapatinib | Lapatinib | Breast Cancer, Non-Small Cell Lung Cancer, Esophageal Cancer, Gastric Cancer, Metastatic Pancreatic Cancer, Adenocarcinoma Of The Gastroesophageal Junction, Head And Neck Cancer Squamous Cell Carcinoma, Metastatic Colorectal Cancer, Non-Neoplastic Neuromas, Vestibular Schwannoma (Acoustic Neuroma) | Epidermal growth factor receptor antagonists, ERBB 2 receptor antagonists |
| Lazabemide | Lazabemide | Parkinson's disease, Alzheimer's disease, Smoking withdrawal | Monoamine oxidase B inhibitors, Antioxidants |
| L-dopa | L-dopa | Parkinson's Disease | Aromatic L Amino Acid Decarboxylase (AADC or Dopa Decarboxylase or DDC or EC 4.1.1.28) Inhibitor; Catechol O Methyltransferase (Epididymis Secretory Sperm Binding Protein Li 98n or COMT or EC 2.1.1.6) Inhibitor; Dopamine Receptor (DRD) Agonist |
| leflunomide | leflunomide | Rheumatoid Arthritis | |
| Lenalidomide | Lenalidomide | | |
| lenvatinib | lenvatinib | | |
| Letermovir | Letermovir | | Cytomegalovirus replication inhibitors |
| Leucovorin | Leucovorin | | |
| Leuprolide | Leuprolide acetate | | |
| Levetiracetam | Levetiracetam | | SV2A protein modulators |
| Levocarnitine | Levocarnitine | | |
| Levofloxacin | Levofloxacin | | DNA gyrase inhibitors, Type II DNA topoisomerase inhibitors |
| Levoleucovorin | Levoleucovorin | | |
| Levothyroxine | Levothyroxine sodium | Thyroid Cancer, Goiter, Hypothyroidism, Hashimoto Thyroiditis | Thyroid hormone receptor agonists |
| Lidocaine | Lidocaine transdermal patch | | Sodium channel antagonists |
| lidocane | lidocane | Postherpetic Neuralgia | Voltage Gated Sodium Channel (SCN) Blocker |
| Linezolid | Linezolid | | Protein 30S ribosomal subunit inhibitors |
| Lobaplatin | Lobaplatin | Small cell lung cancer, Chronic myeloid leukaemia, Breast cancer, Cancer | Alkylating agents |
| Lodoxamide | Lodoxamide tromethamine | | |

TABLE 1-continued

Exemplary Therapeutic Agents and Associated Diseases and Disorders

| Abbreviated Drug Name | Drug Name | Indication | Mechanism Of Action |
|---|---|---|---|
| Lomitapide | Lomitapide | Hyperlipoproteinaemia type IIa | Microsomal triglyceride transfer protein inhibitors |
| lopinavir | lopinavir | HIV-1 Infection | |
| lovastatin | lovastatin | Myocardial Infarction, Hypercholesterolemia, Atherosclerosis, Unstable Angina, Dyslipidemia, Hyperlipidemia, Coronary Disease, Familial Hypercholesterolemia (Type II Hyperlipoproteinemia) | |
| Lumacaftor | Lumacaftor/ivacaftor | | |
| macitentan | macitentan | | |
| maraviroc | maraviroc | HIV-1 Infection | |
| Mefloquine HCl | Mefloquine HCl | | |
| Meloxicam | Meloxicam injection | | Cyclo-oxygenase 2 inhibitors |
| melphalan | melphalan | Breast Cancer, Ovarian Cancer, Retinoblastoma, Soft Tissue Sarcoma, Bone Marrow Transplantation, Melanoma, Multiple Myeloma (Kahler Disease), Metastatic Breast Cancer, Polycythemia Vera, Adenocarcinoma, Metastatic Ovarian Cancer, Neuroblastoma | |
| mercaptopurine | mercaptopurine oral solution | Acute Lymphocytic Leukemia (ALL, Acute Lymphoblastic Leukemia), Acute Myelocytic Leukemia (AML, Acute Myeloblastic Leukemia), Chronic Myelocytic Leukemia (CML, Chronic Myeloid Leukemia), Leukemias, Pediatric Cancer | |
| Meropenem | Meropenem | Febrile neutropenia, Bacterial infections, Community-acquired pneumonia, Skin and soft tissue infections | Cell wall inhibitors |
| Mesna | Mesna | | Undefined mechanism |
| methotrexate | methotrexate | Psoriasis, Rheumatoid Arthritis, Polyarticular Juvenile Idiopathic Arthritis (PJIA) | Tetrahydrofolate dehydrogenase inhibitors, Thymidylate synthase inhibitors |
| Methylnaltrexone | Methylnaltrexone bromide | | Opioid mu receptor antagonists |
| Methylphenidate | Methylphenidate transdermal | | Adrenergic receptor modulators, Dopamine release stimulants |
| metoprolol | metoprolol | Angina (Angina Pectoris), Hypertension, Myocardial Infarction, Migraine | Beta 1 Adrenergic Receptor (Beta 1 Adrenoreceptor or ADRB1) Antagonist |
| Mifepristone | Mifepristone | | |
| Miglustat | Miglustat | | |
| Miltefosine | Miltefosine | Visceral leishmaniasis, Cutaneous leishmaniasis, Cancer metastases, Leishmaniasis, Chagas disease, Malignant melanoma | Signal transduction pathway inhibitors |
| Minocycline | Minocycline IV | | Glial cell inhibitors, Protein 30S ribosomal subunit inhibitors |
| mitomycin C | mitomycin C | Breast Cancer, Lung Cancer, Prostate Cancer, Anal Cancer, Bone Cancer, Non-Small Cell Lung Cancer, Squamous Cell Carcinoma, Uterine Cancer, Malignant Mesothelioma, Colorectal Cancer, Cervical Cancer, Chronic Lymphocytic Leukemia (CLL), Chronic Myelocytic Leukemia (CML, Chronic Myeloid Leukemia), Liver Cancer, Head And Neck Cancer, Pancreatic Cancer, Gastric Cancer, Bladder Cancer, Leukemias, Metastatic Breast Cancer, Sarcomas, Solid Tumor, Adenocarcinoma Of The Gastroesophageal Junction, Colon | |

TABLE 1-continued

Exemplary Therapeutic Agents and Associated Diseases and Disorders

| Abbreviated Drug Name | Drug Name | Indication | Mechanism Of Action |
|---|---|---|---|
| Mitoxantrone | Mitoxantrone | Cancer, Metastatic Adenocarcinoma of The Pancreas, Non Muscle Invasive Bladder Cancer (NMIBC) (Superficial Bladder Cancer), Skin Cancer | DNA inhibitors, DNA topoisomerase inhibitors, Type II DNA topoisomerase inhibitors, Immunosuppressants |
| Modafinil | Modafinil | | |
| Morphine | Morphine | Acute Pain, Chronic Pain, Dyspnea | Mu Type Opioid Receptor (MOR1 or Mu Opiate Receptor or Mu Opioid Receptor or OPRM1) Agonist |
| Motexafin gadolinium | Motexafin gadolinium | Brain cancer, Non-small cell lung cancer, Glioma, Lymphoma, Chronic lymphocytic leukaemia, Glioblastoma, Multiple myeloma, Non-Hodgkin's lymphoma, Renal cancer, Cardiovascular disorders, Head and neck cancer, Solid tumours, Amyotrophic lateral sclerosis | Thioredoxin reductase inhibitors |
| Moxifloxacin | Moxifloxacin | Intra-abdominal infections, Acute exacerbations of chronic bronchitis, Community-acquired pneumonia, Skin and soft tissue infections, Acute sinusitis, Bacterial infections, Respiratory tract infections, Pelvic inflammatory disorders, Plague, Tuberculosis | Type II DNA topoisomerase inhibitors |
| Mycophenolate mofetil | Mycophenolate mofetil | Liver Transplantation, Heart Transplantation, Kidney Transplantation | Immunosuppressants, Inosine monophosphate dehydrogenase inhibitors |
| Nafarelin | Nafarelin acetate | | |
| Naloxone | Naloxone injection | | Opioid receptor antagonists |
| naproxen | naproxen | Osteoarthritis Pain, Gastric Ulcers, Ankylosing Spondylitis (Bekhterev's Disease), Rheumatoid Arthritis Pain, Migraine | |
| nelarabine | nelarabine | Acute Lymphocytic Leukemia (ALL, Acute Lymphoblastic Leukemia), Acute Lymphoblastic Lymphoma | |
| nelfinavir | nelfinavir | HIV-1 Infection | |
| Neostigmine | Neostigmine | | |
| Nevirapine | Nevirapine | HIV-1 infections | Non-nucleoside reverse transcriptase inhibitors |
| nilotinib | Nilotinib | Anaplastic Astrocytoma, Oligodendroglioma, Colorectal Cancer, Pulmonary Arterial Hypertension, Acute Lymphocytic Leukemia (ALL, Acute Lymphoblastic Leukemia), Acute Myelocytic Leukemia (AML, Acute Myeloblastic Leukemia), Chronic Myelocytic Leukemia (CML, Chronic Myeloid Leukemia), Systemic Sclerosis (Scleroderma), Graft Versus Host Disease (GVHD), Gastrointestinal Stromal Tumor (GIST), Anaplastic Oligoastrocytoma, Head And Neck Cancer Squamous Cell Carcinoma, Metastatic Melanoma, Pigmented Villonodular Synovitis, Recurrent Glioblastoma Multiforme (GBM), Tenosynovitis, Vestibular Schwannoma (Acoustic Neuroma) | |

TABLE 1-continued

Exemplary Therapeutic Agents and Associated Diseases and Disorders

| Abbreviated Drug Name | Drug Name | Indication | Mechanism Of Action |
|---|---|---|---|
| Nilutamide | Nilutamide | Prostate cancer | Testosterone congener inhibitors |
| nintedanib | nintedanib | | |
| Nitazoxanide | Nitazoxanide | | |
| Nitisinone | Nitisinone | | |
| nitrosoureas | nitrosoureas | Astrocytoma, Glioblastoma Multiforme (GBM), Metastatic Brain Tumor, Glioma, Ependymoma, Lymphoma, Melanoma, Multiple Myeloma (Kahler Disease), Non-Hodgkin Lymphoma, Hodgkin Lymphoma, Solid Tumor, Brain Tumor, Gastrointestinal Tract Cancer, Medulloblastoma | |
| nortriptyline | nortriptyline | Depression | |
| NSC 361456 | NSC 361456 | Cancer | Undefined mechanism |
| obeticholic acid | obeticholic acid | | |
| olaparib | olaparib | | |
| Omacetaxine mepesuccinate | Omacetaxine mepesuccinate | Chronic Myelocytic Leukemia (CML, Chronic Myeloid Leukemia) | Apoptosis stimulants, Cyclin D1 inhibitors, MCL1 protein inhibitors, Protein synthesis inhibitors, Proto oncogene protein c-myc inhibitors |
| Omadacycline | Omadacycline | | Protein synthesis inhibitors |
| Omeprazole | Omeprazole | Peptic ulcer, Helicobacter infections, Duodenal ulcer, Gastric ulcer, Gastro-oesophageal reflux, Zollinger-Ellison syndrome, Gastritis, Dyspepsia | Proton pump inhibitors |
| opioids | opioids | Pain | |
| Oritavancin | Oritavancin | | |
| Orlistat | Orlistat | Obesity | Lipase inhibitors |
| Oxaliplatin | Oxaliplatin | | DNA cross linking agents, DNA synthesis inhibitors |
| oxprenolol | oxprenolol | Hypertension | |
| Oxybate | Oxybate | | |
| Oxybutynin | Oxybutynin | | Cholinergic receptor antagonists, Muscarinic receptor antagonists |
| Oxymetholone | Oxymetholone | Anaemia, Cachexia | Protein synthesis stimulants, Stem cell stimulants, Testosterone congener stimulants |
| Paclitaxel | Paclitaxel | Ovarian cancer, Breast cancer, Gastric cancer, Kaposi's sarcoma, Non-small cell lung cancer, Cervical cancer, Multiple myeloma, Head and neck cancer, Prostate cancer, Cancer metastases, Bladder cancer, Testicular cancer, Endometrial cancer, Non-Hodgkin's lymphoma, Sarcoma, Lung cancer, Mesothelioma, Leukaemia, Pleural effusion, Small cell lung cancer | Mitosis inhibitors, Proto-oncogene protein c-bcl-2 inhibitors, Tubulin polymerisation promoters |
| Hemin | Hemin | | |
| Pantoprazole | Pantoprazole | | |
| Paracetamol | Paracetamol intravenous | Fever; Pain | |
| Paricalcitol | Paricalcitol | | Calcitriol receptor agonists, Parathyroid hormone receptor antagonists |
| Pazopanib | Pazopanib | | |
| Pemetrexed | Pemetrexed | Non-small cell lung cancer, Mesothelioma, Breast cancer, Non-Hodgkin's lymphoma, Head and neck cancer, Ovarian cancer, Osteosarcoma, Renal cancer, Small cell lung cancer | Antimetabolites, Tetrahydrofolate dehydrogenase inhibitors, Thymidylate synthase inhibitors |

TABLE 1-continued

Exemplary Therapeutic Agents and Associated Diseases and Disorders

| Abbreviated Drug Name | Drug Name | Indication | Mechanism Of Action |
|---|---|---|---|
| Pentamidine isethionate | Pentamidine isethionate | | |
| pentazocine | pentazocine (acetaminophen + pentazocine hydrochloride) | Pain, Moderate Pain | |
| Pentosan | Pentosan polysulfate sodium | | |
| Pentostatin | Pentostatin | Hairy cell leukaemia, Cutaneous T cell lymphoma, Graft-versus-host disease, Non-Hodgkin's lymphoma, Rheumatoid arthritis | Adenosine deaminase inhibitors, Immunomodulators |
| Peramivir | Peramivir | | |
| Perflexane | Perflexane | | |
| Perflutren | Perflutren | | Undefined mechanism |
| Phenylephrine | Phenylephrine intravenous | | |
| Piperacillin/ tazobactam | Piperacillin/ tazobactam | | Beta lactamase inhibitors, Cell wall inhibitors |
| Pirmenol | Pirmenol | Ventricular arrhythmias | Calcium channel antagonists, Muscarinic M2 receptor antagonists, Potassium channel antagonists, Sodium channel antagonists |
| Plazomicin | Plazomicin | | Protein synthesis inhibitors |
| Plerixafor | Plerixafor | | CXCR4 receptor antagonists |
| Polidocanol | Polidocanol | | |
| Pomalidomide | Pomalidomide | | |
| ponatinib | ponatinib hydrochloride | Glioblastoma Multiforme (GBM), Non-Small Cell Lung Cancer, Acute Lymphocytic Leukemia (ALL, Acute Lymphoblastic Leukemia), Acute Myelocytic Leukemia (AML, Acute Myeloblastic Leukemia), Chronic Myelocytic Leukemia (CML, Chronic Myeloid Leukemia), Gastrointestinal Stromal Tumor (GIST), Biliary Tumor, Medullary Thyroid Cancer | |
| Posaconazole | Posaconazole | | |
| pralatrexate | Pralatrexate | Non-Small Cell Lung Cancer, Esophageal Cancer, Cutaneous T-Cell Lymphoma, Hodgkin Lymphoma, Gastric Cancer, Bladder Cancer, Oral Mucositis, Metastatic Breast Cancer, B-Cell Non-Hodgkin Lymphoma, Peripheral T-Cell Lymphomas (PTCL), Transitional Cell Cancer (Urothelial Cell Cancer) | Antimetabolites, Tetrahydrofolate dehydrogenase inhibitors |
| prednisolone | prednisolone | Burns, Keratitis, Blepharitis, Conjunctivitis, Anterior Uveitis, Herpetic Keratitis, Ocular Inflammation, Scleritis | |
| prednisone | predisone | Multiple Sclerosis, Asthma, Sicca Syndrome (Sjogren), Proteinuria, Uveitis, Juvenile Rheumatoid Arthritis, Vasculitis, Chronic Obstructive Pulmonary Disease (COPD), Idiopathic Pulmonary Fibrosis, Hypoxemia, Serum Sickness, Polymyositis, Tuberculous Meningitis, Gouty Arthritis (Gout), Ankylosing Spondylitis (Bekhterev's Disease), Idiopathic Thrombocytopenic Purpura (Immune Thrombocytopenic Purpura), Psoriatic Arthritis, Polymyalgia Rheumatica, Dermatomyositis, Ulcerative Colitis, Transplantation, Rheumatoid Arthritis, Crohn's Disease (Regional Enteritis), Systemic Lupus Erythematosus, | |

TABLE 1-continued

Exemplary Therapeutic Agents and Associated Diseases and Disorders

| Abbreviated Drug Name | Drug Name | Indication | Mechanism Of Action |
|---|---|---|---|
| | | Dermatitis, Thrombocytopenia, Acquired (Autoimmune) Hemolytic Anemia, Adrenal Insufficiency, Allergic Bronchopulmonary Aspergillosis, Aspiration Pneumonitis, Atopic Dermatitis, Bronchiolitis Obliterans, Congenital Adrenal Hyperplasia (Adrenogenital Syndrome), Contact Dermatitis, Dermatitis Herpetiformis (Duhring's Disease), Drug Hypersensitivity Reactions, Edema, Erythema Multiforme, Idiopathic Eosinophilic Pneumonia, Idiopathic Interstitial Pneumonia (IIP), Nonsuppurative Thyroiditis, Ocular Inflammation, Pemphigus, Perennial Allergic Rhinitis, Pneumocystis carinii Pneumonia, Pulmonary Tuberculosis, Respiratory Hypersensitivity, Seasonal Allergic Rhinitis, Sympathetic Ophthalmia, Symptomatic Sarcoidosis | |
| Propofol | Propofol | | GABA receptor agonists |
| propranolol | propranolol | Angina (Angina Pectoris), Hypertension, Myocardial Infarction, Migraine, Atrial Fibrillation, Essential Tremor, Pheochromocytoma, Tachycardia (Tachyarrhythmias), Hyperthyroidism, Ventricular Arrhythmia, Wolff-Parkinson-White Syndrome | Beta 1 Adrenergic Receptor (Beta 1 Adrenoreceptor or ADRB1) Antagonist; Beta 2 Adrenergic Receptor (Beta 2 Adrenoreceptor or ADRB2) Antagonist |
| Quinapril | Quinapril | | ACE inhibitors |
| Quinine sulfate | Quinine sulfate | | |
| Quinupristin/ dalfopristin | Quinupristin/ dalfopristin | Enterococcal infections, Gram-positive infections, Skin and soft tissue infections, Nosocomial pneumonia | Protein synthesis inhibitors |
| Raloxifene | Raloxifene | Postmenopausal osteoporosis, Breast cancer, Fracture, Cardiovascular disorders, Endometriosis, Vasomotor symptoms, Hypercholesterolaemia, Leiomyoma | Selective estrogen receptor modulators |
| raltegravir | raltegravir | HIV/AIDS, HIV-1 Infection | |
| Raltitrexed | Raltitrexed | Colorectal cancer, Mesothelioma | Thymidylate synthase inhibitors |
| Ramatroban | Ramatroban | Allergic rhinitis, Asthma, Ischaemic heart disorders, Thrombosis | Thromboxane A2 receptor antagonists |
| Regadenoson | Regadenoson | Coronary disorders | Adenosine A2 receptor agonists |
| Regorafenib | Regorafenib | | |
| Remacemide | Remacemide | Huntington's disease, Epilepsy, Stroke, Neurological disorders, Parkinson's disease, Neuropathic pain | Glutamate receptor antagonists, NMDA receptor antagonists |
| riboflavin | riboflavin ophthalmic solution & ultraviolet A | | |
| Rifabutin | Rifabutin | | |
| Rifampin | Rifampin | | |
| Rifapentine | Rifapentine | Tuberculosis, Mycobacterium avium complex infections | Protein 50S ribosomal subunit inhibitors |
| Rifaximin | Rifaximin | | |
| rilpivirine | rilpivirine | HIV-1 Infection | |
| Riluzole | Riluzole | | |
| Riociguat | Riociguat | | |
| Ritonavir | Ritonavir | Hepatitis C, HIV-1 Infection | HIV protease inhibitors |
| RO 316840 | RO 316840 | Hepatitis B, HIV infections | RNA-directed DNA polymerase inhibitors |
| Romidepsin | Romidepsin | | |
| Ropeginterferon alfa-2b | Ropeginterferon alfa-2b | | Interferon alpha 2b stimulants |
| rosuvastatin | rosuvastatin | | |
| Rotigotine | Rotigotine | | Dopamine D2 receptor agonists |

TABLE 1-continued

Exemplary Therapeutic Agents and Associated Diseases and Disorders

| Abbreviated Drug Name | Drug Name | Indication | Mechanism Of Action |
|---|---|---|---|
| Rufinamide | Rufinamide | | |
| Ruxolitinib | Ruxolitinib Phosphate | | |
| Sabril | Sabril | | |
| salbutamol | salbutamol | Asthma, Bronchospasm, Obstructive Pulmonary Disease, Chronic Obstructive Pulmonary Disease (COPD), Chronic Bronchitis, Emphysema, Exercise-Induced Bronchoconstriction (EBI), Premature Labor (Tocolysis), Pulmonary Tuberculosis, Status Asthmaticus | |
| Salmeterol | Salmeterol injection | | Arachidonic acid inhibitors, Beta 2 adrenergic receptor agonists |
| Samarium 153 lexidronam | Samarium 153 lexidronam | | Ionising radiation emitters, Reactive oxygen species stimulants |
| Sapropterin | Sapropterin | | |
| saquinavir | saquinavir | HIV-1 Infection | HIV 1 Retropepsin (HIV Aspartyl Protease or HIV Proteinase or Retroproteinase or Gag Protease or HIV Aspartyl Protease or EC 3.4.23.16) Inhibitor; HIV 2 Retropepsin (HIV 2 Protease or EC 3.4.23.47) Inhibitor |
| Satraplatin | Satraplatin | Squamous cell cancer, Prostate cancer, Non-small cell lung cancer, Breast cancer, Solid tumours | DNA cross linking agents, DNA synthesis inhibitors |
| Sedoxantrone | Sedoxantrone | Prostate cancer, Colorectal cancer, Solid tumours | DNA helicase inhibitors, DNA inhibitors |
| Selexipag | Selexipag | | |
| Semaxanib | Semaxanib | Kaposi's sarcoma, Colorectal cancer, Non-small cell lung cancer, Acute myeloid leukaemia, Solid tumours, Cancer metastases | Angiogenesis inhibitors, Protein tyrosine kinase inhibitors, Vascular endothelial growth factor receptor-2 antagonists |
| Sertraline | Sertraline | Major depressive disorder, Panic disorder, Post-traumatic stress disorders, Social phobia, Obsessive-compulsive disorders, Premenstrual dysphoric disorder, Generalised anxiety disorder, Premature ejaculation, Obesity | Serotonin uptake inhibitors |
| Sildenafil | Sildenafil | | |
| Simvastatin | Simvastatin | Hypertriglyceridaemia, Hypercholesterolaemia, Low HDL cholesterol, Hyperlipoproteinaemias, Diabetic cardiomyopathy, Cystic fibrosis, Multiple sclerosis, Alzheimer's disease, Bone resorption, Rheumatoid arthritis | HMG-CoA reductase inhibitors, Nitric oxide synthase type II inhibitors |
| sirolimus | sirolimus | Arteriovenous Fistula, Benign Cardiovascular Tumor, Dermatological Disorders, Kidney Transplantation, Choroidal Neovascularization, Diabetic Macular Edema, Keratoconjunctivitis sicca (Dry Eye), Dry (Atrophic) Macular Degeneration, Posterior Uveitis, Wet (Neovascular/Exudative) Macular Degeneration | |

TABLE 1-continued

Exemplary Therapeutic Agents and Associated Diseases and Disorders

| Abbreviated Drug Name | Drug Name | Indication | Mechanism Of Action |
|---|---|---|---|
| Sodium ferric gluconate | Sodium ferric gluconate complex | | Iron replacements |
| Sodium nitrite-sodium thiosulfate combination therapy | Sodium nitrite-sodium thiosulfate combination therapy | | |
| Sodium phenylacetate/ sodium benzoate | Sodium phenylacetate/ sodium benzoate | | Ammonia scavengers |
| Sodium phenylbutyrate | Sodium phenylbutyrate | | |
| Sorafenib | Sorafenib | | |
| Sorivudine | Sorivudine | Herpes zoster | RNA-directed DNA polymerase inhibitors |
| Sotalol | IV Sotalol | | |
| Stavudine | Stavudine | HIV-1 infections | Nucleoside reverse transcriptase inhibitors |
| sulfasalazine | sulfasalazine | Colitis, Ulcerative Colitis, Crohn's Disease (Regional Enteritis), Proctitis | |
| Sumatriptan | Sumatriptan transdermal | | Serotonin 1D receptor agonists |
| Sunitinib | Sunitinib | Pancreatic cancer, Gastrointestinal stromal tumours, Renal cancer, Prostate cancer, Oesophageal cancer, Thyroid cancer, Bladder cancer, Malignant melanoma, Soft tissue sarcoma, Hepatocellular carcinoma, Germ cell and embryonal neoplasms, Non-small cell lung cancer, Breast cancer, Colorectal cancer, Gastric cancer, Urogenital cancer, Acute myeloid leukaemia | Colony stimulating factor receptor antagonists, Fms-like tyrosine kinase 3 inhibitors, Platelet derived growth factor alpha receptor antagonists, Platelet-derived growth factor beta receptor antagonists, Proto oncogene protein c ret inhibitors, Proto oncogene protein c-kit inhibitors, Vascular endothelial growth factor receptor 3 antagonists, Vascular endothelial growth factor receptor-1 antagonists, Vascular endothelial growth factor receptor-2 antagonists |
| Tacrine | Tacrine | Alzheimer's disease, HIV infections | Acetylcholinesterase inhibitors |
| Tacrolimus | Tacrolimus | Transplant rejection, Atopic dermatitis, Ulcerative colitis, Myasthenia gravis, Intestinal transplant rejection, Graft-versus-host disease, Interstitial lung diseases, Lupus nephritis, Allergic conjunctivitis, Rheumatoid arthritis, Coronary artery restenosis, Open-angle glaucoma, Psoriasis, Eye disorders, Dry eyes, Lupus Nephritis, Myasthenia Gravis, Pneumonia, Liver Transplantation, Heart Transplantation, Bone Marrow Transplantation, Lung Transplantation, Ulcerative Colitis, Rheumatoid Arthritis, Crohn's Disease (Regional Enteritis), Eczema, Kidney Transplantation, Atopic Dermatitis | Calcineurin inhibitors, Cytokine inhibitors, Immunosuppressants, T cell activation inhibitors |
| Tanomastat | Tanomastat | Non-small cell lung cancer, Ovarian cancer, Pancreatic cancer, Small cell lung cancer, Osteoarthritis | Angiogenesis inhibitors, Matrix metalloproteinase inhibitors |
| tasimelteon | tasimelteon | | |
| Tc 99m apcitide | Tc 99m apcitide | | Radionuclide imaging enhancers |

TABLE 1-continued

Exemplary Therapeutic Agents and Associated Diseases and Disorders

| Abbreviated Drug Name | Drug Name | Indication | Mechanism Of Action |
|---|---|---|---|
| Tc 99m ethylenedicysteine deoxyglucose | Tc 99m ethylenedicysteine deoxyglucose | | Single-photon emission-computed tomography enhancers |
| Tedizolid | Tedizolid | | |
| Teicoplanin | Teicoplanin | Gram-positive infections, Bacterial infections | Cell wall inhibitors |
| Telavancin | Telavancin | | Cell membrane permeability enhancers, Cell wall inhibitors |
| Telithromycin | Telithromycin | Acute sinusitis, Gram-positive infections, Community-acquired pneumonia, Tonsillitis, Acute exacerbations of chronic bronchitis, Pharyngitis, Respiratory tract infections, Obstetric and gynaecological infections, Pelvic inflammatory disorders, Skin and soft tissue infections, Toxoplasmosis | Protein 50S ribosomal subunit inhibitors |
| Temafloxacin | Temafloxacin | Bacterial infections | Type II DNA topoisomerase inhibitors |
| Temozolomide | Temozolomide | | |
| Temsirolimus | Temsirolimus | Mantle-cell lymphoma, Renal cancer, Glioblastoma, Hodgkin's disease, Glioma, Non-Hodgkin's lymphoma, Head and neck cancer, Follicular lymphoma, Lymphoma, Acute lymphoblastic leukaemia, Colorectal cancer, Solid tumours, Prostate cancer, Multiple myeloma, Breast cancer, Soft tissue sarcoma, Pancreatic cancer | MTOR protein inhibitors |
| Teniposide | Teniposide | | |
| tenofovir | tenofovir | HIV-1 Infection | |
| Terbinafine | Terbinafine | Mycoses, Tinea cruris, Pityriasis versicolor, Tinea pedis, Tinea corporis, Tinea capitis | Squalene monooxygenase inhibitors |
| Testosterone propionate | Testosterone propionate | Breast cancer, Delayed puberty, Hypogonadism, Menopausal syndrome, Decreased libido, Male Hypogonadism, Secondary (Hypogonadotropic) Hypogonadism, Testicular (Primary) Hypogonadism, Testicular Diseases | Androgen Receptor (Dihydrotestosterone Receptor or Nuclear Receptor Subfamily 3 Group C Member 4 or DHTR or NR3C4 or AR) Agonist |
| Thalidomide | Thalidomide | | |
| Tianeptine | Tianeptine | Anxiety disorders, Major depressive disorder, Alcoholism, Irritable bowel syndrome, Asthma | Serotonin uptake stimulants |
| Tigecycline | Tigecycline | | |
| Tinzaparin sodium | Tinzaparin sodium | | Factor Xa inhibitors, Thrombin inhibitors |
| Tiopronin | Tiopronin | | |
| Tizanidine | Tizanidine | Muscle spasticity, Migraine, Fibromyalgia | Alpha 2 adrenergic receptor agonists |
| Tobramycin | Tobramycin for inhalation | | |
| Tolcapone | Tolcapone | Parkinson's disease | Catechol-O-methyltransferase inhibitors |
| Tolrestat | Tolrestat | Diabetic complications | Aldehyde reductase inhibitors |
| Tolvaptan | Tolvaptan | Oedema, Hyponatraemia, Cardiac oedema, Autosomal dominant polycystic kidney disease, Renal failure, Ascites | Vasopressin V2 receptor antagonists |
| Topiramate | Topiramate | Epilepsy, Migraine, Lennox-Gastaut syndrome, Obesity, Post-traumatic stress disorders, Diabetic neuropathies, Bipolar disorders | AMPA receptor antagonists, Carbonic anhydrase inhibitors, GABA-A receptor antagonists, Kainic acid receptor antagonists, Sodium channel antagonists, |

TABLE 1-continued

Exemplary Therapeutic Agents and Associated Diseases and Disorders

| Abbreviated Drug Name | Drug Name | Indication | Mechanism Of Action |
|---|---|---|---|
| | | | GABA A receptor agonists |
| Topotecan | Topotecan | Small cell lung cancer, Ovarian cancer, Cervical cancer, Brain cancer | DNA topoisomerase I inhibitors |
| Trabectedin | Trabectedin | | |
| Trametinib | Trametinib | | |
| Treprostinil | Treprostinil | Pulmonary Arterial Hypertension | Prostacyclin Receptor (Prostaglandin I2 Receptor or Prostanoid IP Receptor or PTGIR) Agonist |
| Tretinoin | Tretinoin | | |
| Triciribine | Triciribine | Ovarian cancer, Breast cancer, Acute myeloid leukaemia, Solid tumours, Haematological malignancies, Pancreatic cancer, HIV infections, Cancer | DNA synthesis inhibitors, Protein kinase inhibitors, Proto oncogene protein c-akt inhibitors |
| Trientine | Trientine HCl | | |
| Trimetrexate | Trimetrexate | Pneumocystis pneumonia, Colorectal cancer, Bladder cancer, Lung cancer, Cancer, Pancreatic cancer, Cervical cancer, Non-small cell lung cancer, Breast cancer, Gastric cancer, Psoriasis, Leukaemia, Rheumatoid arthritis | Tetrahydrofolate dehydrogenase inhibitors |
| Trovafloxacin | Trovafloxacin | Bacterial infections, Genital tract infections, Respiratory tract infections, Toxoplasmosis | Type II DNA topoisomerase inhibitors |
| Uridine triacetate | Uridine triacetate | | |
| Ursodiol | Ursodiol | | |
| Vandetanib | Vandetanib | | |
| venetoclax | venetoclax | | |
| verapamil | verapamil | Angina (Angina Pectoris), Hypertension, Unstable Angina, Renal (Renovascular) Hypertension, Atrial Fibrillation, Ischemia, Atrial Flutter, Chronic Stable Angina, Idiopathic (Essential) Hypertension, Paroxysmal Ventricular Tachycardia, Supraventricular Tachycardia, Vasospastic Angina, Wolff-Parkinson-White Syndrome | |
| Verteporfin | Verteporfin | | |
| vinblastine | vinblastine | Breast Cancer, Testicular Cancer, Lymphoma, Hodgkin Lymphoma, Carcinomas, Gestational Trophoblastic Disease, Kaposi Sarcoma, Letterer-Siwe Disease (Multifocal and multisystemic (disseminated) Langerhans-cell histiocytosis), Mycosis Fungoides | |
| vincristine sulfate | vincristine sulfate | Metastatic Uveal Melanoma, Non-Hodgkin Lymphoma, Acute Lymphocytic Leukemia (ALL, Acute Lymphoblastic Leukemia) | Tubulin polymerisation inhibitors |
| Vinorelbine | Vinorelbine | Non-small cell lung cancer, Breast cancer, Ovarian cancer, Head and neck cancer, Prostate cancer, Small cell lung cancer, Cervical cancer, Malignant melanoma, Multiple myeloma | Mitosis inhibitors, Tubulin polymerisation inhibitors |
| Vismodegib | Vismodegib | Basal cell cancer, Pancreatic cancer, Basal cell nevus syndrome, Gastric cancer, Small cell lung cancer, Medulloblastoma, Breast cancer, Chondrosarcoma, Myelofibrosis, Idiopathic pulmonary fibrosis, Glioblastoma, Colorectal cancer, Chronic lymphocytic leukaemia, Ovarian cancer, B cell lymphoma, Myelodysplastic syndromes, Acute myeloid leukaemia, Prostate cancer, Sarcoma | Hedgehog cell-signalling pathway inhibitors |

TABLE 1-continued

Exemplary Therapeutic Agents and Associated Diseases and Disorders

| Abbreviated Drug Name | Drug Name | Indication | Mechanism Of Action |
|---|---|---|---|
| Vitamin B12 fluorescent-analogues | Vitamin B12 fluorescent-analogues | | |
| Voglibose | Voglibose | Type 2 diabetes mellitus | Alpha-glucosidase inhibitors, Glucagon-like peptide 1 stimulants |
| Voriconazole | Voriconazole | | |
| Zafirlukast | Zafirlukast | Asthma | Leukotriene D4 receptor antagonists, Leukotriene E4 receptor antagonists |
| zalcitabine | zalcitabine | HIV/AIDS | |
| zidovudine | zidovudine | HIV-1 Infection, HIV-2 Infection | |
| Zileuton | Zileuton | Asthma, Ulcerative colitis, Chronic obstructive pulmonary disease, Acute asthma, Acne, Atopic dermatitis, Rheumatoid arthritis, Cancer, Allergic rhinitis, Atherosclerosis, Nasal polyps | 5-lipoxygenase inhibitors |
| Zoledronic acid | Zoledronic acid | Osteitis deformans, Bone metastases, Malignant hypercalcaemia, Postmenopausal osteoporosis, Corticosteroid-induced osteoporosis, Multiple myeloma, Male osteoporosis, Fracture, Mesothelioma, Osteoporosis, Breast cancer, Osteogenesis imperfecta, Osteosarcoma, Rheumatoid arthritis | Bone resorption factor inhibitors, Geranyltranstransferase inhibitors, Osteoclast inhibitors |

In some embodiments, the therapeutic agent is an antimicrobial, antiviral, antiparasitic, anticancer agent, or other therapeutic agent selected from those in Table 2, below; or a pharmaceutically acceptable salt thereof.

TABLE 2

Exemplary Therapeutic Agents and Associated Diseases and Disorders

| Therapeutic Agent Name | Indication | Mechanism of Action | Therapeutic Area |
|---|---|---|---|
| Amikacin liposomal inhaled - Insmed | Cystic fibrosis-associated respiratory tract infections, Mycobacterial infections, Bronchiectasis | Protein 30S ribosomal subunit inhibitors | Bacterial Infections, Drug Delivery Systems |
| Azithromycin | Community-acquired pneumonia, Bacterial infections, Acute sinusitis, Pelvic inflammatory disorders, Otitis media, Sexually transmitted infections, Cystic fibrosis-associated respiratory tract infections, Cholera, Asthma, Pertussis, Typhoid, Gastroparesis, Acute coronary syndromes | Protein 50S ribosomal subunit inhibitors | Bacterial Infections, Digestive System Disorders, Ischaemic Heart Disease, Obstructive Airways Disease |
| Cefepime | Intra-abdominal infections, Bacterial infections, Skin and soft tissue infections, Urinary tract infections, Respiratory tract infections, Febrile neutropenia | Cell wall inhibitors | Bacterial Infections |
| Ceftaroline fosamil | Community-acquired pneumonia, Skin and soft tissue infections, Methicillin-resistant *Staphylococcus aureus* infections, Bacteraemia, Sepsis, Bacterial infections, Osteomyelitis | Cell wall inhibitors, Penicillin-binding protein inhibitors | Bacterial Infections |
| Ceftazidime - B Braun Medical | CNS infections, Skin and soft tissue infections, Bacteraemia, Intra-abdominal infections, Gynaecological infections, Bone and joint infections, Respiratory tract infections | Cell wall inhibitors | Bacterial Infections |
| Ceftolozane/ tazobactam | Intra-abdominal infections, Gram-negative infections, Urinary tract infections, Pyelonephritis, Nosocomial pneumonia | Beta lactamase inhibitors, Cell wall inhibitors | Bacterial Infections |
| Ceftriaxone injectable | Pelvic inflammatory disorders, Respiratory tract infections, Skin and soft tissue infections, Otitis media, Gonorrhoea, Bone and joint infections, Epididymitis, Urinary tract infections, Meningococcal infections | Cell wall inhibitors | Bacterial Infections |
| Cidofovir | Cytomegalovirus retinitis, Cystitis, Polyomavirus infections, Herpes simplex virus infections, Human papillomavirus infections, Kaposi's sarcoma, Viral infections, Molluscum contagiosum, Cancer, Rheumatic disorders | DNA-directed DNA polymerase inhibitors, Immunomodulators | Cancer, Genitourinary Disorders, Rheumatic Disease, Viral Infections |

TABLE 2-continued

Exemplary Therapeutic Agents and Associated Diseases and Disorders

| Therapeutic Agent Name | Indication | Mechanism of Action | Therapeutic Area |
|---|---|---|---|
| Delafloxacin | Skin and soft tissue infections, Community-acquired pneumonia, Nosocomial pneumonia, Urinary tract infections, Intra-abdominal infections, Gonorrhoea, Acute exacerbations of chronic bronchitis, Anthrax | DNA gyrase inhibitors, DNA topoisomerase IV inhibitors | Bacterial Infections |
| Doripenem | Gram-positive infections, Gram-negative infections, Paediatric infections, Intra-abdominal infections, Urinary tract infections, Meningococcal infections, Nosocomial pneumonia, Respiratory tract infections, Pneumonia, Bacterial infections | Cell wall inhibitors | Bacterial Infections |
| Eravacycline | Urinary tract infections, Intra-abdominal infections, Respiratory tract infections | Protein 30S ribosomal subunit inhibitors | Bacterial Infections |
| Fosfomycin intravenous - Zavante Therapeutics | Urinary tract infections, Intra-abdominal infections, Skin and soft tissue infections, Pseudomonal infections | Cell wall inhibitors, Peptidoglycan inhibitors | Bacterial Infections |
| Gentamicin implant - Innocoll | Postoperative infections, Diabetic foot ulcer | Protein 30S ribosomal subunit inhibitors | Bacterial Infections, Drug Delivery Systems, Skin Disorders |
| Iclaprim | Skin and soft tissue infections, Nosocomial infections, Nosocomial pneumonia, Gonorrhoea, Chlamydial infections | Tetrahydrofolate dehydrogenase inhibitors | Bacterial Infections, Mycoses |
| Isavuconazonium | Aspergillosis, Zygomycosis, Candidiasis, Mycoses | 14-alpha demethylase inhibitors | Mycoses |
| Lefamulin | Community-acquired pneumonia, Skin and soft tissue infections, Bone and joint infections, Osteomyelitis, Sexually transmitted infections, Nosocomial pneumonia | Peptidyltransferase modulators, Protein 50S ribosomal subunit modulators | Bacterial Infections |
| Letermovir | Cytomegalovirus infections | Cytomegalovirus replication inhibitors | Viral Infections |
| Levofloxacin | Respiratory tract infections, Skin and soft tissue infections, Prostatitis, Bacterial infections, Urinary tract infections, Acute sinusitis, Acute exacerbations of chronic bronchitis, Community-acquired pneumonia, Anthrax, Nosocomial pneumonia, Sinusitis, Pneumonia, Pyelonephritis, Postoperative infections, Tuberculosis, Gynaecological infections | DNA gyrase inhibitors, Type II DNA topoisomerase inhibitors | Bacterial Infections, Viral Infections |
| Linezolid | Vancomycin-resistant enterococcal infections, Nosocomial pneumonia, Nosocomial infections, Diabetic foot ulcer, Gram-positive infections, Methicillin-resistant *Staphylococcus aureus* infections, Community-acquired pneumonia, Skin and soft tissue infections, Bacterial infections | Protein 30S ribosomal subunit inhibitors | Bacterial Infections |
| Meropenem | Febrile neutropenia, Bacterial infections, Community-acquired pneumonia, Skin and soft tissue infections | Cell wall inhibitors | Bacterial Infections |
| Meropenem - B Braun Medical | Skin and soft tissue infections, Intra-abdominal infections, Bacterial meningitis | Cell wall inhibitors | Bacterial Infections |
| Meropenem/ vaborbactam | Pyelonephritis, Bacteraemia, Gram-negative infections, Urinary tract infections, Pneumonia | Beta lactamase inhibitors, Cell wall inhibitors | Bacterial Infections, Genitourinary Disorders |
| Minocycline IV - Rempex Pharmaceuticals | Gram-positive infections, Gram-negative infections | Glial cell inhibitors, Protein 30S ribosomal subunit inhibitors | Bacterial Infections |
| Moxifloxacin | Intra-abdominal infections, Acute exacerbations of chronic bronchitis, Community-acquired pneumonia, Skin and soft tissue infections, Acute sinusitis, Bacterial infections, Respiratory tract infections, Pelvic inflammatory disorders, Plague, Tuberculosis | Type II DNA topoisomerase inhibitors | Bacterial Infections |
| Moxifloxacin injection | Community-acquired pneumonia, Intra-abdominal infections, Acute exacerbations of chronic bronchitis, Skin and soft tissue infections, Acute sinusitis | Type II DNA topoisomerase inhibitors | Bacterial Infections |
| Omadacycline | Skin and soft tissue infections, Community-acquired pneumonia, Urinary tract infections, Nosocomial infections, Acute sinusitis, Anthrax, Plague | Protein synthesis inhibitors | Bacterial Infections |
| Oseltamivir | Influenza virus infections | Neuraminidase inhibitors | Viral Infections |
| Peramivir | Influenza A virus H1N1 subtype, Influenza virus infections | Neuraminidase inhibitors | Viral Infections |
| Plazomicin | Urinary tract infections, Bacteraemia, Pyelonephritis, Nosocomial pneumonia, Gram-negative infections, Respiratory tract infections, Yersinia infections, Tularaemia | Protein synthesis inhibitors | Bacterial Infections |
| Ropeginterferon alfa-2b | Polycythaemia vera, Essential thrombocythaemia, Hepatitis B, Hepatitis C, Myelofibrosis, Chronic myeloid leukaemia, Cancer | Interferon alpha 2b stimulants | Cancer, Haematological Disorders, Viral Infections |
| Rose bengal sodium | Malignant melanoma, Psoriasis, Atopic dermatitis, Liver metastases, Hepatocellular carcinoma, Breast cancer, Neuroendocrine tumours, Acne vulgaris | Cell death stimulants, Cell membrane modulators, Immunostimulants | Cancer, Skin Disorders |

TABLE 2-continued

Exemplary Therapeutic Agents and Associated Diseases and Disorders

| Therapeutic Agent Name | Indication | Mechanism of Action | Therapeutic Area |
|---|---|---|---|
| Solithromycin | Community-acquired pneumonia, Chlamydial infections, Gonorrhoea, Urethritis, Chronic obstructive pulmonary disease, Non-alcoholic steatohepatitis, Otorhinolaryngological infections, Tularaemia, Bacterial infections, Anthrax, Obstetric and gynaecological infections, Otitis media, Cystic fibrosis, Mycoplasma infections, Legionella infections, Enterococcal infections, Mycobacterium avium complex infections, Malaria | Protein 50S ribosomal subunit inhibitors | Bacterial Infections, Liver Disorders, Parasitic Infections, Respiratory Tract Disorders |
| Tedizolid | Skin and soft tissue infections, Nosocomial pneumonia, Bacteraemia, Gram-positive infections | Ribosomal protein inhibitors | Bacterial Infections |

In some embodiments, the therapeutic agent is selected from Gentamicin, Tobramycin, Amikacin, Kanamycin, Neomycin, Netilmicin, Paromomycin, Spectinomycin, Ampicillin, Ampicillin-sulbactam, Azithromycin, Aztreonam, Benzathine Penicillin, Cefotaxime, Ceftaroline, Fosamil, Ceftriaxone, Ciprofloxacin, Clindamycin, Doxycycline, Ertapenem, Imipenem-cistlastin, Levofloxacin, Merropenem, Metronidazole, Moxifloxacin, Rifampin, Tigecycline, Vancomycin, Oritavancin, Tedizolid, Telavancin Nafcillin, or Oxacillin; or a pharmaceutically acceptable salt thereof.

2. Definitions

While the terms used herein are believed to be well understood by one of ordinary skill in the art, definitions are set forth herein to facilitate explanation of the presently-disclosed subject matter.

As used herein, the term "about," when referring to a numerical value or range of a parameter such as mass, weight, volume, time, concentration, biological activity, c log P, or percentage, is meant to encompass variations of, e.g., ±20%, in some embodiments ±10%, in some embodiments ±5%, in some embodiments ±1%, in some embodiments ±0.5%, and in some embodiments ±0.1% from the specified value or range.

As used herein, the terms "treatment," "ctreat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The term "lipid," as used herein, refers to natural and non-natural hydrophobic and/or lipophilic fats, oils, polymers, hydrocarbons, and other such materials. In some embodiments, suitable lipids, when incorporated into a lipid prodrug, are processed or metabolized similarly to triglyercides in the GI tract or mimic such processing or metabolism. The term "glyceride" refers to an ester of glycerol (1,2,3-propanetriol) with acyl radicals of fatty acids or other lipids and is also known as an acylglycerol. If only one position of the glycerol molecule is esterified with a fatty acid, a "monoglyceride" is produced; if two positions are esterified, a "diglyceride" is produced; and if all three positions of the glycerol are esterified with fatty acid a "triglyceride" or "triacylglycerol" is produced. A glyceride is called "simple" if all esterified positions contain the same fatty acid; or "mixed" if different fatty acids are involved. The carbons of the glycerol backbone are designated sn-1, sn-2 and sn-3, with sn-2 being in the middle and sn-1 and sn-3 being the ends of the glycerol.

Naturally occurring oils and fats consist largely of triglycerides wherein the 3 fatty acyl residues may or may not be identical. The term "long chain triglycerides" (or "LCT") means both a simple and mixed triglyceride containing fatty acids with more than 12 carbon atoms (long chain fatty acids, "LCFA"), whereas the term "medium chain triglycerides" (or "MCT") means both a simple and mixed triglyceride containing fatty acids with 4 to 12 carbon atoms.

The term "ECN" or "equivalent carbon number" means the sum of the number of carbon atoms in the acyl chains of a glyceride molecule. For example, tripalmitin (tripalmitic glycerol), which is a simple triglyceride containing 3 acyl radicals of 16 carbon atoms, has an ECN of 3×16=48. Conversely, a triglyceride with an ECN=40 may have "mixed" acyl chain lengths of 8, 16 and 16; 10, 14 and 16; 8, 14 and 18, etc. Naturally occurring oils are frequently "mixed" with respect to specific fatty acids, but tend not to contain LCFAs and MCFAs on the same glycerol backbone. Thus, triacylglycerols with ECNs of 24-30 typically contain predominately medium chain fatty acids, while triacylglycerols with ECNs of greater than 43 typically contain predominantly long chain fatty acids. Triacylglycerols having an ECNs of 32-42 typically contain one or two MCFA in combination with one or two LCFAs to "fill" the triglyceride. Triacylglycerols with ECNs in the range of greater than 30 to less than 48 typically represent mixed triacylglycerol species that are absent from or are present in significantly lower concentrations in physical mixtures. The fatty acids that occur in foods usually contain an even number of carbon atoms in an unbranched chain, e.g., lauric or dodecanoic acid.

The term "self-immolative group," as used herein, refers to a bivalent chemical moiety that comprises a covalent, scissile bond as one of its bivalent bonds and a stable, covalent bond with a therapeutic agent as its other bivalent bond, wherein the bond with the therapeutic agent becomes labile upon cleavage of the scissile bond. Examples of self-immolative groups include, but are not limited to, disulfide groups, hydrazones, acetal self-immolative groups, carboxyacetal self-immolative groups, carboxy(methylacetal) self-immolative groups, p-hydroxybenzyl self-immolative groups, para-hydroxybenzyl carbonyl self-immolative groups, flipped ester self-immolative groups, and trimethyl lock, or 2-hydroxyphenyl carbamate (2-HPC) self-immolative groups. A number of other suitable self-immolative groups are known in the art as described, for example, in C. A. Blencowe et al., *Polym. Chem.* 2011, 2, 773-790 and F. Kratz et al., ChemMedChem. 2008, 3(1), 20-53; Huvelle, S. et al., *Org. Biomol. Chem.* 2017, 15(16), 3435-3443; and Alouane, A. et al., *Angewandte Chemie International Edition* 2015, 54 (26), 7492-7509; and Levine, M. N. et al., *Chem. Sci. VL-IS*-3 (8), 2412-2420; each of which is hereby incorporated by reference in its entirety.

As used here in, the term "therapeutic agent," "active pharmaceutical agent," "active agent," or "pharmaceutical agent" includes any therapeutic agent or imaging (contrasting) agent which would benefit from transport via the intestinal lymphatic system, for example, to enable oral administration (e.g. of an intravenously administered therapeutic agent), to avoid first pass metabolism, avoid liver toxicity or other toxicity, or for targeted delivery within the lymphatic system.

Lipid prodrug compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, Handbook of Chemistry and Physics, 98th Ed. Additionally, general principles of organic chemistry are described in "Organic Chemistry," Thomas Sorrell, University Science Books, Sausalito: 1999, and *March's Advanced Organic Chemistry: Reactions, Mechanisms, and Structure*, M. B. Smith and J. March, 7th Edition, John Wiley & Sons, 2013, the entire contents of which are hereby incorporated by reference.

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bicyclic ring" or "bicyclic ring system" refers to any bicyclic ring system, i.e. carbocyclic or heterocyclic, saturated or having one or more units of unsaturation, having one or more atoms in common between the two rings of the ring system. Thus, the term includes any permissible ring fusion, such as ortho-fused or spirocyclic. As used herein, the term "heterobicyclic" is a subset of "bicyclic" that requires that one or more heteroatoms are present in one or both rings of the bicycle. Such heteroatoms may be present at ring junctions and are optionally substituted, and may be selected from nitrogen (including N-oxides), oxygen, sulfur (including oxidized forms such as sulfones and sulfonates), phosphorus (including oxidized forms such as phosphates), boron, etc. In some embodiments, a bicyclic group has 7-12 ring members and 0-4 heteroatoms independently selected from nitrogen, oxygen, or sulfur. As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bicyclic rings include:

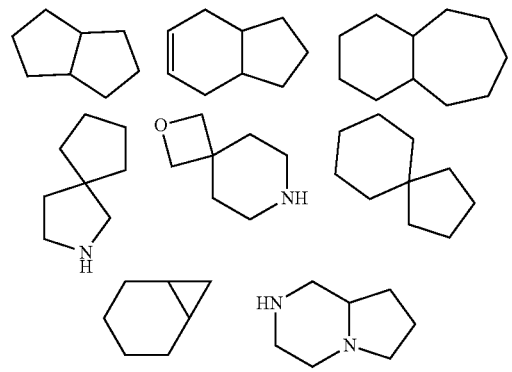

Exemplary bridged bicyclics include:

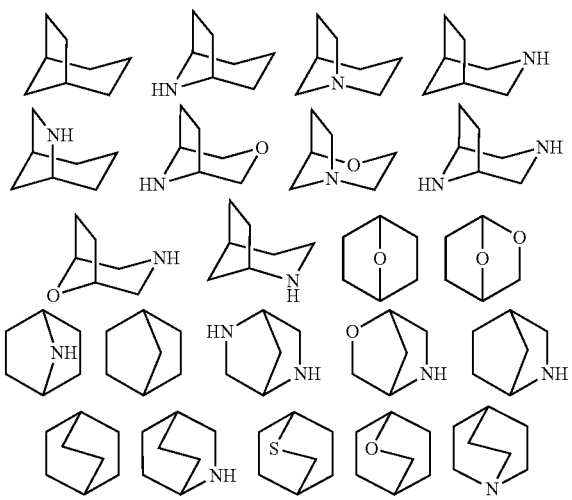

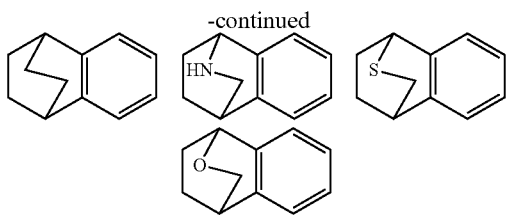

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain" refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3 (4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Each optional substituent on a substitutable carbon is a monovalent substituent independently selected from halogen; —$(CH_2)_{0-4}R^\circ$; —$(CH_2)_{0-4}OR^\circ$; —$O(CH_2)_{0-4}R^\circ$, —$O$—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; $(CH_2)_{0-4}O(CH_2)_{0-1}Ph$ which may be substituted with $R^\circ$; —CH=CHPh, which may be substituted with $R^\circ$; —$(CH_2)_{0-4}O(CH_2)_{0-1}$-pyridyl which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR$—, $SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$SC(S)SR^\circ$, —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$S(O)(NR^\circ)R^\circ$; —$S(O)_2N=C(NR^\circ_2)_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; $SiR^\circ_3$; —$(C_{1-4}$ straight or branched alkylene$)O$—$N(R^\circ)_2$; or —$(C_{1-4}$ straight or branched alkylene$)C(O)O$—$N(R^\circ)_2$.

Each $R^\circ$ is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted by a divalent substituent on a saturated carbon atom of $R^\circ$ selected from =O and =S; or each $R^\circ$ is optionally substituted with a monovalent substituent independently selected from halogen, —$(CH_2)_{0-2}R^\bullet$, -(halo$R^\bullet$), —$(CH_2)_{0-2}OH$, —$(CH_2)_{0-2}OR^\bullet$, —$(CH_2)_{0-2}CH(OR^\bullet)_2$; —$O(haloR^\bullet)$, —CN, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR^\bullet_3$, —$C(O)SR^\bullet$, —$(C_{1-4}$ straight or branched alkylene$)C(O)OR^\bullet$, or —$SSR^\bullet$.

Each $R^\bullet$ is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, and wherein each $R^\bullet$ is unsubstituted or where preceded by halo is substituted only with one or more halogens; or wherein an optional substituent on a saturated carbon is a divalent substituent independently selected from =O, =S, =$NNR^*_2$, =$NNHC(O)R^*$, =$NNHC(O)OR^*$, =$NNHS(O)_2R^*$, =$NR^*$, =$NOR^*$, —$O(C(R^*_2))_{2-3}O$—, or —$S(C(R^*_2))_{2-3}S$—, or a divalent substituent bound to vicinal substitutable carbons of an "optionally substituted" group is —$O(CR^*_2)_{2-3}O$—, wherein each independent occurrence of $R^*$ is selected from hydrogen, $C_{1-6}$ aliphatic or an unsubstituted 5-6-membered saturated, partially unsaturated, or aryl ring having 0-4 heteroatoms independently selected from nitrogen, oxygen, or sulfur.

When $R^*$ is $C_{1-6}$ aliphatic, $R^*$ is optionally substituted with halogen, —$R^\bullet$, -(halo$R^\bullet$), —OH, —$OR^\bullet$, —$O(haloR^\bullet)$, —CN, —C(O)OH, —$C(O)OR^\bullet$, —$NH_2$, —$NHR^\bullet$, —$NR^\bullet_2$, or —$NO_2$, wherein each $R^\bullet$ is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, and wherein each $R^\bullet$ is unsubstituted or where preceded by halo is substituted only with one or more halogens.

An optional substituent on a substitutable nitrogen is independently —$R^\dagger$, —$NR^\dagger_2$, —$C(O)R^\dagger$, —$C(O)OR^\dagger$, —$C(O)C(O)R^\dagger$, —$C(O)CH_2C(O)R^\dagger$, —$S(O)_2R^\dagger$, —$S(O)_2NR^\dagger_2$, —$C(S)NR^\dagger_2$, —$C(NH)NR^\dagger_2$, or —$N(RT)S(O)_2R^\dagger$; wherein each RT is independently hydrogen, $C_{1-6}$ aliphatic, unsubstituted —OPh, or an unsubstituted 5-6-membered saturated, partially unsaturated, or aryl ring having 0-4 heteroatoms independently selected from nitrogen, oxygen, or sulfur, or, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur; wherein when RT is $C_{1-6}$ aliphatic, RT is optionally substituted with halogen, —$R^\bullet$, -(halo$R^\bullet$), —OH, —$OR^\bullet$, —$O(haloR^\bullet)$, —CN, —C(O)OH, —$C(O)OR^\bullet$, —$NH_2$, —$NHR^\bullet$, —$NR^\bullet_2$, or —$NO_2$, wherein each $R^\bullet$ is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, and wherein each $R^\bullet$ is unsubstituted or where preceded by halo is substituted only with one or more halogens.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts include salts of an amino group (or other basic group) formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid, or by using other methods used in the art such as ion exchange. Other pharmaceutically acceptable salts include adipate, alginate, ascorbate, aspartate, benzenesulfonate, benzoate, besylate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

3. Uses, Formulation and Administration

Uses of Lymphatic-Directing Lipid Prodrugs

Disclosed lymphatic-directing lipid prodrugs, as well as pharmaceutically acceptable compositions comprising a disclosed lipid prodrug, and a pharmaceutically acceptable excipient, diluent, or carrier, are useful for treating a variety of diseases, disorders or conditions. Such diseases, disorders, or conditions include those described herein.

One of ordinary skill in the art will recognize and appreciate that each of the therapeutic agents described herein are known to be associated with treatment of one or more diseases, disorders, or conditions. Accordingly, it will be appreciated that, in certain embodiments, the present invention provides a method of treating a disease, disorder, or condition in a patient in need thereof comprising administering to said patient a disclosed lipid prodrug.

The presently disclosed lipid prodrugs are useful for the stable transport of pharmaceutical agents to the intestinal lymph and release of the pharmaceutical agents in the lymph, lymphocytes, lymphoid tissues, tissues with high lipase activity such as adipose tissue, certain cancers, the liver, or in the systemic circulation. Disclosed lipid prodrugs are particularly useful for the transport and release of pharmaceutical agents that benefit from avoidance of first pass metabolism, for example, therapeutic agents that exhibit greater than about 50% first pass metabolism when administered orally. In some embodiments, the therapeutic agent exhibits greater than about 60% first pass metabolism when administered orally. In some embodiments, the therapeutic agent exhibits greater than about 70%, 80%, or 90% first pass metabolism when administered orally.

The presently disclosed lipid prodrugs are also useful for the targeted release of the therapeutic agent within the lymphatic system, for example, in the lymph, lymphocytes and lymphoid tissues, as well as in tissues with high lipase activity such as adipose tissue, certain cancers, or the liver. In some embodiments, the therapeutic agent exhibits poor lymphatic transport when administered orally. In some embodiments, the therapeutic exhibits less than 70%, 60%, 50%, 40%, 30%, 20%, 15%, 10%, 8%, 5%, 4%, 3% 2%, 1%, 0.5%, 0.25%, 0.2%, 0.15%, or 0.1% lymphatic transport when administered orally. In contrast, the present invention provides for improved lymphatic transport of such therapeutic agents. In some embodiments, a disclosed lipid prodrug exhibits at least 1%, 5%, 7.5%, 10%, 12.5%, 15%, 20%, 25%, 30%, 35%, 40%, or 50% lymphatic transport when administered orally. In some embodiments, a disclosed lipid prodrug exhibits about 1-50%, 5-40%, 10-30%, 15-25%, or about 50%, 40%, 30%, 25%, 20%, 15%, 12.5%, 10%, 7.5%, 5%, 2.5%, or 1% lymphatic transport when administered orally, as measured by either w/w % of the lipid prodrug administered or w/w % of the therapeutic agent in its lipid prodrug form vs. the unmodified therapeutic agent.

In some embodiments, a disclosed lipid prodrug is delivered to the central nervous system (CNS) or crosses the blood-brain barrier (BBB) via the lymphatic system.

In some embodiments, the present invention provides a method of modulating an immune response, comprising administering to a patient in need thereof an effective amount of a disclosed lipid prodrug that comprises an immunomodulatory therapeutic agent. In some embodiments, the immune response includes one or more immune responses mediated by the lymphatic system, or mediated by immune cells in the lymphatic system. In some embodiments, the patient is suffering from a hyperproliferative disease, disorder, or condition such as cancer. In some embodiments, the patient is suffering from an autoimmune disease, disorder, or condition. In certain embodiments, the disease, disorder, or condition is any of those listed in any of Tables 1 through 7.

Therapeutic agents that may benefit from the stable transport to the intestinal lymph and release in the lymph, lymphocytes, lymphoid tissues, tissues with high lipase activity such as adipose tissue, certain cancers, the liver or in the systemic circulation include, but are not limited to, testosterone, mycophenolic acid, oestrogens (estrogen), morphine, tetrahydrocannabinol, cannabidiol, metoprolol, raloxifene, alphaxolone, statins such as atorvastatin, pentazocine, propranolol, L-DOPA, buprenorphine, midazolam, lidocaine, chlorpromazine, amitriptyline, nortriptyline, pentazocine, isosorbidedinitrate, glyceryl trinitrate, oxprenolol, labetalol, verapamil, salbutamol, epitiostanol, melphalan, and lovastatin.

Pharmaceutically Acceptable Compositions

According to another embodiment, the present invention provides a composition comprising a lipid prodrug of the present disclosure and a pharmaceutically acceptable carrier, adjuvant, or vehicle. The amount of lipid prodrug in the composition is an amount effective to treat the relevant disease, disorder, or condition in a patient in need thereof (an "effective amount"). In some embodiments, a composition of the present disclosure is formulated for oral administration to a patient.

The term "patient," as used herein, means an animal, for example a mammal, such as a human.

The term "pharmaceutically acceptable carrier, adjuvant, or vehicle" refers to a nontoxic carrier, adjuvant, or vehicle that does not destroy the pharmacological activity of the agent with which it is formulated. Pharmaceutically acceptable carriers, adjuvants or vehicles that may be used in the disclosed compositions include, but are not limited to, ion exchangers, alumina, stearates such as aluminum stearate, lecithin, serum proteins such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. In some embodiments, the composition is formulated as a lipophilic mixture, such as a lipid-based composition.

Compositions of the present invention may be administered orally, parenterally, enterally, intracisternally, intraperitoneally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the composition is administered orally, intraperitoneally, or intravenously. In some embodiments, the composition is a transmucosal formulation. In some embodiments, the composition is injected directly into the lymphatic system. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

To aid in delivery of the composition, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, may also be added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, pharmaceutically acceptable compositions may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

In some embodiments, the pharmaceutically acceptable composition is formulated for oral administration. Such formulations may be administered with or without food. In some embodiments, the pharmaceutically acceptable composition is administered without food. In other embodiments, the pharmaceutically acceptable composition is administered with food.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

Therapeutic agents can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In some embodiments, the lipid prodrug is formulated as an orally administrable, lipid-based formulation. Lipid-based formulations for oral delivery are known in the art and may include, for example, substantially non-aqueous vehicles which typically contain one or more lipid components. The lipid vehicles and resulting lipid formulations may be usefully classified as described below according to their shared common features according to the lipid formulation classification system (LFCS) (Pouton, C. W., Eur. J. Pharm. Sci. 11 (Supp 2), S93-S98, 2000; Pouton, C. W., Eur. J. Pharm. Sci. 29 278-287, 2006).

Lipid vehicles, and the resulting lipid formulations, may contain oil/lipids and/or surfactants, optionally with co-solvents. In the LFCS terminology, Type I formulations include oils or lipids which require digestion, such as mono, di and tri-glycerides and combinations thereof. Type II formulations are water-insoluble self emulsifying drug delivery systems (SEDDS) which contain lipids and oils used in Type I formulations, with additional water insoluble surfactants. Type III formulations are SEDDS or self-microemulsifying drug delivery systems (SMEDDS) which contain lipids and oils used in Type I formulations, with additional water-soluble surfactants and/or co-solvents (Type IIIa) or a greater proportion of water-soluble components (Type IIIb). Type IV formulations contain predominantly hydrophilic surfactants and co-solvents (e.g. PEG, propylene glycol and diethylene glycol monoethyl ether) and are useful for drugs which are poorly water soluble but not lipophilic. Any such lipid formulation (Type I-IV) is contemplated herein for use with a disclosed lipid prodrug or pharmaceutical composition thereof.

In some embodiments, the lipid vehicle contains one or more oils or lipids, without additional surfactants, co-surfactants or co-emulsifiers, or co-solvents, i.e. it consists essentially of one or more oils or lipids. In some further embodiments, the lipid vehicle contains one or more oils or lipids together with one or more water-insoluble surfactants, optionally together with one or more co-solvents. In some embodiments, the lipid vehicle contains one or more oils or lipids together with one or more water-soluble surfactants, optionally together with one or more co-solvents. In some embodiments, the lipid vehicle contains a mixture of oil/lipid, surfactant and co-solvent. In some embodiments, the lipid vehicle consists essentially of one or more surfactants/co-surfactants/co-emulsifiers, and/or solvents/co-solvents.

Examples of oils or lipids which may be used in the present invention include almond oil, babassu oil, blackcurrant seed oil, borage oil, canola oil, castor oil, coconut oil, cod liver oil, corn oil, cottonseed oil, evening primrose oil, fish oil, grape seed oil, mustard seed oil, olive oil, palm kernel oil, palm oil, peanut oil, rapeseed oil, safflower oil, sesame oil, shark liver oil, soybean oil, sunflower oil, walnut oil, wheat germ oil, avocado oil, bran oil, hydrogenated castor oil, hydrogenated coconut oil, hydrogenated cottonseed oil, hydrogenated palm oil, hydrogenated soybean oil, partially hydrogenated soybean oil, hydrogenated vegetable oil, caprylic/capric glycerides, fractionated triglycerides, glyceryl tricaprate, glyceryl tricaproate, glyceryl tricaprylate, glyceryl tricaprylate/caprate, glyceryl tricaprylate/caprate, glyceryl tricaprylate/caprate/laurate, glyceryl tricaprylate/caprate/linoleate, glyceryl tricaprylate/caprate/stearate, glyceryl trilaurate, glyceryl monolaurate, glyceryl behenate, glyceryl monolinoleate, glyceryl trilinolenate, glyceryl trioleate, glyceryl triundecanoate, glyceryl tristearate linoleic glycerides, saturated polyglycolized glycerides, synthetic medium chain triglycerides containing primarily $C_{8-12}$ fatty acid chains, medium chain triglycerides containing primarily $C_{8-12}$ fatty acid chains, long chain triglycerides containing primarily $>C_{12}$ fatty acid chains, modified triglycerides, fractionated triglycerides, and mixtures thereof.

Examples of mono and diglycerides which may be used in such formulations include glycerol mono- and diesters having fatty acid chains from 8 to 40 carbon atoms, including hydrolysed coconut oils (e.g. Capmul® MCM), hydrolysed corn oil (e.g. Maisine™35-1). In some embodiments, the monoglycerides and diglycerides are mono- or di-saturated fatty acid esters of glycerol having fatty acid chains of 8 to 18 carbon chain length (e.g. glyceryl monostearate, glyceryl distearate, glyceryl monocaprylate, glyceryl dicaprylate, glyceryl monocaprate and glyceryl dicaprate). Mixtures of fatty acids ("structured glycerides") adapted for enhancing the absorption and transport of lipid soluble compounds are disclosed in, e.g., U.S. Pat. No. 6,013,665, which is hereby incorporated by reference.

Suitable surfactants for use in the lipid formulations include propylene glycol mono- and di-esters of $C_{8-22}$ fatty acids, such as, but not limited to, propylene glycol monocaprylate, propylene glycol dicaprylate, propylene glycol monolaurate, sold under trade names such as Capryol® 90, Labrafac® PG, Lauroglycol® FCC, sugar fatty acid esters, such as, but not limited to, sucrose palmitate, sucrose laurate, and sucrose stearate; sorbitan fatty acid esters such as, but not limited to, sorbitan laurate, sorbitan palmitate, and sorbitan oleate; polyoxyethylene sorbitan fatty acid esters such as, but not limited to, polysorbate 20, polysorbate 40, polysorbate 60, polysorbate 80, and polysorbate 85; polyoxyethylene mono- and di-fatty acid esters including, but not limited to, polyoxyl 40 stearate and polyoxyl 40 oleate; a mixture of polyoxyethylene mono- and di-esters of $C_{8-22}$ fatty acids and glyceryl mono-, di-, and tri-esters of $C_{8-22}$ fatty acids as sold under tradenames such as Labrasol®, Gelucire® 44/14, Gelucire® 50/13, and Labrafil®; polyoxyethylene castor oils compound such as, but not limited to, polyoxyl 35 castor oil, polyoxyl 40 hydrogenated castor oil, and polyoxyl 60 hydrogenated castor oil, as are sold under tradenames such as Cremophor®/Kolliphor EL, Cremophor®/Kolliphor® RH40, and Cremophor®/Kolliphor® RH60; polyoxyethylene alkyl ethers including, but not limited to, polyoxyl 20 cetostearyl ether and polyoxyl 10 oleyl ether; DL-α-tocopheryl polyethylene glycol succinate; glyceryl mono-, di-, and tri-esters; glyceryl mono-, di-, and tri-esters of $C_{8-22}$ fatty acids; sucrose mono-, di-, and tri-esters; sodium dioctylsulfosuccinate; polyoxyethylene-polyoxypropylene copolymers such as, but not limited to poloxamer 124, poloxamer 188, and poloxamer 407; polyoxyethylene ethers of $C_{8-22}$ fatty alcohols including, but not limited to, polyoxyethylenelauryl alcohol, polyoxyethylenecetyl alcohol, polyoxyethylene stearyl alcohol, polyoxyethyleneoleyl alcohol, as sold under tradenames such as Brij® 35, Brij® 58, Brij® 78, Brij® 98, or a mixture of any two or more thereof.

A co-emulsifier, or co-surfactant, may be used in the formulation. A suitable co-emulsifier or co-surfactant may be a phosphoglyceride; a phospholipid, for example lecithin, or a free fatty acid that is liquid at room temperature, for example, iso-stearic acid, oleic acid, linoelic acid, linolenic acid, palmitic acid, stearic acid, lauric acid, capric acid, caprylic acid, and caproic acid.

Suitable solvents/co-solvents include ethanol, propylene glycol, polyethylene glycol, diethylene glycol monoethyl ether, and glycerol.

A polymer may also be used in the formulation to inhibit drug precipitation or to alter the rate of drug release. A range of polymers have been shown to impart these properties and are well known to those skilled in the art. Suitable polymers include hydroxypropylmethylcellulose, hydroxypropylmethylcellulose acetyl succinate, other cellulose-derived polymers such as methylcellulose; poly(meth)acrylates, such as the Eudragit series of polymers, including Eudragit E100, polyvinylpyrrolidone, or others as described in, e.g. Warren et al., Mol. Pharmaceutics 2013, 10, 2823-2848.

Formulations may be chosen specifically to provide for sustained release of the active in the gastrointestinal (GI) tract in order to control the rate of absorption. Many different approaches may be used to achieve these ends including the use of high melting point lipids that disperse/erode slowly in the GI tract, or polymers that form a matrix that slowly erodes. These formulations may take the form of large monolithic dose forms or may be present as micro or nano-particulate matrices as described in, for example, in Mishra, Handbook of Encapsulation and Controlled Release, CRC Press, Boca Raton, (2016) ISBN 978-1-4822-3234-9, Wilson and Crowley Controlled Release in Oral Drug Delivery, Springer, NY, ISBN 978-1-4614-1004-1 (2011) or Wise, Handbook of Pharmaceutical Controlled Release Technology, Marcel Dekker, NY, ISBN 0-82467-0369-3 (2000).

Formulations may also contain materials commonly known to those skilled in the art to be included in lipid based formulations, including antioxidants, for example, butylated hydroxyanisole (BHA) or butylated hydroxytoluene (BHT) and solidifying agents such as microporous silica, for example magnesium alumino-metasilicate (Neusilin).

In some embodiments, the lipid prodrug may be co-administered orally with an enzyme inhibitor to increase stability of the prodrug in the gastrointestinal tract or enterocyte. In certain embodiments, the enzyme inhibitor inhibits pancreatic lipases, examples of which include, but are not limited to, Alli® (orlistat). In other embodiments it is envisaged that the enzyme inhibitor will inhibit cellular lipase enzymes such as monoacylglycerol lipase, an example of which includes, but is not limited to, JZL184 (4-nitrophenyl-4-[bis(1,3-benzodioxol-5-yl)(hydroxy) methyl]piperidine-1-carboxylate).

Combination Therapies

A provided lipid prodrug, or pharmaceutically acceptable composition thereof, may be administered to a patient in need thereof in combination with one or more additional therapeutic agents and/or therapeutic processes.

The lipid prodrug or pharmaceutically acceptable composition thereof can be administered alone or in combination with one or more other therapeutic compounds, possible combination therapy taking the form of fixed combinations or the administration of the lipid prodrug or composition and one or more other therapeutic compounds being staggered or given independently of one another, or the combined administration of fixed combinations and one or more other therapeutic compounds. A disclosed lipid prodrug or composition can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Such additional agents may be administered separately from a provided lipid prodrug or composition, as part of a multiple dosage regimen. Alternatively, those agents may be part of a single dosage form, mixed together with a disclosed lipid prodrug in a single composition. If administered as part of a multiple dosage regime, the two active agents may be submitted simultaneously, sequentially or within a period of time from one another.

As used herein, the term "combination," "combined," and related terms refers to the simultaneous or sequential administration of therapeutic agents in accordance with the present disclosure. For example, a disclosed lipid prodrug may be administered with another therapeutic agent simultaneously or sequentially in separate unit dosage forms or together in a single unit dosage form. Accordingly, the present disclosure provides a single unit dosage form comprising a disclosed lipid prodrug, an additional therapeutic agent, and a pharmaceutically acceptable carrier, adjuvant, or vehicle. In some embodiments, the additional agent is formulated in a separate composition from the lipid prodrug.

The amount of both a disclosed lipid prodrug and additional therapeutic agent (in those compositions which comprise an additional therapeutic agent as described above) that may be combined with the carrier materials to produce a single dosage form will vary depending upon the patient treated and the particular mode of administration. In certain embodiments, compositions of this invention should be formulated so that a dosage of between 0.01-100 mg/kg body weight/day of a disclosed lipid prodrug can be administered.

In those compositions which comprise an additional therapeutic agent, that additional therapeutic agent and the disclosed lipid prodrug may act synergistically. Therefore, the amount of additional therapeutic agent in such compositions will be less than that required in a monotherapy utilizing only that therapeutic agent. In such compositions, a dosage of between 0.01-1,000 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Examples of agents with which the lipid prodrugs of this invention may be combined include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention include a monoclonal antibody or a siRNA therapeutic.

In another embodiment, the present invention provides a method of treating an inflammatory disease, disorder or condition by administering to a patient in need thereof a disclosed lipid prodrug and one or more additional therapeutic agents. Such additional therapeutic agents may be small molecules or a biologic and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), JAK inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating gout comprising administering to a patient in need thereof a disclosed lipid prodrug and one or more additional therapeutic agents selected from non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol and febuxostat (Uloric®).

In another embodiment, the present invention provides a method of treating rheumatoid arthritis comprising administering to a patient in need thereof a disclosed lipid prodrug and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a disclosed lipid prodrug and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating lupus comprising administering to a patient in need thereof a disclosed lipid prodrug and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating inflammatory bowel disease comprising administering to a patient in need thereof a disclosed lipid prodrug and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a disclosed lipid prodrug and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophylline (Theo-Dur®, Theolair®, Slo-bid®, Uniphyl®, Theo-24®) and aminophylline, and IgE antibodies such as omalizumab (Xolair®).

In some embodiments, the present invention provides a method of treating COPD comprising administering to a patient in need thereof a disclosed lipid prodrug and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, and combinations thereof.

In some embodiments, the present invention provides a method of treating HIV comprising administering to a patient in need thereof a disclosed lipid prodrug and one or more additional therapeutic agents selected from nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), and combinations thereof.

In another embodiment, the present invention provides a method of treating a hematological malignancy comprising administering to a patient in need thereof a disclosed lipid prodrug and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a Bcl-2 inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a solid tumor comprising administering to a patient in need thereof a disclosed lipid prodrug and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a Bcl-2 inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a hematological malignancy comprising administering to a patient in need thereof a disclosed lipid prodrug and a Hedgehog (Hh) signaling pathway inhibitor. In some embodiments, the hematological malignancy is DLBCL.

In another embodiment, the present invention provides a method of treating diffuse large B-cell lymphoma (DLBCL) comprising administering to a patient in need thereof a disclosed lipid prodrug and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a disclosed lipid prodrug and one or more additional therapeutic agents selected from bortezomib (Velcade®), and dexamethasone (Decadron®), a hedgehog signaling inhibitor, a Bcl-2 inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating Waldenstrom's macroglobulinemia comprising administering to a patient in need thereof a disclosed lipid prodrug and one or more additional therapeutic agents selected from chlorambucil (Leukeran®), cyclophosphamide (Cytoxan®, Neosar®), fludarabine (Fludara®), cladribine (Leustatin®), rituximab (Rituxan®), a hedgehog signaling inhibitor, a Bcl-2 inhibitor, a BTK inhibitor, a JAK/pan-JAK inhibitor, a TYK2 inhibitor, a PI3K inhibitor, and a SYK inhibitor.

In some embodiments, the present invention provides a method of treating Alzheimer's disease comprising administering to a patient in need thereof a disclosed lipid prodrug and one or more additional therapeutic agents selected from donepezil (Aricept®), rivastigmine (Excelon®), galantamine (Razadyne®), tacrine (Cognex®), and memantine (Namenda®).

In another embodiment, the present invention provides a method of treating organ transplant rejection or graft vs. host disease comprising administering to a patient in need thereof a disclosed lipid prodrug and one or more additional therapeutic agents selected from a steroid, cyclosporin, FK506, rapamycin, a hedgehog signaling inhibitor, a Bcl-2 inhibitor, a BTK inhibitor, a JAK/pan-JAK inhibitor, a TYK2 inhibitor, a PI3K inhibitor, and a SYK inhibitor.

In another embodiment, the present invention provides a method of treating or lessening the severity of a disease comprising administering to a patient in need thereof a disclosed lipid prodrug and a BTK inhibitor, wherein the disease is selected from inflammatory bowel disease, arthritis, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, caused by HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, atopic dermatitis, degenerative joint disease, vitiligo, autoimmune hypopituitarism, Behcet's disease, scleraderma, mycosis fungoides, acute inflammatory responses (such as acute respiratory distress syndrome and ischemia/reperfusion injury), and Graves' disease.

In some embodiments the present invention provides a method of treating or lessening the severity of a disease comprising administering to a patient in need thereof a disclosed lipid prodrug and a Bcl-2 inhibitor, wherein the disease is an inflammatory disorder, an autoimmune disorder, a proliferative disorder, an endocrine disorder, a neurological disorder, or a disorder associated with transplantation. In some embodiments, the disorder is a proliferative disorder, lupus, or lupus nephritis. In some embodiments, the proliferative disorder is chronic lymphocytic leukemia, diffuse large B-cell lymphoma, Hodgkin's disease, small-cell lung cancer, non-small-cell lung cancer, myelodysplastic syndrome, lymphoma, a hematological neoplasm, or a solid tumor.

In another embodiment, the present invention provides a method of treating or lessening the severity of a disease comprising administering to a patient in need thereof a disclosed lipid prodrug and a PI3K inhibitor, wherein the disease is selected from a cancer, a neurodegenerative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a disclosed lipid prodrug and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

A disclosed lipid prodrug of the current invention may also be used to advantage in combination with an antiproliferative compound. Such antiproliferative compounds include, but are not limited to, aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethyl-amino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Letrozole is marketed under the trade names Femara™ or Femar™ Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™) daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™ Docetaxel is marketed under the trade name Taxotere™. Vinblastine sulfate is marketed under the trade name Vinblastin R. P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS—354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; Ilmofosine; RO 318220 and RO 320432; GO 6976; lsis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases (EGFR1 ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof, see WO2008118802), navitoclax (and analogs thereof, see U.S. Pat. No. 7,390,799), NH-1 (Shenayng Pharmaceutical University), obatoclax (and analogs thereof, see WO 2004/106328, hereby incorporated by reference), 5-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

Further examples of BTK inhibitory compounds, and conditions treatable by such compounds in combination with compounds of this invention can be found in WO 2008/039218 and WO 2011/090760, the entirety of which are incorporated herein by reference.

Further examples of SYK inhibitory compounds, and conditions treatable by such compounds in combination with compounds of this invention can be found in WO 2003/063794, WO 2005/007623, and WO 2006/078846, the entirety of which are incorporated herein by reference.

Further examples of PI3K inhibitory compounds, and conditions treatable by such compounds in combination with compounds of this invention can be found in WO 2004/019973, WO 2004/089925, WO 2007/016176, U.S. Pat. No. 8,138,347, WO 2002/088112, WO 2007/084786, WO 2007/129161, WO 2006/122806, WO 2005/113554, and WO 2007/044729 the entirety of which are incorporated herein by reference.

Further examples of JAK inhibitory compounds, and conditions treatable by such compounds in combination with compounds of this invention can be found in WO 2009/114512, WO 2008/109943, WO 2007/053452, WO 2000/142246, and WO 2007/070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with a disclosed lipid prodrug include, but are not limited to, bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term "cyclooxygenase inhibitor" as used herein includes, but is not limited to, Cox-2 inhibitors, 5-alkyl substituted 2-arylaminophenylacetic acid and derivatives, such as celecoxib (Celebrex™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase enzyme, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), a disclosed lipid prodrug can be used in combination with standard leukemia therapies, especially in combination with therapies used for the treatment of AML. In particular, a disclosed lipid prodrug can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

Disclosed lipid prodrugs are also useful as co-therapeutic compounds for use in combination with other drug substances such as anti-inflammatory, bronchodilatory or anti-histamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A disclosed lipid prodrug may be mixed with the other drug substance in a fixed pharmaceutical composition or it may be administered separately, before, simultaneously with or after the other drug substance. Accordingly the invention includes a combination of a disclosed lipid prodrug as hereinbefore described with an anti-inflammatory, bronchodilatory, antihistamine or anti-tussive drug substance, said disclosed lipid prodrug and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zafirlukast;

PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of disclosed lipid prodrugs with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzo-cyclohepten-8-yl]carbonyl]amino]phenyl]-methyl] tetrahydro-N,N-dimethyl-2H-pyran-4-aminium chloride (TAK-770).

In some embodiments, the additional therapeutic agent is selected from Abacavir, Abiraterone, Acetylcysteine, acyclovir, adefovir dipivoxil, Alatrofloxacin, Albendazole, albuterol, Alendronic acid, Altropane, Amifostine, Aminolevulinic acid, amiodarone (e.g. cosolvent-free), Amisulpride, amitriptyline, amprenavir, anastrozole, Apomorphine, apremilast, Arbutamine, Argatroban, Arsenic trioxide, aspirin, Atazanavir/cobicistat, Atorvastatin, Avibactam/ceftazidime, Azacitidine, azathioprine, Azithromycin, Belinostat, bendamustine, Bexarotene, Biapenem, Bicalutamide, Bortezomib, Bosentan, bosutinib, Bromfenac, Buprenorphine, Bupropion, Busulfan, C1 esterase inhibitor, Caffeine, calcium levofolinate, Cangrelor, capecitabine, capsaicin, Carfilzomib, Carvedilol, Cefepime, Ceftaroline fosamil, Ceftazidime, Ceftibuten, Ceftolozane/tazobactam, celecoxib, Celgosivir, chlorambucil, Cidofovir, Ciprofloxacin, Cladribine, Clazosentan, Clofarabine, Clopidogrel, cyclophosphamide, cytarabine, danazol, Dantrolene, dasatinib, Daunorubicin, Decitabine, Deferiprone, delavirdine, Deoxycholic acid, deoxythymidine, Dexamethasone, Dexmedetomidine, Dexrazoxane, Diclofenac, Didanosine, diethylcarbamazine, Docetaxel, Dolasetron, Doripenem, Doxapram, Doxercalciferol, Doxorubicin, doxycycline, Efavirenz, Eflapegrastim, elvitegravir, emtricitabine, Entacapone, Epacadostat, epinephrine, epitiostanol, Epoprostenol, ergotamine, Eribulin, Esomeprazole, estradiol, estrogen, etonogestrel, Ezetimibe, Ezetimibe/simvastatin, Fasudil, Fenoldopam, Fentanyl, Ferric carboxymaltose, Finasteride, Fingolimod, Florbenazine F18, Florbetaben F 18, florbetapir F 18, Fludarabine, Fluorine 18 AV 1451, fluorouracil, Fluoxymesterone, Flurpiridaz F-18, Flutafuranol F 18, Flutemetamol F 18, Fomepizole, Fosaprepitant, Fosphenytoin, Fospropofol, fulvestrant, Furosemide, Gadobenic acid, Gadobutrol, Gadoversetamide, Gadoxetate disodium, gemcitabine, Glimepiride, Granisetron, Guadecitabine, hydroxychloroquine, Ibandronic acid, ibuprofen, imatinib, Imiquimod, Iobenguane I-123, Ioflupane 1231, Ioxilan, Irinotecan, Isavuconazonium, isosorbidedinitrate, ivermectin, ixabepilone, labelalol, Lacosamide, lamivudine, Lamotrigine, Lansoprazole, Lapatinib, L-dopa, leflunomide, Letermovir, Letrozole, Levetiracetam, Levofloxacin, Levothyroxine, Lidocaine, lidocaine, Linezolid, Lobaplatin, Lomitapide, lopinavir, maraviroc, Meloxicam, melphalan, mercaptopurine, Meropenem, Mesna, methotrexate, Methylnaltrexone, Methylphenidate, metoprolol, midazolam, Minocycline IV, Mitoxantrone, Moxifloxacin, Mycophenolate mofetil, naloxone, naltrexone, naproxen, Nefazodone, nelarabine, nelfinavir, Nevirapine, nilotinib, Nilutamide, nitrosoureas, nortriptyline, Omacetaxine mepesuccinate, Omadacycline, Omeprazole, an opioid such as codeine, meperidine, fentanyl, morphine, oxycodone, hydrocodone, hydromorphone, or methadone, Oxaliplatin, oxprenolol, Oxybutynin, Oxymetholone, paclitaxel (Taxol®), Palonosetron, Pantoprazole, Paracetamol, Pemetrexed, pentazocine, Pentostatin, Phenylephrine, Pirmenol, platinum, Plazomicin, Plerixafor, ponatinib, pralatrexate, predisone, prednisolone, Propofol, propranolol, Quinapril, Radium-223 chloride, Raloxifene, raltegravir, Raltitrexed, Ramatroban, Regadenoson, Remifentanil, Remimazolam besylate, rilpivirine, rinotecan, Risperidone, Ritonavir, Rivastigmine, rofecoxib, Romidepsin, Ropeginterferon alfa-2b, Rotigotine, salbutamol, Salmeterol, Samarium 153 lexidronam, saquinavir, Selegiline, Sertraline, Sildenafil, Simvastatin, Sorivudine, Stavudine, sulfasalazine, Sulfur hexafluoride, Sumatriptan, Sunitinib, Tacrine, tamoxifen, Technetium Tc 99m trofolastat, Tedizolid, Temozolomide, tenofovir, Terbinafine, Testosterone propionate, thiotepa, Tianeptine, Tigecycline, Tizanidine, Topiramate, Topotecan, toremifene, Treprostinil, Tretinoin, Triciribine, verapamil, Verteporfin, Vinorelbine, Vismodegib, Voglibose, zalcitabine, zidovudine, Zileuton, or Zoledronic acid; or a pharmaceutically acceptable salt thereof.

The structure of the active compounds identified by code numbers, generic or trade names may be taken from the actual edition of the standard compendium "The Merck Index" or from databases, e.g. Patents International (e.g. IMS World Publications).

A disclosed lipid prodrug may also be used in combination with known therapeutic processes, for example, the administration of hormones or radiation. In certain embodiments, a disclosed lipid prodrug is used as a radiosensitizer, especially for the treatment of tumors which exhibit poor sensitivity to radiotherapy.

The disclosed lipid prodrugs and compositions, and any co-administered additional therapeutic agents, according to the method of the present invention, may be administered using any amount and any route of administration effective for treating or lessening the severity of a disease, disorder, or condition such as cancer, an autoimmune disorder, a proliferative disorder, an inflammatory disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. Disclosed lipid prodrugs are preferably formulated in dosage unit form for ease of administration and uniformity of dosage. The expression "dosage unit form" as used herein refers to a physically discrete unit of agent appropriate for the patient to be treated. It will be understood, however, that the total daily usage of a disclosed lipid prodrug or composition thereof and any co-administered additional therapeutic agents will be decided by the attending physician within the scope of sound medical judgment. The specific effective dose level for any particular patient or organism will depend upon a variety of factors including the disorder being treated and the severity of the disorder; the activity of the specific lipid prodrug employed; the specific composition employed; the age, body weight, general health, sex and diet of the patient; the time of administration, route of administration, and rate of excretion of the specific lipid prodrug or composition; the duration of the treatment; drugs used in combination or coincidental with the specific lipid prodrug or composition employed, and like factors well known in the medical arts. The term "patient," as used herein, means an animal, preferably a mammal, and most preferably a human.

4. Methods of Making Lipid Prodrugs

General Methods for Making Lipid Prodrugs

The lipid prodrug compounds of this invention may be prepared or isolated in general by synthetic and/or semi-synthetic methods known to those skilled in the art for analogous compounds and by methods described in detail in the Examples, herein.

The therapeutic agents comprised in disclosed lipid prodrugs (e.g., conjugated to a glyceride-based prodrug) may be purchased commercially or prepared by organic synthesis, semi-synthesis, fermentation (e.g. with viral vectors), and like methods known in the art.

In some embodiments, protecting groups (as defined below) can be used to manipulate therapeutic agents in preparation for conjugation to the remainder of the lipid prodrug structure, for example, to prevent undesired side reactions from taking place.

In the synthesis methods described herein, where a particular protecting group ("PG"), leaving group ("LG"), or transformation condition is depicted, one of ordinary skill in the art will appreciate that other protecting groups, leaving groups, and transformation conditions are also suitable and are contemplated. Such groups and transformations are described in detail in *March's Advanced Organic Chemistry: Reactions, Mechanisms, and Structure*, M. B. Smith and J. March, 7$^{th}$ Edition, John Wiley & Sons, 2013, *Comprehensive Organic Transformations*, R. C. Larock, 3$^{rd}$ Edition, John Wiley & Sons, 2018, and *Protective Groups in Organic Synthesis*, P. G. M. Wuts, 5$^{th}$ edition, John Wiley & Sons, 2014, the entirety of each of which is hereby incorporated herein by reference.

As used herein, the phrase "leaving group" (LG) includes, but is not limited to, halogens (e.g., fluoride, chloride, bromide, iodide), sulfonates (e.g., mesylate, tosylate, benzenesulfonate, brosylate, nosylate, triflate), diazonium, and the like.

As used herein, the phrase "oxygen protecting group" includes, for example, carbonyl protecting groups, hydroxyl protecting groups, etc. Hydroxyl protecting groups are well known in the art and include those described in detail in *Protective Groups in Organic Synthesis*, P. G. M. Wuts, 5$^{th}$ edition, John Wiley & Sons, 2014, and Philip Kocienski, in *Protecting Groups*, Georg Thieme Verlag Stuttgart, New York, 1994, the entireties of which are incorporated herein by reference. Examples of suitable hydroxyl protecting groups include, but are not limited to, esters, allyl ethers, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetyl), crotonate, 4-methoxy-crotonate, benzoate, p-benzylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy) methyl, benzyloxymethyl, beta-(trimethylsilyl)ethoxymethyl, and tetrahydropyranyl ethers. Examples of arylalkyl ethers include benzyl, p-methoxybenzyl (MPM), 3,4-dimethoxybenzyl, o-nitrobenzyl, p-nitrobenzyl, p-halobenzyl, 2,6-dichlorobenzyl, p-cyanobenzyl, and 2- and 4-picolyl.

Amino protecting groups are well known in the art and include those described in detail in *Protective Groups in Organic Synthesis*, P. G. M. Wuts, 5$^{th}$ edition, John Wiley & Sons, 2014, and Philip Kocienski, in *Protecting Groups*, Georg Thieme Verlag Stuttgart, New York, 1994, the entireties of which are incorporated herein by reference. Suitable amino protecting groups include, but are not limited to, aralkylamines, carbamates, cyclic imides, allyl amines, amides, and the like. Examples of such groups include t-butyloxycarbonyl (Boc), ethyloxycarbonyl, methyloxycarbonyl, trichloroethyloxycarbonyl, allyloxycarbonyl (Alloc), benzyloxocarbonyl (Cbz), allyl, phthalimide, benzyl (Bn), fluorenylmethylcarbonyl (Fmoc), formyl, acetyl, chloroacetyl, dichloroacetyl, trichloroacetyl, phenylacetyl, trifluoroacetyl, benzoyl, and the like.

One of skill in the art will appreciate that various functional groups present in compounds of the invention such as aliphatic groups, alcohols, carboxylic acids, esters, amides, aldehydes, halogens and nitriles can be interconverted by techniques well known in the art including, but not limited to reduction, oxidation, esterification, hydrolysis, partial oxidation, partial reduction, halogenation, dehydration, partial hydration, and hydration. See, for example, *March's Advanced Organic Chemistry: Reactions, Mechanisms, and Structure*, M. B. Smith and J. March, 7$^{th}$ Edition, John Wiley & Sons, 2013, *Comprehensive Organic Transformations*, R. C. Larock, 3$^{rd}$ Edition, John Wiley & Sons, 2018, the entirety of each of which is incorporated herein by reference. Such interconversions may require one or more of the aforementioned techniques, and certain methods for synthesizing compounds of the invention are described below.

As a general strategy, compounds of the present invention may be synthesized via one of the following routes:

Scheme 1. Synthesis of compounds of formula iii.

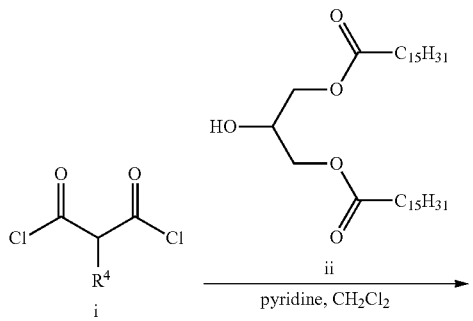

223

-continued

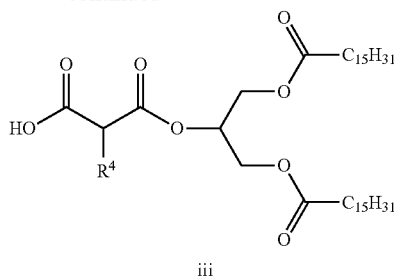

iii

Diacid chlorides i, which are readily available from the corresponding malonic acids, can be reacted with a diglyceride such as ii in the presence of pyridine or another appropriate base to give acid-triglyceride (acid-TG) iii (see Scheme 1). Formula iii is shown with $C_{15}H_{31}$ fatty acid side chains, but other fatty acids (such as those described above) can be substituted in this and other Formulas described below.

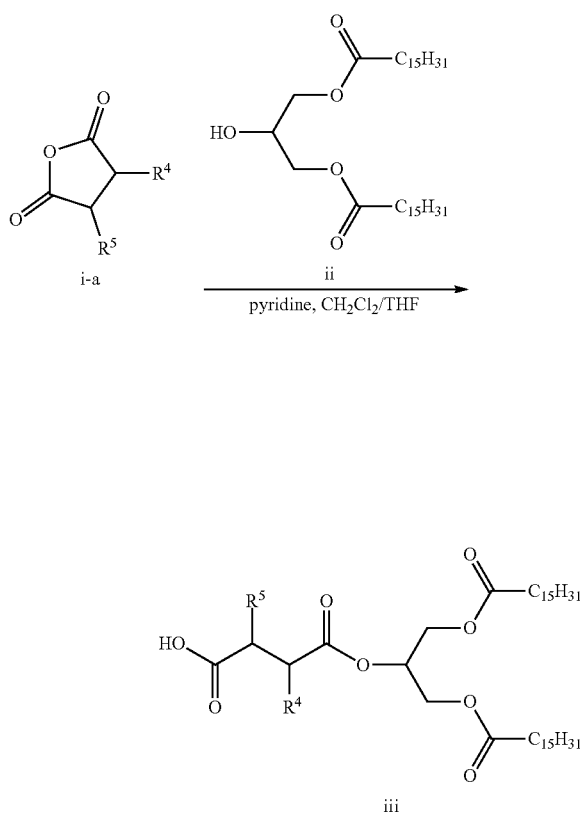

In cases where acid anhydride i-a is available, acid-TG iii can be generated by ring-opening with diglyceride ii in the presence of pyridine or another appropriate base (Scheme 2). This method works best when $R^4$ and $R^5$ of acid anhydride i-a are identical, e.g. both Me, but will result in a regioisomeric mixture of acid-TG products iv when $R^4$ and $R^5$ differ from each other. Consequently, other methods, such as that outlined in Scheme 3, can advantageously be employed in this circumstance.

224

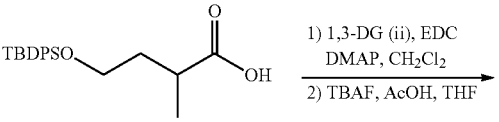

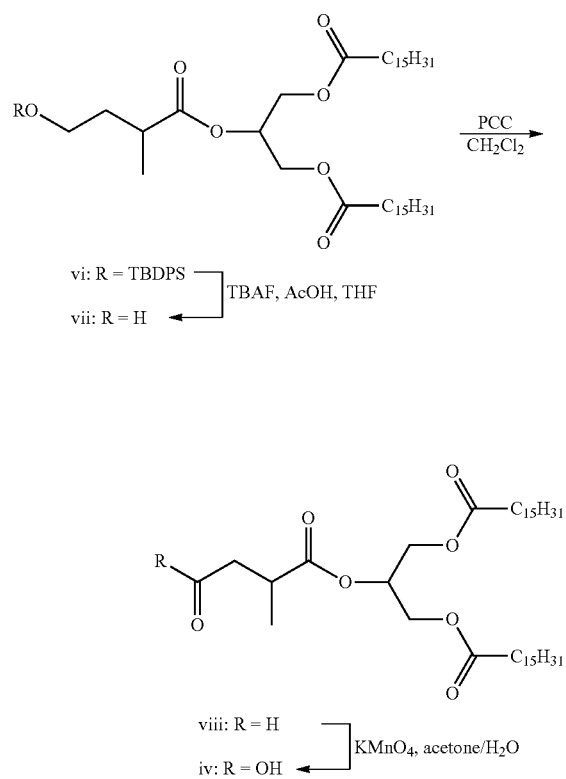

To obtain acid-TG iv as a single regioisomer in the specific example where $R^4$=Me or other alkyl or substitution and $R^5$=H, the known carboxylic acid v (Lienard, B. M. R. et al., *Org. Biomol. Chem.* 2008, 6, (13), 2282-2292) can be used as a starting point (see Scheme 3). Coupling of acid v with 1,3-DG ii under standard conditions produces TBDPS protected triglyceride vi, which can be treated with appropriate conditions such as TBAF and AcOH to afford alcohol vii. A two-step oxidation process (for example, PCC, then $KMnO_4$) can then be used to transform alcohol vii into the desired acid-TG iv via the intermediate aldehyde viii.

Scheme 4. Synthesis of compounds of formula x wherein ——M—— is an acetal self-immolative (ASI) group.

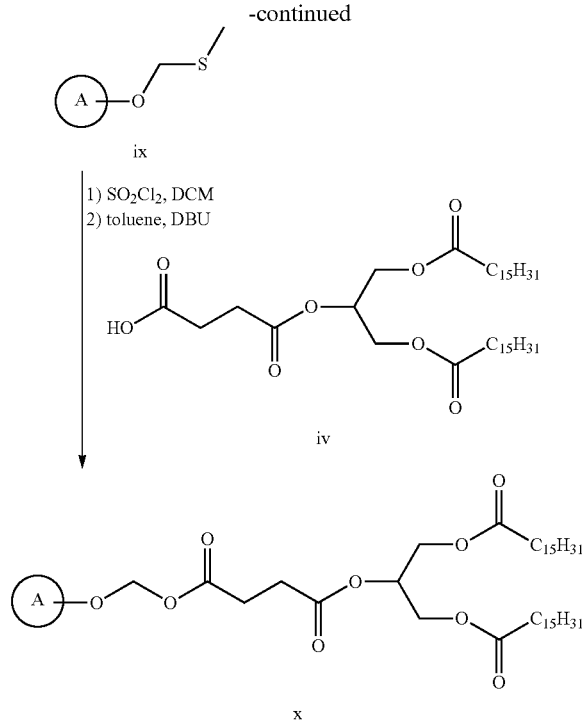

ix

1) SO₂Cl₂, DCM
2) toluene, DBU iv x

Scheme 5. Synthesis of compounds of formula xii wherein —M— is a carboxyacetal (CASI) or carboxy(methylacetal) (CMSI) self-immolative group.

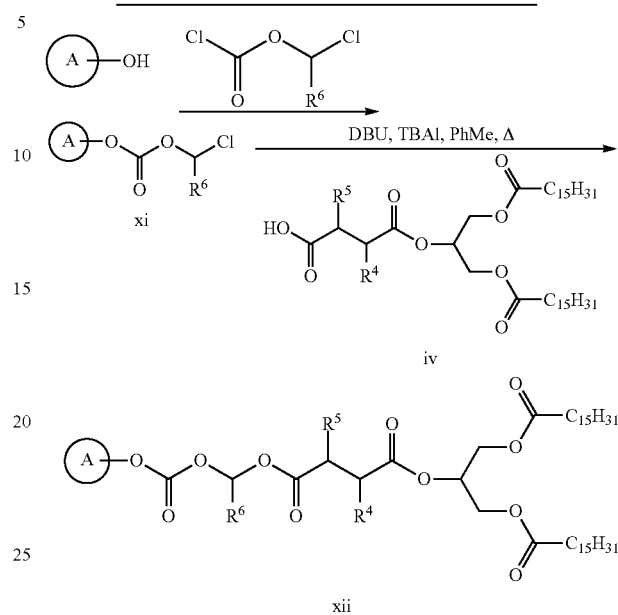

xi

DBU, TBAI, PhMe, Δ iv xii

For the synthesis of compounds containing an acetal self-immolative (ASI) group between the pharmaceutical agent and the alkyl spacer, the alcohol-bearing parent molecule must be functionalized and activated prior to conjugation with acid-triglyceride iii as outlined above in Scheme 4. Treatment of an alcohol with DMSO in a mixture of acetic anhydride and acetic acid results in the formation of (methylthio)methyl (MTM) ether ix. Activation of MTM ether ix using sulfuryl chloride forms a presumed sulfoxide species that can react with the carboxylate of acid-triglyceride iv to give the target compound x.

In cases where the pharmaceutical agent contains an alcohol, phenol or amine (primary or secondary) functional group, a modified version of the acetal self-immolative group can be used where an additional carboxy group is included. Reaction of the parent drug with a chloroalkyl chloroformate gives chloroalkyl carbonates (shown) or carbamates xi (see Scheme 5). Displacement of the halide leaving group is then accomplished by treatment with the carboxylate derived from acid-TG iv in an appropriate solvent such as refluxing toluene to afford the target compound xii.

Scheme 6. Synthesis of compounds of formula xviii wherein —M— is a trimethyl-lock (TML) self-immolative group.

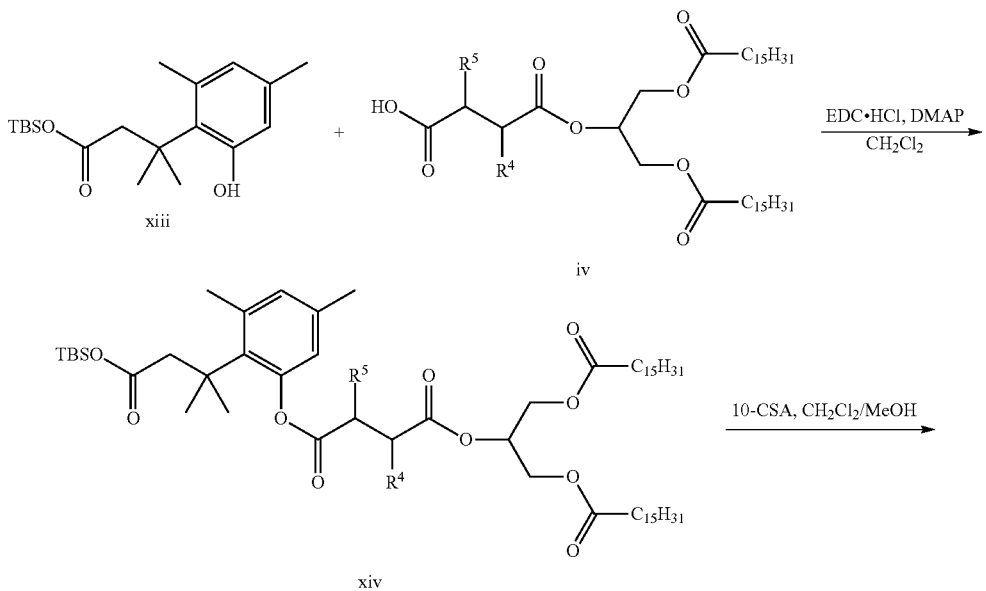

xiii + iv

EDC·HCl, DMAP
CH₂Cl₂ xiv

10-CSA, CH₂Cl₂/MeOH

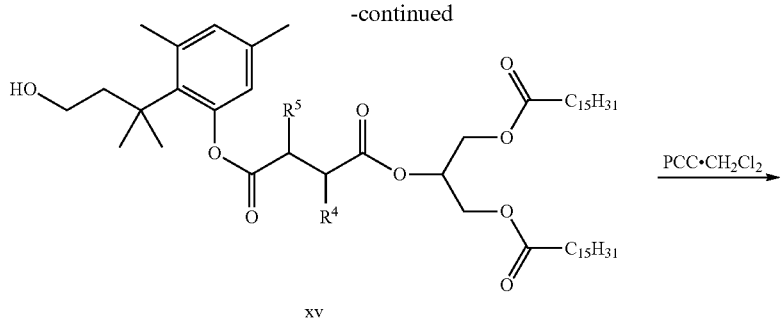

xv

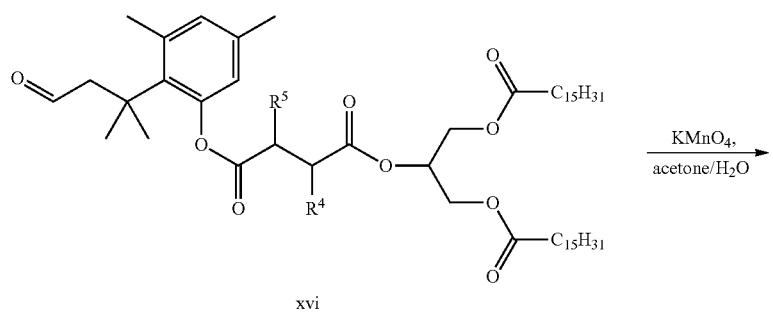

xvi

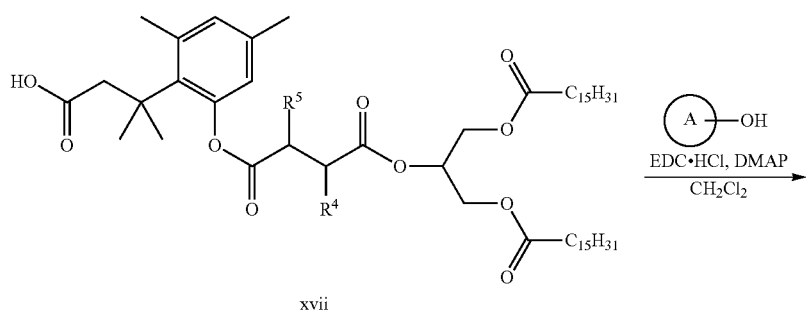

xvii

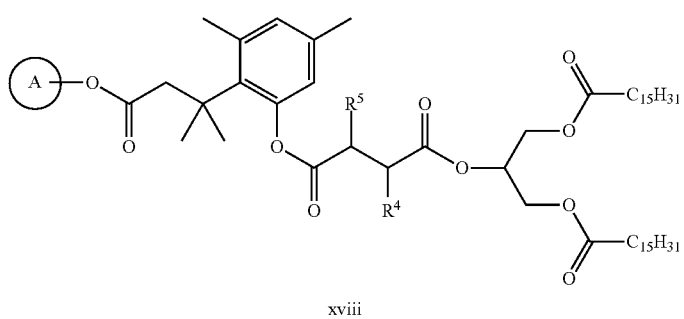

xviii

For the synthesis of prodrugs containing a trimethyl lock (TML) self-immolative group (Levine, M. N.; Raines, R. T. Chem. Sci. 2012, 3, 2412-2420, hereby incorporated by reference) between the pharmaceutical agent and the alkyl spacer to facilitate systemic release of the parent molecule, the acid-triglyceride iv must be functionalized with the TML moiety prior to conjugation with a pharmaceutical agent as outlined in Scheme 6. Coupling of acid-TG iv with TML phenol xiii under standard conditions gives triglyceride xiv, which can be deprotected under acidic conditions (10-camphorsulfonic acid) to give alcohol xv. Sequential oxidation of alcohol xv firstly to aldehyde xvi and then acid xvii, followed by coupling to either an alcohol (shown), amine or sulfonamide-containing pharmaceutical agent under standard conditions can give the target compound xviii.

Scheme 7. Synthesis of compounds of formula xxiv wherein —M— is a p-hydroxybenzyl carbonyl (PHB) self-immolative group.

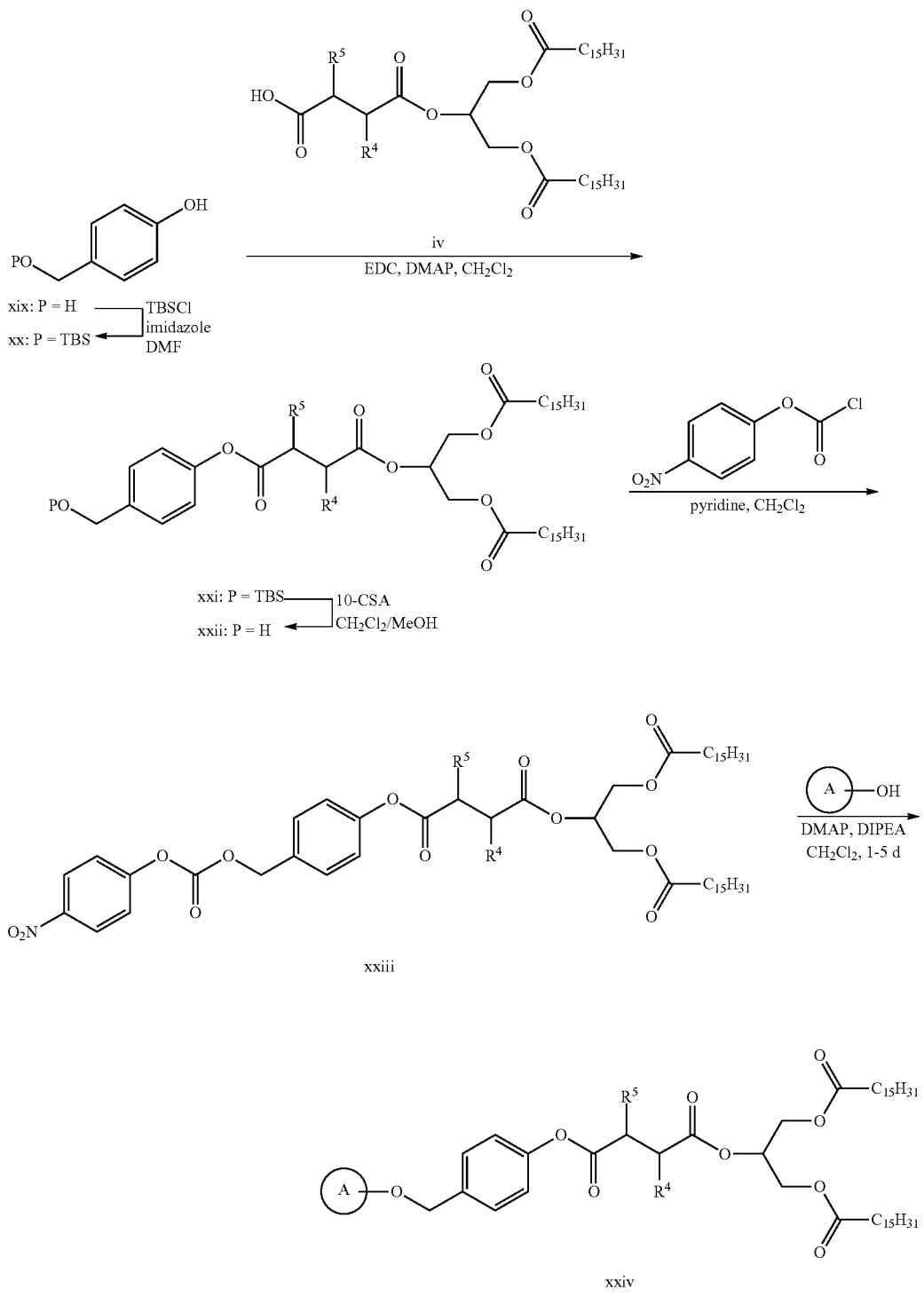

For the synthesis of compounds containing a p-hydroxybenzyl (PHB) carbonyl self-immolative group, the primary hydroxyl group of p-hydroxybenzyl alcohol (xix) is first protected as a silyl ether and the free phenolic hydroxyl group coupled with acid-TG iv to give PHB triglyceride xxi (see Scheme 7). After removal of the silicon protecting group, primary alcohol xxii can be activated by treatment with p-nitrophenyl (PNP) chloroformate to give PNP carbonate xxiii. Displacement of the PNP group is then achieved by reaction with a pharmaceutical agent (A-OH shown) under basic conditions to give the desired compound xxiv.

Scheme 8. Synthesis of compounds of formula III wherein —M— is a flipped-ester self-immolative(FSI) group.

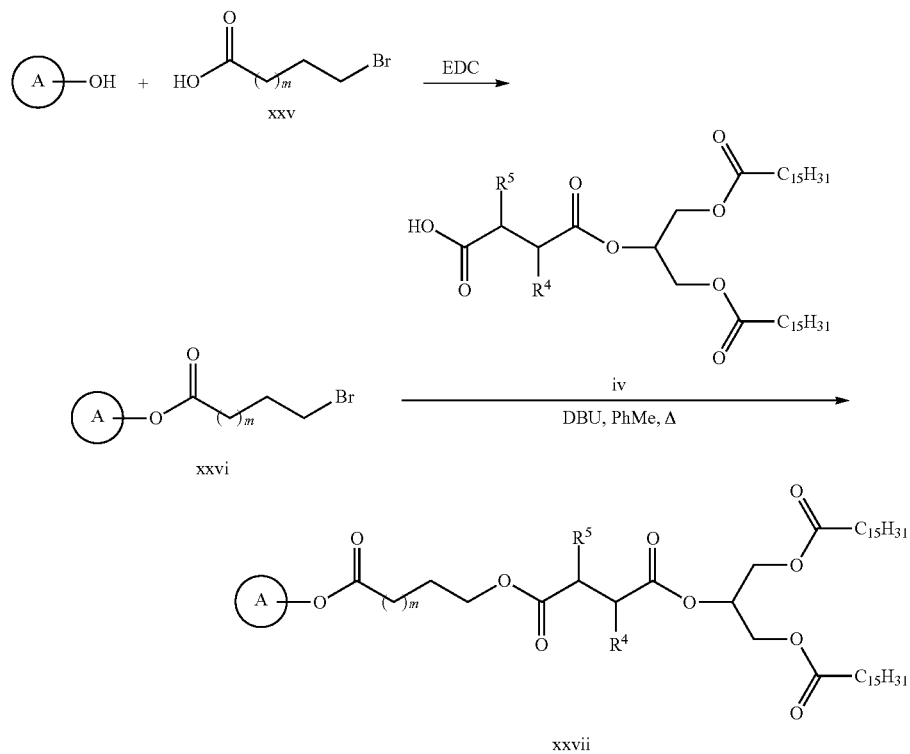

Without wishing to be bound by theory, it is believed that the flipped-ester self-immolative (FSI) group can liberate the free pharmaceutical agent by a cyclization mechanism, resulting in loss of either a four-carbon (FSI-4) or five-carbon (FSI-5) lactone. Alternatively, liberation of the agent may occur by a chemical or enzymatic mechanism in vivo. FSI prodrugs can be synthesized by coupling the pharmaceutical agent (A-OH shown) with either 4-bromobutyric acid (m=1) or 5-bromovaleric acid (m=2) (xxv) to give bromide xxvi (see Scheme 8). Displacement of bromide xxvi using the carboxylate derived from acid-TG iv generates the desired ester bond in target compound xxvii.

EXEMPLIFICATION

Example 1: Synthesis of Intermediates

List of Abbreviations equiv or eq: molar equivalents
rt or RT: room temperature
UV: ultra violet
HPLC: high pressure liquid chromatography
Rt: retention time
LCMS or LC-MS: liquid chromatography-mass spectrometry
NMR: nuclear magnetic resonance
TLC: thin layer chromatography
sat: saturated
aq: aqueous
Ac: acetyl
BINAP: (±)-2,2'-Bis(diphenylphosphino)-1,1'-binaphthalene
Bn: Benzyl
DBU: 1,8-Diazabicyclo[5.4.0]undec-7-ene
DCC: N,N'-Dicyclohexylcarbodiimide
DCM: Dichloromethane
DCE: Dichloroethane
DEA: Diethylamine
DIPA: Diisopropylamine
DMF: N,N-dimethylformamide
DMSO: dimethylsulfoxide
DMPU: N,N'-Dimethylpropyleneurea
ACN or MeCN: acetonitrile
DIPEA: diisopropylethylamine
EA or EtOAc: ethyl acetate
EDCI, EDC, or EDAC: 1-Ethyl-3-(3-dimethylaminopropyl)carbodiimide
TEA: triethylamine
THF: tetrahydrofuran
TBS: tert-butyldimethylsilyl
KHMDS: potassium hexamethyl disilylazide
Tf: trifluoromethanesulfonate
Ms: methanesulfonyl
NBS: N-bromosuccinimide
PCC: Pyridinium chlorochromate
PE: petroleum ether
TFA: trifluoroacetic acid
MMPP: magnesium monoperoxyphthalate
HATU: 1-[Bis(dimethylamino)methylene]-1H-1,2,3-triazolo[4,5-b]pyridinium 3-oxide Hexafluorophosphate
Cy: cyclohexyl
Tol: toluene
DMP: Dess-Martin periodinane
IBX: 2-iodoxybenzoic acid
PMB: p-methoxybenzyl
SEM: [2-(Trimethylsilyl)ethoxy]methyl

1,3-DG (Int-2)

Scheme 9. Synthesis of Int-2.

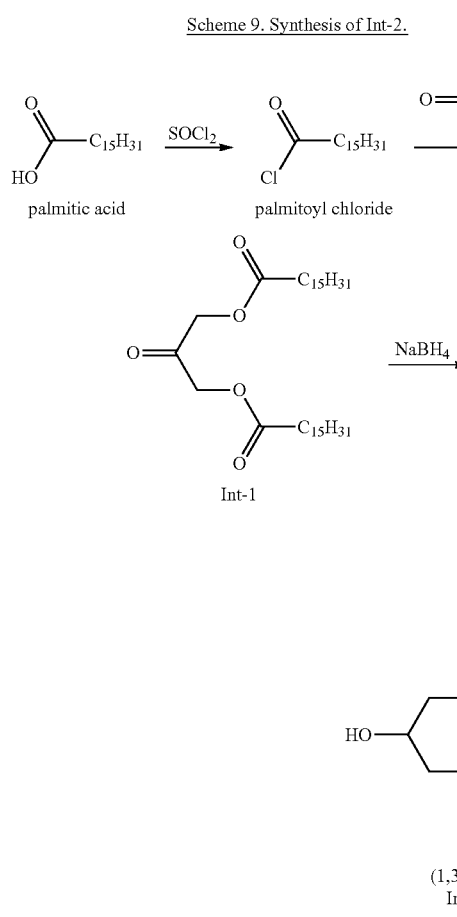

DMF (1 mL, 13.7 mmol) was added into a mixture of palmitic acid (433 g, 1.69 mol) in thionyl chloride (500 mL, 6.3 mol) at room temperature. The resultant reaction mixture was heated under reflux for 3 h. It was concentrated to dryness to afford palmitoyl chloride (453 g, 1.64 mol, 97% yield) as a yellowish oil, which was used in the next step without further purification.

To a mixture of 1,3-dihydroxypropan-2-one (77 g, 0.855 mol) and anhydrous pyridine (140 g, 1.76 mol) in anhydrous dichloromethane (2500 mL) under nitrogen at room temperature, was added with palmitic chloride (453 g, 1.64 mol). The mixture was stirred at room temperature for 16 h. It was diluted with MeOH (1000 mL) and water (2000 mL) and stirred for 30 min. The precipitate was collected by filter and dried to afford Int-1 (462 g, 0.815 mmol, 95% yield) as a white solid.

Int-1 (220 g, 388 mmol) was dissolved in a solution of THF (3000 mL) and water (200 mL) at 0° C. Sodium borohydride (22 g, 579 mmol) was added portion wise. After addition, the mixture was filtered to afford a cake, which was dried to afford compound Int-2 (1,3-DG) (177 g, 311 mmol, 80% yield) as a white solid. LC-MS: MS m/z=591 (M+Na+), RT=4.39 min; $^1$H NMR (400 MHz, chloroform-d) δ 4.20-4.05 (m, 5H), 2.35 (t, J=7.6 Hz, 4H), 1.62 (t, J=7.6 Hz, 4H), 1.25 (s, 48H), 0.88 (t, J=6.6 Hz, 6H).

C5βMe-Acid-2-TG (Int-4):

Scheme 10. Syntheisis of Int-4.

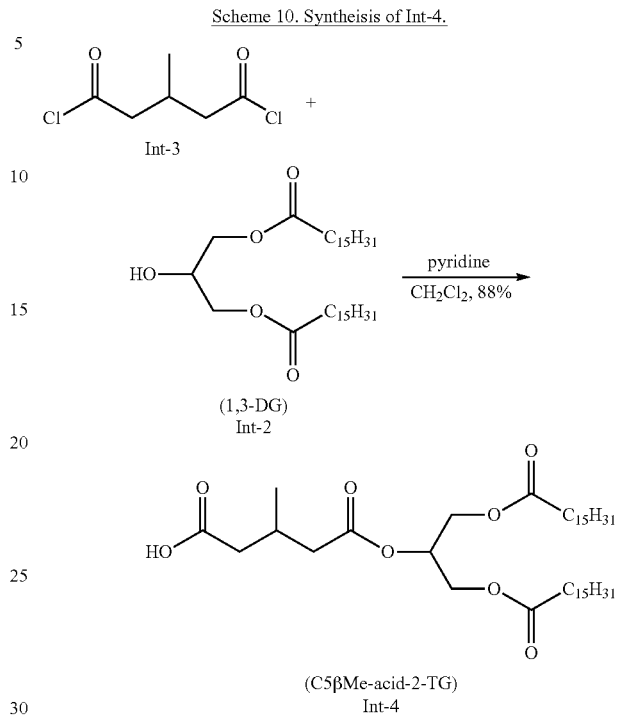

A mixture of 3-methylglutaric acid (500 mg, 3.42 mmol) and DMF (two drops) in thionyl chloride (2.48 mL, 34.2 mmol) was heated at reflux for two hours. The reaction was cooled to room temperature, diluted with toluene (5 mL) and concentrated under reduced pressure to give diacid chloride Int-3 (584 mg, 83%) as a yellow oil that was used without purification. $^1$H NMR (400 MHz, CDCl$_3$) δ 3.02 (dd, J=17.3, 6.1 Hz, 2H), 2.89 (dd, J=17.3, 7.2 Hz, 2H), 2.61 (m, 1H), 1.13 (d, J=6.8 Hz, 2H).

A solution of Int-2 (1,3-DG) (50.0 mg, 0.0879 mmol) and pyridine (71.1 µL, 0.879 mmol) in dichloromethane (2 mL) was added to acid chloride Int-3 (80.4 mg, 0.439) in dichloromethane (1.5 mL) and the mixture heated at reflux for two hours. The reaction was cooled to room temperature, diluted with ethyl acetate (15 mL) and 1 M HCl (5 mL) and the organic phase separated. The aqueous layer was further extracted with ethyl acetate (2×20 mL) and the combined organic extracts washed with 1 M HCl (20 mL) and brine (2×30 mL), dried (MgSO$_4$) and concentrated under reduced pressure to give the crude product. Purification by silica gel chromatography (20% to 45% ethyl acetate/hexanes) gave Int-4 (54.0 mg, 88%) as a colorless solid. $^1$H NMR (400 MHz, CDCl$_3$) δ 5.27 (m, 1H), 4.311 (dd, J=11.9, 4.2 Hz, 1H), 4.305 (dd, J=11.9, 4.2 Hz, 1H), 4.14 (dd, J=11.9, 5.6 Hz, 2H), 2.52-2.39 (m, 3H), 2.36-2.24 (m, 6H), 1.66-1.55 (m, 4H), 1.37-1.17 (m, 48H), 1.06 (d, J=6.3 Hz, 3H), 0.88 (t, J=6.8 Hz, 6H); $^{13}$C NMR (101 MHz, CDCl$_3$) δ 178.1 (C), 173.5 (2C; C), 171.4 (C), 69.3 (CH), 62.2 (2C; CH$_2$), 40.7 (CH$_2$), 40.4 (CH$_2$), 34.1 (2C; CH$_2$), 32.1 (2C; CH$_2$), 29.82 (6C; CH$_2$), 29.78 (4C; CH$_2$), 29.74 (2C; CH$_2$), 29.6 (2C; CH$_2$), 29.5 (2C; CH$_2$), 29.4 (2C; CH$_2$), 29.2 (2C; CH$_2$), 27.3 (CH), 25.0 (2C; CH$_2$), 22.8 (2C; CH$_2$), 19.8 (CH$_3$), 14.2 (2C; CH$_3$); ESI-HRMS: calcd. for C$_{41}$H$_{76}$NaO$_8$ [M+Na$^+$] 719.5432; found 719.5451.

Alternate Procedure (Larger Scale):

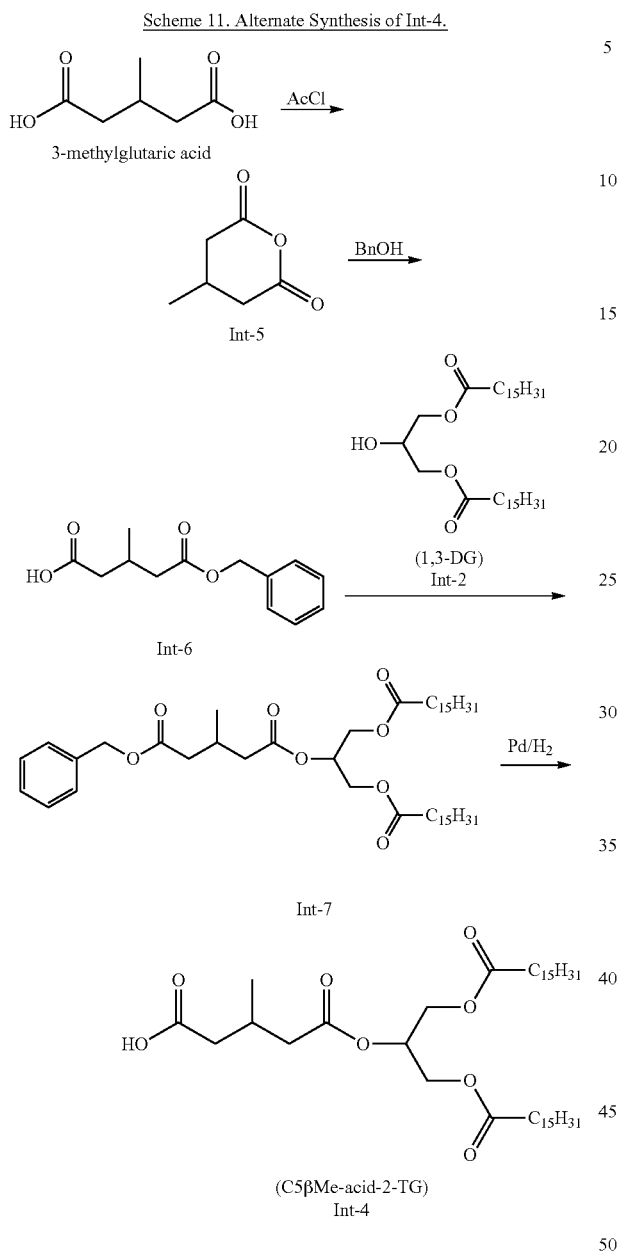

Scheme 11. Alternate Synthesis of Int-4.

A mixture of 3-methylglutaric acid (100 g, 685 mmol) and acetyl chloride (250 mL, 3.53 mol) was heated under reflux for 16 h, then concentrated to dryness before adding into a solution of pyridine (270 g, 3.4 mol) and benzyl alcohol (100 g, 926 mmol) in dichloromethane (1500 mL) at room temperature. The mixture was stirred for 72 h. The reaction was concentrated and the residue was purified by silica column chromatography, eluting with from 0 to 50% ethyl acetate in petroleum ether to afford Int-6 (70 g, 297 mmol, 43% yield) as a yellowish oil. $^1$H NMR (400 MHz, chloroform-d) δ 7.39-7.30 (m, 5H), 5.12 (s, 2H), 2.52-2.25 (m, 5H), 1.04 (d, J=6.6 Hz, 3H).

To a mixture of Int-6 (70 g, 297 mmol) and Int-2 (1,3-DG) (80 g, 140 mmol) in dichloromethane (1500 mL) was added EDCI (115 g, 600 mmol) and DMAP (3.66 g, 30 mmol). Triethylamine (100 mL, 719 mmol) was added drop wise at 0° C. The mixture was stirred at room temperature for 72 h. The reaction was concentrated to dryness and the residue was purified by silica column chromatography, eluting with ethyl acetate in petroleum ether from 0 to 50% to afford Int-7 (68 g, 86.5 mmol, 29% yield) as a white solid. $^1$H NMR (400 MHz, chloroform-d) δ 7.40-7.32 (m, 5H), 5.30-5.24 (m, 1H), 5.12 (s, 2H), 4.31-4.27 (m, 2H), 4.17-4.10 (m, 2H), 2.50-2.38 (m, 3H), 2.34-2.28 (m, 6H), 1.61-1.55 (m, 4H), 1.35-1.20 (m, 48H), 1.02 (d, J=6.4 Hz, 3H), 0.88 (t, J=6.6 Hz, 6H).

Int-7 (68 g, 86.5 mmol) and palladium on carbon (3 g) were suspended in THF (400 mL). The mixture was hydrogenated under hydrogen atmosphere at 30° C. for 16 h, then filtered and concentrated to dryness. The residue was further purified by trituration with hexane to afford Int-4 (C5βMe-acid-2-TG) (51 g, 73.2 mmol, 84% yield) as a white solid. LC-MS: MS m/z=719 (M+Na+), RT=3.83 min. $^1$H NMR (400 MHz, chloroform-d) δ 5.31-5.25 (m, 1H), 4.34-4.29 (m, 2H), 4.16-4.12 (m, 2H), 2.49-2.40 (m, 3H), 2.33-2.28 (m, 6H), 1.62-1.57 (m, 4H), 1.35-1.20 (m, 48H), 1.06 (d, J=6.4 Hz, 3H), 0.88 (t, J=6.6 Hz, 6H).

C10-Acid-2-TG:

Scheme 12. Synthesis of Int-9.

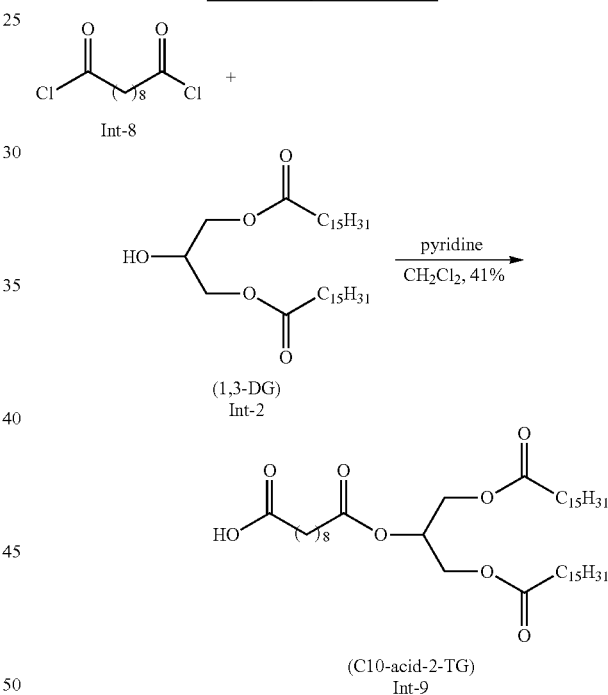

A mixture of sebacic acid (88.0 mg, 0.435 mmol) and DMF (one drop) in thionyl chloride (316 μL, 4.35 mmol) was heated at reflux for 1.5 hours. The reaction was cooled to RT, diluted with toluene (5 mL) and concentrated under reduced pressure to give diacid chloride Int-8 (104 mg, quant.) as a yellow oil that was used without purification. $^1$H NMR (400 MHz, chloroform-d) δ 2.88 (t, J=7.3 Hz, 4H), 1.76-1.66 (m, 4H), 1.42-1.26 (m, 8H).

A solution of Int-2 (1,3-DG) (45.0 mg, 0.0791 mmol) and pyridine (64.0 μL, 0.791 mmol) in dichloromethane (1.5 mL) was added to diacid chloride Int-8 (104 mg, 0.435 mmol) in dichloromethane (1.5 mL) and the mixture stirred at rt for 1.5 hours. The reaction was diluted with ethyl acetate (5 mL), water (10 mL) and 1 M HCl (3 mL) and the aqueous layer extracted with ethyl acetate (3×15 mL). The combined organic extracts were washed with 1 M HCl (30 mL) and brine (30 mL), dried (MgSO$_4$) and concentrated under reduced pressure to give the crude product. Purification by silica gel chromatography (20% to 50% ethyl acetate/hexanes) gave Int-9 (C10-acid-2-TG) (24.3 mg, 41%) as a pale yellow solid. $^1$H NMR (400 MHz, CDCl$_3$) δ 5.26 (m, 1H), 4.29 (dd, J=11.9, 4.4 Hz, 2H), 4.14 (dd, J=11.9, 5.9 Hz, 2H), 2.37-2.27 (m, 8H), 1.70-1.53 (m, 8H), 1.39-1.19 (m, 56H), 0.87 (t, J=6.9 Hz, 6H); $^{13}$C NMR (101 MHz, CDCl$_3$) δ 178.6 (C), 173.5 (2C; C), 173.0 (C), 69.0 (CH), 62.2 (CH$_2$), 34.3 (CH$_2$), 34.2 (2C; CH$_2$), 33.9 (CH$_2$), 32.01 (2C; CH$_2$), 29.85 (6C; CH$_2$), 29.81 (4C; CH$_2$), 29.77 (2C; CH$_2$), 29.6 (2C; CH$_2$), 29.5 (2C; CH$_2$), 29.4 (2C; CH$_2$), 29.3 (2C; CH$_2$), 29.2 (2C; CH$_2$), 29.11 (CH$_2$), 29.10 (CH$_2$), 25.00 (2C; CH$_2$), 24.95 (CH$_2$), 24.8 (CH$_2$), 22.8 (2C; CH$_2$), 14.3 (2C; CH$_3$).

Alternate Procedure (Larger Scale):

h, then cooled and concentrated to dryness. It was added into a solution of pyridine (270 g, 3.4 mol) and benzyl alcohol (100 g, 926 mmol) in dichloromethane (1500 mL) at room temperature and the mixture was stirred for 72 h. The reaction was concentrated and the residue was purified by column chromatography, eluting with from 0 to 50% ethyl acetate in petroleum ether to afford Int-11 (82 g, 281 mmol, 57% yield) as a yellowish oil. LC-MS: MS m/z=293 (M+H+), RT=1.45 min.

To a mixture of Int-11 (82 g, 281 mmol) and Int-2 (1,3-DG) (80 g, 140 mmol) in dichloromethane (1500 mL) was added EDCI (115 g, 600 mmol) and DMAP (3.66 g, 30 mmol). Then triethylamine (100 mL, 719 mmol) was added dropwise at 0° C. The mixture was stirred at room temperature for 72 h. The reaction was concentrated to dryness and the residue was purified by column chromatography, eluting

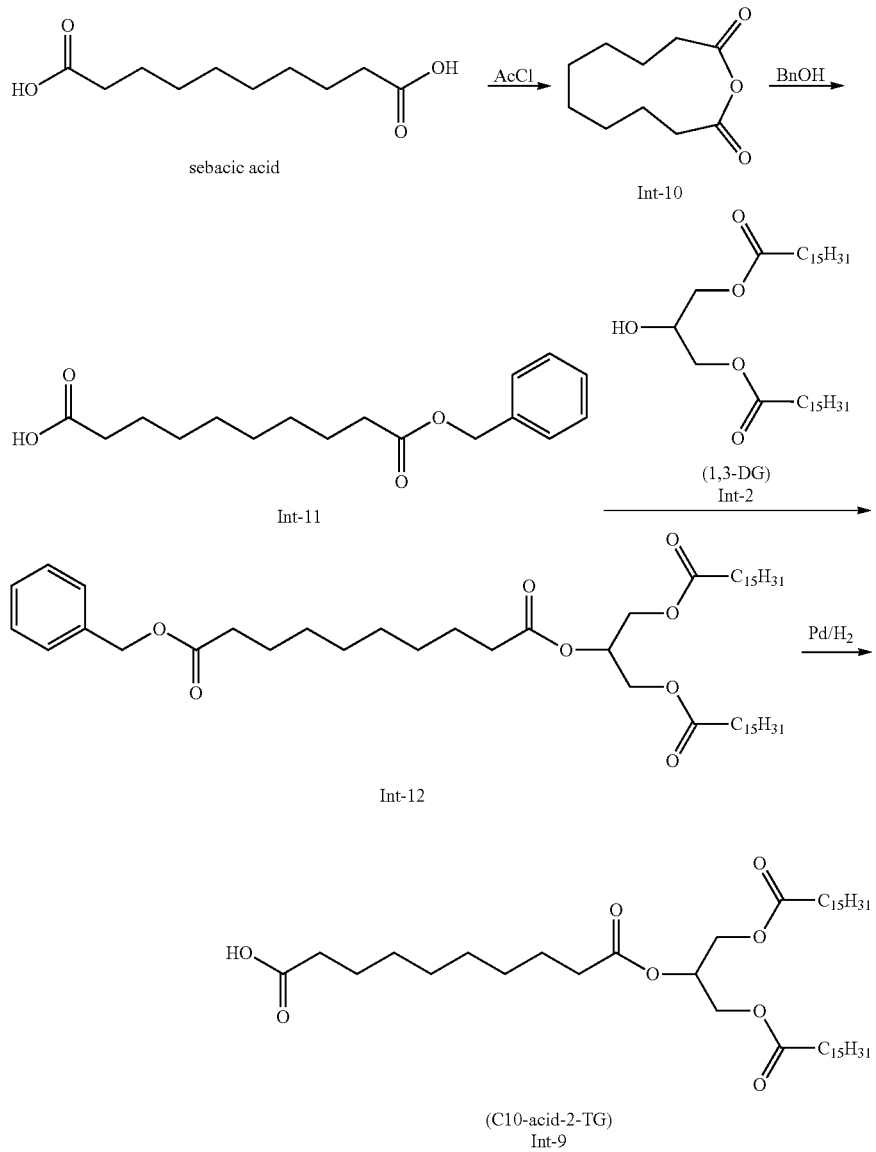

Scheme 13. Synthesis of Int-9.

A mixture of sebacic acid (100 g, 495 mmol) and acetyl chloride (250 mL, 3.53 mol) was heated under reflux for 16 with ethyl acetate in petroleum ether from 0 to 50% to afford Int-12 (65 g, 77 mmol, 27% yield) as a white solid. $^1$H NMR (400 MHz, chloroform-d) δ 7.38-7.29 (m, 5H), 5.27-5.25 (m, 1H), 5.11 (s, 2H), 4.31-4.27 (m, 2H), 4.17-4.12 (m, 2H), 2.37-2.29 (m, 8H), 1.65-1.57 (m, 8H), 1.35-1.20 (m, 56H), 0.88 (t, J=6.6 Hz, 6H).

Int-12 (65 g, 77 mmol) and palladium on carbon (3 g) were suspended in THF (400 mL). The mixture was hydrogenated under hydrogen atmosphere at 30° C. for 16 h, then it was filtered and the filtrate concentrated to dryness and then further purified by trituration with hexane to afford Int-9 (C10-acid-2-TG) (50 g, 66.4 mmol, 86% yield) as a white solid. LC-MS: MS m/z=775 (M+Na+), RT=5.95 min; $^1$H NMR (400 MHz, chloroform-d) δ 5.29-5.24 (m, 1H), 4.31-4.27 (m, 2H), 4.19-4.12 (m, 2H), 2.37-2.39 (m, 8H), 1.65-1.58 (m, 8H), 1.35-1.20 (m, 56H), 0.88 (t, J=6.6 Hz, 6H).

Int-120 was Prepared Using Similar Methods:

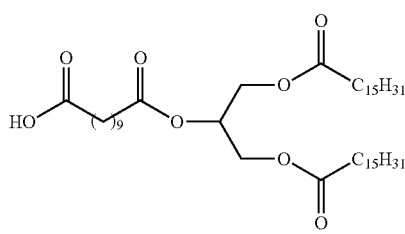

$^1$H NMR (401 MHz, CDCl$_3$) δ 5.25 (m, 1H), 4.28 (dd, J=11.9, 4.3 Hz, 2H), 4.13 (dd, J=11.9, 5.9 Hz, 2H), 2.35-2.26 (m, 8H), 1.65-1.54 (m, 8H), 1.35-1.18 (m, 58H), 0.86 (t, J=6.9 Hz, 6H); $^{13}$C NMR (101 MHz, CDCl$_3$) δ 179.9 (C), 173.4 (2C; C), 173.0 (C), 69.0 (CH), 62.2 (2C; CH$_2$), 34.3 (CH$_2$), 34.2 (2C; CH$_2$), 34.1 (CH$_2$), 32.0 (2C; CH$_2$), 29.81 (6C; CH$_2$), 29.77 (4C; CH$_2$), 29.74 (2C; CH$_2$), 29.59 (2C; CH$_2$), 29.48 (2C; CH$_2$), 29.38 (2C; CH$_2$), 29.36 (CH$_2$), 29.31 (2C; CH$_2$), 29.22 (2C; CH$_2$), 29.15 (CH$_2$), 29.13 (CH$_2$), 25.0 (3C; CH$_2$), 24.8 (CH$_2$), 22.8 (2C; CH$_2$), 14.2 (2C; CH$_3$). ESI-HRMS: calcd. for C$_{46}$H$_{86}$NaO$_8$ [M+Na$^+$] 789.6215; found 789.6218.

C12α'βMe-Acid-2-TG (Int-23 and Int-27):

Scheme 14. Synthesis of Int-23 and Int-27.

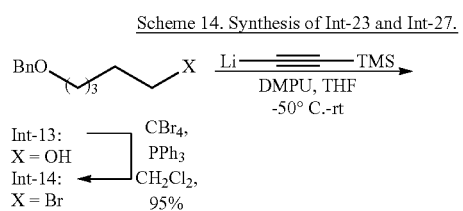

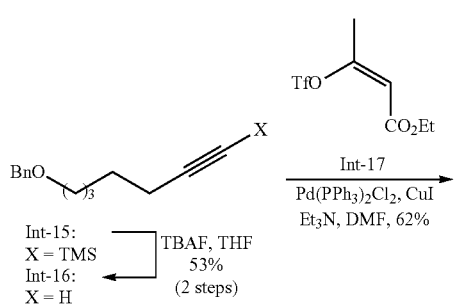

-continued

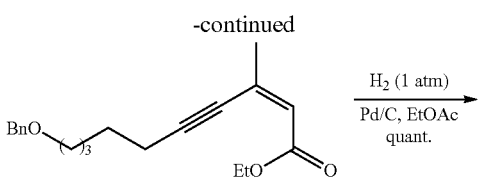
Int-18

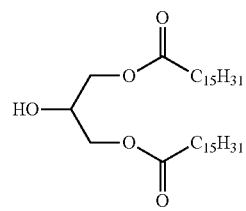
(1,3-DG)

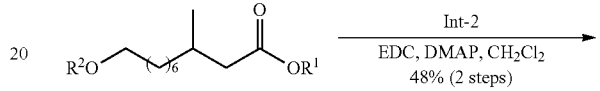

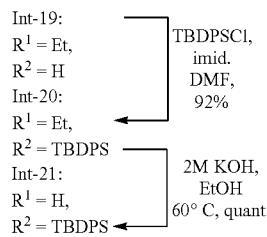

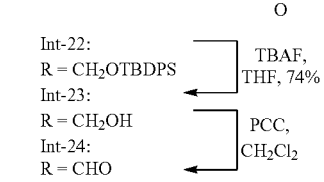
Int-26

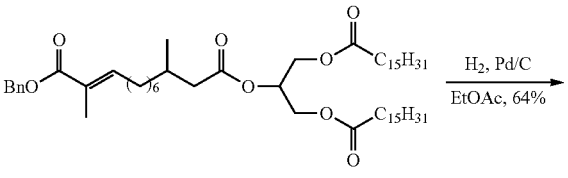
(C12α'βMe-acid-2-TG
Int-27

Int-13: prepared according to: Young, I. S.; Kerr, M. A. *J. Am. Chem. Soc.* 2007, 129, 1465-1469.

Int-14: prepared according to: Chowdhury, R.; Ghosh, S. K. *Org. Lett.* 2009, 11, 3270-3273.

n-Butyllithium (n-BuLi, 1.6 M in hexanes, 765 µL, 1.23 mmol) was added slowly to a solution of TMS-acetylene (198 µL, 1.40 mmol) in THF (1.5 mL) at −78° C. and the mixture stirred at −78° C. for five minutes then warmed to rt and stirred for a further 15 minutes. The reaction was re-cooled to −50° C., a solution of bromide Int-14 (90.0 mg, 0.350 mmol) in THF (1 mL) was added dropwise and the mixture stirred at −50° C. for 15 minutes and then at room temperature for 17 hours. The reaction was diluted with brine (15 mL) and the aqueous phase extracted with ethyl acetate (3×15 mL). The combined organic extracts were washed with brine (30 mL), dried (MgSO$_4$) and concentrated under reduced pressure to give the crude product. Purification by silica gel chromatography (4% to 5% ethyl acetate/hexanes) gave TMS alkyne Int-15 (45.9 mg, 48%) as a colorless oil also containing desilylated alkyne Int-16 (9.7 mg, 14% by $^1$H NMR integration) and small amounts of PPh$_3$. $^1$H NMR (400 MHz, CDCl$_3$) δ 7.37-7.26 (m, 5H), 4.50 (s, 2H), 3.48 (t, J=6.5 Hz, 2H), 2.23 (t, J=7.0 Hz, 2H), 1.68-1.60 (m, 2H), 1.58-1.42 (m, 4H), 0.14 (s, J=3.4 Hz, 7H).

Tetrabutylammonium fluoride (TBAF, 1.0 M in THF, 201 µL, 0.201 mmol) was added dropwise to a 7:2 mixture of silylalkyne Int-15 and alkyne Int-16 (55.6 mg combined, 0.215 mmol) in THF (1 mL) at 0° C. and the mixture stirred at room temperature for one hour. The reaction was diluted with water (5 mL) and sat. aq. NH$_4$Cl (3 mL) and the aqueous phase extracted with ethyl acetate (3×10 mL). The combined organic extracts were washed with brine (20 mL), dried (MgSO$_4$) and concentrated under reduced pressure to give the crude product. Purification by silica gel chromatography (4% ethyl acetate/hexanes) gave alkyne Int-16 (37.5 mg, 53% over two steps) as a colorless oil. $^1$H NMR (400 MHz, CDCl$_3$) δ 7.39-7.27 (m, 5H), 4.51 (s, 2H), 3.49 (t, J=6.5 Hz, 2H), 2.21 (td, J=6.9, 2.6 Hz, 2H), 1.95 (t, J=2.7 Hz, 1H), 1.70-1.61 (m, 2H), 1.60-1.48 (m, 4H); $^{13}$C NMR (101 MHz, CDCl$_3$) δ 138.7 (C), 128.5 (2C; CH), 127.7 (2C; CH), 127.6 (CH), 84.6 (C), 73.0 (CH$_2$), 70.3 (CH$_2$), 68.4 (CH), 29.4 (CH$_2$), 28.4 (CH$_2$), 25.5 (CH$_2$), 18.5 (CH$_2$).

Int-17: prepared according to: Kim, H.-O. et al. *Synlett* 1998, 1059-1060.

A suspension of PdCl$_2$(PPh$_3$)$_2$ (16.8 mg, 0.0240 mmol) in DMF (1.5 mL) was degassed using N$_2$ gas for five minutes, and then CuI (9.1 mg, 0.0480 mmol), Et$_3$N (66.8 µL, 0.480 mmol) and a degassed solution of alkyne Int-16 (48.5 mg, 0.240 mmol) and enol triflate Int-17 (94.3 mg, 0.360 mmol) in DMF (2 mL) were added. The mixture was degassed using a stream of N$_2$ for a further five minutes and then heated at 0° C. for one hour. The reaction was cooled to room temperature, diluted with ethyl acetate (30 mL), washed with 1 M HCl, sat. aq. NaHCO$_3$, water and brine (20 mL each), dried (MgSO$_4$) and concentrated under reduced pressure to give the crude product. Silica gel chromatography (4% to 5% ethyl acetate/hexanes) gave enyne Int-18 (46.6 mg, 62%) as a pale yellow oil. $^1$H NMR (400 MHz, CDCl$_3$) δ 7.37-7.24 (m, 5H), 5.92 (m, 1H), 4.50 (s, 2H), 4.17 (q, J=7.1 Hz, 2H), 3.48 (t, J=6.5 Hz, 2H), 2.45 (t, J=7.0 Hz, 2H), 2.01 (d, J=1.4 Hz, 3H), 1.69-1.59 (m, 4H), 1.56-1.49 (m, 2H), 1.27 (t, J=7.1 Hz, 3H); $^{13}$C NMR (101 MHz, CDCl$_3$) δ 165.4 (C), 138.8 (C), 135.9 (C), 128.5 (2C; CH), 127.7 (2C; CH), 127.6 (CH), 123.4 (CH), 102.9 (C), 80.0 (C), 73.0 (CH$_2$), 70.4 (CH$_2$), 60.0 (CH$_2$), 29.4 (CH$_2$), 28.4 (CH$_2$), 26.0 (CH$_3$), 25.7 (CH$_2$), 20.1 (CH$_2$), 14.4 (CH$_3$).

A solution of benzyl ether Int-18 (31.4 mg, 0.100 mmol) in ethyl acetate (8 mL) in a three-neck round-bottom flask was twice evacuated and flushed with N$_2$ gas, then palladium on carbon (10% w/w, 26.6 mg, 0.0250 mmol) was added and the resulting suspension re-evacuated and flushed with N$_2$ three times. The flask was fitted with a H$_2$ balloon, evacuated and flushed with H$_2$ three times and the reaction mixture stirred at RT under 1 atm of H$_2$ for one hour. The flask was then evacuated and flushed with N$_2$ and the reaction mixture filtered through a pad of Celite, washing with ethyl acetate (30 mL). The filtrate was concentrated under reduced pressure to give saturated alcohol Int-19 (23.0 mg, quant.) as a colorless oil that was used without purification. $^1$H NMR (400 MHz, CDCl$_3$) δ 4.12 (q, J=7.1 Hz, 2H), 3.63 (t, J=6.6 Hz, 2H), 2.28 (dd, J=14.6, 6.1 Hz, 1H), 2.09 (dd, J=14.6, 8.1 Hz, 1H), 1.94 (m, 1H), 1.60-1.50 (m, 2H), 1.25 (t, J=6.6 Hz, 3H), 1.40-1.13 (m, 10H), 0.92 (d, J=6.6 Hz, 3H); $^{13}$C NMR (101 MHz, CDCl$_3$) δ 173.6 (C), 63.2 (CH$_2$), 60.2 (CH$_2$), 42.1 (CH$_2$), 36.8 (CH$_2$), 32.9 (CH$_2$), 30.5 (CH), 29.8 (CH$_2$), 29.5 (CH$_2$), 26.9 (CH$_2$), 25.8 (CH$_2$), 19.9 (CH$_3$), 14.4 (CH$_3$).

Imidazole (9.6 mg, 0.141 mmol) and tert-butyl(chloro)diphenylsilane (TBDPSCl, 50.8 µL, 0.195 mmol) were added to a solution of alcohol Int-19 (18.0 mg, 0.0781 mmol) in DMF (3 mL) and the mixture stirred at RT for 16 hours. The reaction was diluted with ethyl acetate (20 mL), washed with brine (2×20 mL), dried (MgSO$_4$), and concentrated under reduced pressure to give the crude product. Purification by silica gel chromatography (4% ethyl acetate/hexanes with 0.5% Et$_3$N) gave TBDPS ether Int-20 (33.7 mg, 92%) as a colorless oil. $^1$H NMR (400 MHz, CDCl$_3$) δ 7.70-7.64 (m, 4H), 7.45-7.33 (m, 6H), 4.13 (q, J=7.1 Hz, 2H), 3.65 (t, J=6.5 Hz, 2H), 2.28 (dd, J=14.6, 6.0 Hz, 1H), 2.09 (dd, J=14.6, 8.2 Hz, 1H), 1.94 (m, 1H), 1.60-1.50 (m, 2H), 1.38-1.21 (m, 3H), 1.05 (s, J=2.9 Hz, 2H), 1.05 (s, 9H), 0.93 (d, J=6.6 Hz, 3H); $^{13}$C NMR (101 MHz, CDCl$_3$) δ 173.6 (C), 135.7 (4C; CH), 134.3 (2C; C), 129.6 (2C; CH), 127.7 (4C; CH), 64.1 (CH$_2$), 60.2 (CH$_2$), 42.1 (CH$_2$), 36.9 (CH$_2$), 32.7 (CH$_2$), 30.5 (CH), 29.9 (CH$_2$), 29.5 (CH$_2$), 27.01 (3C; CH$_3$), 26.99 (CH$_2$), 25.9 (CH$_2$), 19.9 (CH$_3$), 19.4 (C), 14.4 (CH$_3$).

A solution of potassium hydroxide (2.0 M, 427 µL, 0.853 mmol) was added to ester Int-20 (40.0 mg, 0.0853 mmol) in ethanol (2 mL) and the mixture heated at 80° C. for two hours. The reaction was cooled to RT, acidified to pH 1 by addition of 1 M HCl and the organic solvent removed under reduced pressure. The residue was diluted with water (5 mL) and the aqueous phase extracted with ethyl acetate (3×15 mL). The combined organic extracts were washed with brine (30 mL), dried (MgSO$_4$) and concentrated under reduced pressure to give crude acid Int-21 (37.6 mg, quant.) as a colorless oil that was used without purification. $^1$H NMR (400 MHz, CDCl$_3$) δ 7.74-7.63 (m, 4H), 7.45-7.34 (m, 6H), 3.65 (t, J=6.5 Hz, 2H), 2.35 (dd, J=15.0, 5.9 Hz, 1H), 2.14 (dd, J=15.0, 8.2 Hz, 1H), 1.95 (m, 1H), 1.61-1.50 (m, 2H), 1.38-1.18 (m, 10H), 1.04 (s, 9H), 0.96 (d, J=6.6 Hz, 3H); $^{13}$C NMR (101 MHz, CDCl$_3$) δ 179.5 (C), 135.7 (4C; CH), 134.3 (2C; C), 129.6 (2C; CH), 127.7 (4C; CH), 64.1 (CH$_2$), 41.7 (CH$_2$), 36.8 (CH$_2$), 32.7 (CH$_2$), 30.3 (CH), 29.8 (CH$_2$), 29.5 (CH$_2$), 27.01 (3C; CH$_3$), 26.97 (CH$_2$), 25.9 (CH$_2$), 19.8 (CH$_3$), 19.4 (C). Note: While two sets of signals were observed in both the $^1$H and $^{13}$C NMR spectra, only the major set of signals are reported above. It was unclear if the doubling was due to the presence of two closely-related compounds or the presence of both monomeric and dimeric species due to the high concentration of the NMR sample.

DMAP (10.1 mg, 0.0831 mmol), EDC·HCl (39.8 mg, 0.208 mmol) and Int-2 (1,3-DG) (70.9 mg, 0.125 mmol) were added to a solution of acid Int-21 (36.6 mg, 0.0831 mmol) in dichloromethane (2.5 mL) and the mixture stirred at room temperature for 21 hours. The reaction was diluted with dichloromethane (5 mL), silica gel was added and the mixture concentrated under reduced pressure. Purification by silica gel chromatography (4% to 5% ethyl acetate/hexanes) gave triglyceride Int-22 (39.9 mg, 48% over two steps) as a colorless solid. $^1$H NMR (400 MHz, CDCl$_3$) δ 7.69-7.64 (m, 4H), 7.44-7.34 (m, 6H), 5.28 (m, 1H), 4.289/4.287 (each dd, J=11.8, 4.2 Hz, 2H), 4.14 (dd, J=12.0, 5.9 Hz, 2H), 3.65 (t, J=6.5 Hz, 2H), 2.37-2.27 (m, 5H), 2.11 (dd, J=14.7, 8.4 Hz, 1H), 1.92 (m, 1H), 1.67-1.50 (m, 8H), 1.39-1.14 (m, 56H), 1.04 (s, 9H), 0.93 (d, J=6.6 Hz, 3H), 0.88 (t, J=6.9 Hz, 6H); $^{13}$C NMR (101 MHz, CDCl$_3$) δ 173.5 (2C; C), 172.5 (C), 135.7 (4C; CH), 134.3 (2C; C), 129.6 (2C; CH), 127.7 (4C; CH), 68.9 (CH), 64.1 (CH$_2$), 62.3 (2C; CH$_2$), 41.8 (CH$_2$), 36.8 (CH$_2$), 34.2 (2C; CH$_2$), 32.7 (CH$_2$), 32.1 (2C; CH$_2$), 30.5 (CH), 29.9 (CH$_2$), 29.84 (6C; CH$_2$), 29.80 (4C; CH$_2$), 29.76 (2C; CH$_2$), 29.6 (2C; CH$_2$), 29.54 (CH$_2$), 29.51 (2C; CH$_2$), 29.4 (2C; CH$_2$), 29.3 (2C; CH$_2$), 27.02 (CH$_2$), 27.00 (3C; CH$_3$), 25.9 (CH$_2$), 25.0 (2C; CH$_2$), 22.8 (2C; CH$_2$), 19.7 (CH$_3$), 19.4 (C), 14.3 (2C; CH$_3$).

Tetrabutylammonium fluoride (TBAF, 1.0 M in THF, 98.3 µL, 98.3 µmol) was added to a solution of TBDPS ether Int-22 (39.0 mg, 39.3 µmol) in THF (2.5 mL) at 0° C. and the mixture stirred at room temperature for three hours. The reaction was diluted with water (10 mL), extracted with ethyl acetate (3×15 mL), and the organic extracts washed with brine (30 mL), dried (MgSO$_4$) and concentrated under reduced pressure to give the crude product. Purification by silica gel chromatography (10% to 20% ethyl acetate/hexanes) gave alcohol Int-23 (21.8 mg, 74%) as a colorless solid. $^1$H NMR (400 MHz, CDCl$_3$) δ 5.28 (m, 1H), 4.29 (dd, J=11.9, 4.3 Hz, 2H), 4.14 (dd, J=11.9, 5.9 Hz, 2H), 3.64 (t, J=6.6 Hz, 2H), 2.36-2.27 (m, 5H), 2.12 (dd, J=14.7, 8.2 Hz, 1H), 1.93 (m, 1H), 1.65-1.52 (m, 6H), 1.39-1.16 (m, 58H), 0.93 (d, J=6.6 Hz, 3H), 0.88 (t, J=6.9 Hz, 6H); $^{13}$C NMR (101 MHz, CDCl$_3$) δ 173.5 (2C; C), 172.5 (C), 68.9 (CH), 63.2 (CH$_2$), 62.3 (2C; CH$_2$), 41.8 (CH$_2$), 36.7 (CH$_2$), 34.2 (2C; CH$_2$), 32.9 (CH$_2$), 32.1 (2C; CH$_2$), 30.5 (CH), 29.84 (4C; CH$_2$), 29.83 (2C; CH$_2$), 29.80 (4C; CH$_2$), 29.77 (2C; CH$_2$), 29.6 (2C; CH$_2$), 29.5 (3C; CH$_2$), 29.4 (2C; CH$_2$), 29.3 (3C; CH$_2$), 26.9 (CH$_2$), 25.8 (CH$_2$), 25.0 (2C; CH$_2$), 22.8 (2C; CH$_2$), 19.7 (CH$_3$), 14.3 (2C; CH$_3$).

Pyridinium chlorochromate (PCC, 12.0 mg, 55.8 µmol) was added to a suspension of alcohol Int-23 (21.0 mg, 27.9 µmol) and celite (15 mg) in dichloromethane (1.5 mL) at 0° C. and the mixture stirred at room temperature for 1.75 hours. The reaction was filtered through a short pad of silica gel, eluting with ethyl acetate, and the filtrate concentrated under reduced pressure to give crude aldehyde Int-24 (20.9 mg, quant.) as a yellow oil that was used without purification.

$^1$H NMR (400 MHz, CDCl$_3$) δ 9.76 (s, 1H), 5.28 (m, 1H), 4.29 (dd, J=11.6, 3.5 Hz, 2H), 4.14 (dd, J=11.6, 5.7 Hz, 2H), 2.42 (t, J=7.1 Hz, 2H), 2.36-2.25 (m, 5H), 2.12 (dd, J=14.5, 8.3 Hz, 1H), 1.93 (m, 1H), 1.72-1.53 (m, 6H), 1.42-1.05 (m, 56H), 0.93 (d, J=6.5 Hz, 3H), 0.88 (t, J=6.6 Hz, 6H).

Int-25: prepared according to: Gossauer, A.; Kuhne, G. Liebigs. Ann. Chem. 1977, 664-686.

A solution of ylide Int-25 (8.1 mg, 19.0 µmol) in toluene (0.4 mL) was added to aldehyde Int-24 (11.0 mg, 14.6 µmol) in toluene (0.6 mL) and the mixture heated at reflux for four hours. The reaction was cooled to rt and concentrated under reduced pressure to give the crude product. Purification by silica gel chromatography (5% to 10% ethyl acetate/hexanes) gave α,β-unsaturated benzyl ester Int-26 (7.1 mg, 54%) as a yellow oil. $^1$H NMR (401 MHz, CDCl$_3$) δ 7.41-7.27 (m, 5H), 6.81 (td, J=7.5, 1.4 Hz, 1H), 5.27 (m, 1H), 5.18 (s, 2H), 4.29 (dd, J=11.9, 4.3 Hz, 2H), 4.14 (dd, J=11.9, 6.0 Hz, 2H), 2.36-2.27 (m, 5H), 2.20-2.08 (m, 3H), 1.93 (m, 1H), 1.85 (d, J=1.2 Hz, 3H), 1.67-1.54 (m, 6H), 1.47-1.38 (m, 2H), 1.37-1.19 (m, 54H), 0.93 (d, J=6.6 Hz, 3H), 0.88 (t, J=6.9 Hz, 6H); $^{13}$C NMR (101 MHz, CDCl$_3$) δ 173.4 (2C; C), 172.4 (C), 168.2 (C), 143.2 (CH), 136.6 (C), 128.7 (2C; CH), 128.2 (CH), 128.1 (2C; CH), 127.6 (C), 69.0 (CH), 66.3 (CH$_2$), 62.3 (2C; CH$_2$), 41.8 (CH$_2$), 36.8 (CH$_2$), 34.2 (2C; CH$_2$), 32.1 (2C; CH$_2$), 30.5 (CH), 29.85 (6C; CH$_2$), 29.81 (4C; CH$_2$), 29.77 (2C; CH$_2$), 29.74 (CH$_2$), 29.63 (2C; CH$_2$), 29.56 (CH$_2$), 29.51 (2C; CH$_2$), 29.4 (2C; CH$_2$), 29.3 (2C; CH$_2$), 28.9 (CH$_2$), 28.7 (CH$_2$), 27.0 (CH$_2$), 25.0 (2C; CH$_2$), 22.8 (2C; CH$_2$), 19.7 (CH$_2$), 14.3 (2C; CH$_2$), 12.6 (CH$_2$).

A solution of benzyl ether Int-26 (48.5 mg, 54.0 µmol) in ethyl acetate (2.5 mL) in a two-neck flask was evacuated and flushed with N$_2$ gas (three times each), then palladium on carbon (10% w/w, 11.5 mg, 10.8 µmol) was added and the resulting suspension re-evacuated and flushed with N$_2$ (three times each). The flask was fitted with a H$_2$ balloon, evacuated and flushed with H$_2$ (three times each) and the reaction mixture stirred at room temperature under 1 atm of H$_2$ for three hours. The reaction was filtered through a pad of celite, washing with ethyl acetate, and concentrated under reduced pressure to give the crude product. Purification by silica gel chromatography (10% to 20% ethyl acetate/hexanes) gave saturated acid Int-27 (C12α'βMe-acid-2-TG) (28.1 mg, 64%) as a colorless oil. $^1$H NMR (401 MHz, CDCl$_3$) δ 5.27 (m, 1H), 4.29 (dd, J=11.9, 4.3 Hz, 2H), 4.14 (dd, J=11.9, 6.1 Hz, 2H), 2.46 (m, 1H), 2.37-2.26 (m, 5H), 2.12 (dd, J=14.7, 8.2 Hz, 1H), 1.94 (m, 1H), 1.73-1.55 (m, 5H), 1.41 (m, 1H), 1.37-1.20 (m, 60H), 1.18 (d, J=7.0 Hz, 3H), 0.93 (d, J=6.6 Hz, 3H), 0.88 (t, J=6.9 Hz, 6H); $^{13}$C NMR (101 MHz, CDCl$_3$) δ 182.3 (C), 173.5 (2C; C), 172.5 (C), 69.0 (CH), 62.3 (2C; CH$_2$), 41.8 (CH$_2$), 39.4 (CH), 36.8 (CH$_2$), 34.2 (2C; CH$_2$), 33.7 (CH$_2$), 32.1 (2C; CH$_2$), 30.5 (CH), 29.84 (6C; CH$_2$), 29.80 (4C; CH$_2$), 29.77 (2C; CH$_2$), 29.62 (2C; CH$_2$), 29.60 (CH$_2$), 29.57 (CH$_2$), 29.5 (2C; CH$_2$), 29.4 (2C; CH$_2$), 29.3 (2C; CH$_2$), 27.3 (CH$_2$), 27.0 (CH$_2$), 25.0 (2C; CH$_2$), 22.8 (2C; CH$_2$), 19.7 (CH$_3$), 17.0 (CH$_3$), 14.3 (2C; CH$_3$).

C4-Acid-2-TG (Int-28):

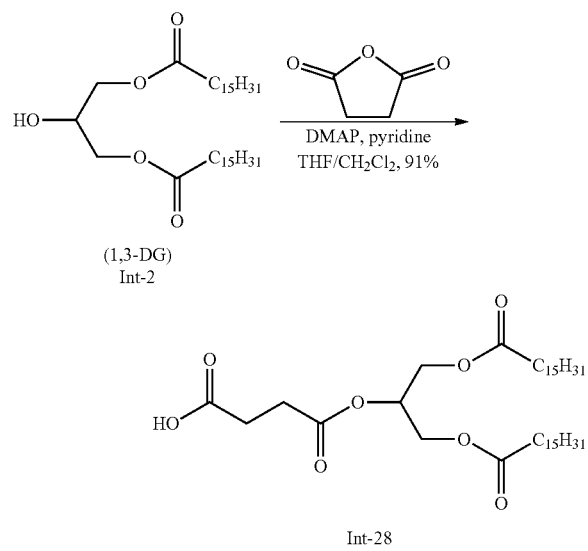

Scheme 15. Synthesis of Int-28.

4-(Dimethylamino)pyridine (DMAP, 15.5 mg, 0.127 mmol) was added to a solution of 1,3-diglyceride Int-2 (72.2 mg, 0.127 mmol) and succinic anhydride (25.4 mg, 0.254 mmol) in pyridine/THF/CH$_2$Cl$_2$ (0.5 mL each) and the mixture stirred at room temperature for 17 hours. An extra portion of succinic anhydride (25.4 mg, 0.254 mmol) and DMAP (15.5 mg, 0.127 mmol) was added and the solution heated at 40° C. for a further 22 hours. The reaction was diluted with ethyl acetate (25 mL), washed with 1 M HCl (20 mL) and brine (2×30 mL), dried (MgSO$_4$) and concentrated under reduced pressure to give the crude product. Silica gel chromatography (15% to 25% ethyl acetate/hexanes) gave acid-TG Int-28 (77.0 mg, 91%) as a colorless solid. $^1$H NMR (400 MHz, CDCl$_3$) δ 5.27 (m, 1H), 4.30 (dd, J=12.0, 4.3 Hz, 2H), 4.15 (dd, J=12.0, 5.8 Hz, 2H), 2.72-2.61 (m, 4H), 2.31 (t, J=7.6 Hz, 4H), 1.67-1.54 (m, 4H), 1.36-1.19 (m, 48H), 0.88 (t, J=6.9 Hz, 6H); $^{13}$C NMR (101 MHz, CDCl$_3$) δ 176.9 (C), 173.5 (2C; C), 171.4 (C), 69.8 (CH), 62.0 (2C; CH$_2$), 34.2 (2C; CH$_2$), 32.1 (2C; CH$_2$), 29.84 (6C; CH$_2$), 29.81 (4C; CH$_2$), 29.77 (2C; CH$_2$), 29.6 (2C; CH$_2$), 29.5 (2C; CH$_2$), 29.4 (2C; CH$_2$), 29.3 (2C; CH$_2$), 29.0 (CH$_2$), 28.8 (CH$_2$), 25.0 (2C; CH$_2$), 22.8 (2C; CH$_2$), 14.3 (2C; CH$_3$).

C6-Acid-2-TG (Int-29):

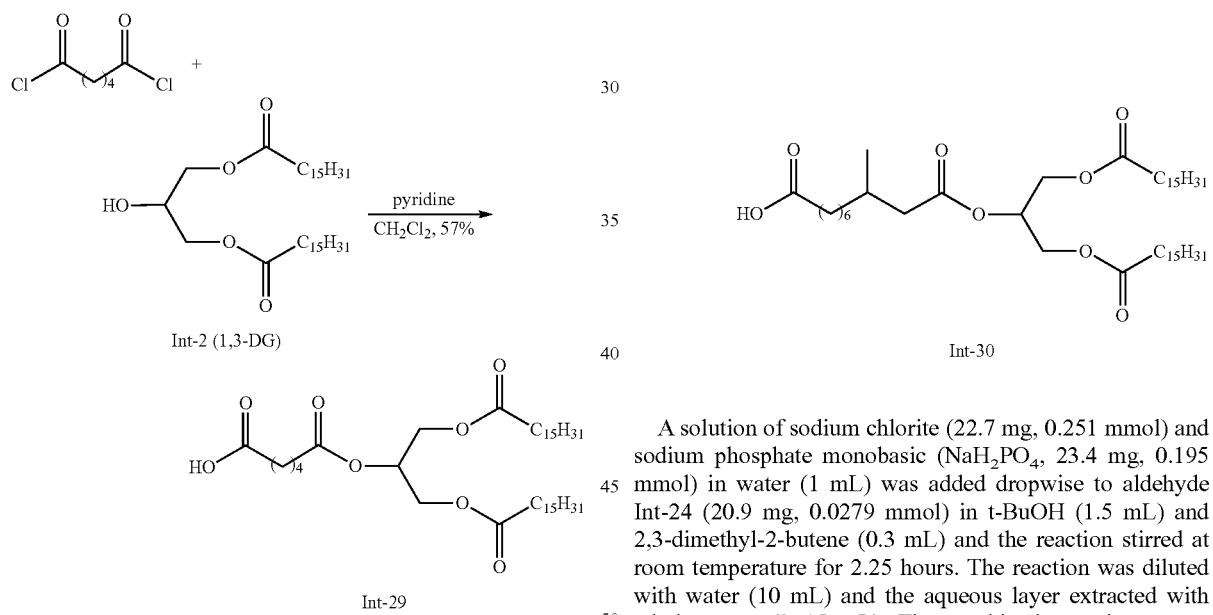

Int-2 (1,3-DG)

Int-29

A solution of 1,3-diglyceride Int-2 (75.0 mg, 0.132 mmol) and pyridine (107 μL, 1.32 mmol) in CH$_2$Cl$_2$ (2.5 mL) was added to diacid chloride 1 (96.1 mL, 0.659 mmol) in CH$_2$Cl$_2$ (2.5 mL) and the mixture heated at reflux for 3.5 hours. The reaction was cooled to room temperature, diluted with ethyl acetate (30 mL) and the organic extract washed with 1 M HCl (20 mL) and brine (2×20 mL), dried (MgSO$_4$) and concentrated under reduced pressure to give the crude product. Purification by silica gel chromatography (15% to 25% ethyl acetate/hexanes) gave acid-TG Int-29 (52.7 mg, 57%) as a colorless solid. $^1$H NMR (400 MHz, CDCl$_3$) δ 5.26 (m, 1H), 4.30 (dd, J=11.9, 4.3 Hz, 2H), 4.14 (dd, J=11.9, 5.9 Hz, 2H), 2.41-2.34 (m, 4H), 2.31 (t, J=7.6 Hz, 4H), 1.72-1.65 (m, 4H), 1.65-1.56 (m, 4H), 1.35-1.20 (m, 48H), 0.88 (t, J=6.8 Hz, 6H); $^{13}$C NMR (101 MHz, CDCl$_3$) δ 178.3 (C), 173.5 (2C; C), 172.4 (C), 69.3 (CH), 62.2 (2C; CH$_2$), 34.2 (2C; CH$_2$), 33.8 (CH$_2$), 33.5 (CH$_2$), 32.1 (2C; CH$_2$), 29.84 (6C; CH$_2$), 29.81 (4C; CH$_2$), 29.77 (2C; CH$_2$), 29.6 (2C; CH$_2$), 29.5 (2C; CH$_2$), 29.4 (2C; CH$_2$), 29.3 (2C; CH$_2$), 25.0 (2C; CH$_2$), 24.3 (CH$_2$), 24.1 (CH$_2$), 22.8 (2C; CH$_2$), 14.3 (2C; CH$_2$).

C10βMe-Acid-2-TG (Int-30):

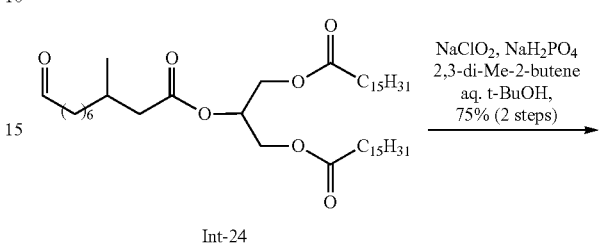

Int-24

Int-30

A solution of sodium chlorite (22.7 mg, 0.251 mmol) and sodium phosphate monobasic (NaH$_2$PO$_4$, 23.4 mg, 0.195 mmol) in water (1 mL) was added dropwise to aldehyde Int-24 (20.9 mg, 0.0279 mmol) in t-BuOH (1.5 mL) and 2,3-dimethyl-2-butene (0.3 mL) and the reaction stirred at room temperature for 2.25 hours. The reaction was diluted with water (10 mL) and the aqueous layer extracted with ethyl acetate (3×15 mL). The combined organic extracts were washed with brine (30 mL), dried (MgSO$_4$) and concentrated under reduced pressure to give the crude product. Purification by silica gel chromatography (10% to 20% ethyl acetate/hexanes with 0.5% acetic acid) gave acid Int-30 (16.1 mg, 75%) as a colorless solid. $^1$H NMR (400 MHz, CDCl$_3$) δ 5.27 (m, 1H), 4.29 (dd, J=11.9, 4.3 Hz, 2H), 4.14 (dd, J=12.0, 6.0 Hz, 2H), 2.37-2.27 (m, 7H), 2.12 (dd, J=14.7, 8.2 Hz, 1H), 1.93 (m, 1H), 1.67-1.55 (m, 6H), 1.40-1.14 (m, 56H), 0.93 (d, J=6.6 Hz, 3H), 0.88 (t, J=6.9 Hz, 6H); $^{13}$C NMR (101 MHz, CDCl$_3$) δ 179.7 (C), 173.5 (2C; C), 172.4 (C), 69.0 (CH), 62.3 (2C; CH$_2$), 41.8 (CH$_2$), 36.7 (CH$_2$), 34.2 (2C; CH$_2$), 34.1 (CH$_2$), 32.1 (2C; CH$_2$), 30.4 (CH), 29.82 (6C; CH$_2$), 29.79 (4C; CH$_2$), 29.75 (2C; CH$_2$), 29.6 (2C; CH$_2$), 29.5 (3C; CH$_2$), 29.4 (2C; CH$_2$), 29.24 (2C; CH$_2$), 29.16 (CH$_2$), 26.8 (CH$_2$), 25.0 (2C; CH$_2$), 24.8 (CH$_2$), 22.8 (2C; CH$_2$), 19.7 (CH$_3$), 14.2 (2C; CH$_3$).

Using similar methods to those described above, Int-121 was prepared:

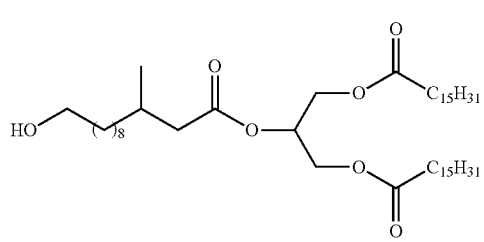

¹H NMR (401 MHz, CDCl₃) δ 5.28 (m, 1H), 4.29 (dd, J=11.9, 4.3 Hz, 2H), 4.14 (dd, J=11.8, 6.0 Hz, 2H), 3.64 (t, J=6.6 Hz, 2H), 2.32 (dd, J=14.6, 5.8 Hz, 1H), 2.30 (t, J=7.5 Hz, 4H), 2.12 (dd, J=14.6, 8.2 Hz, 1H), 1.94 (m, 1H), 1.64-1.49 (m, 6H), 1.40-1.13 (m, 62H), 0.93 (d, J=6.6 Hz, 3H), 0.88 (t, J=6.9 Hz, 6H); ¹³C NMR (101 MHz, CDCl₃) δ 173.3 (2C; C), 172.4 (C), 68.9 (CH), 62.9 (CH₂), 62.2 (2C; CH₂), 41.7 (CH₂), 36.7 (CH₂), 34.1 (2C; CH₂), 32.9 (CH₂), 32.0 (2C; CH₂), 30.4 (CH), 29.80 (CH₂), 29.76 (6C; CH₂), 29.72 (4C; CH₂), 29.68 (2C; CH₂), 29.65 (CH₂), 29.62 (CH₂), 29.53 (2C; CH₂), 29.50 (CH₂), 29.4 (2C; CH₂), 29.3 (2C; CH₂), 29.2 (2C; CH₂), 27.0 (CH₂), 25.8 (CH₂), 24.9 (2C; CH₂), 22.7 (2C; CH₂), 19.6 (CH₃), 14.2 (2C; CH₃).

C12-Acid-2-TG (Int-37):

Scheme 18. Synthesis of Int-37.

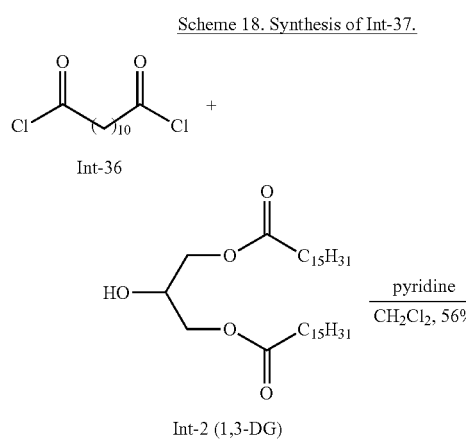

A mixture of dodecanedioic acid (700 mg, 3.04 mmol) and DMF (two drops) in thionyl chloride (2.20 mL, 30.4 mmol) was heated at reflux for two hours. The reaction was cooled to room temperature, diluted with toluene (5 mL) and concentrated under reduced pressure to give diacid chloride Int-36 (812 mg, quant.) as a yellow oil that was used without purification. ¹H NMR (400 MHz, CDCl₃): δ 2.88 (t, J=7.3 Hz, 4H), 1.76-1.65 (m, 4H), 1.42-1.23 (m, 12H).

A solution of 1,3-diglyceride Int-2 (40.0 mg, 0.0703 mmol) and pyridine (56.9 μL, 0.703 mmol) in CH₂Cl₂ (1.5 mL) was added to diacid chloride Int-36 (93.9 mg, 0.352 mmol) in CH₂Cl₂ (1.5 mL) and the mixture stirred at room temperature for 16 hours. The reaction was diluted with ethyl acetate (3 mL), water (10 mL) and 1 M HCl (2 mL) and the aqueous layer extracted with ethyl acetate (3×15 mL). The combined organic extracts were washed with 1 M HCl (30 mL) and brine (2×30 mL), dried (MgSO₄) and concentrated under reduced pressure to give the crude product. Purification by silica gel chromatography (20% to 45% ethyl acetate/hexanes) gave acid-TG Int-37 (30.7 mg, 56%) as a colorless solid. ¹H NMR (400 MHz, CDCl₃): δ 5.26 (m, 1H), 4.29 (dd, J=11.9, 4.3 Hz, 2H), 4.14 (dd, J=11.9, 5.9 Hz, 2H), 2.38-2.26 (m, 8H), 1.69-1.54 (m, 8H), 1.38-1.19 (m, 60H), 0.87 (t, J=6.9 Hz, 6H).

C15βMe-Acid-2-TG (Int-49):

Scheme 19. Synthesis of Int-49.

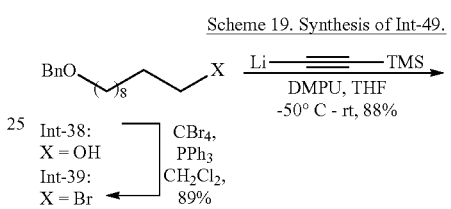

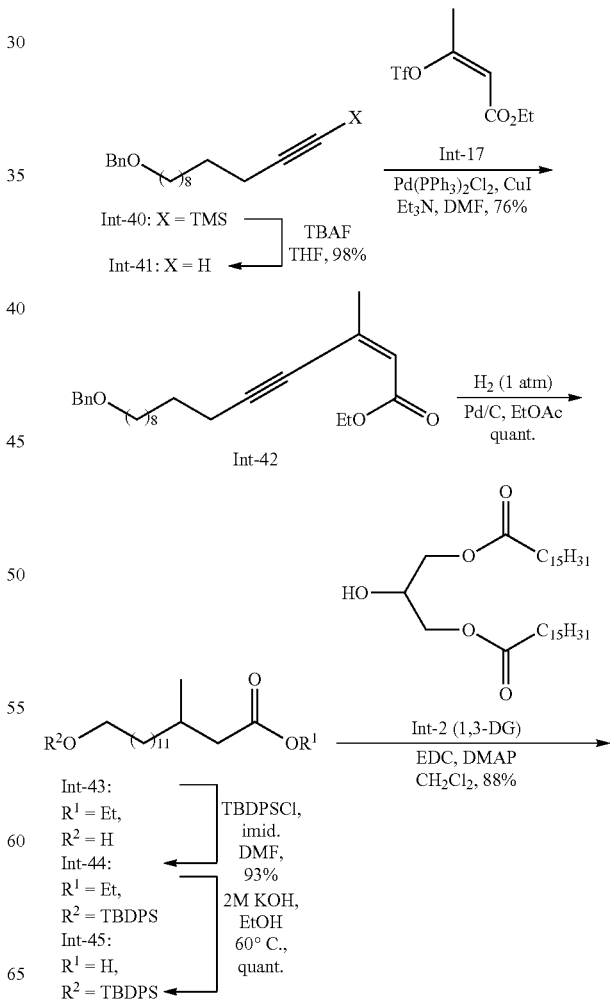

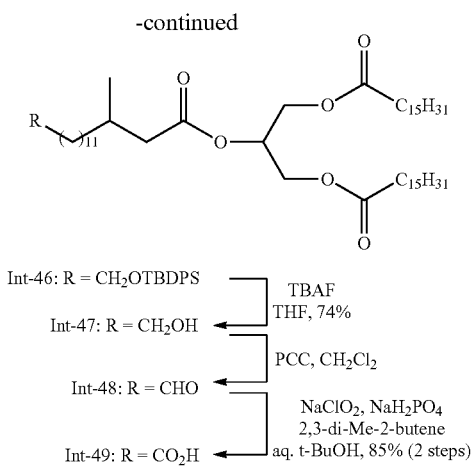

Int-46: R = CH₂OTBDPS
Int-47: R = CH₂OH      ← TBAF, THF, 74%
Int-48: R = CHO        ← PCC, CH₂Cl₂
Int-49: R = CO₂H       ← NaClO₂, NaH₂PO₄, 2,3-di-Me-2-butene, aq. t-BuOH, 85% (2 steps)

A solution of 1,10-decanediol (1.05 g, 6.00 mmol) in DMF (7 mL) was added dropwise to a suspension of sodium hydride (60% w/w in mineral oil, washed twice with dry petrol, 240 mg, 6.00 mmol) in DMF (8 mL) at 0° C. and the mixture stirred at room temperature for one hour. Benzyl bromide (784 µL, 3.50 mmol) was added dropwise and the mixture stirred at room temperature for 1.5 hours. The reaction was diluted with ethyl acetate (30 mL), quenched with water (20 mL) and the aqueous phase extracted with ethyl acetate (3×30 mL). The combined organic extracts washed with water and brine (60 mL each), dried (MgSO₄) and concentrated under reduced pressure to give the crude product. Purification by silica gel chromatography (20% to 30% ethyl acetate/hexanes) gave benzyl ether Int-38 (657 mg, 41%) as a colorless oil. $^1$H NMR (400 MHz, CDCl₃) δ 7.39-7.24 (m, 5H), 4.50 (s, 2H), 3.64 (t, J=6.6 Hz, 2H), 3.46 (t, J=6.7 Hz, 2H), 1.65-1.52 (m, 4H), 1.40-1.25 (m, 12H).

Carbon tetrabromide (1.05 g, 3.17 mmol) and triphenylphosphine (1.07 g, 4.08 mmol) were added to a solution of alcohol Int-38 (600 mg, 1.11 mmol) in CH₂Cl₂ (20 mL) at 0° C. and the mixture stirred at room temperature for 2.5 hours. The reaction was diluted with CH₂Cl₂ (20 mL), silica gel was added and the solvent evaporated under reduced pressure. Purification by silica gel chromatography (3% to 4% ethyl acetate/hexanes) gave bromide Int-39 (658 mg, 89%) as a colorless oil. $^1$H NMR (400 MHz, CDCl₃) δ 7.41-7.26 (m, 5H), 4.50 (s, 2H), 3.46 (t, J=6.6 Hz, 2H), 3.40 (t, J=6.9 Hz, 2H), 1.91-1.79 (m, 2H), 1.68-1.56 (m, 2H), 1.47-1.23 (m, 12H).

n-Butyllithium (n-BuLi, 1.6 M in hexanes, 4.01 mL, 6.42 mmol) was added slowly to a solution of TMS-acetylene (1.02 mL, 7.22 mmol) in THF (9 mL) at −78° C. and the mixture stirred at −78° C. for five minutes then warmed to room temperature and stirred for a further 15 minutes. The reaction was re-cooled to −50° C., a solution of bromide Int-39 (525 mg, 1.60 mmol) and DMPU (1.06 mL, 8.82 mmol) in THF (6 mL) was added dropwise and the mixture stirred at −50° C. for 30 minutes and then at room temperature for 22 hours. The reaction was diluted with brine (15 mL) and the organic solvent evaporated under reduced pressure. The aqueous residue was extracted with ethyl acetate (3×25 mL) and the combined organic extracts washed with brine (50 mL), dried (MgSO₄) and concentrated under reduced pressure to give the crude product. Purification by silica gel chromatography (3.5% to 4.5% ethyl acetate/hexanes) gave TMS alkyne Int-40 (489 mg, 88%) as a colorless oil containing small amounts of desilylated alkyne Int-41 (<10%). $^1$H NMR (400 MHz, CDCl₃) δ 7.37-7.25 (m, 5H), 4.50 (s, 2H), 3.46 (t, J=6.7 Hz, 2H), 2.21 (t, J=7.2 Hz, 2H), 1.65-1.58 (m, 2H), 1.54-1.46 (m, 2H), 1.41-1.24 (m, 12H), 0.14 (s, 9H).

Tetrabutylammonium fluoride (TBAF, 1.0 M in THF, 1.61 mL, 1.61 mmol) was added dropwise to silylalkyne Int-40 (463 mg, 1.34 mmol) in THF (12 mL) at 0° C. and the mixture stirred at room temperature for 40 minutes. The reaction was diluted with water (10 mL) and the aqueous phase extracted with ethyl acetate (3×20 mL). The combined organic extracts were washed with brine (40 mL), dried (MgSO₄) and concentrated under reduced pressure to give the crude product. Purification by silica gel chromatography (4% to 5% ethyl acetate/hexanes) gave alkyne Int-41 (361 mg, 98%) as a colorless oil. $^1$H NMR (400 MHz, CDCl₃) δ 7.38-7.25 (m, 5H), 4.50 (s, 2H), 3.46 (t, J=6.7 Hz, 2H), 2.18 (td, J=7.1, 2.6 Hz, 2H), 1.94 (t, J=2.7 Hz, 1H), 1.65-1.57 (m, 2H), 1.55-1.48 (m, 2H), 1.43-1.24 (m, 12H). $^{13}$C NMR (101 MHz, CDCl₃) δ 138.86 (C), 128.49 (2C; CH), 127.77 (2C; CH), 127.61 (CH), 84.97 (C), 73.00 (CH₂), 70.67 (CH₂), 68.18 (CH), 29.91 (CH₂), 29.67 (CH₂), 29.59 (CH₂), 29.57 (CH₂), 29.23 (CH₂), 28.89 (CH₂), 28.63 (CH₂), 26.33 (CH₂), 18.54 (CH₂).

A suspension of PdCl₂(PPh₃)₂ (32.2 mg, 0.0459 mmol) in DMF (4 mL) was degassed using a stream of N₂ gas for five minutes, and then CuI (35.0 mg, 0.184 mmol), Et₃N (256 µL, 1.84 mmol) and a degassed solution of alkyne Int-41 (250 mg, 0.918 mmol) and enol triflate Int-17 (313 mg, 1.19 mmol) in DMF (6 mL) were added. The mixture was degassed using a stream of N₂ for a further five minutes and then heated at 70° C. for one hour. The reaction was cooled to room temperature, diluted with ethyl acetate (40 mL), washed with 1 M HCl, sat. aq. NaHCO₃, water and brine (30 mL each), dried (MgSO₄) and concentrated under reduced pressure to give the crude product. Silica gel chromatography (4% to 5% ethyl acetate/hexanes) gave enyne Int-42 (269 mg, 76%) as a pale yellow oil. $^1$H NMR (400 MHz, CDCl₃) δ 7.38-7.24 (m, 5H), 5.92 (m, 1H), 4.50 (s, 2H), 4.18 (t, J=7.1 Hz, 2H), 3.46 (t, J=6.7 Hz, 2H), 2.43 (t, J=7.2 Hz, 2H), 2.01 (d, J=1.4 Hz, 3H), 1.65-1.55 (m, 4H), 1.46-1.24 (m, 12H); $^{13}$C NMR (101 MHz, CDCl₃) δ 165.4 (C), 138.8 (C), 135.9 (C), 128.5 (2C; CH), 127.7 (2C; CH), 127.6 (CH), 123.3 (CH), 103.3 (C), 79.9 (C), 73.0 (CH₂), 70.6 (CH₂), 60.0 (CH₂), 29.9 (CH₂), 29.65 (CH₂), 29.59 (CH₂), 29.56 (CH₂), 29.2 (CH₂), 29.1 (CH₂), 28.6 (CH₂), 26.3 (CH₂), 26.0 (CH₃), 20.1 (CH₂), 14.4 (CH₃).

A solution of benzyl ether Int-42 (246 mg, 0.640 mmol) in ethyl acetate (25 mL) in a three-neck round-bottom flask was twice evacuated and flushed with N₂ gas, then palladium on carbon (10% w/w, 102 mg, 0.0960 mmol) was added and the resulting suspension re-evacuated and flushed with N₂ three times. The flask was fitted with a H₂ balloon, evacuated and flushed with H₂ three times and the reaction mixture stirred at room temperature under 1 atm of H₂ for one hour. The reaction mixture was then filtered through a pad of celite and the pad washed with ethyl acetate (40 mL). The filtrate was concentrated under reduced pressure to give saturated alcohol Int-43 (192 mg, quant.) as a colorless oil that was used without purification. $^1$H NMR (400 MHz, CDCl₃) δ 4.12 (q, J=7.1 Hz, 2H), 3.63 (t, J=6.6 Hz, 2H), 2.28 (dd, J=14.6, 6.0 Hz, 1H), 2.08 (dd, J=14.6, 8.1 Hz, 1H), 1.93 (m, 1H), 1.60-1.51 (m, 2H), 1.43-1.12 (m, 23H), 0.92 (d, J=6.6 Hz, 3H). $^{13}$C NMR (101 MHz, CDCl₃) δ 173.6 (C), 63.2 (CH₂), 60.2 (CH₂), 42.1 (CH₂), 36.9 (CH₂), 32.9 (CH₂), 30.5 (CH), 29.9 (CH₂), 29.74 (4C; CH₂), 29.70 (CH₂), 29.6 (CH₂), 27.0 (CH₂), 25.9 (CH₂), 19.9 (CH₃), 14.4 (CH₃).

Imidazole (32.0 mg, 0.0.469 mmol) and tert-butyl(chloro)diphenylsilane (TBDPSCl, 183 µL, 0.704 mmol) were added to a solution of alcohol Int-43 (70.5 mg, 0.235 mmol) in DMF (7 mL) and the mixture stirred at room temperature for 17 hours. The reaction was diluted with ethyl acetate (20 mL), washed with water (20 mL) and brine (2×20 mL), dried (MgSO$_4$) and concentrated under reduced pressure to give the crude product. Purification by silica gel chromatography (3% to 4% ethyl acetate/hexanes with 0.5% Et$_3$N) gave TBDPS ether Int-44 (117 mg, 93%) as a colorless oil. $^1$H NMR (400 MHz, CDCl$_3$) δ 7.70-7.63 (m, 4H), 7.44-7.34 (m, 6H), 4.12 (q, J=7.1 Hz, 2H), 3.65 (t, J=6.5 Hz, 2H), 2.29 (dd, J=14.6, 6.0 Hz, 1H), 2.09 (dd, J=14.6, 8.2 Hz, 1H), 1.95 (m, 1H), 1.60-1.50 (m, 2H), 1.38-1.14 (m, 23H), 1.04 (s, J=2.8 Hz, 9H), 0.92 (d, J=6.6 Hz, 3H); $^{13}$C NMR (101 MHz, CDCl$_3$) δ 173.5 (C), 135.7 (4C; CH), 134.3 (2C; C), 129.6 (2C; CH), 127.7 (4C; CH), 64.1 (CH$_2$), 60.2 (CH$_2$), 42.1 (CH$_2$), 36.9 (CH$_2$), 32.7 (CH$_2$), 30.5 (CH), 29.9 (CH$_2$), 29.79 (3C; CH$_2$), 29.77 (2C; CH$_2$), 29.5 (CH$_2$), 27.1 (CH$_2$), 27.0 (3C; CH$_3$), 25.9 (CH$_2$), 19.9 (CH$_3$), 19.4 (C), 14.4 (CH$_3$).

A solution of potassium hydroxide (2.0 M, 390 μL, 0.781 mmol) was added to ester Int-44 (42.1 mg. 0.0781 mmol) in ethanol (2 mL) and the mixture heated at 60° C. for 1.5 hours. The reaction was acidified to pH 1 by addition of 1 M HCl, diluted with water (10 mL) and the aqueous phase extracted with ethyl acetate (3×15 mL). The combined organic extracts were washed with brine (30 mL), dried (MgSO$_4$) and concentrated under reduced pressure to give crude acid Int-45 (39.9 mg, quant.) as a colorless oil that was used without purification. $^1$H NMR (400 MHz, CDCl$_3$) δ 7.75-7.66 (m, 4H), 7.46-7.35 (m, 6H), 3.67 (t, J=6.5 Hz, 2H), 2.36 (dd, J=15.0, 5.9 Hz, 1H), 2.15 (dd, J=14.9, 8.2 Hz, 1H), 1.97 (m, 1H), 1.61-1.52 (m, 2H), 1.41-1.17 (m, 20H), 1.06 (s, 9H), 0.98 (d, J=6.6 Hz, 3H); $^{13}$C NMR (101 MHz, CDCl$_3$) δ 179.7 (C), 135.7 (4C; CH), 134.3 (2C; C), 129.6 (2C; CH), 127.7 (4C; CH), 64.2 (CH$_2$), 41.7 (CH$_2$), 36.8 (CH$_2$), 32.7 (CH$_2$), 30.3 (CH), 29.9 (CH$_2$), 29.80 (2C; CH$_2$), 29.78 (2C; CH$_2$), 29.75 (CH$_2$), 29.5 (CH$_2$), 27.1 (CH$_2$), 27.0 (3C; CH$_3$), 25.9 (CH$_2$), 19.8 (CH$_3$), 19.4 (C).

4-(Dimethylamino)pyridine (DMAP, 9.5 mg, 0.0781 mmol), EDC·HCl (29.9 mg, 0.156 mmol) and 1,3-diglyceride Int-2 (53.3 mg, 0.0937 mmol) were added to a solution of acid Int-45 (39.9 mg, 0.0781 mmol) in CH$_2$Cl$_2$ (2.5 mL) and the mixture stirred at room temperature for 19 hours. The reaction was diluted with CH$_2$Cl$_2$ (5 mL), silica gel was added and the mixture concentrated under reduced pressure. Purification by silica gel chromatography (4% to 5% ethyl acetate/hexanes) gave triglyceride Int-46 (72.8 mg, 88% over two steps) as a colorless solid. $^1$H NMR (400 MHz, CDCl$_3$) δ 7.73-7.63 (m, 4H), 7.49-7.31 (m, 6H), 5.29 (m, 1H), 4.30 (dd, J=11.9, 4.2 Hz, 2H), 4.15 (dd, J=11.9, 6.1 Hz, 2H), 3.66 (t, J=6.5 Hz, 2H), 2.34 (dd, J=14.6, 6.0 Hz, 1H), 2.31 (t, J=7.5 Hz, 4H), 2.13 (dd, J=14.6, 8.3 Hz, 1H), 1.94 (m, 1H), 1.68-1.52 (m, 6H), 1.44-1.16 (m, 68H), 1.05 (s, 9H), 0.94 (d, J=6.6 Hz, 3H), 0.88 (t, J=6.8 Hz, 6H); $^{13}$C NMR (101 MHz, CDCl$_3$) δ 173.4 (2C; C), 172.5 (C), 135.7 (4C; CH), 134.3 (2C; C), 129.6 (2C; CH), 127.7 (4C; CH), 68.9 (CH), 64.1 (CH$_2$), 62.3 (2C; CH$_2$), 41.8 (CH$_2$), 36.8 (CH$_2$), 34.2 (2C; CH$_2$), 32.7 (CH$_2$), 32.1 (2C; CH$_2$), 30.5 (CH), 30.0 (CH$_2$), 29.84 (8C; CH$_2$), 29.80 (6C; CH$_2$), 29.76 (2C; CH$_2$), 29.61 (2C; CH$_2$), 29.54 (CH$_2$), 29.50 (3C; CH$_2$), 29.4 (2C; CH$_2$), 29.3 (2C; CH$_2$), 27.2 (CH$_2$), 27.0 (3C; CH$_3$), 25.9 (CH$_2$), 25.0 (2C; CH$_2$), 22.8 (2C; CH$_2$), 19.7 (CH$_3$), 19.3 (C), 14.3 (2C; CH$_3$).

Tetrabutylammonium fluoride (TBAF, 1.0 M in THF, 186 μL, 0.186 mmol) and acetic acid (10.6 μL, 0.186 mmol) were added dropwise to TBDPS ether Int-46 (65.7 mg, 0.0619 mmol) in THF (3 mL) at 0° C. and the mixture stirred at room temperature for 19 hours. The reaction was diluted with water (10 mL) and the aqueous phase extracted with ethyl acetate (3×15 mL). The combined organic extracts were washed with sat. aq. NaHCO$_3$ and brine (30 mL each), dried (MgSO$_4$) and concentrated under reduced pressure to give the crude product. Purification by silica gel chromatography (10% to 15% ethyl acetate/hexanes) gave alcohol Int-47 (34.2 mg, 67%) as a colorless oil. $^1$H NMR (400 MHz, CDCl$_3$) δ 5.27 (m, 1H), 4.28 (dd, J=11.9, 4.3 Hz, 2H), 4.14 (dd, J=11.8, 6.0 Hz, 2H), 3.63 (t, J=6.6 Hz, 2H), 2.32 (dd, J=14.6, 5.9 Hz, 1H), 2.30 (t, J=7.6 Hz, 4H), 2.11 (dd, J=14.6, 8.3 Hz, 1H), 1.92 (m, 1H), 1.66-1.52 (m, 6H), 1.40-1.13 (m, 68H), 0.92 (d, J=6.6 Hz, 3H), 0.87 (t, J=6.9 Hz, 6H); $^{13}$C NMR (101 MHz, CDCl$_3$) δ 173.5 (2C; C), 172.5 (C), 68.9 (CH), 63.2 (CH$_2$), 62.3 (2C; CH$_2$), 41.8 (CH$_2$), 36.8 (CH$_2$), 34.2 (2C; CH$_2$), 32.9 (CH$_2$), 32.1 (2C; CH$_2$), 30.5 (CH), 29.9 (CH$_2$), 29.84 (8C; CH$_2$), 29.80 (6C; CH$_2$), 29.76 (2C; CH$_2$), 29.73 (CH$_2$), 29.62 (2C; CH$_2$), 29.57 (CH$_2$), 29.5 (2C; CH$_2$), 29.4 (2C; CH$_2$), 29.3 (2C; CH$_2$), 27.1 (CH$_2$), 25.9 (CH$_2$), 25.0 (2C; CH$_2$), 22.8 (2C; CH$_2$), 19.7 (CH$_3$), 14.3 (2C; CH$_3$).

Pyridinium chlorochromate (PCC, 14.7 mg, 68.0 μmol) was added to a suspension of alcohol Int-47 (28.0 mg, 34.0 μmol) and celite (15 mg) in CH$_2$Cl$_2$ (1.5 mL) at 0° C. and the mixture stirred at room temperature for one hour. The reaction was filtered through a short pad of silica gel, eluting with ethyl acetate, and the filtrate concentrated under reduced pressure to give crude aldehyde Int-48 (27.9 mg, quant.) as a yellow oil that was used without purification. $^1$H NMR (400 MHz, CDCl$_3$) δ 9.76 (s, 1H), 5.28 (m, 1H), 4.29 (dd, J=11.6, 3.5 Hz, 2H), 4.14 (dd, J=11.9, 5.8 Hz, 2H), 2.42 (t, J=6.8 Hz, 2H), 2.36-2.25 (m, 5H), 2.12 (dd, J=14.4, 8.5 Hz, 1H), 1.94 (m, 1H), 1.69-1.51 (m, 6H), 1.42-1.09 (m, 66H), 0.93 (d, J=6.4 Hz, 3H), 0.88 (t, J=6.3 Hz, 6H).

A solution of sodium chlorite (27.6 mg, 0.306 mmol) and sodium phosphate monobasic (NaH$_2$PO$_4$, 28.8 mg, 0.238 mmol) in water (1.2 mL) was added dropwise to aldehyde Int-48 (27.9 mg, 0.0340 mmol) in t-BuOH (1.8 mL) and 2,3-dimethyl-2-butene (0.4 mL) and the reaction stirred at room temperature for 16 hours. The reaction was acidified to pH 2 using 1 M HCl, diluted with water (10 mL) and the aqueous layer extracted with ethyl acetate (3×15 mL). The combined organic extracts were washed with brine (30 mL), dried ((MgSO$_4$) and concentrated under reduced pressure to give the crude product. Purification by silica gel chromatography (10% to 15% ethyl acetate/hexanes with 0.5% acetic acid) gave acid Int-49 (24.3 mg, 85%) as a colorless solid. $^1$H NMR (400 MHz, CDCl$_3$) δ 5.29 (m, 1H), 4.29 (dd, J=11.9, 3.8 Hz, 2H), 4.14 (dd, J=11.9, 6.1 Hz, 2H), 2.37-2.27 (m, 7H), 2.11 (dd, J=14.7, 8.3 Hz, 1H), 1.92 (m, 1H), 1.68-1.54 (m, 6H), 1.40-1.13 (m, 66H), 0.93 (d, J=6.6 Hz, 3H), 0.87 (t, J=6.8 Hz, 6H); $^{13}$C NMR (101 MHz, CDCl$_3$) δ 179.5 (C), 173.5 (2C; C), 172.5 (C), 68.9 (CH), 62.3 (2C; CH$_2$), 41.9 (CH$_2$), 36.8 (CH$_2$), 34.2 (2C; CH$_2$), 34.1 (CH$_2$), 32.1 (2C; CH$_2$), 30.5 (CH), 29.93 (CH$_2$), 29.85 (8C; CH$_2$), 29.81 (4C; CH$_2$), 29.77 (2C; CH$_2$), 29.73 (CH$_2$), 29.62 (2C; CH$_2$), 29.58 (CH$_2$), 29.51 (2C; CH$_2$), 29.42 (2C; CH$_2$), 29.39 (CH$_2$), 29.26 (2C; CH$_2$), 29.2 (CH$_2$), 27.1 (CH$_2$), 25.0 (2C; CH$_2$), 24.8 (CH$_2$), 22.8 (2C; CH$_2$), 19.7 (CH$_2$), 14.3 (2C; CH$_2$).

Using similar methods, Int-118 was prepared from 1,8-octanediol:

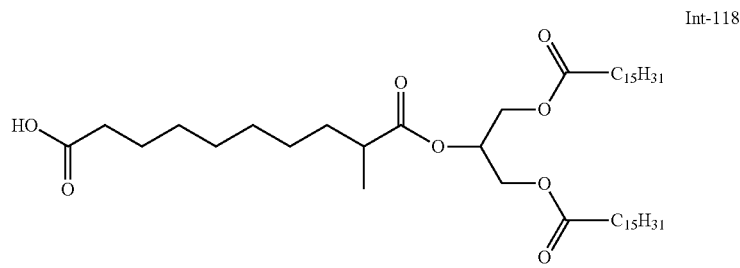

Int-118

$^1$H NMR (400 MHz, CDCl$_3$) δ 5.31 (s, 1H), 4.33 (dd, J=8.4, 4.4 Hz, 2H), 4.19 (dd, J=11.8, 5.9 Hz, 2H), 2.47 (m, 1H), 2.37 (dt, J=15.6, 7.4 Hz, 6H), 1.65 (s, 7H), 1.31 (d, J=13.3 Hz, 58H), 1.18 (d, J=6.9 Hz, 3H), 0.92 (t, J=6.6 Hz, 6H); $^{13}$C NMR (10 MHz, CDCl$_3$) δ 179.73 (1C), 175.87 (1C), 173.31 (2C), 68.70 (1C), 62.13 (1C), 39.50 (1C), 34.04 (3C), 33.57 (1C), 31.93 (4C), 29.71-29.01 (18C), 27.07 (1C), 24.85 (3C), 24.62 (1C), 22.70 (4C), 17.03 (1C), 14.14 (3C). MASS (ESI, −ve) m/z: 766.0 (M−1). (ESI, +ve) m/z: 785.0 (M+18).

C15α'βMe-Acid-2-TG (Int-62):

Scheme 20. Synthesis of Int-62.

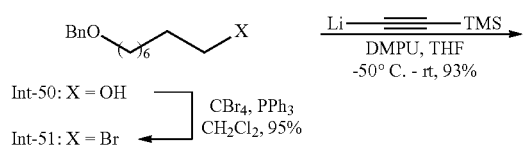

Int-50: X = OH
Int-51: X = Br    CBr$_4$, PPh$_3$
              CH$_2$Cl$_2$, 95%

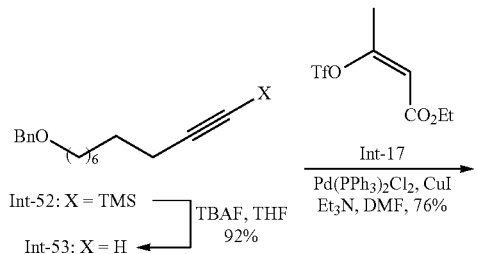

Int-52: X = TMS
Int-53: X = H    TBAF, THF
              92%

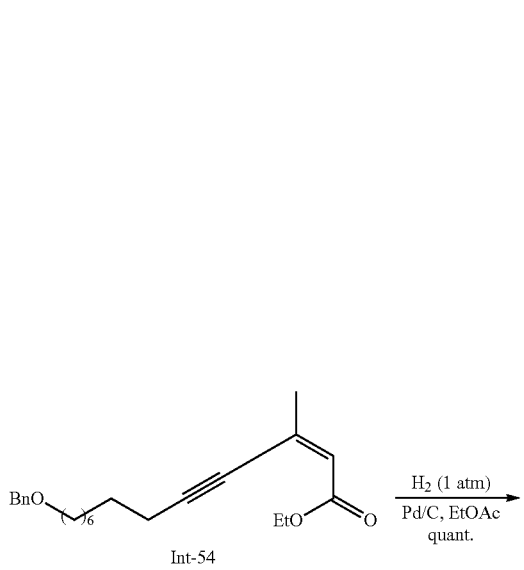

Int-54

H$_2$ (1 atm)
Pd/C, EtOAc
quant.

-continued

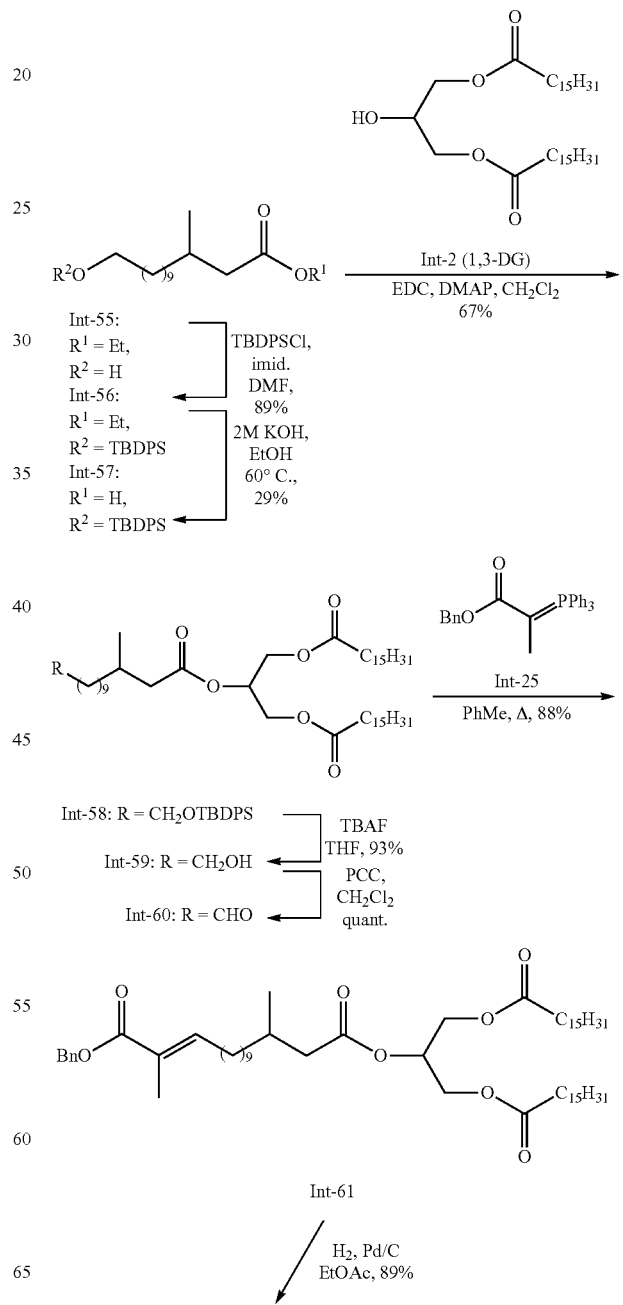

Int-55: R$^1$ = Et, R$^2$ = H
Int-56: R$^1$ = Et, R$^2$ = TBDPS
Int-57: R$^1$ = H, R$^2$ = TBDPS

Int-2 (1,3-DG)
EDC, DMAP, CH$_2$Cl$_2$
67%

TBDPSCl, imid. DMF, 89%

2M KOH, EtOH
60° C., 29%

Int-58: R = CH$_2$OTBDPS
Int-59: R = CH$_2$OH
Int-60: R = CHO

TBAF THF, 93%
PCC, CH$_2$Cl$_2$ quant.

Int-25
PhMe, Δ, 88%

Int-61

H$_2$, Pd/C
EtOAc, 89%

-continued

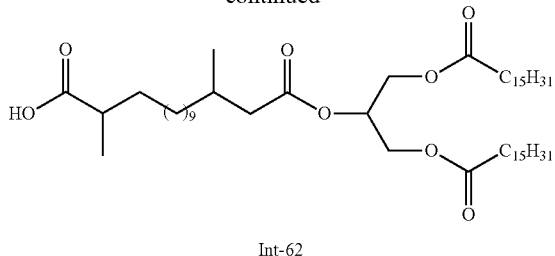

Int-62

Int-50: prepared according to: Subba Reddy, B. V. et al. Helv. Chim. Acta. 2013, 96, 1983-1990.

Int-51: known compound that may be prepared as disclosed in Takagi, Y. et al. Tetrahedron: Asymm. 2004, 15, 2591-2594). $^1$H NMR (401 MHz, CDCl$_3$) δ 7.39-7.23 (m, 5H), 4.50 (s, 2H), 3.47 (t, J=6.6 Hz, 2H), 3.40 (t, J=6.9 Hz, 2H), 1.90-1.80 (m, 2H), 1.66-1.57 (m, 2H), 1.48-1.26 (m, 8H).

n-Butyllithium (n-BuLi, 2.0 M in cyclohexane, 18.1 mL, 36.3 mmol) was added slowly to a solution of TMS-acetylene (5.7 mL, 41.5 mmol) in THF (45 mL) at −78° C. and the mixture stirred at −78° C. for five minutes then warmed to room temperature and stirred for a further 15 minutes. The reaction was re-cooled to −78° C., a solution of bromide Int-51 (3.10 g, 10.4 mmol) and DMPU (6.3 mL, 51.8 mmol) in THF (30 mL) was added slowly and the mixture stirred at −78° C. for 30 minutes and then at room temperature for 18 hours. The reaction was diluted with water (60 mL) and the majority of the organic solvent removed under reduced pressure. The residue was diluted with brine (120 mL) and the aqueous phase extracted with ethyl acetate (3×100 mL). The combined organic extracts were washed with brine (3×100 mL), dried (MgSO$_4$) and concentrated under reduced pressure to give the crude product. Purification by silica gel chromatography (Reveleris 80 g column, 60 mL/min, 4% to 40% ethyl acetate/hexanes) gave TMS alkyne Int-52 (3.05 g, 93%) as a colorless oil. $^1$H NMR (401 MHz, CDCl$_3$) δ 7.36-7.25 (m, 5H), 4.50 (s, 2H), 3.46 (t, J=6.6 Hz, 2H), 2.21 (t, J=7.2 Hz, 2H), 1.65-1.57 (m, 2H), 1.55-1.46 (m, 2H), 1.41-1.27 (m, 8H), 0.15 (s, 9H).

Tetrabutylammonium fluoride (TBAF, 1.0 M in THF, 9.7 mL, 9.70 mmol) was added dropwise to silylalkyne Int-52 (3.05 g, 9.62 mmol) in THF (40 mL) at 0° C. and the mixture stirred at room temperature for one hour. The reaction was diluted with water (25 mL) and the organic solvent removed under reduced pressure. The resulting solution was diluted with brine (100 mL) and the aqueous phase extracted with ethyl acetate (3×50 mL). The combined organic extracts were washed with brine (3×50 mL), dried (MgSO$_4$) and concentrated under reduced pressure to give the crude product. Purification by silica gel chromatography (Reveleris 80 g column, 60 mL/min, 3% to 10% ethyl acetate/hexanes) gave alkyne Int-53 (2.17 g, 92%). $^1$H NMR (401 MHz, CDCl$_3$) δ 7.38-7.25 (m, 5H), 4.50 (s, 2H), 3.46 (t, J=6.6 Hz, 2H), 2.18 (td, J=7.1, 2.6 Hz, 2H), 1.94 (t, J=2.7 Hz, 1H), 1.66-1.56 (m, 2H), 1.57-1.48 (m, 2H), 1.43-1.27 (m, 8H); $^{13}$C NMR (101 MHz, CDCl$_3$) δ 138.8 (C), 128.4 (2C; CH), 127.7 (2C; CH), 127.6 (CH), 84.8 (C), 73.0 (CH), 70.6 (CH$_2$), 68.2 (CH), 29.8 (CH$_2$), 29.4 (CH$_2$), 29.1 (CH$_2$), 28.8 (CH$_2$), 28.6 (CH$_2$), 26.2 (CH$_2$), 18.5 (CH$_2$).

Int-17 was prepared as described above.

A suspension of PdCl$_2$(PPh$_3$)$_2$ (605 mg, 0.862 mmol) in DMF (40 mL) was degassed using N$_2$ gas for five minutes, and then CuI (335 mg, 1.76 mmol), Et$_3$N (2.40 mL, 17.2 mmol) and a degassed solution of alkyne 4 (2.11 g, 8.62 mmol) and enol triflate Int-17 (3.40 g, 13.00 mmol) in DMF (50 mL) were added. The mixture was degassed using a stream of N$_2$ for a further five minutes and then heated at 70° C. for one hour. The reaction was cooled to room temperature and concentrated under reduced pressure to about one-quarter of its original volume. The resulting solution was diluted with ethyl acetate (80 mL), washed with 1 M HCl, sat. aq. NaHCO$_3$, water and brine (30 mL each), dried (MgSO$_4$) and concentrated under reduced pressure to give the crude product. Silica gel chromatography (Reveleris 80 g column, 60 mL/min, 5% to 20% ethyl acetate/hexanes) gave enyne Int-54 (2.35 g, 76%) as a pale yellow oil. $^1$H NMR (401 MHz, CDCl$_3$) δ 7.37-7.24 (m, 5H), 5.92 (d, J=1.4 Hz, 1H), 4.50 (s, 2H), 4.18 (q, J=7.1 Hz, 2H), 3.46 (t, J=6.6 Hz, 2H), 2.43 (t, J=7.2 Hz, 2H), 2.01 (d, J=1.4 Hz, 3H), 1.65-1.55 (m, 4H), 1.46-1.30 (m, 8H), 1.28 (t, J=7.1 Hz, 3H); $^{13}$C NMR (101 MHz, CDCl$_3$) δ 165.4 (C), 138.8 (C), 135.9 (C), 128.5 (2C; CH), 127.7 (2C; CH), 127.6 (CH), 123.4 (CH), 103.2 (C), 79.9 (C), 73.0 (CH$_2$), 70.6 (CH$_2$), 60.0 (CH$_2$), 29.9 (CH$_2$), 29.4 (CH$_2$), 29.2 (CH$_2$), 29.0 (CH$_2$), 28.6 (CH$_2$), 26.3 (CH$_2$), 26.0 (CH$_3$), 20.1 (CH$_2$), 14.4 (CH$_3$).

A solution of benzyl ether Int-54 (707 mg, 1.98 mmol) in ethyl acetate (80 mL) in a three-neck round-bottom flask was twice evacuated and flushed with N$_2$ gas, then palladium on carbon (10% w/w, 525 mg, 0.494 mmol) was added and the resulting suspension re-evacuated and flushed with N$_2$ three times. The flask was fitted with a H$_2$ balloon, evacuated and flushed with H$_2$ three times and the reaction mixture stirred at room temperature under 1 atm of H$_2$ for two hours. The flask was then evacuated and flushed with N$_2$ and the reaction mixture filtered through a pad of celite, washing with ethyl acetate (80 mL). The filtrate was concentrated under reduced pressure to give saturated alcohol Int-55 (540 mg, quant.) as a colorless oil that was used without purification. $^1$H NMR (401 MHz, CDCl$_3$) δ 4.13 (q, J=7.1 Hz, 2H), 3.64 (t, J=6.6 Hz, 2H), 2.28 (dd, J=14.6, 6.0 Hz, 1H), 2.09 (dd, J=14.6, 8.1 Hz, 1H), 1.94 (m, 1H), 1.62-1.51 (m, 2H), 1.39-1.21 (m, 16H), 1.25 (t, J=7.1 Hz, 3H), 0.93 (d, J=6.6 Hz, 3H).

Imidazole (670 mg, 9.85 mmol) and tert-butyl(chloro)diphenylsilane (TBDPSCl, 3.5 mL, 13.6 mmol) were added to a solution of alcohol Int-55 (1.48 g, 5.42 mmol) in CH$_2$Cl$_2$ (80 mL) at 0° C. and the mixture stirred at room temperature for 2.5 hours. The reaction was concentrated to half its volume under reduced pressure, washed with water (2×20 mL) and brine (30 mL), dried (MgSO$_4$) and concentrated under reduced pressure to give the crude product. Purification by silica gel chromatography (Reveleris 80 g column, 60 mL/min, 1% to 16% ethyl acetate/hexanes) gave TBDPS ether Int-56 (2.46 g, 89%) as a colorless oil. $^1$H NMR (401 MHz, CDCl$_3$) δ 7.75-7.64 (m, 4H), 7.46-7.35 (m, 6H), 4.13 (q, J=7.1 Hz, 2H), 3.65 (t, J=6.5 Hz, 2H), 2.29 (dd, J=14.6, 6.0 Hz, 1H), 2.09 (dd, J=14.6, 8.2 Hz, 1H), 1.95 (m, 1H), 1.61-1.50 (m, 2H), 1.38-1.20 (m, 19H), 1.05 (s, 9H), 0.93 (d, J=6.6 Hz, 3H).

A solution of potassium hydroxide (2.0 M, 11.3 mL, 22.6 mmol) was added to ester Int-56 (1.15 g, 2.26 mmol) in ethanol (40 mL) and the mixture stirred at room temperature for 19 hours. The reaction was adjusted to pH 2 by addition of 1 M HCl and the organic solvent removed under reduced pressure. The residue was diluted with water (15 mL) and the aqueous phase extracted with ethyl acetate (3×20 mL). The combined organic extracts were washed with brine (30 mL), dried (MgSO$_4$) and concentrated under reduced pressure to give the crude product. Silica gel chromatography (5% to 25% ethyl acetate/hexanes) gave a pure sample of acid Int-57 (321 mg, 29%) as a pale yellow oil that was used for analytical purposes. An additional >750 mg of 9 was obtained containing slight contamination by an unknown TBDPS species—this material was carried forward and purified at a later stage in the reaction sequence. $^1$H NMR (401 MHz, CDCl$_3$) δ 7.70-7.64 (m, 4H), 7.44-7.34 (m, 6H), 3.65 (t, J=6.5 Hz, 2H), 2.35 (dd, J=15.0, 5.9 Hz, 1H), 2.14 (dd, J=15.0, 8.2 Hz, 1H), 1.95 (m, 1H), 1.60-1.51 (m, 2H), 1.39-1.16 (m, 16H), 1.04 (s, 9H), 0.96 (d, J=6.6 Hz, 3H); $^{13}$C NMR (101 MHz, CDCl$_3$) δ 179.3 (C), 135.7 (4C; CH), 134.4 (2C; C), 129.6 (2C; CH), 127.7 (4C; CH), 64.2 (CH$_2$), 41.7 (CH$_2$), 36.8 (CH$_2$), 32.7 (CH$_2$), 30.3 (CH), 29.9 (CH$_2$), 29.76 (2C; CH$_2$), 29.72 (CH$_2$), 29.5 (CH$_2$), 27.1 (CH$_2$), 27.0 (3C; CH$_3$), 25.9 (CH$_2$), 19.8 (CH$_3$), 19.4 (C).

DMAP (80.8 mg, 0.661 mmol), EDC·HCl (230 mg, 1.20 mmol) and 1,3-diglyceride Int-2 (374 mg, 0.658 mmol) were added to a solution of acid Int-57 (288 mg, 0.597 mmol) in CH$_2$Cl$_2$ (20 mL) and the mixture stirred at room temperature for 20 hours. The reaction was diluted with CH$_2$Cl$_2$ (20 mL), silica gel was added and the mixture concentrated under reduced pressure. Purification by silica gel chromatography (5% to 8% ethyl acetate/hexanes) gave triglyceride Int-58 (416 mg, 67%) as a colorless solid. $^1$H NMR (401 MHz, CDCl$_3$) δ 7.69-7.64 (m, 4H), 7.44-7.34 (m, 6H), 5.28 (m, 1H), 4.289/4.288 (each dd, J=11.9, 4.3 Hz, 2H), 4.14 (dd, J=12.0, 6.0 Hz, 2H), 3.65 (t, J=6.5 Hz, 2H), 2.34 (dd, J=15.0, 5.9 Hz, 1H), 2.30 (t, J=7.5 Hz, 4H), 2.12 (dd, J=14.6, 8.3 Hz, 1H), 1.93 (m, 1H), 1.66-1.50 (m, 6H), 1.45-1.14 (m, 64H), 1.04 (s, 9H), 0.93 (d, J=6.6 Hz, 3H), 0.88 (t, J=6.6 Hz, 6H).

Tetrabutylammonium fluoride (TBAF, 1.0 M in THF, 574 μL, 0.574 mmol) and acetic acid (32.8 μL, 0.574 mmol) were added to a solution of TBDPS ether Int-58 (395 mg, 0.383 mmol) in THF (15 mL) at 0° C. and the mixture stirred at room temperature for 17 hours. The reaction was concentrated under reduced pressure and the residue diluted with ethyl acetate (30 mL), washed with water (2×20 mL) and brine (30 mL), dried (MgSO$_4$) and concentrated under reduced pressure to give the crude product. Purification by silica gel chromatography (5% to 25% ethyl acetate/hexanes) gave alcohol Int-59 (282 mg, 93%) as a colorless solid. $^1$H NMR (401 MHz, CDCl$_3$) δ 5.28 (m, 1H), 4.286/4.285 (each dd, J=11.8, 4.2 Hz, 2H), 4.14 (dd, J=11.9, 5.7 Hz, 2H), 3.63 (t, J=6.6 Hz, 2H), 2.33 (dd, J=15.0, 5.9 Hz, 1H), 2.30 (t, J=7.5 Hz, 4H), 2.12 (dd, J=14.7, 8.3 Hz, 1H), 1.93 (m, 1H), 1.68-1.52 (m, 6H), 1.49-1.15 (m, 64H), 0.93 (d, J=6.6 Hz, 3H), 0.88 (t, J=6.6 Hz, 6H); $^{13}$C NMR (101 MHz, CDCl$_3$) δ 173.5 (2C; C), 172.5 (C), 69.0 (CH), 63.2 (CH$_2$), 62.3 (2C; CH$_2$), 41.9 (CH$_2$), 36.8 (CH$_2$), 34.2 (2C; CH$_2$), 33.0 (CH$_2$), 32.1 (2C; CH$_2$), 30.5 (CH), 29.9 (CH$_2$), 29.84 (6C; CH$_2$), 29.81 (4C; CH$_2$), 29.77 (2C; CH$_2$), 29.74 (CH$_2$), 29.71 (CH$_2$), 29.62 (2C; CH$_2$), 29.57 (CH$_2$), 29.5 (2C; CH$_2$), 29.4 (2C; CH$_2$), 29.3 (3C; CH$_2$), 27.1 (CH$_2$), 25.9 (CH$_2$), 25.0 (2C; CH$_2$), 22.8 (2C; CH$_2$), 19.7 (CH$_3$), 14.3 (2C; CH$_3$).

Pyridinium chlorochromate (PCC, 143 mg, 0.664 mmol) was added to a suspension of alcohol Int-59 (263 mg, 0.331 mmol) and Celite (150 mg) in CH$_2$Cl$_2$ (18 mL) at 0° C. and the mixture stirred at room temperature for four hours. The reaction was filtered through a short pad of silica gel, eluting with ethyl acetate, and the filtrate concentrated under reduced pressure to give crude aldehyde Int-60 (262 mg, quant.) as a yellow oil that was used without purification. $^1$H NMR (401 MHz, CDCl$_3$) δ 9.76 (t, J=1.8 Hz, 1H), 5.27 (m, 1H), 4.29 (dd, J=11.8, 4.1 Hz, 2H), 4.14 (dd, J=11.8, 6.0 Hz, 2H), 2.42 (td, J=7.4, 1.8 Hz, 2H), 2.33 (dd, J=15.0, 5.9 Hz, 1H), 2.30 (t, J=7.5 Hz, 4H), 2.12 (dd, J=14.7, 8.3 Hz, 1H), 1.93 (m, 1H), 1.69-1.53 (m, 6H), 1.45-1.16 (m, 62H), 0.93 (d, J=6.6 Hz, 3H), 0.88 (t, J=6.8 Hz, 6H).

Int-25 was prepared as described above.

A solution of ylide Int-25 (270 mg, 0.637 mmol) in toluene (10 mL) was added to aldehyde Int-60 (262 mg, 0.331 mmol) in toluene (8 mL) and the mixture heated at reflux for 20 hours. The reaction was cooled to room temperature and concentrated under reduced pressure to give the crude product. Purification by silica gel chromatography (5% to 15% ethyl acetate/hexanes) gave α,β-unsaturated benzyl ester Int-61 (273 mg, 88%) as a yellow oil. $^1$H NMR (401 MHz, CDCl$_3$) δ 7.40-7.27 (m, 5H), 6.82 (td, J=7.5, 1.4 Hz, 1H), 5.28 (m, 1H), 5.18 (s, 2H), 4.29 (dd, J=11.9, 4.3 Hz, 2H), 4.14 (dd, J=11.9, 6.0 Hz, 2H), 2.33 (dd, J=15.0, 5.9 Hz, 1H), 2.30 (t, J=7.5 Hz, 4H), 2.20-2.07 (m, 3H), 1.92 (m, 1H), 1.85 (d, J=1.2 Hz, 3H), 1.65-1.53 (m, 4H), 1.47-1.37 (m, 2H), 1.36-1.14 (m, 62H), 0.93 (d, J=6.6 Hz, 3H), 0.88 (t, J=6.9 Hz, 6H); $^{13}$C NMR (101 MHz, CDCl$_3$) δ 173.4 (2C; C), 172.5 (C), 168.2 (C), 143.3 (CH), 136.6 (C), 128.6 (2C; CH), 128.13 (CH), 128.11 (2C; CH), 127.5 (C), 68.9 (CH), 66.3 (CH$_2$), 62.3 (2C; CH$_2$), 41.8 (CH$_2$), 36.8 (CH$_2$), 34.2 (2C; CH$_2$), 32.1 (2C; CH$_2$), 30.5 (CH), 29.9 (CH$_2$), 29.84 (6C; CH$_2$), 29.80 (4C; CH$_2$), 29.76 (2C; CH$_2$), 29.70 (CH$_2$), 29.61 (3C; CH$_2$), 29.57 (CH$_2$), 29.5 (2C; CH$_2$), 29.4 (2C; CH$_2$), 29.3 (3C; CH$_2$), 28.9 (CH$_2$), 28.7 (CH$_2$), 27.1 (CH$_2$), 25.0 (2C; CH$_2$), 22.8 (2C; CH$_2$), 19.7 (CH$_3$), 14.3 (2C; CH$_3$), 12.5 (CH$_3$).

A solution of benzyl ester Int-61 (246 mg, 0.262 mmol) in ethyl acetate (10 mL) in a two-neck flask was evacuated and flushed with N$_2$ gas (three times each), then palladium on carbon (10% w/w, 55.7 mg, 0.0524 mmol) was added and the resulting suspension re-evacuated and flushed with N$_2$ (three times each). The flask was fitted with a H$_2$ balloon, evacuated and flushed with H$_2$ (three times each) and the reaction mixture stirred at room temperature under 1 atm of H$_2$ for 1.5 hours. The reaction was filtered through a pad of celite, washing with ethyl acetate, and concentrated under reduced pressure to give the crude product. Purification by silica gel chromatography (5% to 20% ethyl acetate/hexanes) gave saturated acid Int-62 (193 mg, 87%) as a colorless solid. $^1$H NMR (401 MHz, CDCl$_3$) δ 5.28 (m, 1H), 4.291/4.289 (each dd, J=11.8, 4.2 Hz, 2H), 4.147/4.144 (each dd, J=11.9, 6.0 Hz, 2H), 2.46 (m, 1H), 2.33 (dd, J=15.0, 5.9 Hz, 1H), 2.31 (t, J=7.5 Hz, 4H), 2.12 (dd, J=14.7, 8.2 Hz, 1H), 1.94 (m, 1H), 1.73-1.55 (m, 5H), 1.50-1.21 (m, 67H), 1.18 (d, J=7.0 Hz, 3H), 0.93 (d, J=6.6 Hz, 3H), 0.88 (t, J=6.9 Hz, 6H).

Ph-C3-Phenol-2-TG (Int-67):

Scheme 21. Synthesis of Int-67.

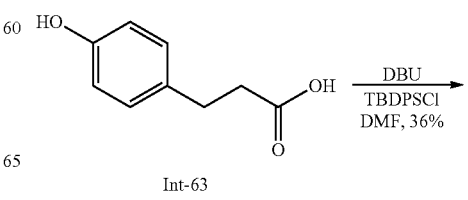

Int-63

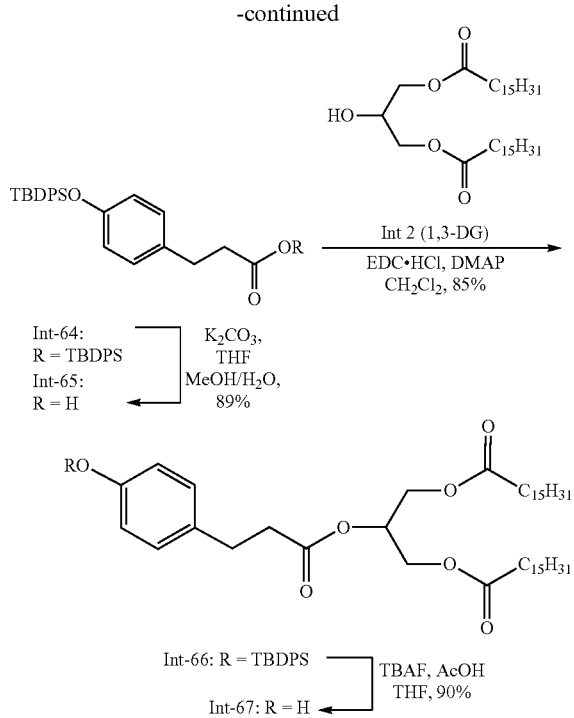

DBU (108 µL, 1.08 mmol) and t-butyldiphenylsilyl chloride (TBDPSCl, 338 µL, 1.30 mmol) were added to a solution of (4-hydroxyphenyl)propionic acid (Int-63; commercially available) (120 mg, 0.722 mmol) in DMF (4 mL) and the mixture stirred at room temperature for one hour. The reaction was diluted with ethyl acetate (15 mL) and organic phase washed with water and brine (15 mL each), dried (MgSO$_4$) and concentrated under reduced pressure to give the crude product. Silica gel chromatography (4.5% ethyl acetate/hexanes) gave silyl ester Int-64 (165 mg, 36%) as a colorless oil. $^1$H NMR (400 MHz, CDCl$_3$): δ 7.75-7.70 (m, 4H), 7.63-7.58 (m, 4H), 7.46-7.31 (m, 12H), 6.97-6.91 (m, 2H), 6.71-6.67 (m, 2H), 2.87 (t, J=7.6 Hz, 2H), 2.72 (t, J=7.6 Hz, 2H), 1.11 (s, 9H), 1.07 (s, 9H); $^{13}$C NMR (101 MHz, CDCl$_3$): δ 172.3 (C), 154.1 (C), 135.7 (4C; CH), 135.4 (4C; CH), 133.2 (2C; C), 133.0 (C), 132.0 (2C; C), 130.1 (2C; CH), 130.0 (2C; CH), 129.2 (2C; CH), 127.9 (4C; CH), 127.8 (4C; CH), 119.7 (2C; CH), 37.9 (CH$_2$), 30.4 (CH$_2$), 27.0 (3C; CH$_3$), 26.7 (3C; CH$_3$), 19.6 (C), 19.2 (C).

Potassium carbonate (157 mg, 1.14 mmol) was added to a solution of TBDPS ester Int-64 (147 mg, 0.228 mmol) in THF (3 mL), methanol (1.5 mL) and water (1.5 mmol) and the mixture stirred at room temperature for 2.5 hours. The reaction was acidified to pH 2 by the addition of 1 M HCl and the aqueous layer extracted with ethyl acetate (3×15 mL). The combined organic extracts were washed with water (30 mL), sat. aq. NaHCO$_3$ (30 mL) and brine (30 mL), dried (MgSO$_4$) and concentrated under reduced pressure to give the crude product. Purification by silica gel chromatography (20% to 35% to 50% ethyl acetate/hexanes) gave acid Int-65 (82.4 mg, 89%) as a colorless solid. $^1$H NMR (400 MHz, CDCl$_3$) δ 7.74-7.67 (m, 4H), 7.45-7.32 (m, 6H), 6.95-6.88 (m, 2H), 6.71-6.65 (m, 2H), 2.82 (t, J=7.8 Hz, 2H), 2.58 (t, J=7.8 Hz, 2H), 1.09 (s, 9H); $^{13}$C NMR (101 MHz, CDCl$_3$): δ 179.2 (C), 154.3 (C), 135.7 (4C; CH), 133.1 (2C; C), 132.7 (C), 130.0 (2C; CH), 129.1 (2C; CH), 127.9 (4C; CH), 119.8 (2C; CH), 35.9 (CH$_2$), 29.9 (CH$_2$), 26.7 (3C; CH$_3$), 19.6 (C).

DMAP (8.2 mg, 0.0667 mmol), EDC·HCl (25.6 mg, 0.133 mmol) and 1,3-diglyceride Int-2 (41.7 mg, 0.0734 mmol) were added to a solution of acid Int-65 (27.0 mg, 0.0666 mmol) in CH$_2$Cl$_2$ (2 mL) and the mixture stirred at room temperature for 19 hours. The reaction was diluted with CH$_2$Cl$_2$ (3 mL), silica gel was added and the mixture concentrated under reduced pressure. Purification by silica gel chromatography (5% to 7.5% ethyl acetate/hexanes) gave triglyceride Int-66 (54.4 mg, 85%) as a colorless solid. $^1$H NMR (400 MHz, CDCl$_3$) δ 7.74-7.66 (m, 4H), 7.45-7.33 (m, 6H), 6.94-6.87 (m, 2H), 6.71-6.64 (m, 2H), 5.24 (m, 1H), 4.25 (dd, J=11.9, 4.3 Hz, 2H), 4.11 (dd, J=11.9, 5.9 Hz, 2H), 2.81 (t, J=7.8 Hz, 2H), 2.60-2.51 (m, 2H), 2.28 (t, J=7.5 Hz, 4H), 1.64-1.56 (m, 4H), 1.35-1.20 (m, 48H), 1.09 (s, 9H), 0.88 (t, J=6.8 Hz, 6H); $^{13}$C NMR (101 MHz, CDCl$_3$) δ 173.4 (2C; C), 172.2 (C), 154.2 (C), 135.7 (4C; CH), 133.1 (2C; C), 132.7 (C), 130.0 (2C; CH), 129.1 (2C; CH), 127.9 (4C; CH), 119.8 (2C; CH), 69.2 (CH), 62.1 (2C; CH$_2$), 36.0 (CH$_2$), 34.2 (2C; CH$_2$), 32.1 (2C; CH$_2$), 30.1 (CH$_2$), 29.85 (2C; CH$_2$), 29.81 (2C; CH$_2$), 29.76 (2C; CH$_2$), 29.6 (2C; CH$_2$), 29.5 (2C; CH$_2$), 29.4 (2C; CH$_2$), 29.3 (2C; CH$_2$), 26.7 (3C; CH$_3$), 25.0 (2C; CH$_2$), 22.8 (2C; CH$_2$), 19.6 (C), 14.3 (2C; CH$_3$).

Acetic acid (6.5 µL, 0.114 mmol) and tetrabutylammonium fluoride (TBAF, 1.0 M in THF, 114 µL, 0.114 mmol) were added to a solution of TBDPS ether Int-66 (54.5 mg, 0.0570 mmol) in THF (1.2 mL) at 0° C. and the mixture stirred at room temperature for 30 minutes. The reaction was diluted with water (10 mL) and the aqueous layer extracted with ethyl acetate (3×10 mL). The combined organic extracts were washed with sat. aq. NaHCO$_3$ (20 mL) and brine (20 mL), dried (MgSO$_4$) and concentrated under reduced pressure to give the crude product. Purification by silica gel chromatography (10% to 15% ethyl acetate/hexanes) gave phenol Int-67 (37.0 mg, 90%) as a colorless solid. $^1$H NMR (400 MHz, CDCl$_3$) δ 7.09-7.03 (m, 2H), 6.78-6.72 (m, 2H), 5.25 (m, 1H), 4.62 (s, 1H), 4.25 (dd, J=11.9, 4.4 Hz, 2H), 4.11 (dd, J=11.9, 5.8 Hz, 2H), 2.88 (t, J=7.7 Hz, 2H), 2.61 (t, J=7.7 Hz, 2H), 2.29 (t, J=7.6 Hz, 4H), 1.64-1.56 (m, 4H), 1.34-1.18 (m, 48H), 0.88 (t, J=6.9 Hz, 6H); $^{13}$C NMR (101 MHz, CDCl$_3$) δ 173.6 (2C; C), 172.3 (C), 154.4 (C), 132.3 (C), 129.5 (2C; CH), 115.5 (2C; CH), 69.2 (CH), 62.2 (2C; CH$_2$), 36.2 (CH$_2$), 34.2 (2C; CH$_2$), 32.1 (2C; CH$_2$), 30.2 (CH$_2$), 29.83 (6C; CH$_2$), 29.79 (4C; CH$_2$), 29.76 (2C; CH$_2$), 29.6 (2C; CH$_2$), 29.5 (2C; CH$_2$), 29.4 (2C; CH$_2$), 29.2 (2C; CH$_2$), 25.0 (2C; CH$_2$), 22.8 (2C; CH$_2$), 14.3 (2C; CH$_3$).

C6-ET-alcohol-2-TG (Int-73):

Scheme 22. Synthesis of Int-73.

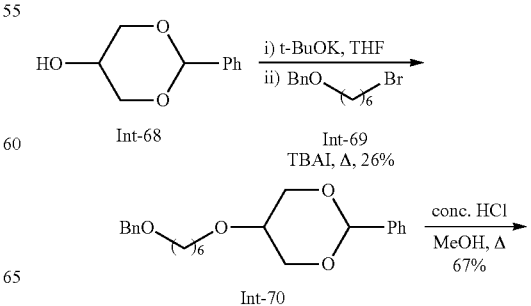

-continued

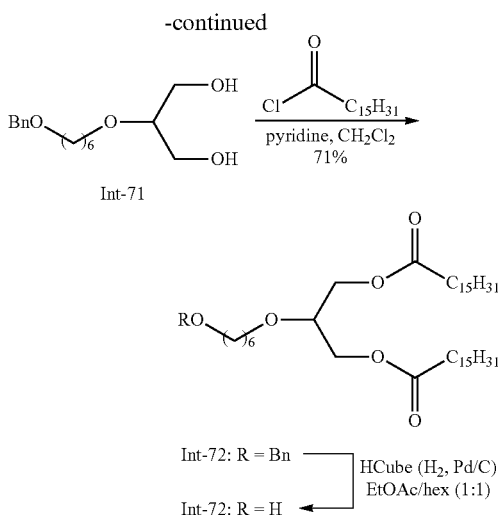

Int-69 is a known compound that may be prepared as described in, e.g., Sang-sup, J. et al. *Tetrahedron: Asymmetry* 1997, 8, 1187-1192).

Alcohol Int-68 (commercially available; 90.0 mg, 0.499 mmol) was added in a single portion to a suspension of t-BuOK (84.1 mg, 0.749 mmol) in THF (2 mL) and the mixture stirred at room temperature for one hour. A solution of bromide Int-69 (190 mg, 0.699 mmol) in THF (1 mL) and TBAI (36.9 mg, 0.100 mmol) were then added and the resulting mixture heated at reflux for 20 hours. The reaction was cooled to room temperature and diluted with ethyl acetate (10 mL), quenched with water (15 mL) and the aqueous phase extracted with ethyl acetate (3×20 mL). The combined organic extracts were washed with water and brine (50 mL each), dried (MgSO$_4$) and concentrated under reduced pressure to give the crude product. Silica gel chromatography (5 to 15% to 25% ethyl acetate/hexanes) gave a sample of semi-pure product, which was re-subjected to column chromatography (5% to 12.5% ethyl acetate/toluene) to give ether-linked glycerol Int-70 (48.0 mg, 26%) as a colorless oil. $^1$H NMR (400 MHz, CDCl$_3$): δ 7.54-7.49 (m, 2H), 7.39-7.26 (m, 8H), 5.55 (s, 1H), 4.50 (s, 2H), 4.33 (dd, J=12.5, 1.4 Hz, 2H), 4.07-4.01 (m, 2H), 3.55 (t, J=6.7 Hz, 2H), 3.47 (t, J=6.6 Hz, 2H), 3.25 (m, 1H), 1.71-1.59 (m, 4H), 1.45-1.39 (m, 4H).

A mixture of benzylidene acetal Int-70 (46.0 mg, 0.124 mmol), conc. HCl (2 drops) and MeOH (1.5 mL) was heated at reflux for two hours and then cooled to room temperature. The reaction was diluted with ethyl acetate (30 mL) and water (10 mL), and the organic phase washed sat. aq. NaHCO$_3$, water and brine (30 mL each), dried (MgSO$_4$) and concentrated under reduced pressure to give the crude product. Silica gel chromatography (40% to 80% ethyl acetate/hexanes) gave diol Int-71 (23.5 mg, 67%) as a colorless oil. $^1$H NMR (400 MHz, CDCl$_3$): δ 7.36-7.27 (m, 5H), 4.50 (s, 2H), 3.76 (dd, J=11.6, 4.4 Hz, 2H), 3.67 (dd, J=11.6, 5.1 Hz, 2H), 3.57 (t, J=6.6 Hz, 2H), 3.50-3.42 (m, 3H), 1.67-1.56 (m, 4H), 1.43-1.36 (m, 4H).

A solution of freshly-prepared palmitoyl chloride (91.6 mg, 0.333 mmol) in CH$_2$Cl$_2$ (1.5 mL) and pyridine (30.3 µL, 0.375 mmol) were added to the diol Int-71 (23.5 mg, 0.0833 mmol) and the reaction stirred at room temperature for 16 hours. The reaction mixture was diluted with CH$_2$Cl$_2$ (30 mL) and quenched with water (10 mL). The organic phase was washed with water, sat. aq. NaHCO$_3$ and brine (30 mL each), dried (MgSO$_4$) and concentrated under reduced pressure to give the crude product. Silica gel chromatography (5% to 10% ethyl acetate/hexanes) gave glyceride Int-72 (44.8 mg, 71%) as a colorless solid. $^1$H NMR (400 MHz, CDCl$_3$): δ 7.36-7.26 (m, 5H), 4.50 (s, 2H), 4.18 (dd, J=11.6, 4.9 Hz, 2H), 4.11 (dd, J=11.6, 5.5 Hz, 2H), 3.68 (dd, J=10.4, 5.3 Hz, 1H), 3.55 (t, J=6.6 Hz, 2H), 3.46 (t, J=6.6 Hz, 2H), 2.32 (t, J=7.6 Hz, 4H), 1.67-1.54 (m, 8H), 1.34-1.21 (m, 52H), 0.88 (t, J=6.9 Hz, 6H); $^{13}$C NMR (100 MHz, CDCl$_3$): δ 173.7 (2C; C), 138.8 (C), 128.5 (2C; CH), 127.7 (2C; CH), 127.6 (CH), 75.3 (CH), 73.0 (CH$_2$), 70.7 (CH$_2$), 70.5 (CH$_2$), 63.2 (2C; CH$_2$), 34.3 (2C; CH$_2$), 32.1 (2C; CH$_2$), 30.0 (CH$_2$), 29.87 (CH$_2$), 29.84 (2C; CH$_2$), 29.80 (2C; CH$_2$), 29.76 (2C; CH$_2$), 29.6 (2C; CH$_2$), 29.5 (2C; CH$_2$), 29.4 (2C; CH$_2$), 29.3 (2C; CH$_2$), 26.2 (CH$_2$), 26.0 (CH$_2$), 25.1 (2C; CH$_2$), 22.8 (2C; CH$_2$), 14.3 (2C; CH$_3$).

A solution of benzyl ether Int-72 (43.5 mg, 57.3 µmol) in ethyl acetate/hexanes (10 mL each) was subjected to hydrogenolysis using an HCube hydrogenation apparatus under recycling conditions (10% Pd/C cartridge, full H$_2$ mode at 6 bar, flow rate=1 mL/min), with the column temperature set at 25° C. for 1.5 hours then at 35° C. for a further hour. Concentration of the reaction mixture under reduced pressure gave alcohol Int-73 (38.2 mg, quant.) as a colorless solid that was used without purification. $^1$H NMR (400 MHz, CDCl$_3$): δ 4.19 (dd, J=11.6, 4.9 Hz, 2H), 4.11 (dd, J=11.6, 5.5 Hz, 2H), 3.67 (m, 1H), 3.64 (t, J=6.5 Hz, 2H), 3.55 (t, J=6.5 Hz, 2H), 2.32 (t, J=7.6 Hz, 4H), 1.66-1.56 (m, 8H), 1.41-1.34 (m, 4H), 1.33-1.18 (m, 48H), 0.88 (t, J=6.8 Hz, 6H).

C4-ET-alcohol-2-TG (Int-78):

Scheme 23. Synthesis of Int-78.

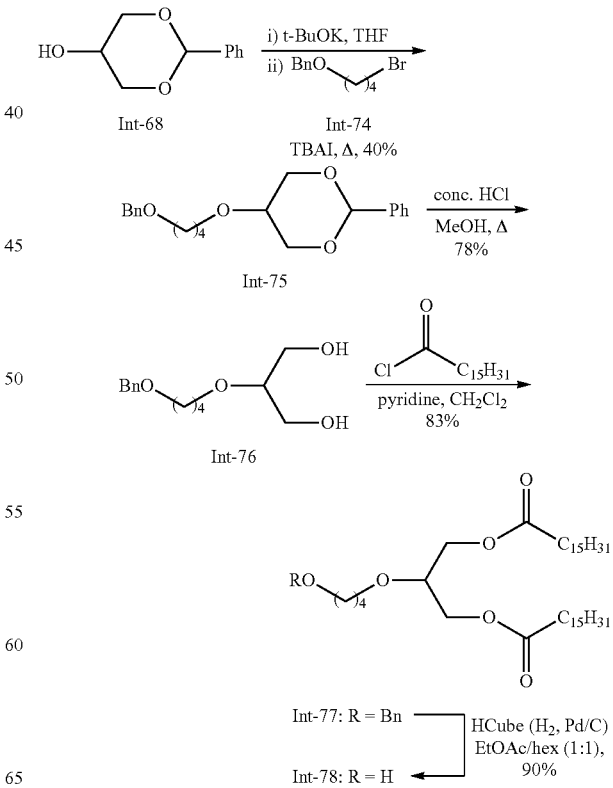

Int-74 is a known compound that may be prepared as described in Charette, A. B. et al. *J. Am. Chem. Soc.* 2001, 123, 11829-11830.

Alcohol Int-68 (commercially available; 135 mg, 0.749 mmol) was added in a single portion to a suspension of t-BuOK (118 mg, 1.05 mmol) in THF (2.5 mL) and the mixture stirred at RT for one hour. A solution of bromide Int-74 (273 mg, 1.12 mmol) in THF (2 mL) was then added and the resulting mixture heated at reflux for 26 hours. The reaction was cooled to room temperature and diluted with ethyl acetate (10 mL), quenched with water (20 mL) and the aqueous phase extracted with ethyl acetate (3×25 mL). The combined organic extracts were washed with water and brine (60 mL each), dried (MgSO$_4$) and concentrated under reduced pressure to give the crude product. Silica gel chromatography (10% to 20% ethyl acetate/hexanes) gave ether-linked glycerol Int-75 (103 mg, 40%) as a colorless oil. $^1$H NMR (400 MHz, CDCl$_3$): δ 7.53-7.48 (m, 2H), 7.38-7.27 (m, 8H), 5.55 (s, 1H), 4.50 (s, 2H), 4.37-4.27 (m, 2H), 4.08-3.98 (m, 2H), 3.61-3.55 (m, 2H), 3.54-3.50 (m, 2H), 3.25 (m, 1H), 1.82-1.65 (m, 4H); $^{13}$C NMR (100 MHz, CDCl$_3$): δ 138.8 (C), 138.3 (C), 128.9 (CH), 128.4 (2C; CH), 128.3 (2C; CH), 127.7 (2C; CH), 127.6 (CH), 126.3 (2C; CH), 101.4 (C), 73.0 (CH$_2$), 70.7 (CH), 70.3 (CH$_2$), 69.1 (2C; CH$_2$), 68.7 (CH$_2$), 26.7 (CH$_2$), 26.6 (CH$_2$).

A mixture of benzylidene acetal Int-75 (102 mg, 0.298 mmol), conc. HCl (2 drops) and MeOH (4 mL) was heated at reflux for two hours and then cooled to RT. The reaction was diluted with ethyl acetate (40 mL) and water (15 mL), and the organic phase washed sat. aq. NaHCO$_3$, water and brine (40 mL each), dried (MgSO$_4$) and concentrated under reduced pressure to give the crude product. Silica gel chromatography (25% to 65% to 90% ethyl acetate/hexanes) gave diol Int-76 (58.8 mg, 78%) as a colorless oil. $^1$H NMR (400 MHz, CDCl$_3$): δ 7.38-7.24 (m, 5H), 4.50 (s, 2H), 3.71 (dd, J=11.6, 4.6 Hz, 2H), 3.64 (dd, J=11.6, 4.9 Hz, 2H), 3.60-3.55 (m, 2H), 3.52-3.46 (m, 2H), 3.41 (m, 1H), 2.59 (br s, 2H), 1.75-1.61 (m, 4H); $^{13}$C NMR (100 MHz, CDCl$_3$): δ 138.5 (C), 128.5 (2C; CH), 127.8 (2C; CH), 127.7 (CH), 78.8 (CH), 73.0 (CH$_2$), 70.2 (CH$_2$), 69.8 (CH$_2$), 62.2 (2C; CH$_2$), 27.1 (CH$_2$), 26.4 (CH$_2$).

A solution of palmitoyl chloride (131 mg, 0.475 mmol) in CH$_2$Cl$_2$ (2 mL) and pyridine (48.0 μL, 0.594 mmol) were added to the diol Int-76 (30.2 mg, 0.119 mmol) and the reaction stirred at room temperature for 19 hours. The reaction mixture was diluted with CH$_2$Cl$_2$ (40 mL) and quenched with water (20 mL). The organic phase was washed with water, sat. aq. NaHCO$_3$ and brine (40 mL each), dried (MgSO$_4$) and concentrated under reduced pressure to give the crude product. Silica gel chromatography (6% ethyl acetate/hexanes) gave triglyceride Int-77 (72.4 mg, 83%) as a colorless solid. $^1$H NMR (400 MHz, CDCl$_3$): δ 7.38-7.26 (m, 5H), 4.50 (s, 2H), 4.18 (dd, J=11.6, 4.9 Hz, 2H), 4.11 (dd, J=11.6, 5.5 Hz, 2H), 3.67 (m, 1H), 3.58 (t, J=6.1 Hz, 2H), 3.48 (t, J=6.1 Hz, 2H), 2.31 (t, J=7.6 Hz, 4H), 1.73-1.55 (m, 8H), 1.37-1.19 (m, 48H), 0.88 (t, J=6.9 Hz, 6H); $^{13}$C NMR (100 MHz, CDCl$_3$): δ 173.7 (2C; C), 138.7 (C), 128.5 (2C; CH), 127.7 (2C; CH), 127.6 (CH), 75.4 (CH), 73.0 (CH$_2$), 70.4 (CH$_2$), 70.2 (CH$_2$), 63.1 (2C; CH$_2$), 34.3 (2C; CH$_2$), 32.1 (2C; CH$_2$), 29.82 (6C; CH$_2$), 29.79 (4C; CH$_2$), 29.74 (2C; CH$_2$), 29.6 (2C; CH$_2$), 29.5 (2C; CH$_2$), 29.4 (2C; H2), 29.3 (2C; CH$_2$), 26.8 (CH$_2$), 26.5 (CH$_2$), 25.0 (2C; CH$_2$), 22.8 (2C; CH$_2$), 14.2 (2C; CH$_3$).

A solution of benzyl ether Int-77 (70.0 mg, 95.8 μmol) in ethyl acetate/hexanes (25 mL each) was subjected to hydrogenolysis using an HCube hydrogenation apparatus under recycling conditions (10% Pd/C cartridge, full H$_2$ mode at 6 bar, flow rate=1 mL/min), with the column temperature set at 50° C. for 2.5 hours. Concentration of the reaction mixture under reduced pressure gave the crude product, which was purified by silica gel chromatography (10% to 30% ethyl acetate/hexanes) to give alcohol Int-78 (55.0 mg, 90%) as a colorless solid. $^1$H NMR (400 MHz, CDCl$_3$): δ 4.20 (dd, J=11.7, 4.8 Hz, 2H), 4.11 (dd, J=11.7, 5.5 Hz, 2H), 3.69 (m, 1H), 3.64 (t, J=5.9 Hz, 2H), 3.60 (t, J=5.8 Hz, 2H), 2.32 (t, J=7.5 Hz, 4H), 1.70-1.55 (m, 8H), 1.33-1.19 (m, 48H), 0.87 (t, J=6.8 Hz, 6H); $^{13}$C NMR (100 MHz, CDCl$_3$): δ 173.7 (2C; C), 75.5 (CH), 70.5 (CH$_2$), 63.0 (2C; CH$_2$), 62.6 (CH$_2$), 34.3 (2C; CH$_2$), 32.0 (2C; CH$_2$), 29.9 (CH$_2$), 29.82 (2C; CH$_2$), 29.78 (2C; CH$_2$), 29.7 (2C; CH$_2$), 29.6 (2C; CH$_2$), 29.5 (2C; CH$_2$), 29.4 (2C; CH$_2$), 29.3 (2C; CH$_2$), 26.7 (CH$_2$), 25.0 (2C; CH$_2$), 22.8 (2C; CH$_2$), 14.2 (2C; CH$_3$).

C5ββDiMe-Acid-2-TG (Int-79):

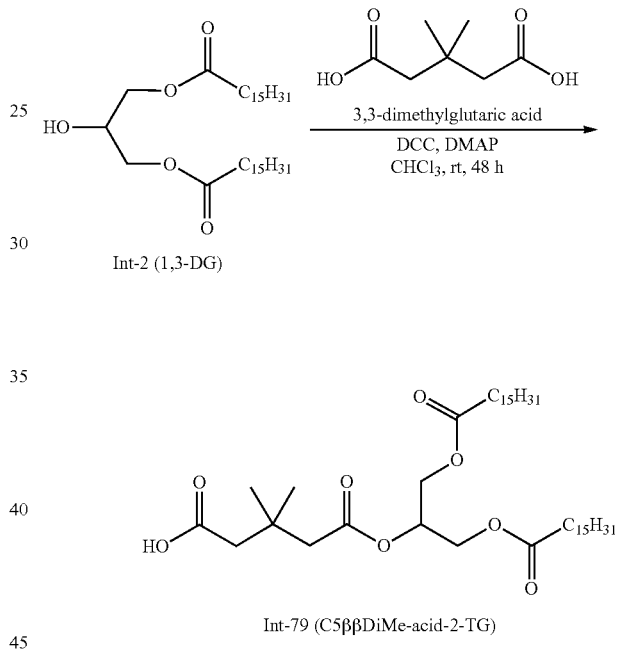

Int-79 (C5ββDiMe-acid-2-TG)

To a solution of compound Int-2 (5.0 g, 8.78 mmol) in chloroform (150 ml) was added DCC (3.62 g, 17.57 mmol) and DMAP (0.53 g, 4.39 mmol), followed by addition of 3,3-dimethylglutaric acid (2.81 g, 17.57 mmol) at room temperature and then stirring for 48 h. The reaction was monitored by TLC. After completion of the reaction, the reaction mixture was filtered through a celite bed and washed with dichloromethane (100 ml) and the filtrate was evaporated to give the crude desired compound, which was purified by combi-flash purification. The compound was eluted using 6% ethyl acetate in hexane and concentrated to give Int-79 (C5ββDiMe-acid-2-TG) (2.0 g, 32%) as off-white solid. $^1$H NMR (400 MHz, CDCl$_3$) δ 5.33 (m, 1H), 4.33 (m, 2H), 4.18 (m, 2H), 2.51 (s, 4H), 2.35 (t, 4H), 1.64 (t, 4H), 1.29 (m, 49H), 1.19 (s, 6H), 0.92 (t, 6H); $^{13}$C NMR (101 MHz, CDCl$_3$) δ 176.4 (1C), 173.3 (2C), 171.0 (1C), 69.1 (1C), 62.1 (2C), 45.0 (1C) 44.7 (1C), 34.0 (3C), 32.6 (1C), 31.9 (3H), 29.7-29.1 (14C), 27.7 (3C), 24.8 (3C), 22.7 (3C), 14.1 (3C); HPLC (ELSD): 10.07 min, 97.74% purity; MASS (ESI, −ve) m/z: 710 (M−1).

C12a'aMe-Acid-2-TG (Int-81):

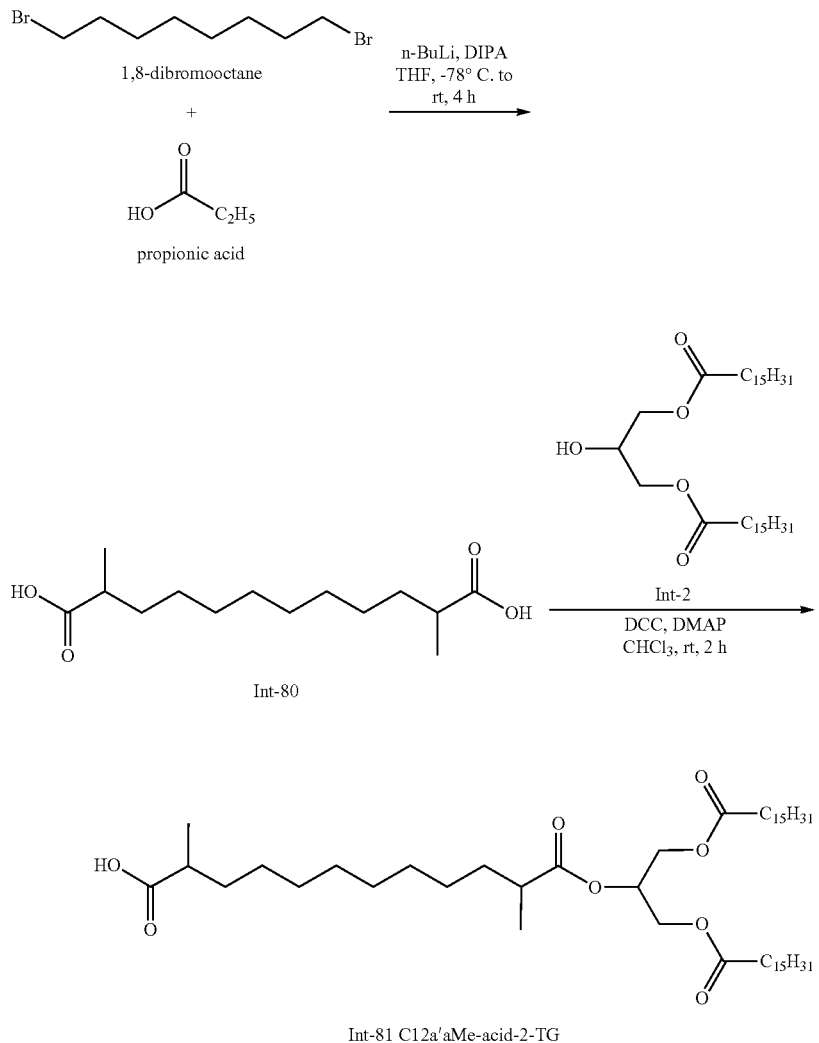

To a solution of diisopropylamine (DIPA) (3.18 g, 81.08 mmol) in dry THF (45 mL) was added n-BuLi (2.5 M in hexane) (32 mL, 81.08 mmol) at −78° C. The reaction mixture was stirred at −78° C. for 30 min, then then propionic acid (1.5 g, 20.27 mmol) was added and the reaction mixture was stirred at −78° C. for further 30 min. 1,8-dibromooctane (2.75 g, 10.13 mmol) was added and the reaction mixture was stirred and allowed to warm from −78° C. to room temperature over 3 h. The reaction was monitored by TLC for completeness. An additional identical batch starting with 1.5 g propionic acid was prepared and the two batches combined before workup. The combined reaction mixture was diluted with water (100 mL) and acidified with 1N HCl (25 ml) and extracted with ethyl acetate (3×100 ml), and the combined organic layer was dried over $Na_2SO_4$ and evaporated to give crude compound. The title compound was purified by combi flash purification, eluting with 10% ethyl acetate/hexane as the mobile phase. After evaporation, Int-80 (0.99 g, 9.5%) was obtained as an off-white solid. $^1$H NMR (400 MHz, $CDCl_3$) δ 2.57-2.39 (m, 2H), 1.71 (m, 2H), 1.50-1.43 (m, 2H), 1.40-1.25 (m, 14H), 1.22 (d, J=7.2 Hz 6H).

To a solution of compound Int-2 (2.7 g, 4.74 mmol) in chloroform (50 ml) was added DCC (1.95 g, 9.49 mmol) and DMAP (0.28 g, 2.30 mmol), then the reaction was stirred at room temperature for 30 min. Int-80 (2.44 g, 9.49 mmol) was added at room temperature and stirred for 2 h. The reaction was monitored by TLC until completion, after which the reaction mixture was filtered through celite and washed with DCM (45 ml), then evaporated to give the crude product, which was purified by combi flash purification, eluting with 7% ethyl acetate/hexane. After evaporation, Int-81 (C12a'aMe-acid-2-TG) (1.7 g, 44.3%) was obtained as an off-white solid. $^1$H NMR (400 MHz, $CDCl_3$) δ 5.32 (m, 1H), 4.33 (m, 2H), 4.19 (m, 2H), 2.49 (m, 2H), 2.34 (m, 4H), 1.72-1.62 (m, 4H), 1.49-1.40 (m, 4H). 1.38-1.29 (m, 59H), 1.24-1.17 (m, 8H), 0.92 (m, 6H); $^{13}$C NMR (101 MHz, $CDCl_3$) δ 181.7 (1C), 176.0 (1C), 173.4 (2C), 68.7 (2C), 62.2 (3C), 39.6 (2C), 39.2 (1C), 34.1 (3C), 33.7 (1C), 32.0 (3C), 29.7-29.2 (17C), 27.2 (1C), 24.9 (3C), 22.7 (3C), 17.1 (2C), 16.9 (1C), 14.2 (3C).

Scheme 26. Synthesis of Int-91.

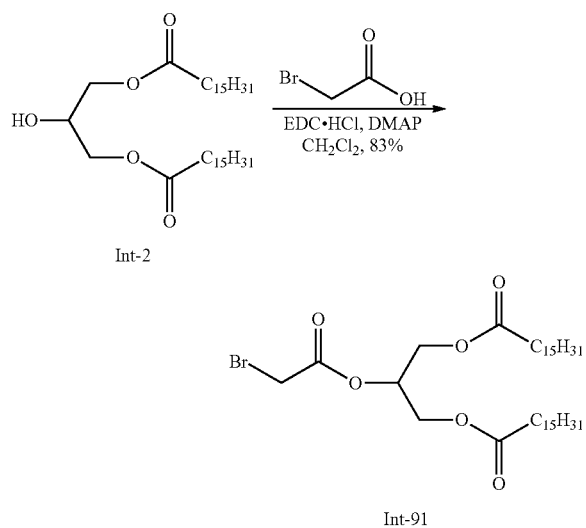

Bromotriglyceride Int-91:

DMAP (10.7 mg, 0.0979 mmol) and EDC·HCl (41.8 mg, 0.220 mmol) were added to a solution of bromoacetic acid (24.4 mg, 0.176 mmol) and Int-2 (50.0 mg, 0.0879 mmol) in CH$_2$Cl$_2$ (2 mL) and the mixture stirred at RT for 22 hours. The reaction was diluted with CH$_2$Cl$_2$ (5 mL), silica gel was added, and the solvent removed under reduced pressure. Silica gel chromatography (4% ethyl acetate/hexanes) gave bromotriglyceride Int-91 (50.3 mg, 83%) as a colorless solid. $^1$H NMR (400 MHz, CDCl$_3$) δ 5.31 (m, 1H), 4.34 (dd, J=12.1, 4.0 Hz, 2H), 4.17 (dd, J=12.1, 6.1 Hz, 2H), 3.84 (s, 2H), 2.32 (t, J=7.6 Hz, 4H), 1.66-1.56 (m, 4H), 1.35-1.20 (m, 48H), 0.88 (t, J=6.9 Hz, 6H); $^{13}$C NMR (101 MHz, CDCl$_3$) δ 173.4 (2C; C), 166.7 (C), 71.3 (CH), 61.9 (2C; CH$_2$), 34.1 (2C; CH$_2$), 32.1 (2C; CH$_2$), 29.84 (2C; CH$_2$), 29.80 (2C; CH$_2$), 29.75 (2C; CH$_2$), 29.6 (2C; CH$_2$), 29.5 (2C; CH$_2$), 29.4 (2C; CH$_2$), 29.3 (2C; CH$_2$), 25.5 (CH$_2$), 25.0 (2C; CH$_2$), 22.8 (2C; CH$_2$), 14.3 (2C; CH$_2$).

Iodotriglyceride Int-95:

Scheme 27. Synthesis of Int-95.

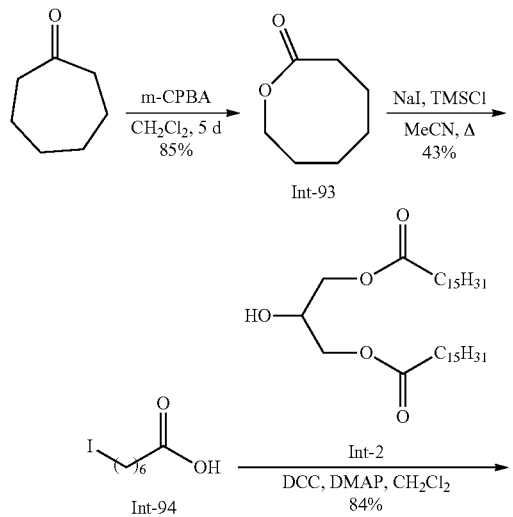

Int-93 is a known compound prepared from cycloheptanone as shown above (see Kai, K. et al. *Tetrahedron* 2008, 64, 6760-6769). To prepare Int-94, chlorotrimethylsilane (TMSCl, 208 µL, 1.64 mmol) was added to a suspension of lactone Int-93 (70.0 mg, 0.546 mmol) and sodium iodide (246 mg, 1.64 mmol) in acetonitrile (1.5 mL) and the mixture heated at reflux for 16 hours. The reaction was cooled to RT, diluted with ethyl acetate and water (10 mL each), and extracted with ethyl acetate (3×15 ml). The combined organic extracts were washed with 1 M Na$_2$S$_2$O$_3$ and brine (40 mL each), dried (MgSO$_4$) and concentrated under reduced pressure to give the crude product. Silica gel chromatography (100% CH$_2$Cl$_2$ to 50% ethyl acetate/hexanes) gave semi-pure acid Int-94 (59.8 mg, 43%) as a yellow oil. However, an accurate yield and clean NMR spectra could not be obtained due to the presence of the m-CPBA impurities, which were carried forward to the next step. $^1$H NMR (400 MHz, CDCl$_3$) δ 3.19 (t, J=7.0 Hz, 2H), 2.37 (t, J=7.4 Hz, 2H), 1.88-1.80 (m, 2H), 1.71-1.61 (m, 2H), 1.46-1.33 (m, 4H).

DMAP (15.2 mg, 0.124 mmol) and DCC (51.3 mg, 0.248 mmol) were added sequentially to a solution of acid Int-94 (35.0 mg, 0.137 mmol) and 1,3-diglyceride Int-2 (70.7 mg, 0.124 mmol) in CH$_2$Cl$_2$ (4 mL) and the mixture stirred at RT for 17 hours. The resulting suspension was diluted with CH$_2$Cl$_2$, cooled to 0° C. and filtered through Celite, washing with further CH$_2$Cl$_2$. The organic phase was washed with 1 M HCl, sat. aq. NaHCO$_3$ and brine, dried (MgSO$_4$) and concentrated under reduced pressure to give the crude product. Silica gel chromatography (3.5% to 4.5% ethyl acetate/hexanes) gave semi-pure iodotriglyceride Int-95 (83.6 mg, 84%) as a colorless solid. However, an accurate yield and clean NMR spectra could not be obtained due to the presence of the m-CPBA impurities, which were carried forward to the next step. $^1$H NMR (400 MHz, CDCl$_3$) δ 5.26 (m, 1H), 4.30 (dd, J=11.9, 4.4 Hz, 2H), 4.14 (dd, J=11.9, 5.9 Hz, 2H), 3.18 (t, J=7.0 Hz, 2H), 2.36-2.27 (m, 6H), 1.86-1.77 (m, 2H), 1.68-1.52 (m, 6H), 1.45-1.18 (m, 52H), 0.88 (t, J=6.9 Hz, 6H).

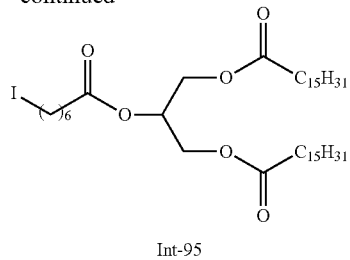

Int-95

Scheme 28. Synthesis of Int-97.

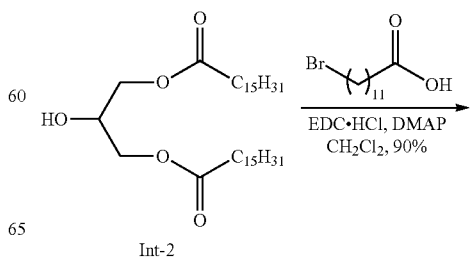

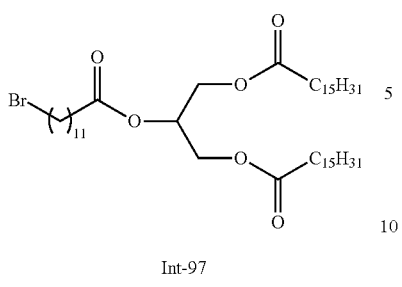

Int-97

DMAP (17.2 mg, 0.141 mmol) and EDC·HCl (67.4 mg, 0.352 mmol) were added to a solution of 1,3-diglyceride Int-2 (80.0 mg, 0.141 mmol) and 12-bromododecanoic acid (51.0 mg, 0.183 mmol) in $CH_2Cl_2$ (2.5 mL) and the mixture stirred at RT for 18 hours. The reaction was diluted with $CH_2Cl_2$ (10 mL), silica gel was added, and the mixture concentrated under reduced pressure. Purification by silica gel chromatography (5% to 10% ethyl acetate/hexanes) gave bromotriglyceride Int-97 (105 mg, 90%) as a colorless solid. $^1H$ NMR (401 MHz, $CDCl_3$) δ 5.25 (m, 1H), 4.28 (dd, J=11.9, 4.3 Hz, 2H), 4.13 (dd, J=11.9, 5.9 Hz, 2H), 3.38 (t, J=6.9 Hz, 2H), 2.30 (t, J=7.5 Hz, 2H), 2.29 (t, J=7.5 Hz, 4H), 1.88-1.79 (m, 2H), 1.65-1.55 (m, 6H), 1.45-1.36 (m, 2H), 1.34-1.18 (m, 60H), 0.86 (t, J=6.8 Hz, 6H); $^{13}C$ NMR (101 MHz, $CDCl_3$) δ 173.4 (2C; C), 172.9 (C), 69.0 (CH), 62.2 (2C; $CH_2$), 34.3 ($CH_2$), 34.2 (2C; $CH_2$), 34.0 ($CH_2$), 33.0 ($CH_2$), 32.1 (2C; $CH_2$), 29.82 (6C; $CH_2$), 29.78 (4C; $CH_2$), 29.74 (2C; $CH_2$), 29.60 (3C; $CH_2$), 29.54 (2C; $CH_2$), 29.48 (2C; $CH_2$), 29.39 (2C; $CH_2$), 29.38 ($CH_2$), 29.23 (2C; $CH_2$), 29.17 ($CH_2$), 28.9 ($CH_2$), 28.3 ($CH_2$), 25.0 (2C; $CH_2$), 22.8 (2C; $CH_2$), 14.2 (2C; $CH_3$).

Int-105:

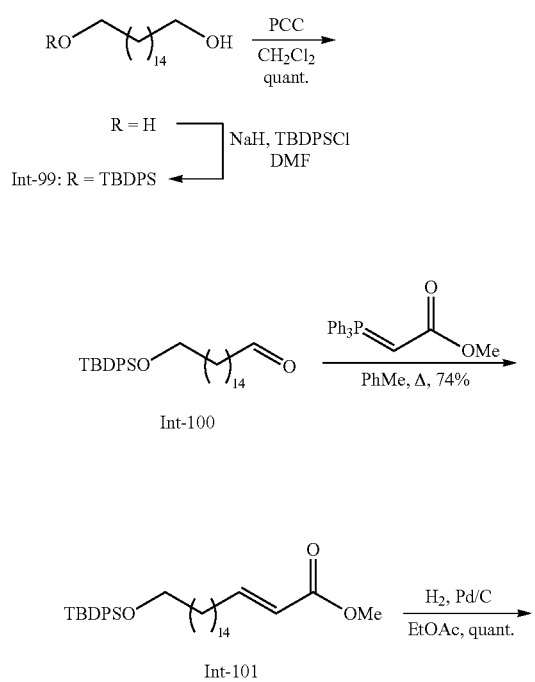

Scheme 29. Synthesis of Int-105.

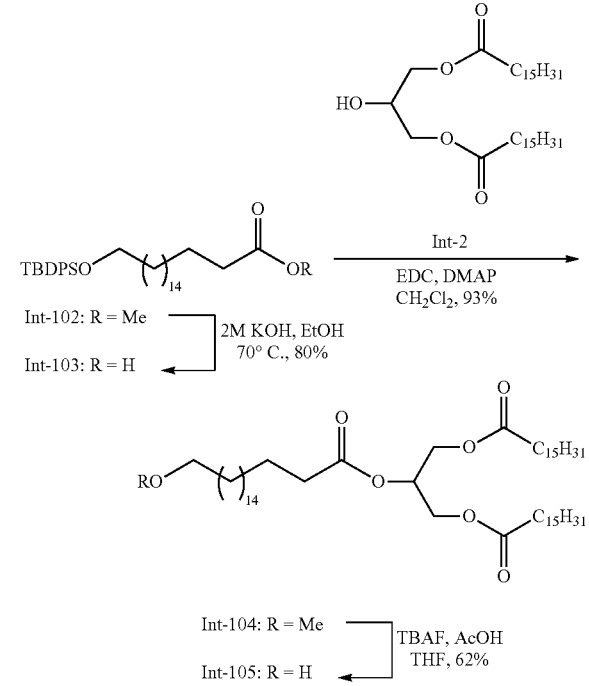

Int-99:

A suspension of 1,16-hexanediol (200 mg, 0.774 mmol) in DMF (2 mL) was added a suspension of NaH (34.1 mg, 60% w/w dispersion in mineral oil, washed twice with dry petrol, 8.51 mmol) in DMF (1 mL) at 0° C. and the mixture stirred at 0° C. for 10 minutes and then at rt for 30 minutes. TBDPSCl (221 μL, 0.851 mmol) was added and the mixture stirred at rt for 17 hours. The reaction was diluted with ethyl acetate (50 mL), washed with water and brine (2×40 mL each), dried ($MgSO_4$) and concentrated under reduced pressure to give the crude product. Silica gel chromatography (15% ethyl acetate/hexanes) gave TBDPS ether Int-99 (124 mg, 32%) as a colorless solid. $^1H$ NMR (401 MHz, $CDCl_3$) δ 7.70-7.63 (m, 4H), 7.45-7.34 (m, 6H), 3.64 (td, J=6.5, 3.6 Hz, 4H), 1.61-1.46 (m, 4H), 1.39-1.19 (m, 24H), 1.04 (s, 9H).

Int-100:

Pyridinium chlorochromate (PCC, 106 mg, 0.491 mmol) and Celite (100 mg) were added to alcohol Int-99 (122 mg, 0.246 mmol) in $CH_2Cl_2$ (6 mL) at 0° C. and the mixture stirred at 0° C. for 10 minutes and then at rt for 1.5 hours. The reaction was filtered through a short pad of silica gel, eluting with 50% ethyl acetate/hexanes (80 mL), and the filtrate concentrated under reduced pressure to give crude aldehyde Int-100 (121 mg, quant.) as a yellow oil that was immediately used without purification.

Int-101:

Ylide methyl 2-(triphenyl-λ$^5$-phosphaneylidene)acetate (205 mg, 0.614 mmol) was added to crude aldehyde Int-100 (121 mg, 0.246 mmol) in toluene (6 mL) and the mixture heated at reflux for one hour. The reaction was cooled to rt and concentrated under reduced pressure to give the crude product. Purification by silica gel chromatography (4% ethyl acetate/hexanes) gave alpha,beta-unsaturated methyl ester Int-101 (100 mg, 74%, 6:1 mixture of E/Z isomers) as a yellow oil. NMR data is provided for the major isomer. $^1H$ NMR (401 MHz, $CDCl_3$) δ 7.74-7.66 (m, 4H), 7.48-7.36 (m, 6H), 7.01 (dt, J=15.6, 7.0 Hz, 1H), 5.85 (dt, J=15.6, 1.5 Hz, 1H), 3.74 (s, 3H), 3.69 (t, J=6.5 Hz, 2H), 2.22 (qd, J=7.3, 1.5 Hz, 2H), 1.64-1.55 (m, 2H), 1.47 (dd, J=13.9, 6.9 Hz, 2H), 1.42-1.25 (m, 22H), 1.09 (s, 9H); $^{13}$C NMR (101 MHz, CDCl$_3$) δ 167.3 (C), 149.9 (CH), 135.7 (4C; CH), 134.3 (2C; C), 129.6 (2C; CH), 127.7 (4C; CH), 120.9 (CH), 64.1 (CH$_2$), 51.4 (CH$_3$), 32.7 (CH$_2$), 32.3 (CH$_2$), 29.79 (2C; CH$_2$), 29.75 (2C; CH$_2$), 29.74 (CH$_2$), 29.66 (CH$_2$), 29.52 (CH$_2$), 29.50 (CH$_2$), 29.3 (CH$_2$), 28.1 (CH$_2$), 27.0 (3C; CH$_2$), 25.9 (CH$_2$), 19.3 (C).

Int-102:

A solution of alkene Int-101 (99.0 mg, 0.180 mmol) in ethyl acetate (5 mL) in a two-neck flask was evacuated and flushed with N$_2$ gas three times each, then palladium on carbon (10% w/w, 28.7 mg, 0.0270 mmol) was added and the resulting suspension re-evacuated and flushed with N$_2$ three times. The flask was fitted with a H$_2$ balloon, evacuated and flushed with H$_2$ three times and the reaction mixture stirred at rt under 1 atm of H$_2$ for one hour. The reaction was filtered through a pad of Celite, washing with ethyl acetate (80 mL), and concentrated under reduced pressure to give saturated methyl ester Int-102 (99.4 mg, quant.) as a colorless oil that was used without purification. $^1$H NMR (401 MHz, CDCl$_3$) δ 7.75-7.67 (m, 4H), 7.47-7.36 (m, 6H), 3.69 (t, J=6.5 Hz, 2H), 3.68 (s, 3H), 2.33 (t, J=7.5 Hz, 2H), 1.70-1.54 (m, 4H), 1.43-1.23 (m, 26H), 1.09 (s, 9H); $^{13}$C NMR (101 MHz, CDCl$_3$) δ 174.4 (C), 135.7 (4C; CH), 134.3 (2C; C), 129.6 (2C; CH), 127.7 (4C; CH), 64.1 (CH$_2$), 51.5 (CH$_3$), 34.2 (CH$_2$), 32.7 (CH$_2$), 29.82 (2C; CH$_2$), 29.81 (2C; CH$_2$), 29.78 (CH$_2$), 29.76 (CH$_2$), 29.75 (CH$_2$), 29.73 (CH$_2$), 29.6 (CH$_2$), 29.5 (CH$_2$), 29.4 (CH$_2$), 29.3 (CH$_2$), 27.0 (3C; CH$_3$), 25.9 (CH$_2$), 25.1 (CH$_2$), 19.3 (C).

Int-103:

A solution of potassium hydroxide (2.0 M, 530 μL, 1.06 mmol) was added to ester Int-102 (26.0 mg. 0.0854 mmol) in ethanol (3 mL) and the mixture heated at 70° C. for 50 minutes. The reaction was acidified to pH 3 by addition of 1 M HCl and diluted with ethyl acetate (40 mL). The organic phase was washed with water (2×30 mL) and brine (30 mL), dried (MgSO$_4$) and concentrated under reduced pressure to give the crude product. Purification by silica gel chromatography (15% ethyl acetate/hexanes) gave acid Int-103 (76.8 mg, 80%) as a colorless oil. $^1$H NMR (401 MHz, CDCl$_3$) δ 7.73-7.67 (m, 4H), 7.44-7.37 (m, 6H), 3.68 (t, J=6.5 Hz, 2H), 2.37 (t, J=7.5 Hz, 2H), 1.70-1.53 (m, 4H), 1.41-1.23 (m, 26H), 1.07 (s, 9H); $^{13}$C NMR (101 MHz, CDCl$_3$) δ 180.4 (C), 135.7 (4C; CH), 134.3 (2C; C), 129.6 (2C; CH), 127.7 (4C; CH), 64.2 (CH$_2$), 34.2 (CH$_2$), 32.7 (CH$_2$), 29.83 (4C; CH$_2$), 29.81 (CH$_2$), 29.78 (2C; CH$_2$), 29.76 (CH$_2$), 29.6 (CH$_2$), 29.5 (CH$_2$), 29.4 (CH$_2$), 29.2 (CH$_2$), 27.0 (3C; CH$_3$), 25.9 (CH$_2$), 24.8 (CH$_2$), 19.4 (C).

Int-104:

DMAP (10.2 mg, 0.0839 mmol), EDC·HCl (40.2 mg, 0.210 mmol) and 1,3-diglyceride Int-2 (52.5 mg, 0.0923 mmol) were added to a solution of acid Int-103 (45.2 mg, 0.0839 mmol) in CH$_2$Cl$_2$ (4 mL) and the mixture stirred at RT for 22 hours. The reaction was diluted with CH$_2$Cl$_2$ (10 mL), silica gel was added and the mixture concentrated under reduced pressure. Purification by silica gel chromatography (4% to 6% ethyl acetate/hexanes) gave triglyceride Int-104 (84.9 mg, 93%) as a colorless solid. $^1$H NMR (401 MHz, CDCl$_3$) δ 7.71-7.65 (m, 4H), 7.45-7.34 (m, 6H), 5.28 (m, 1H), 4.31 (dd, J=11.9, 4.3 Hz, 2H), 4.16 (dd, J=11.9, 6.0 Hz, 2H), 3.66 (t, J=6.5 Hz, 2H), 2.325 (t, J=7.5 Hz, 2H), 2.319 (t, J=7.5 Hz, 4H), 1.69-1.52 (m, 8H), 1.42-1.20 (m, 74H), 1.06 (s, 9H), 0.89 (t, J=6.8 Hz, 6H); $^{13}$C NMR (101 MHz, CDCl$_3$) δ 173.4 (2C; C), 173.0 (C), 135.7 (4C; CH), 134.3 (2C; C), 129.6 (2C; CH), 127.7 (4C; CH), 69.0 (CH), 64.1 (CH$_2$), 62.2 (2C; CH$_2$), 34.3 (CH$_2$), 34.2 (2C; CH$_2$), 32.7 (CH$_2$), 32.1 (2C; CH$_2$), 29.86 (2C; CH$_2$), 29.84 (9C; CH$_2$), 29.80 (5C; CH$_2$), 29.77 (2C; CH$_2$), 29.76 (2C; CH$_2$), 29.65 (CH$_2$), 29.61 (2C; CH$_2$), 29.53 (CH$_2$), 29.50 (2C; CH$_2$), 29.44 (CH$_2$), 29.41 (2C; CH$_2$), 29.25 (2C; CH$_2$), 29.22 (CH$_2$), 27.0 (3C; CH$_3$), 25.9 (CH$_2$), 25.04 (CH$_2$), 24.99 (2C; CH$_2$), 22.8 (2C; CH$_2$), 19.3 (C), 14.2 (2C; CH$_3$).

Int-105:

Tetrabutylammonium fluoride (TBAF, 1.0 M in THF, 154 μL, 0.154 mmol) and acetic acid (8.8 μL, 0.154 mmol) were added to a solution of TBDPS ether Int-104 (84.0 mg, 0.0771 mmol) in THF (3 mL) at 0° C. and the mixture stirred at 0° C. for 15 minutes and then at rt for seven hours. The reaction was diluted with ethyl acetate (40 mL), washed with water (30 mL) and brine (2×30 mL), dried (MgSO$_4$) and concentrated under reduced pressure to give the crude product. Purification by silica gel chromatography (7.5% to 20% ethyl acetate/hexanes) gave alcohol Int-105 (40.5 mg, 62%) as a colorless solid. $^1$H NMR (401 MHz, CDCl$_3$) δ 5.26 (m, 1H), 4.29 (dd, J=11.9, 4.3 Hz, 2H), 4.14 (dd, J=11.9, 6.0 Hz, 2H), 3.64 (t, J=6.6 Hz, 2H), 2.31 (t, J=7.5 Hz, 2H), 2.30 (t, J=7.5 Hz, 4H), 1.67-1.51 (m, 8H), 1.44-1.17 (m, 74H), 0.88 (t, J=6.8 Hz, 6H); $^{13}$C NMR (101 MHz, CDCl$_3$) δ 173.5 (2C; C), 173.1 (C), 69.0 (CH), 63.3 (CH$_2$), 62.3 (2C; CH$_2$), 34.4 (CH$_2$), 34.2 (2C; CH$_2$), 33.0 (CH$_2$), 32.1 (2C; CH$_2$), 29.82 (10C; CH$_2$), 29.80 (6C; CH$_2$), 29.76 (3C; CH$_2$), 29.75 (CH$_2$), 29.65 (CH$_2$), 29.63 (2C; CH$_2$), 29.59 (CH$_2$), 29.51 (2C; CH$_2$), 29.45 (CH$_2$), 29.42 (2C; CH$_2$), 29.27 (2C; CH$_2$), 29.23 (CH$_2$), 25.9 (CH$_2$), 25.1 (CH$_2$), 25.0 (2C; CH$_2$), 22.8 (2C; CH$_2$), 14.3 (2C; CH$_3$).

Int-110 (TML(CO$_2$H)-C4-2-TG):

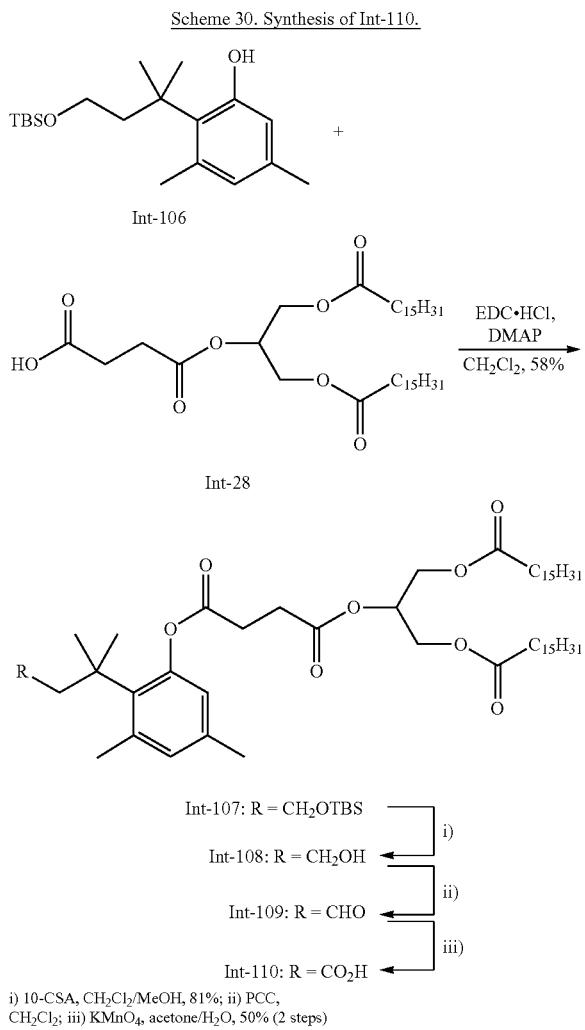

Scheme 30. Synthesis of Int-110.

Int-107: R = CH$_2$OTBS
Int-108: R = CH$_2$OH
Int-109: R = CHO
Int-110: R = CO$_2$H i) 10-CSA, CH$_2$Cl$_2$/MeOH, 81%; ii) PCC, CH$_2$Cl$_2$; iii) KMnO$_4$, acetone/H$_2$O, 50% (2 steps)

Int-106: prepared according to: Amsberry, K. L. et al. Pharm Res. 1991, 8, 455-461.

DMAP (18.3 mg, 0.149 mmol) and EDC·HCl (71.6 mg, 0.374 mmol) were added to a solution of Int-28 (100 mg, 0.149 mmol) and phenol Int-106 (53.0 mg, 0.164 mmol) in $CH_2Cl_2$ (4 mL) and the mixture stirred at room temperature for 19 hours. The reaction was diluted with $CH_2Cl_2$ (5 mL), silica gel was added, and the mixture concentrated under reduced pressure. Purification by silica gel chromatography (3% to 7.5% ethyl acetate/hexanes) gave TML-TG Int-107 (84.6 mg, 58%) as a colourless oil. $^1$H NMR (400 MHz, $CDCl_3$) δ 6.80 (d, J=2.0 Hz, 1H), 6.55 (d, J=1.9 Hz, 1H), 5.29 (m, 1H), 4.31 (dd, J=11.9, 4.4 Hz, 2H), 4.16 (dd, J=12.0, 5.8 Hz, 2H), 3.51-3.44 (m, 2H), 2.85 (t, J=6.9 Hz, 2H), 2.75 (t, J=6.9 Hz, 2H), 2.51 (s, 3H), 2.30 (t, J=7.6 Hz, 4H), 2.22 (s, 3H), 2.06-1.99 (m, 2H), 1.65-1.56 (m, 4H), 1.46 (s, 6H), 1.37-1.20 (m, 48H), 0.88 (t, J=6.9 Hz, 6H), 0.84 (s, 9H), −0.03 (s, 6H); $^{13}$C NMR (101 MHz, $CDCl_3$) δ 173.4 (2C; C), 171.5 (C), 171.3 (C), 149.7 (C), 138.5 (C), 136.1 (C), 134.1 (C), 132.5 (CH), 123.1 (CH), 69.8 (CH), 62.0 (2C; $CH_2$), 60.9 ($CH_2$), 46.1 ($CH_2$), 39.2 (C), 34.1 (2C; $CH_2$), 32.1 (2C; $CH_2$), 31.9 (2C; $CH_3$), 29.9 ($CH_2$), 29.83 (6C; $CH_2$), 29.79 (4C; $CH_2$), 29.75 (2C; $CH_2$), 29.6 (2C; $CH_2$), 29.5 (2C; $CH_2$), 29.4 (2C; $CH_2$), 29.2 (2C; $CH_2$), 29.0 ($CH_2$), 26.1 (3C; $CH_3$), 25.4 ($CH_3$), 25.0 (2C; $CH_2$), 22.8 (2C; $CH_2$), 20.3 ($CH_3$), 18.3 (C), 14.3 (2C; $CH_3$), −5.21 (2C; $CH_3$). ESI-HRMS: calcd. for $C_{58}H_{105}O_9Si$ [M+H]$^+$ 973.7522; found 973.7515.

10-Camphorsulfonic acid (3.0 mg, 12.9 µmol) was added to TBS ether Int-107 (83.7 mg, 86.0 µmol) in $CH_2Cl_2$ (1 mL) and MeOH (1 mL) and the mixture stirred at room temperature for one hour. The reaction was diluted with $CH_2Cl_2$ (20 mL) and the organic phase washed with sat. aq. $NaHCO_3$ and brine (20 mL each), dried ($MgSO_4$) and concentrated under reduced pressure to give the crude product. Purification by silica gel chromatography (15% to 25% ethyl acetate/hexanes) gave alcohol Int-108 (59.9 mg, 81%) as a colourless oil. $^1$H NMR (400 MHz, $CDCl_3$) δ 6.81 (d, J=2.0 Hz, 1H), 6.56 (d, J=1.4 Hz, 1H), 5.28 (m, 1H), 4.30 (dd, J=12.0, 4.4 Hz, 2H), 4.17 (dd, J=12.0, 5.8 Hz, 2H), 3.51 (t, J=6.8 Hz, 2H), 2.88 (t, J=6.6 Hz, 2H), 2.75 (t, J=6.6 Hz, 2H), 2.52 (s, 3H), 2.29 (t, J=7.6 Hz, 4H), 2.22 (s, 3H), 2.05 (t, J=7.4 Hz, 2H), 1.65-1.57 (m, 4H), 1.50 (s, 6H), 1.37-1.20 (m, 48H), 0.88 (t, J=6.9 Hz, 6H); $^{13}$C NMR (101 MHz, $CDCl_3$) δ 173.5 (2C; C), 171.71 (C), 171.70 (C), 149.8 (C), 138.5 (C), 136.3 (C), 133.9 (C), 132.6 (CH), 123.2 (CH), 69.8 (CH), 62.0 (2C; $CH_2$), 60.5 ($CH_2$), 45.9 ($CH_2$), 39.2 (C), 34.1 (2C; $CH_2$), 32.1 (2C; $CH_3$), 32.0 (2C; $CH_2$), 29.84 ($CH_2$), 29.80 (6C; $CH_2$), 29.77 (4C; $CH_2$), 29.72 (2C; $CH_2$), 29.6 (2C; $CH_2$), 29.5 (2C; $CH_2$), 29.4 (2C; $CH_2$), 29.2 (2C; $CH_2$), 28.9 ($CH_2$), 25.5 ($CH_3$), 24.9 (2C; $CH_2$), 22.8 (2C; $CH_2$), 20.3 ($CH_3$), 14.2 (2C; $CH_3$). ESI-HRMS: calcd. for $C_{52}H_{90}NaO_9$ [M+Na]$^+$ 881.6477; found 881.6489.

Pyridinium chlorochromate (PCC, 30.1 mg, 0.139 mmol) was added to a suspension of alcohol Int-108 (59.9 mg, 0.0697 mmol) and Celite (30 mg) in $CH_2Cl_2$ (3 mL) at 0° C. and the mixture stirred at room temperature for two hours. The reaction was filtered through a short pad of silica gel, eluting with 50% ethyl acetate/hexanes (50 mL), and the filtrate concentrated under reduced pressure to give crude aldehyde Int-109 (59.8 mg, quant.) as a yellow oil that was used without purification. $^1$H NMR (400 MHz, $CDCl_3$) δ 9.54 (t, J=2.6 Hz, 1H), 6.84 (d, J=2.0 Hz, 1H), 6.60 (d, J=1.4 Hz, 1H), 5.28 (m, 1H), 4.30 (dd, J=12.0, 4.3 Hz, 2H), 4.16 (dd, J=12.0, 5.8 Hz, 2H), 2.86 (t, J=6.7 Hz, 2H), 2.83 (d, J=2.6 Hz, 2H), 2.75 (t, J=6.3 Hz, 2H), 2.53 (s, 3H), 2.30 (t, J=7.6 Hz, 4H), 2.23 (s, 3H), 1.64-1.58 (m, 4H), 1.56 (s, 3H), 1.55 (s, 3H), 1.32-1.22 (m, 48H), 0.88 (t, J=6.9 Hz, 6H).

Potassium permanganate (12.2 mg, 76.7 µmol) in 1:1 acetone/water (1.6 mL total) was added to aldehyde Int-109 (59.8 mg, 69.7 µmol) in acetone (1.6 mL) and the mixture stirred at room temperature for 17 hours. The reaction was diluted with water (10 mL), acidified to pH 2 using 1 M HCl, and the aqueous layer extracted with $CH_2Cl_2$ (3×15 mL). The combined organic extracts were washed with brine (40 mL), dried ($MgSO_4$) and concentrated under reduced pressure to give the crude product. Purification by silica gel chromatography (10% to 25% ethyl acetate/hexanes) gave acid Int-110 (30.4 mg, 50%) as a colorless solid. $^1$H NMR (400 MHz, $CDCl_3$) δ 6.81 (d, J=1.6 Hz, 1H), 6.58 (d, J=1.4 Hz, 1H), 5.28 (m, 1H), 4.30 (dd, J=11.9, 4.4 Hz, 2H), 4.16 (dd, J=12.0, 5.8 Hz, 2H), 2.88 (t, J=6.6 Hz, 2H), 2.84 (s, 2H), 2.75 (t, J=6.6 Hz, 2H), 2.53 (s, 3H), 2.29 (t, J=7.6 Hz, 4H), 2.22 (s, 3H), 1.64-1.58 (m, J=9.3 Hz, 4H), 1.57 (s, 6H), 1.34-1.20 (m, 48H), 0.88 (t, J=6.8 Hz, 6H); $^{13}$C NMR (101 MHz, $CDCl_3$) δ 176.1 (C), 173.6 (2C; C), 171.6 (C), 171.4 (C), 149.5 (C), 138.2 (C), 136.5 (C), 133.4 (C), 132.7 (CH), 123.0 (CH), 69.8 (CH), 62.0 (2C; $CH_2$), 47.6 ($CH_2$), 38.8 (C), 34.1 (2C; $CH_2$), 32.1 (2C; $CH_2$), 31.5 (2C; $CH_3$), 29.9 ($CH_2$), 29.84 (6C; $CH_2$), 29.80 (4C; $CH_2$), 29.76 (2C; $CH_2$), 29.6 (2C; $CH_2$), 29.5 (2C; $CH_2$), 29.4 (2C; $CH_2$), 29.2 (2C; $CH_2$), 29.0 ($CH_2$), 25.4 ($CH_3$), 25.0 (2C; $CH_2$), 22.8 (2C; $CH_2$), 20.4 ($CH_3$), 14.3 (2C; $CH_3$). ESI-HRMS: calcd. for $C_{52}H_{88}NaO_{10}$ [M+Na]$^+$ 895.6270; found 895.6266.

Using similar methods, Int-119 was prepared by EDC coupling with Int-37 in 84% yield:

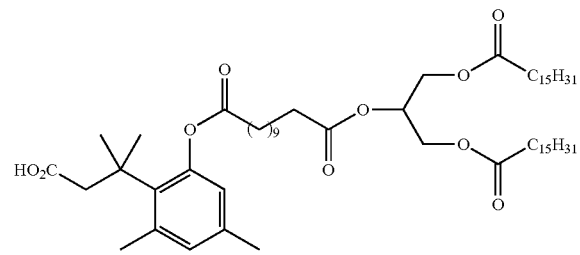

Int-119

$^1$H NMR (401 MHz, $CDCl_3$) δ 6.80 (d, J=1.9 Hz, 1H), 6.55 (d, J=1.7 Hz, 1H), 5.26 (m, 1H), 4.29 (dd, J=11.9, 4.4 Hz, 2H), 4.14 (dd, J=11.9, 5.9 Hz, 2H), 2.83 (s, 2H), 2.55 (t, J=7.5 Hz, 2H), 2.53 (s, 3H), 2.32 (t, J=7.5 Hz, 2H), 2.31 (t, J=7.5 Hz, 4H), 2.22 (s, 3H), 1.78-1.69 (m, 2H), 1.67-1.54 (m, 6H), 1.57 (s, 6H), 1.45-1.20 (m, 60H), 0.88 (t, J=6.8 Hz, 6H); $^{13}$C NMR (101 MHz, $CDCl_3$) δ 176.3 (C), 173.5 (2C; C), 173.1 (C), 173.0 (C), 149.7 (C), 138.2 (C), 136.4 (C), 133.5 (C), 132.5 (CH), 123.2 (CH), 69.0 (CH), 62.2 (2C; $CH_2$), 47.4 ($CH_2$), 38.9 (C), 35.2 ($CH_2$), 34.3 ($CH_2$), 34.2 (2C; $CH_2$), 32.1 (2C; $CH_2$), 31.4 (2C; $CH_3$), 29.84 (6C; $CH_2$), 29.80 (4C; $CH_2$), 29.76 (2C; $CH_2$), 29.62 (2C; $CH_2$), 29.53 (2C; $CH_2$), 29.50 (2C; $CH_2$), 29.41 (2C; $CH_2$), 29.38 (2C; $CH_2$), 29.30 ($CH_2$), 29.26 (2C; $CH_2$), 29.19 ($CH_2$), 25.4 ($CH_3$), 25.0 (3C; $CH_2$), 24.8 ($CH_2$), 22.8 (2C; $CH_2$), 20.4 ($CH_3$), 14.3 (2C; $CH_3$).

Int-122 was also prepared using similar methods:

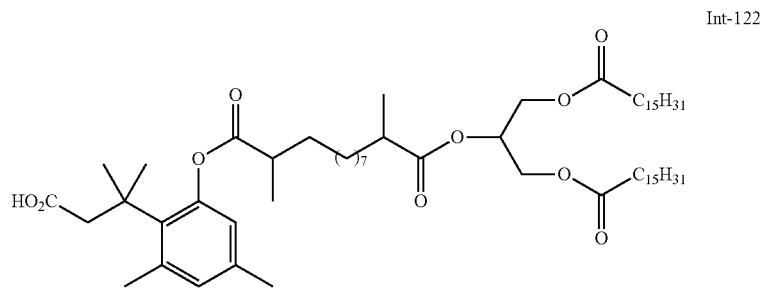

Int-122

$^1$H NMR (401 MHz, CDCl$_3$) δ 6.79 (d, J=1.9 Hz, 1H), 6.51 (d, J=1.8 Hz, 1H), 5.26 (m, 1H), 4.292/4.284 (each dd, J=11.8, 4.2 Hz, 2H), 4.14 (dd, J=11.9, 6.1 Hz, 2H), 2.84 (s, 2H), 2.67 (m, 1H), 2.53 (s, 3H), 2.44 (m, 1H), 2.30 (t, J=7.6 Hz, 4H), 2.22 (s, 3H), 1.84 (m, 1H), 1.69-1.45 (m, 7H), 1.573 (s, 3H), 1.567 (s, 3H), 1.45-1.19 (m, 63H), 1.14 (d, J=7.0 Hz, 3H), 0.88 (t, J=6.9 Hz, 6H); $^{13}$C NMR (101 MHz, CDCl$_3$) δ 176.1 (2C; C), 175.9 (C), 173.5 (2C; C), 150.1 (C), 138.2 (C), 136.4 (C), 133.6 (C), 132.5 (CH), 123.0 (CH), 68.9 (CH), 62.30/62.27 (2C; CH$_2$), 47.3 (CH$_2$), 40.2 (CH), 39.7 (CH), 39.0 (C), 34.2 (2C; CH$_2$), 33.8 (CH$_2$), 33.6 (CH$_2$), 32.1 (2C; CH$_2$), 31.5 (CH$_3$), 29.84 (2C; CH$_2$), 29.80 (2C; CH$_2$), 29.76 (2C; CH$_2$), 29.65 (2C; CH$_2$), 29.61 (2C; CH$_2$), 29.59 (2C; CH$_2$), 29.5 (2C; CH$_2$), 29.4 (2C; CH$_2$), 29.28/29.27 (2C; CH$_2$), 27.34 (CH$_2$), 27.28 (CH$_2$), 25.5 (CH$_3$), 25.0 (2C; CH$_2$), 22.8 (2C; CH$_2$), 20.4 (CH$_3$), 17.2 (CH$_3$), 16.9 (CH$_3$), 14.3 (2C; CH$_3$).

Int-112 1,3-Di-Oleoyl Glycerol (1,3-DG-Oleate):

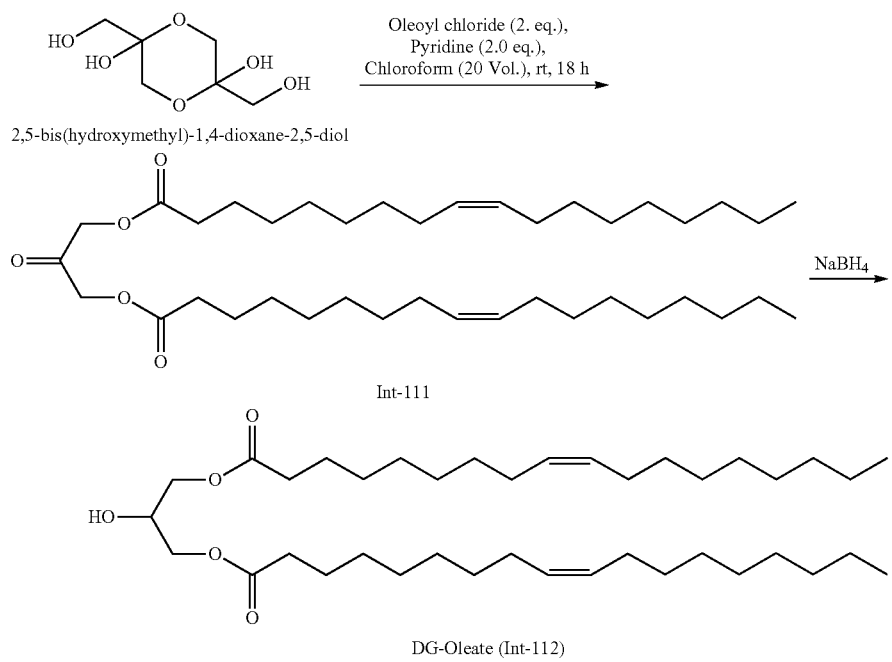

Scheme 31. Synthesis of Int-112.

To a solution of 2,5-bis(hydroxymethyl)-1,4-dioxane-2,5-diol (5 g, 27.7 mol) in chloroform (20 vol) was added pyridine (5.5 mL, 69.4 mol) followed by oleoyl chloride (11 mL, 54.9 mol) and the mixture was stirred at room temperature for 1 h. The solvent was evaporated and the reaction mixture dissolved in ethyl acetate (30 vol) and washed with 1N HCl (10 vol). The organic layer was dried and solvent evaporated under vacuum. The crude material was recrystallized with cold methanol (20 vol). The solid obtained was further washed with cold methanol, and dried to give ketone Int-111 (11 g, 62%) as a white solid. $^1$H NMR (400 MHz, CDCl$_3$) δ 5.36 (t, J=11.6 Hz, 4H), 4.78 (s, 4H), 2.47 (m, 4H), 2.38 (m, 8H), 1.71 (m, 2H), 1.34-1.30 (m, 42H), 0.93 (m, 6H).

Sodium borohydride (NaBH$_4$, 307 mg, 8.09 mmol), was added to a solution of Int-111 (5 g, 8.09 mmol) in THF (20 vol) at 0° C. and then the reaction mixture was stirred at room temperature for 15 mins. The reaction was monitored by TLC and after completion, the reaction mixture was filtered through a celite bed to remove excess of sodium borohydride and the celite bed was washed with ethyl acetate (30 vol), the organic layer was washed with 1N solution of acetic acid (10 vol). The solvent was dried over Na$_2$SO$_4$ and solvent removed under vacuum. The crude material was column purified. The product was eluted at 5%-10% ethyl acetate/hexane to afford 1,3-DG-oleate (Int-112) (2 g, 39%) as viscous liquid. $^1$H NMR (400 MHz, CDCl$_3$) δ 5.39 (m, 4H), 4.20 (m, 5H), 2.44 (d, 1H), 2.36 (m, 4H), 2.01 (m, 8H), 2.47-2.25 (m, 12H), 2.17 (m, 1H), 2.02 (ddd, J=13.4, 4.9, 3.3 Hz, 1H), 1.85 (m, 1H), 1.77 (m, 1H), 1.64 (m, 2H), 1.57-1.26 (m, 42H), 0.9 (t, 6H); $^{13}$C NMR (101 MHz, CDCl$_3$) δ 173.9 (2C, C=O), 130.1 (2C), 129.7 (2C), 68.4 (C, CH), 65.1 (2C), 34.1 (2C), 31.9 (2C), 29.8-29.1 (18C), 27.3 (2C), 24.9 (2C), 22.7 (2C), 14.1 (2C). HPLC (ELSD): 9.62 min, 99.27% purity. MS (ESI, +ve) m/z: 639.2 (MH$^+$+H$_2$O).

Int-113 (C10-Acid-TG-Oleate)

Int-115 (1,3-DG-Butyrate):

Scheme 33. Synthesis of Int-115.

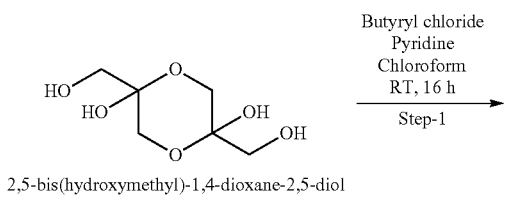

2,5-bis(hydroxymethyl)-1,4-dioxane-2,5-diol

Scheme 32. Synthesis of Int-113.

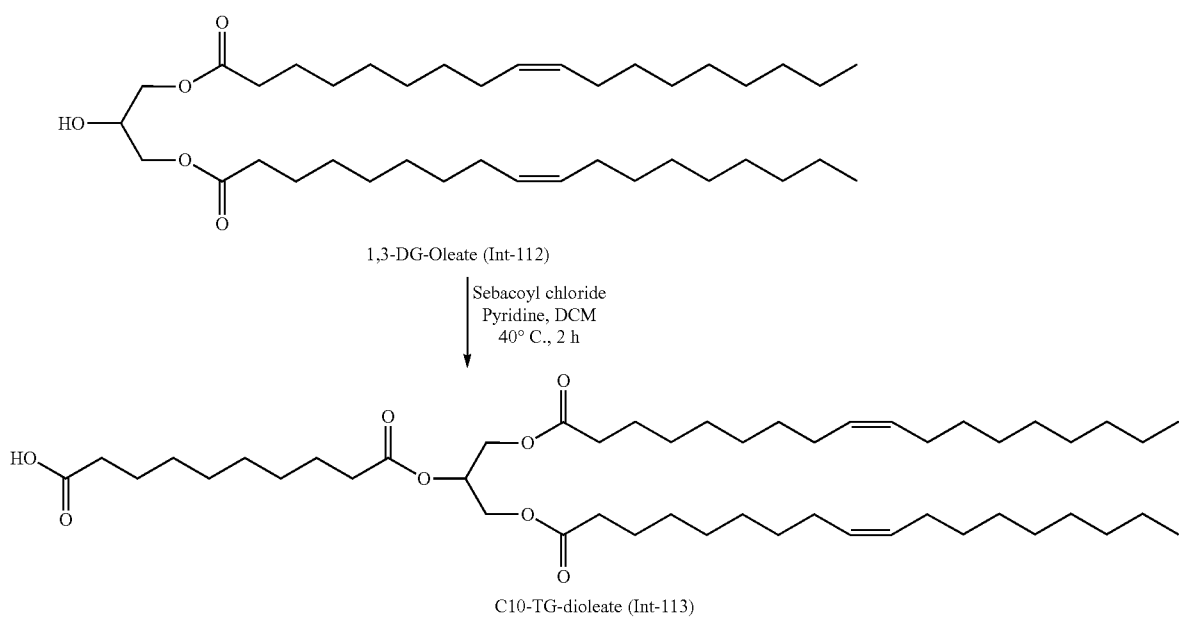

Pyridine (0.19 mL, 2.41 mmol) was added to a suspension of DG-oleate Int-112 (150 mg, 0.241 mmol) in DCM (20 Vol). After 5 min, sebacoyl chloride (289 mg, 1.2 mmol) was added dropwise with stirring at room temperature. Reaction mixture allowed to stir at 40° C. for 2 h. The reaction was monitored by TLC and after completion, diluted with DCM (20 vol), washed with water (20 vol), aqueous sodium bicarbonate (10 vol) and brine (10 vol). The obtained organic layer was dried over Na$_2$SO$_4$, filtered and solvent was removed under reduced pressure. The crude material was column purified. The product was eluted at 5-10% ethyl acetate/hexane to afford C10-acid-TG-oleate Int-113 (60 mg, 30%) as viscous liquid. $^1$H NMR (400 MHz, CDCl$_3$) δ 5.43 (m, 4H), 5.29 (m, 1H), 4.35 (d, 2H), 4.20 (m, 2H), 2.40 (m, 8H), 2.05 (m, 8H), 1.65 (m, 10H), 1.33-1.18 (m 46H), 0.93 (t, 6H); $^{13}$C NMR (101 MHz, CDCl$_3$) δ 1.78 (1C, C=O, 173.3 (2C, C=O), 172.8 (1C, C=O), 130.1 (2C), 129.8 (2C), 68.9 (C, CH), 62.1 (2C), 60.5 (2C), 34.2 (4C), 31.9 (2C), 29.8-29.0 (18C), 27.3 (4C), 24.9 (4C), 22.7 (2C), 14.2 (2C). HPLC (ELSD): 10.90 min, 99% purity. MS (ESI, +ve) m/z: 823.8 (MH$^+$+H$_2$O).

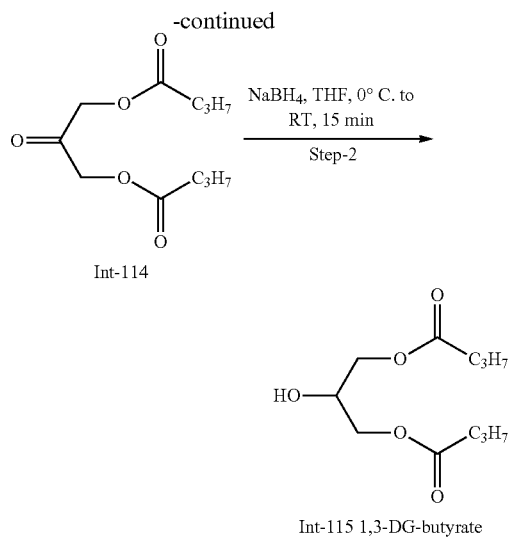

To a solution of 2,5-bis-(hydroxymethyl)-1,4-dioxane-2,5-diol (2.0 g, 1.11 mmol) in chloroform (40 ml) was added pyridine (2.2 mL, 2.77 mmol) followed by butyryl chloride (2.3 mL, 2.22 mol) before stirring at room temperature for 16 h. After completion, the solvent was evaporated and re-dissolved in ethyl acetate (60 ml) and washed with 1N HCl (20 ml). The combined organic layer was dried and evaporated under vacuum. The crude material was purified by column. The product was eluted at 5-10% ethyl acetate/hexane to afford Int-114 (1.4 g, 54%) as viscous liquid. $^1$H NMR (400 MHz, CDCl$_3$) δ 4.8 (s, 4H), 2.45 (t, 4H), 1.79-1.69 (m, 4H), 1.04-0.98 (t, 6H); $^{13}$C NMR (101 MHz, CDCl$_3$) δ 198.2 (1C=O), 172.2 (2C=O), 66.1 (2C), 35.9 (2C), 18.3 (2C), 14.1 (2C). HPLC (ELSD): 1.73 min, 99.8% purity.

Sodium borohydride (NaBH$_4$, 230 mg, 6.10 mmol), was added to a solution of Int-114 (1.3 g, 6.1 mmol) in THF (26 ml) at 0° C. and then the reaction mixture was stirred at room temperature for 15 mins. The reaction was monitored by TLC and after completion, the reaction mixture was filtered through a celite bed to remove excess sodium borohydride, the celite bed was washed with ethyl acetate (40 ml), and the combined organic layer was washed with a 1N solution of acetic acid (13 ml). The organic layer was dried over Na$_2$SO$_4$ and solvent removed under vacuum. The crude material was purified by column. The product was eluted at 5-10% ethyl acetate/hexane to afford Int-115 (1.0 g, 70.6%) as a viscous liquid. $^1$H NMR (400 MHz, CDCl$_3$) δ 4.25-4.13 (m, 5H), 2.4 (s, 1H), 2.38 (t, 4H), 1.75-1.66 (m, 4H), 1.01-0.98 (t, 6H); $^{13}$C NMR (101 MHz, CDCl$_3$) δ 173.8 (2C=O), 68.3 (1C), 65.0 (2C), 35.9 (2C), 18.4 (2C), 13.6 (2C). HPLC (ELSD): 1.8 min, 100% purity. MS (ESI, +ve) m/z: 255.37 (M$^+$+23).

Int-125:

Scheme 34-A. Synthesis of Int-125.

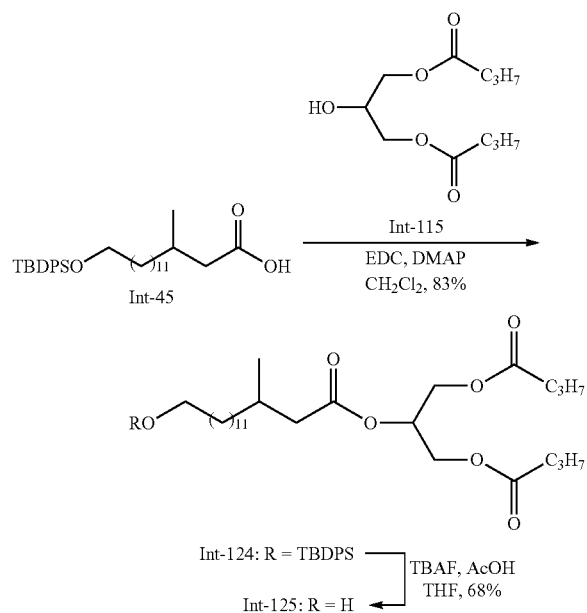

Int-45 was prepared as described above and coupled with Int-115 using EDC and DMAP similarly to methods described above to provide Int-124. Int-124: $^1$H NMR (401 MHz, CDCl$_3$) δ 7.70-7.64 (m, 4H), 7.42-7.35 (m, 6H), 5.29 (m, 1H), 4.307/4.305 (each dd, J=11.9, 4.2 Hz, 2H), 4.159/4.157 (each dd, J=11.9, 6.0 Hz, 2H), 3.66 (t, J=6.5 Hz, 2H), 2.34 (dd, J=14.7, 5.9 Hz, 1H), 2.30 (t, J=7.4 Hz, 4H), 2.13 (dd, J=14.7, 8.3 Hz, 1H), 1.95 (m, 1H), 1.70-1.50 (m, 6H), 1.37-1.17 (m, 20H), 1.05 (s, 9H), 0.95 (t, J=7.5 Hz, 6H), 0.94 (d, J=6.4 Hz, 3H); $^{13}$C NMR (101 MHz, CDCl$_3$) δ 173.2 (2C; C), 172.5 (C), 135.7 (4C; CH), 134.3 (2C; C), 129.6 (2C; CH), 127.7 (4C; CH), 68.9 (CH), 64.1 (CH$_2$), 62.3 (2C; CH$_2$), 41.8 (CH$_2$), 36.8 (CH$_2$), 36.0 (2C; CH$_2$), 32.7 (CH$_2$), 30.5 (CH), 29.9 (CH$_2$), 29.80 (3C; CH$_2$), 29.76 (CH$_2$), 29.75 (CH$_2$), 29.5 (CH$_2$), 27.1 (CH$_2$), 27.0 (3C; CH$_3$), 25.9 (CH$_2$), 19.7 (CH$_3$), 19.3 (C) 18.5 (2C; CH$_2$), 13.7 (2C; CH$_3$).

Int-125:

Tetrabutylammonium fluoride (TBAF, 1.0 M in THF, 243 μL, 0.243 mmol) and AcOH (13.9 L, 0.243 mmol) were added dropwise to TBDPS ether 3 (58.7 mg, 0.0809 mmol) in THF (4 mL) at 0° C. and the mixture stirred at rt for 19 hours. The reaction was diluted with water (10 mL) and the aqueous phase extracted with ethyl acetate (3×15 mL). The combined organic extracts were washed with sat. aq. NaHCO$_3$ and brine (30 mL each), dried (MgSO$_4$) and concentrated under reduced pressure to give the crude product. Purification by silica gel chromatography (6% to 20% ethyl acetate/hexanes) gave alcohol Int-125 (26.7 mg, 68%) as a colorless oil. $^1$H NMR (401 MHz, CDCl$_3$) δ 5.28 (m, 1H), 4.298/4.295 (each dd, J=11.9, 4.3 Hz, 2H), 4.153/4.151 (each dd, J=11.9, 6.0 Hz, 2H), 3.64 (t, J=6.6 Hz, 2H), 2.33 (dd, J=14.7, 5.9 Hz, 1H), 2.30 (t, J=8.4, 6.5 Hz, 4H), 2.12 (dd, J=14.7, 8.3 Hz, 1H), 1.93 (m, 1H), 1.70-1.46 (m, 8H), 1.38-1.16 (m, 18H), 0.95 (t, J=7.4 Hz, 6H), 0.93 (d, J=6.7 Hz, 3H); $^{13}$C NMR (101 MHz, CDCl$_3$) δ 173.3 (2C; C), 172.5 (C), 69.0 (CH), 63.2 (CH$_2$), 62.3 (2C; CH$_2$), 41.9 (CH$_2$), 36.8 (CH$_2$), 36.1 (2C; CH$_2$), 33.0 (CH$_2$), 30.5 (CH), 29.9 (CH$_2$), 29.78 (CH$_2$), 29.76 (2C; CH$_2$), 29.74 (CH$_2$), 29.71 (CH$_2$), 29.6 (CH$_2$), 27.1 (CH$_2$), 25.9 (CH$_2$), 19.7 (CH$_3$), 18.5 (2C; CH$_2$), 13.8 (2C; CH$_3$).

Int-126:

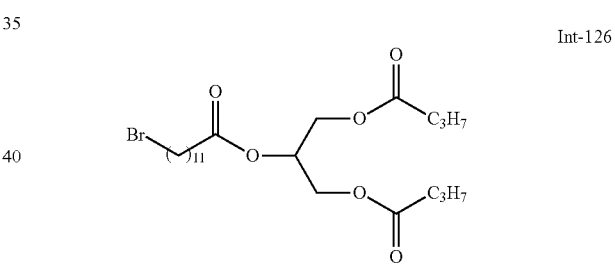

Prepared using similar methods as those shown above. $^1$H NMR (401 MHz, CDCl$_3$) δ 5.23 (m, 1H), 4.26 (dd, J=11.9, 4.3 Hz, 2H), 4.11 (dd, J=11.9, 6.0 Hz, 2H), 3.36 (t, J=6.9 Hz, 2H), 2.28 (t, J=7.4 Hz, 2H), 2.26 (t, J=7.4 Hz, 4H), 1.84-1.75 (m, 2H), 1.66-1.52 (m, 6H), 1.42-1.33 (m, 2H), 1.31-1.19 (m, 12H), 0.90 (t, J=7.4 Hz, 6H); $^{13}$C NMR (101 MHz, CDCl$_3$) δ 173.1 (2C; C), 172.9 (C), 68.9 (CH), 62.1 (2C; CH$_2$), 35.9 (2C; CH$_2$), 34.2 (CH$_2$), 34.0 (CH$_2$), 32.9 (CH$_2$), 29.5 (CH$_2$), 29.43 (CH$_2$), 29.42 (CH$_2$), 29.3 (CH$_2$), 29.1 (CH$_2$), 28.8 (CH$_2$), 28.2 (CH$_2$), 24.9 (CH$_2$), 18.4 (2C; CH$_2$), 13.7 (2C; CH$_3$); ESI-HRMS: calcd. for C$_{23}$H$_{41}$$^{79}$BrNaO$_6$ [M+Na$^+$]515.1979; found 515.1995.

Int-117 1,3-Bis-Decanoyl Glycerol (1,3-DG-Decanoate):

Scheme 34-B. Synthesis of Int-117.

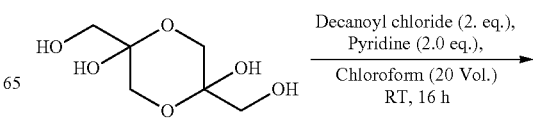

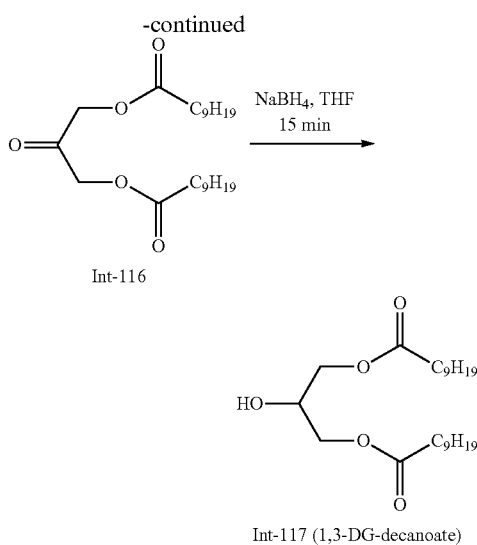

Int-116

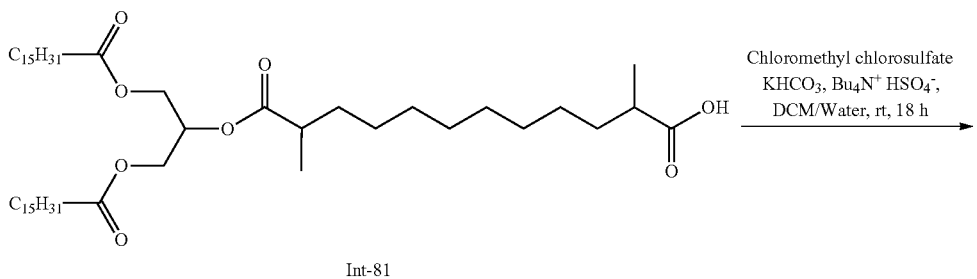

Int-117 (1,3-DG-decanoate)

To a solution of 2, 5-bis-(hydroxymethyl)-1,4-dioxane-2, 5-diol (0.2 g, 1.11 mmol) in chloroform (4.0 ml) was added pyridine (0.22 mL, 2.77 mmol) followed by decanoyl chloride (0.45 mL, 2.22 mmol) and stirred at room temperature for 16 h. The solvent was evaporated and re-dissolved in ethyl acetate (6 ml) and washed with 1N HCl (2 ml). The organic layer was dried and solvent evaporated under vacuum. The crude material was purified by column. The product was eluted at 5-10% ethyl acetate/hexane to afford Int-116 (0.09 g, 20.36%) as viscous liquid. $^1$H NMR (400 MHz, CDCl$_3$) δ 4.8 (m, 4H), 2.46 (m, 4H), 1.73-1.66 (m, 4H), 1.30 (m, 24H), 0.91 (t, 6H); $^{13}$C NMR (101 MHz, CDCl$_3$) δ 198.2 (1C=O), 172.0 (2C=O), 66.1 (2C), 33.7 (2C), 31.8 (2C), 29.3 (2C), 29.2 (2C), 29.0 (2C), 24.8 (2C), 22.6 (2C), 14.12 (2C). HPLC (ELSD): 2.88 min, 100% purity.

Sodium borohydride (NaBH$_4$) (7 mg, 0.2 mmol), was added to a solution of Int-116 (80 mg, 0.2 mmol) in THF (2 ml) at 0° C. and then the reaction mixture was stirred at room temperature for 15 mins. The reaction was monitored by TLC and after completion, the reaction mixture was filtered through a celite bed to remove excess sodium borohydride and the celite bed was washed with ethyl acetate (3 ml). The organic layer was washed with 1 M acetic acid (1 ml). The solvent was dried over Na$_2$SO$_4$ and solvent removed under vacuum. The crude material was purified by column. The product was eluted at 5-10% ethyl acetate/hexane to afford Int-117 (70 mg, 100%) as viscous liquid. $^1$H NMR (400 MHz, CDCl$_3$) δ 4.2-4.1 (m, 5H), 2.51 (s, 1H), 2.38 (t, 4H), 1.68-1.64 (m, 4H), 1.32-1.29 (m, 22H), 0.91 (t, 6H); $^{13}$C NMR (101 MHz, CDCl$_3$) δ 173.0 (2C=O), 68.3 (1C), 65.0 (2C), 34.1 (2C), 31.8 (2C), 29.7 (2C), 29.4 (2C), 29.3 (2C), 29.1 (2C), 24.9 (2C), 22.7 (2C), 14.1 (2C). HPLC (ELSD): 10.70 min, 97.6% purity.

Int-123:

Scheme 34-C. Synthesis of Int-123.

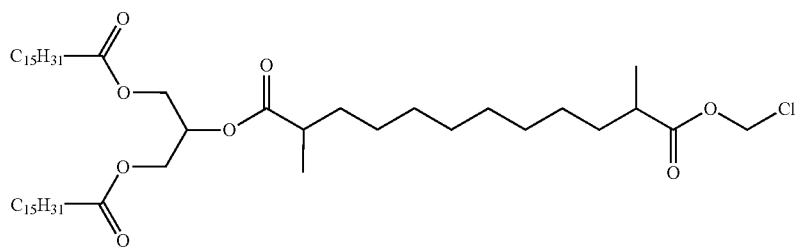

Int-123

Tetra-n-butyl ammonium hydrogen sulfate (0.034 g, 0.098 mmol) and potassium bicarbonate (0.198 g, 1.977 mmol) in distilled water (10 ml) was added to a stirred solution of Int-81 (0.4 g, 0.494 mmol) and tetra-n-butyl ammonium hydrogen sulfate (0.034 g, 0.098 mmol) in dichloromethane (10 ml) at rt and stirred for 0.5 h. Then chloromethyl chlorosulfate (0.062 ml, 0.618 mmol) was added dropwise at rt and stirred vigorously at rt for 18 h. The reaction was monitored by TLC, and after completion of reaction, the reaction mixture was diluted with DCM (25 ml). The organic phase was separated and the aqueous phase extracted with DCM (2×50 ml). Combined organic layers were washed with water (50 ml), brine (50 mL), dried over sodium sulphate, filtered and concentrated at reduced pressure to get crude material. Crude material was purified by column chromatography over silica 100-200 mesh; compound eluted at 20% ethyl acetate/hexane as a mobile phase; visualization was with $KMnO_4$ solution. Int-123 (0.250 g, 59%) was obtained as a viscous liquid. $^1$H NMR (400 MHz, $CDCl_3$) δ 5.75 (m, 2H), 5.32-5.30 (m, 1H), 4.33 (dd, J=11.9, 4.3 Hz, 2H), 4.18 (dd, J=11.9, 6.0 Hz, 2H), 2.56-2.45 (m, 2H), 2.36-2.32 (t, J=7.2 Hz, 4H), 1.66-1.62 (m, 4H), 1.48-1.40 (m, 8H), 1.29 (m, 56H), 1.19 (dd, J=11.2, 7.0 Hz, 6H), 0.92 (t, J=6.7 Hz, 6H).

Example 2: Synthesis of (4-acetamidophenoxy)methyl (1,3-bis(palmitoyloxy)propan-2-yl) succinate, I-1

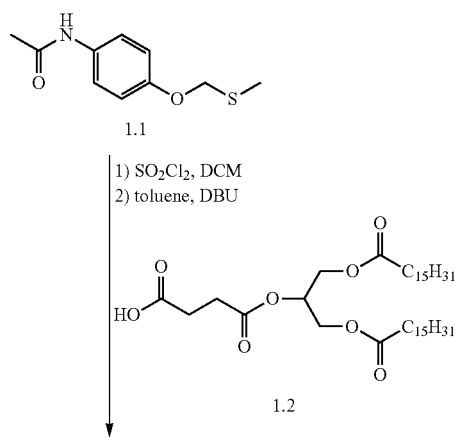

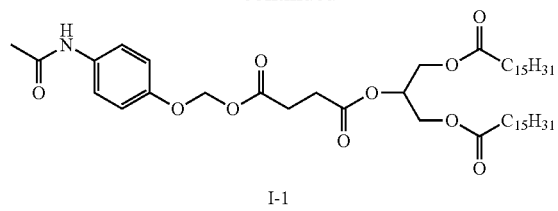

I-1

Synthesis of I-1. I-1 is prepared according to the following procedure. N-(4-((methylthio)methoxy)phenyl)acetamide, 1.1, is prepared by treating acetaminophen with chloromethyl methyl thioether as described in WO 2009/143295, which is hereby incorporated by reference in its entirety. A solution of sulfuryl chloride (2.2 equiv.) in $CH_2Cl_2$ (0.16 M) is added to a solution of 1.1 (1.8 equiv.) in $CH_2Cl_2$ (0.07 M) at 0° C. and the mixture stirred at 0° C. for 30 minutes and then at rt for a further hour. The reaction is concentrated under a stream of $N_2$, co-evaporated from toluene (twice) and dried under reduced pressure. The crude residue is re-dissolved in toluene (0.1 M based on 1.1), added to a solution of acid 1.2 (1 equiv.), as prepared in WO 2017/041139, and DBU (1.5 equiv.) in toluene (0.05 M) that had been pre-stirred for one hour, and the mixture is stirred at rt for two hours. The reaction is diluted with $CH_2Cl_2$ (20 mL) and the organic phase washed with sat. aq. $NaHCO_3$ (20 mL) and brine (20 mL), dried ($MgSO_4$) and concentrated under reduced pressure to give the crude product. Purification by silica gel chromatography with a suitable solvent mixture affords I-1.

Example 3: Synthesis of (((4-acetamidophenoxy)carbonyl)oxy)methyl (1,3-bis(palmitoyloxy)propan-2-yl) succinate, I-2

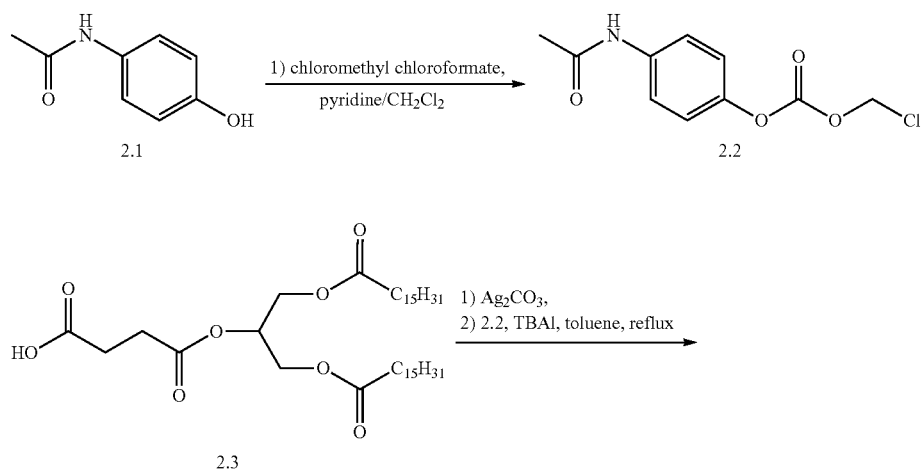

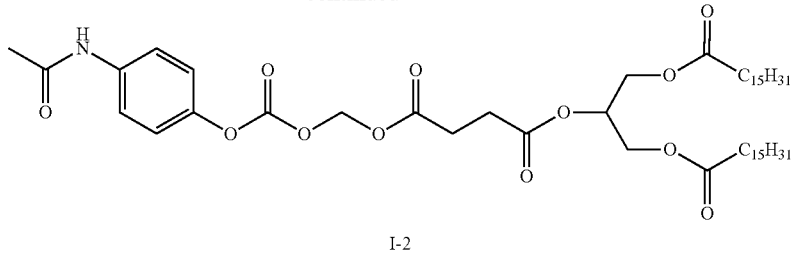

I-2

Synthesis of 2.2. 2.2 is prepared according to the following procedure. Chloromethyl chloroformate (1.6 equiv.) and pyridine (3.0 equiv.) are added to acetaminophen 2.1 (1.0 equiv.) in $CH_2Cl_2$ (0.03 M) at 0° C. and the mixture is stirred at 0° C. for 15 minutes and then at rt for one hour. The reaction is diluted with $CH_2Cl_2$ and the organic phase washed with sat. aq. $NaHCO_3$ and brine, dried ($MgSO_4$) and concentrated under reduced pressure to give 2.2 which is used without purification.

Synthesis of I-2. I-2 is prepared according to the following procedure. Silver carbonate (0.7 equiv.) is added to acid 2.3 (1.2 equiv.) as prepared in WO 2017/041139, in DMF (0.03 M) and the mixture stirred at rt for one hour. The reaction is concentrated under reduced pressure to give a grey residue, to which is added chloromethyl carbonate 2.2 (1.0 equiv.) in toluene (0.03 M) and TBAI (0.3 equiv.) and the mixture heated at reflux for 1.5 hours. The reaction is cooled to rt, then diluted with ethyl acetate. The organic phase is washed with water and brine, dried ($MgSO_4$) and concentrated under reduced pressure to give the crude product. Purification by silica gel chromatography with a suitable solvent mixture affords I-2.

Example 4: Synthesis of 2-(4-(4-acetamidophenoxy)-2-methyl-4-oxobutan-2-yl)-3,5-dimethylphenyl (1,3-bis(palmitoyloxy)propan-2-yl) succinate, I-3

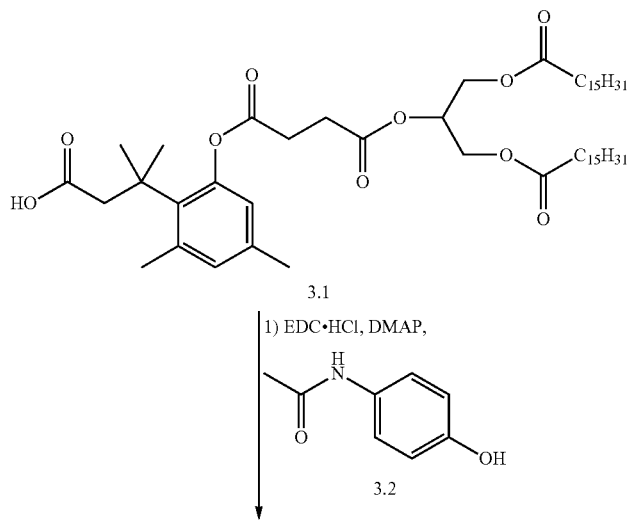

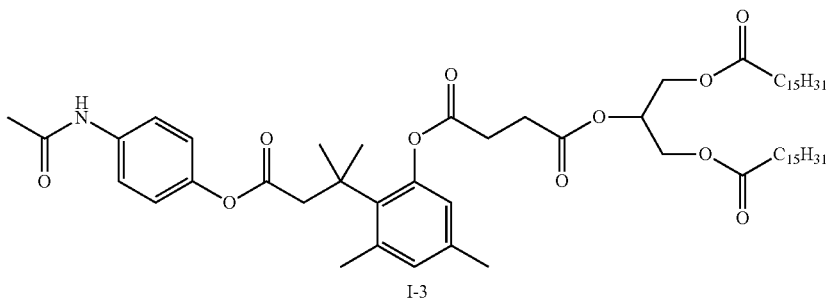

I-3

Synthesis of I-3. I-3 is prepared according to the following procedure. 4-(Dimethylamino)pyridine (DMAP, 1.3 equiv.) and EDC·HCl (2.1 equiv.) is added to a solution of acid 3.1 (1.0 equiv.) as prepared in WO 2017/041139, and acetaminophen 3.2 (1.3 equiv.) in $CH_2Cl_2$ (0.02 M) and the mixture stirred at rt for 19 hours. The reaction is diluted with $CH_2Cl_2$ (10 mL), silica gel is added and the mixture concentrated under reduced pressure. Purification by silica gel chromatography with a suitable solvent mixture affords I-3.

Example 5: Synthesis of 4-((((4-acetamidophenoxy)carbonyl)oxy)methyl)phenyl (1,3-bis(palmitoyloxy)propan-2-yl) succinate, I-4

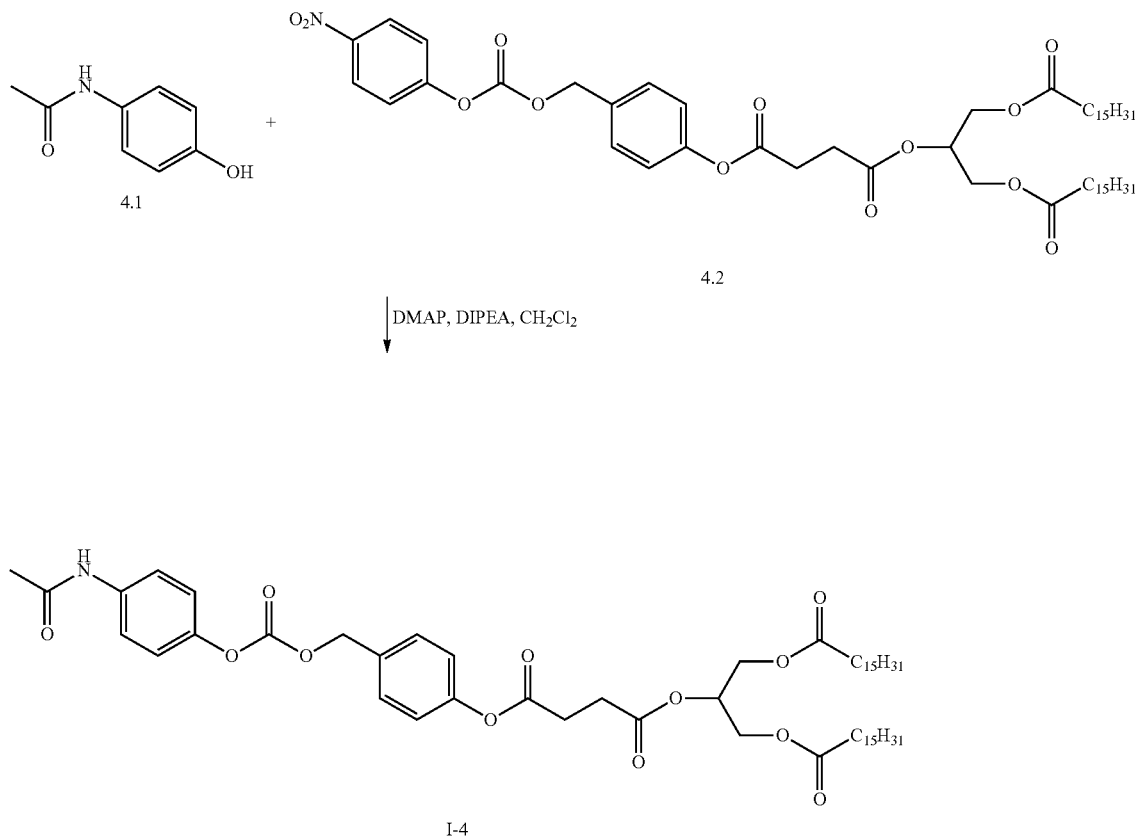

Synthesis of I-4. I-4 is prepared according to the following procedure. 4-(Dimethylamino)pyridine (DMAP, 1.3 equiv.) and DIPEA (0.3 equiv.) were added to a solution of acetaminophen, 4.1 (1.2 equiv.) and PNP carbonate 4.2 (1.0 equiv.) as prepared in WO 2017/041139, in $CH_2Cl_2$ (0.01 M) and the mixture stirred at rt for five days. The reaction was diluted with $CH_2Cl_2$, washed with 1 M HCl, water and brine, dried ($MgSO_4$) and concentrated under reduced pressure to give the crude product. Purification by silica gel chromatography with a suitable solvent mixture affords I-4.

Example 6: Synthesis of 4-(4-acetamidophenoxy)-4-oxobutyl (1,3-bis(palmitoyloxy)propan-2-yl) succinate (I-5) and Additional Paracetamol (Acetaminophen) Lipid Prodrugs

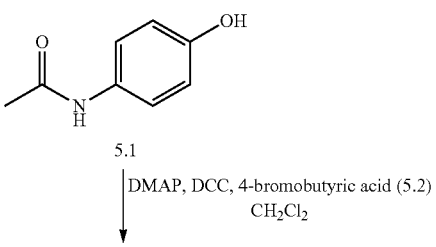

-continued

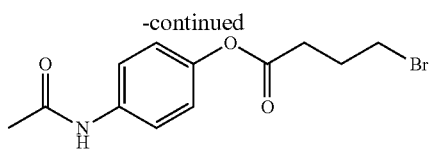
5.3

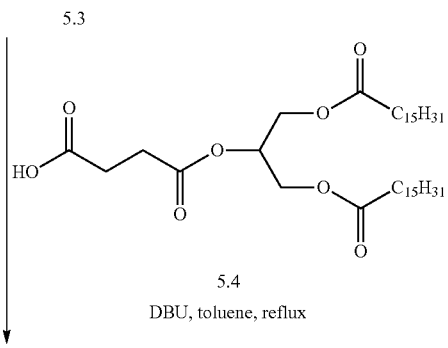
5.4

DBU, toluene, reflux

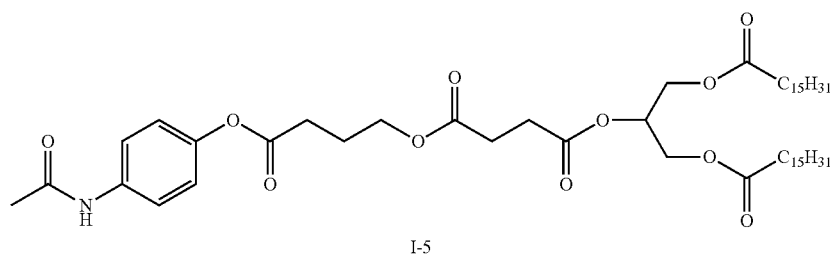
I-5

Synthesis of 5.3. 5.3 is prepared according to the following procedure. 4-(Dimethylamino)pyridine (1.3 equiv.) and DCC (2.1 equiv.) are added to a solution of acetaminophen (1.0 equiv.) and 4-bromobutyric acid 5.2 (1.3 equiv.) in $CH_2Cl_2$ (0.03 M) and the mixture is stirred at rt for 24 hours. Another 0.6 eq. of acid, 1 eq. of DCC, 0.6 eq. of DMAP are added and the mixture is stirred at rt for a further two days. The reaction is diluted with $CH_2Cl_2$, silica gel is added and the mixture is concentrated under reduced pressure. Purification by silica gel chromatography gives bromide 5.3.

Synthesis of I-5. I-5 is prepared according to the following procedure. 1,8-Diazabicyclo[5.4.0]undec-7-ene (DBU) (1.6 equiv.) is added to a suspension of acid 5.4 (1.1 equiv.) as prepared in WO 2017/041139, and bromide 5.3 (1.0 equiv.) in toluene (0.03 M) and the mixture is heated at reflux for 21 hours. The reaction is cooled to rt, then diluted with ethyl acetate. The organic phase is washed with water and brine, dried ($MgSO_4$) and concentrated under reduced pressure to give the crude product. Purification by silica gel chromatography with a suitable solvent mixture affords I-5.

Additional compounds were prepared according to methods similar to those described in this and the foregoing Examples. These compounds and their characterization data are shown below in Table 8.

TABLE 8

Additional Lipid Prodrugs of Paracetamol (Acetaminophen)

| Cmpd. # | Structure | $^1$H NMR; $^{13}$C NMR; MS |
|---|---|---|
| I-6 | ![structure] | $^1$H NMR (401 MHz, $CDCl_3$) δ 7.50 (d, J = 8.9 Hz, 2H), 7.15 (s, 1H), 7.03 (d, J = 8.9 Hz, 2H), 5.29 (m, 1H), 4.318/4.313 (each dd, J = 11.9, 4.2 Hz, 2H), 4.146/4.144 (each dd, J = 11.9, 6.0 Hz, 2H), 2.68-2.45 (m, 4H), 2.39-2.27 (m, 5H), 2.17 (s, 3H), 1.66-1.53 (m, 4H), 1.25 (s, 48H), 1.12 (d, J = 6.5 Hz, 3H), 0.88 (t, J = 6.8 Hz, 6H). |

TABLE 8-continued

Additional Lipid Prodrugs of Paracetamol (Acetaminophen)

| Cmpd. # | Structure | $^1$H NMR; $^{13}$C NMR; MS |
|---|---|---|
| I-7 | 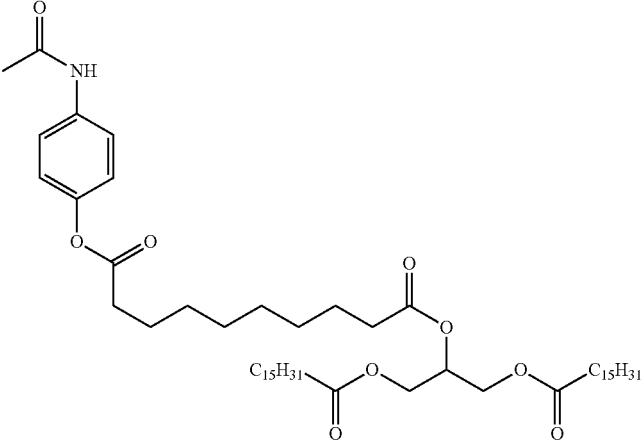 | $^1$H NMR (401 MHz, CDCl$_3$) δ 7.49 (d, J = 8.8 Hz, 2H), 7.30 (br s, 1H), 7.02 (d, J = 8.8 Hz, 2H), 5.26 (m, 1H), 4.29 (dd, J = 11.9, 4.4 Hz, 2H), 4.14 (dd, J = 11.9, 5.9 Hz, 2H), 2.53 (t, J = 7.5 Hz, 2H), 2.32 (t, J = 7.5 Hz, 2H), 2.31 (t, J = 7.5 Hz, 4H), 2.16 (s, 3H), 1.78-1.69 (m, 2H), 1.68-1.54 (m, 6H), 1.44-1.19 (m, 56H), 0.88 (t, J = 6.8 Hz, 6H); $^{13}$C NMR (101 MHz, CDCl$_3$) δ 173.5 (2C; C), 173.0 (C), 172.5 (C), 168.3 (C), 147.1 (C), 135.6 (C), 122.1 (2C; CH), 120.9 (2C; CH), 69.0 (CH), 62.2 (2C, CH$_2$), 34.5 (CH$_2$), 34.3 (CH$_2$), 34.2 (2C; CH$_2$), 32.1 (2C; CH$_2$), 29.84 (6C; CH$_2$), 29.80 (4C; CH$_2$), 29.77 (2C; CH$_2$), 29.6 (2C; CH$_2$), 29.5 (2C; CH$_2$), 29.4 (2C; CH$_2$), 29.26 (2C; CH$_2$), 29.22 (CH$_2$), 29.20 (CH$_2$), 29.17 (CH$_2$), 29.12 (CH$_2$), 25.01 (2C; CH$_2$), 24.96 (CH$_2$), 24.7 (CH$_3$), 22.8 (2C; CH$_2$), 14.3 (2C; CH$_3$). |
| I-8 | 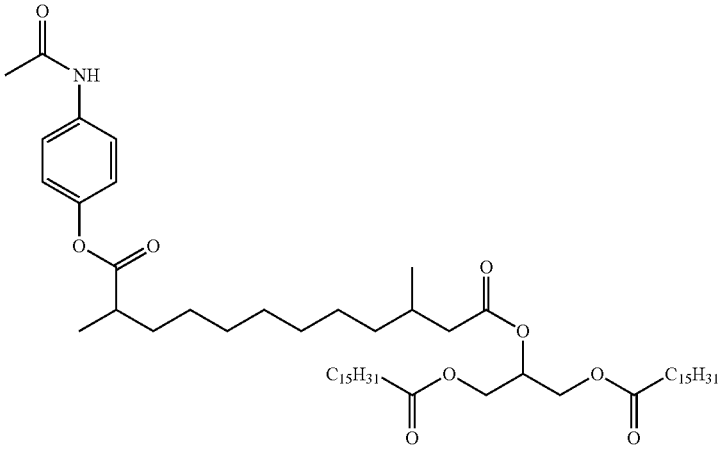 | $^1$H NMR (401 MHz, CDCl$_3$) δ 7.49 (d, J = 8.9 Hz, 2H), 7.31 (br s, 1H), 7.01 (d, J = 8.9 Hz, 2H), 5.28 (m, 1H), 4.288/4.284 (each dd, J = 11.9, 4.3 Hz, 2H), 4.14 (dd, J = 11.9, 5.9 Hz, 2H), 2.66 (m, 1H), 2.32 (dd, J = 14.7, 5.8 Hz, 1H), 2.30 (t, J = 7.5 Hz, 4H), 2.16 (s, 3H), 2.12 (dd, J = 14.7, 8.3 Hz, 1H), 1.93 (m, 1H), 1.79 (m, 1H), 1.68-1.47 (m, 6H), 1.45-1.15 (m, 62H), 0.93 (d, J = 6.6 Hz, 3H), 0.88 (t, J = 6.9 Hz, 6H); $^{13}$C NMR (101 MHz, CDCl$_3$) δ 175.6 (C), 173.5 (2C; C), 172.5 (C), 168.3 (C), 147.1 (C), 135.6 (C), 122.1 (2C; CH), 120.9 (2C; CH), 68.9 (CH), 62.3 (2C; CH$_2$), 41.8 (CH$_2$), 39.8 (CH), 36.8 (CH$_2$), 34.2 (2C; CH$_2$), 33.9 (CH$_2$), 32.1 (2C; CH$_2$), 30.5 (CH), 29.84 (7C; CH$_2$), 29.80 (4C; CH$_2$), 29.76 (2C; CH$_2$), 29.6 (4C; CH$_2$), 29.5 (2C; CH$_2$), 29.4 (2C; CH$_2$), 29.3 (2C; CH$_2$), 27.4 (CH$_2$), 27.0 (CH$_2$), 25.0 (2C; CH$_2$), 24.6 (CH$_3$), 22.8 (2C; CH$_2$), 19.7 (CH$_3$), 17.2 (CH$_3$), 14.3 (2C; CH$_3$); ESI-HRMS: calcd. for C$_{57}$H$_{99}$NNaO$_9$ [M + Na$^+$] 964.7212; found 964.7214. |
| I-9 | 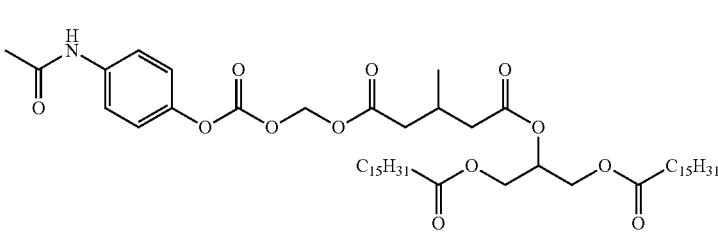 | $^1$H NMR (401 MHz, CDCl$_3$) δ 7.53 (d, J = 8.9 Hz, 2H), 7.20 (br s, 1H), 7.15 (d, J = 9.0 Hz, 2H), 5.85 (s, 2H), 5.27 (m, 1H), 4.33-4.27 (m, 2H), 4.13 (dd, J = 11.9, 6.0 Hz, 2H), 2.56-2.24 (m, 9H), 2.18 (s, 3H), 1.67-1.53 (m, 4H), 1.37-1.19 (m, 48H), 1.06 (d, J = 6.4 Hz, 3H), 0.88 (t, J = 6.8 Hz, 6H); $^{13}$C NMR (101 MHz, CDCl$_3$) δ 173.5 (2C; C), 171.4 (C), 170.7 (C), 152.7 (C), 121.5 (2C; CH), 120.9 (2C; CH), 82.4 (CH$_2$), 69.4 (CH), 62.2 (2C; CH$_2$), 40.6 (CH$_2$), 40.3 (CH$_2$), 34.2 (2C; CH$_2$), 32.1 (2C; CH$_2$), 29.85 (6C; CH$_2$), 29.81 (4C; CH$_2$), 29.77 (2C; CH$_2$), 29.6 (2C; CH$_2$), 29.5 (2C; CH$_2$), 29.4 (2C; CH$_2$), 29.3 (2C; CH$_2$), 27.3 (CH), 25.0 (2C; CH$_2$), 24.7 (CH$_3$), 22.8 (2C; CH$_2$), 19.8 (CH$_3$), 14.3 (2C; CH$_3$). |

TABLE 8-continued

Additional Lipid Prodrugs of Paracetamol (Acetaminophen)

| Cmpd. # | Structure | $^1$H NMR; $^{13}$C NMR; MS |
|---|---|---|
| I-10 | 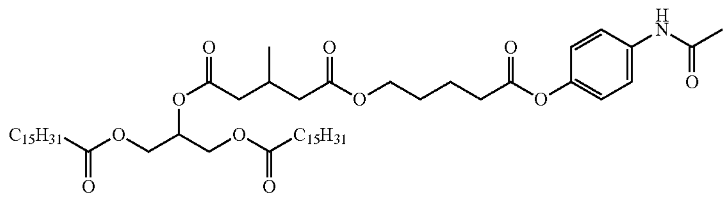 | $^1$H NMR (401 MHz, CDCl$_3$) δ 7.49 (d, J = 8.9 Hz, 2H), 7.41 (br s, 1H), 7.01 (d, J = 8.9 Hz, 2H), 5.26 (m, 1H), 4.288/4.281 (each dd, J = 11.9, 4.3 Hz, 2H), 4.16-4.09 (m, 4H), 2.58 (t, J = 7.1 Hz, 2H), 2.50-2.35 (m, 3H), 2.30 (t, J = 7.5 Hz, 4H), 2.33-2.20 (m, 2H), 2.15 (s, 3H), 1.86-1.71 (m, 4H), 1.65-1.54 (m, 4H), 1.34-1.18 (m, 48H), 1.02 (d, J = 6.5 Hz, 3H), 0.87 (t, J = 6.8 Hz, 6H); $^{13}$C NMR (101 MHz, CDCl$_3$) δ 173.5 (2C; C), 172.3 (C), 172.0 (C), 171.5 (C), 168.4 (C), 146.9 (C), 135.8 (C), 122.0 (2C; CH), 120.9 (2C; CH), 69.2 (CH), 64.0 (CH$_2$), 62.2 (2C; CH$_2$), 40.8 (2C; CH$_2$), 34.12 (2C; CH$_2$), 33.9 (CH$_2$), 32.1 (2C; CH$_2$), 29.83 (6C; CH$_2$), 29.79 (4C; CH$_2$), 29.75 (2C; CH$_2$), 29.6 (2C; CH$_2$), 29.5 (2C; CH$_2$), 29.4 (2C; CH$_2$), 29.3 (2C; CH$_2$), 28.2 (CH$_2$), 27.5 (CH), 25.0 (2C; CH$_2$), 24.6 (CH$_3$), 22.8 (2C; CH$_2$), 21.6 (CH$_2$), 19.8 (CH$_3$), 14.2 (2C; CH$_3$). |

Example 7: Synthesis of Buprenorphine Lipid Prodrugs

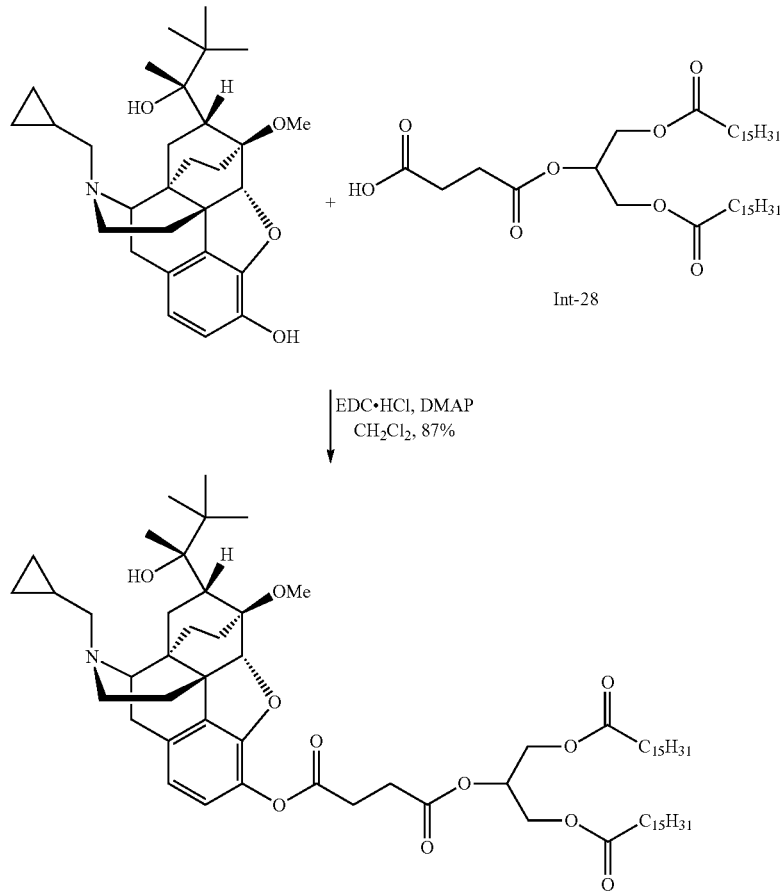

Synthesis of I-12. DMAP (2.0 mg, 16.0 µmol) and EDC·HCl (7.7 mg, 40.0 µmol) were added to a solution of Int-28 (13.9 mg, 20.8 µmol) and buprenorphine (7.5 mg, 16.0 µmol) in $CH_2Cl_2$ (0.8 mL) and the mixture stirred at rt for two hours. The reaction was diluted with $CH_2Cl_2$ (5 mL), silica gel was added, and the solvent removed under reduced pressure. Purification by silica gel chromatography (10% to 15% ethyl acetate/hexanes with 0.5% $Et_3N$) gave BUP prodrug I-12 (15.6 mg, 87%) as a colorless oil. $^1$H NMR (401 MHz, $CDCl_3$) δ 6.78 (d, J=8.1 Hz, 1H), 6.58 (d, J=8.1 Hz, 1H), 5.89 (s, 1H), 5.26 (m, 1H), 4.42 (d, J=1.6 Hz, 1H), 4.29 (dt, J=11.9, 4.4 Hz, 2H), 4.19-4.12 (m, 2H), 3.45 (s, 3H), 3.05-2.97 (m, 2H), 2.93-2.83 (m, 3H), 2.70 (t, J=6.9 Hz, 2H), 2.62 (dd, J=11.8, 4.9 Hz, 1H), 2.37-2.20 (m, 8H), 2.11 (t, J=9.8 Hz, 1H), 1.96 (m, 1H), 1.91-1.75 (m, 2H), 1.70 (dd, J=13.0, 2.4 Hz, 1H), 1.65-1.53 (m, 4H), 1.35 (s, 3H), 1.37-1.16 (m, 49H), 1.06 (m, 1H), 1.03 (s, 9H), 0.88 (t, J=6.9 Hz, 6H), 0.80 (m, 1H), 0.67 (m, 1H), 0.54-0.42 (m, 2H), 0.15-0.08 (m, 2H).

Additional compounds were prepared according to methods similar to those described in this and the foregoing Examples. These compounds and their characterization data are shown below in Table 9.

TABLE 9

Additional Lipid Prodrugs of Buprenorphine

| Cmpd. # | Structure | $^1$H NMR; $^{13}$C NMR; MS |
|---|---|---|
| I-13 | 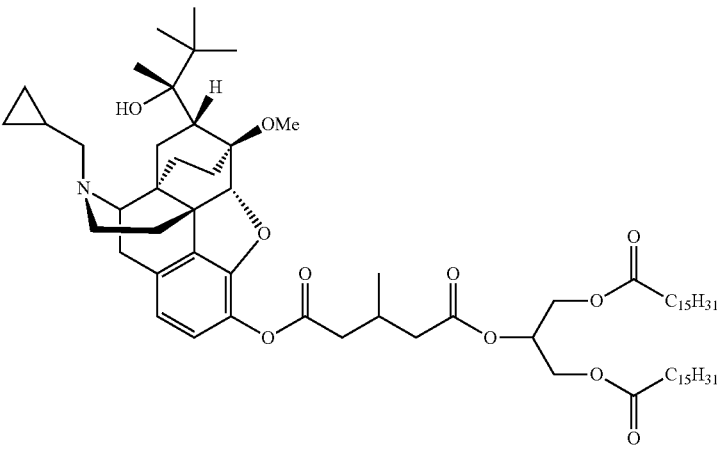 | $^1$H NMR (401 MHz, $CDCl_3$) δ $^1$H NMR (401 MHz, $CDCl_3$) δ 6.76 (d, J = 7.6 Hz, 1H), 6.59 (d, J = 8.1 Hz, 1H), 5.88 (s, 1H), 5.28 (m, 1H), 4.42 (s, 1H), 4.34-4.26 (m, 2H), 4.13 (dd, J = 11.9, 6.0 Hz, 2H), 3.45 (s, 3H), 3.06-2.98 (m, 2H), 2.88 (m, 1H), 2.67-2.59 (m, 2H), 2.57-2.41 (m, 3H), 2.39-2.21 (m, 9H), 2.11 (m, 1H), 2.02-1.78 (m, 3H), 1.71 (m, 1H), 1.65-1.54 (m, 4H), 1.35 (s, 3H), 1.38-1.19 (m, 49H), 1.102/1.091 (each d, J = 6.4 Hz, 3H), 1.04 (m, 1H), 1.03 (s, 9H), 0.87 (t, J = 6.9 Hz, 8H), 0.79 (m, 1H), 0.70 (m, 1H), 0.55-0.42 (m, 2H), 0.15-0.08 (m, 2H); $^{13}$C NMR (101 MHz, $CDCl_3$) δ 173.4 (2C; C), 171.4 (C), 170.1 (C), 149.9 (C), 134.6 (C), 133.9 (C), 131.3 (C), 122.1 (CH), 119.4 (CH), 98.2 (CH), 80.9 (C), 79.4 (C), 69.3 (CH), 62.2 (2C; $CH_2$), 59.7 ($CH_2$), 58.3 (CH), 52.7 ($CH_3$), 46.4 (C), 44.4 (CH), 43.7 ($CH_2$), 40.69/40.60 ($CH_2$), 40.5 (C), 40.36/40.32 ($CH_2$), 36.1 (C), 35.6 ($CH_2$), 34.1 (2C; $CH_2$), 33.5 ($CH_2$), 32.1 (2C; $CH_2$), 29.9 ($CH_2$), 29.85 (6C; $CH_2$), 29.81 (4C; $CH_2$), 29.77 (2C; $CH_2$), 29.6 (2C; $CH_2$), 29.5 (2C; $CH_2$), 29.4 (2C; $CH_2$), 29.3 (2C; $CH_2$), 27.68/27.64 (CH), 26.6 (3C; $CH_3$), 25.0 (2C; $CH_2$), 23.5 ($CH_2$), 22.8 (2C; $CH_2$), 2.01 ($CH_3$), 19.62/19.60 ($CH_3$), 17.7 ($CH_2$), 14.3 (2C; $CH_3$), 9.6 (CH), 4.3 ($CH_2$), 3.4 ($CH_2$). |
| I-14 | 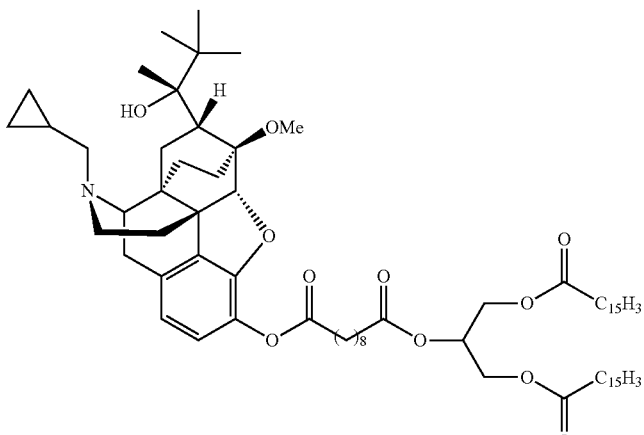 | $^1$H NMR (400 MHz, $CDCl_3$) δ 6.76 (d, J = 8.1 Hz, 1H), 6.59 (d, J = 8.1 Hz, 1H), 5.90 (s, 1H), 5.26 (m, 1H), 4.42 (d, J = 1.7 Hz, 1H), 4.29 (dd, J = 11.9, 4.4 Hz, 2H), 4.14 (dd, J = 11.9, 5.9 Hz, 2H), 3.45 (s, 3H), 3.05-2.98 (m, 2H), 2.88 (m, 1H), 2.62 (dd, J = 11.8, 4.9 Hz, 1H), 2.51 (t, J = 7.5 Hz, 2H), 2.38-2.21 (m, 10H), 2.12 (m, 1H), 2.03-1.77 (m, 3H), 1.73-1.66 (m, 3H), 1.65-1.52 (m, 6H), 1.35 (s, 3H), 1.43-1.18 (m, 57H), 1.06 (m, 1H), 1.03 (s, 9H), 0.88 (t, J = 6.9 Hz, 6H), 0.80 (m, 1H), 0.68 (m, 1H), 0.54-0.42 (m, 2H), 0.15-0.08 (m, 2H); $^{13}$C NMR (101 MHz, $CDCl_3$) δ 173.4 (2C; C), 172.9 (C), 171.7 (C), 150.0 (C), 134.5 (C), 133.8 (C), 131.6 (C), 122.2 (CH), 119.4 (CH), 98.3 (CH), 80.9 (C), 79.4 (C), 69.0 (CH), 62.2 (2C; $CH_2$), 59.7 ($CH_2$), 58.3 (CH), 52.7 ($CH_3$), 46.4 (C), 44.5 (CH), 43.7 ($CH_2$), 40.5 (C), 36.1 (C), 35.6 ($CH_2$), 34.3 ($CH_2$), 34.2 (2C; $CH_2$), 34.0 ($CH_2$), 33.5 |

TABLE 9-continued

Additional Lipid Prodrugs of Buprenorphine

| Cmpd. # | Structure | $^1$H NMR; $^{13}$C NMR; MS |
|---|---|---|
| | | (CH$_2$), 32.1 (2C; CH$_2$), 29.9 (CH$_2$), 29.84 (6C; CH$_2$), 29.80 (4C; CH$_2$), 29.76 (2C; CH$_2$), 29.6 (2C; CH$_2$), 29.5 (2C; CH$_2$), 29.4 (2C; CH$_2$), 29.25 (2C; CH$_2$), 29.23 (2C; CH$_2$), 29.15 (2C; CH$_2$), 26.6 (3C; CH$_3$), 25.2 (CH$_2$), 25.00 (2C; CH$_2$), 24.96 (CH$_2$), 23.5 (CH$_2$), 22.8 (2C; CH$_2$), 20.1 (CH$_3$), 17.6 (CH$_2$), 14.3 (2C; CH$_3$), 9.6 (CH), 4.3 (CH$_2$), 3.4 (CH$_2$). |
| I-15 | 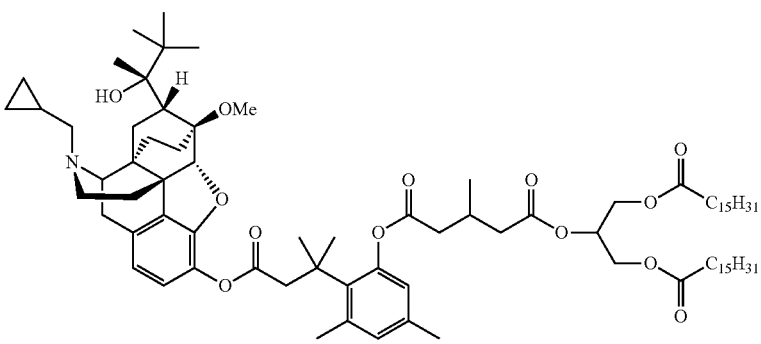 | $^1$H NMR (401 MHz, CDCl$_3$) δ 6.79 (d, J = 1.8 Hz, 1H), 6.59 (d, J = 8.1 Hz, 1H), 6.57 (d, J = 1.4 Hz, 1H), 6.53 (d, J = 8.1 Hz, 1H), 5.90 (s, 1H), 5.28 (m, 1H), 4.39 (d, J = 1.4 Hz, 1H), 4.30 (dt, J = 11.9, 3.7 Hz, 2H), 4.14 (dd, J = 11.9, 6.0 Hz, 2H), 3.37 (s, 3H), 3.10-2.95 (m, 4H), 2.87 (m, 1H), 2.70 (dd, J = 14.8, 5.0 Hz, 1H), 2.64-2.49 (m, 4H), 2.55 (s, 3H), 2.40-2.18 (m, 9H), 2.22 (s, 3H), 2.10 (t, J = 9.8 Hz, 1H), 1.97 (m, 1H), 1.88-1.73 (m, 2H), 1.71-1.53 (m, 11H), 1.35 (s, 3H), 1.44-1.19 (m, 49H), 1.13 (d, J = 6.3 Hz, 3H), 1.05 (m, 1H), 1.02 (s, 9H), 0.87 (t, J = 6.8 Hz, 6H), 0.79 (m, 1H), 0.66 (m, 1H), 0.53-0.42 (m, 2H), 0.15-0.07 (m, 2H); $^{13}$C NMR (101 MHz, CDCl$_3$) δ 173.4 (2C; C), 171.4 (C), 171.3 (C), 169.4 (C), 150.0 (C), 149.5 (C), 138.2 (C), 136.4 (C), 134.4 (C), 133.7 (C), 133.5 (C), 132.6 (CH), 131.3 (C), 123.1 (CH), 122.3 (CH), 119.3 (CH), 98.1 (CH), 80.8 (C), 79.4 (C), 69.3 (CH), 62.2 (2C; CH$_2$), 59.6 (CH$_2$), 58.3 (CH), 52.7 (CH$_3$), 47.3 (CH$_2$), 46.3 (C), 44.3 (CH), 43.7 (CH$_2$), 41.3 (CH$_2$), 40.7 (CH$_2$), 40.5 (C), 39.0 (C), 36.1 (C), 35.5 (CH$_2$), 34.1 (2C; CH$_2$), 33.5 (CH$_2$), 32.1 (2C; CH$_2$), 31.4 (CH$_3$), 31.33/31.31 (CH$_3$), 29.9 (CH$_2$), 29.83 (6C; CH$_2$), 29.79 (4C; CH$_2$), 29.75 (2C; CH$_2$), 29.6 (2C; CH$_2$), 29.5 (2C; CH$_2$), 29.4 (2C; CH$_2$), 29.2 (2C; CH$_2$), 27.3 (CH), 26.5 (3C; CH$_3$), 25.5 (CH$_3$), 25.0 (2C; CH$_2$), 23.4 (CH$_2$), 22.8 (2C; CH$_2$), 20.4 (CH$_3$), 20.1 (CH$_3$), 19.9 (CH$_3$), 17.7 (CH$_2$), 14.3 (2C; CH$_3$), 9.6 (CH), 4.3 (CH$_2$), 3.4 (CH$_2$). |
| I-16 | 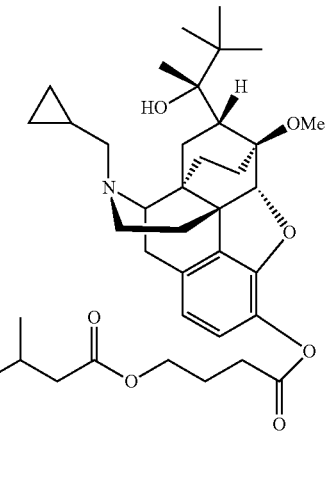 | $^1$H NMR (401 MHz, CDCl$_3$) δ 6.78 (d, J = 8.1 Hz, 1H), 6.59 (d, J = 8.1 Hz, 1H), 5.89 (s, 1H), 5.27 (m, 1H), 4.42 (d, J = 1.7 Hz, 1H), 4.299/4.296 (each dd, J = 11.9, 4.3 Hz, 2H), 4.20-4.09 (m, 4H), 3.45 (s, 3H), 3.06-2.98 (m, 2H), 2.88 (m, 1H), 2.67-2.58 (m, 3H), 2.52-2.20 (m, 13H), 2.19-1.78 (m, 6H), 1.70 (dd, J = 13.2, 5.5 Hz, 1H), 1.66-1.49 (m, 4H), 1.35 (s, 3H), 1.38-1.17 (m, 49H), 1.04 (m, 1H), 1.03 (s, 9H), 1.02 (d, J = 6.6 Hz, 3H), 0.88 (t, J = 6.9 Hz, 6H), 0.80 (m, 1H), 0.68 (m, 1H), 0.54-0.43 (m, 2H), 0.16-0.08 (m, 2H). |

TABLE 9-continued

Additional Lipid Prodrugs of Buprenorphine

| Cmpd. # | Structure | $^1$H NMR; $^{13}$C NMR; MS |
|---|---|---|
| I-17 | 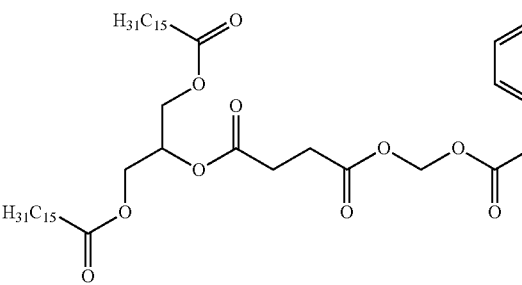 | $^1$H NMR (401 MHz, CDCl$_3$) δ 6.88 (d, J = 8.2 Hz, 1H), 6.60 (d, J = 8.1 Hz, 1H), 5.86 (s, 1H), 5.82 (s, 2H), 5.27 (m, 1H), 4.46 (s, 1H), 4.30 (dd, J = 12.0, 4.3 Hz, 2H), 4.15 (dd, J = 12.0, 5.9 Hz, 2H), 3.49 (s, 3H), 3.06-2.98 (m, 2H), 2.89 (m, 1H), 2.73-2.60 (m, 5H), 2.39-2.22 (m, 8H), 2.12 (t, J = 9.2 Hz, 1H), 2.01 (m, 1H), 1.93-1.80 (m, 2H), 1.75-1.49 (m, 5H), 1.35 (s, 3H), 1.34-1.20 (m, 49H), 1.05 (m, 1H), 1.03 (s, 9H), 0.88 (t, J = 6.9 Hz, 6H), 0.80 (m, 1H), 0.66 (m, 1H), 0.56-0.44 (m, 2H), 0.16-0.09 (m, 2H); ESI-HRMS: Calcd. for C$_{70}$H$_{114}$NO$_{14}$ [M + H$^+$] 1192.8234; found 1192.8244. |
| I-18 | 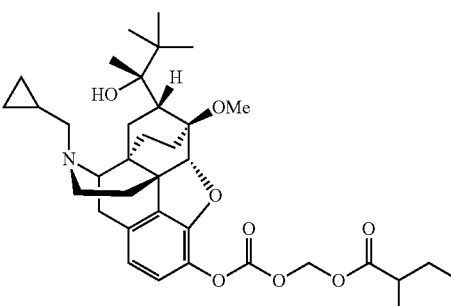 | $^1$H NMR (401 MHz, CDCl$_3$) δ 6.87 (d, J = 8.2 Hz, 1H), 6.60 (d, J = 8.2 Hz, 1H), 5.89 (s, 1H), 5.81 (ddd, J = 8.5, 5.6, 2.5 Hz, 2H), 5.27 (m, 1H), 4.46 (s, 1H), 4.285/4.283 (each dd, J = 11.9, 4.3 Hz, 2H), 4.14 (dd, J = 11.8, 5.9 Hz, 2H), 3.48 (s, 3H), 3.07-2.97 (m, 2H), 2.89 (m, 1H), 2.63 (dd, J = 11.9, 4.8 Hz, 1H), 2.47 (m, 1H), 2.41-2.22 (m, 9H), 2.16-2.06 (m, 2H), 2.03-1.77 (m, 4H), 1.75-1.50 (m, 7H), 1.48-1.20 (m, 61H), 1.35 (s, 3H), 1.172/1.167 (each d, J = 7.0 Hz, 3H), 1.05 (m, 1H), 1.03 (s, 9H), 0.92 (d, J = 6.6 Hz, 3H), 0.88 (t, J = 6.9 Hz, 6H), 0.80 (m, 1H), 0.67 (m, 1H), 0.54-0.43 (m, 2H), 0.15-0.08 (m, 2H). |
| I-19 | 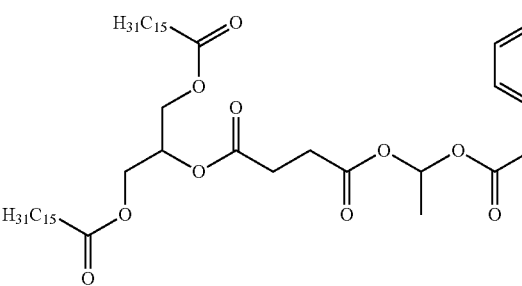 | $^1$H NMR (401 MHz, CDCl$_3$) δ 6.88/6.87 (each d, J = 8.2 Hz, 1H), 6.77 (m, 1H), 6.59 (d, J = 8.2 Hz, 1H), 5.89/5.88 (each s, 1H), 5.25 (m, 1H), 4.46 (br s, 1H), 4.33-4.26 (m, 2H), 4.19-4.11 (m, 2H), 3.49/3.48 (each s, 3H), 3.06-2.98 (m, 2H), 2.89 (m, 1H), 2.74-2.57 (m, 5H), 2.38-2.20 (m, 8H), 2.12 (t, J = 10.0 Hz, 1H), 1.98 (td, J = 12.5, 5.5 Hz, 1H), 1.91-1.77 (m, 2H), 1.70 (dd, J = 13.4, 2.9 Hz, 1H), 1.64-1.52 (m, 7H), 1.35 (s, 3H), 1.33-1.18 (m, 49H), 1.06 (m, 1H), 1.03 (s, 5H), 0.88 (t, J = 6.9 Hz, 6H), 0.81 (m, 1H), 0.66 (m, 1H), 0.55-0.43 (m, 2H), 0.15-0.07 (m, 2H); ESI-HRMS: Calcd. for C$_{71}$H$_{116}$NO$_{14}$ [M + H$^+$] 1206.8390; found 1206.8401. |

Example 8: Synthesis of BODIPY and Cy5 Lipid Prodrugs

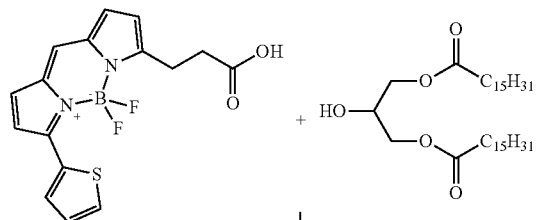

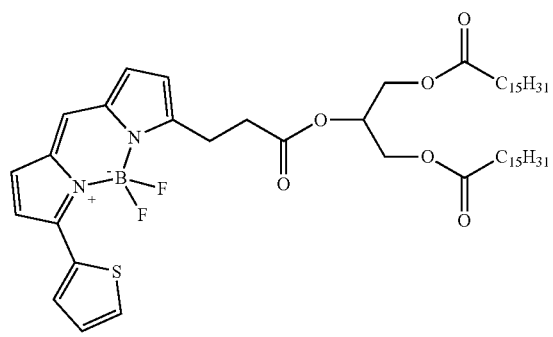

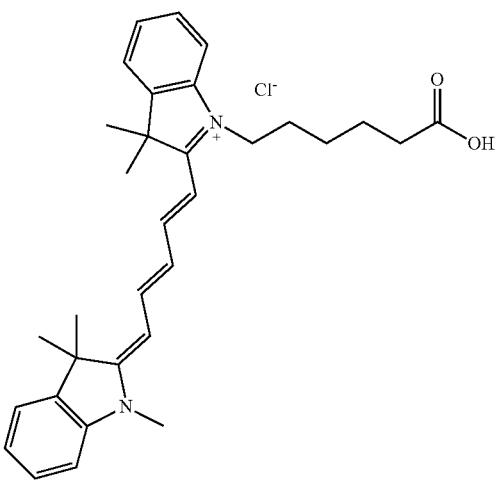

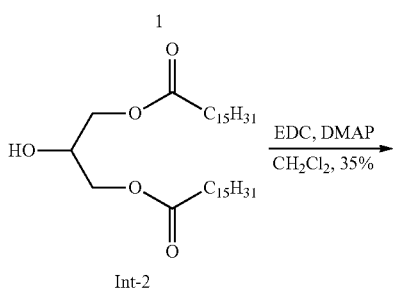

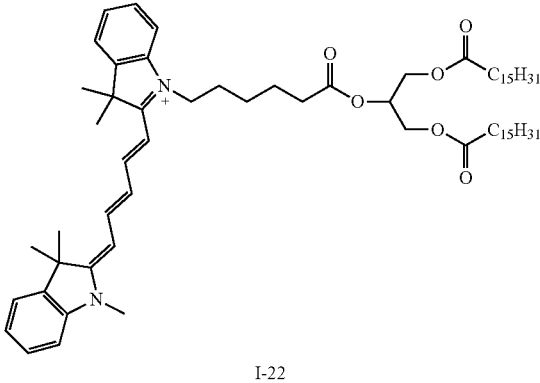

DMAP (2.9 mg, 24.1 μmol) and EDC·HCl (11.5 mg, 60.2 μmol) were added to a solution of 1,3-diglyceride Int-2 (13.7 mg, 24.1 μmol) and BODIPY-558 acid (10.0 mg, 28.9 μmol) in CH$_2$Cl$_2$ (1 mL) and the mixture stirred at rt for 18 hours. The reaction was concentrated under reduced pressure to give the crude product. Purification by silica gel chromatography (7.5% to 9% ethyl acetate/hexanes) gave BODIPY-TG I-11 (8.0 mg, 37%) as a purple solid. $^1$H NMR (401 MHz, CDCl$_3$) δ 8.16 (dd, J=3.9, 1.0 Hz, 1H), 7.50 (dd, J=5.1, 1.0 Hz, 1H), 7.18 (dd, J=5.0, 3.9 Hz, 1H), 7.12 (s, 1H), 7.04 (d, J=4.4 Hz, 1H), 6.97 (d, J=4.1 Hz, 1H), 6.80 (d, J=4.2 Hz, 1H), 6.38 (d, J=4.1 Hz, 1H), 5.28 (m, 1H), 4.29 (dd, J=11.9, 4.3 Hz, 2H), 4.14 (dd, J=12.1, 5.8 Hz, 2H), 3.37 (t, J=7.4 Hz, 2H), 2.82 (t, J=7.4 Hz, 2H), 2.29 (t, J=7.6 Hz, 4H), 1.65-1.52 (m, 4H), 1.37-1.19 (m, 48H), 0.88 (t, J=6.9 Hz, 6H); $^{13}$C NMR (101 MHz, CDCl$_3$) δ 173.5 (C), 171.7 (C), 131.5 (CH), 130.8 (CH), 129.7 (CH), 129.2 (CH), 126.8 (CH), 120.6 (CH), 118.8 (CH), 114.2 (CH), 69.6 (CH), 62.2 (2C; CH$_2$), 34.2 (2C; CH$_2$), 33.2 (CH$_2$), 32.1 (2C; CH$_2$), 29.85 (2C; CH$_2$), 29.81 (2C; CH$_2$), 29.77 (2C; CH$_2$), 29.6 (2C; CH$_2$), 29.5 (2C; CH$_2$), 29.4 (2C; CH$_2$), 29.3 (2C; CH$_2$), 25.0 (2C; CH$_2$), 24.1 (CH$_2$), 22.8 (2C; CH$_2$), 14.3 (2C; CH$_3$). Note: All five aromatic quaternary carbon signals were too weak to be observed, while several of the aromatic CH signals were also relatively weak.

DMAP, 2.2 mg, 18.0 μmol) and EDC·HCl (8.6 mg, 44.9 μmol) were added to a solution of 1,3-diglyceride Int-2 (10.2 mg, 18.0 μmol) and cyanine-5 acid 1 (9.8 mg, 18.9 μmol) in CH$_2$Cl$_2$ (1 mL) and the mixture stirred at rt for two days and 21 hours. The reaction was concentrated under reduced pressure to give the crude product. Purification by silica gel chromatography (1% to 4% MeOH/CH$_2$Cl$_2$) gave Cy5-TG I-22 (6.5 mg, 35%) as a blue solid. $^1$H NMR (401 MHz, CDCl$_3$) δ 8.19 (t, J=11.9 Hz, 2H), 7.41-7.31 (m, 4H), 7.29-7.18 (m, 2H), 7.13-7.02 (m, 2H), 6.92 (t, J=12.5 Hz, 1H), 6.40 (dd, J=13.5, 3.5 Hz, 2H), 5.23 (m, 1H), 4.30 (dd, J=11.9, 4.4 Hz, 2H), 4.17-4.02 (m, 4H), 3.71 (s, 3H), 2.38 (t, J=7.4 Hz, 2H), 2.31 (t, J=7.5 Hz, 4H), 1.78 (s, 6H), 1.74 (s, 6H), 1.88-1.49 (m, 10H), 1.39-0.98 (m, 48H), 0.91-0.84 (m, 6H).

Example 9: Synthesis of Cannabidiol Lipid Prodrugs

Lipid prodrugs of cannabidiol (CBD) were synthesized as follows.

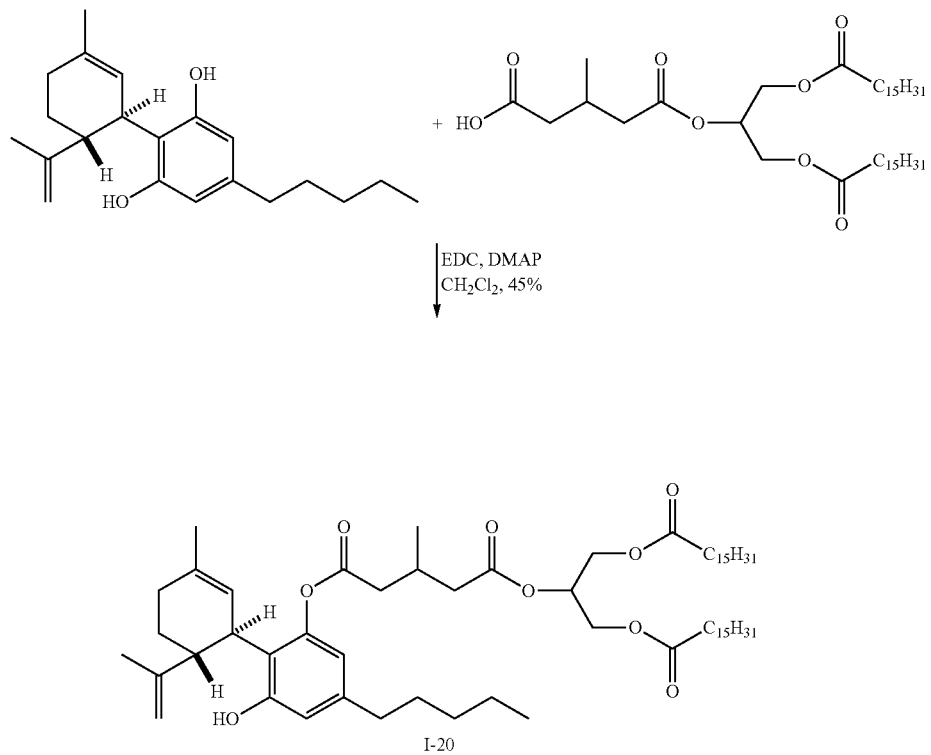

DMAP (2.7 mg, 22.3 µmol) and EDC·HCl (10.7 mg, 55.6 µmol) were added to a solution of triglyceride intermediate Int-4 (18.6 mg, 26.7 µmol) and cannabidiol (7.0 mg, 22.3 µmol) in $CH_2Cl_2$ (1 mL) and the mixture stirred at rt for 19 hours. The reaction was then concentrated under reduced pressure to give the crude product. Purification by silica gel chromatography (5% to 7.5% to 10% ethyl acetate/hexanes) gave CBD prodrug CBD-C5bMe-2-TG (I-20) (9.9 mg, 45%); $^1$H NMR (401 MHz, $CDCl_3$) δ 6.55 (s, 1H), 6.38 (dd, J=3.4, 1.7 Hz, 1H), 5.97 (br s, 1H), 5.52 (br s, 1H), 5.28 (m, 1H), 4.60 (m, 1H), 4.44 (br s, 1H), 4.36-4.27 (m, 2H), 4.14 (dd, J=11.9, 5.9 Hz, 2H), 3.47 (m, 1H), 2.67-2.27 (m, 8H), 2.30 (t, J=7.6 Hz, 4H), 2.21 (m, 1H), 2.06 (m, 1H), 1.86-1.67 (m, 5H), 1.65-1.51 (m, 9H), 1.47-1.19 (m, 52H), 1.11 (d, J=6.5 Hz, 3H), 0.88 (t, J=6.8 Hz, 9H); $^{13}$C NMR (101 MHz, $CDCl_3$) δ 173.43 (2C; C), 171.44/171.41 (C), 170.68/170.66 (C), 69.34 (CH), 62.20 (2C; $CH_2$), 45.73 (CH), 40.78 ($CH_2$), 40.64 ($CH_2$), 40.58 ($CH_2$), 38.14 (CH), 35.54 ($CH_2$), 34.16 (2C; $CH_2$), 32.07 (2C; $CH_2$), 31.63 ($CH_2$), 30.67 ($CH_2$), 29.85 (6C; $CH_2$), 29.81 (4C; $CH_2$), 29.77 (2C; $CH_2$), 29.63 (2C; $CH_2$), 29.51 (2C; $CH_2$), 29.42 (2C; $CH_2$), 29.27 (2C; $CH_2$), 27.42 (CH), 24.99 (2C; $CH_2$), 23.76 ($CH_3$), 22.84 (2C; $CH_2$), 22.64 ($CH_2$), 19.88/19.85 ($CH_3$), 14.27 (2C; $CH_3$), 14.17 ($CH_3$). Note: i) 37% of bis-prodrug (i.e. coupling of C10-acid-TG to both phenolic hydroxyl groups of cannabidiol) was also isolated; ii) A number of the aromatic signals were not observed in the $^{13}$C NMR spectrum.

Compound CBD-FSI5-C5bMe-2-TG (I-21) was prepared as follows.

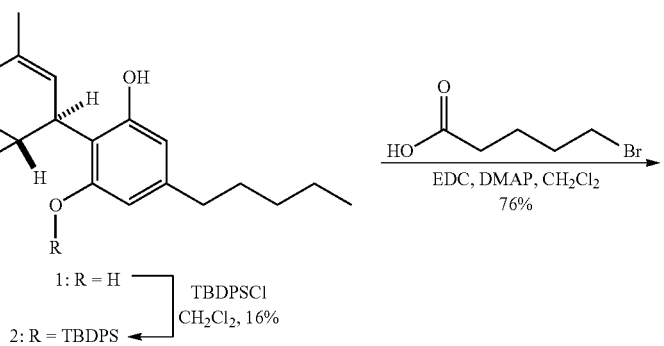

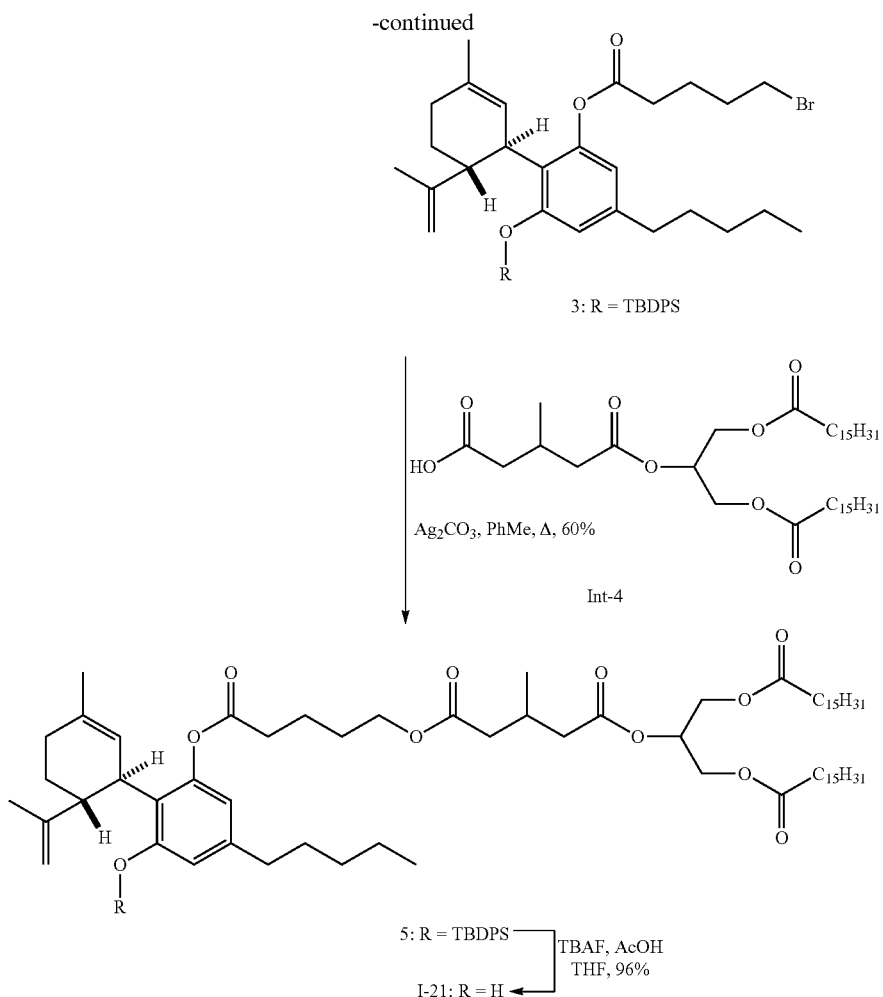

Intermediate 2 in the scheme above was prepared as follows. DMAP (5.2 mg, 42.9 μmol) and tert-butyl(chloro)diphenylsilane (TBDPSCl, 7.4 μL, 28.6 μmol) were added to a solution of cannabidiol (1) (9.0 mg, 28.6 μmol) in $CH_2Cl_2$ (0.8 mL) and the mixture stirred at rt for 23 hours. An additional amount of TBDPS (4.9 μL, 19.1 μmol) was added and the mixture stirred at rt for a further seven hours. The reaction was concentrated under a stream of $N_2$ to give the crude product. Purification by silica gel chromatography (2% to 3% ethyl acetate/hexanes) gave mono-TBDPS ether 2 (2.6 mg, 16%) as a colorless oil; $^1$H NMR (401 MHz, $CDCl_3$) δ 7.76-7.71 (m, 2H), 7.62 (d, J=6.9 Hz, 2H), 7.47-7.27 (m, 6H), 6.18 (br s, 1H), 5.90 (br s, 1H), 5.77 (d, J=1.5 Hz, 1H), 5.58 (br s, 1H), 4.67 (m, 1H), 4.57 (s, 1H), 4.23 (m, 1H), 2.57 (m, 1H), 2.31-2.10 (m, 2H), 2.07 (t, J=7.4 Hz, 2H), 1.92-1.74 (m, 2H), 1.80 (s, 3H), 1.62 (s, 3H), 1.15-0.99 (m, 4H), 1.07 (s, 9H), 0.97-0.86 (m, 2H), 0.74 (t, J=7.3 Hz, 3H).

Intermediate 3 in the scheme above was prepared as follows. DMAP (0.7 mg, 5.8 μmol) and EDC·HCl (3.3 mg, 17.4 μmol) were added to a solution of phenol 2 (3.2 mg, 5.8 μmol) and 5-bromovaleric acid (2.1 mg, 11.6 μmol) in $CH_2Cl_2$ (0.6 mL) and the mixture stirred at rt for 19 hours. The reaction was concentrated under a stream of $N_2$ gas to give the crude product. Purification by silica gel chromatography (4% to 5% ethyl acetate/hexanes) gave bromovalerate ester 3 (3.1 mg, 76%) as a colorless oil. $^1$H NMR (401 MHz, $CDCl_3$) δ 7.76-7.56 (m, 4H), 7.46-7.30 (m, 6H), 6.28 (d, J=1.5 Hz, 1H), 6.05 (s, 1H), 5.24 (m, 1H), 4.61 (s, 2H), 4.22 (m, 1H), 3.46 (t, J=6.5 Hz, 2H), 2.76 (m, 1H), 2.60-2.14 (m, 4H), 2.13-1.94 (m, 6H), 1.93-1.71 (m, 4H), 1.67 (s, 3H), 1.62 (s, 3H), 1.32-1.24 (m, 2H), 1.07 (s, 9H), 1.12-1.01 (m, 2H), 0.97-0.83 (m, 2H), 0.73 (t, J=7.3 Hz, 3H).

Intermediate 5 in the scheme above was prepared as follows. Silver carbonate (2.7 mg, 9.7 μmol) was added to a solution of acid-TG Int-4 (10.2 mg, 14.6 μmol) and bromide 3 (8.7 mg, 12.2 μmol) in toluene (1 mL) and the mixture heated at 80° C. for one hour and at reflux for a further 1.5 hours. The reaction was cooled to rt, tetra-n-butylammonium iodide (TBAI, 4.5 mg, 12.2 μmol) was added and the mixture heated at reflux for an additional hour. The reaction was re-cooled to rt, diluted with ethyl acetate (40 mL) and the organic phase washed with water and brine (40 mL each), dried ($MgSO_4$) and concentrated under reduced pressure to give the crude product. Silica gel chromatography (5% to 12.5% ethyl acetate/hexanes) gave protected CBD prodrug I-21 (9.8 mg, 60%) as a colourless oil. $^1$H NMR (401 MHz, $CDCl_3$) δ 7.76-7.56 (m, 4H), 7.47-7.29 (m, 6H), 6.28 (d, J=1.5 Hz, 1H), 6.05 (s, 1H), 5.27 (m, 1H), 4.61 (br s, 1H), 4.300/4.296 (each dd, J=11.9, 4.3 Hz, 2H), 4.26-4.07 (m, 4H), 2.76 (m, 1H), 2.60-2.36 (m, 5H), 2.31 (t, J=7.5 Hz, 4H), 2.28-2.18 (m, 2H), 2.17-2.02 (m, 2H), 1.89-1.70 (m, 6H), 1.66 (s, 3H), 1.64-1.53 (m, 9H), 1.38-1.18 (m, 52H), 1.07 (s, 9H), 1.03 (d, J=6.5 Hz, 3H), 0.88 (t, J=6.9 Hz, 6H), 0.73 (t, J=7.3 Hz, 3H); ESI-HRMS: Calcd. for $C_{83}H_{131}O_{11}Si$ [M+H]$^+$ 1331.9455; found 1331.9417.

Example 10: Synthesis of Raloxifene, Rasagiline, Testosterone, Tetrahydrocannabinol (THC), and Other Lipid Prodrugs Additional lipid prodrugs were prepared using methods similar to those described herein.

TABLE 10

Additional Lipid Prodrugs

| Cmpd. # | Structure | $^1$H NMR; $^{13}$C NMR; MS |
|---|---|---|
| I-23 | 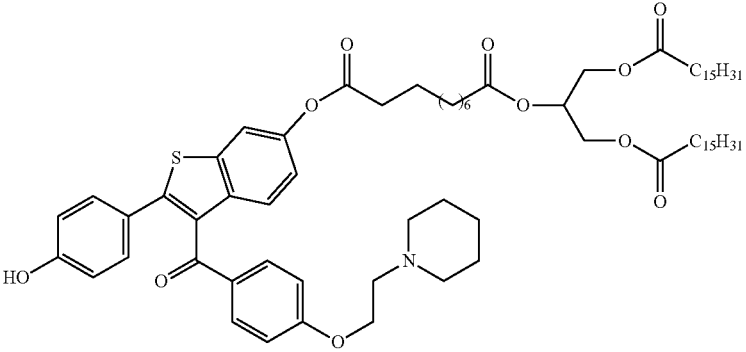 | $^1$H NMR (400 MHz, CDCl$_3$) δ 7.77 (d, J = 8.8 Hz, 1H), 7.66 (d, J = 8.9 Hz, 2H), 7.59 (d, J = 2.1 Hz, 1H), 7.19 (d, J = 8.6 Hz, 2H), 7.08 (dd, J = 8.8, 2.2 Hz, 1H), 6.67 (d, J = 7.3 Hz, 2H), 6.61 (d, J = 8.6 Hz, 2H), 5.26 (m, 1H), 4.30 (dd, J = 11.9, 4.3 Hz, 2H), 4.15 (dd, J = 11.9, 5.9 Hz, 2H), 4.09 (t, J = 5.7 Hz, 2H), 2.77 (t, J = 5.8 Hz, 2H), 2.62-2.50 (m, 6H), 2.37-2.27 (m, 6H), 1.82-1.73 (m, 2H), 1.69-1.55 (m, 10H), 1.50-1.19 (m, 58H), 0.87 (t, J = 6.8 Hz, 6H); ESI-HRMS: calcd. for C$_{73}$H$_{110}$NO$_{11}$S [M + H$^+$] 1208.7794; found 1208.7815. |
| I-24 | 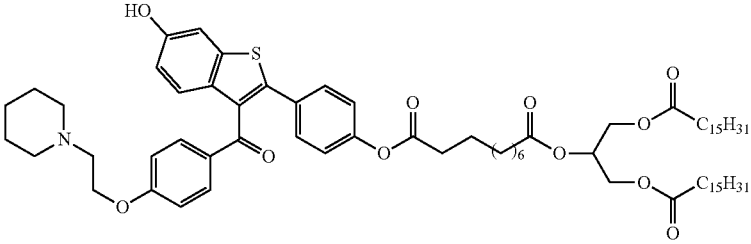 | $^1$H NMR (400 MHz, CDCl$_3$) δ 7.76-7.71 (m, 2H), 7.49 (d, J = 8.8 Hz, 1H), 7.42-7.38 (m, 2H), 7.28 (d, J = 2.1 Hz, 1H), 6.97-6.93 (m, 2H), 6.87 (dd, J = 8.8, 2.3 Hz, 1H), 6.77-6.71 (m, 2H), 5.25 (m, 1H), 4.29 (dd, J = 11.9, 4.4 Hz, 2H), 4.27-4.19 (m, 2H), 4.14 (dd, J = 11.9, 5.9 Hz, 2H), 2.97 (br s, 2H), 2.72 (br s, 4H), 2.51 (t, J = 7.5 Hz, 2H), 2.32 (t, J = 7.5 Hz, 2H), 2.31 (t, J = 7.6 Hz, 4H), 1.84-1.49 (m, 10H), 1.42-1.19 (m, 58H), 0.88 (t, J = 6.9 Hz, 6H). |
| I-25 | 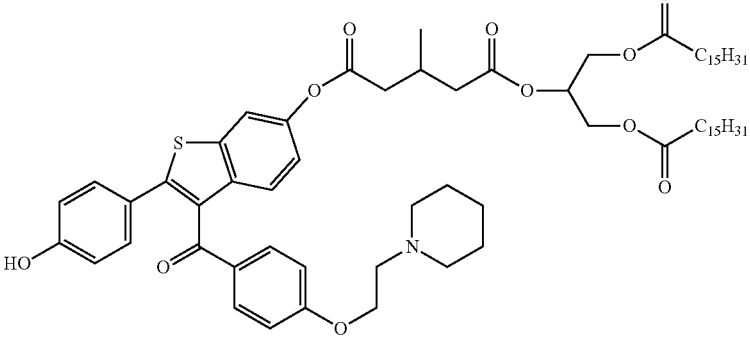 | $^1$H NMR (400 MHz, CDCl$_3$) δ 7.79 (d, J = 8.8 Hz, 1H), 7.64 (d, J = 8.9 Hz, 2H), 7.60 (d, J = 2.0 Hz, 1H), 7.16 (d, J = 8.6 Hz, 2H), 7.09 (dd, J = 8.8, 2.2 Hz, 1H), 6.65 (d, J = 8.9 Hz, 2H), 6.61 (d, J = 8.6 Hz, 2H), 5.31 (m, 1H), 4.331/4.328 (each dd, J = 11.9, 4.2 Hz, 2H), 4.16 (dd, J = 12.1, 5.7 Hz, 3H), 4.13 (t, J = 5.5 Hz, 2H), 2.83 (t, J = 5.2 Hz, 2H), 2.71 (dd, J = 14.8, 5.5 Hz, 1H), 2.67-2.48 (m, 7H), 2.39 (dd, J = 15.3, 7.2 Hz, 1H), 2.310/2.308 (each t, J = 7.8 Hz, 4H), 1.71-1.64 (m, 4H), 1.63-1.55 (m, 4H), 1.53-1.43 (m, 2H), 1.37-1.19 (m, 48H), 1.16 (d, J = 6.5 Hz, 3H), 0.87 (t, J = 6.8 Hz, 6H); $^{13}$C NMR (101 MHz, CDCl$_3$) δ 192.8 (C), 173.5 (2C; C), 171.4 (C), 171.0 (C), 162.0 (C), 157.5 (C), 148.0 (C), 139.1 (C), 137.8 (C), 132.5 (2C; CH), 131.0 (2C; CH), 130.2 (C), 125.1 (C), 124.4 (CH), 119.7 (CH), 116.1 (2C; CH), 114.7 (CH), 114.4 (2C; CH), 69.4 (CH), 65.2 (CH$_2$), 62.2 (2C; CH$_2$), 57.2 (CH$_2$), 55.0 (2C; CH$_2$), 40.8 (2C; CH$_2$), 34.2 (2C; CH$_2$), 32.1 (2C; CH$_2$), 29.84 (6C; CH$_2$), 29.80 (4C; CH$_2$), 29.76 (2C; CH$_2$), 29.6 (2C; CH$_2$), 29.5 (2C; CH$_2$), 29.4 (2C; CH$_2$), 29.3 (2C; CH$_2$), 27.6 (CH), 25.0 (2C; CH$_2$), 24.7 (CH$_2$), 23.3 (CH$_2$), 22.8 (2C; CH$_2$), 19.9 (CH$_3$), |

TABLE 10-continued

Additional Lipid Prodrugs

| Cmpd. # | Structure | $^1$H NMR; $^{13}$C NMR; MS |
|---|---|---|
| | | 14.3 (2C; CH$_3$); ESI-HRMS: calcd. for C$_{69}$H$_{102}$NO$_{11}$S [M + H$^+$] 1152.7168; found 1152.7186. |
| I-26 | 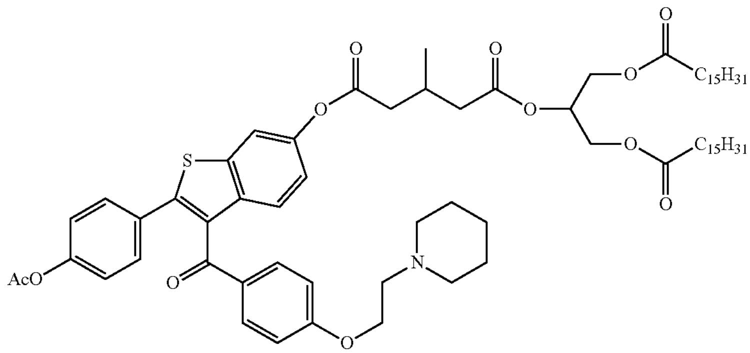 | $^1$H NMR (400 MHz, CDCl$_3$) δ 7.72 (d, J = 8.9 Hz, 2H), 7.65 (d, J = 8.8 Hz, 1H), 7.63 (d, J = 1.9 Hz, 1H), 7.46-7.40 (m, 2H), 7.08 (dd, J = 8.8, 2.2 Hz, 1H), 7.01-6.96 (m, 2H), 6.77 (d, J = 8.9 Hz, 2H), 5.30 (m, 1H), 4.331/4.327 (each dd, J = 11.9, 4.2 Hz, 2H), 4.18-4.13 (m, 4H), 2.88-2.77 (m, 2H), 2.71 (dd, J = 14.8, 5.5 Hz, 1H), 2.66-2.48 (m, 7H), 2.39 (dd, J = 15.3, 7.1 Hz, 1H), 2.309/2.307 (each t, J = 7.8 Hz, 4H), 2.26 (s, 3H), 1.70-1.54 (m, 8H), 1.51-1.41 (m, 2H), 1.34-1.19 (m, 48H), 1.16 (d, J = 6.5 Hz, 3H), 0.87 (t, J = 6.8 Hz, 6H); $^{13}$C NMR (101 MHz, CDCl$_3$) δ 192.6 (C), 173.4 (2C; C), 171.4 (C), 170.9 (C), 169.1 (C), 163.2 (C), 151.1 (C), 148.3 (C), 144.4 (C), 139.5 (C), 137.7 (C), 132.5 (2C; CH), 131.8 (C), 130.9 (C), 130.4 (C), 130.3 (2C; CH), 124.4 (CH), 122.0 (2C; CH), 119.8 (CH), 114.8 (CH), 114.5 (2C; CH), 69.5 (CH), 66.0 (CH$_2$), 62.2 (2C; CH$_2$), 57.6 (CH$_2$), 55.1 (2C; CH$_2$), 40.7 (2C; CH$_2$), 34.2 (2C; CH$_2$), 32.1 (2C; CH$_2$), 29.84 (6C; CH$_2$), 29.80 (4C; CH$_2$), 29.76 (2C; CH$_2$), 29.6 (2C; CH$_2$), 29.5 (2C; CH$_2$), 29.4 (2C; CH$_2$), 29.3 (2C; CH$_2$), 27.6 (CH), 25.6 (2C; CH$_2$), 25.0 (2C; CH$_2$), 24.0 (CH$_2$), 22.8 (2C; CH$_2$), 21.3 (CH$_3$), 19.9 (CH$_3$), 14.3 (2C; CH$_3$); ESI-HRMS: calcd. for C$_{71}$H$_{104}$NO$_{12}$S [M + H$^+$] 1194.7274; found 1194.7285. |
| I-27 | 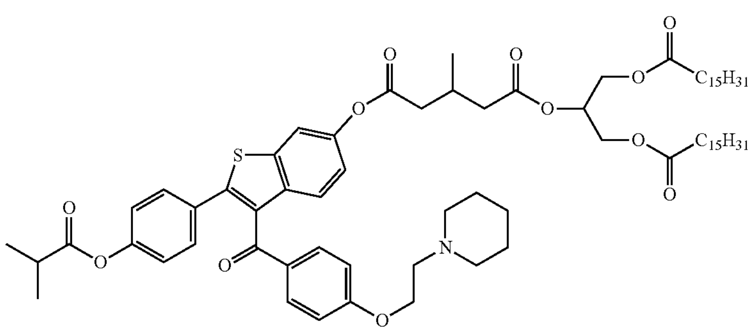 | $^1$H NMR (401 MHz, CDCl$_3$) δ 7.77-7.71 (m, 2H), 7.68-7.61 (m, 2H), 7.46-7.41 (m, 2H), 7.08 (dd, J = 8.8, 2.2 Hz, 1H), 7.00-6.94 (m, 2H), 6.81-6.74 (m, 2H), 5.30 (m, 1H), 4.332/4.329 (each dd, J = 11.9, 4.2 Hz, 2H), 4.24-4.11 (m, 4H), 2.89-2.68 (m, 5H), 2.66-2.48 (m, 6H), 2.39 (dd, J = 15.3, 7.1 Hz, 1H), 2.311/2.307 (each t, J = 7.7 Hz, 4H), 1.73-1.41 (m, 10H), 1.36-1.20 (m, 48H), 1.28 (d, J = 7.0 Hz, 6H), 1.16 (d, J = 6.5 Hz, 3H), 0.87 (t, J = 6.9 Hz, 6H); $^{13}$C NMR (101 MHz, CDCl$_3$) δ 192.7 (C), 175.3 (C), 173.4 (2C; C), 171.4 (C), 170.9 (C), 151.4 (C), 148.3 (C), 139.5 (C), 137.7 (C), 132.5 (2C; CH), 131.7 (C), 130.7 (C), 130.3 (2C; CH), 124.4 (CH), 122.0 (2C; CH), 119.8 (CH), 114.8 (CH), 114.5 (2C; CH), 69.5 (CH), 62.2 (2C; CH$_2$), 40.8 (2C; CH$_2$), 34.3 (CH), 34.2 (2C; CH$_2$), 32.1 (2C; CH$_2$), 29.85 (6C; CH$_2$), 29.81 (4C; CH$_2$), 29.77 (2C; CH$_2$), 29.6 (2C; CH$_2$), 29.5 (2C; CH$_2$), 29.4 (2C; CH$_2$), 29.3 (2C; CH$_2$), 27.6 (CH), 25.0 (2C; CH$_2$), 22.8 (2C; CH$_2$), 19.9 (CH$_3$), 19.0 (2C; CH$_3$), 14.3 (2C; CH$_3$). Note: Some signals were not observed in the $^{13}$C NMR spectrum. |

TABLE 10-continued

Additional Lipid Prodrugs

| Cmpd. # | Structure | $^1$H NMR; $^{13}$C NMR; MS |
|---|---|---|
| I-28 | 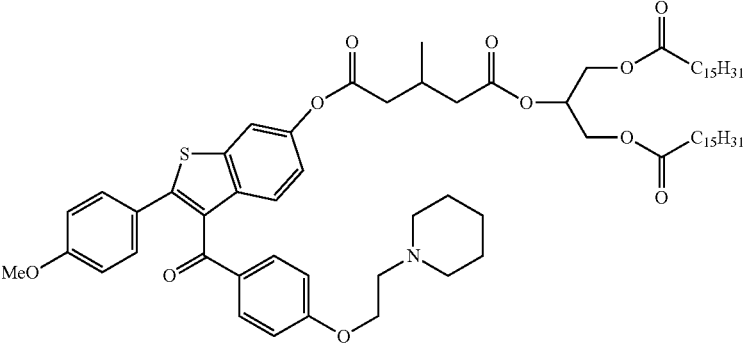 | $^1$H NMR (401 MHz, CDCl$_3$) δ 7.77-7.71 (m, 2H), 7.63 (d, J = 8.9 Hz, 1H), 7.60 (d, J = 1.9 Hz, 1H), 7.38-7.33 (m, 2H), 7.06 (dd, J = 8.8, 2.2 Hz, 1H), 6.79-6.74 (m, 4H), 5.30 (m, 1H), 4.330/4.227 (each dd, J = 11.9, 4.2 Hz, 2H), 4.19-4.10 (m, 4H), 3.76 (s, 3H), 2.84-2.76 (m, 2H), 2.71 (dd, J = 14.8, 5.5 Hz, 1H), 2.66-2.48 (m, 6H), 2.38 (dd, J = 15.3, 7.1 Hz, 1H), 2.310/2.306 (each t, J = 7.6 Hz, 4H), 1.76-1.54 (m, 9H), 1.51-1.42 (m, 2H), 1.35-1.18 (m, 48H), 1.16 (d, J = 6.5 Hz, 3H), 0.87 (t, J = 6.9 Hz, 6H); $^{13}$C NMR (101 MHz, CDCl$_3$) δ 193.0 (C), 173.5 (2C; C), 171.4 (C), 171.0 (C), 160.2 (C), 148.0 (C), 145.6 (C), 139.2 (C), 137.9 (C), 132.5 (2C; C), 130.54 (2C; C), 130.48 (C), 125.8 (C), 124.1 (CH), 119.6 (CH), 114.8 (CH), 114.4 (2C; CH), 114.3 (2C; CH), 69.4 (CH), 66.0* (CH$_2$), 62.2 (2C; CH$_2$), 57.7 (CH$_2$), 55.4 (CH$_3$), 55.1 (CH$_2$), 40.7 (2C; CH$_2$), 34.2 (2C; CH$_2$), 32.1 (2C; CH$_2$), 29.85 (6C; CH$_2$), 29.81 (4C; CH$_2$), 29.77 (2C; CH$_2$), 29.6 (2C; CH$_2$), 29.5 (2C; CH$_2$), 29.4 (2C; CH$_2$), 29.3 (2C; CH$_2$), 27.6 (CH), 25.7* (2C; CH$_2$), 25.0 (2C; CH$_2$), 24.0* (CH$_2$), 22.8 (2C; CH$_2$), 19.9 (CH$_3$), 14.3 (2C; CH$_3$). Note: Two signals were missing from the $^{13}$C NMR spectrum, possibly the quaternary signals of the thiophene ring, while the signals marked with an asterisk (*) were very weak/broad and their presence was supported by cross-peaks in the HSQC spectrum. |
| I-29 | 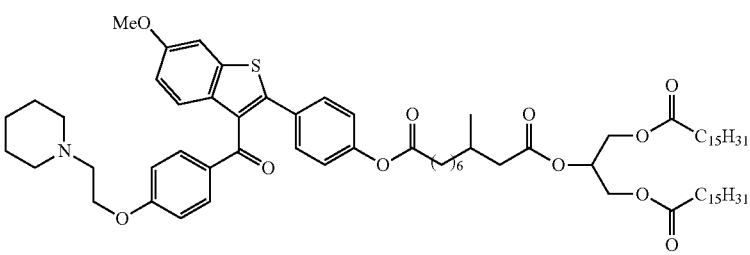 | $^1$H NMR (401 MHz, CDCl$_3$) δ 7.75 (d, J = 8.9 Hz, 2H), 7.51 (d, J = 8.9 Hz, 1H), 7.43 (d, J = 8.7 Hz, 2H), 7.33 (d, J = 2.3 Hz, 1H), 7.00-6.93 (m, 3H), 6.77 (d, J = 9.0 Hz, 2H), 5.27 (m, 1H), 4.29 (dd, J = 11.9, 4.2 Hz, 2H), 4.18-4.09 (m, 4H), 3.89 (s, 3H), 2.84-2.75 (m, 2H), 2.62-2.47 (m, 6H), 2.33 (dd, J = 14.7, 5.8 Hz, 1H), 2.30 (t, J = 7.5 Hz, 4H), 2.12 (dd, J = 14.7, 8.3 Hz, 1H), 1.94 (m, 1H), 1.75-1.56 (m, 9H), 1.50-1.16 (m, 59H), 0.93 (d, J = 6.6 Hz, 3H), 0.87 (t, J = 6.9 Hz, 6H); $^{13}$C NMR (101 MHz, CDCl$_3$) δ 193.1 (C), 173.4 (2C; C), 172.4 (C), 172.0 (C), 158.0 (C), 150.9 (C), 140.5 (C), 134.0 (C), 132.5 (2C; CH), 131.8 (C), 131.2 (C), 130.5 (C), 130.2 (2C; CH), 124.4 (CH), 121.9 (2C; CH), 115.2 (CH), 114.4 (2C; CH), 104.6 (CH), 69.0 (CH), 65.9* (CH$_2$), 62.3 (2C; CH$_2$), 57.6 (CH$_2$), 55.8 (CH$_2$), 55.1 (2C; CH$_2$), 41.8 (CH$_2$), 36.8 (CH$_2$), 34.5 (CH$_2$), 34.2 (2C; CH$_2$), 32.1 (2C; CH$_2$), 30.5 (CH), 29.85 (6C; CH$_2$), 29.81 (4C; CH$_2$), 29.77 (2C; CH$_2$), 29.62 (2C; CH$_2$), 29.55 (CH$_2$), 29.51 (2C; CH$_2$), 29.42 (2C; CH$_2$), 29.27 (2C; CH$_2$), 29.23 (CH$_2$), 26.9 (CH$_2$), 25.6* (2C; CH$_2$), 25.00 (2C; CH$_2$), |

TABLE 10-continued

Additional Lipid Prodrugs

| Cmpd. # | Structure | $^1$H NMR; $^{13}$C NMR; MS |
|---|---|---|
| | | 24.97 (CH$_2$), 23.9* (CH$_2$), 22.8 (2C; CH$_2$), 19.7 (CH$_3$), 14.3 (2C; CH$_3$). Note: One signals was missing from the $^{13}$C NMR spectrum, possibly one of the quaternary signals from the thiophene ring, while the signals marked with an asterisk (*) were very weak/broad and their presence was supported by cross-peaks in the HSQC spectrum. |
| I-30 | 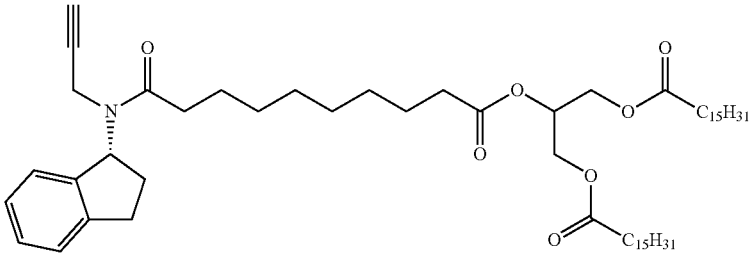 | $^1$H NMR (400 MHz, CDCl$_3$) δ 7.14 (m, 4H), 6.31 (m, 1H), 5.6 (m, 2H), 5.4 (m, 2H) 4.30 (m. 4H), 4.2 (m, 4H), 3.91 (m, 1H), 3.70 (m, 1H), 3.4 (m, 1H), 3.08 (m, 2H), 2.56 (m, 4H), 2.36 (m, 10H), 1.74 (m, 3H), 1.64 (m, 6H), 1.37 (m, 44H), 0.93 (t, 6H); $^{13}$C NMR (101 MHz, CDCl$_3$) δ 173.9 (1C, C=O), 173.3 (2C, C=O), 172.9 (1C, C=O), 144.2-143.3 (2C), 141.03-140.229 (2C), 128.45-128.0 (2C), 126.99-126.72 (2C), 125.33-125.05 (2C), 124.34-123.92 (2C), 81.13-80.60 (2C), 71.78 (1C), 69.85 (1C), 68.88 (2C), 63.29 (1C), 62.10 (2C), 59.36 (1C), 34.04-33.86 (4C), 33.20 (2C), 31.96-31.63 (2C), 30.64-30.08 (2C), 29.73-29.04 (13), 25.40-25.18 (2C), 24.8 (2C), 22.74 (2C), 14.18 (2C). HPLC (ELSD): 14.67 min, 100% purity; HPLC (Chiral): 6.71 min, 100% purity; MS (ESI, +ve) m/z: 907.5 (MH$^+$ + 1). |
| I-31 | 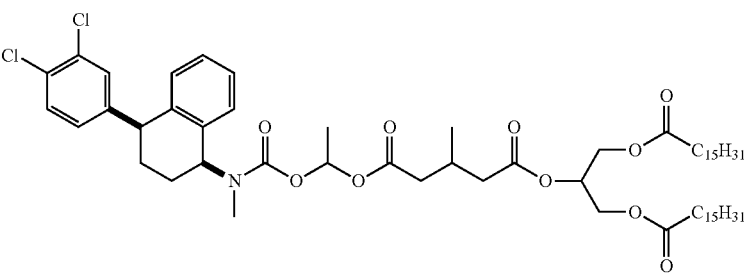 | $^1$H NMR (400 MHz, CDCl$_3$) δ 7.33 (d, J = 8.3 Hz, 1H), 7.31-7.16 (m, 3H), 7.11-7.07 (m, 1H), 6.99-6.88 (m, 2H), 6.85-6.77 (m, 1H), 5.54-5.46 (m, 0.6H), 5.33-5.22 (m, 1.4H), 4.43-4.24 (m, 2H), 4.18 (br s, 1H), 4.15-4.09 (m, 2H), 2.72-2.66 (m, 3H), 2.55-2.36 (m, 3H), 2.34-2.20 (m, 7H), 2.06-1.97 (m, 1H), 1.84-1.70 (m, 2H), 1.64-1.49 (m, 7H), 1.37-1.16 (m, 48H), 1.07/1.02 (each d, J = 6.4 Hz, 3H), 0.87 (t, J = 6.9 Hz, 6H); Note: Fractional integrations, doubled signals and the lack of well-defined signals were observed due to the presence of diastereomers and/or rotational isomers. $^{13}$C NMR (101 MHz, CDCl$_3$) δ 173.4 (C), 69.2 (CH), 62.2 (2C; CH$_2$), 34.1 (2C; CH$_2$), 32.1 (2C; CH$_2$), 29.84 (6C; CH$_2$), 29.80 (4C; CH$_2$), 29.76 (2C; CH$_2$), 29.6 (2C; CH$_2$), 29.5 (2C; CH$_2$), 29.4 (2C; CH$_2$), 29.3 (2C; CH$_2$), 25.0 (2C; CH$_2$), 22.8 (2C; CH$_2$), 14.3 (2C; CH$_2$). Note: Only the signals for the glyceride portion are listed—multiple signals are observed in almost all other cases. |

TABLE 10-continued

Additional Lipid Prodrugs

| Cmpd. # | Structure | $^1$H NMR; $^{13}$C NMR; MS |
|---|---|---|
| I-32 | 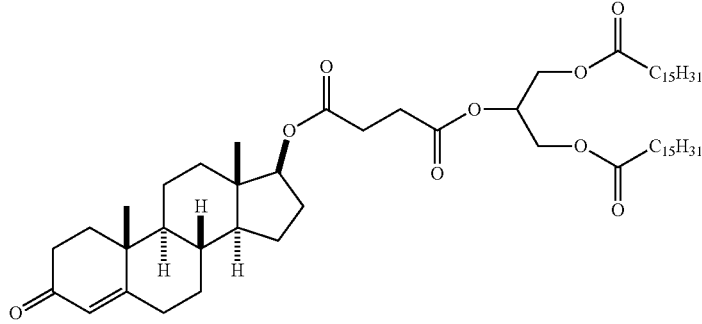 | $^1$H NMR (400 MHz, CDCl$_3$): δ 5.72 (s, 1H), 5.26 (m, 1H), 4.61 (dd, J = 9.0, 7.9 Hz, 1H), 4.291/4.288 (each dd, J = 11.9, 4.3, 1.3 Hz, 2H), 4.15 (dd, J = 12.1, 6.0 Hz, 2H), 2.68-2.58 (m, 4H), 2.47-2.24 (m, 4H), 2.31 (t, J = 7.6 Hz, 4H), 2.17 (m, 1H), 2.02 (m, 1H), 1.84 (m, 1H), 1.78 (m, 1H), 1.73-1.44 (m, 9H), 1.42-1.13 (m, 51H), 1.18 (s, 3H), 1.12-0.91 (m, 3H), 0.87 (t, J = 6.9 Hz, 6H), 0.83 (s, 3H); $^{13}$C NMR (100 MHz, CDCl$_3$): δ 199.6 (C), 173.5 (2C; C), 172.1 (C), 171.6 (C), 171.1 (C), 124.1 (CH), 83.0 (CH), 69.6 (CH), 62.0 (2C; CH$_2$), 53.8 (CH), 50.3 (CH), 42.7 (C), 38.7 (C), 36.7 (CH$_2$), 35.8 (CH$_2$), 35.5 (CH), 34.14 (2C; CH$_2$), 34.05 (CH$_2$), 32.9 (CH$_2$), 32.1 (2C; CH$_2$), 31.6 (CH$_2$), 29.84 (6C; CH$_2$), 29.80 (4C; CH$_2$), 29.77 (2C; CH$_2$), 29.6 (2C; CH$_2$), 29.5 (2C; CH$_2$), 29.42 (2C; CH$_2$), 29.26 (2C; CH$_2$), 29.25 (CH$_2$), 29.22 (CH$_2$), 27.6 (CH$_2$), 25.0 (2C; CH$_2$), 23.6 (CH$_2$), 22.8 (2C; CH$_2$), 20.6 (CH$_2$), 17.5 (CH$_3$), 14.3 (2C; CH$_3$), 12.2 (CH$_3$); ESI-HRMS: calcd. for C$_{59}$H$_{101}$O$_9$ [M + H$^+$] 953.7440; found 953.7452. |
| I-33 | 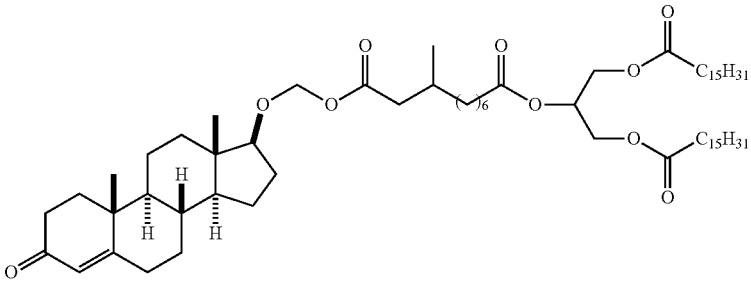 | $^1$H NMR (401 MHz, CDCl$_3$) δ 5.73 (s, 1H), 5.25 (m, 1H), 4.61 (dd, J = 8.1, 8.1 Hz, 1H), 4.29 (dd, J = 11.9, 4.4 Hz, 2H), 4.14 (dd, J = 11.9, 5.9 Hz, 2H), 2.47-2.14 (m, 12H), 2.09 (dd, J = 14.5, 8.2 Hz, 1H), 2.02 (ddd, J = 13.1, 4.7, 3.2 Hz, 1H), 1.92 (m, 1H), 1.85 (m, 1H), 1.78 (m, 1H), 1.74-1.46 (m, 11H), 1.44-1.21 (m, 58H), 1.19 (s, 3H), 1.18-0.96 (m, 4H), 0.93 (d, J = 6.6 Hz, 3H), 0.88 (t, J = 6.9 Hz, 6H), 0.83 (s, 3H); $^{13}$C NMR (101 MHz, CDCl$_3$) δ 199.5 (C), 173.42 (2C; C), 173.39/173.37 (C), 172.9 (C), 171.0 (C), 124.1 (CH), 82.3 (CH), 69.1 (CH), 62.2 (2C; CH$_2$), 53.9 (CH), 50.4 (CH), 42.6 (C), 42.23/42.22 (CH$_2$), 38.8 (C), 36.84 (CH$_2$), 36.81 (CH$_2$), 35.9 (CH$_2$), 35.6 (CH), 34.3 (CH$_2$), 34.2 (2C; CH$_2$), 34.1 (CH$_2$), 32.9 (CH$_2$), 32.1 (2C; CH$_2$), 31.6 (CH$_2$), 30.59/30.55 (CH), 29.84 (6C; CH$_2$), 29.80 (4C; CH$_2$), 29.77 (2C; CH$_2$), 29.62 (2C; CH$_2$), 29.59 (CH$_2$), 29.5 (2C; CH$_2$), 29.4 (2C; CH$_2$), 29.3 (2C; CH$_2$), 29.2 (CH$_2$), 27.68/27.65 (CH$_2$), 26.9 (CH$_2$), 25.01 (2C; CH$_2$), 24.99 (CH$_2$), 23.7 (CH$_2$), 22.8 (2C; CH$_2$), 20.7 (CH$_2$), 19.85/19.83 (CH$_3$), 17.6 (CH$_3$), 14.3 (2C; CH$_3$), 12.2 (CH$_3$). |

TABLE 10-continued

Additional Lipid Prodrugs

| Cmpd. # | Structure | $^1$H NMR; $^{13}$C NMR; MS |
|---|---|---|
| I-34 | 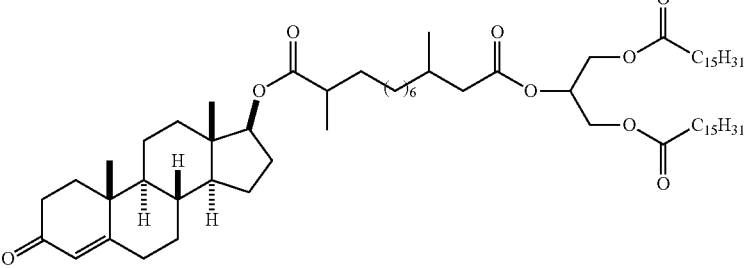 | $^1$H NMR (401 MHz, CDCl$_3$) δ 5.73 (s, 1H), 5.27 (m, 1H), 4.61 (m, 1H), 4.289/4.287 (each dd, J = 11.7, 4.2 Hz, 2H), 4.14 (d, J = 11.9, 6/0 Hz, 2H), 2.47-2.24 (m, 10H), 2.23-2.08 (m, 2H), 2.02 (m, 1H), 1.93 (m, 1H), 1.86 (m, 1H), 1.80-1.76 (m, 1H), 1.72-1.46 (m, 10H), 1.44-1.22 (m, 64H), 1.19 (s, 3H), 1.139/1.132 (each d, J = 7.0 Hz, 3H), 1.11-0.95 (m, 3H), 0.93 (d, J = 6.6 Hz, 3H), 0.88 (d, J = 6.9 Hz, 6H), 0.84 (s, 3H); $^{13}$C NMR (101 MHz, CDCl$_3$) δ 199.6 (C), 176.9 (C), 173.4 (2C; C), 172.5 (C), 171.0 (C), 124.1 (CH), 82.1 (CH), 69.0 (CH), 62.3 (2C; CH$_2$), 53.9 (CH), 50.5 (CH), 42.7 (C), 41.9 (CH$_2$), 39.93/39.88 (CH), 38.8 (C), 36.9 (CH$_2$), 36.8 (CH$_2$), 35.9 (CH$_2$), 35.6 (CH), 34.2 (2C; CH$_2$), 34.1 (CH$_2$), 34.00/33.96 (CH$_2$), 32.9 (CH$_2$), 32.1 (2C; CH$_2$), 31.7 (CH$_2$), 30.5 (CH), 29.92 (CH$_2$), 29.85 (2C; CH$_2$), 29.81 (2C; CH$_2$), 29.78 (2C; CH$_2$), 29.70 (CH$_2$), 29.69 (CH$_2$), 29.6 (2C; CH$_2$), 29.5 (2C; CH$_2$), 29.4 (2C; CH$_2$), 29.3 (2C; CH$_2$), 27.68/27.66 (CH$_2$), 27.4 (CH$_2$), 27.1 (CH$_2$), 25.1 (2C; CH$_2$), 23.7 (CH$_2$), 22.8 (2C; CH$_2$), 20.7 (CH$_2$), 19.7 (CH$_3$), 17.6 (CH$_3$), 17.42/17.26 (CH$_3$), 14.3 (2C; CH$_3$), 12.23/12.21 (CH$_3$). |
| I-35 | 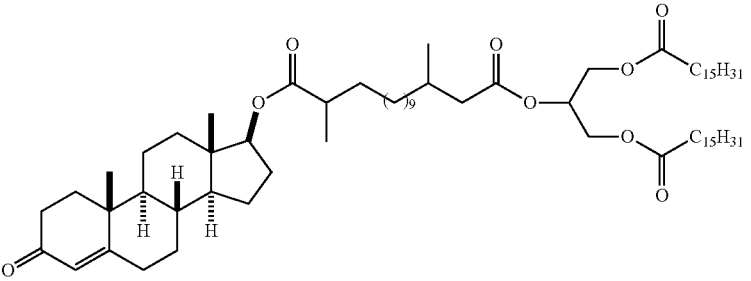 | $^1$H NMR (401 MHz, CDCl$_3$) δ 5.73 (s, 1H), 5.27 (m, 1H), 4.61/4.60 (each dd, J = 9.1, 7.8 Hz, 1H), 4.28 (dd, J = 11.9, 3.8 Hz, 2H), 4.14 (dd, J = 11.9, 5.9 Hz, 2H), 2.47-2.24 (m, 10H), 2.18 (m, 1H), 2.11 (dd, J = 14.7, 8.3 Hz, 1H), 2.02 (m, 1H), 1.93 (m, 1H), 1.85 (m, 1H), 1.77 (m, 1H), 1.73-1.54 (m, 9H), 1.52-1.21 (m, 71H), 1.19 (s, 3H), 1.133/1.126 (each d, J = 7.0 Hz, 3H), 1.11-0.94 (m, 3H), 0.92 (d, J = 6.6 Hz, 3H), 0.87 (t, J = 6.9 Hz, 6H), 0.84 (s, 3H); $^{13}$C NMR (101 MHz, CDCl$_3$) δ 199.6 (C), 177.0 (C), 173.4 (2C; C), 172.5 (C), 171.1 (C), 124.1 (CH), 82.10/82.08 (CH), 69.0 (CH), 62.3 (2C; CH$_2$), 53.9 (CH), 50.4 (CH), 42.7 (C), 41.8 (CH$_2$), 39.90/39.87 (CH), 38.7 (C), 36.84 (CH$_2$), 36.79 (CH$_2$), 35.8 (CH$_2$), 35.6 (CH), 34.2 (2C; CH$_2$), 34.1 (CH$_2$), 34.01/33.97 (CH$_2$), 32.9 (CH$_2$), 32.1 (2C; CH$_2$), 31.6 (CH$_2$), 30.5 (CH), 30.0 (CH$_2$), 29.83 (6C; CH$_2$), 29.80 (4C; CH$_2$), 29.76 (3C; CH$_2$), 29.68 (2C; CH$_2$), 29.6 (2C; CH$_2$), 29.5 (3C; CH$_2$), 29.4 (2C; CH$_2$), 29.3 (3C; CH$_2$), 27.7 (CH$_2$), 27.6 (CH$_2$), 27.4 (CH$_2$), 27.1 (CH$_2$), 25.0 (2C; CH$_2$), 23.6 (CH$_2$), 22.8 (2C; CH$_2$), 20.7 (CH$_2$), 19.7 (CH$_3$), 17.5 (CH$_3$), 17.4/17.3 (CH$_3$), 14.3 (2C; CH$_3$), 12.20/12.18 (CH$_3$). |

TABLE 10-continued

Additional Lipid Prodrugs

| Cmpd. # | Structure | $^1$H NMR; $^{13}$C NMR; MS |
|---|---|---|
| I-36 | 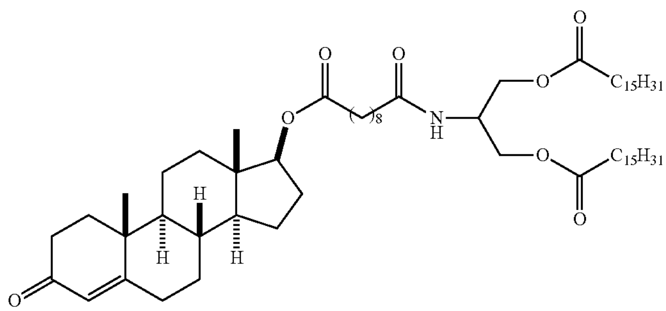 | $^1$H NMR (401 MHz, CDCl$_3$) δ 5.74 (d, J = 8.6 Hz, 1H), 5.73 (s, 1H), 4.60 (dd, J = 8.9, 8.1 Hz, 1H), 4.46 (m, 1H), 4.22 (dd, J = 11.4, 5.4 Hz, 2H), 4.07 (dd, J = 11.4, 5.3 Hz, 2H), 2.47-2.23 (m, 10H), 2.22-2.12 (m, 3H), 2.02 (m, 1H), 1.85 (m, 1H), 1.77 (m, 1H), 1.73-1.45 (m, 13H), 1.43-1.21 (m, 58H), 1.19 (s, 3H), 1.16-0.90 (m, 4H), 0.88 (t, J = 6.8 Hz, 6H), 0.83 (s, 3H); $^{13}$C NMR (101 MHz, CDCl$_3$) δ 199.6 (C), 174.0 (C), 173.9 (2C; C), 173.0 (C), 171.1 (C), 124.1 (CH), 82.3 (CH), 62.8 (2C; CH$_2$), 53.9 (CH), 50.4 (CH), 47.6 (CH), 42.7 (C), 38.8 (C), 36.84 (CH$_2$), 36.80 (CH$_2$), 35.9 (CH$_2$), 35.6 (CH), 34.7 (CH$_2$), 34.2 (2C; CH$_2$), 34.1 (CH$_2$), 32.9 (CH$_2$), 32.1 (2C; CH$_2$), 31.6 (CH$_2$), 29.85 (2C; CH$_2$), 29.81 (2C; CH$_2$), 29.77 (2C; CH$_2$), 29.6 (2C; CH$_2$), 29.5 (2C; CH$_2$), 29.4 (2C; CH$_2$), 29.32 (2C; CH$_2$), 29.30 (2C; CH$_2$), 29.24 (2C; CH$_2$), 27.7 (CH$_2$), 25.7 (CH$_2$), 25.2 (CH$_2$), 25.0 (2C; CH$_2$), 23.6 (CH$_2$), 22.8 (2C; CH$_2$), 20.7 (CH$_2$), 17.5 (CH$_2$), 14.3 (2C; CH$_2$), 12.2 (CH$_2$). |
| I-37 | 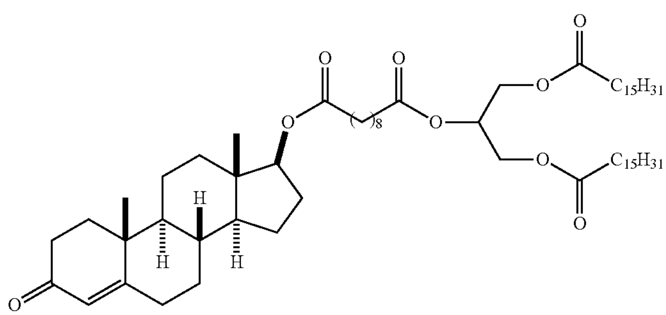 | $^1$H NMR (401 MHz, CDCl$_3$) δ 5.73 (s, 1H), 4.61 (dd, J = 9.0, 7.9 Hz, 1H), 4.18 (dd, J = 11.6, 4.9 Hz, 2H), 4.12 (dd, J = 11.4, 5.4 Hz, 2H), 3.67 (m, 1H), 3.54 (t, J = 6.6 Hz, 2H), 2.48-2.25 (m, 9H), 2.18 (m, 1H), 2.01 (m, 1H), 1.83 (m, 1H), 1.77 (m, 1H), 1.73-1.49 (m, 16H), 1.48-1.22 (m, 58H), 1.19 (s, 3H), 1.17-0.92 (m, 4H), 0.88 (t, J = 6.9 Hz, 6H), 0.84 (s, 3H); $^{13}$C NMR (101 Hz, CDCl$_3$) δ 199.6 (C), 174.0 (C), 173.7 (2C; C), 171.1 (C), 124.1 (CH), 82.3 (CH), 75.3 (CH), 70.8 (CH$_2$), 63.2 (2C; CH$_2$), 53.9 (CH), 50.4 (CH), 42.7 (C), 38.8 (C), 36.8 (CH$_2$), 35.9 (CH$_2$), 35.6 (CH), 34.7 (CH$_2$), 34.3 (2C; CH$_2$), 34.1 (CH$_2$), 32.9 (CH2), 32.1 (2C; CH$_2$), 31.6 (CH$_2$), 30.1 (CH$_2$), 29.84 (6C; CH$_2$), 29.80 (4C; CH$_2$), 29.77 (2C; CH$_2$), 29.62 (2C; CH$_2$), 29.59 (CH$_2$), 29.56 (CH$_2$), 29.50 (2C; CH$_2$), 29.43 (2C; CH$_2$), 29.40 (CH$_2$), 29.29 (3C; CH2), 27.7 (CH$_2$), 26.1 (CH$_2$), 25.2 (CH$_2$), 25.1 (2C; CH$_2$), 23.6 (CH$_2$), 22.8 (2C; CH$_2$), 20.7 (CH$_2$), 17.5 (CH$_3$), 14.3 (2C; CH$_3$), 12.2 (CH$_3$). |
| I-38 | 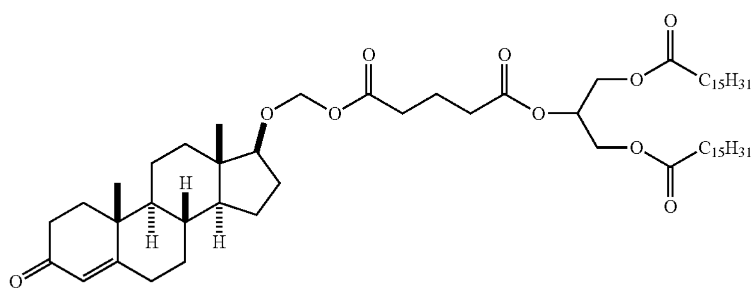 | $^1$H NMR (400 MHz, CDCl$_3$) δ 5.73 (s, 1H), 5.33-5.22 (m, 3H), 4.30 (dd, J = 11.9, 4.4 Hz, 2H), 4.13 (dd, J = 11.9, 5.9 Hz, 2H), 3.54 (dd, J = 8.3, 8.3 Hz, 1H), 2.48-2.23 (m, 12H), 2.08-1.79 (m, 6H), 1.75-1.50 (m, 9H), 1.49-1.21 (m, 49H), 1.19 (s, 3H), 1.17-0.83 (m, 5H), 0.88 (t, J = 6.9 Hz, 6H), 0.80 (s, 3H); $^{13}$C NMR (101 MHz, CDCl$_3$) δ 199.6 (C), 173.4 (2C; C), 172.4 (C), 172.1 (C), 171.2 (C), 124.1 (CH), 89.6 (CH), 89.3 (CH$_2$), 69.4 (CH), 62.1 (2C; CH$_2$), 54.0 (CH), 50.4 (CH), 42.8 (C), 38.8 (C), 36.9 (CH$_2$), |

TABLE 10-continued

Additional Lipid Prodrugs

| Cmpd. # | Structure | $^1$H NMR; $^{13}$C NMR; MS |
|---|---|---|
| | | 35.9 (CH$_2$), 35.5 (CH), 34.2 (2C; CH$_2$), 34.1 (CH$_2$), 33.4 (CH$_2$), 33.2 (CH$_2$), 32.9 (CH$_2$), 32.1 (2C; CH$_2$), 31.6 (CH$_2$), 29.85 (6C; CH$_2$), 29.81 (4C; CH$_2$), 29.77 (2C; CH$_2$), 29.6 (2C; CH$_2$), 29.5 (2C; CH$_2$), 29.4 (2C; CH$_2$), 29.3 (2C; CH$_2$), 28.3 (CH$_2$), 25.0 (2C; CH$_2$), 23.5 (CH$_2$), 22.8 (2C; CH$_2$), 20.7 (CH$_2$), 19.9 (CH$_2$), 17.5 (CH$_3$), 14.3 (2C; CH$_3$), 11.8 (CH$_3$). |
| I-39 | 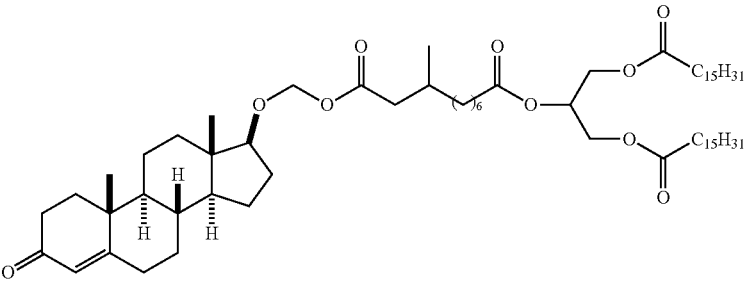 | $^1$H NMR (400 MHz, CDCl$_3$) δ 5.73 (s, 1H), 5.32-5.21 (m, 3H), 4.29 (dd, J = 11.9, 4.4 Hz, 2H), 4.14 (dd, J = 11.9, 5.9 Hz, 2H), 3.55 (dd, J = 8.3, 8.3 Hz, 1H), 2.48-2.23 (m, 11H), 2.11 (dd, J = 14.9, 8.2 Hz, 1H), 2.07-1.99 (m, 2H), 1.98-1.80 (m, 3H), 1.74-1.51 (m, 11H), 1.49-1.21 (m, 57H), 1.19 (s, 3H), 1.17-0.95 (m, 5H), 0.94 (d, J = 6.6 Hz, 3H), 0.88 (t, J = 6.8 Hz, 6H), 0.80 (s, 3H); $^{13}$C NMR (101 MHz, CDCl$_3$) δ 199.6 (C), 173.4 (2C; C), 172.94 (C), 172.90 (C), 171.2 (C), 124.1 (CH), 89.3 (CH), 89.0 (CH$_2$), 69.1 (CH), 62.2 (2C; CH$_2$), 54.0 (CH), 50.5 (CH), 42.8 (C), 42.17/42.16 (CH$_2$), 38.8 (C), 37.0 (CH$_2$), 36.8 (CH$_2$), 35.9 (CH$_2$), 35.6 (CH), 34.3 (CH$_2$), 34.2 (2C; CH$_2$), 34.1 (CH$_2$), 32.9 (CH$_2$), 32.1 (2C; CH$_2$), 31.7 (CH$_2$), 30.29/30.28 (CH), 29.85 (6C; CH$_2$), 29.81 (4C; CH$_2$), 29.77 (2C; CH$_2$), 29.63 (2C; CH$_2$), 29.57 (CH$_2$), 29.5 (2C; CH$_2$), 29.4 (2C; CH$_2$), 29.3 (2C; CH$_2$), 29.2 (CH$_2$), 28.2 (CH$_2$), 26.9 (CH$_2$), 25.01 (2C; CH$_2$), 24.98 (CH$_2$), 23.5 (CH$_2$), 22.8 (2C; CH$_2$), 20.7 (CH$_2$), 19.8 (CH$_3$), 17.5 (CH$_3$), 14.3 (2C; CH$_3$), 11.8 (CH$_3$). |
| I-40 | 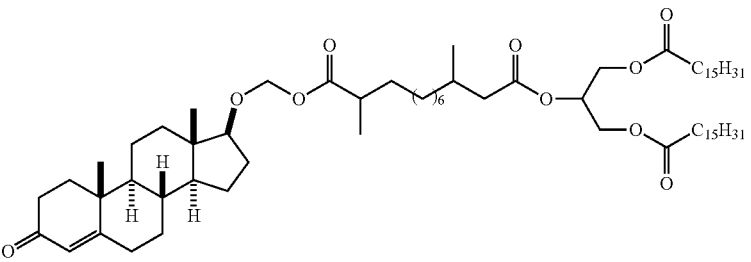 | $^1$H NMR (401 MHz, CDCl$_3$) δ 5.72 (s, 1H), 5.32-5.23 (m, 3H), 4.28 (dd, J = 11.9, 4.0 Hz, 2H), 4.14 (dd, J = 11.9, 6.0 Hz, 2H), 3.55 (dd, J = 8.3, 8.3 Hz, 1H), 2.47-2.23 (m, 10H), 2.11 (dd, J = 14.7, 8.3 Hz, 1H), 2.07-1.98 (m, 2H), 1.95-1.87 (m, 2H), 1.83 (m, 1H), 1.71 (m, 1H), 1.66-1.51 (m, 9H), 1.49-1.35 (m, 2H), 1.49-1.35 (m, 60H), 1.19-0.85 (m, 5H), 1.18 (s, 3H), 1.15 (d, J = 7.0 Hz, 3H), 0.92 (d, J = 6.6 Hz, 3H), 0.87 (t, J = 6.9 Hz, 6H), 0.80 (s, 3H); $^{13}$C NMR (101 MHz, CDCl$_3$) δ 199.6 (C), 176.5 (C), 173.4 (2C; C), 172.4 (C), 171.2 (C), 124.1 (CH), 89.27/89.23 (CH), 89.00/88.97 (CH$_2$), 69.0 (CH), 62.3 (2C; CH$_2$), 54.1 (CH), 50.5 (CH), 42.8 (C), 41.8 (CH$_2$), 39.9 (CH), 38.8 (C), 37.0 (CH$_2$), 36.8 (CH$_2$), 35.9 (CH$_2$), 35.6 (CH), 34.2 (2C; CH$_2$), 34.1 (CH$_2$), 33.7 (CH$_2$), 32.9 (CH$_2$), 32.1 (2C; CH$_2$), 31.7 (CH$_2$), 30.5 (CH), 29.9 (CH$_2$), 29.84 (6C; CH$_2$), 29.80 (4C; CH$_2$), 29.76 (2C; CH$_2$), 29.69 (CH$_2$), 29.68 (CH$_2$), 29.6 (2C; CH$_2$), 29.5 (2C; CH$_2$), 29.4 (2C; CH$_2$), 29.3 (2C; CH$_2$), 28.27 (CH$_2$), 28.26 (CH$_2$), 27.4 |

| Cmpd. # | Structure | $^1$H NMR; $^{13}$C NMR; MS |
|---|---|---|
| | | (CH$_2$), 27.1 (CH$_2$), 25.0 (2C; CH$_2$), 23.5 (CH$_2$), 22.8 (2C; CH$_2$), 20.7 (CH$_2$), 19.7 (CH$_3$), 17.5 (CH$_3$), 17.10/17.08 (CH$_3$), 14.3 (2C; CH$_3$), 11.8 (CH$_3$). |
| I-41 | 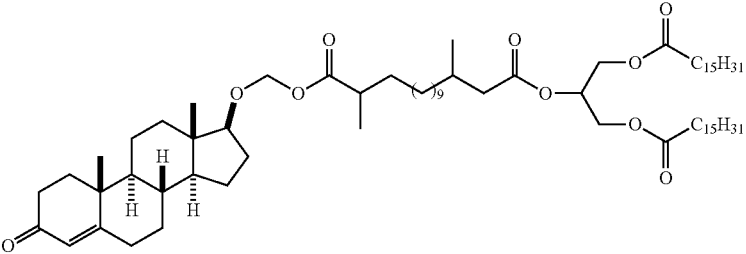 | $^1$H NMR (401 MHz, CDCl$_3$) δ 5.72 (s, 1H), 5.31-5.22 (m, 3H), 4.28 (dd, J = 11.9, 4.2 Hz, 2H), 4.14 (dd, J = 11.9, 6.0 Hz, 2H), 3.55 (dd, J = 8.3, 8.3 Hz, 1H), 2.47-2.23 (m, 10H), 2.11 (dd, J = 14.7, 8.3 Hz, 1H), 2.07-1.98 (m, 2H), 1.96-1.78 (m, 3H), 1.73-1.52 (m, 11H), 1.18 (s, 3H), 1.49-1.06 (m, 68H), 1.15 (d, J = 7.0 Hz, 3H), 1.13-0.94 (m, 4H), 0.92 (d, J = 6.6 Hz, 3H), 0.87 (t, J = 6.8 Hz, 6H), 0.80 (s, 3H); $^{13}$C NMR (101 MHz, CDCl$_3$) δ 199.6 (C), 176.5 (C), 173.4 (2C; C), 172.4 (C), 171.2 (C), 124.0 (CH), 89.18/89.16 (CH$_2$), 88.94/88.92 (CH), 68.9 (CH), 62.3 (2C; CH$_2$), 54.0 (CH), 50.4 (CH), 42.7 (C), 41.8 (CH$_2$), 39.86/39.84 (CH), 38.8 (C), 36.9 (CH$_2$), 36.8 (CH$_2$), 35.9 (CH$_2$), 35.5 (CH), 34.2 (2C; CH$_2$), 34.1 (CH$_2$), 33.7 (CH$_2$), 32.9 (CH$_2$), 32.0 (2C; CH$_2$), 31.6 (CH$_2$), 30.5 (CH), 30.0 (CH$_2$), 29.82 (6C; CH$_2$), 29.78 (4C; CH$_2$), 29.74 (3C; CH$_2$), 29.70 (CH$_2$), 29.69 (CH$_2$), 29.60 (2C; CH$_2$), 29.48 (3C; CH$_2$), 29.39 (2C; CH$_2$), 29.24 (3C; CH$_2$), 28.22/28.21 (CH$_2$), 27.4 (CH$_2$), 27.1 (CH$_2$), 25.0 (2C; CH$_2$), 23.4 (CH$_2$), 22.8 (2C; CH$_2$), 20.7 (CH$_2$), 19.7 (CH$_3$), 17.5 (CH$_3$), 17.09/17.06 (CH$_3$), 14.2 (2C; CH$_3$), 11.7 (CH$_3$). |
| I-42 | 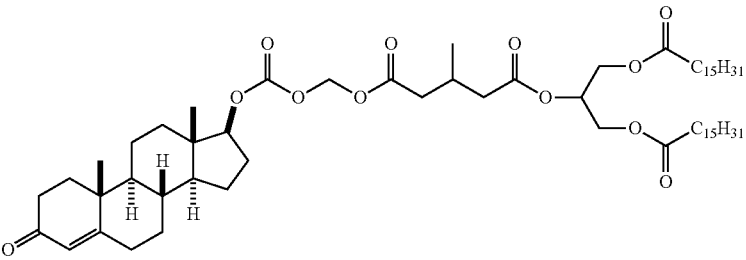 | $^1$H NMR (401 MHz, CDCl$_3$) δ 5.75 (s, 2H), 5.73 (s, 1H), 5.26 (m, 1H), 4.54 (dd, J = 9.0, 7.8 Hz, 1H), 4.301/4.296 (each dd, J = 11.9, 4.3 Hz, 2H), 4.13 (dd, J = 11.9, 6.0 Hz, 2H), 2.52-2.16 (m, 14H), 2.02 (ddd, J = 13.3, 4.8, 3.2 Hz, 1H), 1.90-1.80 (m, 2H), 1.75-1.55 (m, 9H), 1.47-1.17 (m, 51H), 1.19 (s, 3H), 1.04 (d, J = 6.4 Hz, 3H), 1.11-0.90 (m, 3H), 0.88 (t, J = 6.7 Hz, 6H), 0.86 (s, 3H); $^{13}$C NMR (101 MHz, CDCl$_3$) δ 199.6 (C), 173.4 (2C; C), 171.4 (C), 170.87 (C), 170.85 (C), 154.0 (C), 124.2 (CH), 87.1 (CH), 81.9 (CH$_2$), 69.3 (CH), 62.2 (2C; CH$_2$), 53.8 (CH), 50.2 (CH), 42.7 (C), 40.6 (CH$_2$), 40.3 (CH$_2$), 38.7 (C), 36.6 (CH$_2$), 35.9 (CH$_2$), 35.5 (CH), 34.2 (2C; CH$_2$), 34.1 (CH$_2$), 32.8 (CH$_2$), 32.1 (2C; CH$_2$), 31.6 (CH$_2$), 29.85 (6C; CH$_2$), 29.81 (4C; CH$_2$), 29.77 (2C; CH$_2$), 29.6 (2C; CH$_2$), 29.5 (2C; CH$_2$), 29.4 (2C; CH$_2$), 29.3 (2C; CH$_2$), 27.4 (CH$_2$), 27.2 (CH), 25.0 (2C; CH$_2$), 23.5 (CH$_2$), 22.8 (2C; CH$_2$), 20.6 (CH$_2$), 19.7 (CH$_3$), 17.5 (CH$_3$), 14.3 (2C; CH$_3$), 12.1 (CH$_3$). |

TABLE 10-continued

Additional Lipid Prodrugs

| Cmpd. # | Structure | $^1$H NMR; $^{13}$C NMR; MS |
|---|---|---|
| I-43 | 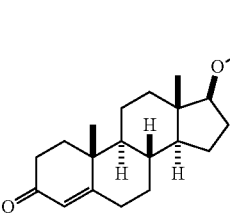 | $^1$H NMR (401 MHz, CDCl$_3$) δ 5.77-5.71 (m, 3H), 5.26 (m, 1H), 4.55 (dd, J = 8.8, 8.0 Hz, 1H), 4.28 (dd, J = 11.9, 4.3 Hz, 2H), 4.13 (dd, J = 11.9, 5.9 Hz, 2H), 2.47 (m, 1H), 2.43-2.17 (m, 10H), 2.11 (dd, J = 13.8, 7.5 Hz, 1H), 2.01 (ddd, J = 14.9, 10.7, 6.8 Hz, 1H), 1.92 (m, 1H), 1.88-1.81 (m, 2H), 1.75-1.55 (m, 4H), 1.47-1.12 (m, 26H), 1.18 (s, 3H), 1.16 (d, J = 7.0 Hz, 3H), 1.11-0.94 (m, 1H), 0.92 (d, J = 6.6 Hz, 1H), 0.88 (d, J = 6.7 Hz, 2H), 0.85 (s, 1H); $^{13}$C NMR (101 MHz, CDCl$_3$) δ 199.6 (C), 175.4 (C), 173.4 (2C; C), 172.5 (C), 170.9 (C), 154.1 (C), 124.2 (CH), 87.0 (CH), 82.0 (CH$_2$), 69.0 (CH), 62.3 (2C; CH$_2$), 53.8 (CH), 50.2 (CH), 42.8 (C), 41.8 (CH$_2$), 39.4 (CH), 38.7 (CH), 36.8 (CH$_2$), 36.7 (CH$_2$), 35.9 (CH$_2$), 35.5 (CH), 34.2 (2C; CH$_2$), 34.1 (CH$_2$), 33.5 (CH$_2$), 32.8 (CH$_2$), 32.1 (2C; CH$_2$), 31.6 (CH$_2$), 30.5 (CH), 29.85 (6C; CH$_2$), 29.81 (4C; CH$_2$), 29.77 (2C; CH$_2$), 29.6 (3C; CH$_2$), 29.5 (3C; CH$_2$), 29.4 (2C; CH$_2$), 29.3 (3C; CH$_2$), 27.4 (CH$_2$), 27.2 (CH$_2$), 27.1 (CH$_2$), 25.0 (2C; CH$_2$), 23.5 (CH$_2$), 22.8 (2C; CH$_2$), 20.6 (CH$_2$), 19.7 (CH$_3$), 17.5 (CH$_3$), 16.83/16.81 (CH$_3$), 14.3 (2C; CH$_3$), 12.1 (CH$_3$). |
| I-44 | 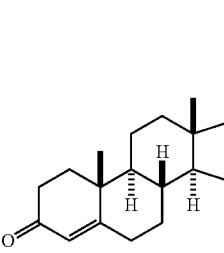 | $^1$H NMR (401 MHz, CDCl$_3$) δ 6.75 (qd, J = 5.4, 2.4 Hz, 1H), 5.73 (s, 1H), 5.26 (m, 1H), 4.53 (dd, J = 14.4, 8.0 Hz, 1H), 4.33-4.26 (m, 2H), 4.132/4.130 (each dd, J = 11.9, 5.9 Hz, 2H), 2.51-2.15 (m, 14H), 2.02 (m, 1H), 1.91-1.81 (m, 2H), 1.75-1.55 (m, 9H), 1.512/1.509 (each d, J = 5.4 Hz, 3H), 1.47-1.20 (m, 50H), 1.19 (s, 3H), 1.03 (d, J = 6.2 Hz, 3H), 1.11-0.84 (m, 4H), 0.87 (t, J = 7.1 Hz, 6H), 0.85 (s, 3H); $^{13}$C NMR (101 MHz, CDCl$_3$) δ 199.5 (C), 173.4 (2C; C), 171.4 (C), 170.88/170.86 (C), 170.33/170.29/170.27 (C), 153.22/153.19 (C), 124.2 (CH), 91.4 (CH), 86.76/86.68 (CH), 69.3 (CH), 62.2 (2C; CH$_2$), 53.8 (CH), 50.2 (CH), 42.80/42.72 (C), 40.69/40.63/40.61 (CH$_2$), 40.58/40.55/40.47/40.44 (CH$_2$), 38.74 (C), 36.69/36.65 (CH$_2$), 35.8 (CH$_2$), 35.5 (CH), 34.2 (2C; CH$_2$), 34.1 (CH$_2$), 32.8 (CH$_2$), 32.1 (2C; CH$_2$), 31.6 (CH$_2$), 29.84 (6C; CH$_2$), 29.80 (4C; CH$_2$), 29.77 (2C; CH$_2$), 29.6 (2C; CH$_2$), 29.5 (2C; CH$_2$), 29.4 (2C; CH$_2$), 29.3 (2C; CH$_2$), 27.38/27.35 (CH$_2$), 27.3 (CH), 25.0 (2C; CH$_2$), 23.5 (CH$_2$), 22.8 (2C; CH$_2$), 20.66/20.63 (CH$_2$), 19.7 (CH$_3$), 19.60/19.57 (CH$_3$), 17.5 (CH$_3$), 14.3 (2C; CH$_3$), 12.08/12.04 (CH$_3$). Note: Doubled/multiple signals were observed in some cases due to the presence of diastereomers. |

TABLE 10-continued

Additional Lipid Prodrugs

| Cmpd. # | Structure | $^1$H NMR; $^{13}$C NMR; MS |
|---|---|---|
| I-45 | 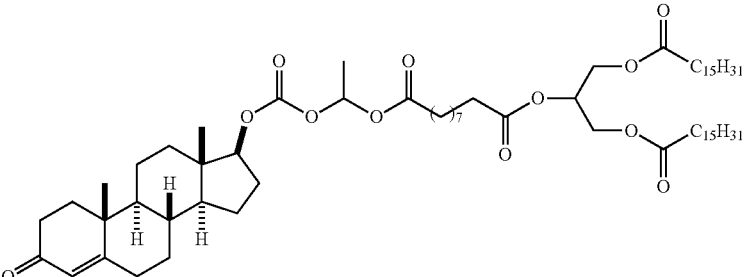 | $^1$H NMR (401 MHz, CDCl$_3$) δ 6.747/6.741 (each q, J = 5.5 Hz, 1H), 5.73 (s, 1H), 5.25 (m, 1H), 4.535/4.527 (each dd, J = 9.0, 7.7 Hz, 1H), 4.29 (dd, J = 11.9, 4.4 Hz, 2H), 4.14 (dd, J = 11.9, 5.9 Hz, 2H), 2.48-2.19 (m, 13H), 2.03 (m, 1H), 1.93-1.80 (m, 2H), 1.75-1.54 (m, 12H), 1.511/1.507 (each d, J = 5.4 Hz, 3H), 1.47-1.20 (m, 59H), 1.19 (s, 3H), 1.12-0.90 (m, 4H), 0.88 (t, J = 7.0 Hz, 6H), 0.86 (s, 3H). Note: Doubled signals were observed in some cases due to the presence of diastereomers. |
| I-46 | 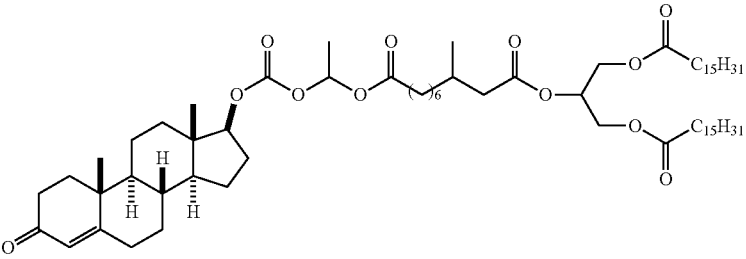 | $^1$H NMR (401 MHz, CDCl$_3$) δ 6.73 (qd, J = 5.4, 2.6 Hz, 1H), 5.72 (s, 1H), 5.26 (m, 1H), 4.52 (m, 1H), 4.28 (dd, J = 11.9, 4.3 Hz, 2H), 4.13 (dd, J = 11.6, 6.2 Hz, 2H), 2.47-2.15 (m, 12H), 2.10 (dd, J = 14.7, 8.3 Hz, 1H), 2.01 (m, 1H), 1.96-1.79 (m, 3H), 1.75-1.53 (m, 11H), 1.501/1.498 (each d, J = 5.4 Hz, 3H), 1.46-1.20 (m, 58H), 1.18 (s, 3H), 1.10-0.92 (m, 4H), 0.92 (d, J = 6.0 Hz, 3H), 0.87 (t, J = 6.9 Hz, 6H), 0.85 (s, 3H); $^{13}$C NMR (101 MHz, CDCl$_3$) δ 199.6 (C), 173.4 (2C; C), 172.4 (C), 171.8 (C), 170.9 (C), 153.2 (C), 124.1 (CH), 91.3 (CH), 86.68/86.62 (CH), 69.0 (CH), 62.3 (2C; CH$_2$), 53.8 (CH), 50.2 (CH), 42.78/42.71 (C), 41.8 (CH$_2$), 38.7 (C), 36.7 (CH$_2$), 36.67/36.65 (CH$_2$), 35.8 (CH$_2$), 35.5 (CH), 34.2 (3C; CH$_2$), 34.0 (CH$_2$), 32.8 (CH$_2$), 32.1 (2C; CH$_2$), 31.5 (CH$_2$), 30.4 (CH), 29.82 (6C; CH$_2$), 29.78 (4C; CH$_2$), 29.75 (2C; CH$_2$), 29.60 (2C; CH$_2$), 29.52 (CH$_2$), 29.49 (2C; CH$_2$), 29.4 (2C; CH$_2$), 29.2 (2C; CH$_2$), 29.13/29.11 (CH$_2$), 27.38/27.33 (CH$_2$), 26.86/26.85 (CH$_2$), 25.0 (2C; CH$_2$), 24.69/24.66 (CH$_2$), 23.4 (CH$_2$), 22.8 (2C; CH$_2$), 20.64/20.61 (CH$_2$), 19.7 (CH$_3$), 19.6 (CH$_3$), 17.5 (CH$_3$), 14.2 (2C; CH$_3$), 12.06/12.03 (CH$_3$). Note: Doubled signals was observed in some cases due to the presence of diastereomers. |
| I-47 | 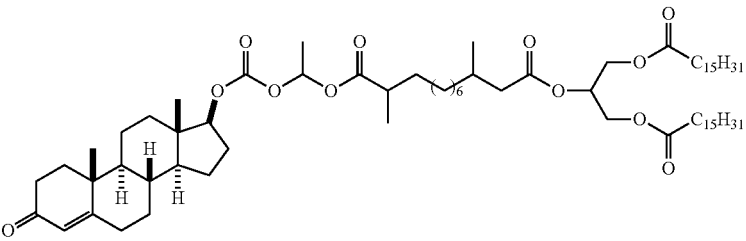 | $^1$H NMR (401 MHz, CDCl$_3$) δ 6.74 (m, 1H), 5.73 (s, 1H), 5.27 (m, 1H), 4.53 (m, 1H), 4.29 (dd, J = 11.9, 4.3 Hz, 2H), 4.14 (dd, J = 11.9, 6.0 Hz, 2H), 2.48-2.25 (m, 10H), 2.20 (m, 1H), 2.11 (m, 1H), 2.02 (m, 1H), 1.97-1.80 (m, 3H), 1.77-1.54 (m, 10H), 1.51 (d, J = 5.4 Hz, 3H), 1.48-1.20 (m, 63H), 1.19 (s, 3H), 1.16-1.12 (m, 3H), 1.11-0.94 (m, 4H), 0.92 (d, J = 6.6 Hz, 3H), 0.88 (t, J = 6.6 Hz, 6H), 0.85 (s, 3H); $^{13}$C NMR (101 MHz, CDCl$_3$) δ 199.6 (C), 174.9 (C), 173.4 (2C; C), 172.5 (C), 170.9 (c), 153.2 (C), 124.2 (CH), 91.4 (CH), 86.6 (CH), 69.0 (CH), 62.3 (2C; CH$_2$), 53.8 (CH), 50.2 (CH), 41.8 (CH$_2$), 39.5 (CH), 36.9 (CH$_2$), 36.7 (CH$_2$), 35.9 (CH$_2$), 35.5 (CH), 34.2 (2C; CH$_2$), 34.1 (CH$_2$), 33.6 (CH$_2$), 32.8 (CH$_2$), 32.1 (2C; CH$_2$), 31.6 (CH$_2$), 30.5 (CH), 29.85 |

TABLE 10-continued

Additional Lipid Prodrugs

| Cmpd. # | Structure | $^1$H NMR; $^{13}$C NMR; MS |
|---|---|---|
| | | (7C; CH$_2$), 29.81 (4C; CH$_2$), 29.77 (2C; CH$_2$), 29.67 (2C; CH$_2$), 29.63 (2C; CH$_2$), 29.51 (2C; CH$_2$), 29.42 (2C; CH$_2$), 29.27 (2C; CH$_2$), 27.5-27.1 (3C; CH$_2$), 25.0 (2C; CH$_2$), 23.5 (CH$_2$), 22.8 (2C; CH$_2$), 20.6 (CH$_2$), 19.69 (CH$_3$), 19.67 (CH$_3$), 17.53 (CH$_3$), 16.9/16.8 (CH$_3$), 14.3 (2C; CH$_3$), 12.1 (CH$_3$). Note: Doubled signals were observed in some cases due to the presence of diastereomers. |
| I-48 | 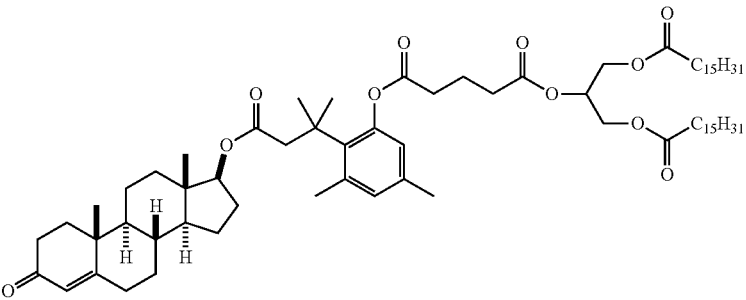 | $[\alpha]^D_{27}$ + 42.0 (c 0.340, CH$_2$Cl$_2$); $^1$H NMR (400 MHz, CDCl$_3$) δ 6.80 (d, J = 1.9 Hz, 1H), 6.56 (d, J = 1.8 Hz, 1H), 5.72 (s, 1H), 5.28 (m, 1H), 4.45 (dd, J = 9.1, 7.3 Hz, 1H), 4.32 (dd, J = 11.9, 4.4 Hz, 2H), 4.15 (dd, J = 11.9, 5.8 Hz, 2H), 2.79 (ABq, J = 14.5 Hz, 2H), 2.64 (t, J = 7.4 Hz, 2H), 2.54 (s, 3H), 2.49 (t, J = 7.1 Hz, 2H), 2.44-2.24 (m, 8H), 2.22 (s, 3H), 2.11-1.96 (m, 4H), 1.81 (m, 1H), 1.70 (dd, J = 13.7, 5.1 Hz, 1H), 1.65-1.48 (m, 8H), 1.55 (s, 6H), 1.44-1.18 (m, 51H), 1.17 (s, 3H), 1.11-0.92 (m, 4H), 0.88 (t, J = 6.9 Hz, 6H), 0.65 (s, 3H); $^{13}$C NMR (101 MHz, CDCl$_3$) δ 199.6 (C), 173.4 (2C; C), 172.1 (C), 171.88 (C), 171.85 (C), 171.1 (C), 149.6 (C), 138.2 (C), 136.3 (C), 133.6 (C), 132.5 (CH), 124.1 (CH), 123.1 (CH), 82.5 (CH), 69.5 (CH), 62.1 (2C; CH$_2$), 53.8 (CH), 50.2 (CH), 48.2 (CH$_2$), 42.4 (C), 39.2 (C), 38.7 (C), 36.5 (CH$_2$), 35.8 (CH$_2$), 35.5 (CH), 34.2 (2C; CH$_2$), 34.1 (CH$_2$), 34.0 (CH$_2$), 33.2 (CH$_2$), 32.9 (CH$_2$), 32.1 (2C; CH$_2$), 31.66 (CH$_3$), 31.60 (CH$_2$), 31.58 (CH$_3$), 29.84 (6C; CH$_2$), 29.81 (4C; CH$_2$), 29.77 (2C; CH$_2$), 29.6 (2C; CH$_2$), 29.5 (2C; CH$_2$), 29.4 (2C; CH$_2$), 29.3 (2C; CH$_2$), 27.4 (CH$_2$), 25.4 (CH$_3$), 25.0 (2C; CH$_2$), 23.6 (CH$_2$), 22.8 (2C; CH$_2$), 20.6 (CH$_2$), 20.4 (CH$_3$), 19.9 (CH$_2$), 17.5 (CH$_3$), 14.3 (2C; CH$_3$), 12.0 (CH$_3$); ESI-HRMS: calcd. for C$_{72}$H$_{116}$NaO$_{11}$ [M + Na$^+$] 1179.8410; found 1179.8461; purity (LC-MS): >99% TST prodrug. |
| I-49 | 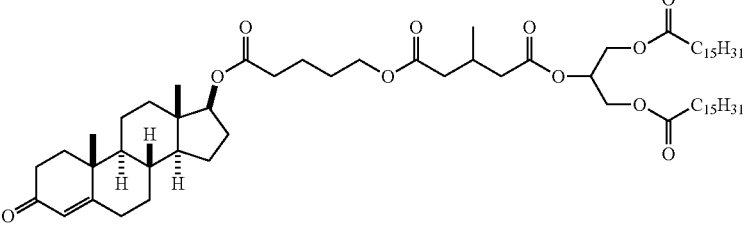 | $^1$H NMR (400 MHz, CDCl$_3$) δ 5.72 (s, 1H), 5.25 (m, 1H), 4.60 (dd, J = 9.0, 7.9 Hz, 1H), 4.29/4.28 (each dd, J = 11.9, 4.3 Hz, 2H), 4.12 (dd, J = 12.0, 5.9 Hz, 2H), 4.07 (t, J = 5.8 Hz, 2H), 2.49-2.09 (m, 12H), 2.29 (t, J = 7.4 Hz, 4H), 2.01 (m, 1H), 1.83 (m, 1H), 1.76 (m, 1H), 1.72-1.43 (m, 13H), 1.43-1.19 (m, 50H), 1.18 (s, 3H), 1.15-0.88 (m, 4H), 1.01 (d, J = 6.5 Hz, 3H), 0.86 (t, J = 6.8 Hz, 6H), 0.82 (s, 3H); $^{13}$C NMR (101 MHz, CDCl$_3$) δ 199.6 (C), 173.4 (2C; C), 173.3 (C), 172.3 (C), 171.5 (C), 171.1 (C), 124.1 (CH), 82.5 (CH), 69.2 (CH), 64.0 (CH$_2$), 62.2 (2C; CH$_2$), 53.8 (CH), 50.3 (CH), 42.6 (C), 40.78 (CH$_2$), 40.77 (CH$_2$), 38.7 (C), 36.8 (CH$_2$), 35.8 (CH$_2$), 35.5 (CH), 34.1 (2C; CH$_2$), 34.0 (2C; CH$_2$), 32.8 |

| Cmpd. # | Structure | $^1$H NMR; $^{13}$C NMR; MS |
|---|---|---|
| | | (CH$_2$), 32.0 (2C; CH$_2$), 31.6 (CH$_2$), 29.81 (6C; CH$_2$), 29.77 (4C; CH$_2$), 29.73 (2C; CH$_2$), 29.6 (2C; CH$_2$), 29.5 (2C; CH$_2$), 29.4 (2C; CH$_2$), 29.2 (2C; CH$_2$), 28.2 (CH$_2$), 27.6 (CH$_2$), 27.5 (CH), 24.9 (2C; CH$_2$), 23.6 (CH$_2$), 22.8 (2C; CH$_2$), 21.6 (CH$_2$), 20.6 (CH$_2$), 19.7 (CH$_3$), 17.5 (CH$_3$), 14.2 (2C; CH$_3$), 12.2 (CH$_3$). |
| I-50 | 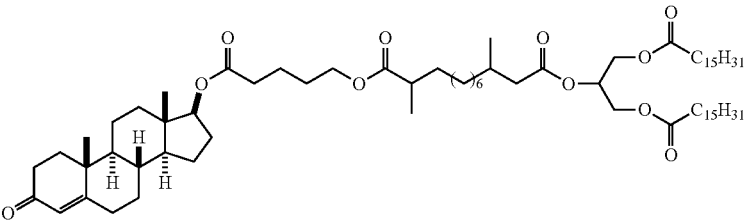 | $^1$H NMR (401 MHz, CDCl$_3$) δ 5.72 (s, 1H), 5.27 (m, 1H), 4.61 (dd, J = 9.0, 7.9 Hz, 1H), 4.28 (dd, J = 11.9, 3.7 Hz, 2H), 4.14 (dd, J = 11.9, 5.9 Hz, 2H), 4.10-4.03 (m, 2H), 2.47-2.25 (m, 13H), 2.17 (m, 1H), 2.11 (dd, J = 14.7, 8.4 Hz, 1H), 2.02 (ddd, J = 13.3, 4.8, 3.2 Hz, 1H), 1.93 (m, 1H), 1.84 (m, 1H), 1.80-1.55 (m, 17H), 1.53-1.21 (m, 72H), 1.19 (s, 4H), 1.13 (d, J = 7.0 Hz, 3H), 1.10-0.95 (m, 3H), 0.92 (d, J = 6.6 Hz, 4H), 0.87 (t, J = 6.7 Hz, 6H), 0.83 (s, 3H); $^{13}$C NMR (101 MHz, CDCl$_3$) δ 199.6 (C), 177.0 (C), 173.43 (2C; C), 173.37 (C), 172.5 (C), 171.0 (C), 124.1 (CH), 82.5 (CH), 69.0 (CH), 63.8 (CH$_2$), 62.3 (2C; CH$_2$), 53.8 (CH), 50.4 (CH), 42.7 (C), 41.8 (CH$_2$), 39.7 (CH), 38.7 (C), 36.84 (CH$_2$), 36.79 (CH$_2$), 35.8 (CH$_2$), 35.5 (CH), 34.18 (2C; CH$_2$), 34.11 (CH$_2$), 34.06 (CH$_2$), 33.9 (CH$_2$), 32.9 (CH$_2$), 32.1 (2C; CH$_2$), 31.6 (CH$_2$), 30.5 (CH), 29.9 (CH$_2$), 29.84 (6C; CH$_2$), 29.80 (4C; CH$_2$), 29.76 (2C; CH$_2$), 29.70 (CH$_2$), 29.67 (CH$_2$), 29.61 (2C; CH$_2$), 29.5 (2C; CH$_2$), 29.4 (2C; CH$_2$), 29.3 (2C; CH$_2$), 28.3 (CH$_2$), 27.7 (CH$_2$), 27.4 (CH$_2$), 27.1 (CH$_2$), 25.0 (2C; CH$_2$), 23.6 (CH$_2$), 22.8 (2C; CH$_2$), 21.7 (CH$_2$), 20.7 (CH$_2$), 19.7 (CH$_3$), 17.5 (CH$_3$), 17.2 (CH$_3$), 14.3 (2C; CH$_3$), 12.2 (CH$_3$). |
| I-51 | 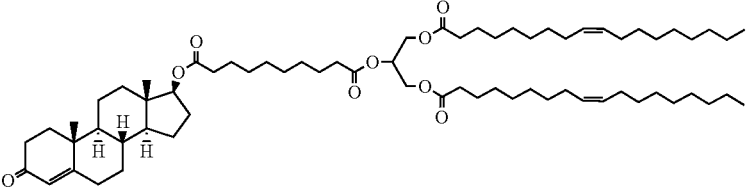 | $^1$H NMR (400 MHz, CDCl$_3$) δ 5.77 (s, 1H), 5.39 (m, 6H), 4.66 (d, 1H), 4.35 (m, 2H), 4.20 (m, 2H), 2.46 (m, 6H), 2.39 (m, 8H), 2.2 (m, 2H), 2.05 (m, 8H), 1.8 (m, 4H), 1.66 (m, 8H), 1.4 (m, 54H), $^{13}$C NMR (101 MHz, CDCl$_3$) δ 199 (1C), 173.3 (2C), 172.8 (1C), 170.98 (1C), 130.02 (2C) 123.9 (1C), 82.1 (1C), 68.87 (1C), 62.12 (1C), 53.69 (1C), 50.23 (1C), 42.4 (1C), 38.6 (1C), 36.6 (1C) 35.6 (2C), 34.5 (6C), 32.7 (2C), 31.9 (2C), 29.7 (30C), 27.5 (3C), 25.05 (2C), 23.49 (2C), 22.6 (2C), 20.5 (1C), 17.3 (1C), 14.1 (2C), 12.0 (1C); HPLC (ELSD): 9.17 min, 99.33% purity; MS (ESI, +ve) m/z: 1.77 (MH$^+$ + 1). |

TABLE 10-continued

Additional Lipid Prodrugs

| Cmpd. # | Structure | $^1$H NMR; $^{13}$C NMR; MS |
|---|---|---|
| I-52 | 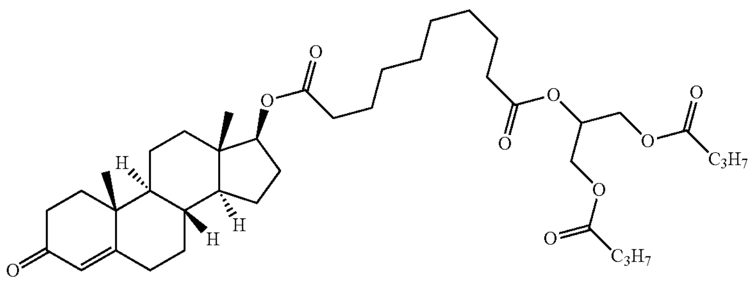 | $^1$H NMR (400 MHz, CDCl$_3$) δ 5.77 (s, 1H), 5.39 (m, 1H), 4.66 (d, 1H), 4.35 (m, 2H), 4.20 (m, 2H), 2.46 (m, 12H), 2.39 (m, 2H), 2.08 (m, 2H), 1.9 (m, 2H), 1.8 (m, 2H), 1.7 (m, 6H), 1.52 (m, 5H) 1.4 (m, 10H), 1.3 (m, 3H), 1.2 (m, 2H), 1.02 (m, 6H), 0.87 (s, 3H); $^{13}$C NMR (101 MHz, CDCl$_3$) δ 199 (1C), 173.3 (2C), 172.9 (1C), 171.03 (1C), 123.9 (1C), 82.2 (1C), 68.9 (1C), 62.08 (2C), 53.72 (1C), 50.26 (1C), 42.53 (1C), 38.6 (1C), 36.6 (1C) 35.7 (3C), 34.5 (1C), 33.9 (1C), 32.7 (1C), 31.5 (1C), 29.1 (4C), 27.4 (2C), 25.08 (1C), 24.8 (2C), 23.52 (1C), 20.5 (1C), 18.38 (2C), 17.43 (1C), 13.67 (2C), 12.1 (1C); HPLC (ELSD): 2.62 min, 100% purity; LCMS (ESI, +ve) m/z: 687.7 (MH$^+$ + 1). |
| I-53 | 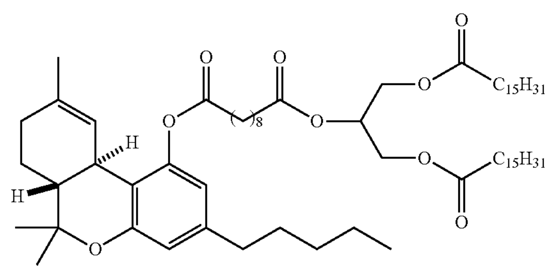 | $^1$H NMR (401 MHz, CDCl$_3$) δ 6.54 (d, J = 1.7 Hz, 1H), 6.38 (d, J = 1.7 Hz, 1H), 5.95 (m, 1H), 5.26 (m, 1H), 4.29 (dd, J = 11.9, 4.4 Hz, 2H), 4.14 (dd, J = 11.9, 5.9 Hz, 2H), 3.05 (m, 1H), 2.54 (t, J = 7.5 Hz, 2H), 2.51-2.46 (m, 2H), 2.32 (t, J = 7.5 Hz, 2H), 2.31 (td, J = 7.5 Hz, 4H), 2.16-2.10 (m, 2H), 1.90 (m, 1H), 1.79-1.71 (m, 2H), 1.65 (s, 3H), 1.70-1.53 (m, 9H), 1.40 (s, 3H), 1.44-1.20 (m, 61H), 1.08 (s, 3H), 0.91-0.85 (m, 9H); $^{13}$C NMR (101 MHz, CDCl$_3$) δ 173.5 (2C; C), 173.0 (C), 171.6 (C), 154.6 (C), 149.5 (C), 142.8 (C), 134.7 (C), 123.6 (CH), 115.31 (CH), 115.25 (C), 114.1 (CH), 77.6 (C), 69.1 (CH), 62.2 (2C; CH$_2$), 45.7 (CH), 35.6 (CH$_2$), 34.6 (CH$_2$), 34.31 (CH$_2$), 34.28 (CH), 34.2 (2C; CH$_2$), 32.1 (2C; CH$_2$), 31.6 (CH$_2$), 31.2 (CH$_2$), 30.7 (CH$_2$), 29.85 (6C; CH$_2$), 29.81 (4C; CH$_2$), 29.78 (2C; CH$_2$), 29.6 (2C; CH$_2$), 29.5 (2C; CH$_2$), 29.4 (2C; CH$_2$), 29.32 (CH$_2$), 29.31 (CH$_2$), 29.29 (CH$_2$), 29.27 (2C; CH$_2$), 29.2 (CH$_2$), 27.6 (CH$_3$), 25.1 (CH$_2$), 25.01 (2C; CH$_2$), 25.00 (CH$_2$), 24.96 (CH$_2$), 23.5 (CH$_3$), 22.8 (2C; CH$_2$), 22.7 (CH$_2$), 19.5 (CH$_3$), 14.3 (2C; CH$_3$), 14.2 (CH$_3$). |
| I-54 | 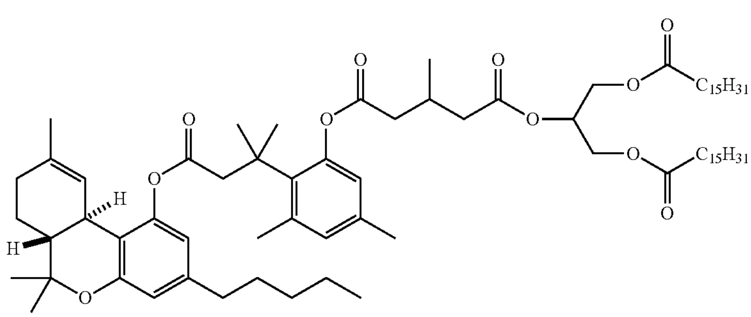 | $^1$H NMR (401 MHz, CDCl$_3$) δ 6.82 (d, J = 1.6 Hz, 1H), 6.60 (s, 1H), 6.48 (d, J = 1.6 Hz, 1H), 5.98 (d, J = 1.6 Hz, 1H), 5.91 (s, 1H), 5.28 (m, 1H), 4.309/4.301 (each dd, J = 11.9, 4.1, 3.2 Hz, 2H), 4.14 (dd, J = 11.9, 6.0 Hz, 2H), 3.13 (d, J = 15.1 Hz, 1H), 2.99 (d, J = 15.2 Hz, 1H), 2.90 (d, J = 10.9 Hz, 1H), 2.70 (dd, J = 15.4, 5.0 Hz, 1H), 2.64-2.49 (m, 3H), 2.58 (s, 3H), 2.45-2.26 (m, 3H), 2.30 (t, J = 7.1 Hz, 4H), 2.24 (s, 3H), 2.15-2.08 (m, 2H), 1.87 (m, 1H), 1.70-1.46 (m, 7H), 1.67 (s, 3H), 1.65 (s, 6H), 1.38 (s, 3H), 1.35-1.21 (m, 53H), 1.13 (d, J = 6.3 Hz, 3H), 1.02 (s, 3H), 0.88 (t, J = 6.9 Hz, 9H); $^{13}$C NMR (101 MHz, CDCl$_3$) δ 173.4 (2C; C), 171.4 |

TABLE 10-continued

Additional Lipid Prodrugs

| Cmpd. # | Structure | $^1$H NMR; $^{13}$C NMR; MS |
|---|---|---|
| | | (C), 171.3 (C), 169.7 (C), 154.4 (C), 149.7 (C), 149.4 (C), 142.7 (C), 138.4 (C), 136.4 (C), 134.4 (C), 133.3 (C), 132.6 (CH), 123.8 (CH), 123.2 (CH), 115.24 (C), 115.20 (CH), 113.9 (CH), 77.5 (C), 69.3 (CH), 62.2 (2C; CH$_2$), 47.8 (CH$_2$), 45.7 (CH), 41.4 (CH$_2$), 40.7 (CH$_2$), 39.4 (C), 35.5 (CH$_2$), 34.19 (CH), 34.15 (2C; CH$_2$), 32.1 (2C; CH$_2$), 31.9 (2C; CH$_3$), 31.6 (CH$_2$), 31.2 (CH$_2$), 30.6 (CH$_2$), 29.85 (6C; CH$_2$), 29.81 (4C; CH$_2$), 29.77 (2C; CH$_2$), 29.6 (2C; CH$_2$), 29.5 (2C; CH$_2$), 29.4 (2C; CH$_2$), 29.3 (2C; CH$_2$), 27.5 (CH$_3$), 27.3 (CH), 25.5 (CH$_3$), 25.0 (3C; CH$_2$), 23.6 (CH$_3$), 22.8 (2C; CH$_2$), 22.7 (CH$_2$), 20.4 (CH$_3$), 19.9 (CH$_3$), 19.4 (CH$_3$), 14.3 (2C; CH$_3$), 14.2 (CH$_3$). |
| I-55 | 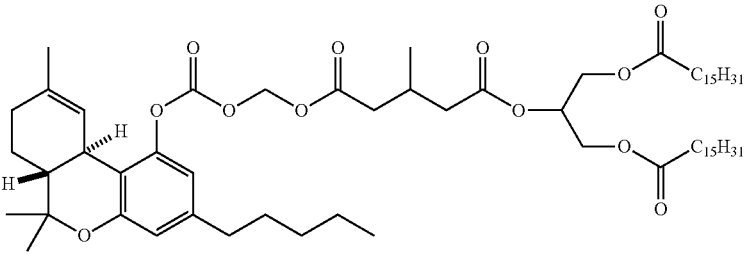 | $^1$H NMR (401 MHz, CDCl$_3$) δ 6.57 (d, J = 1.7 Hz, 1H), 6.51 (d, J = 1.7 Hz, 1H), 5.94 (m, 1H), 5.87 (dd, J = 5.7, 3.3 Hz, 1H), 5.83 (dd, J = 5.6, 4.3 Hz, 1H), 5.27 (m, 1H), 4.306/4.303 (each dd, J = 11.9, 4.2 Hz, 2H), 4.14 (dd, J = 11.9, 6.0 Hz, 2H), 3.15 (m, 1H), 2.55-2.41 (m, 5H), 2.38-2.25 (m, 6H), 2.17-2.09 (m, 2H), 1.90 (m, 1H), 1.66 (s, 3H), 1.71-1.53 (m, 7H), 1.41 (s, 3H), 1.40-1.19 (m, 53H), 1.09 (s, 3H), 1.05 (d, J = 5.8 Hz, 3H), 0.88 (t, J = 6.9 Hz, 9H). |
| I-56 | 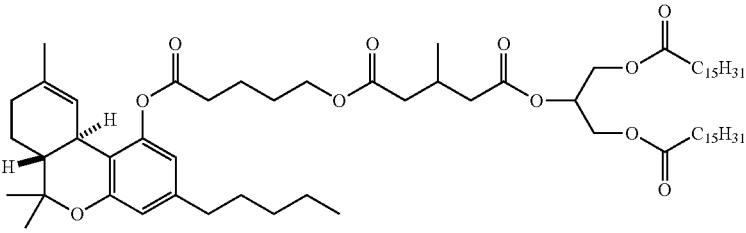 | $^1$H NMR (401 MHz, CDCl$_3$) δ 6.55 (d, J = 1.6 Hz, 1H), 6.38 (d, J = 1.7 Hz, 1H), 5.93 (m, 1H), 5.27 (m, 1H), 4.298/4.294 (each dd, J = 11.9, 4.3 Hz, 2H), 4.18-4.08 (m, 4H), 3.04 (m, 1H), 2.65-2.54 (m, 2H), 2.52-2.36 (m, 5H), 2.33-2.19 (m, 6H), 2.17-2.10 (m, 2H), 1.93-1.71 (m, 5H), 1.65 (s, 3H), 1.70-1.49 (m, 7H), 1.40 (s, 3H), 1.40-1.19 (m, 53H), 1.08 (s, 3H), 1.03 (d, J = 6.5 Hz, 3H), 0.88 (t, J = 6.7 Hz, 9H); $^{13}$C NMR (101 MHz, CDCl$_3$) δ 173.4 (2C; C), 172.3 (C), 171.5 (C), 171.1 (C), 154.6 (C), 149.4 (C), 142.9 (C), 134.9 (C), 123.5 (CH), 115.4 (CH), 115.2 (C), 114.0 (CH), 77.6 (C), 69.3 (CH), 64.0 (CH$_2$), 62.2 (2C; CH$_2$), 45.7 (CH), 40.83 (CH$_2$), 40.81 (CH$_2$), 35.6 (CH$_2$), 34.3 (CH), 34.2 (2C; CH$_2$), 34.0 (CH$_2$), 32.1 (2C; CH$_2$), 31.6 (CH$_2$), 31.1 (CH$_2$), 30.7 (CH$_2$), 29.85 (6C; CH$_2$), 29.81 (4C; CH$_2$), 29.78 (2C; CH$_2$), 29.6 (2C; CH$_2$), 29.5 (2C; CH$_2$), 29.4 (2C; CH$_2$), 29.3 (2C; CH$_2$), 28.3 (CH$_2$), 27.6 (CH$_3$), 27.5 (CH), 25.1 (CH$_2$), 25.0 (2C; CH$_2$), 23.6 (CH$_3$), 22.8 (2C; CH$_2$), 22.7 (CH$_2$), 21.5 (CH$_2$), 19.8 (CH$_3$), 19.5 (CH$_3$), 14.3 (2C; CH$_3$), 14.2 (CH$_3$). |

Example 11: Synthesis of (E)-6-(4-(((4-((1,3-bis(palmitoyloxy)propan-2-yl)oxy)-4-oxobutanoyl)oxy)methoxy)-6-methoxy-7-methyl-3-oxo-1,3-dihydroisobenzofuran-5-yl)-4-methylhex-4-enoic acid (MPA-I-6)

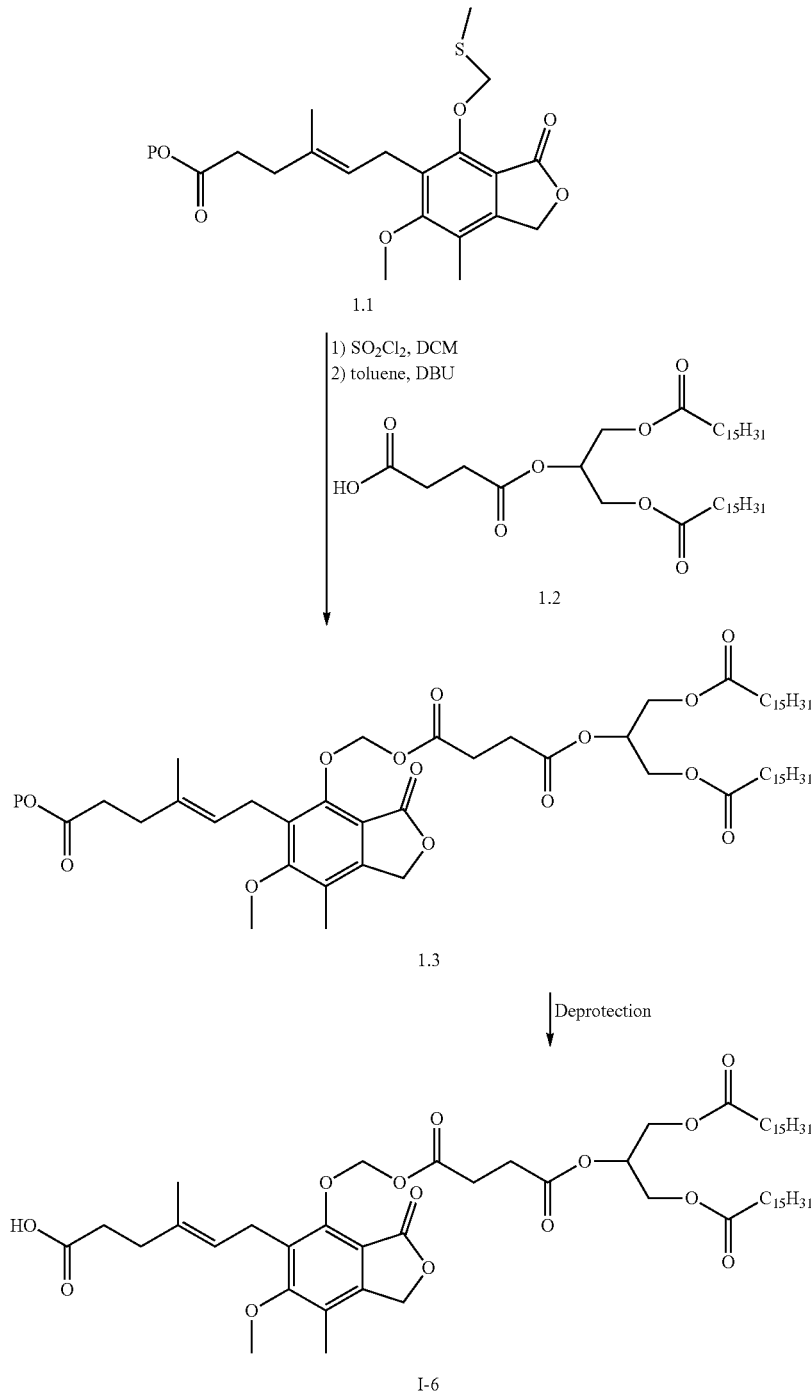

Synthesis of MPA-I-6

Synthesis of MPA-I-6. MPA-I-6 is prepared according to the following procedure. 1.1 is prepared by treating a suitably protected mycophenolic acid (i.e., wherein P is a suitable carboxyl protecting group) with chloromethyl methyl thioether as described in WO 2009/143295, which is hereby incorporated by reference in its entirety. A solution of sulfuryl chloride (2.2 equiv.) in $CH_2Cl_2$ (0.16 M) is added to a solution of 1.1 (1.8 equiv.) in $CH_2Cl_2$ (0.07 M) at 0° C. and the mixture stirred at 0° C. for 30 minutes and then at rt for a further hour. The reaction is concentrated under a stream of $N_2$, co-evaporated from toluene (twice) and dried under reduced pressure. The crude residue is re-dissolved in toluene (0.1 M based on 1.1), added to a solution of acid 1.2 (1 equiv.), as prepared in WO 2017/041139, and DBU (1.5 equiv.) in toluene (0.05 M) that had been pre-stirred for one hour, and the mixture is stirred at rt for two hours. The reaction is diluted with CH$_2$Cl$_2$ (20 mL) and the organic phase washed with sat. aq. NaHCO$_3$ (20 mL) and brine (20 mL), dried (MgSO$_4$) and concentrated under reduced pressure to give the crude product. Deprotection and purification by silica gel chromatography with a suitable solvent mixture affords MPA-I-6.

Example 12: Synthesis of (E)-6-(6-methoxy-7-methyl-3-oxo-4-((5,8,13-trioxo-10-((palmitoyloxy)methyl)-2,4,9,12-tetraoxaoctacosanoyl)oxy)-1,3-dihydroisobenzofuran-5-yl)-4-methylhex-4-enoic acid, MPA-I-7

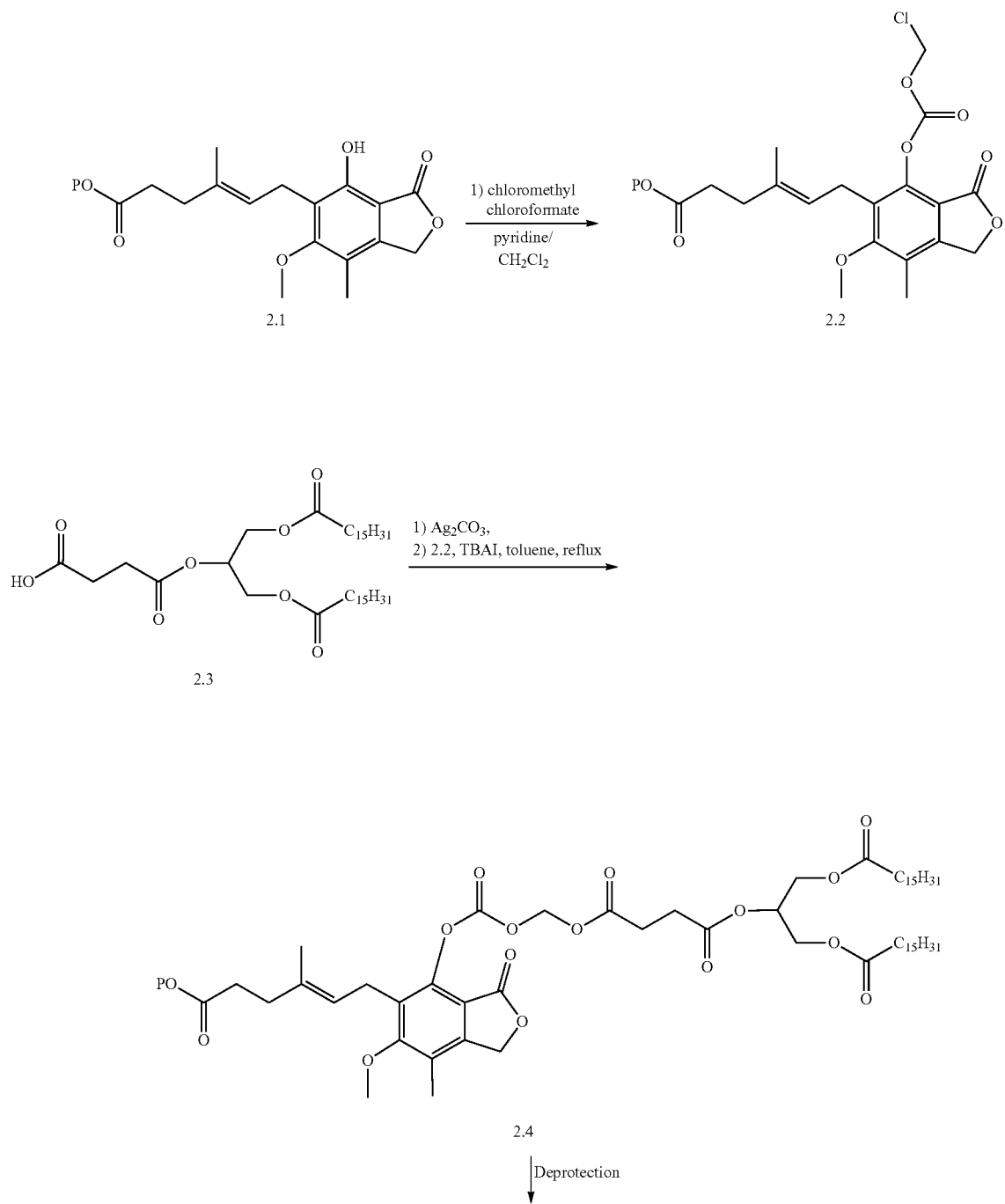

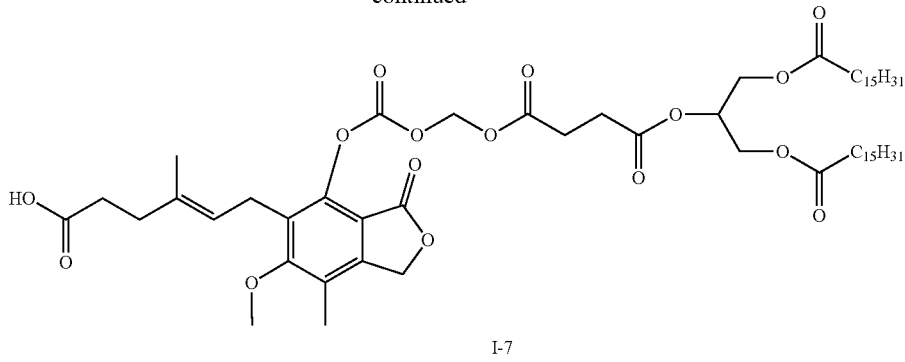

I-7

Synthesis of MPA-I-7

Synthesis of 2.2. 2.2 is prepared according to the following procedure. Chloromethyl chloroformate (1.6 equiv.) and pyridine (3.0 equiv.) are added to a suitably protected mycophenolic acid (ie where P is a suitable carboxyl protecting group) 2.1 (1.0 equiv.) in $CH_2Cl_2$ (0.03 M) at 0° C. and the mixture is stirred at 0° C. for 15 minutes and then at rt for one hour. The reaction is diluted with $CH_2Cl_2$ and the organic phase washed with sat. aq. $NaHCO_3$ and brine, dried ($MgSO_4$) and concentrated under reduced pressure to give 2.2 which is used without purification.

Synthesis of MPA-I-7. 2.4 is prepared according to the following procedure. Silver carbonate (0.7 equiv.) is added to acid 2.3 (1.2 equiv.) as prepared in WO 2017/041139, in DMF (0.03 M) and the mixture stirred at rt for one hour. The reaction is concentrated under reduced pressure to give a grey residue, to which is added chloromethyl carbonate 2.2 (1.0 equiv.) in toluene (0.03 M) and TBAI (0.3 equiv.) and the mixture heated at reflux for 1.5 hours. The reaction is cooled to rt, then diluted with ethyl acetate. The organic phase is washed with water and brine, dried ($MgSO_4$) and concentrated under reduced pressure to give the crude product 2.4. Deprotection and purification by silica gel chromatography with a suitable solvent mixture affords MPA-I-7.

Example 13: Synthesis of (E)-6-(4-((3-(2-((4-((1,3-bis(palmitoyloxy)propan-2-yl)oxy)-4-oxobutanoyl)oxy)-4,6-dimethylphenyl)-3-methylbutanoyl)oxy)-6-methoxy-7-methyl-3-oxo-1,3-dihydroisobenzofuran-5-yl)-4-methylhex-4-enoic acid, MPA-I-8

Synthesis of MPA-I-8.

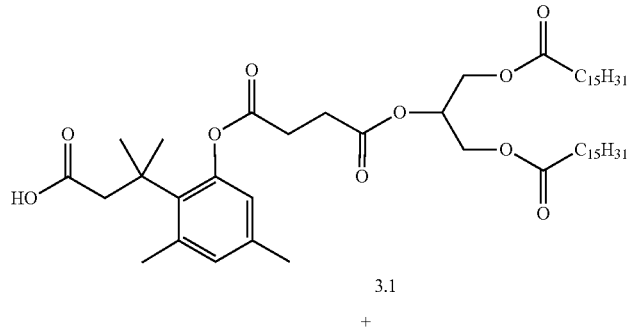

3.1

+

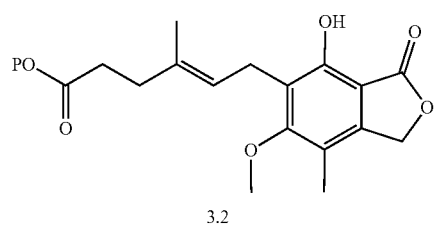

3.2

↓ 1) EDCl•HCl, DMAP

-continued

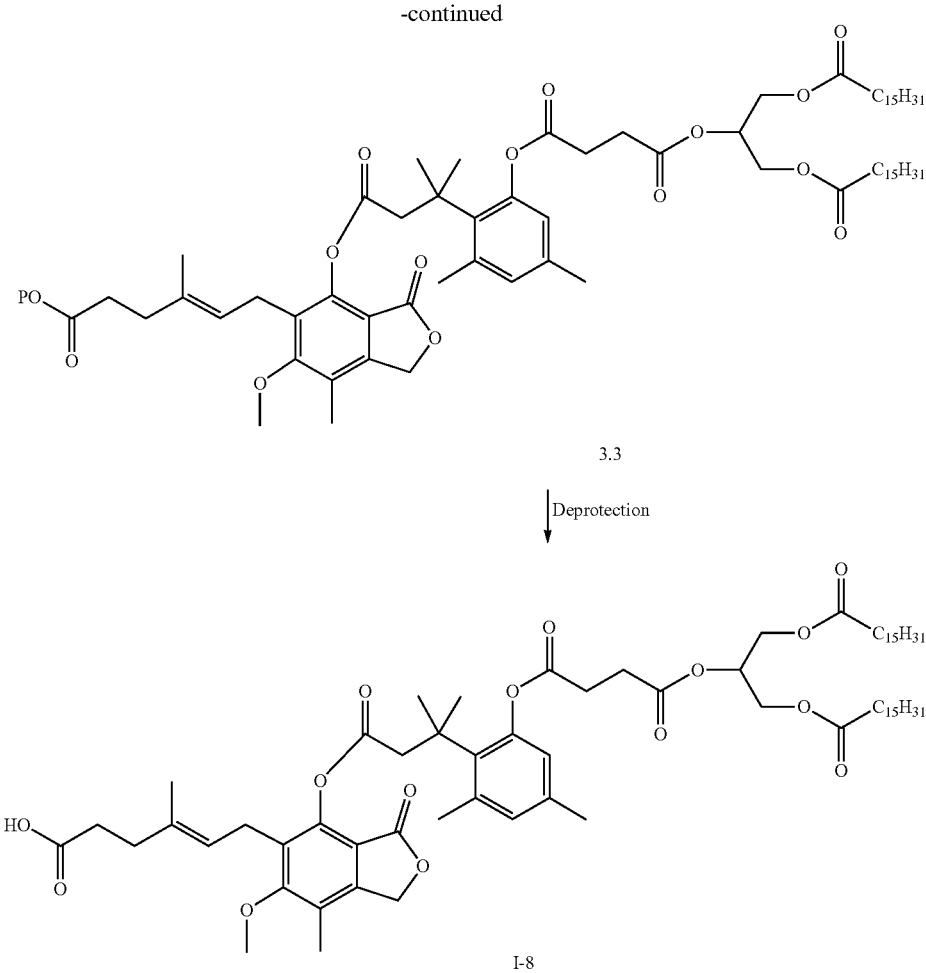

Synthesis of MPA-I-8. MPA-I-8 is prepared according to the following procedure. DMAP (1.3 equiv.) and EDC·HCl (2.1 equiv.) is added to a solution of acid 3.1 (1.0 equiv.) as prepared in WO 2017/041139, and a suitably protected mycophenolic acid (i.e. where P is a suitable carboxyl protecting group such as an alkyl or phenyl ester) 3.2 (1.3 equiv.) in $CH_2Cl_2$ (0.02 M) and the mixture stirred at RT for 19 hours. The reaction is diluted with $CH_2Cl_2$ (10 mL), silica gel is added, and the mixture concentrated under reduced pressure and purified by silica gel chromatography. Deprotection of the ester and purification, e.g. by silica gel chromatography with a suitable solvent mixture, affords MPA-I-8.

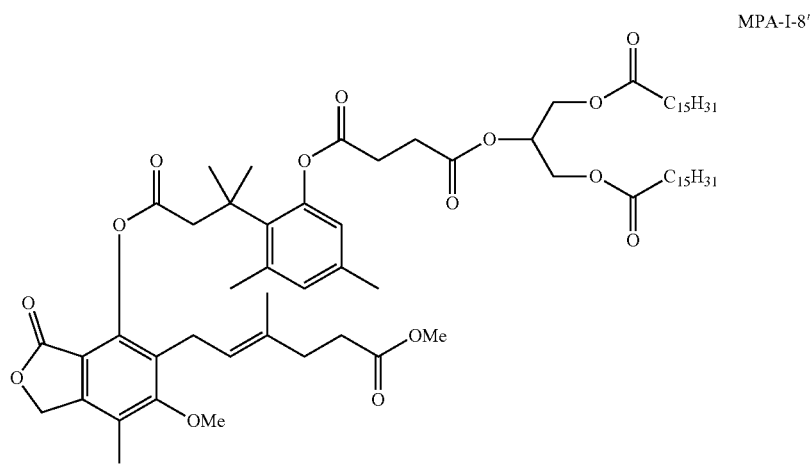

Compound MPA-I-8' was prepared as follows. DMAP (2.4 mg, 19.8 µmol) and EDC·HCl (9.5 mg, 49.4 µmol) were added to a solution of TML acid-TG 3.1 (19.0 mg, 21.8 µmol) and methyl ester 3.2 (6.6 mg, 19.8 µmol, P=Me) in CH$_2$Cl$_2$ (1 mL) and the mixture stirred at RT for 3.5 hours. The reaction was diluted with CH$_2$Cl$_2$ (10 mL), silica gel was added and the mixture concentrated under reduced pressure. Purification by silica gel chromatography (20% to 25% ethyl acetate/hexanes) gave prodrug MPA-(O-TML-C$_{4-2}$-TG)-OMe (MPA-I-8') (22.0 mg, 94%) as a colorless solid. $^1$H NMR (401 MHz, CDCl$_3$) δ 6.78 (d, J=1.9 Hz, 1H), 6.58 (d, J=1.8 Hz, 1H), 5.28 (m, 1H), 5.10 (s, 2H), 4.99 (m, 1H), 4.29 (dd, J=11.9, 4.4 Hz, 2H), 4.16 (dd, J=11.9, 5.8 Hz, 2H), 3.72 (s, 3H), 3.61 (s, 3H), 3.32 (s, 2H), 3.11 (d, J=5.1 Hz, 2H), 2.92 (t, J=6.7 Hz, 2H), 2.76 (t, J=6.7 Hz, 2H), 2.57 (s, 3H), 2.36-2.22 (m, 8H), 2.19 (s, 3H), 2.17 (s, 3H), 1.73 (s, 3H), 1.65 (s, 6H), 1.64-1.54 (m, 4H), 1.35-1.19 (m, 48H), 0.87 (t, J=6.8 Hz, 6H); $^{13}$C NMR (101 MHz, CDCl$_3$) δ 173.8 (C), 173.5 (2C; C), 171.5 (C), 171.4 (C), 170.0 (C), 168.4 (C), 162.8 (C), 149.6 (C), 146.3 (C), 146.0 (C), 138.2 (C), 136.3 (C), 134.2 (C), 133.5 (C), 132.6 (CH), 129.6 (C), 123.1 (CH), 122.79 (C), 122.77 (CH), 113.6 (C), 69.7 (CH), 68.4 (CH$_2$), 62.0 (2C; CH$_2$), 61.2 (CH$_3$), 51.6 (CH$_3$), 47.0 (CH$_2$), 38.9 (C), 34.5 (CH$_2$), 34.1 (2C; CH$_2$), 32.8 (CH$_2$), 32.1 (2C; CH$_2$), 31.4 (2C; CH$_3$), 29.9 (CH$_2$), 29.84 (6C; CH$_2$), 29.80 (4C; CH$_2$), 29.76 (2C; CH$_2$), 29.6 (2C; CH$_2$), 29.5 (2C; CH$_2$), 29.4 (2C; CH$_2$), 29.2 (2C; CH$_2$), 29.0 (CH$_2$), 25.5 (CH$_3$), 25.0 (2C; CH$_2$), 23.5 (CH$_2$), 22.8 (2C; CH$_2$), 20.4 (CH$_3$), 16.4 (CH$_3$), 14.3 (2C; CH$_3$), 11.9 (CH$_3$); ESI-HRMS: calcd. for C$_{70}$H$_{108}$NaO$_{15}$ [M+Na$^+$] 1211.7580; found 1211.7563.

Example 14: Synthesis of (E)-6-(4-(2-((4-(4-((1,3-bis(palmitoyloxy)propan-2-yl)oxy)-4-oxobutanoyl)oxy)benzyl)oxy)-2-oxoethoxy)-6-methoxy-7-methyl-3-oxo-1,3-dihydroisobenzofuran-5-yl)-4-methylhex-4-enoic acid, MPA-I-9

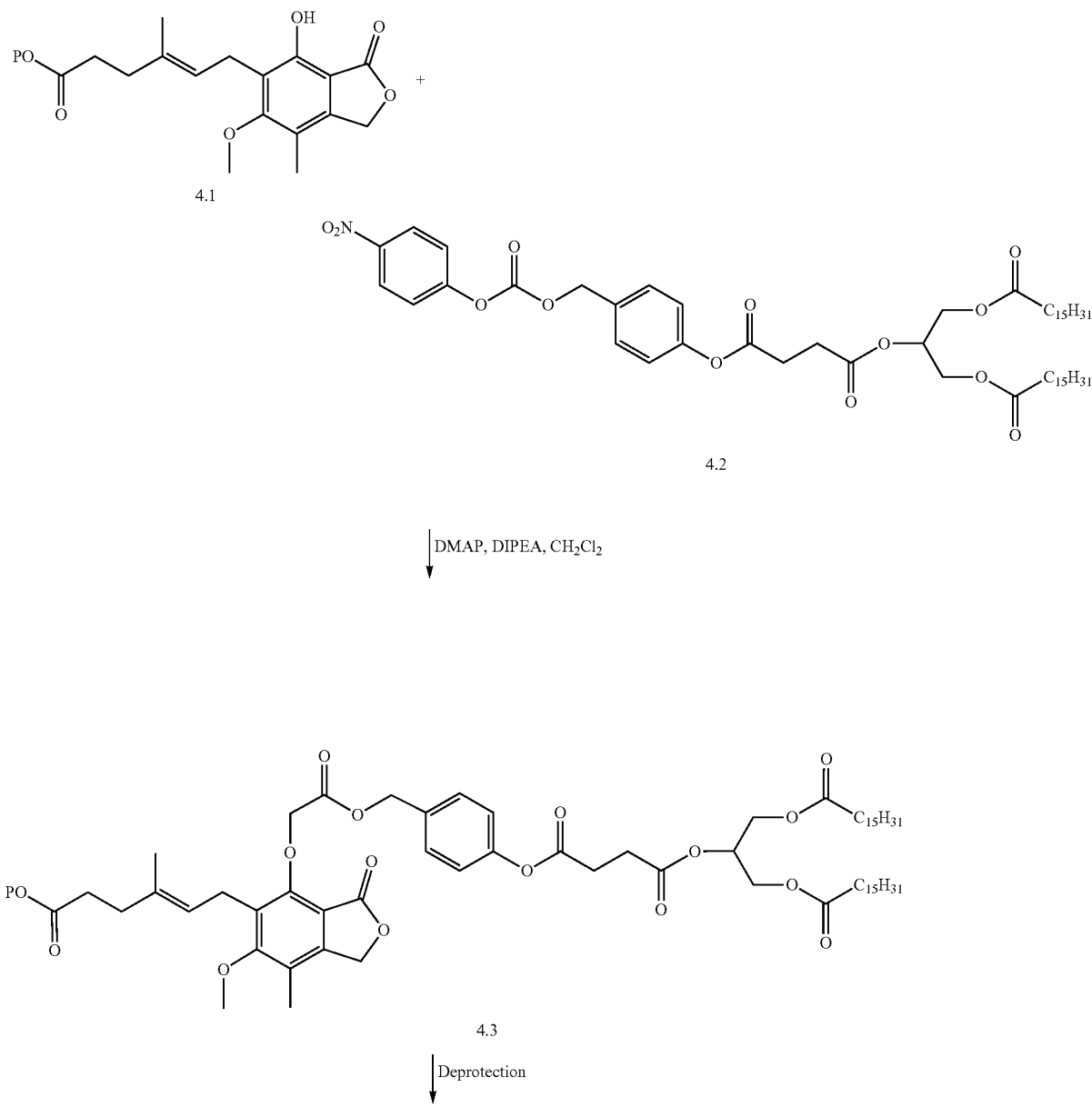

-continued

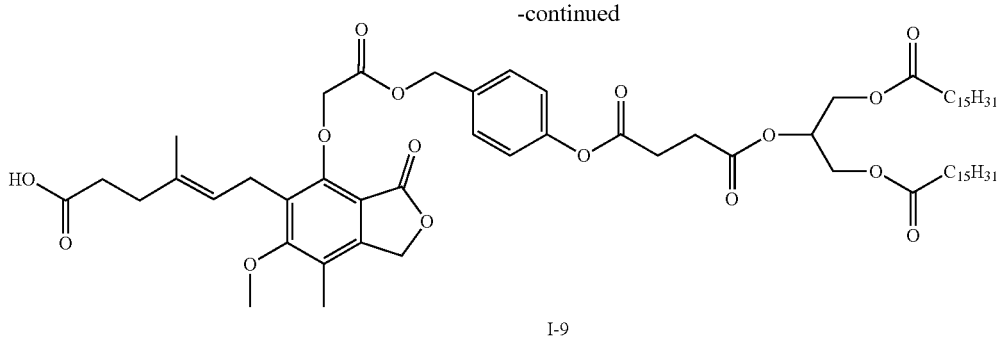

I-9

Synthesis of MPA-I-9

Synthesis of MPA-I-9. MPA-I-9 is prepared according to the following procedure. DMAP (1.3 equiv.) and DIPEA (0.3 equiv.) are added to a solution of a suitably protected mycophenolic acid (i.e. where P is a suitable carboxyl protecting group), 4.1 (1.2 equiv.) and PNP carbonate 4.2 (1.0 equiv.) as prepared in WO 2017/041139, in $CH_2Cl_2$ (0.01 M) and the mixture stirred at rt for about five days. The reaction is diluted with $CH_2Cl_2$, washed with 1 M HCl, water and brine, dried ($MgSO_4$) and concentrated under reduced pressure to give the crude product. Deprotection and purification by silica gel chromatography with a suitable solvent mixture affords MPA-I-9.

Example 15: Synthesis of (E)-6-(4-((4-((4-((1,3-bis (palmitoyloxy)propan-2-yl)oxy)-4-oxobutanoyl)oxy) butanoyl)oxy)-6-methoxy-7-methyl-3-oxo-1,3-dihydroisobenzofuran-5-yl)-4-methylhex-4-enoic acid, MPA-I-10

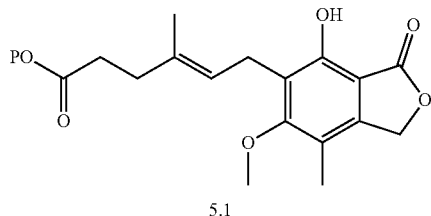

5.1

| DMAP, DCC, 4-bromobutyric acid (5.2)
| $CH_2Cl_2$
↓

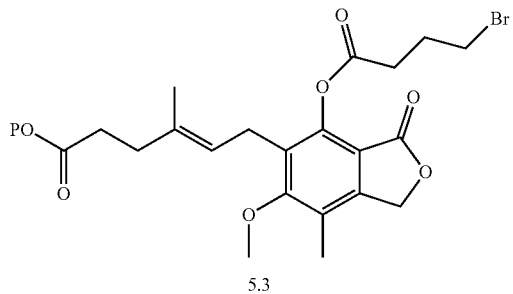

5.3

DBU, toluene, reflux

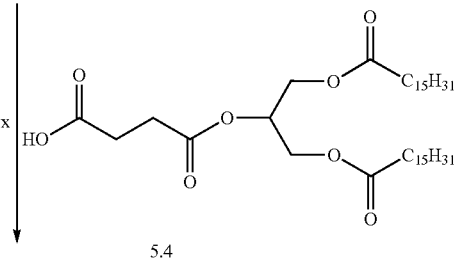

5.4

-continued

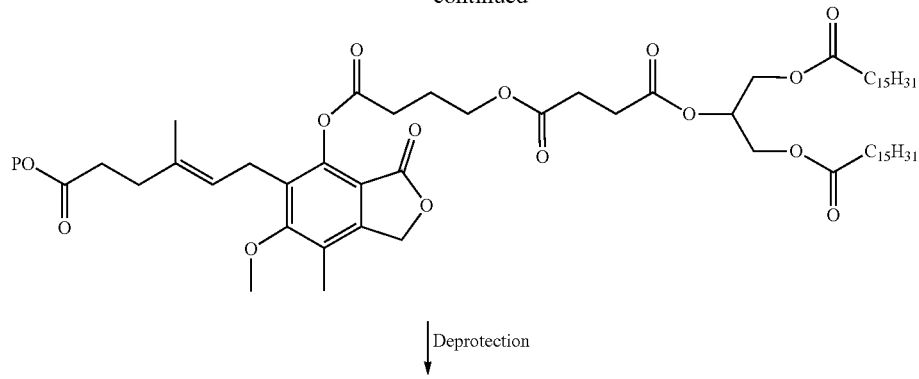

↓ Deprotection

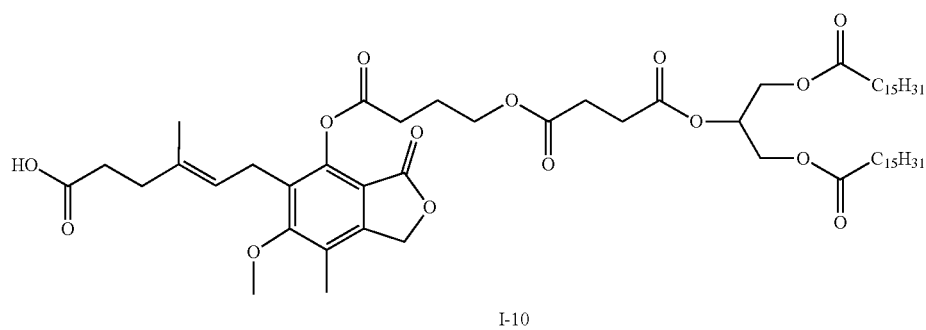

I-10

Synthesis of MPA-T-10

Synthesis of 5.3. DMAP (1.3 equiv.) and DCC (2.1 equiv.) are added to a solution of a suitably protected mycophenolic acid (i.e., where P is a suitable carboxyl protecting group) (1.0 equiv.) and 4-bromobutyric acid 5.2 (1.3 equiv.) in CH$_2$Cl$_2$ (0.03 M) and the mixture is stirred at rt for 24 hours. Another 0.6 eq. of acid, 1 eq. of DCC, 0.6 eq. of DMAP are added and the mixture is stirred at rt for a further two days. The reaction is diluted with CH$_2$Cl$_2$, silica gel is added, and the mixture is concentrated under reduced pressure. Purification by silica gel chromatography gives bromide 5.3.

Synthesis of MPA-I-10. DBU (1.6 equiv.) is added to a suspension of acid 5.4 (1.1 equiv.) as prepared in WO 2017/041139, and bromide 5.3 (1.0 equiv.) in toluene (0.03 M) and the mixture is heated at reflux for 21 hours. The reaction is cooled to rt, then diluted with ethyl acetate. The organic phase is washed with water and brine, dried (MgSO$_4$) and concentrated under reduced pressure to give the crude product. Deprotection and purification by silica gel chromatography with a suitable solvent mixture affords MPA-I-10.

Compounds MPA-I-1, MPA-I-2, MPA-I-3, MPA-I-4, MPA-I-5, MPA-I-11, MPA-I-12, MPA-I-13, MPA-I-14, and MPA-I-15 may be prepared by methods substantially similar to those described in Examples 1 through 5, the General Synthetic Schemes provided herein, and methods known to one of ordinary skill in the art.

Example 16: Synthesis of MPA-Phenol Prodrugs

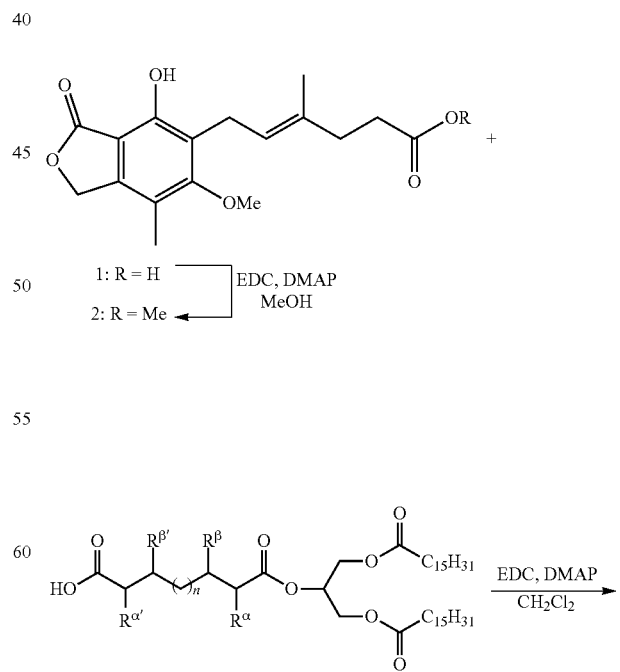

-continued

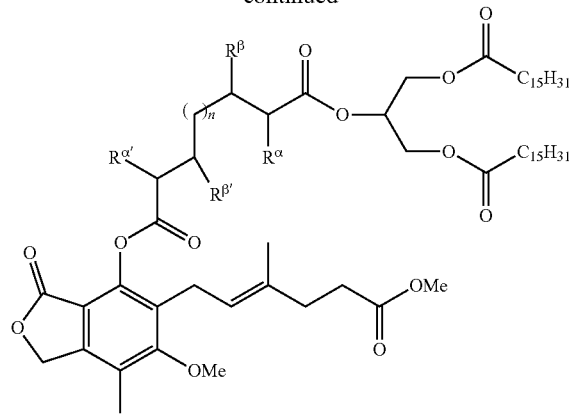

4

$R^α, R^β, R^{α'}, R^{β'}$ = H or Me

Synthesis of MPA-Phenol Prodrugs
(Directly-Linked)

MPA Methyl Ester (Methyl (E)-6-(4-hydroxy-6-methoxy-7-methyl-3-oxo-1,3-dihydroisobenzofuran-5-yl)-4-methylhex-4-enoate) (2)

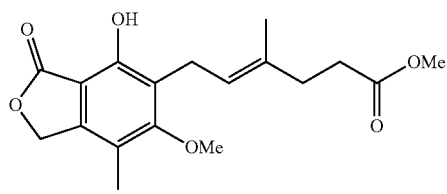

2

DMAP (95.3 mg, 0.280 mmol) and EDC·HCl (300 mg, 1.56 mmol) were added to a solution of mycophenolic acid (1) (250 mg, 0.780 mmol) in CH$_2$Cl$_2$ (5 mL) and MeOH (3 mL) and the mixture stirred at rt for 17 hours. The reaction was diluted with CH$_2$Cl$_2$ (20 mL), silica gel was added and the solvent removed under reduced pressure. Purification by silica gel chromatography (25% to 30% ethyl acetate/hexanes) gave methyl ester 2 (125 mg, 48%) as a colorless solid. $^1$H NMR (401 MHz, CDCl$_3$) δ 7.66 (s, 1H), 5.23 (m, 1H), 5.19 (s, 2H), 3.75 (s, 3H), 3.61 (s, 3H), 3.37 (d, J=6.8 Hz, 2H), 2.42-2.36 (m, 2H), 2.33-2.26 (m, 2H), 2.14 (s, 3H), 1.79 (s, 3H). $^{13}$C NMR (101 MHz, CDCl$_3$) δ 173.9 (C), 173.1 (C), 163.8 (C), 153.8 (C), 144.1 (C), 134.3 (C), 122.9 (CH), 122.3 (C), 116.8 (C), 106.5 (C), 70.2 (CH$_2$), 61.1 (CH$_3$), 51.6 (CH$_3$), 34.7 (CH$_2$), 33.0 (CH$_2$), 22.7 (CH$_2$), 16.2 (CH$_3$), 11.7 (CH$_3$).

(E)-1-(1,3-Bis(palmitoyloxy)propan-2-yl) 10-(6-methoxy-5-(6-methoxy-3-methyl-6-oxohex-2-en-1-yl)-7-methyl-3-oxo-1,3-dihydroisobenzofuran-4-yl) 3-methyldecane-dioate (4d; n=4, $R^β$=Me) (MPA-I-16)

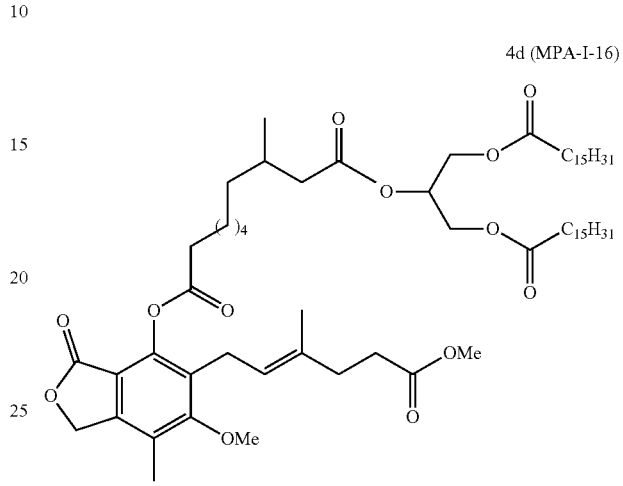

4d (MPA-I-16)

DMAP (2.4 mg, 19.6 μmol) and EDC·HCl (9.4 mg, 48.9 μmol) were added to a solution of methyl ester 2 (6.5 mg, 19.6 μmol) and acid-TG Int-30 (15.0 mg, 19.6 μmol) in CH$_2$Cl$_2$ (1.2 mL) and the mixture stirred at RT for 18 hours. The reaction was diluted with CH$_2$Cl$_2$ (5 mL), silica gel was added and the mixture concentrated under reduced pressure. Purification by silica gel chromatography (25% ethyl acetate/hexanes) gave MPA prodrug MPA-(O-C10bMe-2-TG)-OMe (4d) (MPA-I-16) (19.3 mg, 91%) as a colorless oil. $^1$H NMR (401 MHz, CDCl$_3$) δ 5.27 (m, 1H), 5.13 (s, 2H), 5.10 (m, 1H), 4.28 (dd, J=12.0, 3.9 Hz, 2H), 4.14 (dd, J=11.9, 5.9 Hz, 2H), 3.78 (s, 3H), 3.62 (s, 3H), 3.33 (d, J=6.5 Hz, 2H), 2.67 (t, J=7.5 Hz, 2H), 2.41-2.25 (m, 9H), 2.21 (s, 3H), 2.11 (dd, J=14.7, 8.6 Hz, 1H), 1.94 (m, 1H), 1.83-1.73 (m, 2H), 1.76 (s, 3H), 1.65-1.55 (m, 4H), 1.49-1.16 (m, 56H), 0.93 (d, J=6.6 Hz, 3H), 0.87 (t, J=6.8 Hz, 6H); $^{13}$C NMR (101 MHz, CDCl$_3$) δ 173.8 (C), 173.4 (2C; C), 172.5 (C), 171.8 (C), 168.4 (C), 162.8 (C), 146.3 (C), 146.2 (C), 134.6 (C), 129.4 (C), 122.9 (C), 122.5 (CH), 113.7 (C), 68.9 (CH), 68.4 (CH$_2$), 62.3 (2C; CH$_2$), 61.3 (CH$_3$), 51.6 (CH$_3$), 41.8 (CH$_2$), 36.8 (CH$_2$), 34.6 (CH$_2$), 34.2 (2C; CH$_2$), 34.0 (CH$_2$), 32.9 (CH$_2$), 32.1 (2C; CH$_2$), 30.5 (CH), 29.84 (6C; CH$_2$), 29.80 (4C; CH$_2$), 29.76 (2C; CH$_2$), 29.62 (3C; CH$_2$), 29.50 (2C; CH$_2$), 29.41 (2C; CH$_2$), 29.30 (CH$_2$), 29.26 (2C; CH$_2$), 26.9 (CH$_2$), 25.0 (2C; CH$_2$), 24.7 (CH$_2$), 23.7 (CH$_2$), 22.8 (2C; CH$_2$), 19.6 (CH$_3$), 16.4 (CH$_3$), 14.3 (2C; CH$_3$), 11.9 (CH$_3$).

Further compounds were prepared in a similar manner as described below.

4a (MPA-I-17)

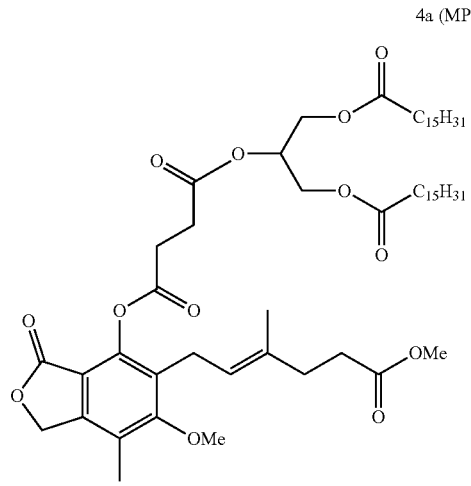

DMAP (11.4 mg, 0.0933 mmol) and EDC·HCl (32.1 mg, 0.167 mmol) were added to a solution of methyl ester 2 (31.0 mg, 0.0930 mmol) and acid-TG Int-28 (62.2 mg, 0.0930 μmol) in CH$_2$Cl$_2$ (4 mL) and the mixture stirred at RT for 18 hours. The reaction was diluted with CH$_2$Cl$_2$ (20 mL), washed with water (20 mL), dried (MgSO$_4$) and concentrated under reduced pressure to give the crude product. Purification by silica gel chromatography (15% ethyl acetate/hexanes) gave MPA prodrug MPA-(O-C4-2-TG)-OMe (MPA-I-17) (38.5 mg, 42%) as a colorless oil. $^1$H NMR (400 MHz, CDCl$_3$) δ 5.28 (m, 1H), 5.14 (s, 2H), 5.12 (m, 1H), 4.29 (dd, J=11.9, 4.4 Hz, 2H), 4.16 (dd, J=11.9, 5.7 Hz, 2H), 3.78 (s, 3H), 3.61 (s, 3H), 3.35 (d, J=6.8 Hz, 2H), 3.03 (t, J=7.1 Hz, 2H), 2.83 (t, J=7.0 Hz, 2H), 2.41-2.35 (m, 2H), 2.33-2.27 (m, 6H), 2.22 (s, 3H), 1.79 (s, 3H), 1.64-1.55 (m, 4H), 1.37-1.17 (m, 48H), 0.87 (t, J=6.9 Hz, 6H).

4b (MPA-I-18)

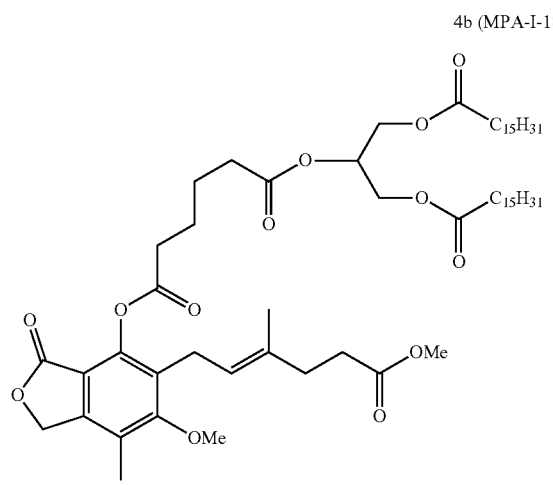

DMAP, 6.0 mg, 49.1 μmol) and DCC (19.0 mg, 92.1 μmol) were added to a solution of methyl ester 2 (17.0 mg, 50.8 μmol) and acid-TG Int-29 (35.0 mg, 50.2 μmol) in CH$_2$Cl$_2$ (2 mL) and the mixture stirred at RT for 18 hours. The reaction was diluted with CH$_2$Cl$_2$ (5 mL), silica gel was added and the mixture concentrated under reduced pressure. Purification by silica gel chromatography (20% ethyl acetate/hexanes) gave MPA prodrug MPA-(O-C6-2-TG)-OMe (4b) (MPA-I-18) (25.0 mg, 49%) as a colorless oil. $^1$H NMR (400 MHz, CDCl$_3$) δ 5.26 (m, 1H), 5.14 (s, 2H), 5.10 (td, J=6.7, 1.1 Hz, 1H), 4.30 (dd, J=11.9, 4.4 Hz, 2H), 4.15 (dd, J=11.9, 5.8 Hz, 2H), 3.78 (s, 3H), 3.62 (s, 3H), 3.33 (d, J=6.5 Hz, 2H), 2.70 (t, J=6.8 Hz, 2H), 2.44-2.25 (m, 10H), 2.22 (s, 3H), 1.89-1.73 (m, 4H), 1.77 (s, 3H), 1.65-1.55 (m, 4H), 1.33-1.20 (m, 48H), 0.88 (t, J=6.9 Hz, 6H).

4c (MPA-I-19)

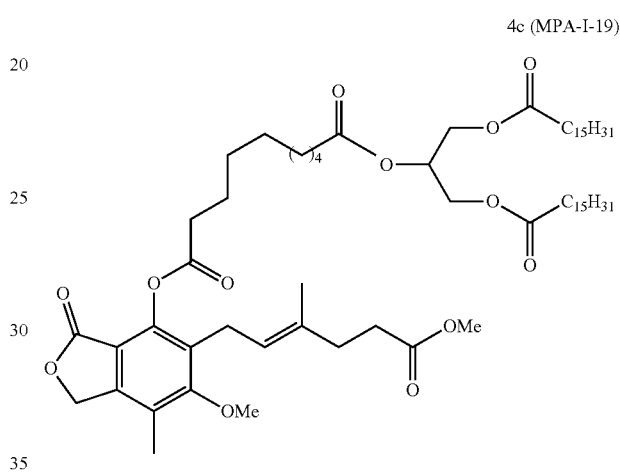

DMAP (5.2 mg, 42.5 μmol) and EDC·HCl (14.1 mg, 73.5 μmol) were added to a solution of methyl ester 2 (12.0 mg, 35.8 μmol) and acid-TG Int-9 (28.0 mg, 19.6 μmol) in CH$_2$Cl$_2$ (0.8 mL) and the mixture stirred at RT for 20 hours. The reaction was diluted with CH$_2$Cl$_2$ (5 mL), silica gel was added and the mixture concentrated under reduced pressure. Purification by silica gel chromatography (10% to 25% ethyl acetate/hexanes) gave MPA prodrug MPA-(O-C10-2-TG)-OMe (4c) (MPA-I-19) (30.5 mg, 80%) as a colorless oil. $^1$H NMR (401 MHz, CDCl$_3$) δ 5.26 (m, 1H), 5.13 (s, 2H), 5.10 (td, J=6.7, 1.1 Hz, 1H), 4.29 (dd, J=11.9, 4.4 Hz, 2H), 4.14 (dd, J=11.9, 5.9 Hz, 2H), 3.77 (s, 3H), 3.62 (s, 3H), 3.33 (d, J=6.6 Hz, 2H), 2.67 (t, J=7.6 Hz, 2H), 2.41-2.25 (m, 10H), 2.21 (s, 3H), 1.82-1.73 (m, 2H), 1.76 (s, 3H), 1.68-1.55 (m, 6H), 1.47-1.19 (m, 66H), 0.87 (t, J=6.8 Hz, 6H).

4e (MPA-I-20)

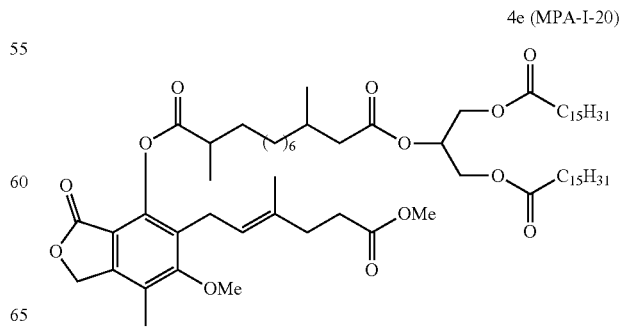

DMAP (2.2 mg, 17.9 µmol) and EDC·HCl (7.1 mg, 37.1 µmol) were added to a solution of methyl ester 2 (6.0 mg, 17.9 µmol) and acid-TG Int-27 (14.5 mg, 17.9 µmol) in CH$_2$Cl$_2$ (1 mL) and the mixture stirred at RT for 18 hours. The reaction was diluted with CH$_2$Cl$_2$ (5 mL), silica gel was added and the mixture concentrated under reduced pressure. Purification by silica gel chromatography (20% ethyl acetate/hexanes) gave MPA prodrug MPA-(O-C12a'bMe-2-TG)-OMe (4e) (MPA-I-20) (18.8 mg, 93%) as a colorless oil. $^1$H NMR (401 MHz, CDCl$_3$) δ 5.27 (m, 1H), 5.13 (s, 2H), 5.10 (td, J=6.5, 1.1 Hz, 1H), 4.284/4.282 (each dd, J=11.8, 4.3 Hz, 2H), 4.14 (dd, J=11.8, 6.0 Hz, 2H), 3.77 (s, 3H), 3.61 (s, 3H), 3.32 (br s, 2H), 2.79 (m, 1H), 2.40-2.34 (m, 2H), 2.33-2.26 (m, 7H), 2.21 (s, 3H), 2.11 (dd, J=14.7, 8.5 Hz, 1H), 1.98-1.85 (m, 2H), 1.76 (s, 3H), 1.65-1.54 (m, 4H), 1.36 (d, J=7.0 Hz, 3H), 1.47-1.16 (m, 61H), 0.93 (d, J=6.6 Hz, 3H), 0.87 (t, J=6.9 Hz, 6H); $^{13}$C NMR (101 MHz, CDCl$_3$) δ 174.6 (C), 173.7 (C), 173.4 (2C; C), 172.5 (C), 168.3 (C), 162.8 (C), 146.3 (C), 146.2 (C), 134.6 (C), 129.4 (C), 122.9 (C), 122.6 (CH), 113.8 (C), 68.9 (CH), 68.3 (CH$_2$), 62.3 (2C; CH$_2$), 61.2 (CH$_3$), 51.6 (CH$_3$), 41.8 (CH$_2$), 39.5 (CH), 36.9 (CH$_2$), 34.5 (CH$_2$), 34.2 (2C; CH$_2$), 33.4 (CH$_2$), 32.9 (CH$_2$), 32.1 (2C; CH$_2$), 30.5 (CH), 29.9 (CH$_2$), 29.82 (6C; CH$_2$), 29.78 (4C; CH$_2$), 29.74 (3C; CH$_2$), 29.68 (CH$_2$), 29.6 (2C; CH$_2$), 29.5 (2C; CH$_2$), 29.4 (2C; CH$_2$), 29.2 (2C; CH$_2$), 27.3 (CH$_2$), 27.1 (CH$_2$), 25.0 (2C; CH$_2$), 23.6 (CH$_2$), 22.8 (2C; CH$_2$), 19.6 (CH$_3$), 16.8 (CH$_3$), 16.5 (CH$_3$), 14.2 (2C; CH$_3$), 11.9 (CH$_3$).

(E)-15-(1,3-bis(palmitoyloxy)propan-2-yl) 1-(6-methoxy-5-(6-methoxy-3-methyl-6-oxohex-2-en-1-yl)-7-methyl-3-oxo-1,3-dihydroisobenzofuran-4-yl) 2,13-dimethylpentadecanedioate (MPA-I-29)

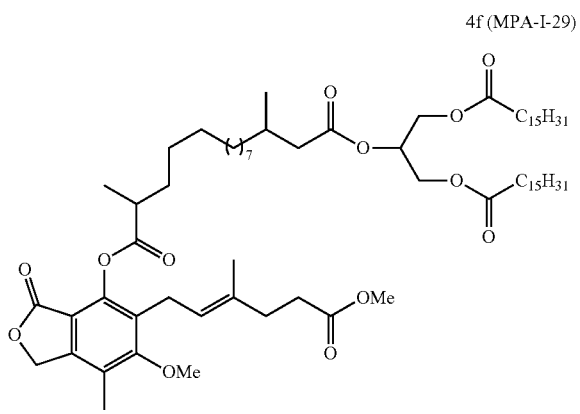

4f (MPA-I-29)

DMAP (4.3 mg, 35.1 µmol) and EDC·HCl (11.8 mg, 61.5 µmol) were added to a solution of methyl ester 2 (10.0 mg, 29.9 µmol) and acid-TG Int-62 (27.5 mg, 32.3 µmol) in CH$_2$Cl$_2$ (0.8 mL) and the mixture stirred at RT for 18 hours. The reaction was diluted with CH$_2$Cl$_2$ (5 mL), silica gel was added, and the mixture was concentrated under reduced pressure. Purification by silica gel chromatography (25% ethyl acetate/hexanes) gave prodrug MPA-(O-C15a'bMe-2-TG)-OMe 4f (MPA-I-29) (34.3 mg, 98%) as a colorless oil. $^1$H NMR (401 MHz, CDCl$_3$) δ 5.27 (m, 1H), 5.14 (s, 2H), 5.10 (td, J=6.6, 1.2 Hz, 1H), 4.29 (dd, J=11.9, 4.3 Hz, 2H), 4.14 (td, J=11.9, 6.0 Hz, 2H), 3.77 (s, 3H), 3.62 (s, 3H), 3.32 (br s, 2H), 2.80 (dd, J=13.9, 7.0 Hz, 1H), 2.41-2.26 (m, 9H), 2.22 (s, 3H), 2.11 (dd, J=14.7, 8.4 Hz, 1H), 1.97-1.86 (s, 2H), 1.76 (s, 3H), 1.65-1.53 (m, 6H), 1.36 (d, J=7.0 Hz, 3H), 1.47-1.15 (m, 69H), 0.92 (d, J=6.6 Hz, 3H), 0.87 (t, J=6.9 Hz, 6H).

(E)-1-(1,3-bis(palmitoyloxy)propan-2-yl) 12-(6-methoxy-5-(6-methoxy-3-methyl-6-oxohex-2-en-1-yl)-7-methyl-3-oxo-1,3-dihydroisobenzofuran-4-yl) dodecanedioate (MPA-I-30)

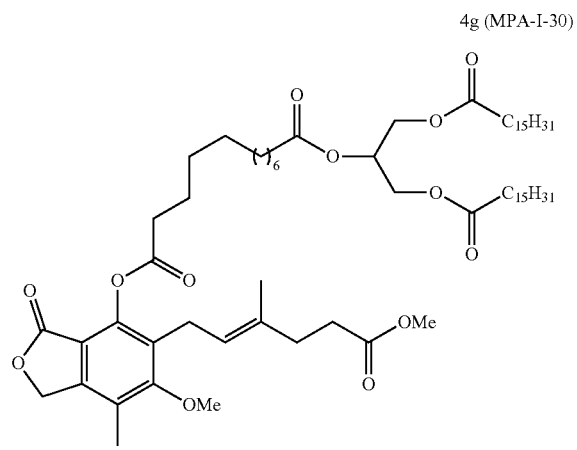

4g (MPA-I-30)

DMAP (2.9 mg, 23.9 µmol) and EDC·HCl (11.5 mg, 59.8 µmol) were added to a solution of methyl ester 2 (8.0 mg, 23.9 µmol) and acid-TG Int-37 (22.4 mg, 28.7 µmol) in CH$_2$Cl$_2$ (0.8 mL) and the mixture stirred at RT for 17 hours. The reaction was diluted with CH$_2$Cl$_2$ (5 mL), silica gel was added and the mixture concentrated under reduced pressure. Purification by silica gel chromatography (4% to 8% ethyl acetate/toluene) gave prodrug MPA(O-C12-2-TG)-OMe 4 g (MPA-I-30) (9.1 mg, 35%) as a colorless oil. $^1$H NMR (400 MHz, CDCl$_3$) δ 5.26 (m, 1H), 5.14 (s, 2H), 5.10 (td, J=6.7, 1.2 Hz, 1H), 4.29 (dd, J=11.9, 4.4 Hz, 2H), 4.14 (dd, J=11.9, 5.9 Hz, 2H), 3.78 (s, 3H), 3.62 (s, 3H), 3.33 (d, J=6.6 Hz, 2H), 2.67 (t, J=7.6 Hz, 2H), 2.41-2.35 (m, 2H), 2.34-2.27 (m, 8H), 2.22 (s, 3H), 1.83-1.73 (m, 2H), 1.76 (s, 3H), 1.66-1.55 (m, 6H), 1.48-1.20 (m, 60H), 0.88 (t, J=6.9 Hz, 6H); $^{13}$C NMR (101 MHz, CDCl$_3$) δ 173.8 (C), 173.5 (2C; C), 173.0 (C), 171.8 (C), 168.4 (C), 162.8 (C), 146.3 (C), 146.2 (C), 134.6 (C), 129.4 (C), 122.9 (C), 122.5 (CH), 113.8 (C), 69.0 (CH), 68.4 (CH$_2$), 62.2 (2C; CH$_2$), 61.3 (CH$_3$), 51.6 (CH$_3$), 34.6 (CH$_2$), 34.4 (CH$_2$), 34.2 (2C; CH$_2$), 34.0 (CH$_2$), 32.9 (CH$_2$), 32.1 (2C; CH$_2$), 29.85 (6C; CH$_2$), 29.81 (4C; CH$_2$), 29.77 (2C; CH$_2$), 29.62 (4C; CH$_2$), 29.51 (2C; CH$_2$), 29.47 (CH$_2$), 29.44 (CH$_2$), 29.42 (2C; CH$_2$), 29.34 (CH$_2$), 29.27 (3C; CH$_2$), 25.1 (CH$_2$), 25.0 (2C; CH$_2$), 24.8 (CH$_2$), 23.7 (CH$_2$), 22.8 (2C; CH$_2$), 16.4 (CH$_3$), 14.3 (2C; CH$_3$), 11.9 (CH$_3$).

357

(E)-1-(1,3-bis(palmitoyloxy)propan-2-yl) 15-(6-methoxy-5-(6-methoxy-3-methyl-6-oxohex-2-en-1-yl)-7-methyl-3-oxo-1,3-dihydroisobenzofuran-4-yl) 3-methylpentadecanedioate (MPA-I-31)

358

(E)-12-(1,3-bis(palmitoyloxy)propan-2-yl) 1-(6-methoxy-7-methyl-5-(3-methyl-6-(2-morpholinoethoxy)-6-oxohex-2-en-1-yl)-3-oxo-1,3-dihydroisobenzofuran-4-yl) 2,10-dimethyldodecanedioate (MPA-I-32)

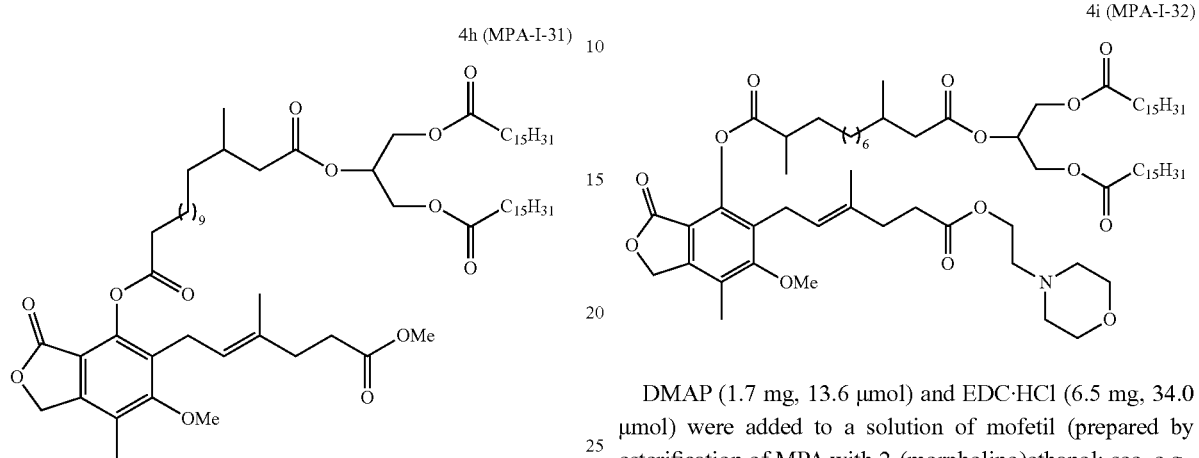

4h (MPA-I-31)

4i (MPA-I-32)

DMAP (1.5 mg, 11.9 μmol) and EDC·HCl (5.7 mg, 29.9 μmol) were added to a solution of methyl ester 2 (4.0 mg, 11.9 μmol) and acid-TG Int-49 (12.0 mg, 14.3 μmol) in $CH_2Cl_2$ (0.8 mL) and the mixture stirred at RT for five hours. The reaction was diluted with $CH_2Cl_2$ (5 mL), silica gel was added, and the mixture concentrated under reduced pressure. Purification by silica gel chromatography (5% to 8% ethyl acetate/toluene) gave prodrug MPA(O-C15bMe-2-TG)-OMe 4h (MPA-I-31) (10.8 mg, 78%) as a colorless oil. $^1$H NMR (400 MHz, $CDCl_3$) δ 5.27 (m, 1H), 5.14 (s, 2H), 5.10 (td, J=6.7, 1.2 Hz, 1H), 4.286/4.285 (each dd, J=11.9, 4.2 Hz, 2H), 4.141-4.139 (dd, J=11.9, 6.0 Hz, 2H), 3.78 (s, 3H), 3.62 (s, 3H), 3.33 (d, J=6.5 Hz, 2H), 2.67 (t, J=7.6 Hz, 2H), 2.41-2.25 (m, 5H), 2.30 (t, J=7.6 Hz, 4H), 2.22 (s, 3H), 2.11 (dd, J=14.7, 8.4 Hz, 1H), 1.93 (m, 1H), 1.83-1.73 (m, 2H), 1.76 (s, 3H), 1.65-1.55 (m, 4H), 1.47-1.14 (m, 66H), 0.93 (d, J=6.6 Hz, 3H), 0.87 (t, J=6.8 Hz, 6H); $^{13}$C NMR (101 MHz, $CDCl_3$) δ 173.8 (C), 173.5 (2C; C), 172.5 (C), 171.8 (C), 168.4 (C), 162.8 (C), 146.3 (C), 146.2 (C), 134.6 (C), 129.4 (C), 122.9 (C), 122.5 (CH), 113.8 (C), 68.9 (CH), 68.4 ($CH_2$), 62.3 (2C; $CH_2$), 61.3 ($CH_3$), 51.7 ($CH_3$), 41.9 ($CH_2$), 36.9 ($CH_2$), 34.6 ($CH_2$), 34.2 (2C; $CH_2$), 34.0 ($CH_2$), 32.9 ($CH_2$), 32.1 (2C; $CH_2$), 30.5 (CH), 30.0 ($CH_2$), 29.85 (7C; $CH_2$), 29.81 (4C; $CH_2$), 29.77 (2C; $CH_2$), 29.67 ($CH_2$), 29.62 (2C; $CH_2$), 29.51 (4C; $CH_2$), 29.42 (2C; $CH_2$), 29.36 ($CH_2$), 29.27 (3C; $CH_2$), 27.1 ($CH_2$), 25.0 (2C; $CH_2$), 24.8 ($CH_2$), 23.7 ($CH_2$), 22.8 (2C; $CH_2$), 19.7 ($CH_3$), 16.4 ($CH_3$), 14.3 (2C; $CH_3$), 11.9 ($CH_3$).

DMAP (1.7 mg, 13.6 μmol) and EDC·HCl (6.5 mg, 34.0 μmol) were added to a solution of mofetil (prepared by esterification of MPA with 2-(morpholino)ethanol; see, e.g., US 2010/0298560, hereby incorporated by reference in its entirety) (5.9 mg, 13.6 μmol) and acid-TG Int-27 (11.0 mg, 13.6 μmol) in $CH_2Cl_2$ (0.8 mL) and the mixture stirred at RT for 18 hours. The reaction was diluted with $CH_2Cl_2$ (5 mL), silica gel was added, and the mixture concentrated under reduced pressure. Purification by silica gel chromatography (50% to 75% ethyl acetate/hexanes) gave prodrug MPA-(O-C12a'bMe-2-TG)-OMF 4i (MPA-I-32) (11.7 mg, 70%) as a colorless oil. $^1$H NMR (400 MHz, $CD_3OD$) δ 5.31-5.24 (m, 3H), 5.07 (td, J=6.3, 1.0 Hz, 1H), 4.357/4.355 (each dd, J=11.9, 3.8 Hz, 2H), 4.21 (t, J=5.4 Hz, 2H), 4.159/4.155 (each dd, J=12.0, 6.3 Hz, 2H), 3.81 (s, 3H), 3.77-3.68 (m, 4H), 3.37 (d, J=5.0 Hz, 2H), 2.94-2.64 (m, 7H), 2.49-2.41 (m, 2H), 2.36-2.24 (m, 7H), 2.27 (s, 3H), 2.15 (dd, J=14.7, 7.7 Hz, 1H), 1.98-1.84 (m, 2H), 1.80 (s, 3H), 1.66-1.54 (m, 4H), 1.34 (d, J=7.0 Hz, 3H), 1.52-1.19 (m, 62H), 0.96 (d, J=6.7 Hz, 3H), 0.90 (t, J=6.8 Hz, 6H); $^{13}$C NMR (101 MHz, $CD_3OD$) δ 174.8 (2C; C), 170.3 (C), 164.2 (C), 148.5 (C), 147.1 (C), 135.8 (C), 130.4 (C), 124.7 (C), 123.8 (CH), 114.5 (C), 70.6 (CH), 69.9 ($CH_2$), 66.9 (2C; $CH_2$), 63.4 (2C; $CH_2$), 61.9 ($CH_3$), 61.3 ($CH_2$), 57.8 ($CH_2$), 54.5 (2C; $CH_2$), 42.6 ($CH_2$), 40.6 (CH), 37.7 ($CH_2$), 35.3 ($CH_2$), 34.9 ($CH_2$), 34.7 ($CH_2$), 33.5 ($CH_2$), 33.1 ($CH_2$), 31.6 (CH), 30.9 ($CH_2$), 30.82 (6C; $CH_2$), 30.81 (5C; $CH_2$), 30.75 (3C; $CH_2$), 30.6 (2C; $CH_2$), 30.5 (2C; $CH_2$), 30.4 (2C; $CH_2$), 30.2 (2C; $CH_2$), 28.3 ($CH_2$), 28.1 ($CH_2$), 26.0 (2C; $CH_2$), 24.4 ($CH_2$), 23.7 (2C; $CH_2$), 20.2 ($CH_3$), 17.4 ($CH_3$), 16.7 ($CH_3$), 14.5 (2C; $CH_3$), 11.8 ($CH_3$). Note: A number of C=O signals were not observed, while a number of other signals were significantly broadened in both the $^1$H and $^{13}$C NMR spectra. A larger amount of sample will be required to re-acquire the $^{13}$C NMR spectrum to observe all signals; ESI-HRMS: calcd. for $C_{72}H_{122}NO_{14}$ [M+H$^+$]1224.8860; found 1224.8866.

(E)-1-(1,3-bis(palmitoyloxy)propan-2-yl) 12-(6-methoxy-5-(6-methoxy-3-methyl-6-oxohex-2-en-1-yl)-7-methyl-3-oxo-1,3-dihydroisobenzofuran-4-yl) 2,11-dimethyldodecanedioate (MPA-I-42)

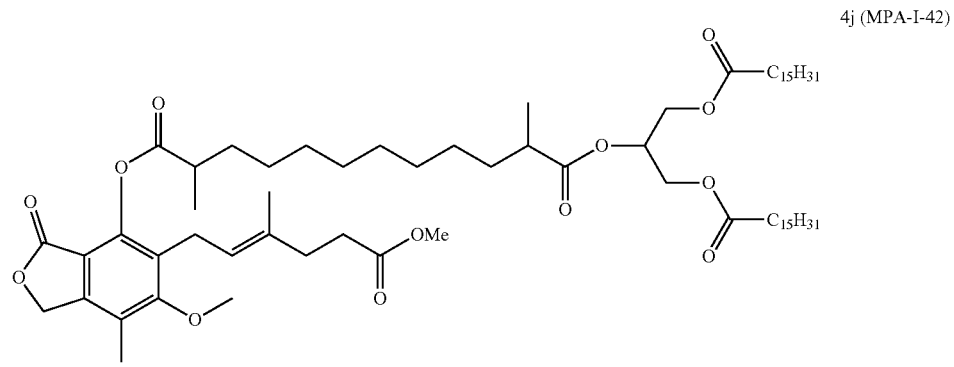

4j (MPA-I-42)

To a solution of methyl ester 2 (0.2 g, 0.247 mmol) in chloroform (10 ml) were added DCC (0.101 g, 0.494 mmol) and DMAP (0.060 g, 0.494 mmol), then the reaction mixture was stirred at rt for 30 min, then Int-81 (0.165 g, 0.494 mmol) was added and stirred at rt for 18 h. The reaction was monitored by TLC. After completion of the reaction, the reaction mixture was filtered through a celite bed and washed with DCM (50 mL), then the filtrate was evaporated to obtain crude product, which was purified by combi flash purification to obtain MPA-(O-C12a'aMe-2-TG)-OMe (MPA-I-42) (0.080 g, 28.7%) as a viscous liquid. $^1$H NMR (400 MHz, CDCl$_3$) δ 5.30 (t, J=5.3 Hz, 1H), 5.16 (s, 2H), 5.13 (d, J=16.8 Hz, 1H), 4.31 (dd, J=11.7, 3.7 Hz, 2H), 4.17 (dd, J=11.9, 6.1 Hz, 2H), 3.79 (s, 3H), 3.64 (s, 3H), 3.34 (bs, 2H), 2.82 (q, J=6.9 Hz, 1H), 2.48-2.30 (m, 10H), 2.24 (s, 3H), 1.92 (s, 2H), 1.78 (s, 3H), 1.64-1.52 (m, 10H), 1.39-1.37 (m, 10H), 1.28 (m, 48H), 1.16 (d, J=6.8 Hz, 3H), 0.89 (t, J=6.8 Hz, 6H); $^{13}$C NMR (101 MHz, CDCl$_3$) δ 175.96 (1C), 174.55 (1C), 173.65 (1C), 173.32 (2C), 168.19 (1C), 162.63 (1C), 146.22 (1C), 146.01 (1C), 134.53 (1C), 129.32 (1C), 122.80 (1C), 122.47 (2C), 113.72 (1C), 68.69 (1C), 68.26 (1C), 62.16 (1C), 61.15 (1C), 51.55 (1C), 39.55 (1C), 39.39 (1C), 34.38 (1C), 34.07 (2C), 33.65 (1C), 33.33 (1C), 32.74 (1C), 31.96 (3C), 29.73-29.16 (23C), 27.22 (1C), 24.88 (2C), 23.53 (1C), 22.73 (2C), 17.04 (1C), 16.74 (1C), 16.39 (1C), 14.17 (3C), 11.79 (1C). HPLC (ELSD): 9.90 min, 100% purity; HPLC (uv-215 nm): 9.86 min, 99.03% purity; LCMS: 9.22 min 100% purity. MASS (ESI, +ve) m/z: 1143.05 (MH+1). ELSD Method: –PDS_ HPLC_ GEMINI_C4_JUPITER_GRA-1. Mobile Phase: 100% MeOH; System: Agilent Technologies 1260 Infinity with PDA Detector & ELSD Detector; Column: Phenomenex JUPITER C4, 100*4.6 mm, 5p; Column Flow: 1.0 ml/min; Column Temp: Ambient; ELSD: SPRAY CHAMBER –50° C.

Compound MPA-(O-C10aMe-2-TG)-OMe (MPA-I-45) was prepared using similar methods as those described above.

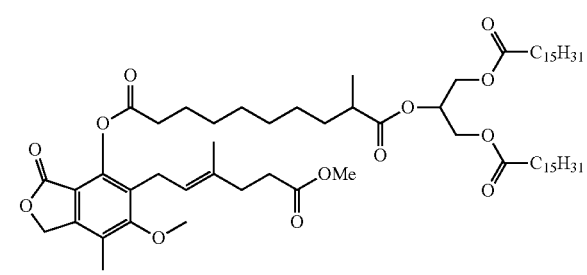

4k (MPA-I-45)

$^1$H NMR (400 MHz, CDCl$_3$) δ 5.31 (t, J=4.8 Hz, 1H), 5.18 (s, 2H), 5.14 (m, 1H), 4.31 (dd, J=11.9, 3.9 Hz, 2H), 4.17 (dd, J=11.9, 6.1 Hz, 2H), 3.82 (s, 3H), 3.67 (s, 3H), 3.38 (d, J=6.0 Hz, 2H), 2.71 (t, J=6.8 Hz, 2H), 2.51-2.49 (m, 1H), 2.47 (m, 2H), 2.38 (dt, J=28.8, 7.3 Hz, 6H), 2.26 (s, 3H), 1.81 (s, 4H), 1.69-1.58 (m, 4H), 1.45 (s, 4H), 1.29 (s, 54H), 1.19 (d, J=7.0 Hz, 4H), 0.92 (t, J=6.7 Hz, 6H); $^{13}$C NMR (101 MHz, CDCl$_3$) δ 175.93 (1C), 173.66 (1C), 173.33 (2C), 171.65 (1C), 168.29 (1C), 162.65 (1C), 146.18 (1C), 146.02 (1C), 134.48 (1C), 129.23 (1C), 122.84 (1C), 122.37 (2C), 113.60 (1C), 68.71 (1C), 68.34 (1C), 62.16 (2C), 61.19 (2C), 51.55 (2C), 39.53 (1C), 34.43 (1C), 34.08 (2C), 33.84 (1C), 33.58 (1C), 32.74 (1C), 31.96 (2C), 29.74-28.95 (20C), 27.16 (1C), 24.89 (2C), 24.60 (1C), 23.57 (1C), 22.73 (2C), 17.04 (1C), 16.30 (1C), 14.17 (2C), 11.82 (1C). HPLC (ELSD): 9.42 min, 100% purity; HPLC (uv-215 nm): 8.95 min, 96.05% purity; LCMS: 9.08 min 100% purity; MS (ESI, +ve) m/z: 1101.10 (MH+18). ELSD Method: –PDS_HPLC_GEMINI_C4_JUPITER_GRA-1; Mobile Phase: 100% MeOH; System: Agilent Technologies 1260 Infinity with PDA Detector & ELSD Detector; Column: Phenomenex JUPITER C4, 100*4.6 mm, 5p; Column Flow: 1.0 ml/min; Column Temp: Ambient; ELSD: SPRAY CHAMBER –50° C.

MPA-phenol lipid prodrugs such as MPA(O-TML-C12-2-TG)-OMe (MPA-I-47), which includes a trimethyl lock SI group, were synthesized in a similar manner, i.e., by coupling of the appropriate carboxylic acid-containing prodrug group with DMAP and EDC.

4l (MPA-I-47)

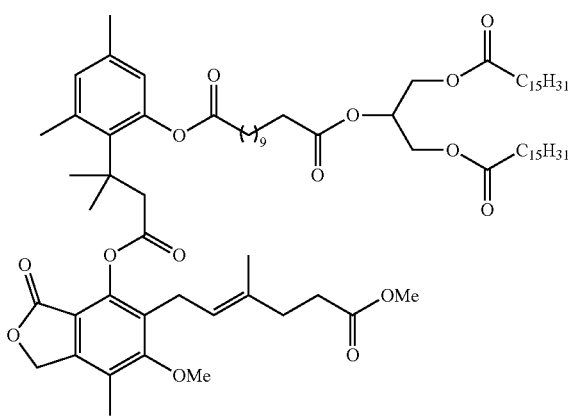

MPA-I-47 was prepared by coupling methyl ester 2 to the appropriate prodrug intermediate in 80% yield using DMAP and EDC. $^1$H NMR (401 MHz, CDCl$_3$) δ 6.77 (d, J=2.0 Hz, 1H), 6.55 (d, J=1.9 Hz, 1H), 5.26 (m, 1H), 5.10 (s, 2H), 4.98 (m, 1H), 4.29 (dd, J=11.9, 4.4 Hz, 2H), 4.14 (dd, J=11.9, 5.9 Hz, 2H), 3.72 (s, 3H), 3.61 (s, 3H), 3.32 (br s, 2H), 3.10 (br d, J=4.9 Hz, 2H), 2.58 (t, J=7.6 Hz, 2H), 2.57 (s, 3H), 2.36-2.20 (m, 10H), 2.19 (s, 3H), 2.17 (s, 3H), 1.79-1.71 (m, 2H), 1.73 (s, 3H), 1.65 (br s, 6H), 1.67-1.56 (m, 6H), 1.43-1.20 (m, 60H), 0.88 (t, J=6.9 Hz, 6H); $^{13}$C NMR (101 MHz, CDCl$_3$) δ 173.8 (C), 173.4 (2C; C), 173.0 (C), 172.9 (C), 170.1 (C), 168.4 (C), 162.8 (C), 149.8 (C), 146.2 (C), 146.0 (C), 138.2 (C), 136.2 (C), 134.1 (C), 133.5 (C), 132.5 (CH), 129.6 (C), 123.2 (CH), 122.82 (CH), 122.77 (C), 113.6 (C), 69.0 (CH), 68.4 (CH$_2$), 62.2 (2C; CH$_2$), 61.2 (CH$_3$), 51.6 (CH$_3$), 47.1 (CH$_2$), 39.0 (C), 35.2 (CH$_2$), 34.5 (CH$_2$), 34.3 (CH$_2$), 34.2 (2C; CH$_2$), 32.8 (CH$_2$), 32.1 (2C; CH$_2$), 31.5 (2C; CH$_3$), 29.84 (6C; CH$_2$), 29.80 (4C; CH$_2$), 29.77 (2C; CH$_3$), 29.62 (4C; CH$_2$), 29.50 (2C; CH$_2$), 29.48 (CH$_2$), 29.44 (CH$_2$), 29.41 (2C; CH$_2$), 29.38 (CH$_2$), 29.26 (3C; CH$_2$), 25.5 (CH$_3$), 25.03 (CH$_2$), 25.00 (2C; CH$_2$), 24.9 (CH$_2$), 23.5 (CH$_2$), 22.8 (2C; CH$_2$), 20.4 (CH$_3$), 16.4 (CH$_3$), 14.3 (2C; CH$_3$), 11.9 (CH$_3$); ESI-HRMS: calcd. for C$_{78}$H$_{124}$NaO$_{15}$ [M+Na$^+$] 1323.8832; found 1323.8844.

Compound MPA(O-TML-C12a'aMe-2-TG)-OMe (MPA-I-52) was prepared using similar methods as those described above and employing Int-122.

MPA-I-52

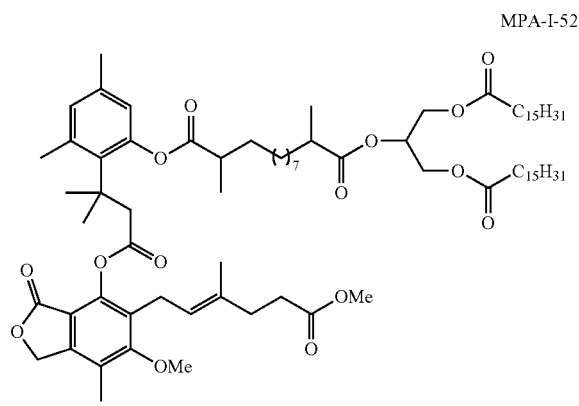

Note: The $^1$H NMR spectrum of this compound suggested the presence of ca. 10% of a related MPA species that could not be removed even after a second attempt at chromatography.

$^1$H NMR (401 MHz, CDCl$_3$) δ 6.76 (d, J=1.8 Hz, 1H), 6.50 (d, J=1.6 Hz, 1H), 5.26 (m, 1H), 5.10 (s, 2H), 4.97 (m, 1H), 4.291/4.283 (each dd, J=11.8, 4.2 Hz, 2H), 4.14 (dd, J=11.9, 6.1 Hz, 2H), 3.72 (s, 3H), 3.61 (s, 3H), 3.33 (br s, 2H), 3.12 (br s, 2H), 2.69 (m, 1H), 2.57 (s, 3H), 2.43 (m, 1H), 2.36-2.27 (m, 6H), 2.25-2.14 (m, 2H), 2.19 (s, 3H), 2.17 (s, 3H), 1.84 (m, 1H), 1.72 (s, 3H), 1.70-1.51 (m, 13H), 1.46-1.19 (m, 63H), 1.13 (d, J=7.0 Hz, 3H), 0.88 (t, J=6.8 Hz, 6H).

Compound MPA(O-C11-2-TG)-OMe (MPA-I-48) was prepared using similar methods as those described above.

4m (MPA-I-48)

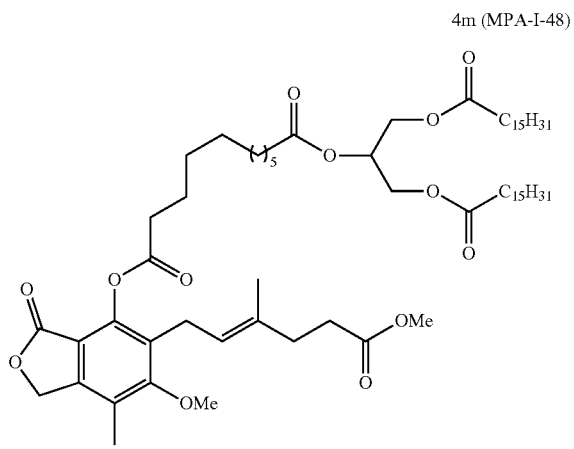

$^1$H NMR (401 MHz, CDCl$_3$) δ 5.25 (m, 1H), 5.13 (s, 2H), 5.10 (m, 1H), 4.28 (dd, J=11.9, 4.4 Hz, 2H), 4.14 (dd, J=11.9, 5.9 Hz, 2H), 3.77 (s, 3H), 3.61 (s, 3H), 3.32 (d, J=6.5 Hz, 2H), 2.66 (t, J=7.6 Hz, 2H), 2.40-2.24 (m, 10H), 2.21 (s, 3H), 1.81-1.72 (m, 2H), 1.76 (d, J=0.8 Hz, 3H), 1.66-1.55 (m, 6H), 1.46-1.18 (m, 58H), 0.87 (t, J=6.8 Hz, 6H); $^{13}$C NMR (101 MHz, CDCl$_3$) δ 173.8 (C), 173.4 (2C; C), 173.0 (C), 171.8 (C), 168.4 (C), 162.8 (C), 146.3 (C), 146.2 (C), 134.6 (C), 129.3 (C), 122.9 (C), 122.5 (CH), 113.7 (C), 69.0 (CH), 68.4 (CH$_2$), 62.2 (2C; CH$_2$), 61.3 (CH$_3$), 51.6 (CH$_3$), 34.5 (CH$_2$), 34.3 (CH$_2$), 34.2 (2C; CH$_2$), 34.0 (CH$_2$), 32.8 (CH$_2$), 32.1 (2C; CH$_2$), 29.83 (6C; CH$_2$), 29.79 (4C; CH$_2$), 29.75 (2C; CH$_2$), 29.60 (2C; CH$_2$), 29.49 (2C; CH$_2$), 29.45 (CH$_2$), 29.42 (CH$_2$), 29.40 (2C; CH$_2$), 29.28 (CH$_2$), 29.24 (2C; CH$_2$), 29.21 (CH$_2$), 25.01 (CH$_2$), 24.99 (2C; CH$_2$), 24.7 (CH$_2$), 23.7 (CH$_2$), 22.8 (2C; CH$_2$), 16.4 (CH$_3$), 14.3 (2C; CH$_3$), 11.9 (CH$_3$); ESI-HRMS: calcd. for C$_{64}$H$_{107}$O$_{13}$ [M+H$^+$] 1083.7706; found 1083.7710.

Compound MPA(O-C12bMe-2-TG)-OMe (MPA-I-53) was prepared using similar methods as those described above.

4n (MPA-I-53)

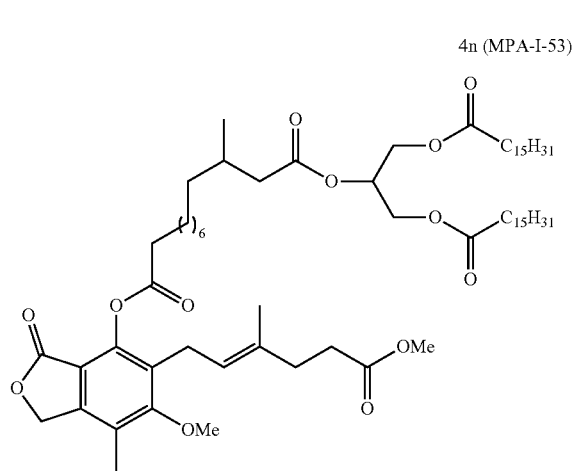

¹H NMR (401 MHz, CDCl₃) δ 5.27 (m, 1H), 5.13 (s, 2H), 5.10 (m, 1H), 4.284/4.282 (each dd, J=11.8, 4.3 Hz, 2H), 4.139/4.138 (each dd, J=11.9, 6.0 Hz, 2H), 3.77 (s, 3H), 3.62 (s, 3H), 3.33 (d, J=6.5 Hz, 2H), 2.67 (t, J=7.6 Hz, 2H), 2.41-2.25 (m, 9H), 2.21 (s, 3H), 2.11 (dd, J=15.4, 9.2 Hz, 1H), 1.93 (m, 1H), 1.82-1.73 (m, 2H), 1.76 (d, J=0.8 Hz, 3H), 1.65-1.55 (m, 4H), 1.47-1.15 (m, 60H), 0.93 (d, J=6.6 Hz, 3H), 0.87 (t, J=6.9 Hz, 6H); ¹³C NMR (101 MHz, CDCl₃) δ 173.8 (C), 173.4 (2C; C), 172.5 (C), 171.8 (C), 168.4 (C), 162.8 (C), 146.3 (C), 146.2 (C), 134.6 (C), 129.4 (C), 122.9 (C), 122.5 (C), 113.7 (C), 68.9 (CH), 68.4 (CH₂), 62.3 (2C; CH₂), 61.3 (CH₃), 51.6 (CH₃), 41.8 (CH₂), 36.9 (CH₂), 34.5 (CH₂), 34.2 (2C; CH₂), 34.0 (CH₂), 32.9 (CH₂), 32.1 (2C; CH₂), 30.5 (CH), 29.9 (CH₂), 29.83 (6C; CH₂), 29.79 (4C; CH₂), 29.76 (2C; CH₂), 29.63 (CH₂), 29.61 (2C; CH₂), 29.50 (2C; CH₂), 29.47 (CH₂), 29.40 (2C; CH₂), 29.33 (CH₂), 29.25 (2C; CH₂), 27.1 (CH₂), 25.0 (2C; CH₂), 24.8 (CH₂), 23.7 (CH₂), 22.8 (2C; CH₂), 19.7 (CH₃), 16.4 (CH₃), 14.3 (2C; CH₃), 11.9 (CH₃).

Example 17: Synthesis of MPA-Phenol Prodrugs with CASI/CMSI Group

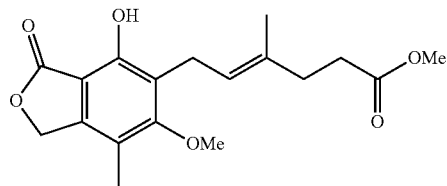

2

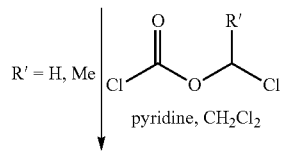

R' = H, Me pyridine, CH₂Cl₂

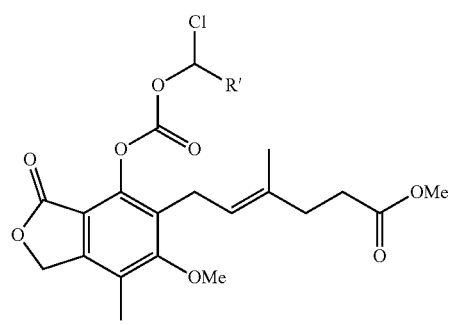

5

+

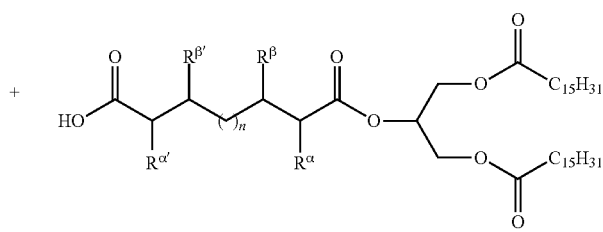

3

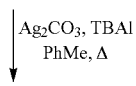

Ag₂CO₃, TBAI
PhMe, Δ

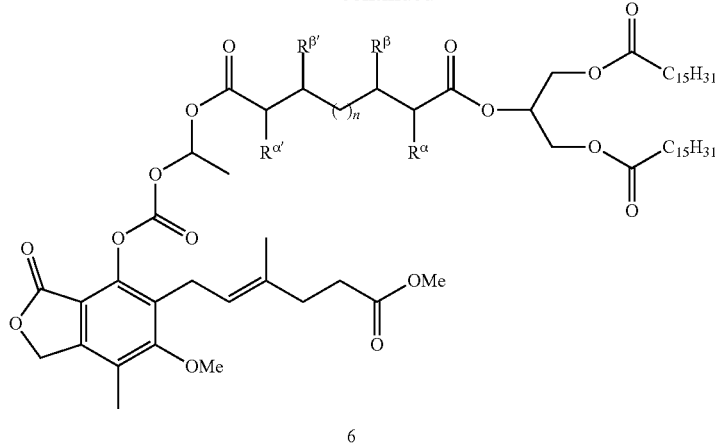

6

Synthesis of MPA-Phenol Prodrugs with CASI/CMSI Group

Methyl (E)-6-(4-(((chloromethoxy)carbonyl)oxy)-6-methoxy-7-methyl-3-oxo-1,3-dihydroisobenzofuran-5-yl)-4-methylhex-4-enoate (5a; R=H)

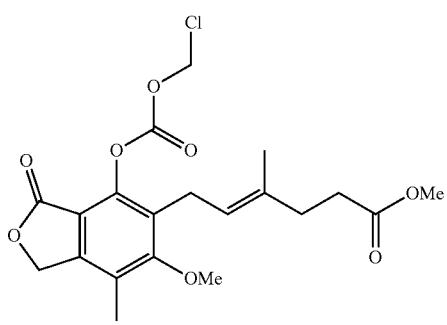

5a

Chloromethyl chloroformate (7.3 µL, 82.2 µmol) and pyridine (12.5 µL, 154 µmol) were added to methyl ester 2 (17.2 mg, 51.4 µmol) in $CH_2Cl_2$ (1.5 mL) at 0° C. and the mixture stirred at 0° C. for 20 minutes and then at RT for one hour. The reaction was diluted with $CH_2Cl_2$ (20 mL) and the organic phase washed with sat. aq. $NaHCO_3$ (3×20 mL) and brine (2×20 mL each), dried ($MgSO_4$) and concentrated under reduced pressure to give chloromethyl carbonate 5a (21.9 mg, quant.) as a colorless oil that was used without purification; $^1H$ NMR (401 MHz, $CDCl_3$) δ 5.85 (s, 2H), 5.18 (s, 2H), 5.10 (m, 1H), 3.81 (s, 3H), 3.62 (s, 3H), 3.41 (d, J=6.8 Hz, 2H), 2.41-2.36 (m, 2H), 2.32-2.26 (m, 2H), 2.25 (s, 3H), 1.78 (d, J=0.8 Hz, 3H).

Methyl (E)-6-(4-(((1-chloroethoxy)carbonyl)oxy)-6-methoxy-7-methyl-3-oxo-1,3-dihydro-isobenzofuran-5-yl)-4-methylhex-4-enoate (5b; R=Me)

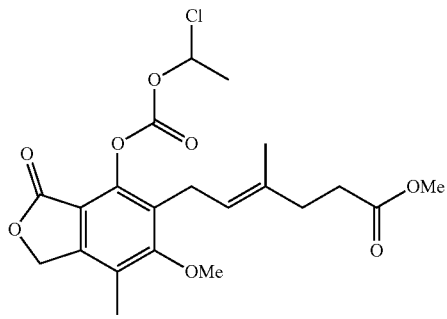

5b

1-Chloroethyl chloroformate (5.8 µL, 53.8 µmol) and pyridine (6.5 µL, 80.7 µmol) were added to methyl ester 2 (15.0 mg, 44.9 µmol) in $CH_2Cl_2$ (1 mL) at 0° C. and the mixture stirred at 0° C. for five minutes and then at rt for 40 minutes. The reaction was diluted with $CH_2Cl_2$ (30 mL) and the organic phase washed with water and brine (30 mL each), dried ($MgSO_4$) and concentrated under reduced pressure to give chloroethyl carbonate 5b (19.8 mg, quant.) as a colorless oil that was used without purification. $^1H$ NMR (401 MHz, $CDCl_3$) δ 6.52 (q, J=5.8 Hz, 1H), 5.18 (s, 2H), 5.11 (td, J=6.9, 1.2 Hz, 1H), 3.80 (s, 3H), 3.62 (s, 3H), 3.46-3.34 (m, 2H), 2.41-2.35 (m, 2H), 2.32-2.25 (m, 2H), 2.24 (s, 3H), 1.94 (d, J=5.8 Hz, 3H), 1.78 (d, J=0.6 Hz, 3H).

(E)-12-(1,3-Bis(palmitoyloxy)propan-2-yl) 1-(((((6-methoxy-5-(6-methoxy-3-methyl-6-oxohex-2-en-1-yl)-7-methyl-3-oxo-1,3-dihydroisobenzofuran-4-yl)oxy)carbonyl)oxy)methyl) 2,10-dimethyldodecanedioate (6a) (MPA-I-21)

Potassium carbonate (13.8 mg, 99.8 µmol) and tetra-n-butylammonium iodide (TBAI, 10.2 mg, 27.6 µmol) were added to a solution of acid-TG Int-27 (50.0 mg, 61.7 µmol) and chloride 5a (24.0 mg, 56.2 µmol) in DMF (2 mL) and the mixture heated at 80° C. for two hours. The reaction was cooled to RT, diluted with water (20 mL) and the aqueous phase extracted with ethyl acetate (3×20 mL). The combined organic extracts were washed with water (2×20 mL), dried (MgSO$_4$) and concentrated under reduced pressure to give the crude product. Silica gel chromatography (5% to 20% ethyl acetate/hexanes) gave MPA-CASI prodrug MPA(O-CASI-C12a'bMe-2-TG)-OMe (6a) (MPA-I-21) (8.6 mg, 13%) as a colorless oil. $^1$H NMR (401 MHz, CDCl$_3$) δ 5.91 (d, J=5.6 Hz, 1H), 5.86 (d, J=5.6 Hz, 1H), 5.37 (m, 1H), 5.16 (s, 2H), 5.11 (m, 1H), 4.28 (dd, J=11.8, 4.2 Hz, 2H), 4.14 (dd, J=12.3, 5.1 Hz, 2H), 3.79 (s, 3H), 3.62 (s, 3H), 3.38 (d, J=7.1 Hz, 2H), 2.55 (m, 1H), 2.41-2.26 (m, 9H), 2.23 (s, 3H), 2.10 (dd, J=14.7, 8.5 Hz, 1H), 1.92 (m, 1H), 1.76 (s, 3H), 1.66-1.50 (m, 6H), 1.38-1.23 (m, 60H), 1.21 (d, J=7.0 Hz, 3H), 0.92 (d, J=6.6 Hz, 3H), 0.88 (t, J=6.9 Hz, 6H).

Example 18: Synthesis of MPA-Phenol Prodrugs with FSI5 Group

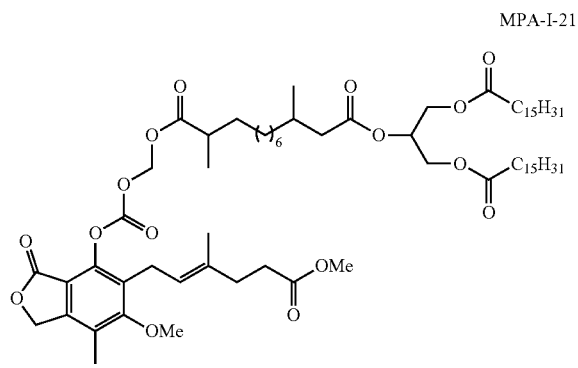

MPA-I-21

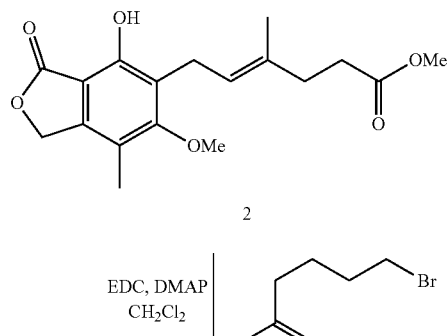

2

EDC, DMAP
CH$_2$Cl$_2$

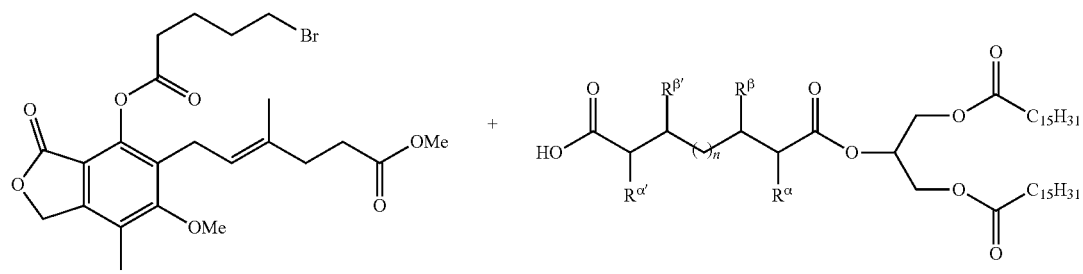

7     3

DBU, TBAI
PhMe, Δ

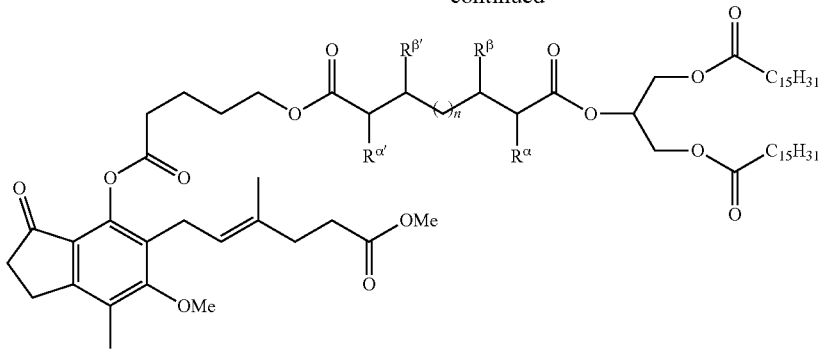

8

Synthesis of MPA-Phenol Prodrugs with FSI5 Group

Methyl (E)-6-(4-((5-bromopentanoyl)oxy)-6-methoxy-7-methyl-3-oxo-1,3-dihydroisobenzofuran-5-yl)-4-methylhex-4-enoate (7)

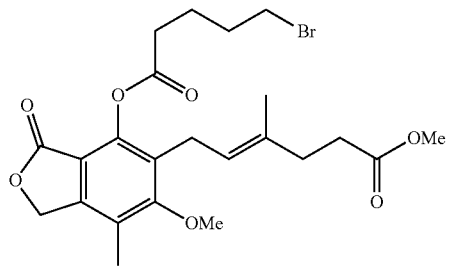

7

DMAP (10.9 mg, 0.0897 mmol) and EDC·HCl (43.0 mg, 0.224 mmol) were added to a solution of 5-bromovaleric acid (24.4 mg, 0.135 mmol) and methyl ester 2 (30.0 mg, 0.0897 mmol) in $CH_2Cl_2$ (2 mL) and the mixture stirred at RT for 30 minutes. The reaction was diluted with $CH_2Cl_2$ (5 mL), silica gel was added, and the mixture concentrated under reduced pressure. Purification by silica gel chromatography (35% ethyl acetate/hexanes) gave 5-bromovalerate ester 7 (38.1 mg, 85%) as a colorless solid; $^1$H NMR (401 MHz, $CDCl_3$) δ 5.13 (s, 2H), 5.08 (m, 1H), 3.77 (s, 3H), 3.61 (s, 3H), 3.47 (t, J=6.4 Hz, 2H), 3.33 (d, J=6.6 Hz, 2H), 2.71 (t, J=7.0 Hz, 2H), 2.40-2.33 (m, 2H), 2.32-2.25 (m, 2H), 2.21 (s, 3H), 2.07-1.88 (m, 4H), 1.76 (d, J=0.7 Hz, 3H). $^{13}$C NMR (101 MHz, $CDCl_3$) δ 173.7 (C), 171.2 (C), 168.4 (C), 162.8 (C), 146.3 (C), 146.0 (C), 134.7 (C), 129.3 (C), 123.1 (C), 122.4 (CH), 113.6 (C), 68.5 ($CH_2$), 61.3 ($CH_3$), 51.6 ($CH_3$), 34.5 ($CH_2$), 33.4 ($CH_2$), 32.82 ($CH_2$), 32.81 ($CH_2$), 31.9 ($CH_2$), 23.7 ($CH_2$), 23.2 ($CH_2$), 16.4 ($CH_3$), 11.9 ($CH_3$).

(E)-12-(1,3-Bis(palmitoyloxy)propan-2-yl) 1-(5-((6-methoxy-5-(6-methoxy-3-methyl-6-oxohex-2-en-1-yl)-7-methyl-3-oxo-1,3-dihydroisobenzofuran-4-yl)oxy)-5-oxopentyl) 2,10-dimethyldodecanedioate (8a) (MPA-I-22)

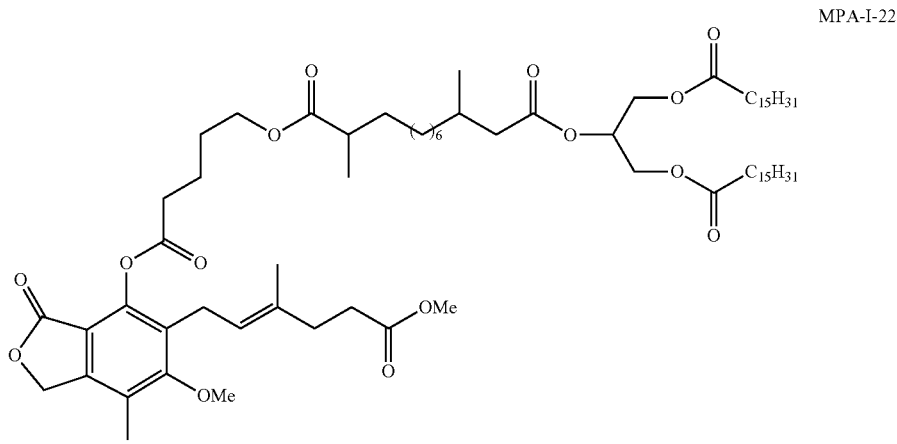

MPA-I-22

Silver carbonate (4.3 mg, 15.4 μmol) and tetra-n-butylammonium iodide (TBAI, 3.5 mg, 9.7 μmol) were added to a solution of acid-TG Int-27 (17.2 mg, 21.2 μmol) and bromide 7 (9.6 mg, 19.3 μmol) in toluene (1 mL) and the mixture heated at 90° C. for two hours. The reaction was cooled to RT, diluted with ethyl acetate (40 mL) and the organic phase washed with water and brine (30 mL each), dried (MgSO$_4$) and concentrated under reduced pressure to give the crude product. Silica gel chromatography (20% to 25% ethyl acetate/hexanes) gave MPA-(O-FSI5-C12a'bMe-2-TG)-OMe prodrug 8a (MPA-I-22) (17.6 mg, 74%) as a colorless oil; $^1$H NMR (401 MHz, CDCl$_3$) δ 5.27 (m, 1H), 5.14 (s, 2H), 5.10 (td, J=6.6, 1.1 Hz, 1H), 4.28 (dd, J=11.9, 3.6 Hz, 2H), 4.17-4.08 (m, 4H), 3.78 (s, 3H), 3.62 (s, 3H), 3.33 (d, J=6.7 Hz, 2H), 2.73 (t, J=6.5 Hz, 1H), 2.46-2.25 (m, 6H), 2.30 (t, J=7.6 Hz, 4H), 2.22 (s, 2H), 2.10 (dd, J=14.7, 8.4 Hz, 1H), 1.97-1.74 (m, 5H), 1.77 (d, J=0.8 Hz, 3H), 1.70-1.52 (m, 6H), 1.45-1.20 (m, 60H), 1.14 (d, J=7.0 Hz, 3H), 0.92 (d, J=6.6 Hz, 3H), 0.88 (t, J=6.9 Hz, 6H); $^{13}$C NMR (101 MHz, CDCl$_3$) δ 177.1 (C), 173.7 (C), 173.4 (2C; C), 172.5 (C), 171.3 (C), 168.4 (C), 162.8 (C), 146.3 (C), 146.1 (C), 134.7 (C), 129.3 (C), 123.0 (C), 122.5 (CH), 113.7 (C), 68.9 (CH), 68.5 (CH$_2$), 63.9 (CH$_2$), 62.3 (2C; CH$_2$), 61.3 (CH$_3$), 51.7 (CH$_3$), 41.8 (CH$_2$), 39.7 (CH), 36.9 (CH$_2$), 34.5 (CH$_2$), 34.2 (2C; CH$_2$), 33.9 (CH$_2$), 33.4 (CH$_2$), 32.9 (CH$_2$), 32.1 (2C; CH$_2$), 30.5 (CH), 29.9 (CH$_2$), 29.84 (6C; CH$_2$), 29.80 (4C; CH$_2$), 29.76 (2C; CH$_2$), 29.72 (CH$_2$), 29.68 (CH$_2$), 29.6 (2C; CH$_2$), 29.5 (2C; CH$_2$), 29.4 (2C; CH$_2$), 29.3 (2C; CH$_2$), 28.2 (CH$_2$), 27.4 (CH$_2$), 27.1 (CH$_2$), 25.0 (2C; CH$_2$), 23.7 (CH$_2$), 22.8 (2C; CH$_2$), 21.3 (CH$_2$), 19.7 (CH$_3$), 17.2 (CH$_3$), 16.4 (CH$_3$), 14.3 (2C; CH$_3$), 11.9 (CH$_3$).

(E)-1-(1,3-bis(palmitoyloxy)propan-2-yl) 10-(5-((6-methoxy-5-(6-methoxy-3-methyl-6-oxohex-2-en-1-yl)-7-methyl-3-oxo-1,3-dihydroisobenzofuran-4-yl)oxy)-4-methyl-5-oxopentyl) 3-methyldecanedioate (MPA-I-33)

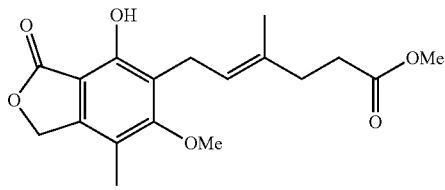

2

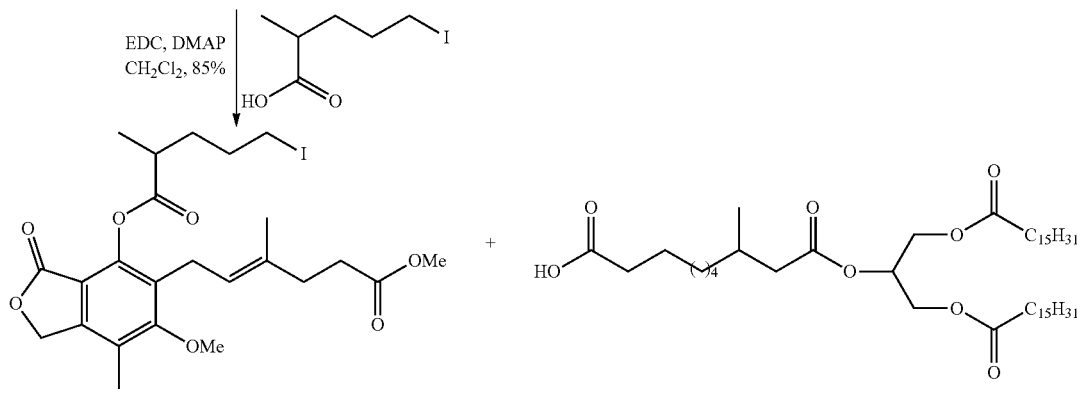

Int-89

Int-30

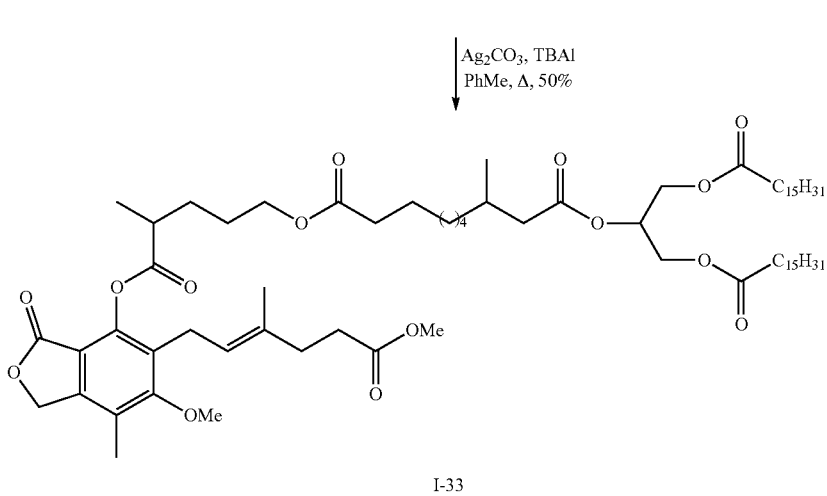

I-33

Synthesis of Additional MPA-Phenol Prodrugs with FSI5 Group

Methyl (E)-6-(4-(((5-iodo-2-methylpentanoyl)oxy)-6-methoxy-7-methyl-3-oxo-1,3-dihydroisobenzofuran-5-yl)-4-methylhex-4-enoate (Int-89)

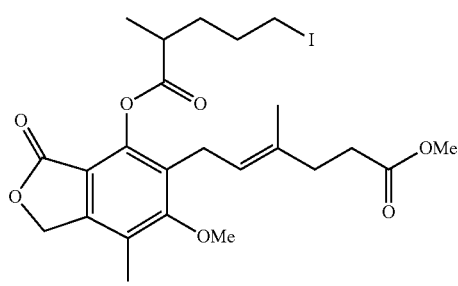

DMAP (3.4 mg, 27.5 µmol) and EDC·HCl (13.2 mg, 68.8 mmol) were added to a solution of 5-iodo-2-valeric acid (9.9 mg, 41.3 mmol) and MPA methyl ester 2 (9.2 mg, 27.5 mmol) in $CH_2Cl_2$ (0.8 mL) and the mixture stirred at RT for 17 hours. The reaction was diluted with $CH_2Cl_2$ (5 mL), silica gel was added, and the mixture concentrated under reduced pressure. Purification by silica gel chromatography (40% ethyl acetate/hexanes) gave semi-pure ester Int-89 (13.0 mg, 85%) as a colorless solid. Note: The quoted yield is not accurate due to significant amounts of inseparable impurities in the sample, presumably carried forward from 5-iodo-2-valeric acid. As a result, the NMR spectra contained a number of additional signals—the major peaks are reported. $^1H$ NMR (401 MHz, $CDCl_3$) δ 5.14 (s, 2H), 5.09 (m, 1H), 3.77 (s, 3H), 3.62 (s, 3H), 3.35-3.22 (m, 4H), 2.83 (m, 1H), 2.40-2.33 (m, 2H), 2.32-2.25 (m, 2H), 2.22 (s, 3H), 2.03-1.93 (m, 2H), 1.77 (s, 3H), 1.67-1.58 (m, 2H), 1.39 (d, J=7.0 Hz, 3H); $^{13}C$ NMR (101 MHz, $CDCl_3$) δ 174.0 (C), 173.7 (C), 168.4 (C), 162.8 (C), 146.4 (C), 146.0 (C), 134.9 (C), 129.5 (C), 123.1 (C), 122.5 (CH), 113.8 (C), 68.4 ($CH_2$), 61.3 ($CH_3$), 51.7 ($CH_3$), 38.6 (CH), 34.5 ($CH_2$), 34.3 ($CH_2$), 32.9 ($CH_2$), 31.0 ($CH_2$), 23.6 ($CH_2$), 17.2 ($CH_3$), 16.6 ($CH_3$), 11.9 ($CH_3$), 6.8 ($CH_2$).

Silver carbonate (2.6 mg, 9.3 µmol) and tetra-n-butylammonium iodide (TBAI, 1.7 mg, 4.7 µmol) were added to a solution of acid-TG Int-30 (9.8 mg, 12.8 µmol) and iodide Int-89 (6.5 mg, 11.6 µmol) in toluene (0.8 mL) and the mixture heated at reflux for two hours. The reaction was cooled to RT, diluted with ethyl acetate (40 mL) and the organic phase washed with water and brine (30 mL each), dried ($MgSO_4$) and concentrated under reduced pressure to give the crude product. Silica gel chromatography (20% to 25% ethyl acetate/hexanes) gave prodrug MPA-(O-FSI5α-C10 (3Me-2-TG)-OMe (MPA-I-33) (6.9 mg, 50%) as a colorless oil. $^1H$ NMR (401 MHz, $CDCl_3$) δ 5.26 (m, 1H), 5.14 (s, 2H), 5.09 (td, J=6.4, 1.0 Hz, 1H), 4.28 (dd, J=12.0, 4.1 Hz, 2H), 4.18-4.06 (m, 4H), 3.77 (s, 3H), 3.62 (s, 3H), 3.32 (br s, 2H), 2.84 (m, 1H), 2.40-2.25 (m, 11H), 2.22 (s, 3H), 2.10 (dd, J=14.7, 8.5 Hz, 1H), 2.01-1.87 (m, 2H), 1.85-1.77 (m, 2H), 1.76 (s, 3H), 1.69-1.52 (m, 7H), 1.39 (d, J=7.0 Hz, 3H), 1.35-1.14 (m, 56H), 0.92 (d, J=6.6 Hz, 3H), 0.88 (t, J=6.8 Hz, 6H); $^{13}C$ NMR (101 MHz, $CDCl_3$) δ 174.2 (C), 174.0 (C), 173.5 (2C; C), 172.5 (C), 168.3 (C), 162.8 (C), 146.4 (C), 146.0 (C), 134.8 (C), 129.4 (C), 123.0 (C), 122.5 (CH), 113.8 (C), 69.0 (CH), 68.4 ($CH_2$), 64.3 ($CH_2$), 62.3 (2C; $CH_2$), 61.3 ($CH_3$), 51.7 ($CH_3$), 41.8 ($CH_2$), 39.2 (CH), 36.8 ($CH_2$), 34.5 ($CH_2$), 34.4 ($CH_2$), 34.2 (2C; $CH_2$), 32.9 ($CH_2$), 32.1 (2C; $CH_2$), 30.5 (CH), 29.85 (6C; $CH_2$), 29.81 (4C; $CH_2$), 29.77 (2C; $CH_2$), 29.6 (3C; $CH_2$), 29.5 (2C; $CH_2$), 29.4 (2C; $CH_2$), 29.34 ($CH_2$), 29.27 (2C; $CH_2$), 26.9 ($CH_2$), 26.4 ($CH_2$), 25.1 ($CH_2$), 25.0 (2C; $CH_2$), 23.6 ($CH_2$), 22.8 (2C; $CH_2$), 19.6 ($CH_3$), 17.1 ($CH_3$), 16.5 ($CH_3$), 14.3 (2C; $CH_3$), 11.9 ($CH_3$). Note: Two signals were not observed in the $^{13}C$ NMR spectrum, possibly due to broadening of signals in proximity to the phenol ester functionality.

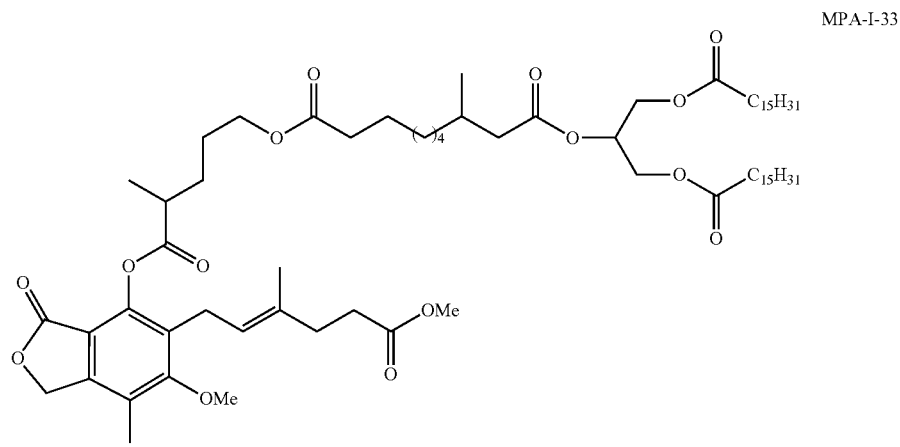

MPA-I-33

Example 19: Synthesis of MPA-Phenol Prodrugs with ASI Group

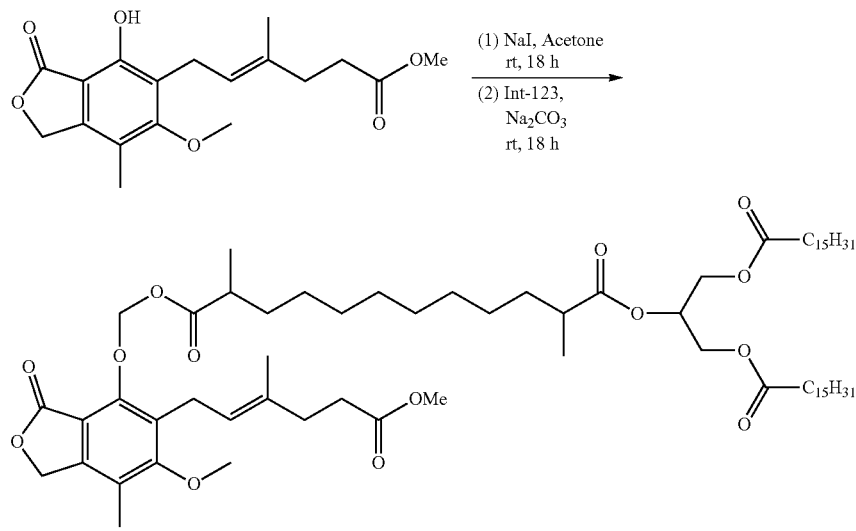

Synthesis of MPA-I-41 and Other MPA-Phenol Prodrugs

To a solution of compound Int-123 (0.190 g, 0.250 mmol) in acetone (10 ml) was added NaI (0.093 g, 0.626 mmol) at room temperature and the mixture stirred at rt for 18 h. Then mycophenolic acid methyl ester 2 (0.084 g, 0.250 mmol) and sodium carbonate (0.066 g, 0.626 mmol) were added at rt and stirred for 18 h. Progress of the reaction was monitored by TLC/Mass analysis; TLC analysis showed one non-polar spot along with some amount of unreacted 2. Then the reaction mixture was diluted with DCM (25 mL) and filtered through celite and washed with DCM (10 ml). Then the organic layer was directly distilled out at reduced pressure; the resulting crude material was purified by combi flash purification, pure product eluted with 10% ethyl acetate/hexane to obtain pure compound MPA-(O-ASI-C12aaDiMe-2-TG)-OMe (MPA-I-41) (50 mg, 17%) as a viscous liquid. $^1$H NMR (400 MHz, CDCl$_3$) δ 6.01 (d, J=6.4 Hz, 1H), 5.96 (d, J=6.4 Hz, 1H), 5.31 (d, J=6.3 Hz, 1H), 5.20 (s, 3H), 4.33 (dd, J=11.9, 4.3 Hz, 2H), 4.18 (dd, J=11.9, 6.0 Hz, 2H), 3.80 (s, 3H), 3.66 (s, 3H), 3.39 (d, J=6.9 Hz, 2H), 2.51-2.34 (m, 12H), 2.23 (s, 3H), 1.81 (s, 2H), 1.61 (s, 15H), 1.35-1.29 (m, 52H), 1.17 (dd, J=11.2, 7.0 Hz, 6H), 0.92 (t, J=6.7 Hz, 6H); $^{13}$C NMR (101 MHz, CDCl$_3$) δ 175.91 (2C), 175.86 (1C), 173.78 (1C), 173.31 (2C), 169.09 (1C), 162.79 (1C), 153.07 (1C), 146.68 (1C), 13.95 (1C), 129.03 (1C), 123.05 (2C), 120.93 (1C), 111.91 (1C), 90.06 (2C), 68.67 (1C), 68.43 (1C), 62.13 (1C), 60.95 (1C), 51.50 (1C), 39.52 (1C), 39.40 (1C), 34.58 (1C), 34.05 (3C), 33.61 (1C), 33.43 (1C), 32.83 (1C), 31.94 (3C), 29.72-29-14 (17C), 27.17 (1C), 24.86 (3C), 23.77 (1C), 22.71 (3C), 17.04 (1C), 16.83 (1C), 16.16 (1C), 14.15 (4C), 11.68 (1C). HPLC (ELSD): 9.73 min, 100% purity; HPLC (uv-215 nm): 9.69 min, 97.28% purity; LCMS: 7.91 min 100% purity. MASS (ESI, +ve) m/z: 1173.10 (MH+18). ELSD Method: –PDS_HPLC_GEMINI_C4_JUPITER_GRA-1; Mobile Phase: 100% Methanol; Column: Phenomenex JUPITER C4 (100*4.6) mm, 5; Column Flow: 1.0 mL/min; Column Temperature: Ambient; ELSD: SPRAY CHAMBER –50° C.

Compound MPA(O-ASI-C12a'bMe-2-TG)-OMe (MPA-I-44) was prepared using similar methods.

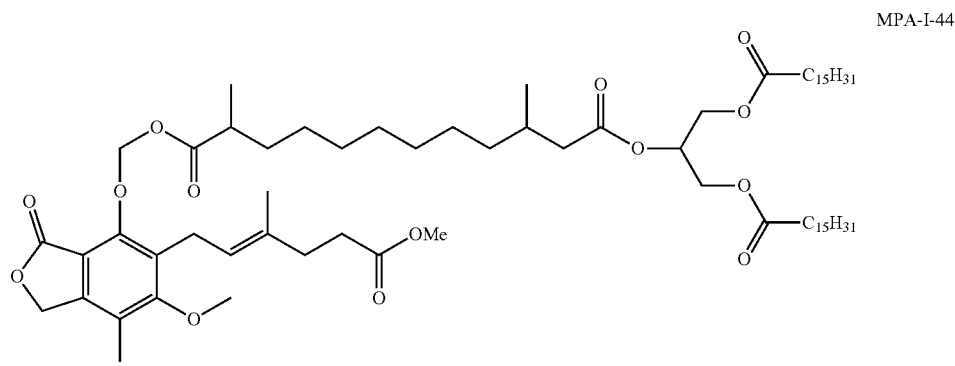

MPA-I-44

$^1$H NMR (400 MHz, CDCl$_3$) δ 6.01-5.99 (dd, J=6.4 Hz, 2H), 5.34-5.30 (m, 1H), 5.19 (s, 3H), 4.34-4.30 (dd, J=11.9, 4.3 Hz, 2H), 4.20-4.16 (dd, J=11.9, 6.0 Hz, 2H), 3.80 (s, 3H), 3.65 (s, 3H), 3.40-3.38 (d, J=6.9 Hz, 2H), 2.48-2.40 (m, 4H), 2.38-2.29 (m, 7H), 2.22 (s, 3H), 1.96 (m, 1H), 1.81 (s, 3H), 1.65-1.62 (m, 4H), 1.38-1.24 (m, 4H), 1.29 (m, 57H), 1.15 (d, J=7.0 Hz, 4H), 0.97-0.93 (d, J=7.0 Hz, 3H), 0.91-0.90 (t, J=6.7 Hz, 6H); $^{13}$C NMR (101 MHz, CDCl$_3$) 175.87 (1C), 173.78 (1C), 173.32 (1C), 172.35 (1C), 169.09 (1C), 162.82 (1C), 153.10 (1C), 146.70 (1C), 133.97 (1C), 129.07 (1C), 123.10 (1C), 120.94 (1C), 111.94 (1C), 90.09 (1C), 68.82 (1C), 68.43 (1C), 62.16 (1C), 60.96 (1C), 51.50 (1C), 41.71 (1C), 39.43 (1C), 36.73 (1C), 34.61 (1C), 34.07 (1C), 33.45 (1C), 32.86 (1C), 31.96 (1C), 30.38 (1C), 29.80-29.15 (30C), 27.17 (1C), 26.96 (1C), 24.88 (1C), 23.80 (1C), 22.73 (1C), 19.55 (1C), 16.84 (1C), 16.18 (1C), 14.16 (1C), 11.68 (1C). HPLC (ELSD): 9.77 min, 98.71% purity; HPLC (uv-215 nm): 9.74 min, 95.42% purity; LCMS: 8.80 min 100% purity; MS (ESI, +ve) m/z: 1173.10 (MH+18). ELSD Method: −PDS_HPLC_GEMINI_C4_JUPITER_GRA-1; Mobile Phase: 100% MEOH; System: Agilent Technologies 1260 Infinity with PDA Detector & ELSD Detector. Column: Phenomenex JUPITER C4, 100*4.6 mm, 5p; Column Flow: 1.0 ml/min; Column Temp: Ambient; ELSD: SPRAY CHAMBER −50° C.

Using similar methods to those described above, compound MPA-(O-ET-C2-2-TG)-OMe (MPA-I-23) was prepared.

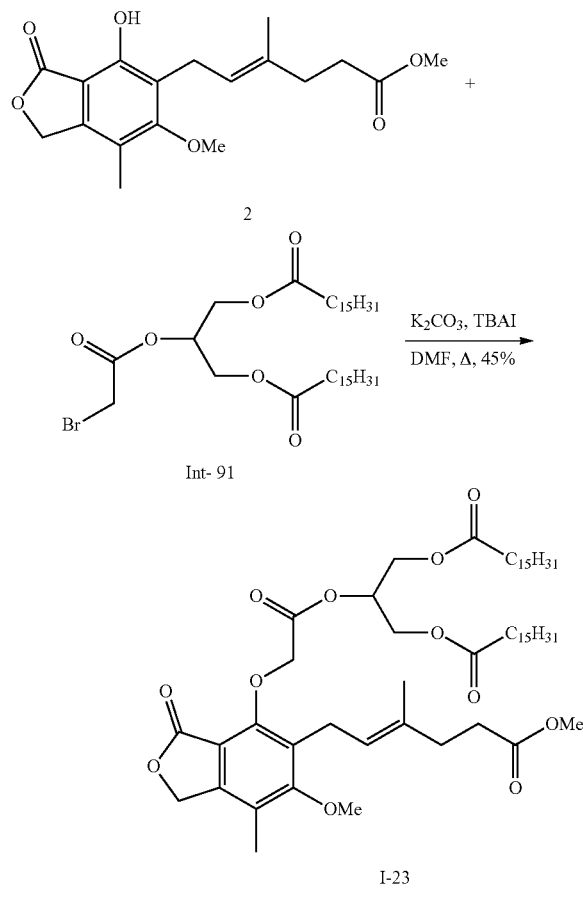

Synthesis of MPA-I-23

Potassium carbonate (6.6 mg, 47.9 μmol) and tetra-n-butylammonium iodide (4.4 mg, 12.0 μmol) were added to a solution of methyl ester 2 (8.0 mg, 23.9 μmol) and bromide Int-91 (20.1 mg, 31.1 μmol) in DMF (1.5 mL) and the mixture heated at 100° C. for 30 minutes. The reaction was cooled to rt, diluted with ethyl acetate (20 mL) and the organic phase washed with water and brine (20 mL each), dried (MgSO$_4$) and concentrated under reduced pressure to give the crude product. Silica gel chromatography (15% to 20% ethyl acetate/hexanes) gave MPA prodrug MPA-I-23 (10.1 mg, 45%) as a colourless solid. $^1$H NMR (401 MHz, CDCl$_3$) δ 5.32 (m, 1H), 5.20 (m, 1H), 5.13 (s, 2H), 5.08 (s, 2H), 4.30 (dd, J=12.0, 4.4 Hz, 2H), 4.15 (dd, J=12.0, 5.9 Hz, 2H), 3.77 (s, 3H), 3.60 (s, 3H), 3.56 (d, J=6.8 Hz, 2H), 2.41-2.34 (m, 2H), 2.32-2.26 (m, 6H), 2.17 (s, 3H), 1.78 (s, 3H), 1.68-1.54 (m, 4H), 1.35-1.19 (m, 48H), 0.88 (t, J=6.8 Hz, 6H); $^{13}$C NMR (101 MHz, CDCl$_3$) δ 173.9 (C), 173.4 (2C; C), 169.2 (C), 168.7 (C), 163.1 (C), 154.6 (C), 146.7 (C), 134.0 (C), 129.1 (C), 123.6 (CH), 120.4 (C), 111.4 (C), 71.0 (CH$_2$), 70.0 (CH), 68.7 (CH$_2$), 62.0 (2C; CH$_2$), 61.1 (CH$_3$), 51.6 (CH$_3$), 34.7 (CH$_2$), 34.1 (2C; CH$_2$), 33.0 (CH$_2$), 32.1 (2C; CH$_2$), 29.85 (6C; CH$_2$), 29.81 (4C; CH$_2$), 29.77 (2C; CH$_2$), 29.6 (2C; CH$_2$), 29.5 (2C; CH$_2$), 29.4 (2C; CH$_2$), 29.3 (2C; CH$_2$), 24.9 (2C; CH$_2$), 23.9 (CH$_2$), 22.8 (2C; CH$_2$), 16.3 (CH$_3$), 14.3 (2C; CH$_3$), 11.7 (CH$_3$); ESI-HRMS: Calcd. for C$_{55}$H$_{91}$O$_{12}$ [M+H$^+$]943.6505; found 943.6508.

Using similar methods to those described above, compound MPA-(O-ET-C5-2-TG)-OMe (MPA-I-24) was prepared.

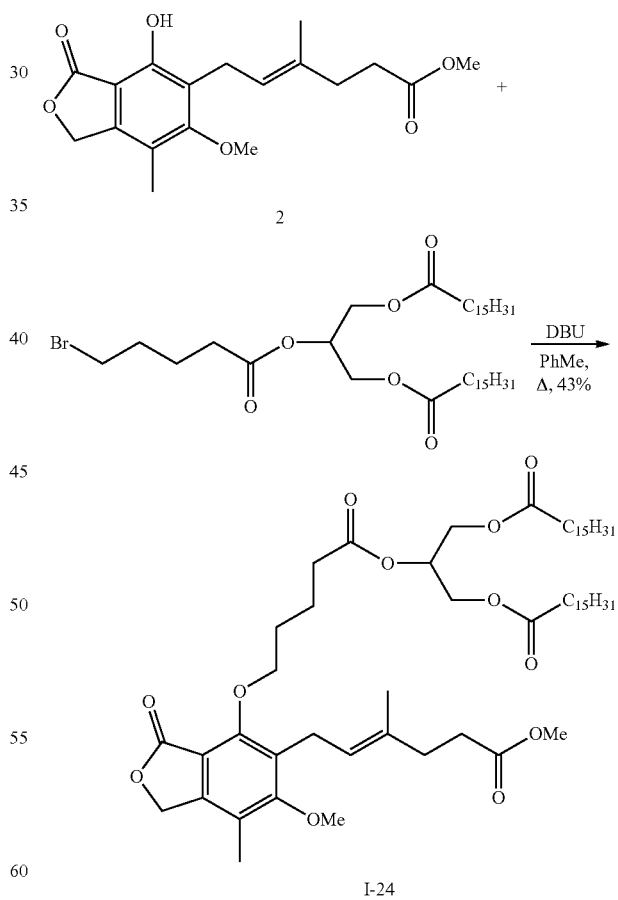

Synthesis of MPA-I-24

DBU (4.4 μL, 29.6 μmol) was added to a suspension of methyl ester 2 (5.5 mg, 16.4 μmol) and the bromide intermediate above (13.2 mg, 18.1 μmol) in toluene (0.8 mL) and the mixture heated at reflux for two hours. The reaction was cooled to rt, then diluted with ethyl acetate (40 mL). The organic phase was washed with water and brine (30 mL each), dried (MgSO$_4$) and concentrated under reduced pressure to give the crude product. Silica gel chromatography (15% to 20% ethyl acetate/hexanes) gave MPA prodrug MPA-I-24 (7.0 mg, 43%) as a colorless solid.

$^1$H NMR (401 MHz, CDCl$_3$) δ 5.26 (m, 1H), 5.15 (m, 1H), 5.11 (s, 2H), 4.29 (dd, J=11.9, 4.4 Hz, 2H), 4.21 (t, J=6.0 Hz, 2H), 4.14 (dd, J=11.9, 5.9 Hz, 2H), 3.76 (s, 3H), 3.61 (s, 3H), 3.40 (d, J=6.6 Hz, 2H), 2.44 (t, J=7.1 Hz, 2H), 2.41-2.26 (m, 4H), 2.31 (t, J=7.5 Hz, 4H), 2.17 (s, 3H), 1.92-1.81 (m, 4H), 1.79 (s, 3H), 1.67-1.55 (m, 4H), 1.36-1.19 (m, 48H), 0.88 (t, J=6.9 Hz, 6H); $^{13}$C NMR (101 MHz, CDCl$_3$) δ 173.48 (3C; C), 172.70 (C), 169.07 (C), 163.00 (C), 155.82 (C), 146.85 (C), 133.91 (C), 129.13 (C), 123.89 (CH), 120.00 (C), 112.75 (C), 74.99 (CH$_2$), 69.11 (CH), 68.37 (CH$_2$), 65.19 (CH$_2$), 62.20 (2C; CH$_2$), 61.07 (CH$_3$), 51.62 (CH$_3$), 34.68 (CH$_2$), 34.26 (CH$_2$), 34.17 (2C; CH$_2$), 33.92 (CH$_2$), 32.97 (CH$_2$), 32.08 (2C; CH$_2$), 29.85 (2C; CH$_2$), 29.81 (2C; CH$_2$), 29.77 (2C; CH$_2$), 29.64 (2C; CH$_2$), 29.51 (3C; CH$_2$), 29.43 (2C; CH$_2$), 29.27 (2C; CH$_2$), 25.00 (2C; CH$_2$), 23.65 (CH$_2$), 22.84 (2C; CH$_2$), 21.41 (CH$_2$), 16.39 (CH$_3$), 14.27 (2C; CH$_3$), 11.68 (CH$_3$); ESI-HRMS: Calcd. for C$_{58}$H$_{97}$O$_{12}$ [M+H$^+$] 985.6975; found 985.6971.

Example 20: Synthesis of (E)-2-(4-((6-(4-hydroxy-6-methoxy-7-methyl-3-oxo-1,3-dihydroisobenzofuran-5-yl)-4-methylhex-4-enoyl)oxy)butoxy)propane-1,3-diyl dipalmitate (MPA-I-25) and (E)-2-((6-((6-(4-hydroxy-6-methoxy-7-methyl-3-oxo-1,3-dihydroisobenzofuran-5-yl)-4-methylhex-4-enoyl)oxy)hexyl)oxy)propane-1,3-diyl dipalmitate (MPA-I-25 and MPA-I-26)

Synthesis of MPA-I-25

Synthesis of Int-82:

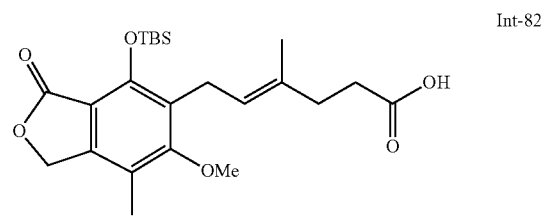 [SMILES: COc1c(C)c2c(c(O[Si](C)(C)C(C)(C)C)c1C/C=C(\C)CCC(=O)O)C(=O)OC2]

Imidazole (128 mg, 1.87 mmol) and tert-butyl(chloro)dimethylsilane (TBSCl, 141 mg, 0.937 mmol) were added to a solution of mycophenolic acid (MPA, 200 mg, 0.624 mmol) in DMF (7 mL) and the mixture stirred at rt for 22 hours. Extra portions of imidazole (65.0 mg, 0.954 mmol) and TBSCl (80.0 mg, 0.531 mmol) were added and the mixture stirred at rt for an additional two days and 18 hours. The reaction was diluted with ethyl acetate (20 mL) and water (30 mL) and the aqueous phase extracted with ethyl acetate (3×30 mL). The combined organic extracts were washed with water and brine (80 mL each), dried (MgSO$_4$) and concentrated under reduced pressure to give the crude product. Purification by silica gel chromatography (10% to 35% ethyl acetate/hexanes) gave MPA(OTBS) Int-82 (164 mg, 60%) as a colorless solid. $^1$H NMR (400 MHz, CDCl$_3$) δ 5.19 (m, 1H), 5.06 (s, 2H), 3.73 (s, 3H), 3.38 (d, J=6.3 Hz, 2H), 2.46-2.36 (m, 2H), 2.33-2.24 (m, 2H), 2.14 (s, 3H), 1.75 (s, 3H), 1.02 (s, 9H), 0.23 (s, 6H); $^{13}$C NMR (101 MHz, CDCl$_3$) δ 179.4 (C), 169.4 (C), 163.3 (C), 151.9 (C), 146.2 (C), 133.5 (C), 127.7 (C), 124.0 (CH), 118.1 (C), 111.8 (C),

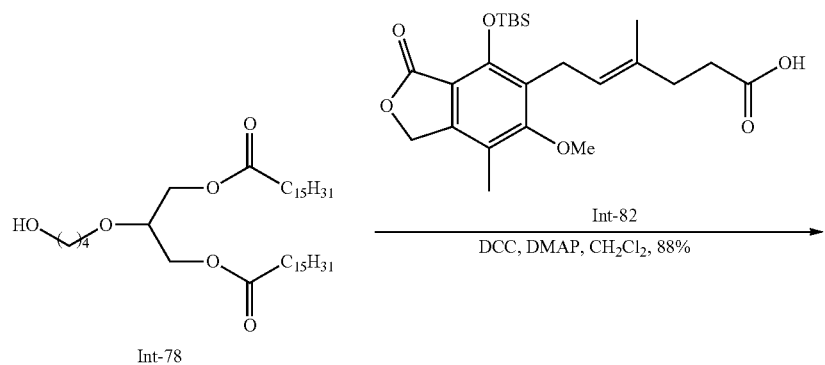

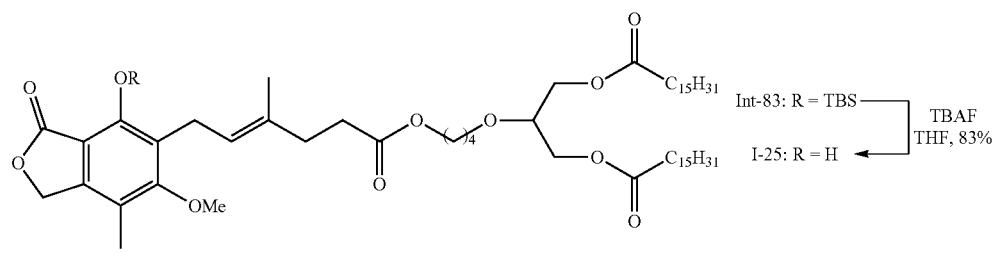

67.8 (CH$_2$), 60.8 (CH$_3$), 34.2 (CH$_2$), 32.9 (CH$_2$), 26.2 (3C; CH$_3$), 23.8 (CH$_2$), 18.9 (C), 16.4 (CH$_3$), 11.5 (CH$_3$), −3.4 (2C; CH$_3$).

Synthesis of Int-83:

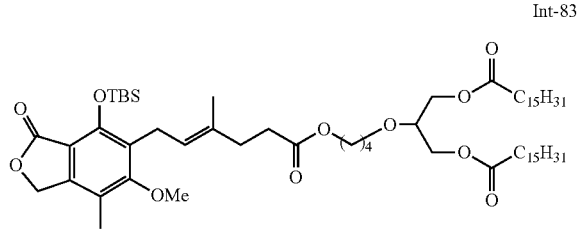

DMAP (5.0 mg, 40.6 µmol) and DCC (11.7 mg, 56.9 µmol) were added to a solution of acid Int-82 (17.8 mg, 40.6 µmol) and alcohol Int-78 (26.0 mg, 40.6 µmol) in CH$_2$Cl$_2$ (1.5 mL) and the mixture stirred at rt for 16 hours. To ensure complete reaction, extra portions of DMAP (4 mg) and DCC (8 mg) were added and stirring continued at rt for a further five hours. The resulting suspension was diluted with CH$_2$Cl$_2$ (15 mL), cooled to 0° C. and filtered through Celite, washing with further CH$_2$Cl$_2$ (50 mL). The organic phase was washed with 1 M HCl, water, sat. aq. NaHCO$_3$ and brine (60 mL each), dried (MgSO$_4$) and concentrated under reduced pressure to give the crude product. Silica gel chromatography (12.5% to 17.5% ethyl acetate/hexanes) gave protected MPA triglyceride Int-83 (37.8 mg, 88%) as a colorless oil. $^1$H NMR (400 MHz, CDCl$_3$): δ 5.17 (dt, J=6.5, 3.2 Hz, 1H), 5.06 (s, 2H), 4.18 (dd, J=11.6, 4.9 Hz, 2H), 4.10 (dd, J=11.6, 5.5 Hz, 2H), 4.03 (t, J=6.4 Hz, 2H), 3.73 (s, 3H), 3.67 (m, 1H), 3.56 (t, J=6.1 Hz, 2H), 3.37 (d, J=6.3 Hz, 2H), 2.41-2.22 (m, 8H), 2.15 (s, 3H), 1.75 (s, 3H), 1.70-1.53 (m, 8H), 1.36-1.16 (m, 48H), 1.03 (s, 9H), 0.88 (t, J=6.9 Hz, 6H), 0.24 (s, 6H); $^{13}$C NMR (100 MHz, CDCl$_3$): δ 173.7 (2C; C), 173.5 (C), 169.3 (C), 163.4 (C), 151.9 (C), 146.2 (C), 133.9 (C), 127.8 (C), 123.7 (CH), 118.0 (C), 111.8 (C), 75.5 (CH), 70.0 (CH$_2$), 67.8 (CH$_2$), 64.2 (CH$_2$), 63.1 (2C; CH$_2$), 60.9 (CH$_3$), 34.6 (CH$_2$), 34.3 (2C; CH$_2$), 33.2 (CH$_2$), 32.1 (2C; CH$_2$), 29.84 (6C; CH$_2$), 29.80 (4C; CH$_2$), 29.76 (2C; CH$_2$), 29.6 (2C; CH$_2$), 29.5 (2C; CH$_2$), 29.4 (2C; CH$_2$), 29.3 (2C; CH$_2$), 26.5 (CH$_2$), 26.2 (CH$_2$), 25.5 (CH$_2$), 25.1 (2C; CH$_2$), 23.8 (CH$_2$), 22.8 (2C; CH$_2$), 18.9 (C), 16.5 (CH$_3$), 14.3 (2C; CH$_3$), 11.6 (CH$_3$), −3.4 (CH$_3$).

Synthesis of MPA-I-25:

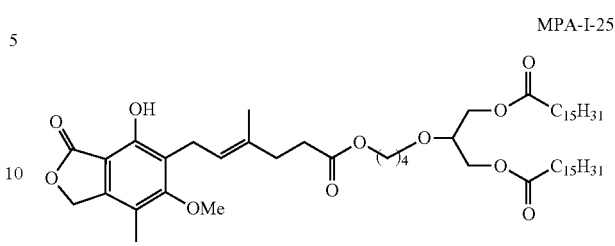

Tetrabutylammonium fluoride (TBAF, 1 M in THF, 38.1 µL, 38.1 µmol) was added to a solution of TBS ether Int-83 (26.9 mg, 38.1 µmol) in THF (1.5 mL) at 0° C. and the mixture was stirred at 0° C. for 50 minutes. The reaction was diluted with ethyl acetate, quenched with water and the aqueous phase extracted with ethyl acetate. The combined organic extracts were washed with water and brine, dried (MgSO$_4$) and concentrated under reduced pressure to give the crude product. Silica gel chromatography (20% ethyl acetate/hexanes) gave prodrug MPA-C4-ET-2-TG (MPA-I-25) (20.0 mg, 83%) as a colorless solid. $^1$H NMR (400 MHz, CDCl$_3$): δ 7.68 (s, 1H), 5.23 (dd, J=7.5, 6.4 Hz, 1H), 5.19 (s, 2H), 4.18 (dd, J=11.6, 4.9 Hz, 2H), 4.10 (dd, J=11.6, 5.5 Hz, 2H), 4.03 (t, J=6.3 Hz, 2H), 3.76 (s, 3H), 3.67 (m, 1H), 3.56 (t, J=6.0 Hz, 2H), 3.38 (d, J=6.9 Hz, 2H), 2.41-2.35 (m, 2H), 2.34-2.26 (m, 6H), 2.14 (s, 3H), 1.79 (s, 3H), 1.69-1.56 (m, 8H), 1.35-1.20 (m, 48H), 0.88 (t, J=6.8 Hz, 6H); $^{13}$C NMR (100 MHz, CDCl$_3$): δ 173.7 (2C; C), 173.5 (C), 173.1 (C), 163.8 (C), 153.8 (C), 144.2 (C), 134.3 (C), 122.8 (CH), 122.3 (C), 116.8 (C), 106.5 (C), 75.5 (CH), 70.2 (CH$_2$), 70.0 (CH$_2$), 64.2 (CH$_2$), 63.1 (2C; CH$_2$), 61.1 (CH$_3$), 34.8 (CH$_2$), 34.3 (2C; CH$_2$), 33.3 (CH$_2$), 32.1 (2C; CH$_2$), 29.84 (6C; CH$_2$), 29.80 (4C; CH$_2$), 29.76 (2C; CH$_2$), 29.6 (2C; CH$_2$), 29.5 (2C; CH$_2$), 29.4 (2C; CH$_2$), 29.3 (2C; CH$_2$), 26.5 (CH$_2$), 25.5 (CH$_2$), 25.1 (2C; CH$_2$), 22.8 (2C; CH$_2$), 22.7 (CH$_2$), 16.3 (CH$_3$), 14.3 (2C; CH$_3$), 11.7 (CH$_3$); ESI-HRMS: calcd. for C$_{56}$H$_{94}$NaO$_{11}$ [M+Na$^+$] 965.6688; found 965.6697.

Using similar procedures employing Int-73 instead of Int-78, compound (E)-2-((6-((6-(4-hydroxy-6-methoxy-7-methyl-3-oxo-1,3-dihydroisobenzofuran-5-yl)-4-methylhex-4-enoyl)oxy)hexyl)oxy)propane-1,3-diyl dipalmitate (MPA-I-26) was prepared.

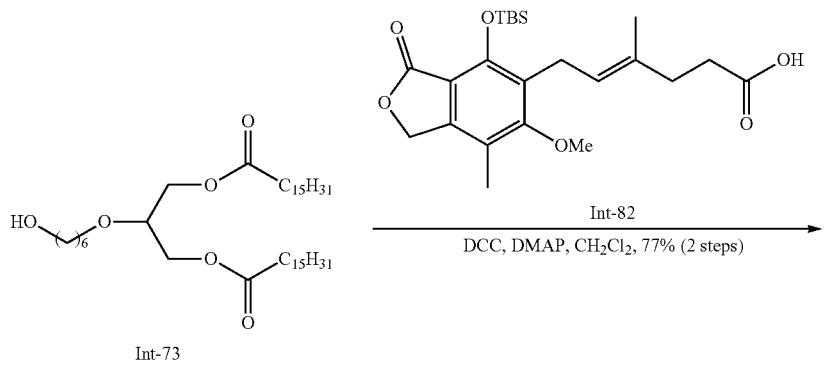

-continued

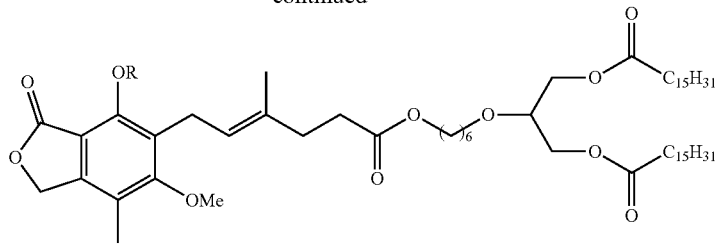

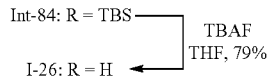

Synthesis of MPA-I-26

Synthesis of Int-84

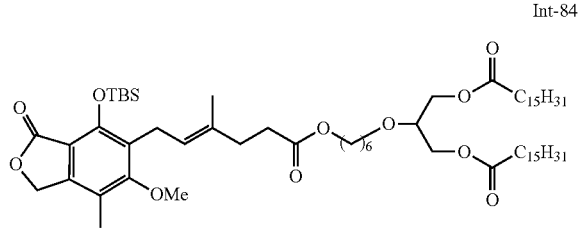

DMAP (6.4 mg, 52.1 µmol) and DCC (15.1 mg, 72.9 µmol) were added to a solution of acid Int-82 (22.7 mg, 52.1 µmol) and alcohol Int-73 (38.2 mg, 57.3 µmol) in $CH_2Cl_2$ (1.5 mL) and the mixture stirred at rt for 16 hours. The resulting suspension was diluted with $CH_2Cl_2$ (10 mL), cooled to 0° C. and filtered through Celite, washing with further $CH_2Cl_2$ (40 mL). The organic phase was washed with 1 M HCl, water, sat. aq. $NaHCO_3$ and brine (40 mL each), dried ($MgSO_4$) and concentrated under reduced pressure to give the crude product. Silica gel chromatography (10% to 15% ethyl acetate/hexanes) gave MPA triglyceride Int-84 (43.6 mg, 77% over two steps) as a colorless oil; $^1H$ NMR (400 MHz, $CDCl_3$): δ 5.18 (dd, J=6.5, 5.3 Hz, 1H), 5.06 (s, 2H), 4.18 (dd, J=11.6, 5.0 Hz, 2H), 4.11 (dd, J=11.6, 5.5 Hz, 2H), 4.00 (t, J=6.7 Hz, 2H), 3.74 (s, 3H), 3.66 (m, 1H), 3.54 (t, J=6.5 Hz, 2H), 3.38 (d, J=6.3 Hz, 2H), 2.40-2.24 (m, 8H), 2.15 (s, 3H), 1.75 (s, 3H), 1.66-1.51 (m, 8H), 1.39-1.18 (m, 52H), 1.03 (s, 9H), 0.88 (t, J=6.9 Hz, 6H), 0.23 (s, 6H); $^{13}C$ NMR (101 MHz, $CDCl_3$) δ 173.7 (2C; C), 173.6 (C), 169.3 (C), 163.3 (C), 151.9 (C), 146.2 (C), 133.9 (C), 127.8 (C), 123.7 (CH), 118.1 (C), 111.8 (C), 75.4 (CH), 70.6 ($CH_2$), 67.8 ($CH_2$), 64.5 ($CH_2$), 63.1 (2C; $CH_2$), 60.9 ($CH_3$), 34.6 ($CH_2$), 34.3 (2C; $CH_2$), 33.2 ($CH_2$), 32.1 (2C; $CH_2$), 30.0 ($CH_2$), 29.85 (6C; $CH_2$), 29.81 (4C; $CH_2$), 29.77 (2C; $CH_2$), 29.6 (2C; $CH_2$), 29.5 (2C; $CH_2$), 29.4 (2C; $CH_2$), 29.3 (2C; $CH_2$), 28.7 ($CH_2$), 26.2 (3C; $CH_3$), 25.9 ($CH_2$), 25.8 ($CH_2$), 25.1 (2C; $CH_2$), 23.8 ($CH_2$), 22.8 (2C; $CH_2$), 18.9 (C), 16.5 ($CH_3$), 14.3 (2C; $CH_3$), 11.6 ($CH_3$), −3.4 (2C; $CH_3$).

Synthesis of MPA-I-26

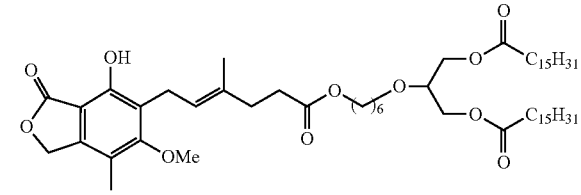

Tetrabutylammonium fluoride (TBAF, 1 M in THF, 60.2 µL, 60.2 µmol) was added to a solution of TBS ether Int-84 (43.6 mg, 40.2 µmol) in THF (2.5 mL) at 0° C. and the mixture was stirred at 0° C. for one hour. The reaction was diluted with ethyl acetate (10 mL) and water (20 mL) and the aqueous phase extracted with ethyl acetate (3×20 mL). The combined organic extracts were washed with water and brine (50 mL each), dried ($MgSO_4$) and concentrated under reduced pressure to give the crude product. Silica gel chromatography (20% ethyl acetate/hexanes) gave MPA prodrug MPA-C6-ET-2-TG (MPA-I-26) (30.8 mg, 79%) as a colorless solid. $^1H$ NMR (400 MHz, $CDCl_3$): δ 7.67 (s, 1H), 5.24 (td, J=6.9, 1.1 Hz, 1H), 5.19 (s, 2H), 4.18 (dd, J=11.6, 5.0 Hz, 2H), 4.11 (dd, J=11.6, 5.5 Hz, 2H), 4.00 (t, J=6.7 Hz, 2H), 3.76 (s, 3H), 3.67 (m, 1H), 3.54 (t, J=6.5 Hz, 2H), 3.38 (d, J=6.9 Hz, 2H), 2.42-2.35 (m, 2H), 2.35-2.26 (m, 6H), 2.14 (s, 3H), 1.80 (s, 3H), 1.66-1.51 (m, 8H), 1.39-1.19 (m, 52H), 0.88 (t, J=6.8 Hz, 6H); $^{13}C$ NMR (100 MHz, $CDCl_3$): δ 173.7 (C), 173.6 (2C; C), 173.1 (C), 163.8 (C), 153.8 (C), 144.1 (C), 134.2 (C), 122.8 (CH), 122.3 (C), 116.8 (C), 106.5 (C), 75.4 (CH), 70.6 ($CH_2$), 70.2 ($CH_2$), 64.5 ($CH_2$), 63.1 (2C; $CH_2$), 61.1 ($CH_3$), 34.8 ($CH_2$), 34.3 ($CH_2$), 33.3 ($CH_2$), 32.1 ($CH_2$), 30.0 ($CH_2$), 29.84 (6C; $CH_2$), 29.80 (4C; $CH_2$), 29.76 (2C; $CH_2$), 29.6 (2C; $CH_2$), 29.5 (2C; $CH_2$), 29.4 (2C; $CH_2$), 29.3 (2C; $CH_2$), 28.7 ($CH_2$), 25.9 ($CH_2$), 25.8 ($CH_2$), 25.1 (2C; $CH_2$), 22.8 (2C; $CH_2$), 22.7 ($CH_2$), 16.3 ($CH_3$), 14.3 (2C; $CH_3$), 11.7 ($CH_3$); ESI-HRMS: calcd. for $C_{58}H_{98}NaO_{11}$ [M+Na$^+$] 993.7001; found 993.7012.

Example 21: Synthesis of (E)-2-(((3-((6-(4-hydroxy-6-methoxy-7-methyl-3-oxo-1,3-dihydroisobenzofuran-5-yl)-4-methylhex-4-enoyl)oxy)propoxy)carbonyl)oxy)propane-1,3-diyl dipalmitate (MPA-I-27)
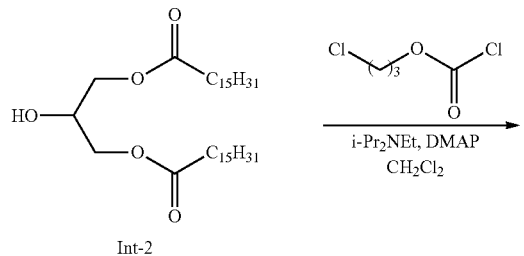
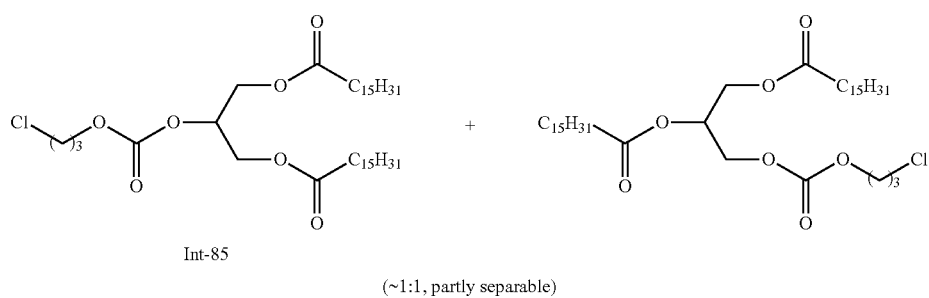
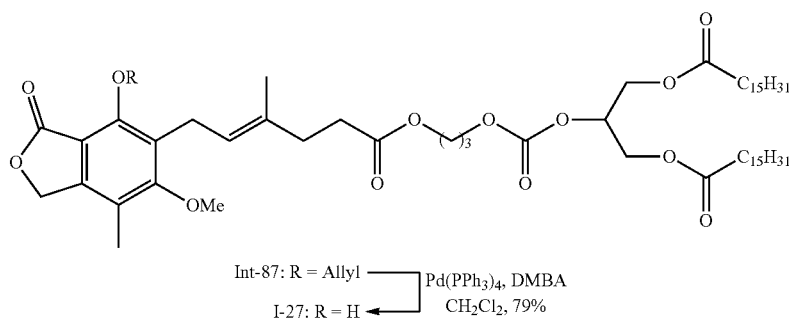

Synthesis of MPA-I-27

3-Chloropropyl chloroformate (20.3 µL, 0.169 mmol) and N,N-diethylisopropylamine (DIPEA, 54.2 µL, 0.316 mmol) were added to 1,3-diglyceride Int-2 (60.0 mg, 0.105 mmol) and DMAP (2.6 mg, 0.0211 mmol) in $CH_2Cl_2$ (3 mL) at 0° C. and the mixture stirred at RT for 18 hours. The reaction was diluted with $CH_2Cl_2$ (30 mL) and the organic phase washed with water, sat. aq. $NaHCO_3$ and brine (25 mL each), dried ($MgSO_4$) and concentrated under reduced pressure to give the crude product. Silica gel chromatography (4% to 5.5% ethyl acetate/hexanes) gave an inseparable mixture of chloropropyl carbonates Int-85 and a regioisomer (ca. 1:1 ratio, 49.8 mg, 69%) as a colorless solid. This mixture was used in the next step without further purification. $^1H$ NMR (400 MHz, $CDCl_3$) δ 5.28 (m, 1H), 4.38-4.13 (m, 6H), 3.63 (t, J=6.3 Hz, 2H), 2.35-2.29 (m, 4H), 2.18-2.10 (m, 2H), 1.66-1.56 (m, 4H), 1.36-1.19 (m, 48H), 0.88 (t, J=6.9 Hz, 6H). Note: The $^1H$ NMR spectrum was acquired using a sample enriched in target carbonate Int-85.

Compound Int-86 is a known compound that may be prepared as described in WO 2016/023082, hereby incorporated by reference in its entirety.

DBU (15.1 µL, 0.101 mmol) was added to a suspension of acid Int-86 (31.2 mg, 0.0867 mmol) and chloride Int-85 and its regioisomer (49.8 mg combined, 0.0722 mmol) and the mixture heated at reflux for 30 minutes. TLC analysis at this time showed very little reaction progress, so tetra-n-butylammonium iodide (TBAI, 5.0 mg, 0.0135 mmol) was added and the mixture heated at reflux for a further 3.5 hours. The reaction was cooled to rt, then diluted with ethyl acetate and water (10 mL each). The aqueous layer was separated and acidified to pH 2 with 1 M HCl, and then extracted with ethyl acetate (3×15 mL). The combined organic extracts were washed with water, sat. aq. $NaHCO_3$ and brine (40 mL each), dried ($MgSO_4$) and concentrated under reduced pressure to give the crude product. Silica gel chromatography (10% to 20% ethyl acetate/hexanes) gave unreacted chlorides Int-85 and its regioisomer (ca. 3:1 ratio, 30 mg) along with protected MPA prodrug Int-87 (14.5 mg) as a colorless oil. Re-subjection of the unreacted starting materials under the same reaction conditions (acid Int-86, DBU, TBAI, reflux for four hours) gave an additional batch of product Int-87 (31.9 mg total, 30% over two steps from 1,3-diglyceride Int-2). $^1H$ NMR (400 MHz, $CDCl_3$): δ 6.09 (ddt, J=16.3, 10.4, 5.9 Hz, 1H), 5.37 (ddd, J=17.2, 3.0, 1.5 Hz, 1H), 5.23 (dd, J=10.4, 1.5 Hz, 1H), 5.13 (s, 2H), 5.06 (m, 1H), 4.78 (dt, J=5.9, 1.2 Hz, 2H), 4.33 (dd, J=12.1, 4.2 Hz, 2H), 4.20 (t, J=6.7 Hz, 2H), 4.18 (dd, J=12.3, 5.9 Hz, 2H), 4.12 (t, J=6.3 Hz, 2H), 3.76 (s, 3H), 3.41 (d, J=6.7 Hz, 2H), 2.42-2.36 (m, 2H), 2.34-2.26 (m, 6H), 2.18 (s, 3H), 2.02-1.93 (m, 2H), 1.78 (s, 3H), 1.64-1.56 (m, 4H), 1.39-1.16 (m, 48H), 0.87 (t, J=6.8 Hz, 3H); $^{13}C$ NMR (100 MHz, $CDCl_3$): δ 173.4 (2C; C), 173.3 (C), 169.2 (C), 162.9 (C), 155.4 (C), 154.4 (C), 146.8 (C), 134.0 (CH), 133.8 (C), 129.3 (C), 123.8 (CH), 120.1 (C), 118.3 ($CH_2$), 112.8 (C), 76.2 ($CH_2$), 73.3 (CH), 68.4 ($CH_2$), 65.2 ($CH_2$), 62.0 (2C; $CH_2$), 61.1 ($CH_3$), 60.8 ($CH_2$), 34.6 ($CH_2$), 34.1 (2C; $CH_2$), 33.0 ($CH_2$), 32.1 (2C; $CH_2$), 29.84 (6C; $CH_2$), 29.81 (4C; $CH_2$), 29.77 (2C; $CH_2$), 29.6 (2C; $CH_2$), 29.5 (2C; $CH_2$), 29.4 (2C; $CH_2$), 29.3 (2C; $CH_2$), 28.1 ($CH_2$), 24.9 (2C; $CH_2$), 23.8 ($CH_2$), 22.8 (2C; $CH_2$), 16.4 ($CH_3$), 14.3 (2C; $CH_3$), 11.7 ($CH_3$).

Synthesis of MPA-I-27

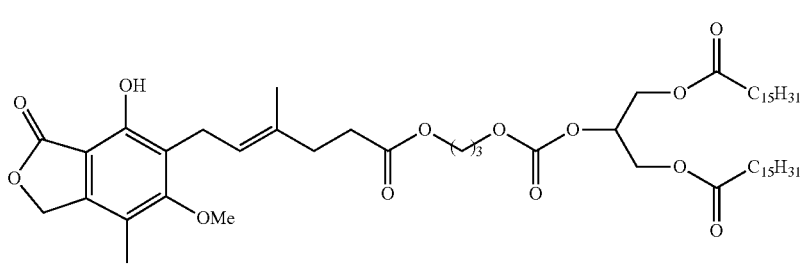

MPA-I-27

1,3-Dimethylbarbituric acid (DMBA; 9.1 mg, 58.2 µmol) and $Pd(PPh_3)_4$ (1.7 mg, 1.5 µmol) were added to allyl ether Int-87 (29.5 mg, 29.1 µmol) in $CH_2Cl_2$ (1.5 mL) and the mixture stirred at rt for one hour. The reaction mixture was directly applied to a short pad of silica gel and eluted with ethyl acetate (50 mL). The eluent was concentrated under reduced pressure to give the crude product. Silica gel chromatography (20% ethyl acetate/hexanes) gave prodrug MPA-C5-CN-2-TG (MPA-I-27) (22.3 mg, 79%) as a colorless solid. $^1H$ NMR (400 MHz, $CDCl_3$): δ 7.68 (s, 1H), 5.23 (td, J=6.9, 1.2 Hz, 1H), 5.19 (s, 2H), 5.07 (tt, J=5.8, 4.3 Hz, 1H), 5.29-5.21 (m, 2H), 4.33 (dd, J=12.1, 4.2 Hz, 2H), 4.20 (t, J=6.5 Hz, 2H), 4.18 (dd, J=12.1, 5.8 Hz, 2H), 4.12 (t, J=6.3 Hz, 2H), 3.76 (s, 3H), 3.38 (d, J=6.9 Hz, 2H), 2.43-2.35 (m, 2H), 2.35-2.26 (m, 6H), 2.14 (s, 3H), 2.01-1.94 (m, 2H), 1.79 (s, 3H), 1.63-1.56 (m, 4H), 1.34-1.19 (m, 48H), 0.87 (t, J=6.9 Hz, 6H); $^{13}C$ NMR (100 MHz, $CDCl_3$): δ 173.4 (2C; C), 173.3 (C), 173.0 (C), 163.8 (C), 154.5 (C), 153.8 (C), 144.2 (C), 134.2 (C), 122.9 (CH), 122.2 (C), 116.9 (C), 106.5 (C), 73.3 (CH), 70.2 ($CH_2$), 65.2 ($CH_2$), 62.0 (2C; $CH_2$), 61.1 ($CH_3$), 60.7 ($CH_2$), 34.7 ($CH_2$), 34.1 (2C; $CH_2$), 33.1 ($CH_2$), 32.1 (2C; $CH_2$), 29.83 (6C; $CH_2$), 29.80 (4C; $CH_2$), 29.75 (2C; $CH_2$), 29.6 (2C; $CH_2$), 29.5 (2C; $CH_2$), 29.4 (2C; $CH_2$), 29.2 (2C; $CH_2$), 28.1 ($CH_2$), 24.9 (2C; $CH_2$), 22.8 (2C; $CH_2$), 22.7 ($CH_2$), 16.3 ($CH_3$), 14.3 (2C; $CH_3$), 11.7 ($CH_3$).

Using similar methods, (E)-2-((3-(4-((6-(4-hydroxy-6-methoxy-7-methyl-3-oxo-1,3-dihydroisobenzofuran-5-yl)-4-methylhex-4-enoyl)oxy)phenyl)propanoyl)oxy)propane-1,3-diyl dipalmitate (MPA-I-28) was prepared.

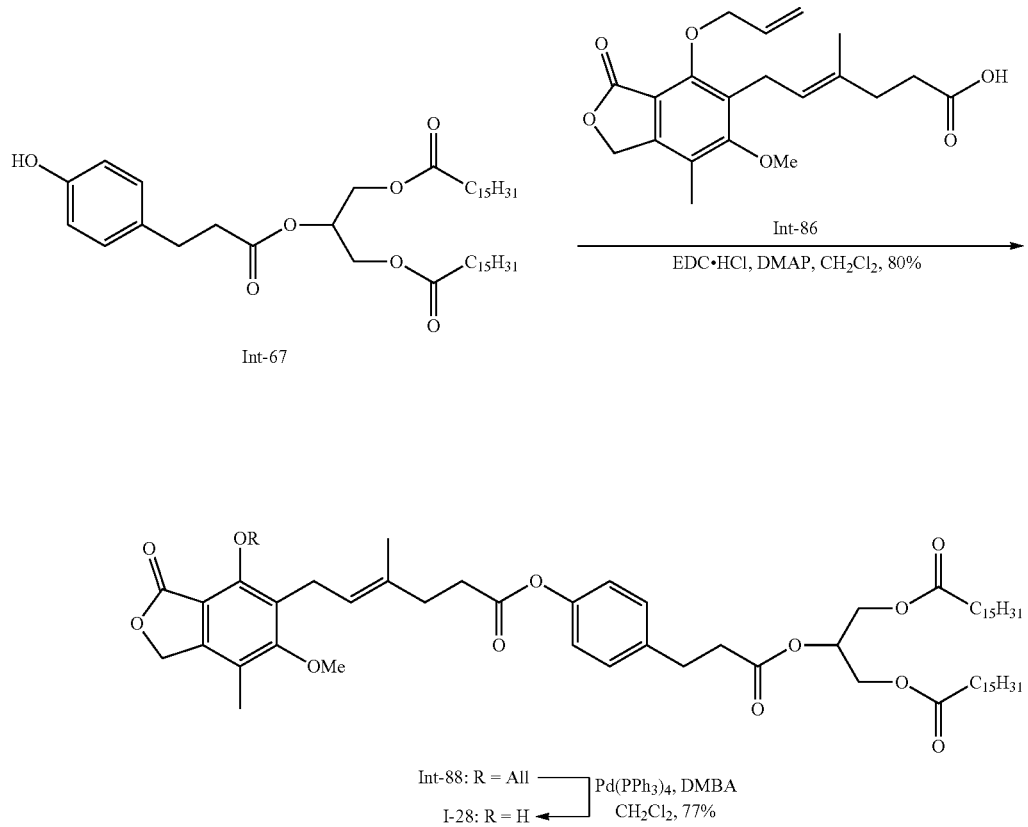

Synthesis of MPA-I-28

The allyl ether Int-88 was prepared as follows. DMAP (5.5 mg, 44.6 μmol), EDC·HCl (17.1 mg, 89.3 μmol) and MPA allyl ether Int-86 (16.1 mg, 44.6 μmol) were added to a solution of phenol intermediate Int-67 (32.0 mg, 44.6 μmol) in $CH_2Cl_2$ (3 mL) and the mixture stirred at RT for 18 hours. The reaction was diluted with $CH_2Cl_2$ (5 mL), silica gel was added and the mixture concentrated under reduced pressure. Purification by silica gel chromatography (15% to 20% ethyl acetate/hexanes) gave the allyl ether Int-88 (37.8 mg, 80%) as a colorless solid. $^1$H NMR (400 MHz, $CDCl_3$) δ 7.18-7.12 (m, 2H), 6.93-6.88 (m, 2H), 6.10 (ddt, J=16.3, 10.4, 5.9 Hz, 1H), 5.37 (ddd, J=17.2, 3.1, 1.5 Hz, 1H), 5.30-5.20 (m, 3H), 5.14 (s, 2H), 4.79 (dt, J=5.9, 1.3 Hz, 2H), 4.28 (dd, J=11.9, 4.4 Hz, 2H), 4.13 (dd, J=11.9, 5.9 Hz, 2H), 3.76 (s, 3H), 3.45 (d, J=6.6 Hz, 2H), 2.92 (t, J=7.8 Hz, 2H), 2.66-2.58 (m, 4H), 2.41 (t, J=7.7 Hz, 2H), 2.29 (t, J=7.6 Hz, 4H), 2.18 (s, 3H), 1.84 (s, 3H), 1.66-1.54 (m, 4H), 1.34-1.17 (m, 48H), 0.88 (t, J=6.9 Hz, 6H); $^{13}$C NMR (101 MHz, $CDCl_3$) δ 173.4 (2C; C), 171.9 (2C; C), 169.1 (C), 162.9 (C), 155.4 (C), 149.3 (C), 146.8 (C), 137.8 (C), 133.9 (CH), 133.6 (C), 129.3 (2C; CH), 129.2 (C), 124.1 (CH), 121.7 (2C; CH), 120.1 (C), 118.3 ($CH_2$), 112.8 (C), 76.2 ($CH_2$), 69.4 (CH), 68.4 ($CH_2$), 62.1 (2C; $CH_2$), 61.1 ($CH_3$), 35.7 ($CH_2$), 34.7 ($CH_2$), 34.1 (2C; $CH_2$), 33.1 ($CH_2$), 32.0 (2C; $CH_2$), 30.3 ($CH_2$), 29.81 (6C; $CH_2$), 29.77 (4C; $CH_2$), 29.73 (2C; $CH_2$), 29.6 (2C; $CH_2$), 29.5. (2C; $CH_2$), 29.4 (2C; $CH_2$), 29.2 (2C; $CH_2$), 25.0 (2C; $CH_2$), 23.8 ($CH_2$), 22.8 (2C; $CH_2$), 16.5 ($CH_3$), 14.2 (2C; $CH_3$), 11.7 ($CH_3$).

DMBA (11.1 mg, 71.4 μmol) and $Pd(PPh_3)_4$ (8.2 mg, 7.1 μmol) were added to allyl ether Int-88 (37.8 mg, 35.7 μmol) in $CH_2Cl_2$ (2 mL) and the mixture stirred at RT for 18 hours. The reaction mixture was directly applied to a short pad of silica gel and eluted with ethyl acetate. The eluent was concentrated under reduced pressure to give the crude product. Silica gel chromatography (15% to 20% ethyl acetate/hexanes) gave prodrug MPA-Ph-$C_{3-2}$-TG MPA-I-28 (28.0 mg, 77%) as a colorless solid. $^1$H NMR (400 MHz, $CDCl_3$) δ 7.69 (s, 1H), 7.17-7.12 (m, 2H), 6.94-6.87 (m, 2H), 5.33 (td, J=6.9, 1.2 Hz, 1H), 5.25 (m, 1H), 5.20 (s, 2H), 4.28 (dd, J=11.9, 4.3 Hz, 2H), 4.13 (dd, J=11.9, 5.8 Hz, 2H), 3.76 (s, 3H), 3.42 (d, J=6.9 Hz, 2H), 2.92 (t, J=7.8 Hz, 2H), 2.68-2.59 (m, 4H), 2.42 (t, J=7.6 Hz, 2H), 2.29 (t, J=7.6 Hz, 4H), 2.15 (s, 3H), 1.85 (s, 3H), 1.66-1.54 (m, 4H), 1.36-1.18 (m, 48H), 0.87 (t, J=6.9 Hz, 6H); $^{13}$C NMR (101 MHz, $CDCl_3$) δ 173.5 (2C; C), 173.0 (C), 171.99 (C), 171.96 (C), 163.8 (C), 153.8 (C), 149.3 (C), 144.2 (C), 137.8 (C), 134.0 (C), 129.3 (2C; CH), 123.2 (CH), 122.2 (C), 121.7 (2C; CH), 116.9 (C), 106.5 (C), 70.2 ($CH_2$), 69.4 (CH), 62.1 (2C; $CH_2$), 61.1 ($CH_3$), 35.8 ($CH_2$), 34.8 ($CH_2$), 34.2 (2C; $CH_2$), 33.2 ($CH_2$), 32.1 (2C; $CH_2$), 30.3 ($CH_2$), 29.83 (6C; $CH_2$), 29.80 (4C; $CH_2$), 29.76 (2C; $CH_2$), 29.6 (2C; $CH_2$), 29.5 (2C; $CH_2$), 29.4 (2C; $CH_2$), 29.3 (2C; $CH_2$), 25.0 (2C; $CH_2$), 22.83 (2C; $CH_2$), 22.76 ($CH_2$), 16.3 ($CH_3$), 14.3 (2C; $CH_3$), 11.7 ($CH_3$).

Using similar methods, (E)-2-((6-(4-hydroxy-6-methoxy-7-methyl-3-oxo-1,3-dihydroisobenzofuran-5-yl)-4-methylhex-4-enoyl)oxy)propane-1,3-diyl dipalmitate (MPA-I-34) was prepared from allyl-protected MPA Int-86 and Int-2 as follows.

MPA-I-34

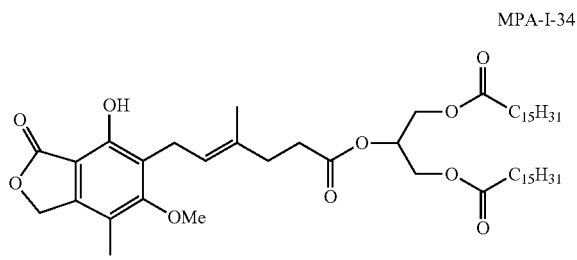

Synthesis of (E)-2-((6-(4-(allyloxy)-6-methoxy-7-methyl-3-oxo-1,3-dihydroisobenzofuran-5-yl)-4-methylhex-4-enoyl)oxy)propane-1,3-diyl dipalmitate (Int-90)

Int-90

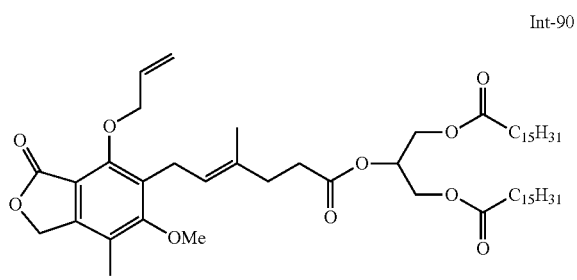

DMAP (55.0 mg, 0.450 mmol) and EDC·HCl (173 mg, 0.900 mmol) were added to a solution of Int-86 (162 mg, 0.450 mmol) and Int-2 (282 mg, 0.495 mmol) in CH$_2$Cl$_2$ (10 mL) and the mixture stirred at RT for 18 hours. The reaction was diluted with CH$_2$Cl$_2$ (20 mL), silica gel was added, and the solvent removed under reduced pressure. Silica gel chromatography (10% to 20% ethyl acetate/hexanes) gave the desired allyl-protected product (E)-2-((6-(4-(allyloxy)-6-methoxy-7-methyl-3-oxo-1,3-dihydroisobenzofuran-5-yl)-4-methylhex-4-enoyl)oxy)propane-1,3-diyl dipalmitate Int-90 (356 mg, 87%) as a colorless solid. $^1$H NMR (400 MHz, CDCl$_3$) δ 6.10 (ddt, J=16.3, 10.4, 5.9 Hz, 1H), 5.37 (dq, J=17.2, 1.5 Hz, 1H), 5.25-5.15 (m, 3H), 5.13 (s, 2H), 4.79 (dt, J=5.9, 1.3 Hz, 2H), 4.24 (dd, J=11.9, 4.5 Hz, 2H), 4.11 (dd, J=11.9, 5.8 Hz, 2H), 3.77 (s, 3H), 3.42 (d, J=6.7 Hz, 2H), 2.43-2.37 (m, 2H), 2.33-2.25 (m, 6H), 2.18 (s, 3H), 1.79 (s, 3H), 1.63-1.51 (m, 8H), 1.35-1.21 (s, 48H), 0.88 (t, J=6.9 Hz, 6H); $^{13}$C NMR (101 MHz, CDCl$_3$) δ 173.1 (2C; C), 172.2 (C), 168.9 (C), 162.8 (C), 155.2 (C), 146.7 (C), 133.9 (CH), 133.5 (C), 129.0 (C), 123.8 (CH), 119.9 (C), 118.0 (CH$_2$), 112.6 (C), 76.0 (CH$_2$), 69.0 (CH), 68.2 (CH$_2$), 61.9 (2C; CH$_2$), 60.9 (CH$_3$), 34.4 (CH$_2$), 34.0 (2C; CH$_2$), 32.9 (CH$_2$), 31.9 (2C; CH$_2$), 29.68 (6C; CH$_2$), 29.64 (4C; CH$_2$), 29.60 (2C; CH$_2$), 29.5 (2C; CH$_2$), 29.4 (2C; CH$_2$), 29.2 (2C; CH$_2$), 29.1 (2C; CH$_2$), 24.8 (2C; CH$_2$), 23.6 (CH$_2$), 22.7 (2C; CH$_2$), 16.2 (CH$_3$), 14.1 (2C; CH$_3$), 11.5 (CH$_3$).

DMBA (122 mg, 0.781 mmol) and Pd(PPh$_3$)$_4$ (67.7 mg, 0.0586 mmol) were added to allyl-protected prodrug Int-90 from the previous step (356 mg, 0.391 mmol) in CH$_2$Cl$_2$ (15 mL) and the mixture stirred at RT for 2.5 hours. The reaction mixture was directly applied to a short pad of silica gel, eluted with ethyl acetate (100 mL) and the filtrate concentrated under reduced pressure to give the crude product. Silica gel chromatography (15% ethyl acetate/hexanes) gave a slightly impure white solid, which was recrystallized from hexanes to give prodrug MPA-2-TG (MPA-I-34) (226 mg, 66%) as a colorless solid. $^1$H NMR (400 MHz, CDCl$_3$) δ 7.68 (s, 1H), 5.26-5.20 (m, 2H), 5.20 (s, 2H), 4.24 (dd, J=11.9, 4.5 Hz, 2H), 4.12 (dd, J=11.9, 5.8 Hz, 2H), 3.76 (s, 3H), 3.38 (d, J=6.9 Hz, 2H), 2.45-2.38 (m, 2H), 2.35-2.26 (m, 6H), 2.15 (s, 3H), 1.80 (s, 3H), 1.64-1.52 (m, 8H), 1.35-1.18 (m, 48H), 0.88 (t, J=6.9 Hz, 6H); $^{13}$C NMR (101 MHz, CDCl$_3$) δ 173.4 (2C; C), 173.0 (C), 172.5 (C), 163.8 (C), 153.8 (C), 144.1 (C), 134.1 (C), 123.0 (CH), 122.2 (C), 116.9 (C), 106.6 (C), 70.2 (CH$_2$), 69.1 (CH), 62.1 (2C; CH$_2$), 61.1 (CH$_3$), 34.6 (CH$_2$), 34.2 (2C; CH$_2$), 33.1 (CH$_2$), 32.1 (2C; CH$_2$), 29.85 (6C; CH$_2$), 29.81 (4C; CH$_2$), 29.77 (2C; CH$_2$), 29.6 (2C; CH$_2$), 29.5 (2C; CH$_2$), 29.4 (2C; CH$_2$), 29.3 (2C; CH$_2$), 25.0 (2C; CH$_2$), 22.8 (2C; CH$_2$), 22.7 (CH$_2$), 16.3 (CH$_3$), 14.3 (2C; CH$_3$), 11.7 (CH$_3$); ESI-HRMS: calcd. for C$_{52}$H$_{87}$O$_{10}$ [M+H$^+$] 871.6294; found 871.6328.

Using similar methods, (E)-2-(2-((6-(4-hydroxy-6-methoxy-7-methyl-3-oxo-1,3-dihydroisobenzofuran-5-yl)-4-methylhex-4-enoyl)oxy)acetoxy)propane-1,3-diyl dipalmitate (MPA-I-35) was prepared from allyl-protected MPA Int-86 and Int-91 as follows.

MPA-I-35

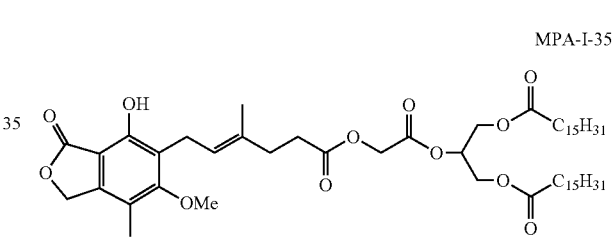

Synthesis of (E)-2-(2-((6-(4-(allyloxy)-6-methoxy-7-methyl-3-oxo-1,3-dihydroisobenzofuran-5-yl)-4-methylhex-4-enoyl)oxy)acetoxy)propane-1,3-diyl dipalmitate (Int-92)

Int-92

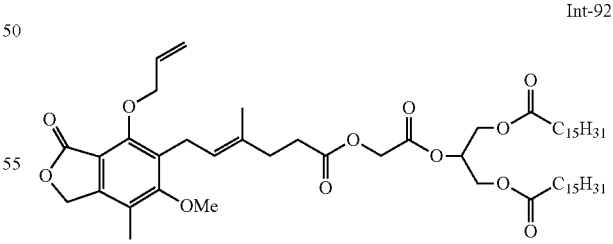

DBU (15.6 µL, 104 µmol) was added to a suspension of acid Int-86 (25.9 mg, 71.7 µmol) and bromide Int-91 (prepared as described above) (45.0 mg, 65.2 µmol) in toluene (3 mL) and the mixture heated at reflux for three hours. The reaction was cooled to RT and diluted with water (10 mL). The aqueous phase was extracted with ethyl acetate (3×15 mL) and the combined organic extracts washed with sat. aq. NaHCO$_3$ and brine (30 mL each), dried (MgSO$_4$) and concentrated under reduced pressure to give the crude product. Silica gel chromatography (12% to 15% ethyl acetate/hexanes) gave the allyl-protected MPA triglyceride Int-92 (45.6 mg, 72%) as a colorless oil. $^1$H NMR (400 MHz, CDCl$_3$) δ 6.09 (ddt, J=16.3, 10.4, 5.9 Hz, 1H), 5.37 (ddd, J=17.2, 3.1, 1.5 Hz, 1H), 5.30 (m, 1H), 5.25-5.17 (m, 2H), 5.13 (s, 2H), 4.78 (dt, J=5.9, 1.3 Hz, 2H), 4.57 (s, 2H), 4.28 (dd, J=12.1, 4.2 Hz, 2H), 4.15 (dd, J=12.0, 5.9 Hz, 2H), 3.76 (s, 3H), 3.42 (d, J=6.7 Hz, 2H), 2.52-2.45 (m, 2H), 2.37-2.27 (m, 6H), 2.17 (s, 3H), 1.79 (s, 3H), 1.63-1.55 (m, 4H), 1.37-1.17 (m, 48H), 0.87 (t, J=6.8 Hz, 6H); $^{13}$C NMR (101 MHz, CDCl$_3$) δ 173.4 (2C; C), 172.6 (C), 169.2 (C), 167.2 (C), 163.0 (C), 155.4 (C), 146.8 (C), 134.0 (CH), 133.7 (C), 129.2 (C), 123.9 (CH), 120.1 (C), 118.2 (CH$_2$), 112.8 (C), 76.2 (CH$_2$), 70.4 (CH), 68.4 (CH$_2$), 61.9 (CH$_2$), 61.1 (CH$_3$), 60.4 (CH$_2$), 34.4 (CH$_2$), 34.1 (2C; CH$_2$), 32.6 (CH$_2$), 32.1 (2C; CH$_2$), 29.82 (6C; CH$_2$), 29.78 (4C; CH$_2$), 29.74 (2C; CH$_2$), 29.6 (2C; CH$_2$), 29.5 (2C; CH$_2$), 29.4 (2C; CH$_2$), 29.2 (2C; CH$_2$), 24.9 (2C; CH$_2$), 23.8 (CH$_2$), 22.8 (2C; CH$_2$), 16.4 (CH$_3$), 14.2 (2C; CH$_3$), 11.7 (CH$_3$).

DMBA (13.4 mg, 85.6 μmol) and Pd(PPh$_3$)$_4$ (2.5 mg, 2.14 μmol) were added to allyl ether Int-92 (41.5 mg, 42.8 μmol) in CH$_2$Cl$_2$ (2.5 mL) and the mixture stirred at rt for 2.5 hours. The reaction mixture was directly applied to a short pad of silica gel, eluted with ethyl acetate (40 mL) and the filtrate concentrated under reduced pressure to give the crude product. Silica gel chromatography (15% ethyl acetate/hexanes) gave prodrug MPA-C2-2-TG (MPA-I-35) (30.9 mg, 78%) as a colorless solid. $^1$H NMR (400 MHz, CDCl$_3$) δ 7.67 (s, 1H), 5.31 (m, 1H), 5.25 (m, 1H), 5.20 (s, 2H), 4.57 (s, 2H), 4.29 (dd, J=12.1, 4.2 Hz, 2H), 4.16 (dd, J=12.1, 6.0 Hz, 2H), 3.76 (s, 3H), 3.38 (d, J=6.9 Hz, 2H), 2.54-2.47 (m, 2H), 2.35-2.29 (m, 6H), 2.14 (s, 3H), 1.80 (s, 3H), 1.64-1.55 (m, 4H), 1.34-1.19 (m, 48H), 0.87 (t, J=6.8 Hz, 6H); $^{13}$C NMR (101 MHz, CDCl$_3$) δ 173.42 (2C; C), 173.04 (C), 172.61 (C), 167.26 (C), 163.79 (C), 153.77 (C), 144.16 (C), 134.01 (C), 123.02 (CH), 122.20 (C), 116.84 (C), 106.51 (C), 70.41 (CH), 70.17 (CH$_2$), 61.86 (2C; CH$_2$), 61.12 (CH$_3$), 60.44 (CH$_2$), 34.46 (CH$_2$), 34.08 (2C; CH$_2$), 32.64 (CH$_2$), 32.06 (2C; CH$_2$), 29.83 (6C; CH$_2$), 29.79 (4C; CH$_2$), 29.75 (2C; CH$_2$), 29.60 (2C; CH$_2$), 29.50 (2C; CH$_2$), 29.39 (2C; CH$_2$), 29.24 (2C; CH$_2$), 24.93 (2C; CH$_2$), 22.82 (2C; CH$_2$), 22.72 (CH$_2$), 16.27 (CH$_3$), 14.26 (2C; CH$_3$), 11.69 (CH$_3$).

Using similar methods, (E)-2-((7-((6-(4-hydroxy-6-methoxy-7-methyl-3-oxo-1,3-dihydroisobenzofuran-5-yl)-4-methylhex-4-enoyl)oxy)heptanoyl)oxy)propane-1,3-diyl dipalmitate (MPA-I-36) was prepared from allyl-protected MPA Int-86 and Int-95 as follows.

Synthesis of (E)-2-((7-((6-(4-(allyloxy)-6-methoxy-7-methyl-3-oxo-1,3-dihydroisobenzofuran-5-yl)-4-methylhex-4-enoyl)oxy)heptanoyl)oxy)propane-1,3-diyl dipalmitate (Int-96)

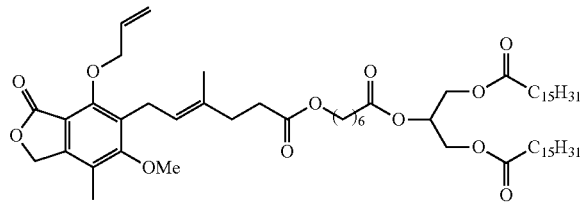

Int-96

DBU (13.6 μL, 90.7 μmol) was added to a suspension of acid Int-86 (26.2 mg, 72.6 μmol) and iodide Int-95 (48.8 mg, 60.5 μmol) and the mixture heated at reflux for 3.5 hours. The reaction was cooled to RT, then diluted with ethyl acetate and water and the aqueous layer extracted with ethyl acetate. The combined organic extracts were washed with water and brine, dried (MgSO$_4$) and concentrated under reduced pressure to give the crude product. Silica gel chromatography (7.5% to 15% to 20% ethyl acetate/hexanes) gave protected MPA prodrug Int-96 (47.5 mg, 76%) as a colorless oil. $^1$H NMR (400 MHz, CDCl$_3$) δ 6.09 (ddt, J=17.1, 10.4, 5.9 Hz, 1H), 5.37 (dq, J=17.2, 1.5 Hz, 1H), 5.28-5.21 (m, 2H), 5.17 (m, 1H), 5.12 (s, 2H), 4.78 (dt, J=5.9, 1.3 Hz, 2H), 4.29 (dd, J=11.9, 4.4 Hz, 2H), 4.13 (dd, J=11.9, 5.9 Hz, 2H), 4.00 (t, J=6.7 Hz, 2H), 3.76 (s, 3H), 3.41 (d, J=6.7 Hz, 2H), 2.40-2.34 (m, 2H), 2.33-2.25 (m, 8H), 2.17 (s, 3H), 1.78 (s, 3H), 1.66-1.54 (m, 8H), 1.36-1.18 (m, 52H), 0.87 (t, J=6.9 Hz, 6H); $^{13}$C NMR (100 MHz, CDCl$_3$) δ 173.5 (C), 173.4 (2C; C), 172.8 (C), 169.2 (C), 163.0 (C), 155.4 (C), 146.8 (C), 133.99 (CH), 133.97 (C), 129.3 (C), 123.7 (CH), 120.1 (C), 118.2 (CH), 112.8 (C), 76.2 (CH$_2$), 69.1 (CH), 68.4 (CH$_2$), 64.4 (CH$_2$), 62.2 (2C; CH$_2$), 61.1 (CH$_3$), 34.7 (CH$_2$), 34.17 (2C; CH$_2$), 34.16 (CH$_2$), 33.2 (CH$_2$), 32.1 (2C; CH$_2$), 29.83 (6C; CH$_2$), 29.79 (4C; CH$_2$), 29.75 (2C; CH$_2$), 29.6 (2C; CH$_2$), 29.5 (2C; CH$_2$), 29.4 (2C; CH$_2$), 29.3 (2C; CH$_2$), 28.8 (CH$_2$), 28.6 (CH$_2$), 25.8 (CH$_2$), 25.0 (2C; CH$_2$), 24.8 (CH$_2$), 23.8 (CH$_2$), 22.8 (2C; CH$_2$), 16.4 (CH$_3$), 14.3 (2C; CH$_3$), 11.7 (CH$_3$).

DMBA (10.8 mg, 69.3 μmol) and Pd(PPh$_3$)$_4$ (2.0 mg, 1.7 μmol) were added to allyl ether Int-96 (36.0 mg, 34.6 μmol) in CH$_2$Cl$_2$ (2 mL) and the mixture stirred at RT for one hour. The reaction mixture was directly applied to a short pad of silica gel and eluted with ethyl acetate (50 mL). The eluent was concentrated under reduced pressure to give the crude product. Silica gel chromatography (5% ethyl acetate/toluene) gave MPA prodrug MPA-C7-2-TG MPA-I-36 (30.6 mg,

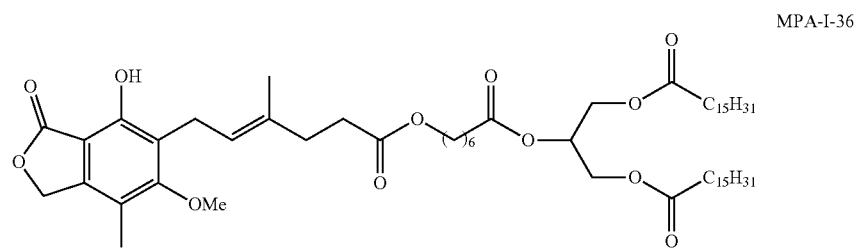

MPA-I-36

88%) as a colorless solid. $^1$H NMR (400 MHz, CDCl$_3$) δ 7.67 (s, 1H), 5.28-5.22 (m, 2H), 5.19 (s, 2H), 4.29 (dd, J=11.9, 4.3 Hz, 2H), 4.14 (dd, J=11.9, 5.9 Hz, 2H), 4.00 (t, J=6.7 Hz, 2H), 3.75 (s, 3H), 3.38 (d, J=6.9 Hz, 2H), 2.40-2.35 (m, 2H), 2.34-2.25 (m, 8H), 2.14 (s, 3H), 1.80 (s, 3H), 1.66-1.52 (m, 8H), 1.37-1.19 (m, 52H), 0.87 (t, J=6.8 Hz, 6H); $^{13}$C NMR (100 MHz, CDCl$_3$) δ 173.6 (C), 173.4 (2C; C), 173.1 (C), 172.8 (C), 163.8 (C), 153.8 (C), 144.1 (C), 134.3 (C), 122.8 (CH), 122.3 (C), 116.8 (C), 106.5 (C), 70.2 (CH$_2$), 69.1 (CH), 64.4 (CH$_2$), 62.2 (2C; CH$_2$), 61.1 (CH$_3$), 34.8 (CH$_2$), 34.2 (3C; CH$_2$), 33.2 (CH$_2$), 32.1 (2C; CH$_2$), 29.83 (6C; CH$_2$), 29.79 (4C; CH$_2$), 29.75 (2C; CH$_2$), 29.6 (2C; CH$_2$), 29.5 (2C; CH$_2$), 29.4 (2C; CH$_2$), 29.2 (2C; CH$_2$), 28.8 (CH$_2$), 28.6 (CH$_2$), 25.8 (CH$_2$), 25.0 (2C; CH$_2$), 24.8 (CH$_2$), 22.8 (2C; CH$_2$), 22.7 (CH$_2$), 16.3 (CH$_3$), 14.3 (2C; CH$_3$), 11.7 (CH$_3$); ESI-HRMS: calcd. for C$_{59}$H$_{98}$NaO$_{12}$ [M+Na$^+$]1021.6951; found 1021.6946.

Using similar methods, (E)-2-((12-((6-(4-hydroxy-6-methoxy-7-methyl-3-oxo-1,3-dihydroisobenzofuran-5-yl)-4-methylhex-4-enoyl)oxy)dodecanoyl)oxy)propane-1,3-diyl dipalmitate (MPA-I-37) was prepared from allyl-protected MPA Int-86 and Int-97 as follows.

MPA-I-37

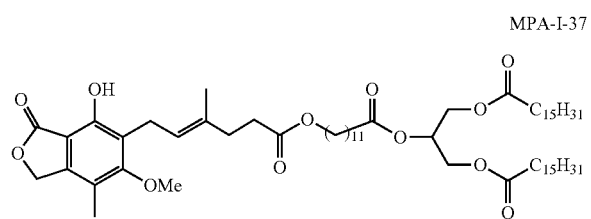

Synthesis of (E)-2-((12-((6-(4-(allyloxy)-6-methoxy-7-methyl-3-oxo-1,3-dihydroisobenzofuran-5-yl)-4-methylhex-4-enoyl)oxy)dodecanoyl)oxy)propane-1,3-diyl dipalmitate (Int-98)

Int-98

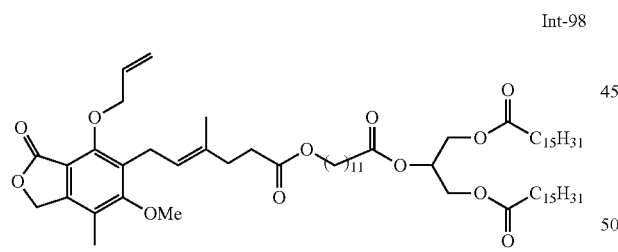

DBU (27.4 μL, 0.183 mmol) was added to a suspension of Int-86 (43.3 mg, 0.120 mmol) and bromide Int-97 (95.0 mg, 0.114 mmol) in toluene (4 mL) and the mixture heated at reflux for two hours. The reaction was cooled to rt, then diluted with ethyl acetate (40 mL). The organic phase was washed with water and brine (30 mL each), dried (MgSO$_4$) and concentrated under reduced pressure to give the crude product. Silica gel chromatography (10% to 20% ethyl acetate/hexanes) gave Int-98 (88.2 mg, 69%) as a colorless solid. $^1$H NMR (401 MHz, CDCl$_3$) δ 6.07 (ddt, J=16.3, 10.4, 5.9 Hz, 1H), 5.35 (dq, J=17.2, 1.5 Hz, 1H), 5.28-5.13 (m, 3H), 5.10 (s, 2H), 4.76 (dt, J=5.9, 1.2 Hz, 2H), 4.27 (dd, J=11.9, 4.3 Hz, 2H), 4.12 (dd, J=11.9, 5.9 Hz, 2H), 3.98 (t, J=6.8 Hz, 2H), 3.74 (s, 3H), 3.39 (d, J=6.7 Hz, 2H), 2.39-2.23 (m, 10H), 2.16 (s, 3H), 1.76 (s, 3H), 1.63-1.51 (m, 8H), 1.35-1.13 (m, 62H), 0.85 (t, J=6.8 Hz, 6H); $^{13}$C NMR (101 MHz, CDCl$_3$) δ 173.5 (C), 173.4 (2C; C), 172.9 (C), 169.1 (C), 162.9 (C), 155.4 (C), 146.7 (C), 133.94 (CH), 133.92 (C), 129.3 (C), 123.6 (CH), 120.0 (C), 118.1 (CH$_2$), 112.7 (C), 76.1 (CH$_2$), 69.0 (CH), 68.4 (CH$_2$), 64.6 (CH$_2$), 62.2 (2C; CH$_2$), 61.0 (CH$_3$), 34.7 (CH$_2$), 34.3 (CH$_2$), 34.1 (2C; CH$_2$), 33.1 (CH$_2$), 32.0 (2C; CH$_2$), 29.78 (6C; CH$_2$), 29.74 (4C; CH$_2$), 29.70 (2C; CH$_2$), 29.63 (CH$_2$), 29.60 (CH$_2$), 29.55 (3C; CH$_2$), 29.44 (2C; CH$_2$), 29.35 (4C; CH$_2$), 29.19 (2C; CH$_2$), 29.15 (CH$_2$), 28.7 (CH$_2$), 26.0 (CH$_2$), 24.9 (2C; CH$_2$), 23.7 (CH$_2$), 22.8 (2C; CH$_2$), 16.4 (CH$_3$), 14.2 (2C; CH$_3$), 11.6 (CH$_3$).

DMBA (24.2 mg, 0.155 mmol) and Pd(PPh$_3$)$_4$ (13.4 mg, 0.0116 mmol) were added to allyl ether Int-98 (86.0 mg, 0.0775 mmol) in CH$_2$Cl$_2$ (3 mL) and the mixture stirred at rt for 4.5 hours. The reaction mixture was directly applied to a short pad of silica gel and eluted with ethyl acetate. The eluent was concentrated under reduced pressure to give the crude product. Silica gel chromatography (15% to 20% ethyl acetate/hexanes) gave prodrug MPA-I-37 (80.0 mg, 96%) as a colorless solid. $^1$H NMR (401 MHz, CDCl$_3$) δ 7.66 (s, 1H), 5.27-5.19 (m, 2H), 5.17 (s, 2H), 4.28 (dd, J=11.9, 4.3 Hz, 2H), 4.13 (dd, J=11.8, 5.9 Hz, 2H), 3.98 (t, J=6.8 Hz, 2H), 3.74 (s, 3H), 3.36 (d, J=6.9 Hz, 2H), 2.40-2.33 (m, 2H), 2.32-2.24 (m, 8H), 2.13 (s, 3H), 1.78 (s, 3H), 1.64-1.50 (m, 8H), 1.37-1.18 (m, 62H), 0.86 (t, J=6.8 Hz, 6H); $^{13}$C NMR (101 MHz, CDCl$_3$) δ 173.5 (C), 173.4 (2C; C), 173.0 (C), 172.9 (C), 163.8 (C), 153.7 (C), 144.1 (C), 134.3 (C), 122.7 (CH), 122.2 (C), 116.8 (C), 106.4 (C), 70.1 (CH$_2$), 69.0 (CH), 64.5 (CH$_2$), 62.2 (2C; CH$_2$), 61.1 (CH$_3$), 34.7 (CH$_2$), 34.3 (CH$_2$), 34.1 (2C; CH$_2$), 33.2 (CH$_2$), 32.0 (2C; CH$_2$), 29.79 (6C; CH$_2$), 29.75 (4C; CH$_2$), 29.71 (2C; CH$_2$), 29.63 (CH$_2$), 29.61 (CH$_2$), 29.56 (2C; CH$_2$), 29.45 (2C; CH$_2$), 29.36 (4C; CH$_2$), 29.20 (2C; CH$_2$), 29.16 (CH$_2$), 28.7 (CH$_2$), 26.0 (CH$_2$), 24.97 (CH$_2$), 24.95 (2C; CH$_2$), 22.8 (2C; CH$_2$), 22.7 (CH$_2$), 16.2 (CH$_3$), 14.2 (2C; CH$_3$), 11.6 (CH$_3$).

Using similar methods, (E)-2-((18-((6-(4-hydroxy-6-methoxy-7-methyl-3-oxo-1,3-dihydroisobenzofuran-5-yl)-4-methylhex-4-enoyl)oxy)octadecanoyl)oxy)propane-1,3-diyl dipalmitate (MPA-I-38) was prepared from allyl-protected MPA Int-86 and Int-105 as follows.

Synthesis of (E)-2-((18-((6-(4-(allyloxy)-6-methoxy-7-methyl-3-oxo-1,3-dihydroisobenzofuran-5-yl)-4-methylhex-4-enoyl)oxy)octadecanoyl)oxy)propane-1,3-diyl dipalmitate (Int-128)

Int-128

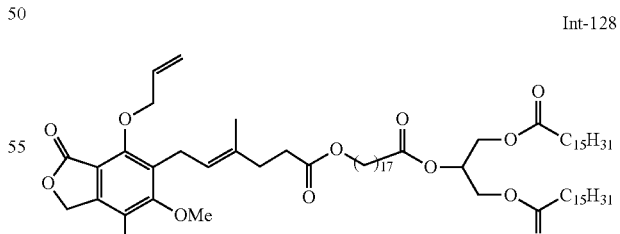

DMAP (4.6 mg, 37.4 μmol), EDC·HCl (17.9 mg, 93.4 μmol) and Int-86 (18.8 mg, 52.3 μmol) were added to a solution of alcohol Int-105 (31.8 mg, 37.4 μmol) in CH$_2$Cl$_2$ (1 mL) and the mixture stirred at RT for 19 hours. The reaction was diluted with CH$_2$Cl$_2$ (5 mL), silica gel was added and the mixture concentrated under reduced pressure. Purification by silica gel chromatography (12.5% to 17.5% ethyl acetate/hexanes) gave allyl-protected prodrug Int-128 (40.6 mg, 91%) as a colorless solid. $^1$H NMR (401 MHz, CDCl$_3$) δ 6.10 (ddt, J=17.1, 10.4, 5.9 Hz, 1H), 5.37 (ddd, J=17.2, 3.1, 1.5 Hz, 1H), 5.30-5.21 (m, 2H), 5.17 (td, J=6.7, 1.1 Hz, 1H), 5.13 (s, 2H), 4.78 (dt, J=5.9, 1.3 Hz, 2H), 4.29 (dd, J=11.9, 4.3 Hz, 2H), 4.14 (dd, J=11.9, 6.0 Hz, 2H), 4.00 (t, J=6.8 Hz, 2H), 3.76 (s, 3H), 3.41 (d, J=6.7 Hz, 2H), 2.39-2.25 (m, 10H), 2.18 (s, 3H), 1.78 (s, 3H), 1.66-1.52 (m, 8H), 1.37-1.18 (m, 74H), 0.88 (t, J=6.9 Hz, 6H); $^{13}$C NMR (101 MHz, CDCl$_3$) δ 173.6 (C), 173.4 (2C; C), 173.0 (C), 169.1 (C), 163.0 (C), 155.4 (C), 146.8 (C), 134.00 (C), 133.97 (CH), 129.3 (C), 123.7 (CH), 120.1 (C), 118.2 (CH$_2$), 112.8 (C), 76.2 (CH$_2$), 69.0 (CH), 68.4 (CH$_2$), 64.6 (CH$_2$), 62.2 (2C; CH$_2$), 61.1 (CH$_3$), 34.7 (CH$_2$), 34.3 (CH$_2$), 34.2 (2C; CH$_2$), 33.2 (CH$_2$), 32.1 (2C; CH$_2$), 29.83 (10C; CH$_2$), 29.79 (6C; CH$_2$), 29.75 (3C; CH$_2$), 29.68 (CH$_2$), 29.65 (CH$_2$), 29.60 (2C; CH$_2$), 29.49 (2C; CH$_2$), 29.44 (CH$_2$), 29.40 (3C; CH$_2$), 29.24 (2C; CH$_2$), 29.22 (CH$_2$), 28.7 (CH$_2$), 26.0 (CH$_2$), 25.03 (CH$_2$), 24.99 (2C; CH$_2$), 23.8 (CH$_2$), 22.8 (2C; CH$_2$), 16.4 (CH$_3$), 14.2 (2C; CH$_3$), 11.7 (CH$_3$).

DMBA (10.6 mg, 68.0 μmol) and Pd(PPh$_3$)$_4$ (7.8 mg, 6.8 μmol) were added to allyl ether Int-128 (40.6 mg, 34.0 μmol) in CH$_2$Cl$_2$ (1.5 mL) and the mixture stirred at RT for 4 h. The reaction was diluted with (10 mL), silica gel was added, and the mixture concentrated under reduced pressure. Silica gel chromatography (15% to 20% ethyl acetate/hexanes) gave MPA prodrug MPA-I-38 (38.3 mg, 98%) as a colorless solid. $^1$H NMR (401 MHz, CDCl$_3$) δ 7.67 (s, 1H), 5.29-5.21 (m, 2H), 5.20 (s, 2H), 4.29 (dd, J=11.9, 4.3 Hz, 2H), 4.14 (dd, J=11.9, 5.9 Hz, 2H), 4.00 (t, J=6.7 Hz, 2H), 3.76 (s, 3H), 3.38 (d, J=6.7 Hz, 2H), 2.42-2.35 (m, 2H), 2.35-2.26 (m, 8H), 2.14 (s, 3H), 1.80 (s, 3H), 1.67-1.51 (m, 8H), 1.45-1.15 (m, 74H), 0.88 (t, J=6.7 Hz, 6H); $^{13}$C NMR (101 MHz, CDCl$_3$) δ 173.6 (C), 173.4 (2C; C), 173.0 (2C; C), 163.8 (C), 153.8 (C), 144.1 (C), 134.4 (C), 122.8 (CH), 122.3 (C), 116.8 (C), 106.5 (C), 70.2 (CH$_2$), 69.0 (CH), 64.6 (CH$_2$), 62.2 (2C; CH$_2$), 61.1 (CH$_3$), 34.8 (CH$_2$), 34.4 (CH$_2$), 34.2 (2C; CH$_2$), 33.3 (CH$_2$), 32.1 (2C; CH$_2$), 29.83 (10C; CH$_2$), 29.79 (6C; CH$_2$), 29.75 (3C; CH$_2$), 29.68 (CH$_2$), 29.65 (CH$_2$), 29.61 (2C; CH$_2$), 29.49 (2C; CH$_2$), 29.44 (CH$_2$), 29.40 (3C; CH$_2$), 29.25 (2C; CH$_2$), 29.22 (CH$_2$), 28.7 (CH$_2$), 26.1 (CH$_2$), 25.04 (CH$_2$), 24.99 (2C; CH$_2$), 22.8 (2C; CH$_2$), 22.7 (CH$_2$), 16.3 (CH$_3$), 14.2 (2C; CH$_3$), 11.7 (CH$_3$).

Using similar methods, (E)-2-((4-((6-(4-hydroxy-6-methoxy-7-methyl-3-oxo-1,3-dihydroisobenzofuran-5-yl)-4-methylhex-4-enoyl)oxy)-3-methylbutanoyl)oxy)propane-1,3-diyl dibutyrate (MPA-I-43) was prepared from Int-86 and Int-125 via the allyl-protected intermediate Int-127:

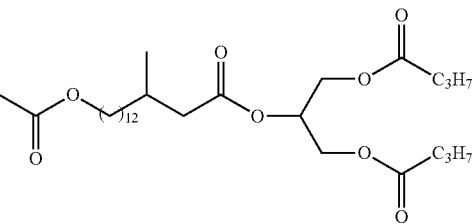

Int-127

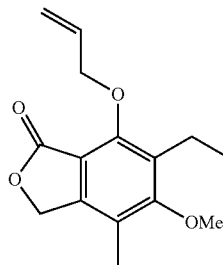

Int-127: $^1$H NMR (401 MHz, CDCl$_3$) δ 6.09 (ddt, J=17.1, 10.4, 5.9 Hz, 1H), 5.37 (dq, J=17.2, 1.5 Hz, 1H), 5.28 (m, 1H), 5.23 (m, 1H), 5.18 (m, 1H), 5.13 (s, 2H), 4.78 (dt, J=5.9, 1.3 Hz, 2H), 4.296/4.293 (each dd, J=11.9, 4.3 Hz, 2H), 4.150/4.148 (each dd, J=11.9, 6.0 Hz, 2H), 4.00 (t, J=6.8 Hz, 2H), 3.76 (s, 3H), 3.41 (d, J=6.7 Hz, 2H), 2.39-2.25 (m, 9H), 2.17 (s, 3H), 2.12 (dd, J=14.7, 8.3 Hz, 1H), 1.93 (m, 1H), 1.78 (d, J=0.7 Hz, 3H), 1.68-1.52 (m, 8H), 1.35-1.17 (m, 18H), 0.94 (t, J=7.4 Hz, 6H), 0.93 (d, J=6.7 Hz, 3H).

MPA-I-43:

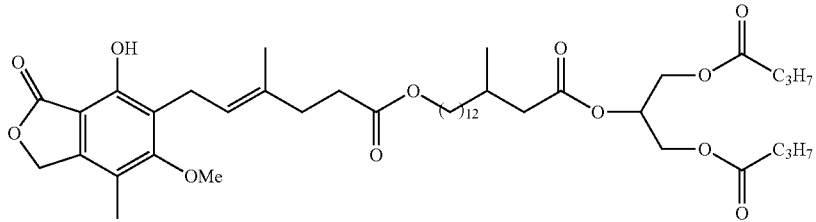

MPA-I-43

MPA-I-43 was prepared from the corresponding allyl-protected compound in 58% yield after Pd-mediated deprotection. $^1$H NMR (401 MHz, CDCl$_3$) δ 7.67 (s, 1H), 5.31-5.21 (m, 2H), 5.19 (s, 2H), 4.295/4.292 (each dd, J=11.9, 4.2 Hz, 2H), 4.149/4.197 (each dd, J=11.9, 6.0 Hz, 2H), 4.00 (t, J=6.8 Hz, 2H), 3.76 (s, 3H), 3.38 (d, J=6.9 Hz, 2H), 2.41-2.26 (m, 9H), 2.14 (s, 3H), 2.12 (dd, J=14.7, 8.3 Hz, 1H), 1.93 (m, 1H), 1.79 (s, 3H), 1.69-1.52 (m, 8H), 1.36-1.15 (m, 18H), 0.94 (t, J=7.4, 2.8 Hz, 6H), 0.92 (d, J=6.7 Hz, 3H); $^{13}$C NMR (101 MHz, CDCl$_3$) δ 173.6 (C), 173.3 (2C; C), 173.1 (C), 172.5 (C), 163.8 (C), 153.8 (C), 144.1 (C), 134.4 (C), 122.8 (CH), 122.3 (C), 116.8 (C), 106.5 (C), 70.2 (CH$_2$), 68.9 (CH), 64.6 (CH$_2$), 62.3 (2C; CH$_2$), 61.1 (CH$_3$), 41.9 (CH$_2$), 36.8 (CH$_2$), 36.1 (2C; CH$_2$), 34.8 (CH$_2$), 33.3 (CH$_2$), 30.5 (CH), 29.9 (CH$_2$), 29.81 (CH$_2$), 29.79 (2C; CH$_2$), 29.74 (CH$_2$), 29.68 (CH$_2$), 29.4 (CH$_2$), 28.8 (CH$_2$), 27.1 (CH$_2$), 26.1 (CH$_2$), 22.7 (CH$_2$), 19.7 (CH$_3$), 18.5 (2C; CH$_2$), 16.3 (CH$_3$), 13.8 (2C; CH$_3$), 11.7 (CH$_3$).

Using similar methods, MPA-C10-2-TG (MPA-I-46) was prepared.

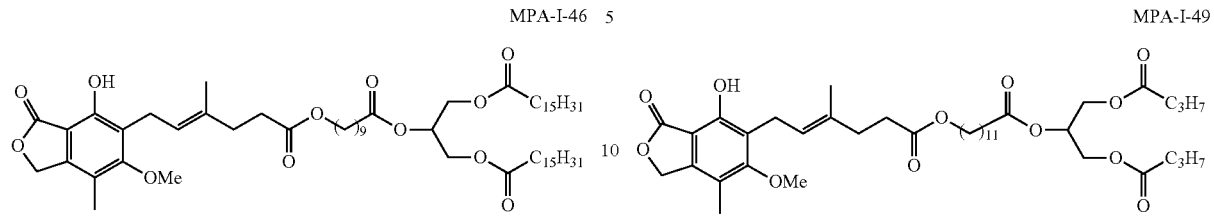

MPA-I-46

$^1$H NMR (401 MHz, CDCl$_3$) δ 7.67 (s, 1H), 5.29-5.21 (m, 2H), 5.19 (s, 2H), 4.29 (dd, J=11.9, 4.4 Hz, 2H), 4.14 (dd, J=11.9, 5.9 Hz, 2H), 4.00 (t, J=6.8 Hz, 2H), 3.76 (s, 3H), 3.38 (d, J=6.9 Hz, 2H), 2.41-2.35 (m, 2H), 2.33-2.24 (m, 8H), 2.14 (s, 3H), 1.80 (s, 3H), 1.66-1.52 (m, 8H), 1.37-1.17 (m, 58H), 0.87 (t, J=6.8 Hz, 6H); $^{13}$C NMR (101 MHz, CDCl$_3$) δ 173.6 (C), 173.4 (2C; C), 173.1 (C), 173.0 (C), 163.8 (C), 153.8 (C), 144.1 (C), 134.4 (C), 122.8 (CH), 122.3 (C), 116.8 (C), 106.5 (C), 70.2 (CH$_2$), 69.0 (CH), 64.6 (CH$_2$), 62.2 (2C; CH$_2$), 61.1 (CH$_3$), 34.8 (CH$_2$), 34.3 (CH$_2$), 34.2 (2C; CH$_2$), 33.3 (CH$_2$), 32.1 (2C; CH$_2$), 29.84 (6C; CH$_2$), 29.80 (4C; CH$_2$), 29.76 (2C; CH$_2$), 29.62 (2C; CH$_2$), 29.50 (3C; CH$_2$), 29.41 (2C; CH$_2$), 29.36 (2C; CH$_2$), 29.26 (2C; CH$_2$), 29.19 (CH$_2$), 28.8 (CH$_2$), 26.1 (CH$_2$), 25.0 (3C; CH$_2$), 22.8 (2C; CH$_2$), 22.7 (CH$_2$), 16.3 (CH$_3$), 14.3 (2C; CH$_3$), 11.7 (CH$_3$).

Using similar methods to those described above, MPA-C12-2-TG-butyrate (MPA-I-49) was prepared using Int-126.

MPA-I-49

$^1$H NMR (401 MHz, CDCl$_3$) δ 7.66 (s, 1H), 5.29-5.19 (m, 2H), 5.18 (s, 2H), 4.29 (dd, J=11.9, 4.3 Hz, 2H), 4.14 (dd, J=11.9, 6.0 Hz, 2H), 3.99 (t, J=6.8 Hz, 2H), 3.75 (s, 3H), 3.37 (d, J=7.0 Hz, 2H), 2.41-2.34 (m, 2H), 2.33-2.24 (m, 8H), 2.13 (s, 3H), 1.78 (s, 3H), 1.69-1.51 (m, 8H), 1.35-1.19 (m, 14H), 0.93 (t, J=7.4 Hz, 6H); $^{13}$C NMR (101 MHz, CDCl$_3$) δ 173.6 (C), 173.2 (2C; C), 173.0 (2C; C), 163.8 (C), 153.8 (C), 144.1 (C), 134.3 (C), 122.8 (CH), 122.3 (C), 116.8 (C), 106.5 (C), 70.2 (CH$_2$), 69.0 (CH), 64.6 (CH$_2$), 62.2 (2C; CH$_2$), 61.1 (CH$_3$), 36.0 (2C; CH$_2$), 34.8 (CH$_2$), 34.3 (CH$_2$), 33.2 (CH$_2$), 29.63 (CH$_2$), 29.61 (CH$_2$), 29.5 (CH$_2$), 29.4 (2C; CH$_2$), 29.2 (CH$_2$), 28.7 (CH$_2$), 26.0 (CH$_2$), 25.0 (CH$_2$), 22.7 (CH$_2$), 18.5 (2C; CH$_2$), 16.3 (CH$_3$), 13.7 (2C; CH$_3$), 11.7 (CH$_3$).

Using similar methods to those described above, MPA-C10bMe-2-TG (MPA-I-50) was prepared using Int-23.

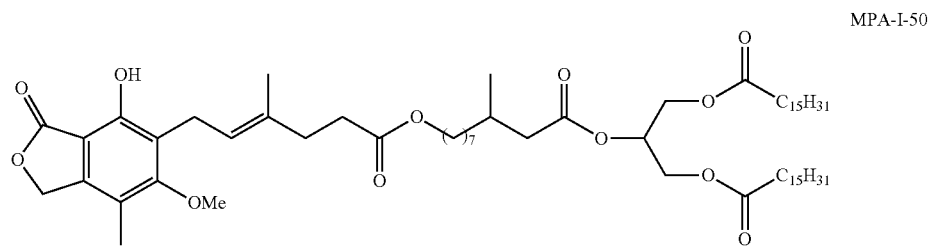

MPA-I-50

$^1$H NMR (401 MHz, CDCl$_3$) δ 7.67 (s, 1H), 5.30-5.20 (m, 2H), 5.19 (s, 2H), 4.28 (dd, J=11.9, 4.3 Hz, 2H), 4.13 (dd, J=13.1, 4.8 Hz, 2H), 4.00 (t, J=6.8 Hz, 2H), 3.75 (s, 3H), 3.38 (d, J=6.9 Hz, 2H), 2.41-2.35 (m, 2H), 2.34-2.26 (m, 7H), 2.14 (s, J=6.2 Hz, 3H), 2.11 (dd, J=14.7, 8.4 Hz, 1H), 1.90 (m, 1H), 1.79 (s, 3H), 1.67-1.52 (m, 6H), 1.36-1.14 (m, 58H), 0.92 (d, J=6.6 Hz, 3H), 0.87 (t, J=6.9 Hz, 6H); $^{13}$C NMR (101 MHz, CDCl$_3$) δ 173.6 (C), 173.4 (2C; C), 173.1 (C), 172.4 (C), 163.8 (C), 153.8 (C), 144.1 (C), 134.4 (C), 122.8 (CH), 122.3 (C), 116.8 (C), 106.5 (C), 70.2 (CH$_2$), 69.0 (CH), 64.6 (CH$_2$), 62.3 (2C; CH$_2$), 61.1 (CH$_3$), 41.8 (CH$_2$), 36.8 (CH$_2$), 34.8 (CH$_2$), 34.2 (2C; CH$_2$), 33.3 (CH$_2$), 32.1 (2C; CH$_2$), 30.5 (CH), 29.83 (7C; CH$_2$), 29.79 (4C; CH$_2$), 29.76 (2C; CH$_2$), 29.6 (2C; CH$_2$), 29.5 (2C; CH$_2$), 29.4 (3C; CH$_2$), 29.3 (2C; CH$_2$), 28.7 (CH$_2$), 27.0 (CH$_2$), 26.1 (CH$_2$), 25.0 (2C; CH$_2$), 22.8 (2C; CH$_2$), 22.7 (CH$_2$), 19.7 (CH$_3$), 16.3 (CH$_3$), 14.3 (2C; CH$_3$), 11.7 (CH$_3$); ESI-HRMS: calcd. for C$_{63}$H$_{106}$NaO$_{12}$ [M+Na$^+$] 1077.7576; found 1077.7576.

Using similar methods to those described above, MPA-C12bMe-2-TG (MPA-I-51) was prepared using Int-121.

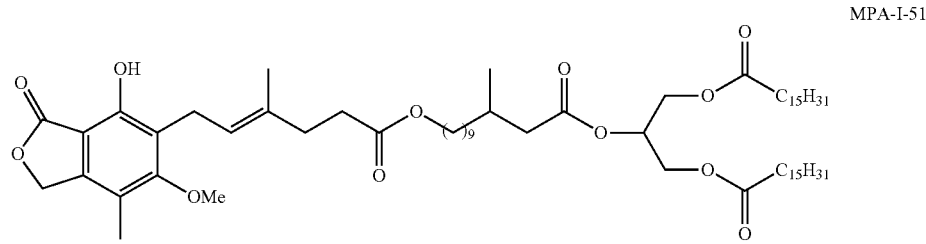

MPA-I-51

$^1$H NMR (401 MHz, CDCl$_3$) δ 7.67 (s, 1H), 5.30-5.21 (m, 2H), 5.19 (s, 2H), 4.285/4.283 (each dd, J=11.8, 4.3 Hz, 2H), 4.14 (dd, J=11.9, 5.9 Hz, 2H), 4.00 (t, J=6.8 Hz, 2H), 3.75 (s, 3H), 3.38 (d, J=6.9 Hz, 2H), 2.41-2.26 (m, 9H), 2.14 (s, 3H), 2.09 (dd, J=14.8, 8.3 Hz, 1H), 1.93 (m, 1H), 1.79 (d, J=0.7 Hz, 3H), 1.64-1.52 (m, 6H), 1.41-1.15 (m, 62H), 0.92 (d, J=6.6 Hz, 3H), 0.87 (t, J=6.9 Hz, 6H); $^{13}$C NMR (101 MHz, CDCl$_3$) δ 173.6 (C), 173.4 (2C; C), 173.1 (C), 172.5 (C), 163.8 (C), 153.8 (C), 144.1 (C), 134.4 (C), 122.8 (CH), 122.3 (C), 116.8 (C), 106.5 (C), 70.2 (CH$_2$), 68.9 (CH), 64.6 (CH$_2$), 62.3 (2C; CH$_2$), 61.1 (CH$_3$), 41.8 (CH$_2$), 36.8 (CH$_2$), 34.8 (CH$_2$), 34.2 (2C; CH$_2$), 33.3 (CH$_2$), 32.1 (2C; CH$_2$), 30.5 (CH), 29.9 (CH$_2$), 29.84 (6C; CH$_2$), 29.80 (4C; CH$_2$), 29.76 (2C; CH$_2$), 29.74 (CH$_2$), 29.68 (CH$_2$), 29.62 (2C; CH$_2$), 29.5 (2C; CH$_2$), 29.4 (3C; CH$_2$), 29.3 (2C; CH$_2$), 28.8 (CH$_2$), 27.1 (CH$_2$), 26.1 (CH$_2$), 25.0 (2C; CH$_2$), 22.8 (2C; CH$_2$), 22.7 (CH$_2$), 19.7 (CH$_3$), 16.3 (CH$_3$), 14.3 (2C; CH$_3$), 11.7 (CH$_3$).

Example 22: Synthesis of TAC-I-1

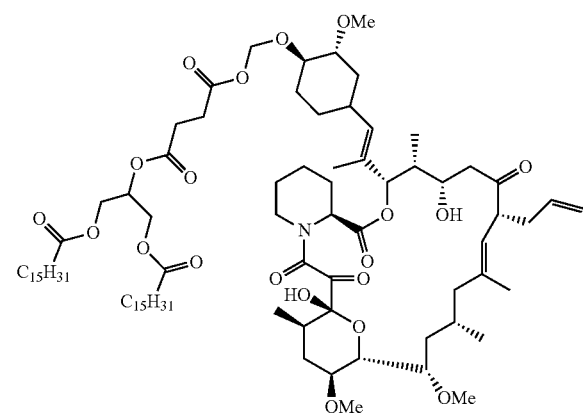

TAC-I-1

Synthesis of TAC-I-1

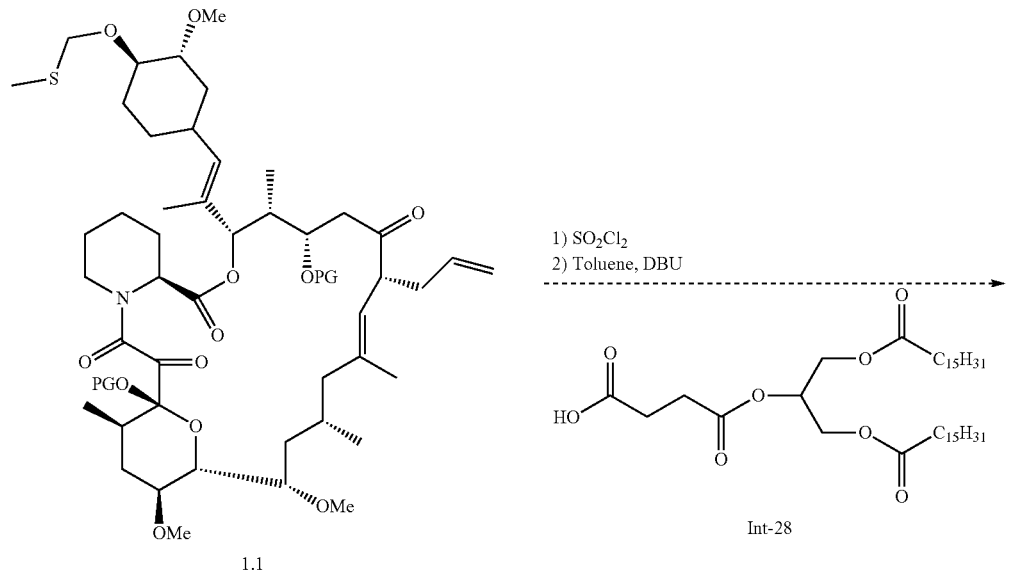

-continued

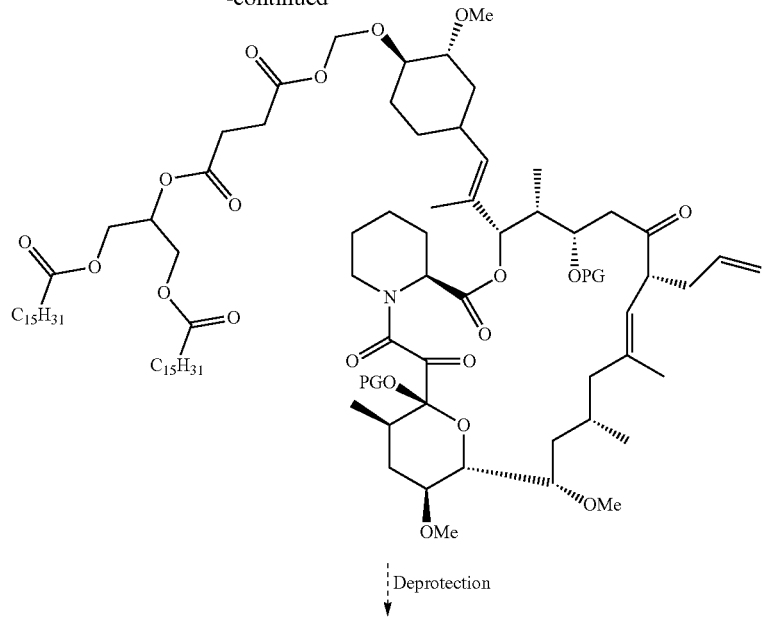

Deprotection ↓

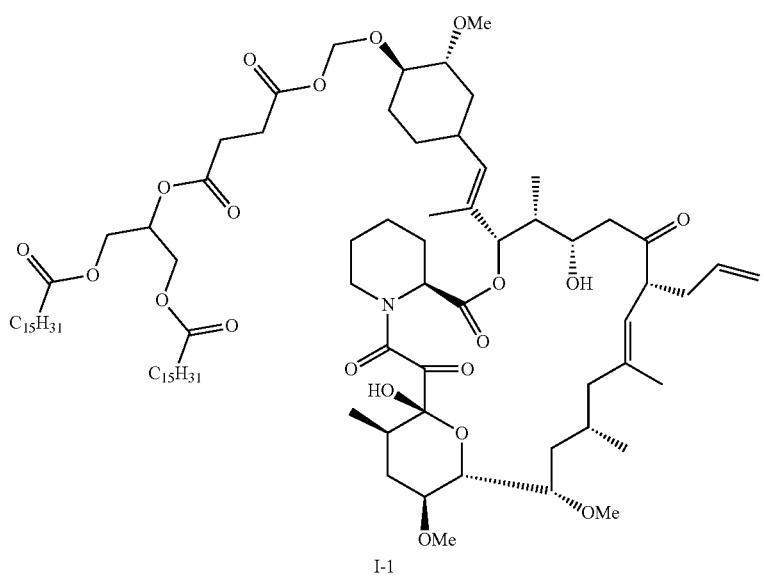

I-1

Synthesis of 1.1: 1.1, is prepared by treating a macrolide with chloromethyl methyl thioether as described in WO 2009/143295, which is hereby incorporated by reference in its entirety. A solution of sulfuryl chloride (2.2 equiv.) in $CH_2Cl_2$ (0.16 M) is added to a solution of 1.1 (1.8 equiv.) in $CH_2Cl_2$ (0.07 M) at 0° C. and the mixture stirred at 0° C. for 30 minutes and then at rt for an additional hour. The reaction is concentrated under a stream of $N_2$, co-evaporated from toluene (twice) and dried under reduced pressure.

Synthesis of TAC-I-1 (TAC-32-(ASI-$C_{4-2}$-TG)): TAC-I-1 is prepared according to the following procedure. The crude residue is re-dissolved in toluene (0.1 M based on 1.1), added to a solution of acid Int-28 (1 eq) as prepared in WO 2017/041139, and DBU (1.5 eq) in toluene (0.05 M) that had been pre-stirred for one hour, and the mixture is stirred at rt for two hours. The reaction is diluted with $CH_2Cl_2$ (20 mL) and the organic phase washed with sat. aq. $NaHCO_3$ (20 mL) and brine (20 mL), dried ($MgSO_4$) and concentrated under reduced pressure to give the crude protected product. Deprotection and purification by silica gel chromatography with a suitable solvent mixture affords TAC-I-1. In the instance protecting groups are not utilized, regioisomers are separated by known purification techniques to afford TAC-I-1 and TAC-I-3.

Example 23: Synthesis of TAC-I-4
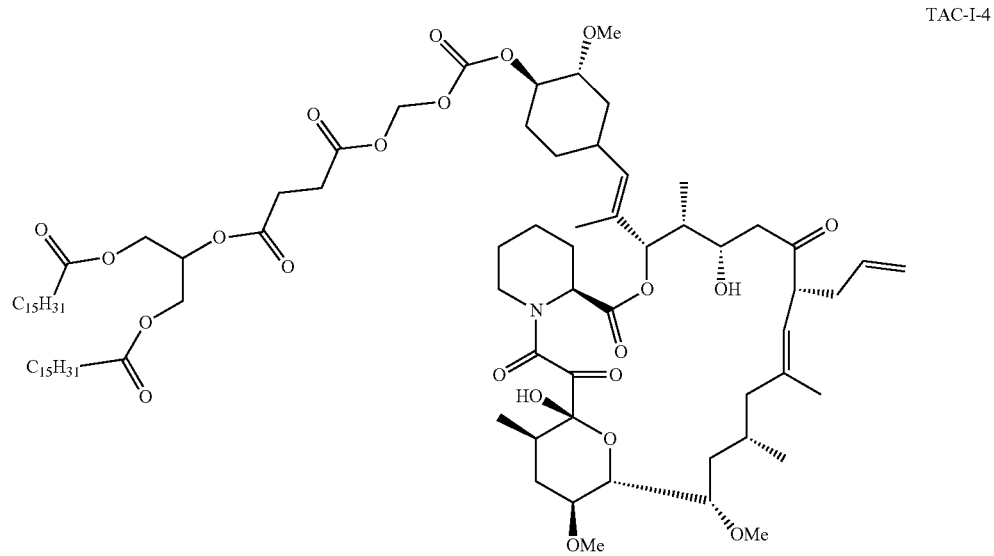
TAC-I-4
Synthesis of TAC-I-4
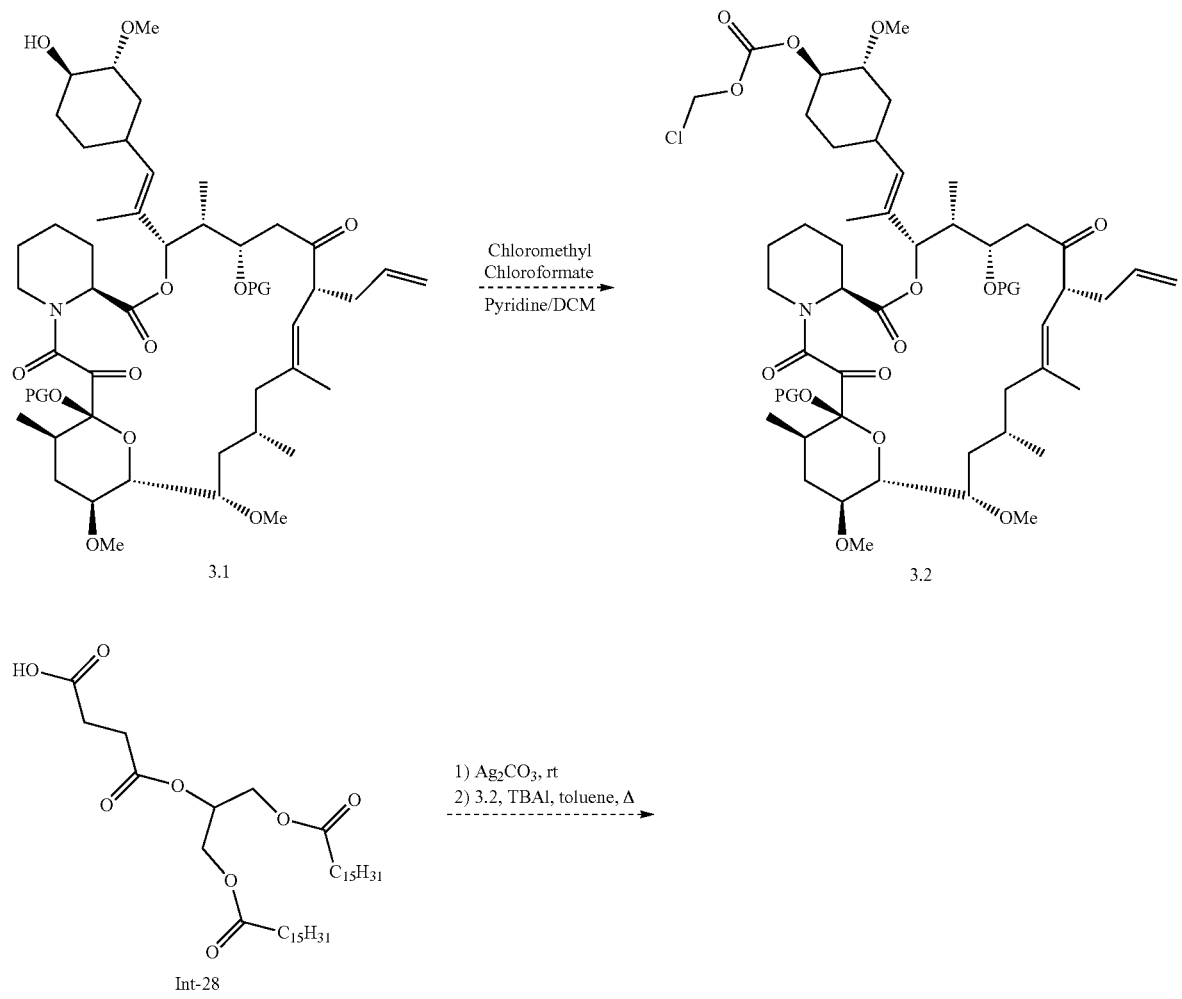

-continued
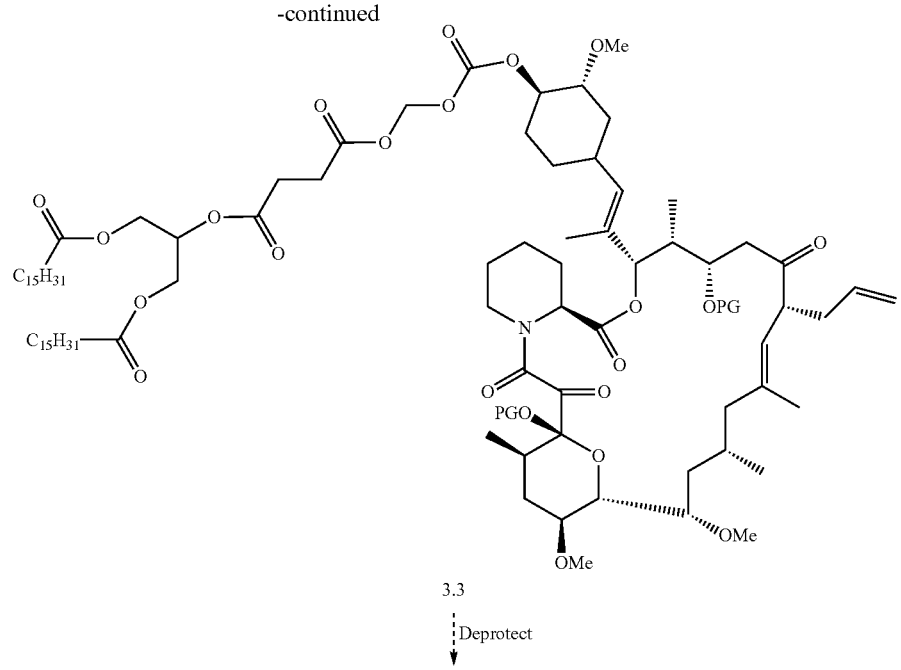
3.3
↓ Deprotect
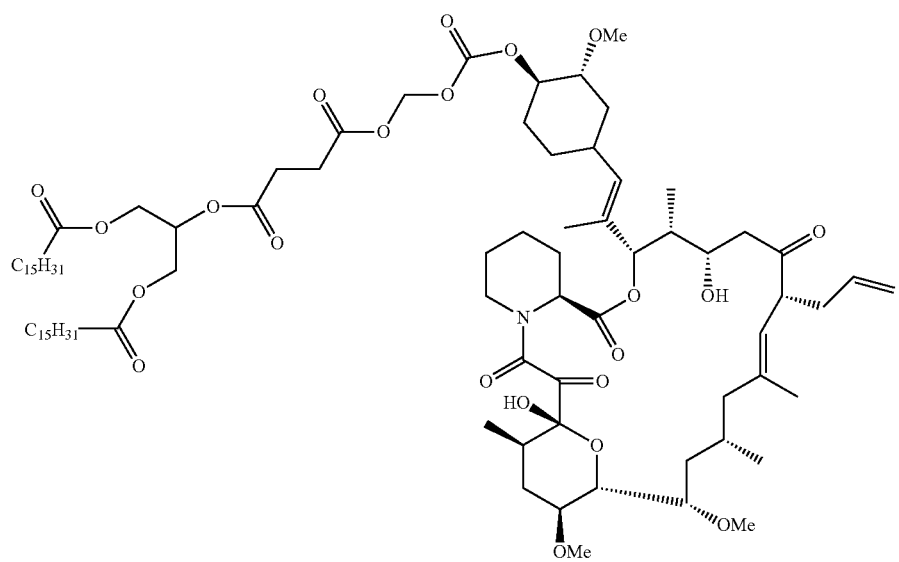
I-4

Synthesis of 3.2: 3.2 is prepared according to the following procedure. PG indicates an optional hydroxyl protecting group. Chloromethyl chloroformate (1.6 equiv.) and pyridine (3.0 equiv.) are added to macrolide 3.1 (1.0 equiv.) in $CH_2Cl_2$ (0.03 M) at 0° C. and the mixture is stirred at 0° C. for 15 minutes and then at rt for one hour. The reaction is diluted with $CH_2Cl_2$ and the organic phase washed with sat. aq. $NaHCO_3$ and brine, dried ($MgSO_4$) and concentrated under reduced pressure to give 3.2 which is used without purification.

Synthesis of TAC-I-4 (TAC-32-(CASI-$C_{4-2}$-TG)): TAC-I-4 is prepared according to the following procedure. Silver carbonate (0.7 equiv.) is added to acid Int-28 (1.2 equiv.) as prepared in WO 2017/041139, in DMF (0.03 M) and the mixture stirred at rt for one hour. The reaction is concentrated under reduced pressure to give a grey residue, to which is added chloromethyl carbonate (1.0 equiv.) in toluene (0.03 M) and TBAI (0.3 equiv.) and the mixture heated at reflux for 1.5 hours. The reaction is cooled to rt, then diluted with ethyl acetate. The organic phase is washed with water and brine, dried ($MgSO_4$) and concentrated under reduced pressure to give the crude 3.3. Deprotection and purification by silica gel chromatography with a suitable solvent mixture affords TAC-I-4. In the instance protecting groups are not utilized, regioisomers are separated via known purification techniques.

Example 24: Synthesis of TAC-I-7 and TAC-I-9

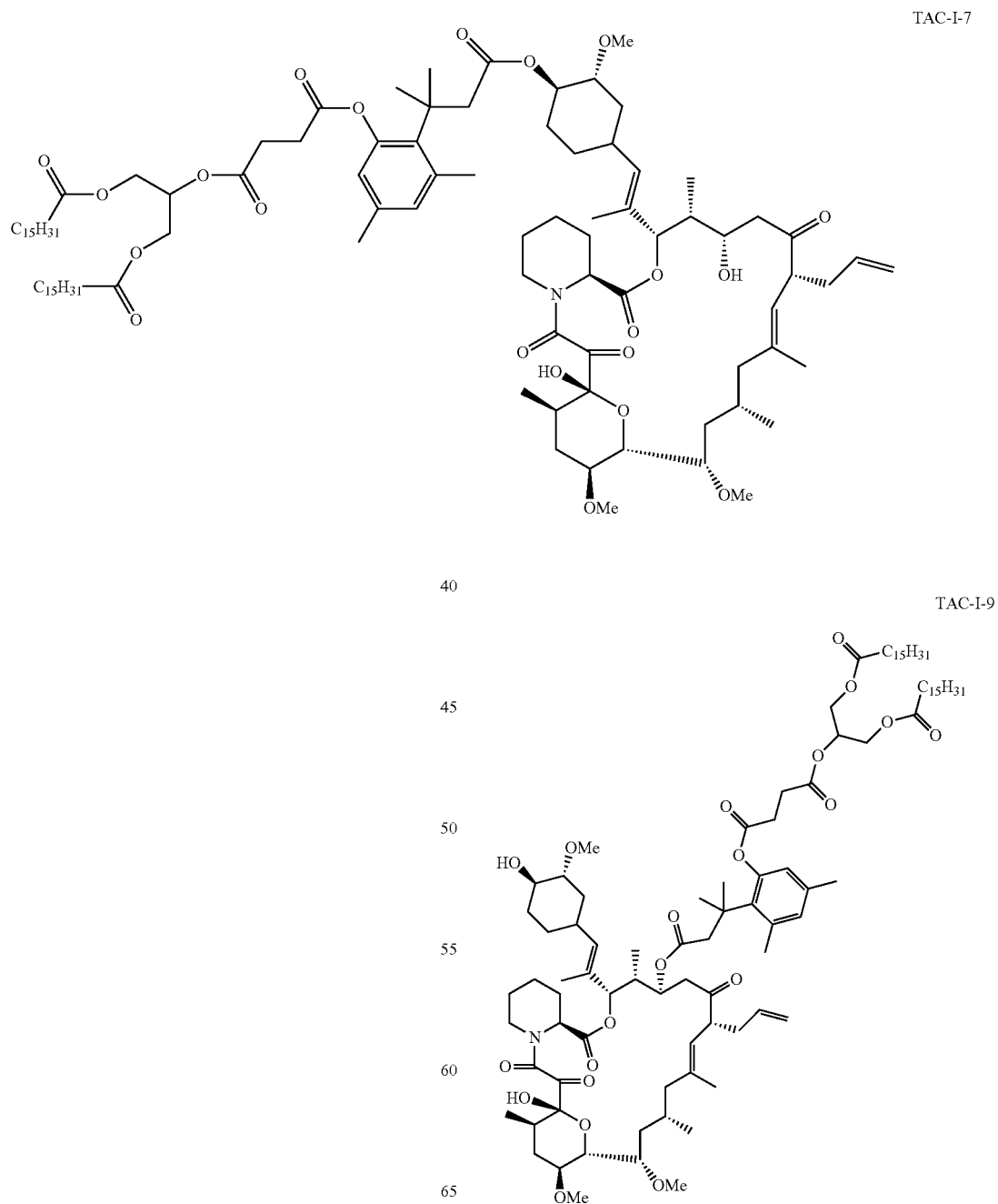

Synthesis of TAC-I-7 and TAC-I-9
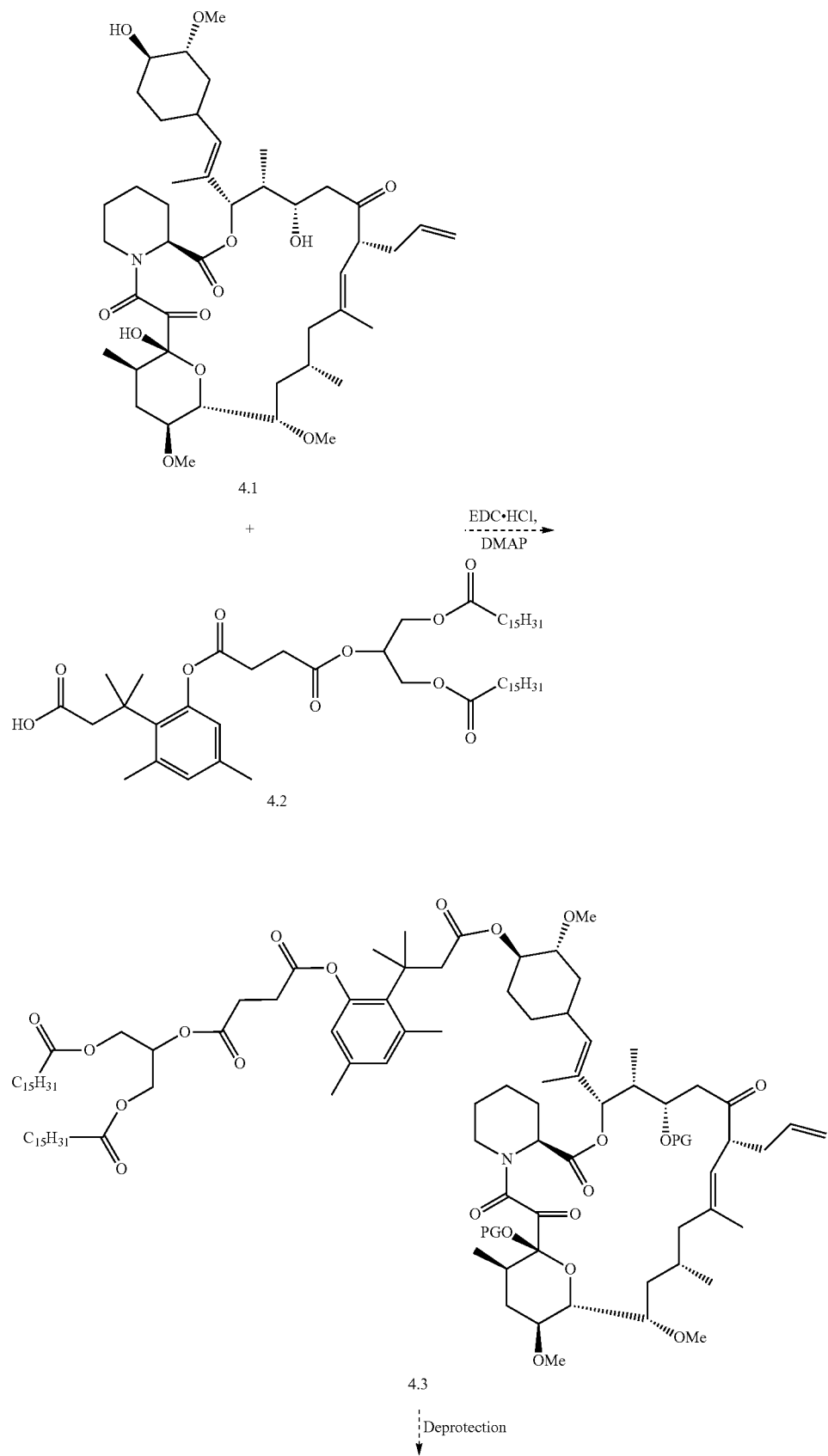

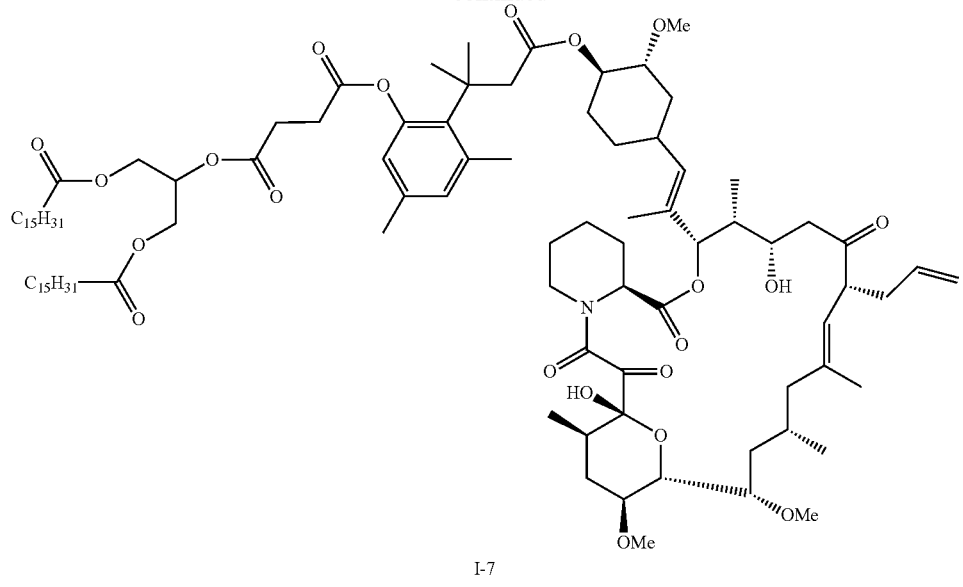

I-7

Synthesis of TAC-I-7 (TAC-32-(TML-C$_{4-2}$-TG): TAC-I-7 is prepared according to the following procedure. 4-(Dimethylamino)pyridine (DMAP, 1.3 equiv.) and EDC·HCl (2.1 equiv.) is added to a solution of macrolide 4.1 (1.3 equiv.) and acid 4.2 (1.0 equiv.), as prepared in WO 2017/041139, in CH$_2$Cl$_2$ (0.02 M) and the mixture stirred at rt for 19 hours. The reaction is diluted with CH$_2$Cl$_2$ (10 mL), silica gel is added and the mixture concentrated under reduced pressure to yield crude. Deprotection and purification by silica gel chromatography with a suitable solvent mixture affords TAC-I-7. In the instance protecting groups are not utilized, regioisomers are separated via known purification techniques.

Example 25: Synthesis of TAC-I-10

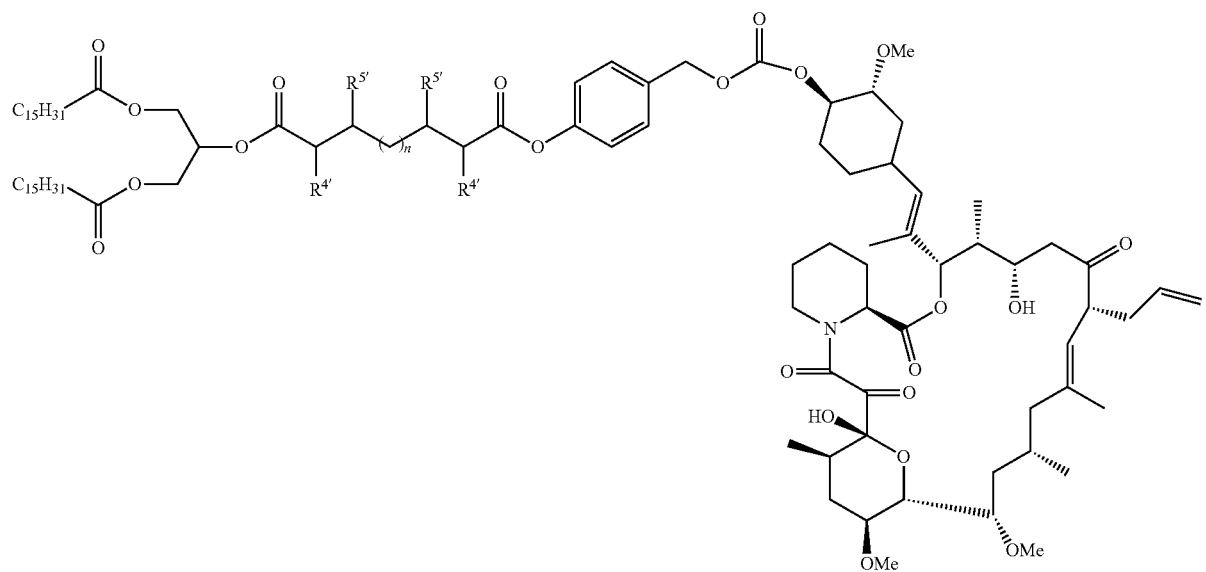

TAC-I-10

Synthesis of TAC-I-10
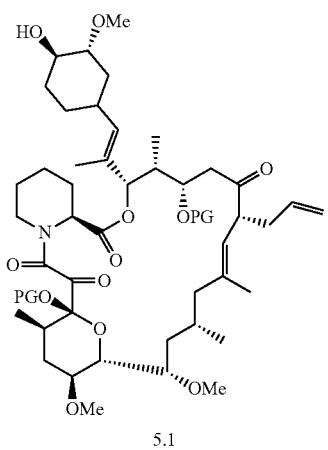
5.1
+
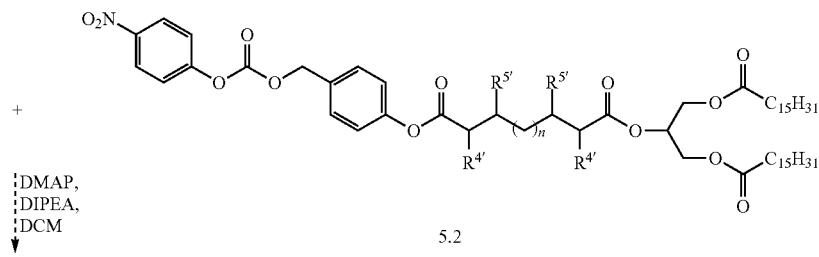
5.2
DMAP,
DIPEA,
DCM
↓
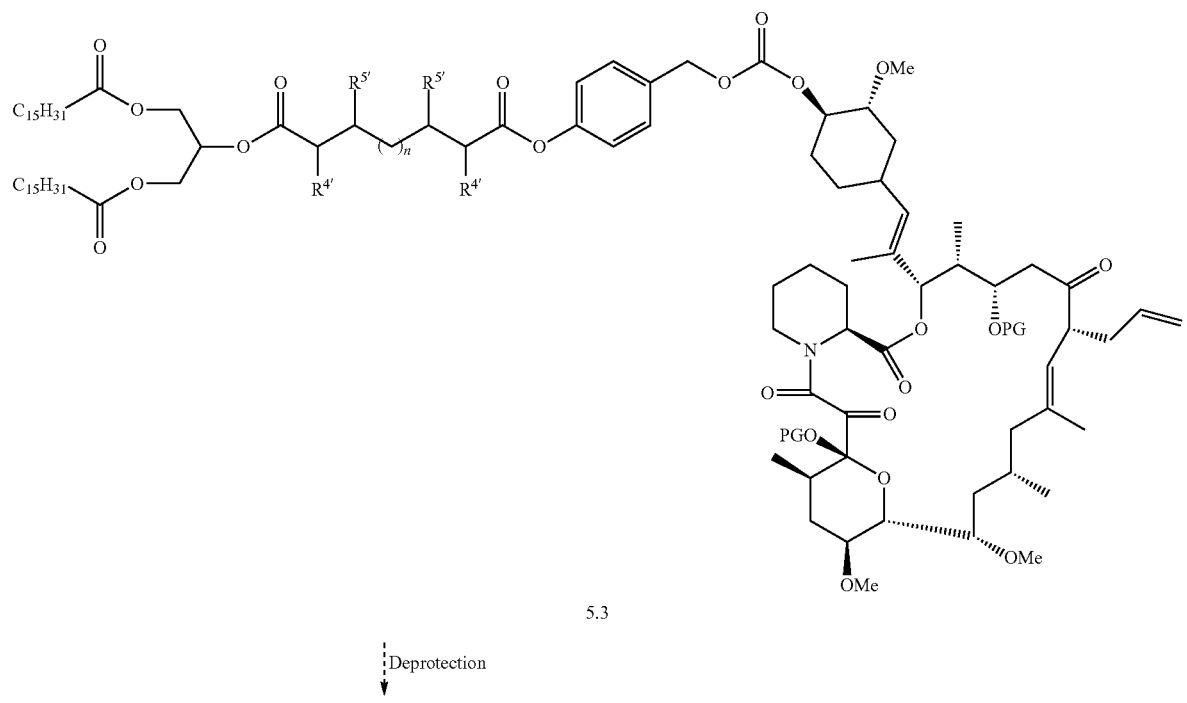
5.3
Deprotection
↓

-continued

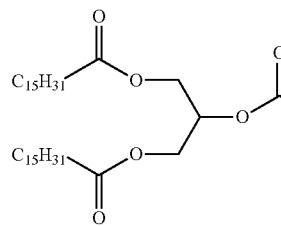
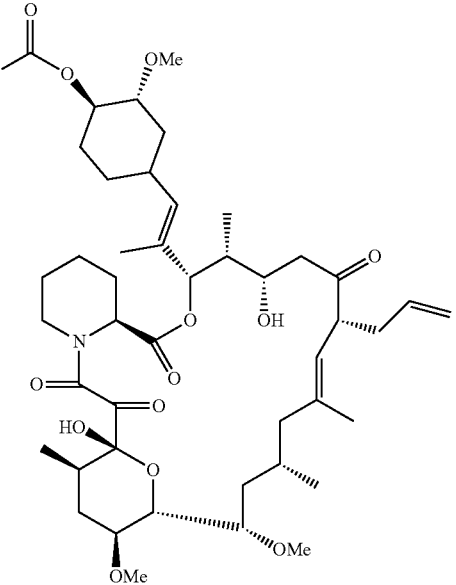

I-10

Synthesis of TAC-I-10. TAC-I-10 is prepared according to the following procedure. PG indicates an optional hydroxyl protecting group. 4-(Dimethylamino)pyridine (DMAP, 1.3 equiv.) and DIPEA (0.3 equiv.) were added to a solution of protected macrolide 5.1 (1.2 equiv.) and PNP carbonate 5.2 (1.0 equiv.) as prepared in WO 2017/041139, in $CH_2Cl_2$ (0.01 M) and the mixture stirred at rt for five days. The reaction was diluted with $CH_2Cl_2$, washed with 1 M HCl, water and brine, dried ($MgSO_4$) and concentrated under reduced pressure to give the crude product 5.3. Deprotection and purification by silica gel chromatography with a suitable solvent mixture affords TAC-I-10. In the instance protecting groups are not utilized, regioisomers are separated by known purification techniques.

Example 26: Synthesis of TAC-I-13

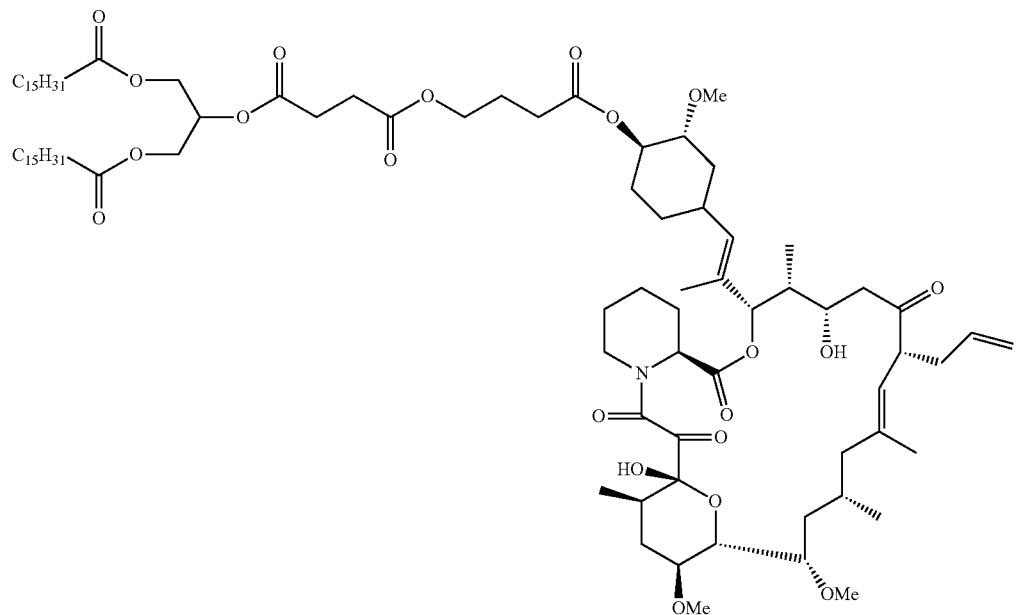

TAC-I-13

Synthesis of TAC-I-13
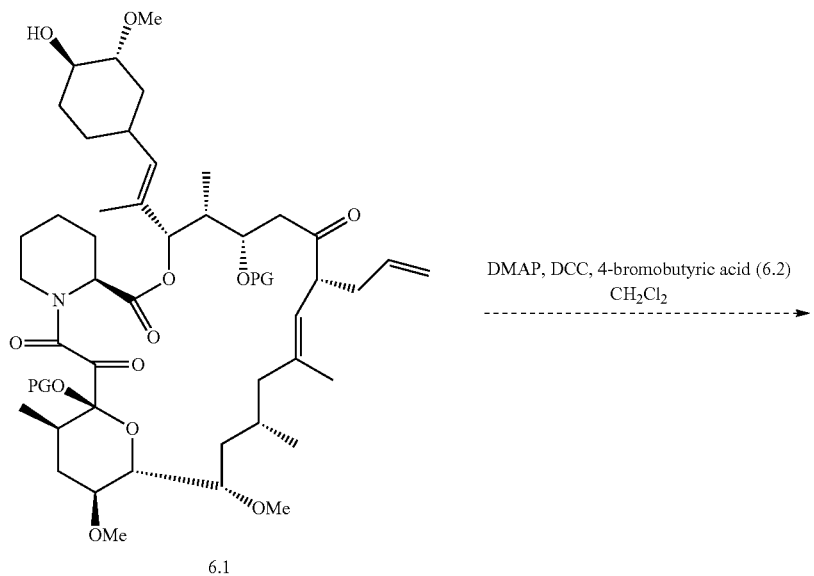
6.1
6.3

-continued

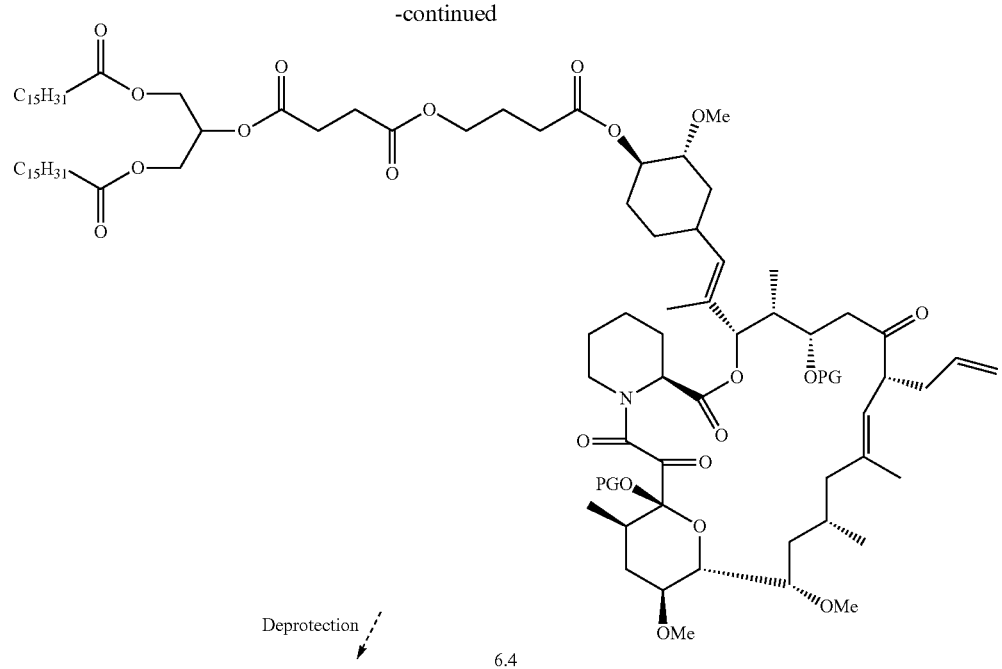

6.4

Deprotection

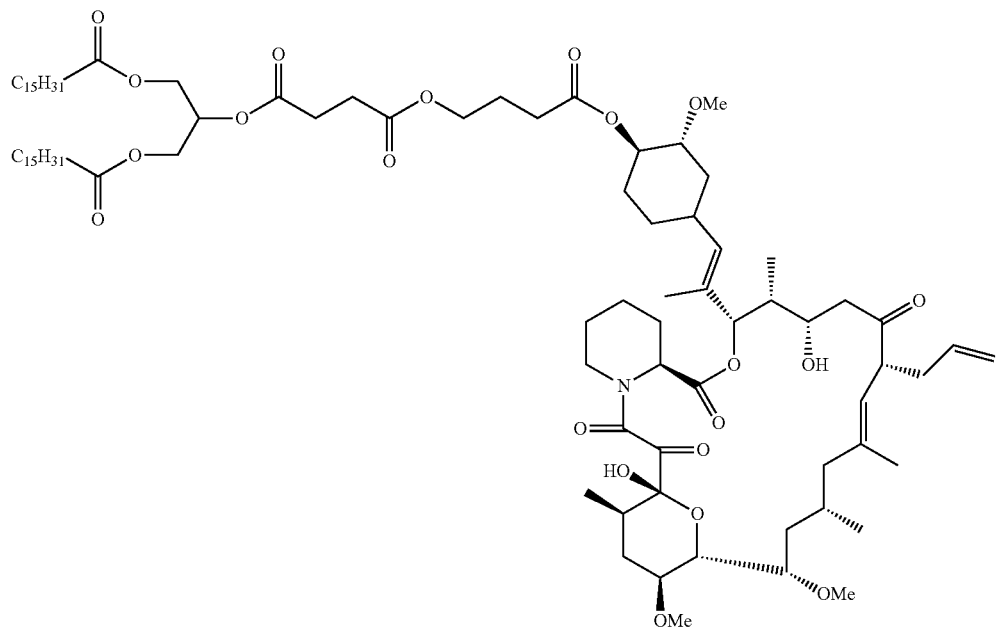

I-13

Synthesis of 6.3: 6.3 is prepared according to the following procedure. PG indicates an optional hydroxyl protecting group. 4-(Dimethylamino)pyridine (1.3 equiv.) and DCC (2.1 equiv.) are added to a solution of macrolide 6.1 (1.0 equiv.) and 4-bromobutyric acid 6.2 (1.3 equiv.) in $CH_2Cl_2$ (0.03 M) and the mixture is stirred at rt for 24 hours. Another 0.6 eq. of acid, 1 eq. of DCC, 0.6 eq. of DMAP are added and the mixture is stirred at rt for an additional two days. The reaction is diluted with $CH_2Cl_2$, silica gel is added and the mixture is concentrated under reduced pressure. Purification by silica gel chromatography gives bromide mixture 6.3.

Synthesis of TAC-I-13 (TAC-32-(FSI-4-C4-2-TG)): TAC-I-13 is prepared according to the following procedure.

1,8-Diazabicyclo[5.4.0]undec-7-ene (DBU) (1.6 equiv.) is added to a suspension of acid Int-28 (1.1 equiv.) as prepared in WO 2017/041139, and bromide 6.3 (1.0 equiv.) in toluene (0.03 M) and the mixture is heated at reflux for 21 hours. The reaction is cooled to rt, then diluted with ethyl acetate. The organic phase is washed with water and brine, dried ($MgSO_4$) and concentrated under reduced pressure to give the crude 6.4. Deprotection and purification by silica gel chromatography with a suitable solvent mixture affords TAC-I-13. In the instance protecting groups are not utilized, regioisomers are separated via known purification techniques.

Example 27: Synthesis of TAC-I-16
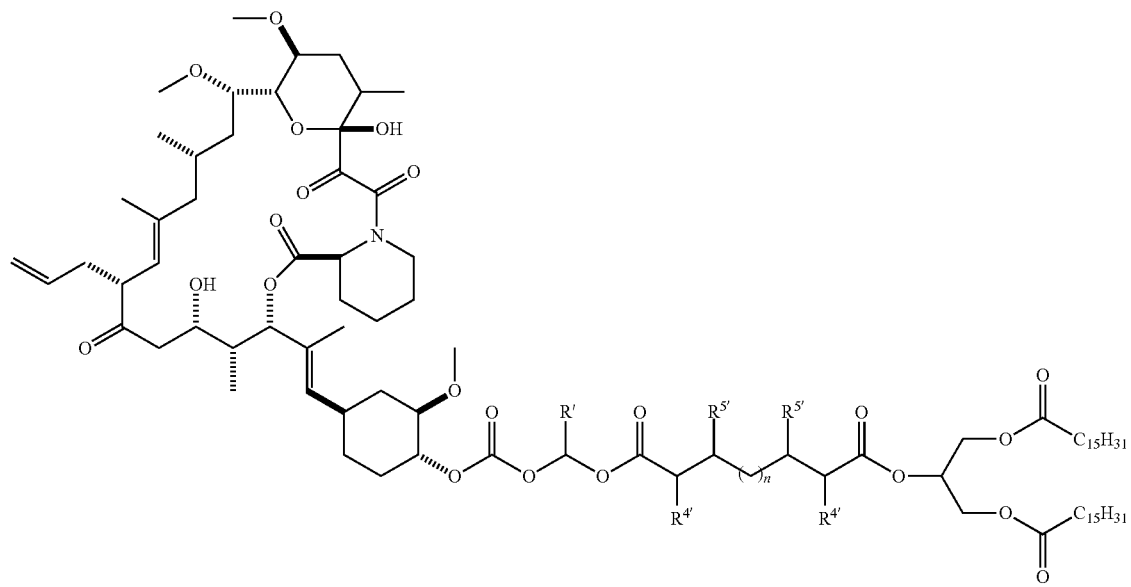
TAC-I-16
Synthesis of TAC-I-16
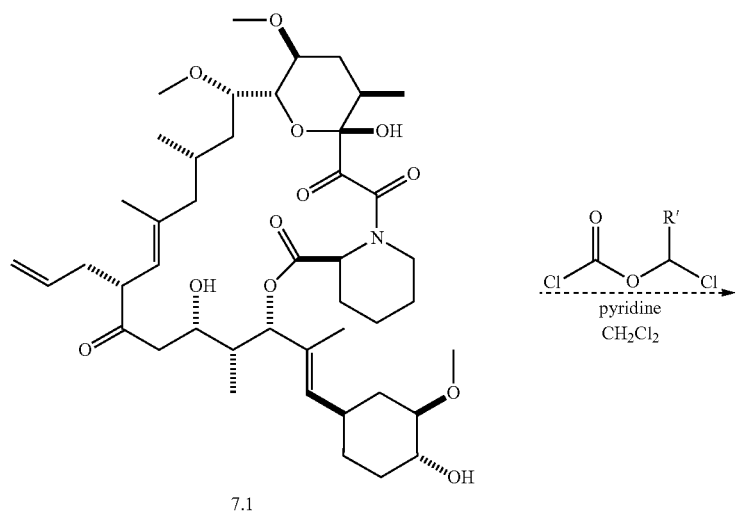
7.1

-continued
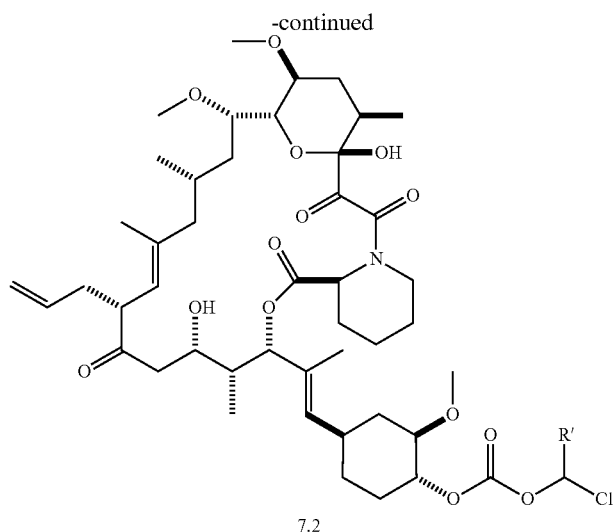
7.2
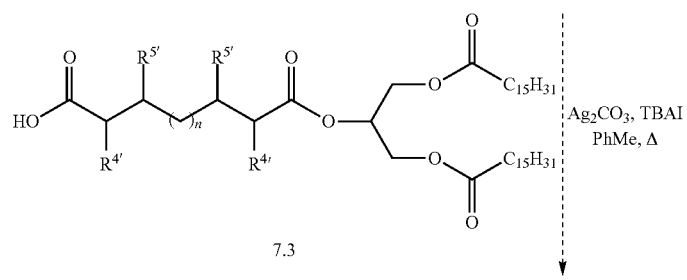
7.3
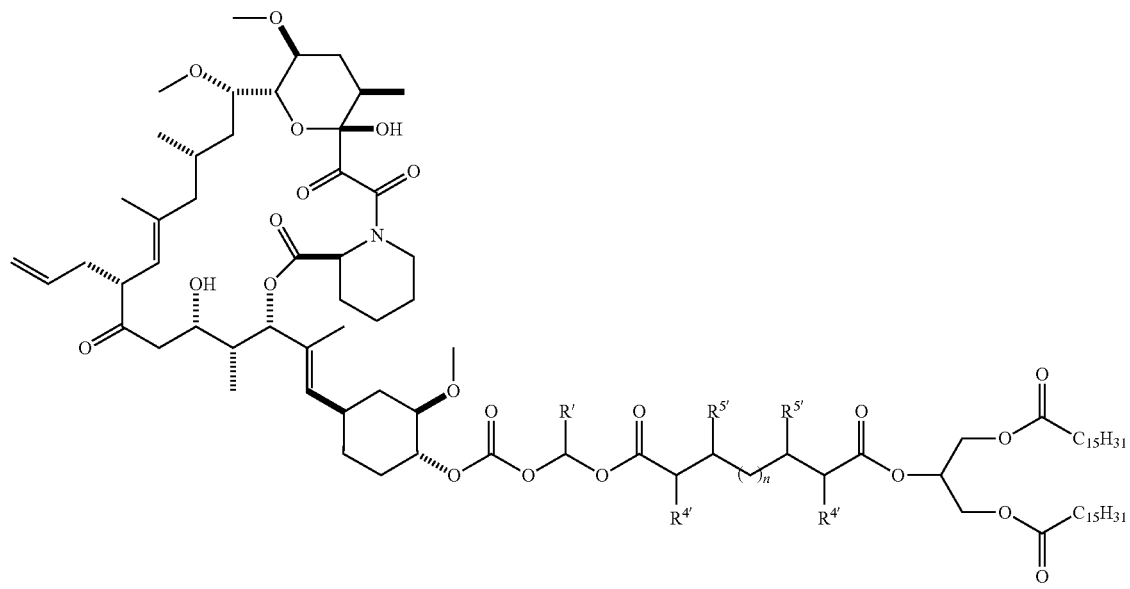
I-16

Synthesis of 7.2: 7.2 is prepared according to the following procedure. PG indicates an optional hydroxyl protecting group. Chloromethyl chloroformate (1.6 equiv.) and pyridine (3.0 equiv.) are added to macrolide 7.1 (1.0 equiv.) in $CH_2Cl_2$ (0.03 M) at 0° C. and the mixture is stirred at 0° C. for 15 minutes and then at rt for one hour. The reaction is diluted with $CH_2Cl_2$ and the organic phase washed with sat. aq. $NaHCO_3$ and brine, dried ($MgSO_4$) and concentrated under reduced pressure to give 7.2 which is used without purification.

Synthesis of TAC-I-16: TAC-I-16 is prepared according to the following procedure. Silver carbonate (0.7 equiv.) is added to acid 7.3 (1.2 equiv.) as prepared in WO 2017/041139, in DMF (0.03 M) and the mixture stirred at rt for one hour. The reaction is concentrated under reduced pressure to give a grey residue, to which is added chloromethyl carbonate 7.2 (1.0 equiv.) in toluene (0.03 M) and TBAI (0.3 equiv.) and the mixture heated at reflux for 1.5 hours. The reaction is cooled to rt, then diluted with ethyl acetate. The organic phase is washed with water and brine, dried ($MgSO_4$) and concentrated under reduced pressure to give the crude TAC-I-16. Purification by silica gel chromatography with a suitable solvent mixture affords TAC-I-16. Regioisomers are separated via known purification techniques.

Example 28: Synthesis of TAC-I-17

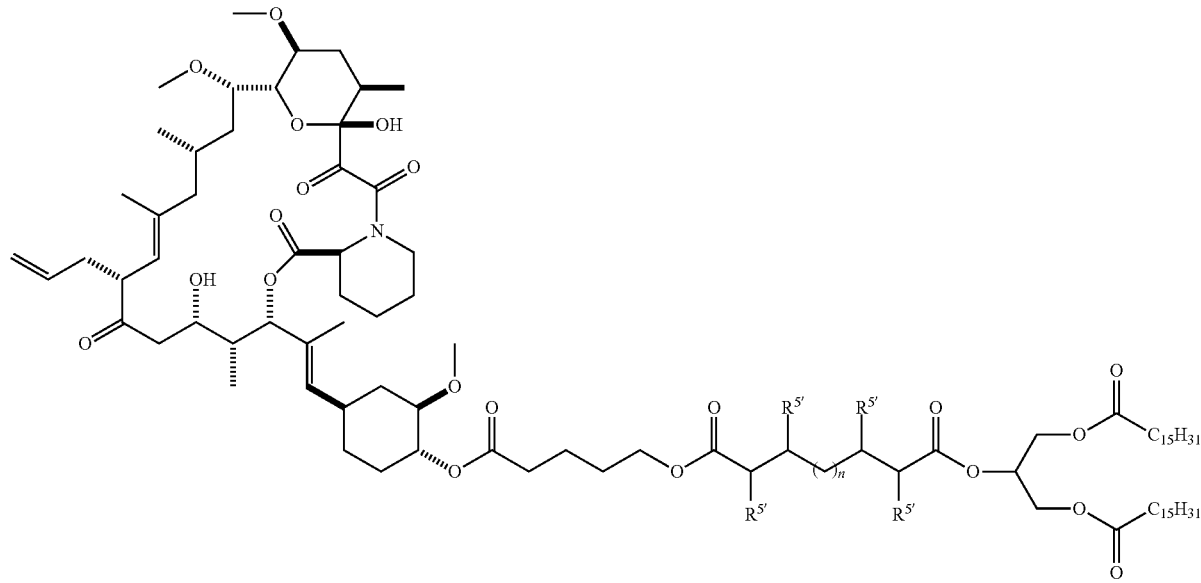

TAC-I-17

Synthesis of TAC-I-17

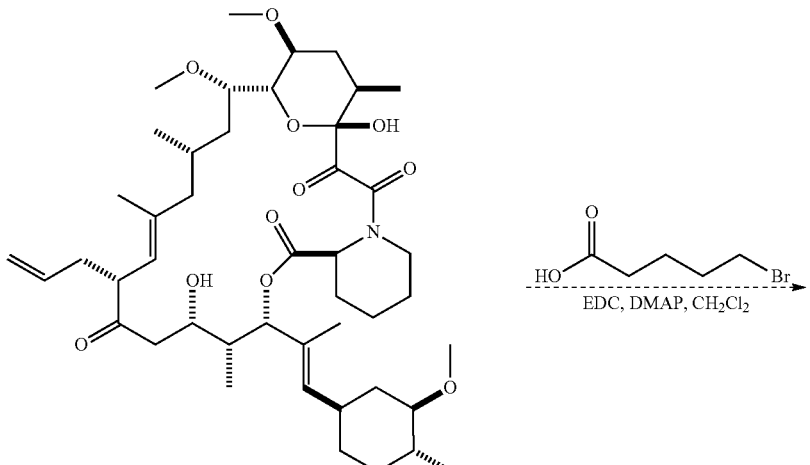

8.1

-continued

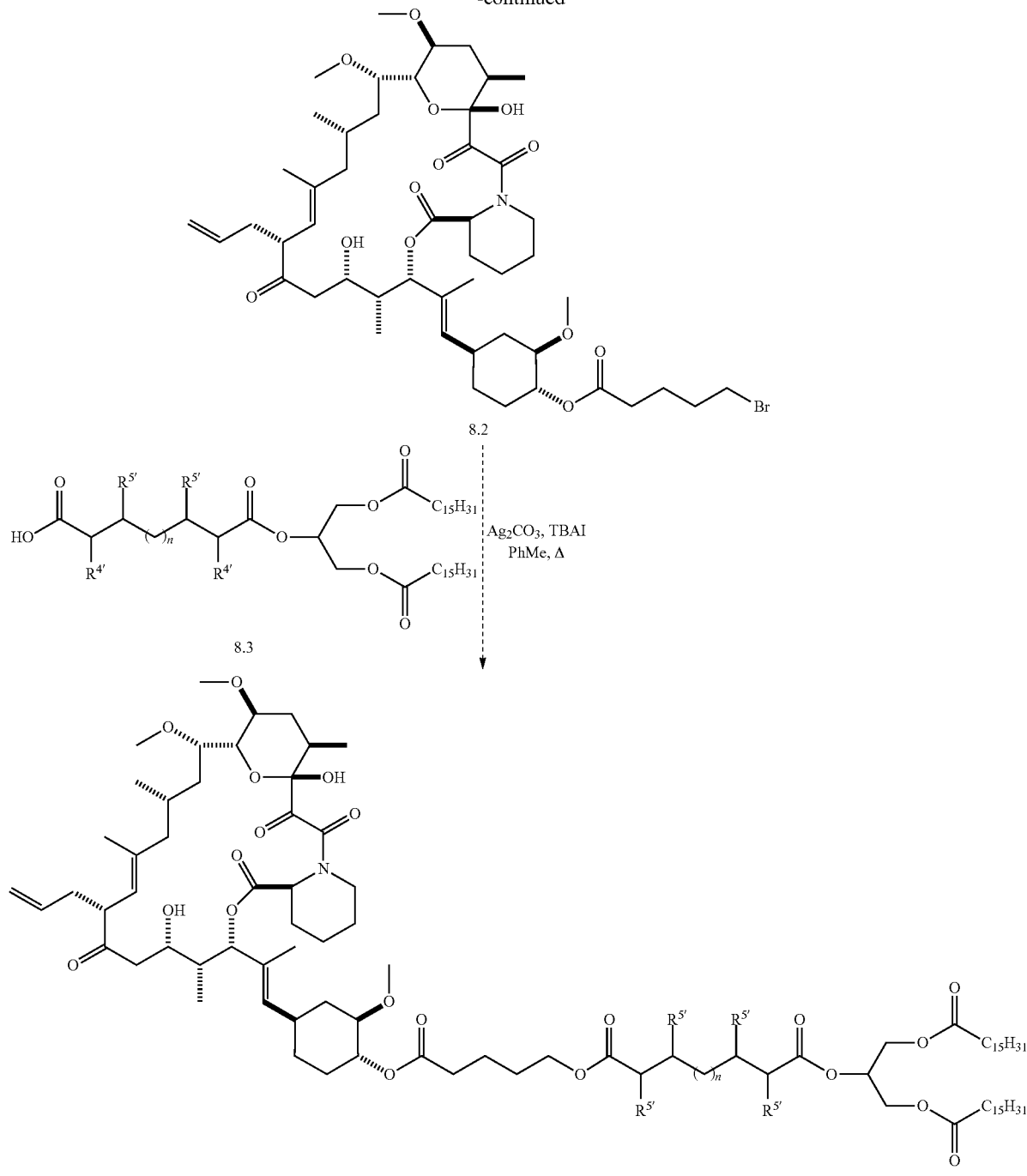

Synthesis of 8.2: 8.2 is prepared according to the following procedure. 4-(Dimethylamino)pyridine (1.3 equiv.) and DCC (2.1 equiv.) are added to a solution of macrolide 8.1 (1.0 equiv.) and 5-bromopentanoic acid (1.3 equiv.) in $CH_2Cl_2$ (0.03 M) and the mixture is stirred at rt for 24 hours. Another 0.6 eq. of acid, 1 eq. of DCC, 0.6 eq. of DMAP are added and the mixture is stirred at rt for an additional two days. The reaction is diluted with $CH_2Cl_2$, silica gel is added and the mixture is concentrated under reduced pressure. Purification by silica gel chromatography gives bromide 8.2.

Synthesis of TAC-I-17: TAC-I-17 is prepared according to the following procedure. Silver carbonate (0.7 equiv.) is added to acid 8.3 (1.2 equiv.) as prepared in WO 2017/041139, in DMF (0.03 M) and the mixture stirred at rt for one hour. The reaction is concentrated under reduced pressure to give a grey residue, to which is added bromide 8.2 (1.0 equiv.) in toluene (0.03 M) and the mixture is heated at reflux for 21 hours. The reaction is cooled to rt, then diluted with ethyl acetate. The organic phase is washed with water and brine, dried ($MgSO_4$) and concentrated under reduced pressure to give the crude TAC-I-17. Purification by silica gel chromatography with a suitable solvent mixture affords TAC-I-17. Regioisomers may be separated via known purification techniques.

TAC-I-18, TAC-I-19, TAC-I-20, TAC-I-21, TAC-I-22, and TAC-I-23:
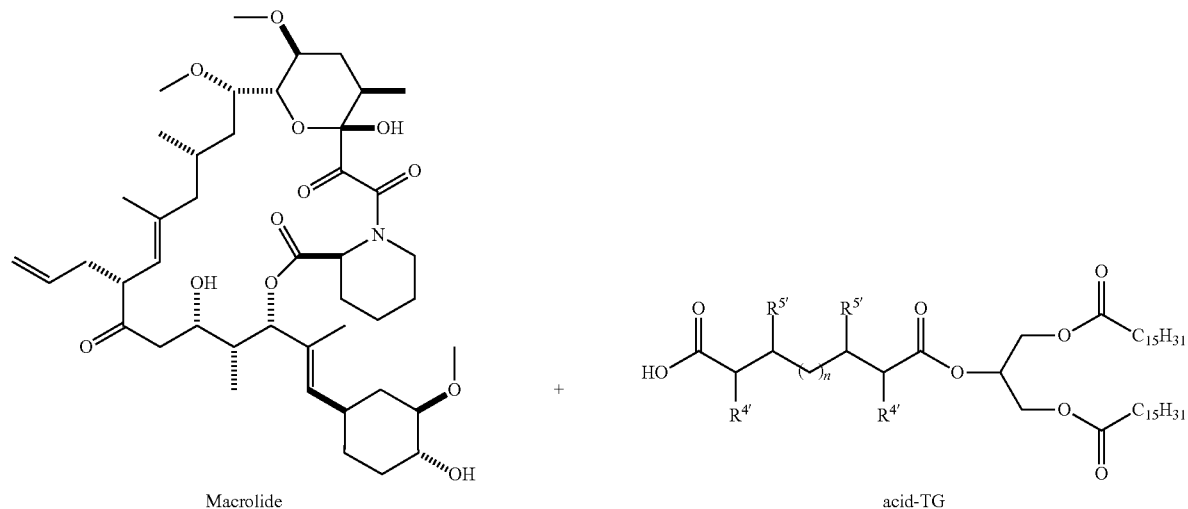
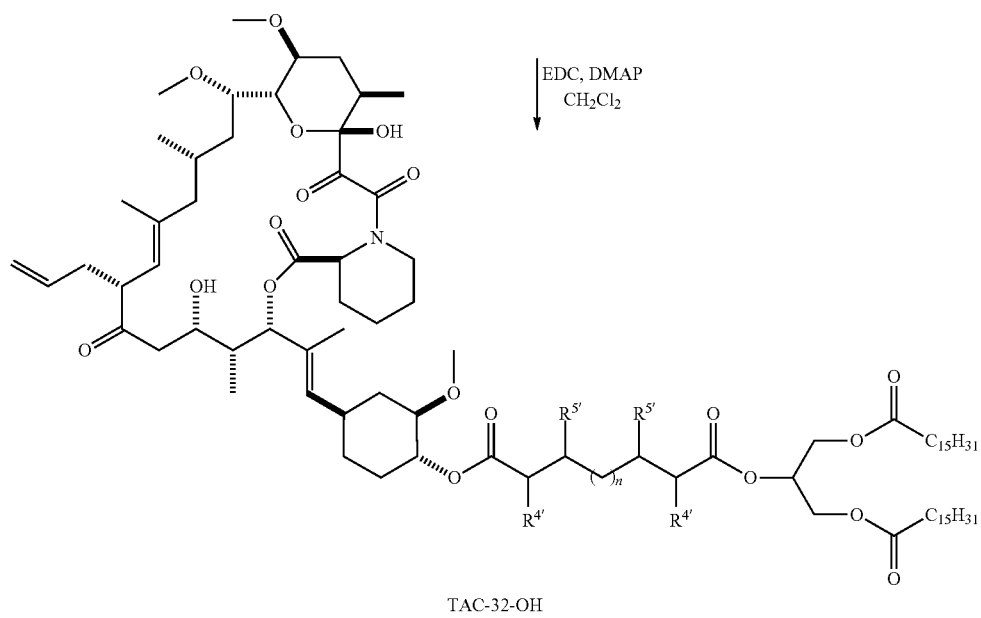

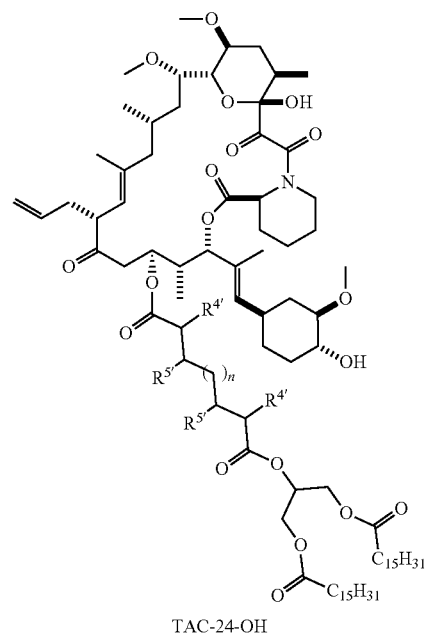
TAC-24-OH
Example 29: Synthesis of TAC-I-18 and TAC-I-19
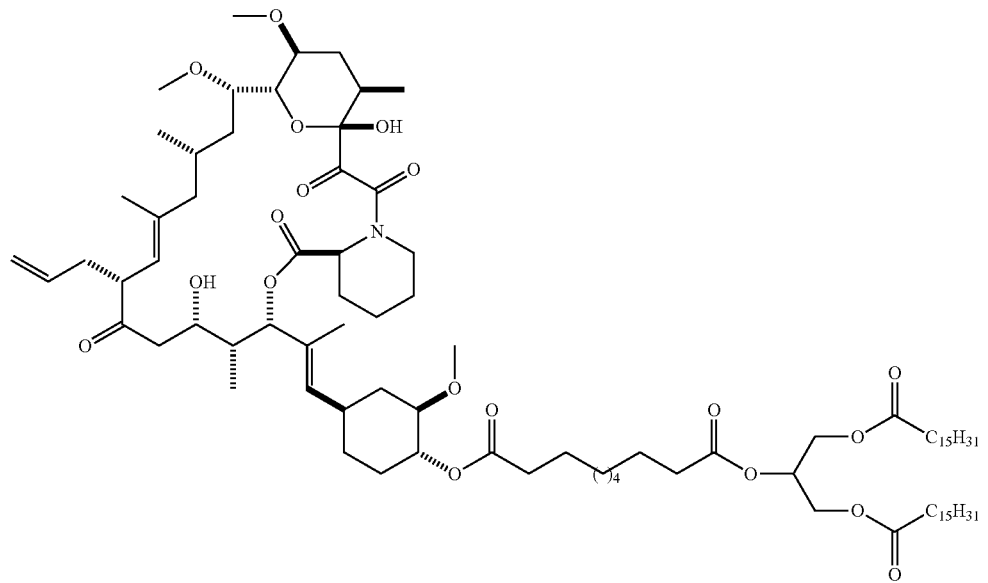
TAC-I-18

-continued
TAC-I-19
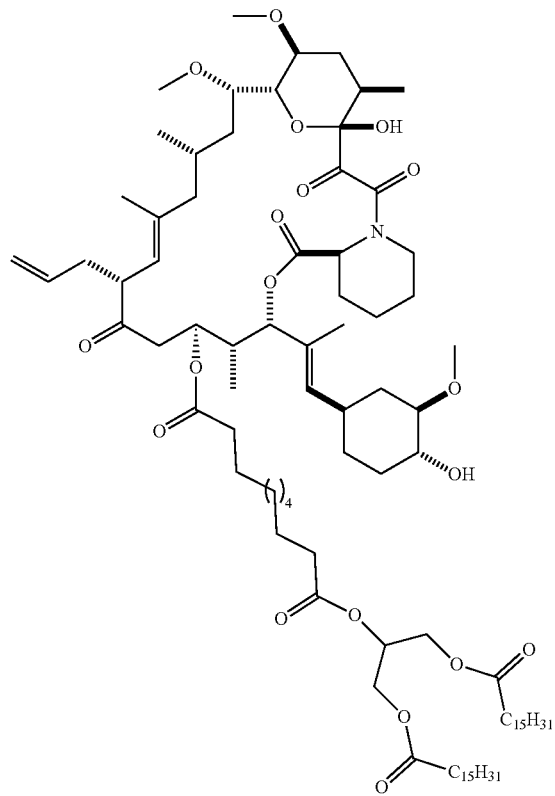
TAC-I-18
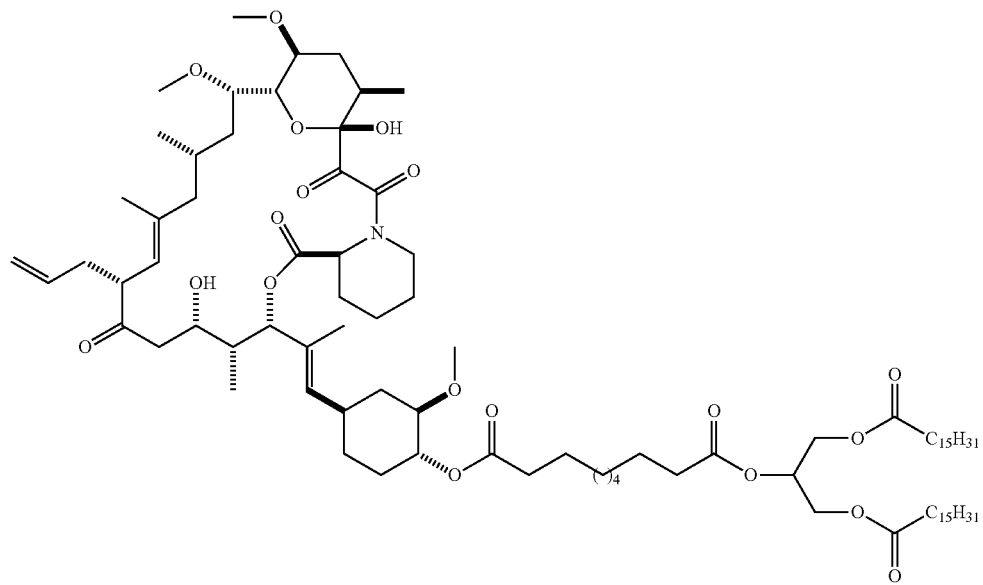

TAC-I-19

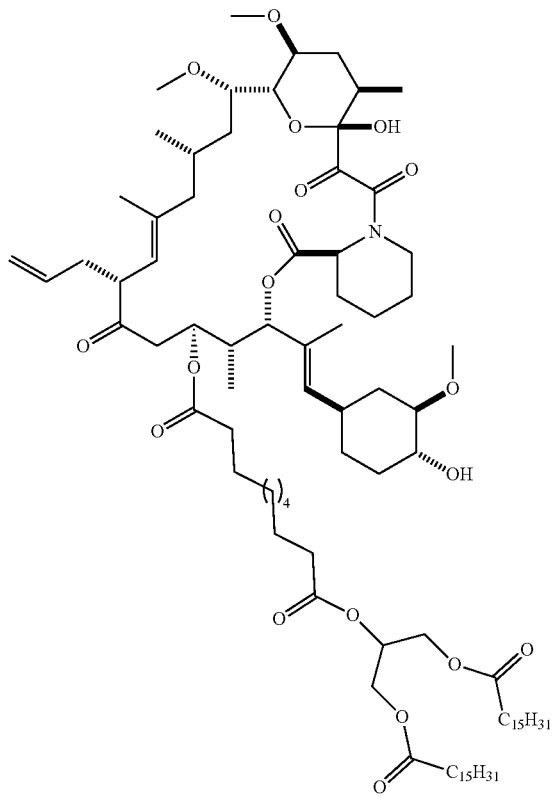

Synthesis of TAC-I-18 (TAC-32(C10-2-TG)) and TAC-I-19 (TAC-24-(C10-2-TG)): 4-(Dimethylamino)pyridine (DMAP, 2.7 mg, 21.9 μmol) and EDC·HCl (12.6 mg, 65.7 mol) were added to a solution of tacrolimus hydrate (18.0 mg, 21.9 μmol) and acid-TG (Int-9; 18.1 mg, 24.1 μmol) in $CH_2Cl_2$ (2 mL) and the mixture stirred at rt for seven days. The reaction was diluted with $CH_2Cl2$ (5 mL), silica gel was added, and the solvent was removed under reduced pressure. Purification by silica gel chromatography (30% to 100% ethyl acetate/hexanes) gave TAC prodrugs TAC-I-18 (9.2 mg, 27%) and TAC-I-19 (8.0 mg, 24%) as colourless oils.

TAC-I-18:

ESI-HRMS: Calcd. for $C_{89}H_{151}NNaO_{19}$ [M+Na$^+$] 1561.0773; found 1561.0745

$R_f$ (50% EtOAc/Hexanes): 0.68.

TAC-I-19:

ESI-HRMS: Calcd. for $C_{89}H_{151}NNaO_{19}$ [M+Na$^+$] 1561.0773; found 1561.0774

$R_f$ (50% EtOAc/Hexanes): 0.41.

Example 30: Synthesis of TAC-I-20 and TAC-I-21

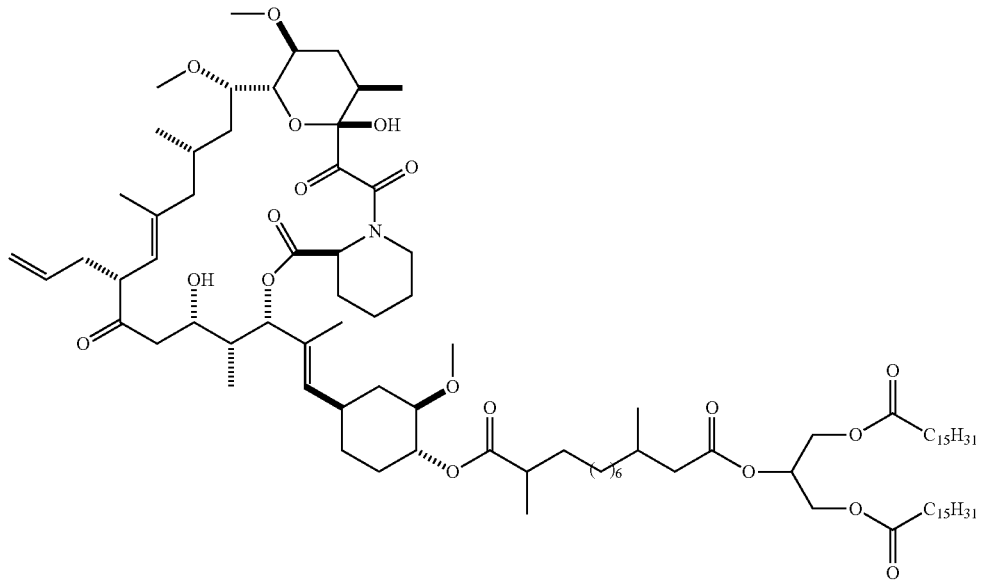

TAC-I-20

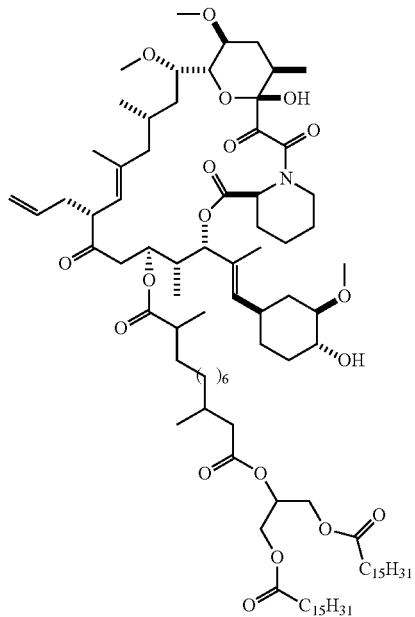

TAC-I-21

Synthesis of TAC-I-20 (TAC-32-(C12α'MeβMe-2TG)) and TAC-I-21 (TAC-24-(C12α'MeβMe-2TG)): 4-(Dimethylamino)pyridine (DMAP, 1.9 mg, 15.5 μmol) and EDC·HCl (6.0 mg, 31.1 μmol) were added to a solution of tacrolimus (12.5 mg, 15.5 μmol) and acid-TG (Int-27; 15.1 mg, 18.7 μmol) in CH$_2$Cl$_2$ (1 mL) and the mixture stirred at rt for seven days. The reaction was diluted with CH$_2$Cl$_2$ (5 mL), silica gel was then added and the solvent was removed under reduced pressure. Purification by silica gel chromatography (30% to 100% ethyl acetate/hexanes) gave TAC prodrugs TAC-I-20 (7.3 mg, 29%) and TAC-I-21 (2.3 mg, 9%) as colourless oils.

TAC-I-20:

ESI-HRMS: Calcd. for C$_{89}$H$_{151}$NNaO$_{19}$ [M+Na$^+$] 1617.1399; found 1617.1357

R$_f$ (50% EtOAc/Hexanes): 0.73.

TAC-I-21:

ESI-HRMS: Calcd. for C$_{89}$H$_{151}$NNaO$_{19}$ [M+Na$^+$] 1617.1399; found 1617.1361

R$_f$ (50% EtOAc/Hexanes): 0.38.

Example 31: Synthesis of TAC-I-22 and TAC-I-23
TAC-I-22
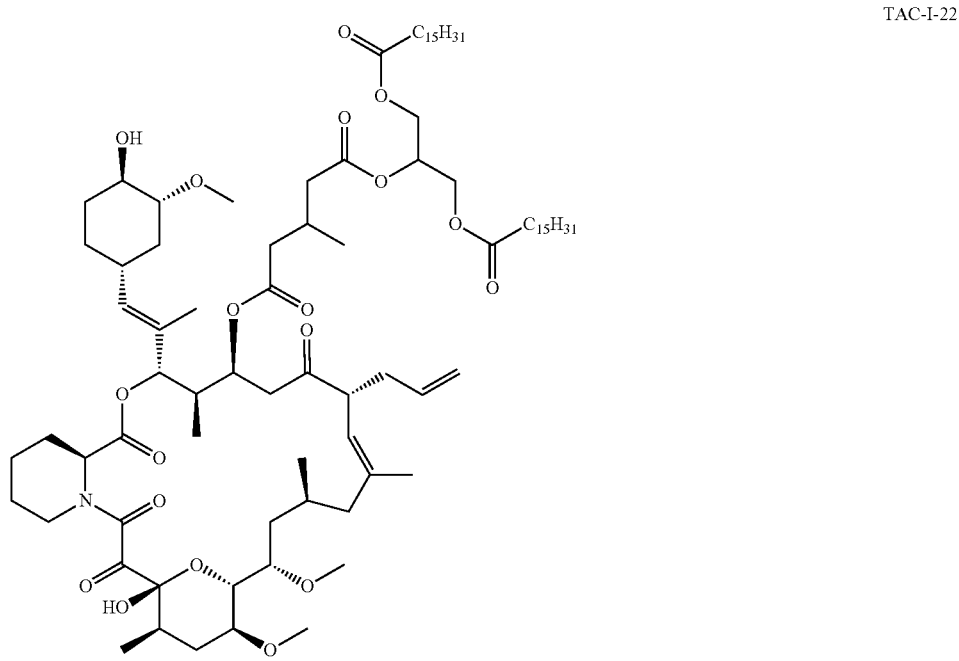
TAC-I-23
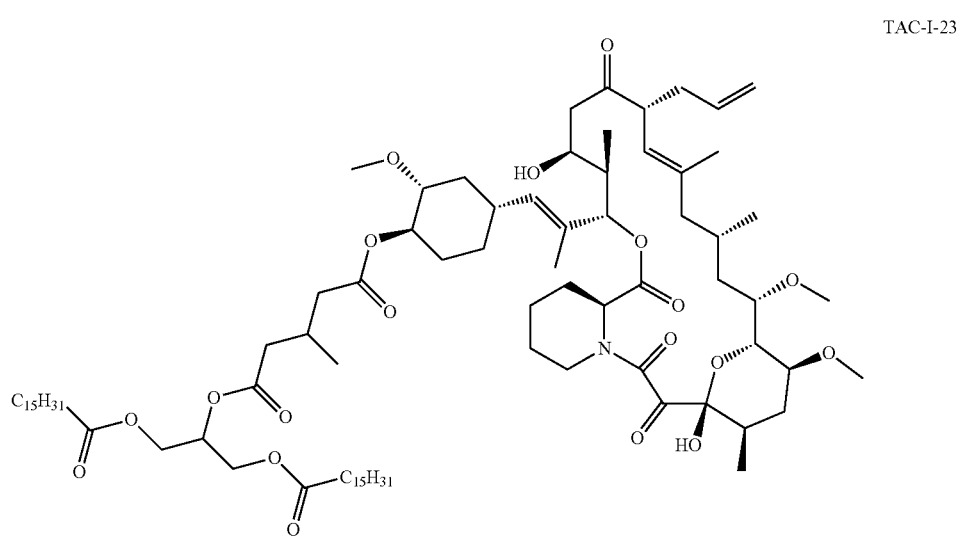

443 444
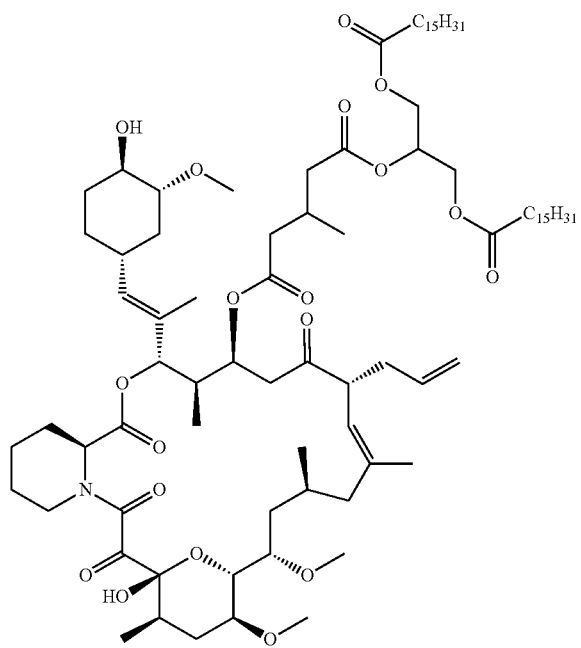
TAC-I-22
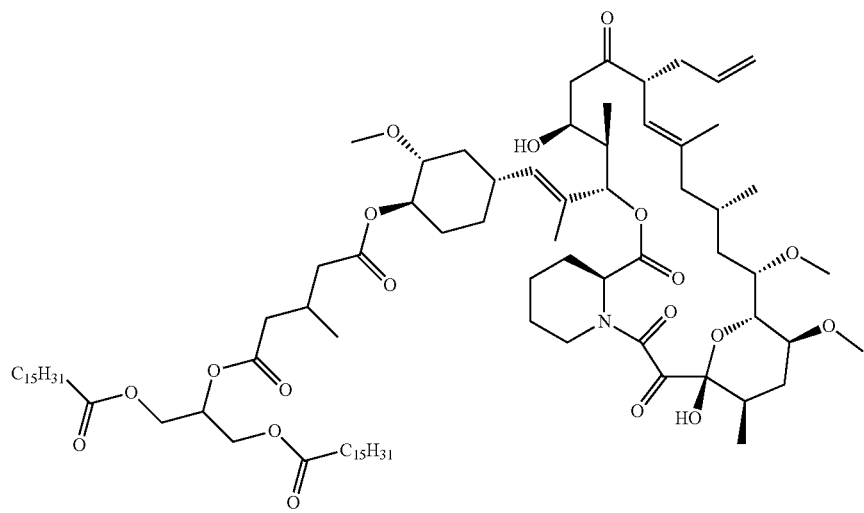
TAC-I-23

Synthesis of TAC-I-22 (TAC-24-C5βMe-2-TG) and TAC-I-23 (TAC-24-C5βMe-2-TG): 4-(Dimethylamino)pyridine (DMAP, 2.1 mg, 17.0 μmol) and EDC·HCl (6.5 mg, 34.1 mol) were added to a solution of tacrolimus hydrate (14.0 mg, 17.0 μmol) and acid-TG 2 (Int-4; 14.2 mg, 20.4 μmol) in CH$_2$Cl$_2$ (1 mL) and the mixture was stirred at rt for five days. The reaction was diluted with CH$_2$Cl$_2$ (5 mL), then silica gel was added and the solvent was removed under reduced pressure. Purification by silica gel chromatography (25% to 60%) EtOAc/hexanes) gave TAC-I-22 (4.3 mg, 17%) and TAC-I-23 (8.6 mg, 34%) as colorless oils.

TAC-I-22:

R$_f$ (50% EtOAc/Hexane): 0.31.

TAC-I-23:

R$_f$ (50% EtOAc/Hexane): 0.65.

Example 32: Synthesis of TAC-I-24 and TAC-I-25

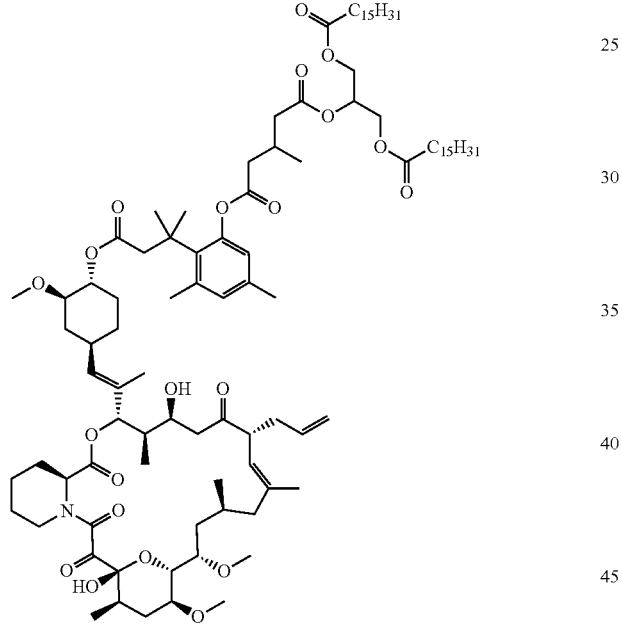

TAC-I-24

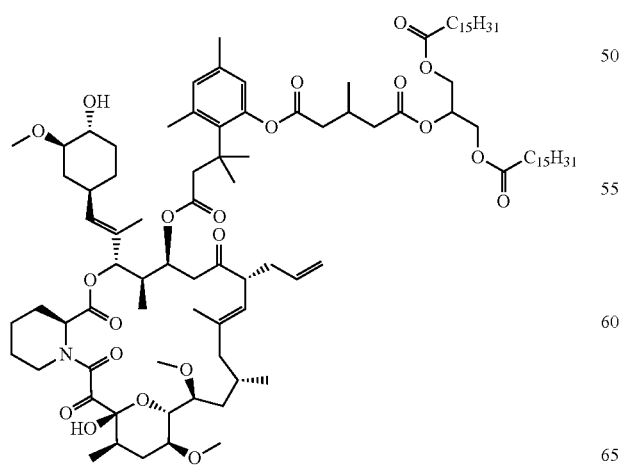

TAC-I-25

Synthesis of TAC-I-24 and TAC-I-25
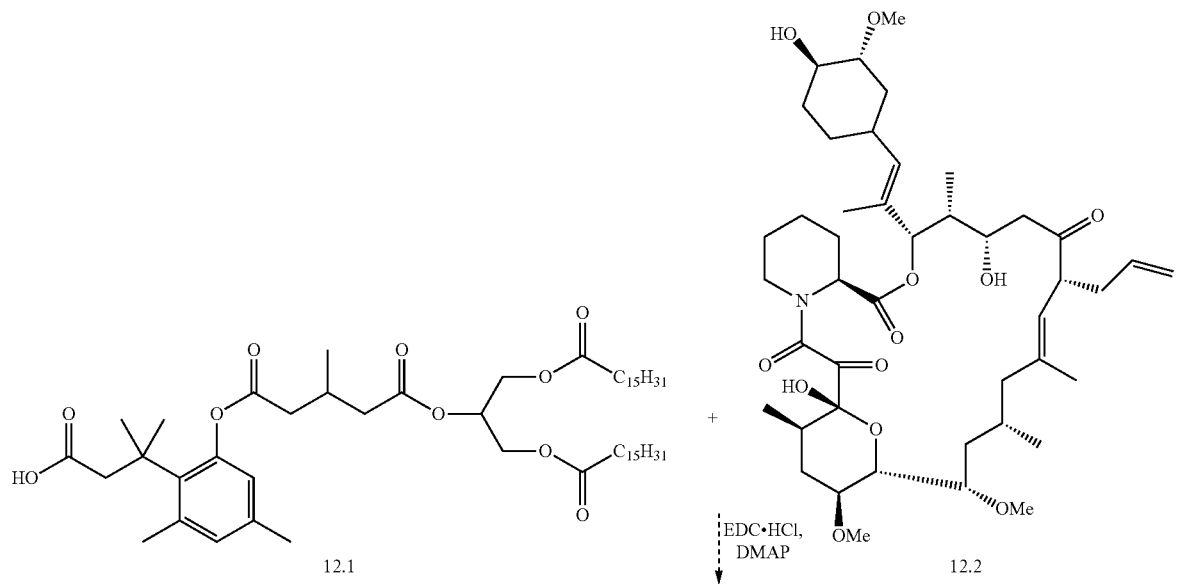
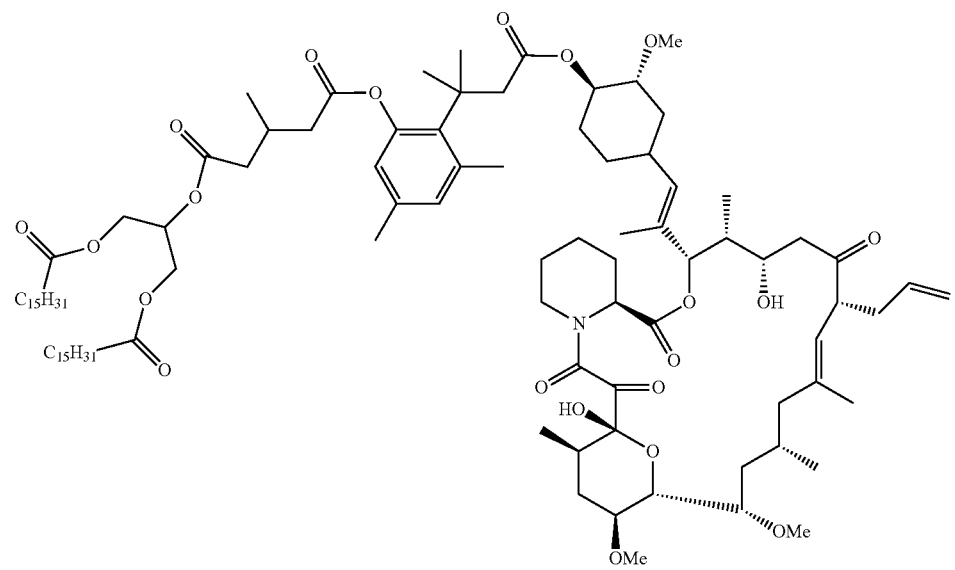
I-24
+

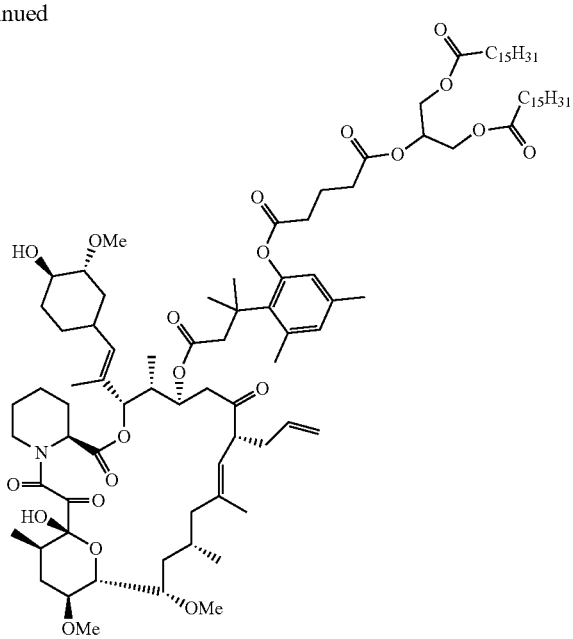

I-25

Synthesis of TAC-I-24 (TAC-32-(TML-CβMe-2-TG)) and TAC-I-25 (TAC-24-(TML-CβMe-2-TG)). TAC-I-24 and TAC-I-25 are prepared according to the following procedure. DMAP (1.3 equiv.) and EDC·HCl (2.1 equiv.) is added to a solution of acid 12.1 (1.0 equiv.) as prepared in WO 2017/041139 with Int-4, and tacrolimus 12.2 (1.3 equiv.) in $CH_2Cl_2$ (0.02 M) and the mixture stirred at RT for 19 hours. The reaction is diluted with $CH_2Cl_2$ (10 mL), silica gel is added, and the mixture concentrated under reduced pressure and purified by silica gel chromatography to affords TAC-I-24 and TAC-I-25. Optionally, hydroxyl protecting groups are utilized to enhance regioselectivity, yielding the target compounds after deprotection and purification.

Example 33: Synthesis of TAC-I-26 and TAC-I-27

TAC-I-26

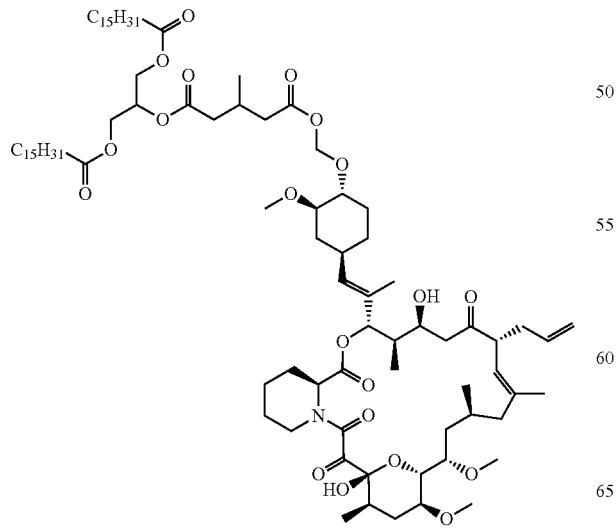

TAC-I-27
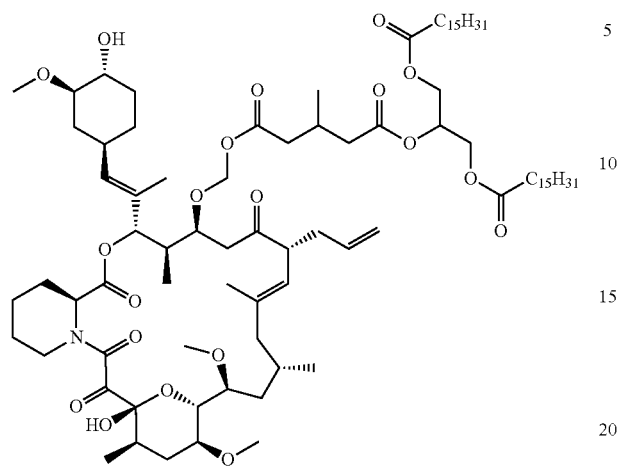
Synthesis of TAC-I-26 and TAC-I-27
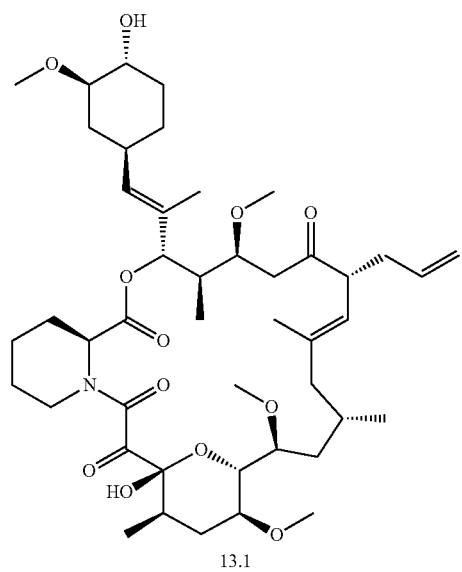
13.1

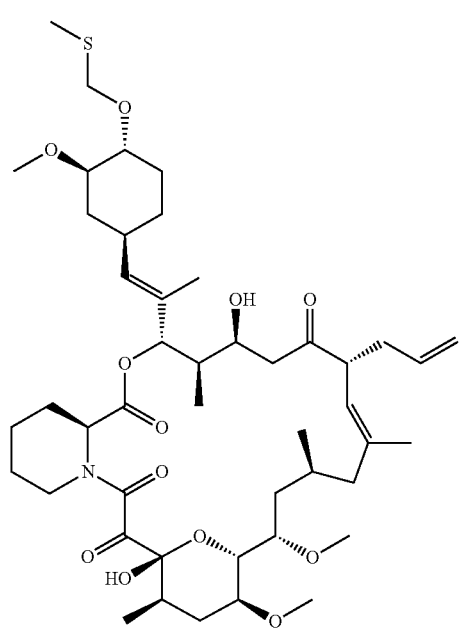

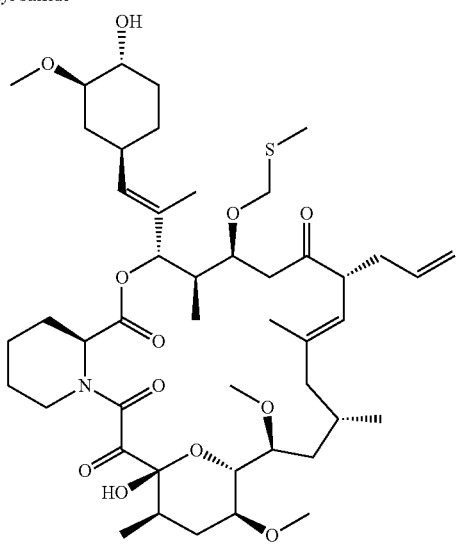

13.2

1) SO₂Cl₂
2) Toluene, DBU

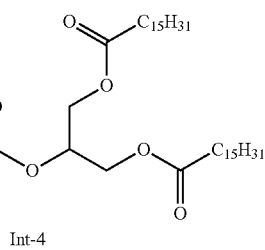

Int-4

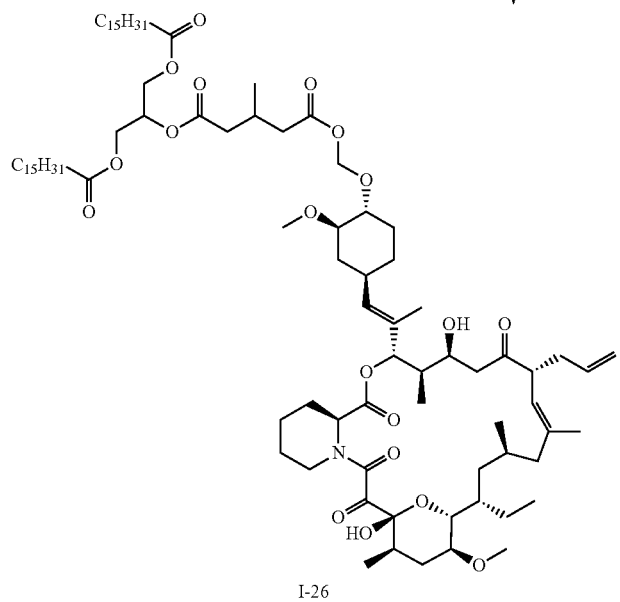

I-26

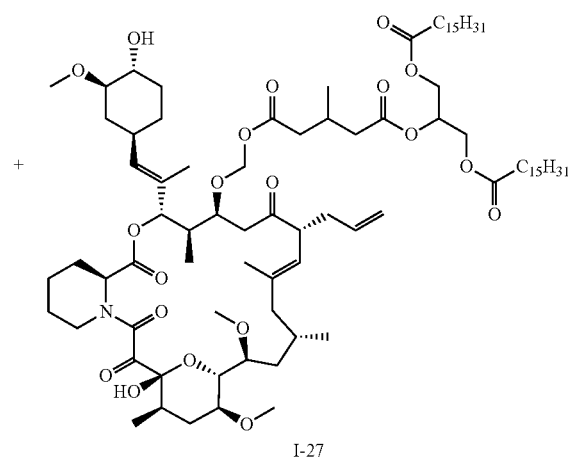

I-27

Synthesis of 13.2: 13.2 is prepared by treating a macrolide 13.1 with chloromethyl methyl thioether as described in WO 2009/143295, which is hereby incorporated by reference in its entirety. A solution of sulfuryl chloride (2.2 equiv.) in $CH_2Cl_2$ (0.16 M) is added to a solution of 13.1 (1.8 equiv.) in $CH_2Cl_2$ (0.07 M) at 0° C. and the mixture stirred at 0° C. for 30 minutes and then at rt for an additional hour. The reaction is concentrated under a stream of $N_2$, co-evaporated from toluene (twice) and dried under reduced pressure.

Synthesis of TAC-I-26 (TAC-32-(ASI-C5βMe-2-TG)) and TAC-I-27 (TAC-24-(ASI-C5βMe-2-TG)): TAC-I-26 and TAC-I-27 are prepared according to the following procedure. The crude residue of 13.2 is re-dissolved in toluene (0.1 M based on 13.1), added to a solution of acid Int-4 (1 eq) as prepared in WO 2017/041139, and DBU (1.5 eq) in toluene (0.05 M) that had been pre-stirred for one hour, and the mixture is stirred at rt for two hours. The reaction is diluted with CH₂Cl₂ (20 mL) and the organic phase washed with sat. aq. NaHCO₃ (20 mL) and brine (20 mL), dried (MgSO₄) and concentrated under reduced pressure to give the crude products. Purification by silica gel chromatography with a suitable solvent mixture affords TAC-I-26 and TAC-I-27.

Example 34: Synthesis of TAC-I-28 and TAC-I-29

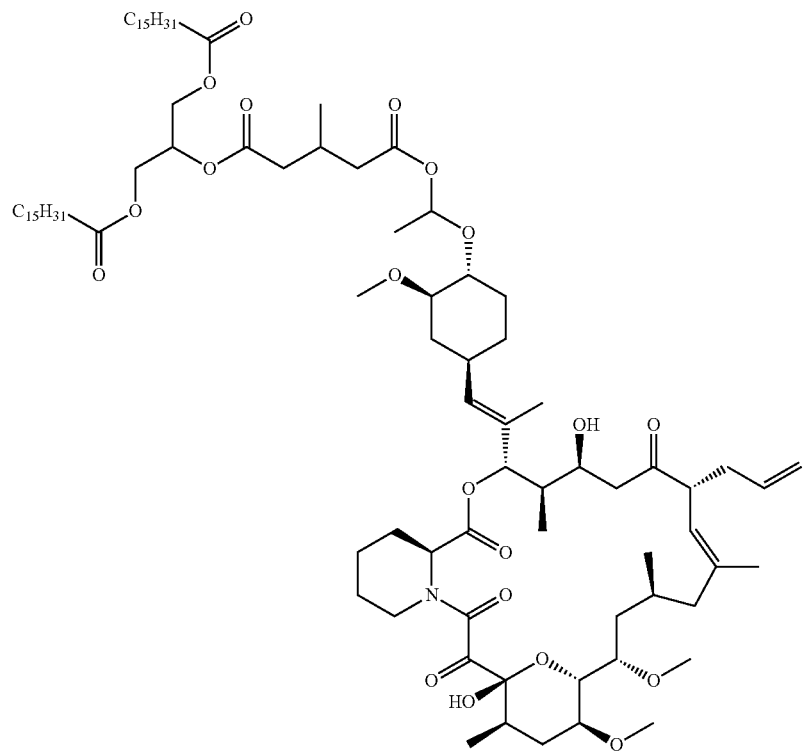

TAC-I-28

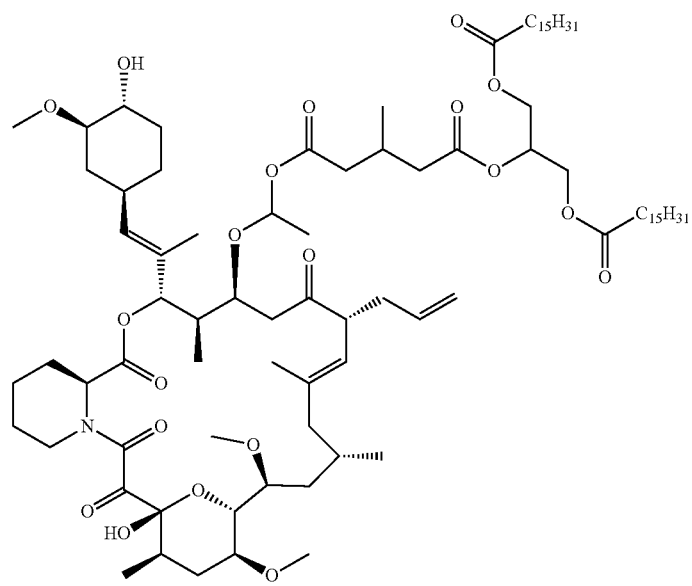

TAC-I-29

Synthesis of TAC-I-28 (TAC-32-(MASI-C5βMe-2-TG)) and TAC-I-29 (TAC-32-(MASI-C5βMe-2-TG)): 4-(Dimethylamino)pyridine (DMAP, 2.7 mg, 21.9 µmol) and EDC·HCl (12.6 mg, 65.7 µmol) are added to a solution of tacrolimus hydrate (18.0 mg, 21.9 µmol) and acid-TG (Int-4; 18.1 mg, 24.1 µmol) in $CH_2Cl_2$ (2 mL) and the mixture is stirred at rt for seven days. The reaction is diluted with $CH_2Cl_2$ (5 mL), silica gel is added, and the solvent is removed under reduced pressure. Purification by silica gel chromatography with suitable solvents gives TAC prodrugs TAC-I-28 and TAC-I-29.

Example 35: Lymphatic Transport Assay in Rats

In order to assess the lymphatic transport of disclosed lipid prodrugs in rats, the mesenteric lymph ducts of the rats used in this study were cannulated to allow continual collection of mesenteric lymph. Lipid formulations containing the compound of interest were then administered to the animals, lymph was collected, and drug concentrations in the lymph samples were quantified.

Lipid-based formulations of the compounds of the invention or control compounds were prepared as previously described (Trevaskis, N. L. et al., *Pharmaceutical Research*, 2005, 22(11), 1863-1870, WO 2016/023082, and WO 2017/041139, hereby incorporated by reference.

In brief, either 1 or 2 mg of test prodrug, 40 mg oleic acid and 25 mg Tween 80 were mixed in a glass vial and incubated at 37° C. for 12-18 h to equilibrate. An aqueous phase consisting of 5.6 ml phosphate buffered saline (PBS, pH 7.4) was subsequently added to the lipid phase (MPA was dissolved in PBS for the preparation of MPA containing formulations) and the formulation emulsified by ultrasonication with a Misonix XL 2020 ultrasonic processor (Misonix, Farmingdale, NY, USA) equipped with a 3.2-mm microprobe tip running at 30% of the maximal amplitude of 240 m and a frequency of 20 kHz for 2 min at room temperature. Doses for administering to more than one animal can be prepared in one batch by suitably increasing the quantities given above. Drug/prodrug concentrations in all formulations were verified using HPLC-MS.

Male Sprague-Dawley (SD) rats were selected for the lymphatic transport studies involving mycophenolic acid lipid prodrugs. Depending on the therapeutic agent, male, female, or both may be selected for study. Rats (typically 240-320 g) were maintained on a standard diet and fasted overnight with free access to water prior to experiments.

Anesthetized rats were placed on a heated pad at 37° C. and cannulas inserted into the duodenum (for formulation administration and rehydration), mesenteric lymph duct (for lymph collection), and carotid artery (in cases where blood collection was conducted). Post-surgery, rats were re-hydrated for 0.5 h via intraduodenal infusion of normal saline at 2.8 mL/h. The lipid formulations were infused into the duodenum at 2.8 mL/h for 2 h after which, normal saline was infused at 2.8 mL/h for the remainder of the experiment. Lymph was continuously collected for up to 8 h into pre-weighed Eppendorf tubes containing 10 µL of 1,000 IU/mL heparin. The collection tubes were changed hourly and lymph flow was measured gravimetrically. Aliquots of hourly lymph samples were stored at −20° C. prior to assay.

Drug concentration in lymph is expressed as total drug and includes free drug and drug associated with different glycerides. Lymph samples are first treated with a lipase or other appropriate conditions to liberate free active agent prior to measurement of active agent levels in the lymph. Treatment with a lipase or other hydrolysis conditions liberates free active agent from any corresponding re-esterified glycerides. Porcine pancreatic lipase is appropriate for this purpose. Alternatively, hydrolysis with 0.5 M NaOH may be used. For MPA "phenol" prodrugs (i.e. prodrugs linked to the triglyceride at the aromatic —OH group of MPA), hydrolysis was performed with 0.5 M NaOH except for the lymph samples collected from 3 rats in the group of compound MPA-I-20 (MPA-O-C12α'βMe-TG), which were hydrolyzed by porcine pancreatic lipase.

Transport of compounds into lymph during each hourly collection period was calculated from the product of the volume of lymph collected and the measured concentrations in lymph. For fluorescently-labelled compounds such as a BDP-conjugate, the concentrations of total compound may be measured by fluorescence spectroscopy without hydrolysis.

The results of the lymphatic transport assays are summarized in Table B, below, and e.g. in the attached Figures. Table B summarizes lymphatic transport of total MPA related compound (% of administered dose) following intraduodenal infusion to anaesthetised, mesenteric lymph-duct cannulated rats. Data are presented as mean±SD when n≥3 or mean±range when n=2. Compounds with a lymphatic transport assay result of greater than 10% (>10%) are designated as "A." Compounds with a lymphatic transport assay result between 1% and 10% (1%-10%) are designated as "B." Compounds with a lymphatic transport assay result of less than 1% and greater than 0.24% (<1% and >0.24%) are designated as "C."

Importantly, the cumulative lymphatic transport percentages of MPA and MMF measured in this assay are very low (0.17±0.12% for MPA and even less for MMF; see FIG. 8). Accordingly, a lymphatic transport assay result of "A" means that the lipid prodrug increases cumulative lymphatic transport relative to MPA or MMF by a factor of >59. A result of "B" indicates an increase by a factor of between 5.9 and 59. A result of "C" indicates an increase by a factor of between about 1.4 and <5.9.

TABLE B

Lymphatic transport of total compounds related to parent therapeutic agent (% of administered dose) following intraduodenal infusion to anesthetised, mesenteric lymph-duct cannulated rats (data are presented as mean ± SD when n ≥ 3 or as mean ± range when n = 2).

| Compound Name | # | Structure | Cumulative lymphatic transport % dose (Mean ± SD, or Range if n = 2) |
|---|---|---|---|
| MPA (n = 5) | — | 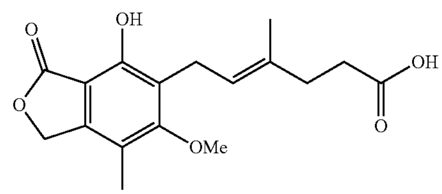 [SMILES: COc1c(C)c2c(c(O)c1C/C=C(\C)CCC(=O)O)C(=O)OC2] | 0.17 ± 0.12 |
| MMF (n = 3) | — | 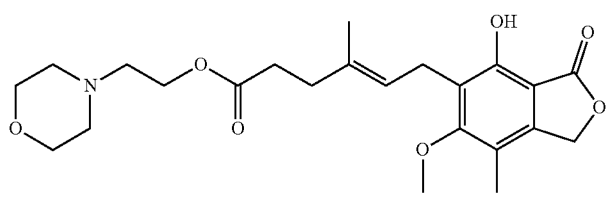 [SMILES: COc1c(C)c2c(c(O)c1C/C=C(\C)CCC(=O)OCCN1CCOCC1)C(=O)OC2] | 0.14 ± 0.08 |
| MPA-TG (n = 5) | MPA-I-34 | 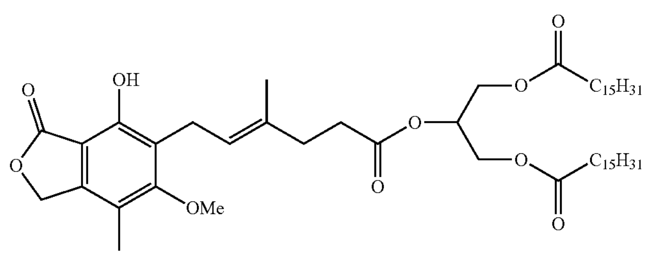 | A |
| MPA-Ph-C3-TG | MPA-I-28 | 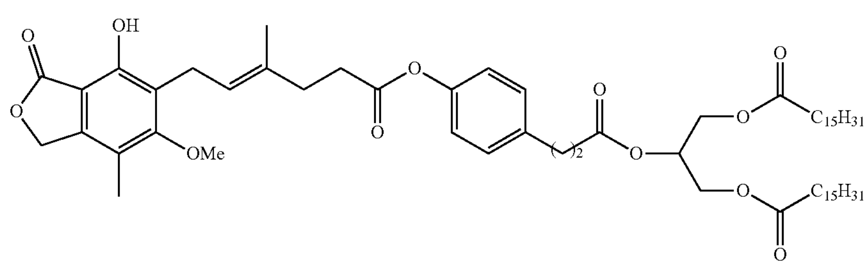 | B |
| MPA-C4(ether)-TG (n = 3) | MPA-I-25 | 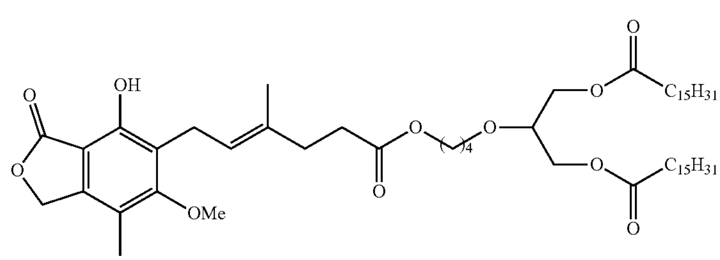 | C |

TABLE B-continued

Lymphatic transport of total compounds related to parent therapeutic agent (% of administered dose) following intraduodenal infusion to anesthetised, mesenteric lymph-duct cannulated rats (data are presented as mean ± SD when n ≥ 3 or as mean ± range when n = 2).

| Compound Name | # | Structure | Cumulative lymphatic transport % dose (Mean ± SD, or Range if n = 2) |
|---|---|---|---|
| MPA-C5-Carbonate-TG (n = 4) | MPA-I-27 | 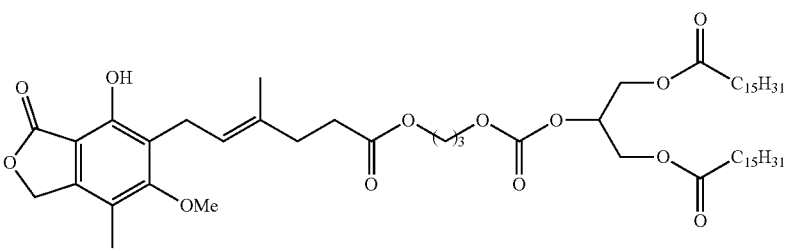 | B |
| MPA-C6(ether)-TG (n = 4) | MPA-I-26 | 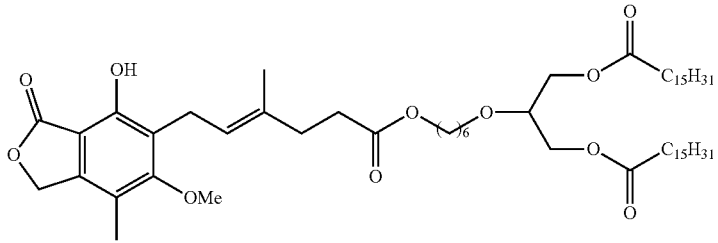 | C |
| MPA-C7-TG (n = 2) | MPA-I-36 | 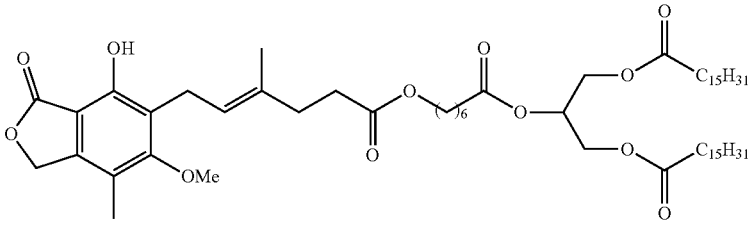 | B |
| MPA-C12-TG (n = 2) (dose 1 mg/rat) | MPA-I-37 | 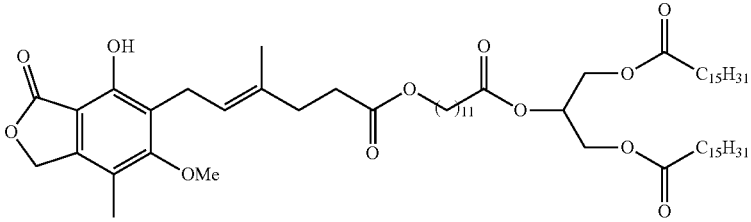 | A |
| MPA-C18-TG (n = 3) (dose 1 mg/rat) | MPA-I-38 | 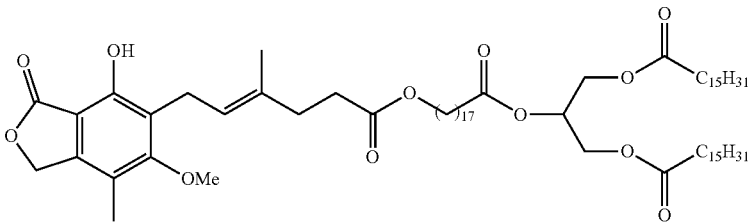 | B |

TABLE B-continued

Lymphatic transport of total compounds related to parent therapeutic agent (% of administered dose) following intraduodenal infusion to anesthetised, mesenteric lymph-duct cannulated rats (data are presented as mean ± SD when n ≥ 3 or as mean ± range when n = 2).

| Compound Name | # | Structure | Cumulative lymphatic transport % dose (Mean ± SD, or Range if n = 2) |
|---|---|---|---|
| MPA-O-C4-TG(OMe) (n = 2) | MPA-I-17 | 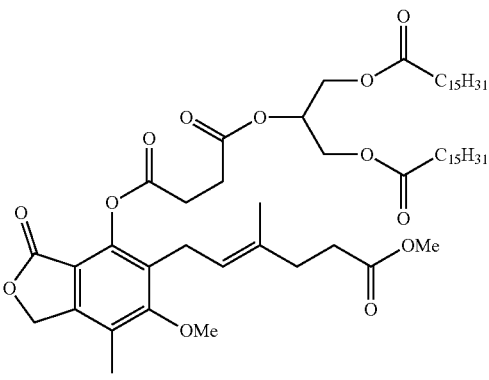 | C |
| MPA-O-C6-TG(OMe) (n = 2) | MPA-I-18 | 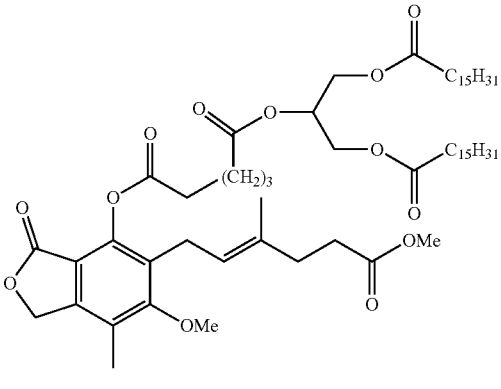 | B |
| MPA-O-C10-TG(OMe) (n = 3) | MPA-I-19 | 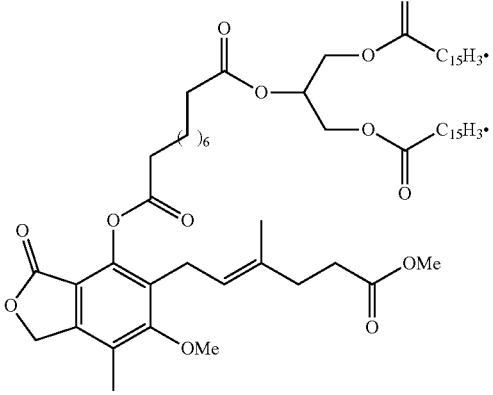 | A |

TABLE B-continued

Lymphatic transport of total compounds related to parent therapeutic agent (% of administered dose) following intraduodenal infusion to anesthetised, mesenteric lymph-duct cannulated rats (data are presented as mean ± SD when n ≥ 3 or as mean ± range when n = 2).

| Compound Name | # | Structure | Cumulative lymphatic transport % dose (Mean ± SD, or Range if n = 2) |
|---|---|---|---|
| MPA-O-C12-TG(OMe) (n = 3) | MPA-I-30 | 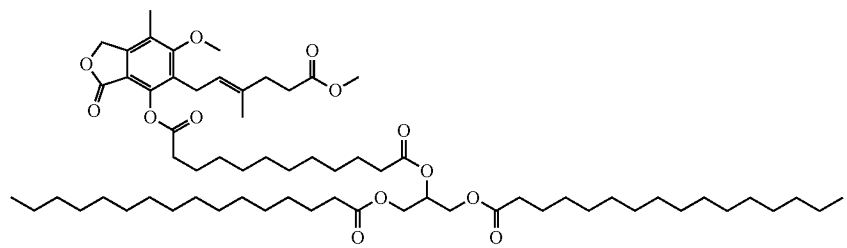 [SMILES: CCCCCCCCCCCCCCCC(=O)OCC(COC(=O)CCCCCCCCCCCCCCC)OC(=O)CCCCCCCCCCC(=O)Oc1c(C/C=C(\C)CCC(=O)OC)c(OC)c(C)c2c1C(=O)OC2] | A |
| MPA-O-C12α'MeβMe-TG(OMe) (n = 5) | MPA-I-20 | 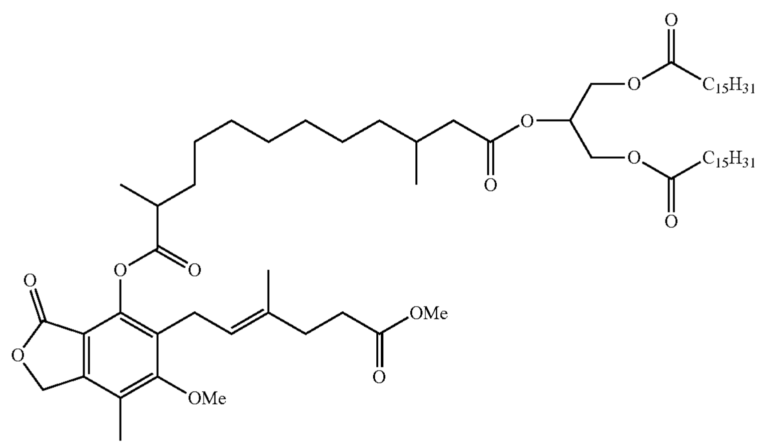 | A |
| MPA-O-CASI-C12α'MeβMe-TG(OMe) (n = 3) | MPA-I-21 | 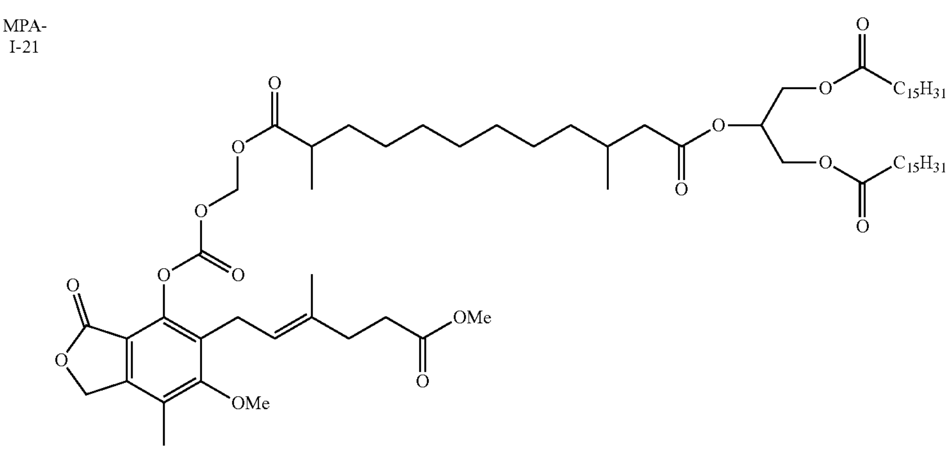 | B |

TABLE B-continued

Lymphatic transport of total compounds related to parent therapeutic agent (% of administered dose) following intraduodenal infusion to anesthetised, mesenteric lymph-duct cannulated rats (data are presented as mean ± SD when n ≥ 3 or as mean ± range when n = 2).

| Compound Name | # | Structure | Cumulative lymphatic transport % dose (Mean ± SD, or Range if n = 2) |
|---|---|---|---|
| MPA-O-C12α'βMe-TG (OMF) (n = 3) | MPA-I-32 | 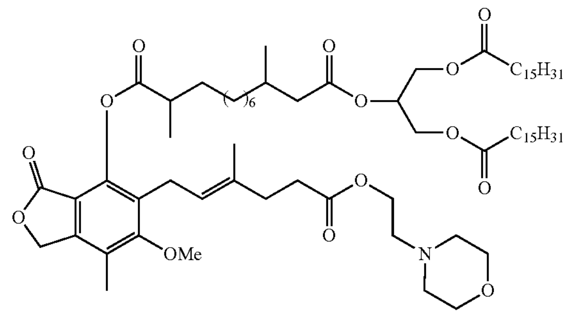 | A |
| MPA-O-FSI(5)-C12α'MeβMe-TG(OMe) (n = 5) | MPA-I-22 | 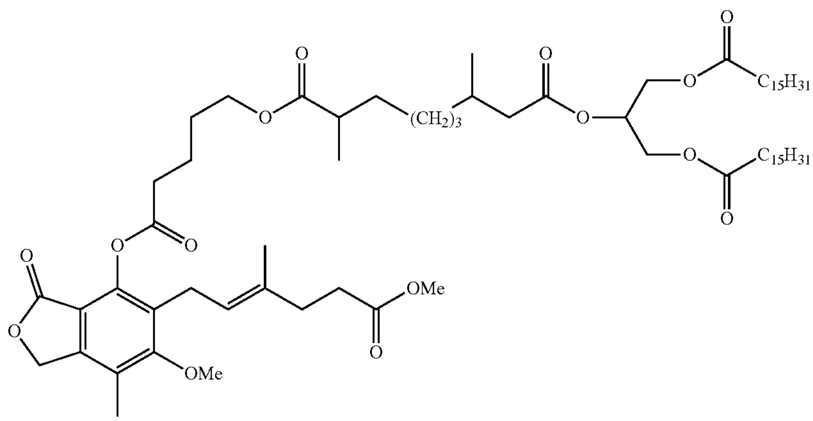 | A |
| MPA-2-PL (n = 4) | MPA-I-39 | 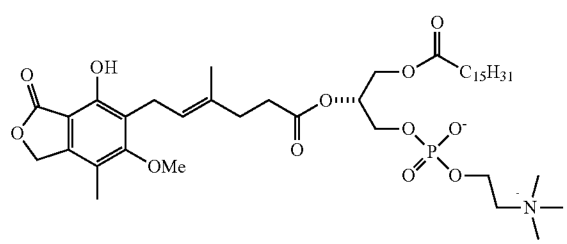 | C |
| MPA-O-TML-C12-TG (n = 3) | MPA-I-47 | 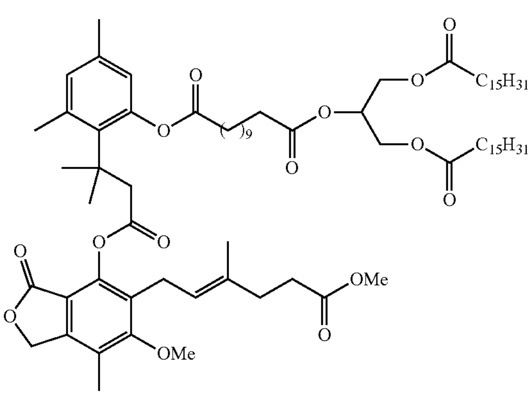 | B |

TABLE B-continued

Lymphatic transport of total compounds related to parent therapeutic agent (% of administered dose) following intraduodenal infusion to anesthetised, mesenteric lymph-duct cannulated rats (data are presented as mean ± SD when n ≥ 3 or as mean ± range when n = 2).

| Compound Name | # | Structure | Cumulative lymphatic transport % dose (Mean ± SD, or Range if n = 2) |
|---|---|---|---|
| MPA-O-ASI-C12α'βMe-TG (n = 3) | MPA-I-44 | 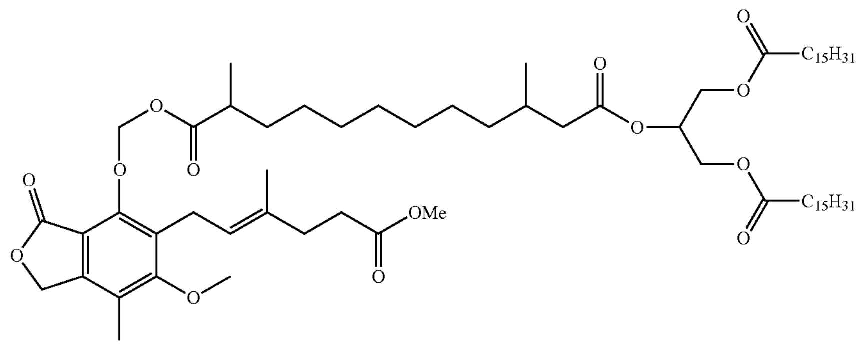 | A |
| MPA-O-C15β-TG (n = 2) | MPA-I-31 | 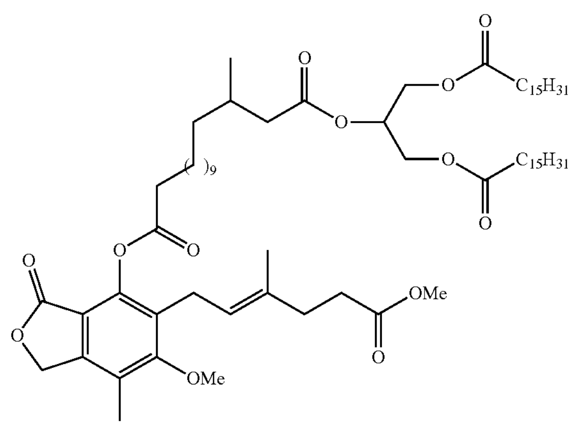 | A |
| MPA-C10-TG (n = 3) | MPA-I-46 | 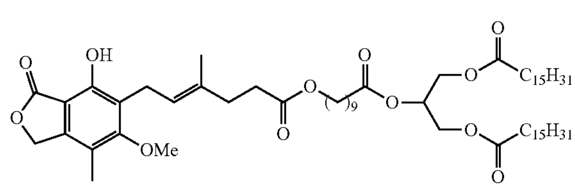 | A |

TABLE B-continued

Lymphatic transport of total compounds related to parent therapeutic agent (% of administered dose) following intraduodenal infusion to anesthetised, mesenteric lymph-duct cannulated rats (data are presented as mean ± SD when n ≥ 3 or as mean ± range when n = 2).

| Compound Name | # | Structure | Cumulative lymphatic transport % dose (Mean ± SD, or Range if n = 2) |
|---|---|---|---|
| MPA(O-C11-2-TG)-OMe | MPA-I-48 | 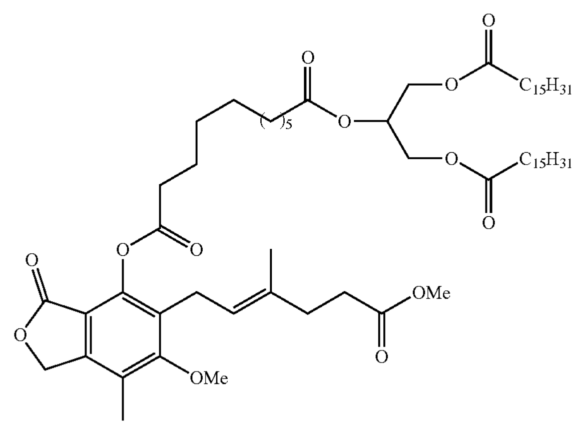 | A |
| MPA-C10β-TG (n = 3) | MPA-I-50 | 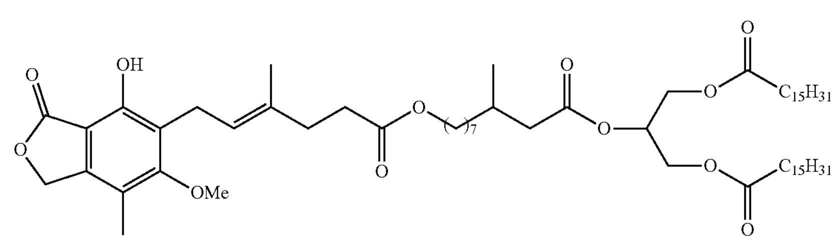 | A |

TABLE B-continued

Lymphatic transport of total compounds related to parent therapeutic agent (% of administered dose) following intraduodenal infusion to anesthetised, mesenteric lymph-duct cannulated rats (data are presented as mean ± SD when n ≥ 3 or as mean ± range when n = 2).

| Compound Name | # | Structure | Cumulative lymphatic transport % dose (Mean ± SD, or Range if n = 2) |
|---|---|---|---|
| MPA-C15β-TG butyrate (n = 3) | MPA-I-43 | 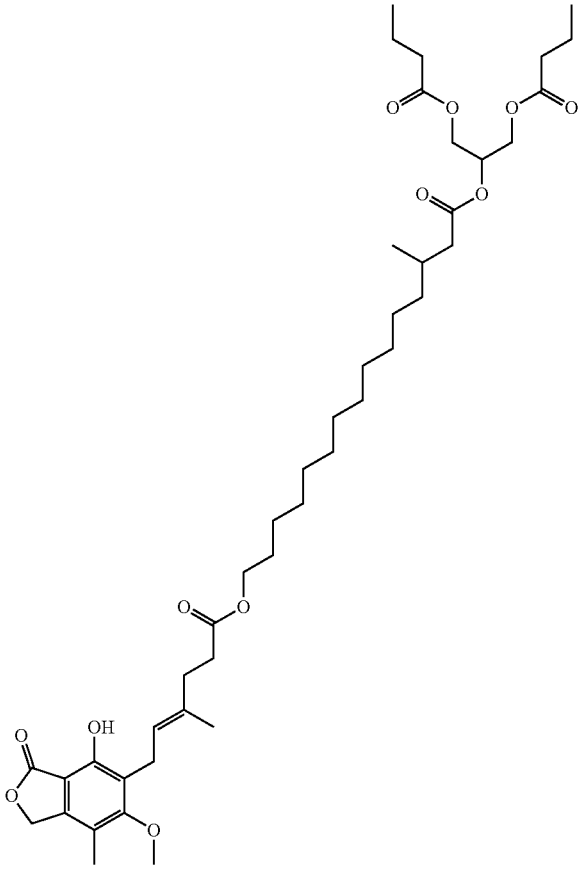 [SMILES: CCCC(=O)OCC(COC(=O)CCC)OC(=O)CC(C)CCCCCCCCCCCCOC(=O)CC/C(C)=C/Cc1c(O)c2c(c(C)c1OC)COC2=O] | A |

The half-life of monoglyceride (MG) intermediates in rat bile and pancreatic fluid was determined for selected compounds. The data are presented in Table 3 below. The designation "A" indicates that the half-life of the MG intermediate was between 15 and 90 minutes. "B" indicates a half-life between >90 minutes and 300 minutes. "C" indicates a half-life between >300 minutes and 600 minutes. "D" indicates a half-life between >600 and 1200 minutes.

The percentage of MPA released at 60 minutes in LPL-supplemented rat plasma was also determined for selected compounds. As shown in Table C below, the designation "*" indicates a release % of 1 to 25%. The designation "" indicates a release % of >25% to 50%. The designation "*" indicates a release % of >50% to 75%. The designation "****" indicates a release % of >75%.

TABLE C

Stability of the Monoglyceride (MG) Intermediates of Lipid Prodrugs in Rat Plasma, Bile, and Pancreatic Fluid.

| Compound Name | # | Half-life of MG intermediates in rat bile and pancreatic fluid (min) (n = 3 unless specified otherwise) | Percentage MPA release at 60 min in LPL supplemented rat plasma (n = 3 unless specified otherwise) |
|---|---|---|---|
| MPA-TG (n = 5) | MPA-I-34 | C | *** |

TABLE C-continued

Stability of the Monoglyceride (MG) Intermediates of Lipid Prodrugs in Rat Plasma, Bile, and Pancreatic Fluid.

| Compound Name | # | Half-life of MG intermediates in rat bile and pancreatic fluid (min) (n = 3 unless specified otherwise) | Percentage MPA release at 60 min in LPL supplemented rat plasma (n = 3 unless specified otherwise) |
|---|---|---|---|
| MPA-C4(ether)-TG (n = 3) | MPA-I-25 | C | |
| MPA-C5-Carbonate-TG (n = 4) | MPA-I-27 | A | |
| MPA-C6(ether)-TG (n = 4) | MPA-I-26 | B | |
| MPA-C7-TG (n = 2) | MPA-I-36 | A | |
| MPA-O-C10-TG(OMe) (n = 3) | MPA-I-19 | | **** |
| MPA-O-C12α'Meβ Me-TG(OMe) (n = 3) | MPA-I-20 | | *** |
| MPA-O-FSI(5)-C12α'Meβ Me-TG(OMe) (n = 2) | MPA-I-22 | | *** |
| MPA-2-PL (n = 4) | MPA-I-39 | | D |

DESCRIPTION OF THE DRAWINGS

FIG. 1: Lymphatic transport of mycophenolic acid prodrug MPA-I-17 in rats following the procedure described above. Rat 1 (●); rat 2 (■).

Figure 2:
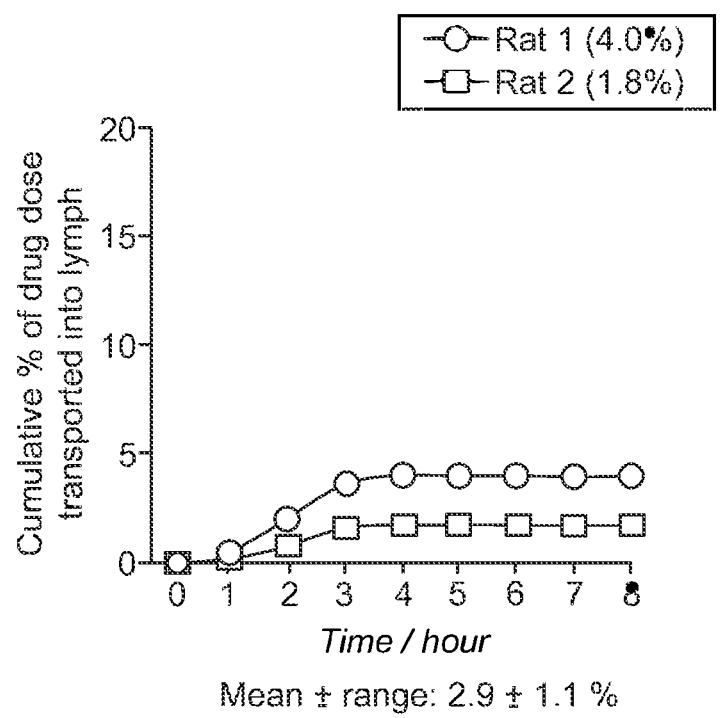
FIG. 2 shows lymphatic transport data for mycophenolic acid prodrug MPA-I-18 in rats.

FIG. 2: Lymphatic transport of mycophenolic acid prodrug MPA-I-18 in rats following the procedure described above. Rat 1 (●); rat 2 (■).

Figure 3:
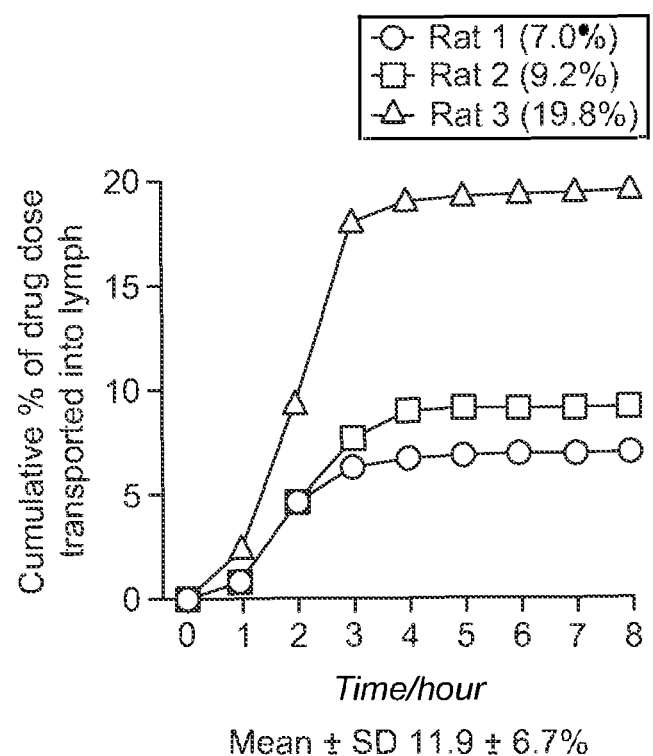
FIG. 3 shows lymphatic transport data for mycophenolic acid prodrug MPA-I-19 in rats.

FIG. 3: Lymphatic transport of mycophenolic acid prodrug MPA-I-19 in rats following the procedure described above. Rat 1 (●); rat 2 (■); rat 3 (▲).

Figure 4:
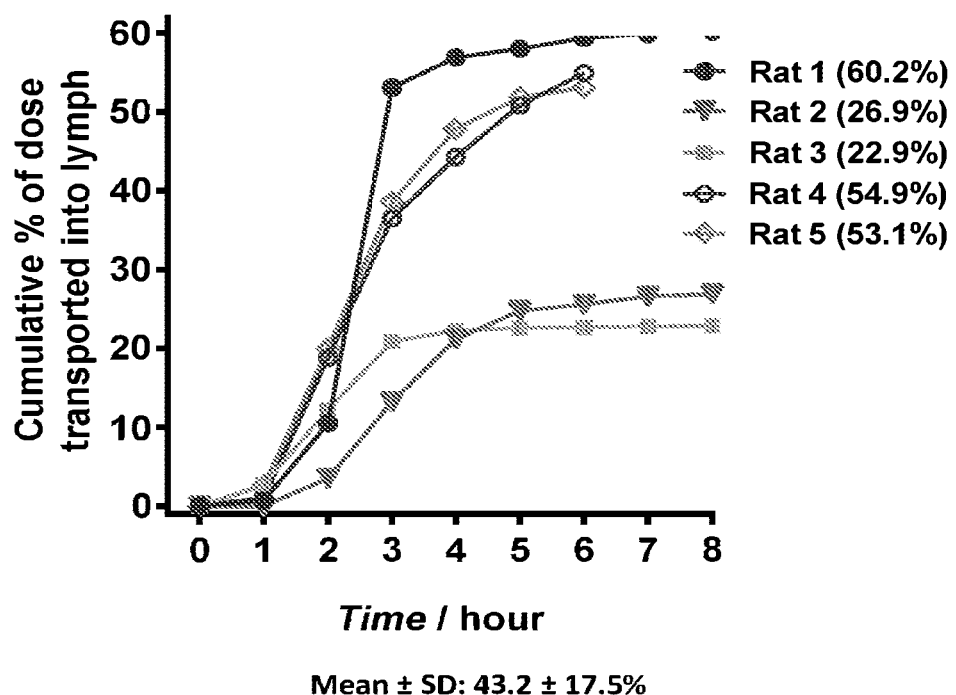
FIG. 4 shows lymphatic transport data for mycophenolic acid prodrug MPA-I-20 in rats.

FIG. 4: Lymphatic transport of mycophenolic acid prodrug MPA-I-20 in rats following the procedure described above. Rat 1 (●); rat 2 (▼); rat 3 (■); rat 4 (○); rat 5 (◇).

Figure 5:
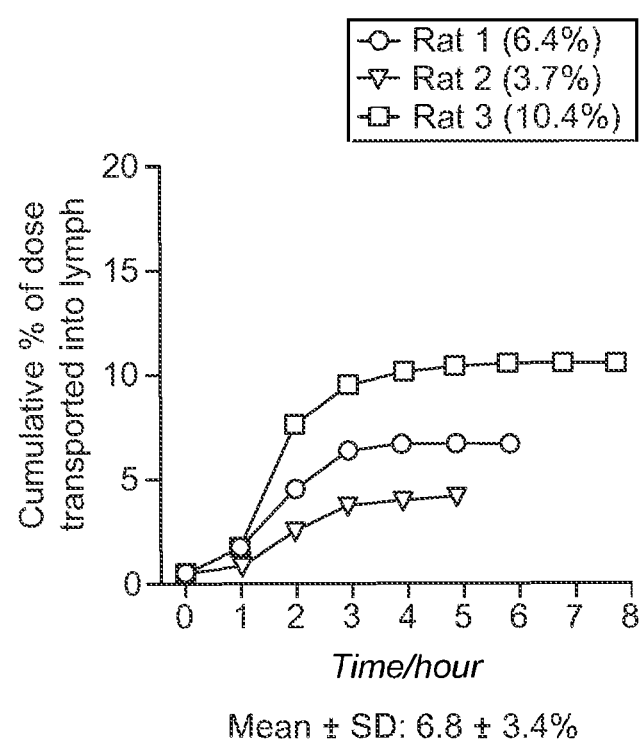
FIG. 5 shows lymphatic transport data for mycophenolic acid prodrug MPA-I-21 in rats.

FIG. 5: Lymphatic transport of mycophenolic acid prodrug MPA-I-21 in rats following the procedure described above. Rat 1 (●); rat 2 (▼); rat 3 (■).

Figure 6:
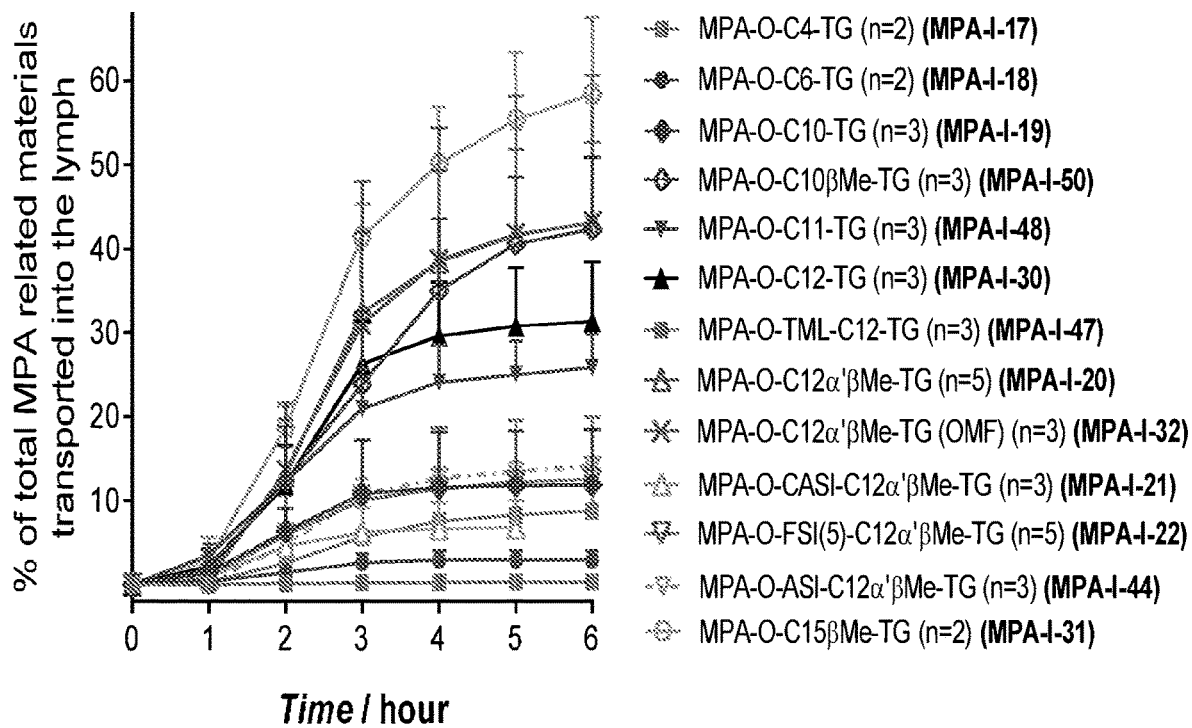
FIG. 6 shows lymphatic transport of phenol-conjugated mycophenolic acid prodrugs (mean SD when n≥3 or as mean±range when n=2).

FIG. 6: lymphatic transport of phenol-conjugated MPA prodrugs (mean±SD when n≥3 or as mean±range when n=2).

Figure 7:
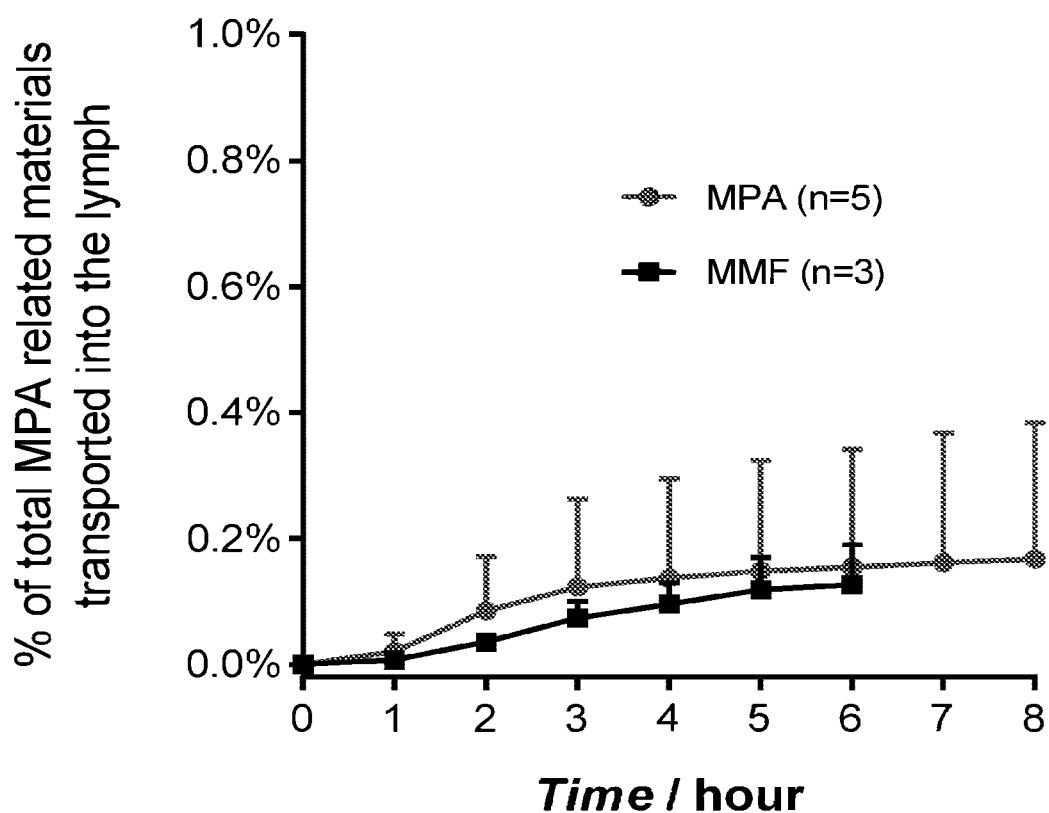
FIG. 7 shows lymphatic transport of mycophenolic acid (MPA) and mycophenolate mofetil (MMF) (mean±SD). MPA (0.13%) and MMF (0.17%) had similar, very low lymphatic transport values in rats. Both compounds were administered as an intraduodenal infusion of 2 mg compound in 5.6 mL of a lipid formulation.

FIG. 7: lymphatic transport of mycophenolic acid (MPA) and mycophenolate mofetil (MMF) (mean±SD).

TABLE D

Pharmacokinetic and Lymph Data for Testosterone Lipid Prodrugs

| Cmd Name and # | Plasma PK measurements: Repeat number | Plasma PK measurements: Mean Plasma AUC (0-24 hr) (nmol · h/L) | Plasma PK measurements: Tmax (h) | Plasma PK measurements: Cmax (nmol/L) | Plasma PK measurements: Fold increase relative to Comparator | Plasma PK measurements: Comparator drug | Rat-cumulative lymphatic transport: Repeat Number | Rat-cumulative lymphatic transport: Mean, lymphatic transport over 6 or 8 hours (%) |
|---|---|---|---|---|---|---|---|---|
| TST-FSI5-C12abMe-2-TG (I-50) | 5 | 504.6 | 1.2 | 293.3 | 74 | TU (testosterone undecanoate) | 2 | 11.3 |
| TST-FSI5-C5bMe-2-TG (I-49) | 4 | 583.3 | 0.9 | 822.1 | 85.5 | TU | | |
| TST-CMSI-C10bMe-2-TG (I-46) | 3 | 591 | 0.92 | 638 | 86.6 | TU | 3 | 11.4 |

TABLE D-continued

Pharmacokinetic and Lymph Data for Testosterone Lipid Prodrugs

| Cmd Name and # | Plasma PK measurements: Repeat number | Plasma PK measurements: Mean Plasma AUC (0-24 hr) (nmol · h/L) | Plasma PK measurements: Tmax (h) | Plasma PK measurements: Cmax (nmol/L) | Plasma PK measurements: Fold increase relative to Comparator | Plasma PK measurements: Comparator drug | Rat-cumulative lymphatic transport: Repeat Number | Rat-cumulative lymphatic transport: Mean, lymphatic transport over 6 or 8 hours (%) |
|---|---|---|---|---|---|---|---|---|
| TST-CMSI-C5bMe-2-TG (1-44) | 4 | 631.6 | 0.9 | 595.8 | 92.6 | TU | | |
| TST-CASI-C5bMe-2-TG (1-42) | 3 | 268.1 | 0.8 | 358.1 | 39.3 | TU | 3 | 2.8 |
| TST-ASI-C15a'bMe-2-TG (I-41) | 3 | 255.4 | 1.1 | 190.8 | 37.4 | TU | 4 | 8.3 |
| TST-ASI-C12a'bMe-2-TG ((I-40) | 3 | 901 | 1.08 | 968 | 132.1 | TU | 3 | 27.2 |
| TST-ASI-C10b'Me-2-TG (I-39) | 4 | 588.7 | 1.8 | 311 | 86.3 | TU | | |
| TST-ASI-C5-2-TG (I-38) | 4 | 236 | 1.2 | 95.6 | 34.6 | TU | 3 | 2.3 |
| TST-C10-ET-2-TG (I-37) | | | | | | | 3 | 6.9 |
| TST-C10-AM-2-TG (I-36) | | | | | | | 3 | 1.8 |
| TST-C15a'bMe-2-TG (I-35) | 3 | 47.7 | 1.5 | 86.8 | 7 | TU | 2 | 14.2 |
| TST-C12a'bMe-2-TG (I-34) | 2 | 187.9 | 1.9 | 24.9 | 27.5 | TU | | |
| TST-C10b'Me-2-TG (I-33) | 3 | 39.6 | 1.5 | 28 | 5.8 | TU | | |
| TST-C4-2-TG (1-32) | 4 | 18.9 | 1.1 | 13.2 | 2.8 | TU | 4 | 13.5 |

TABLE E

Pharmacokinetic and Lymph Data for Additional Lipid Prodrugs

| Cmpd Name and # | Rat-cumulative lymphatic transport: Repeat Number | Rat-cumulative lymphatic transport: Mean, lymphatic transport over 6 or 8 hours (%) | Rat-cumulative lymphatic transport: SD, lymphatic transport over 6 or 8 hours (%) |
|---|---|---|---|
| THC-CASI-C5bMe-2-TG (I-55) | 3 | 66.9 | 18 |
| THC-TML-C5bMe-2-TG (I-54) | 3 | 3.4 | 0.9 |
| THC-C10-2-TG (I-53) | 2 | 82.2 | 1.1 |
| CBD-FSI5-C5bMe-2-TG (I-21) | 2 | 29.1 | 14 |
| CBD-C5bMe-2-TG (I-20) | 3 | 26.1 | 6.6 |
| BUP-TML-C5bMe-2-TG (I-15) | 3 | 44.7 | 19 |
| BUP-C10-2-TG (I-14) | 5 | 59.8 | 17 |
| BUP-C5bMe-2-TG (I-13) | 2 | 45.6 | 14 |
| BUP-C4-2-TG (I-12) | 3 | 12.9 | 4.1 |

Example 36: Prodrug Lymph Node Studies in Mice

This experiment included a single and multiple dose study. In the multiple dose study, dosing of either free MPA or MPA-2-TG (MPA-I-34, structure below) 2 times daily was performed for 2 days followed by collecting samples from mesenteric or peripheral lymph nodes on the 3$^{rd}$ day after dosing.

MPA-I-34

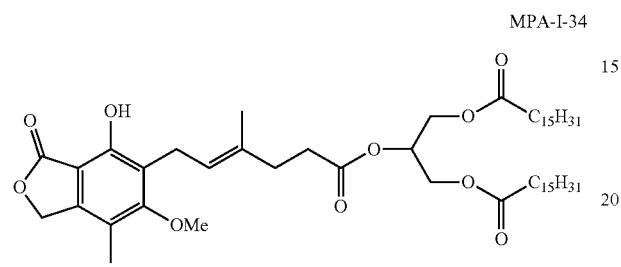

The concentrations of free MPA were measured for both groups of mice.

Figure 8A:
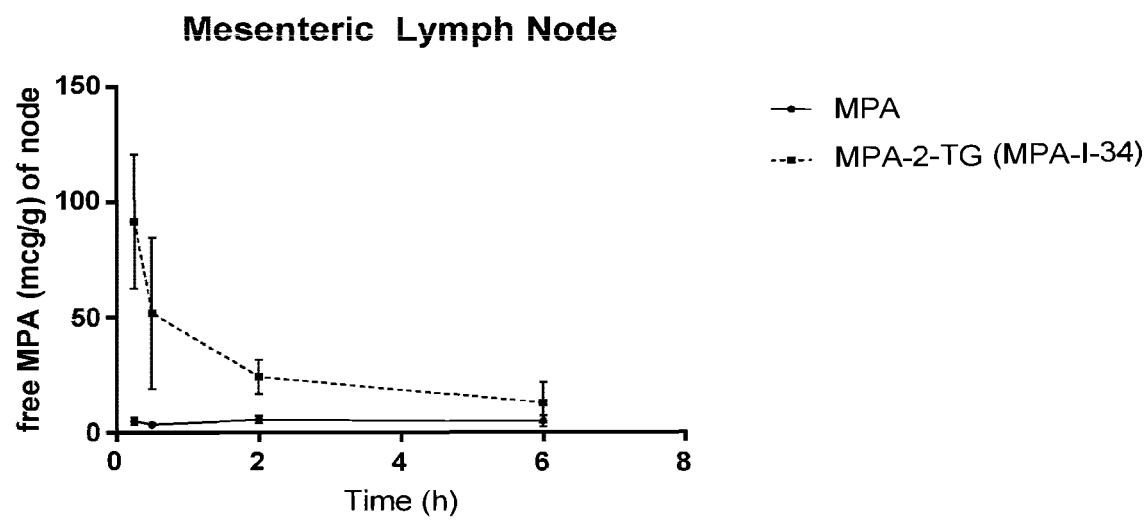
FIG. 8A and FIG. 8B show measured concentrations of free mycophenolic acid (MPA) in mouse mesenteric and peripheral lymph nodes after oral administration of MPA-I-34 or MPA.
Figure 8B:
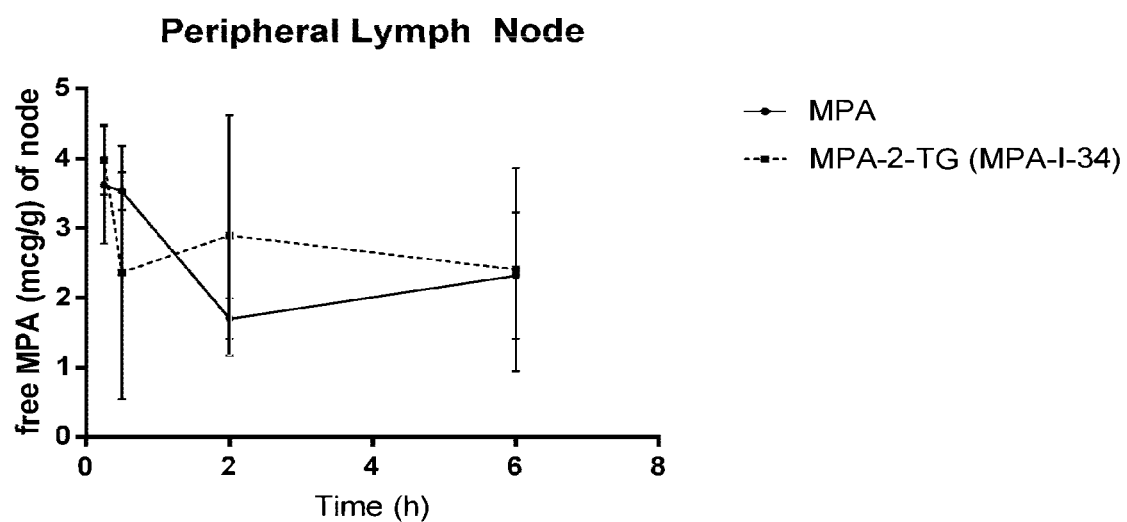

Much higher concentrations in mesenteric lymph nodes after MPA-TG administration were observed compared with MPA. In contrast, the peripheral lymph nodes showed similar concentrations following administration of MPA-TG and MPA. The results of the multi-dose study are shown in FIGS. 8A and 8B.

Figure 9:
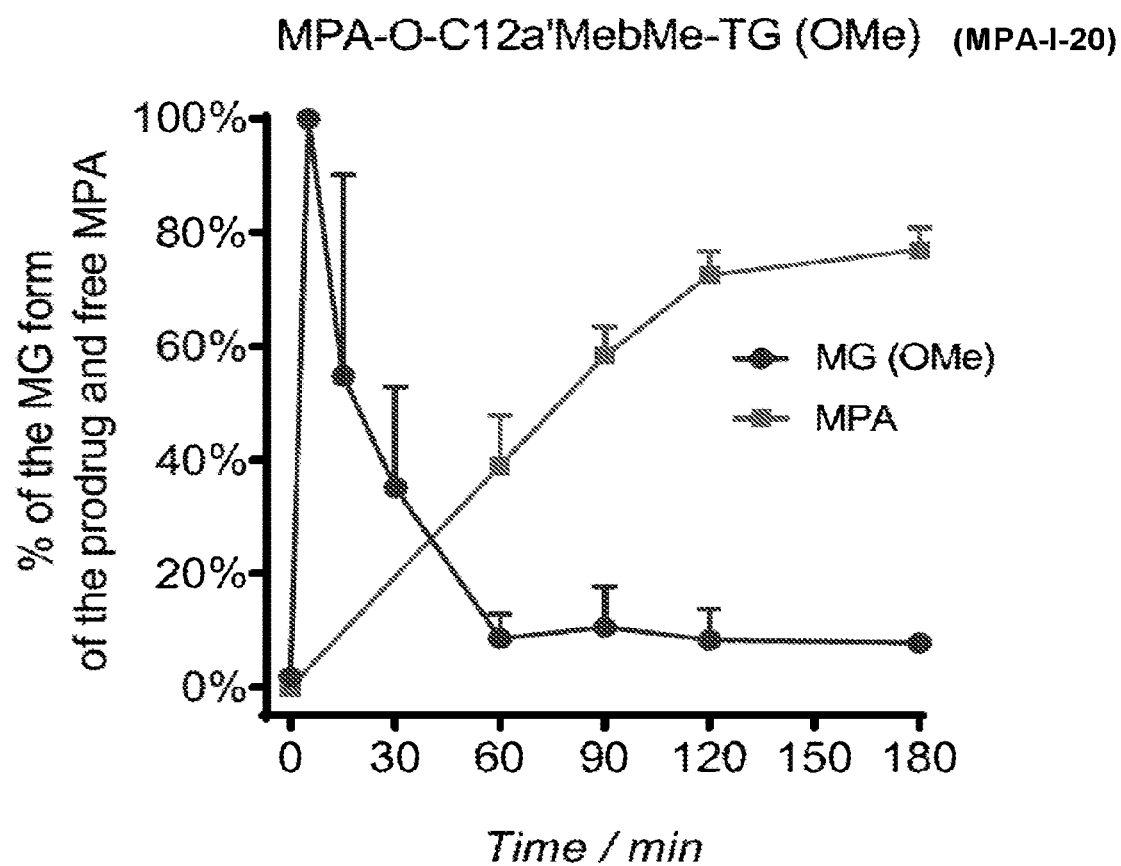
FIG. 9 shows measured concentrations of the monoglyceride form of MPA-I-20 (in which both palmitic acid groups are cleaved) and free MPA released from the monoglyceride over time in rat plasma supplemented with LPL.
Figure 10:
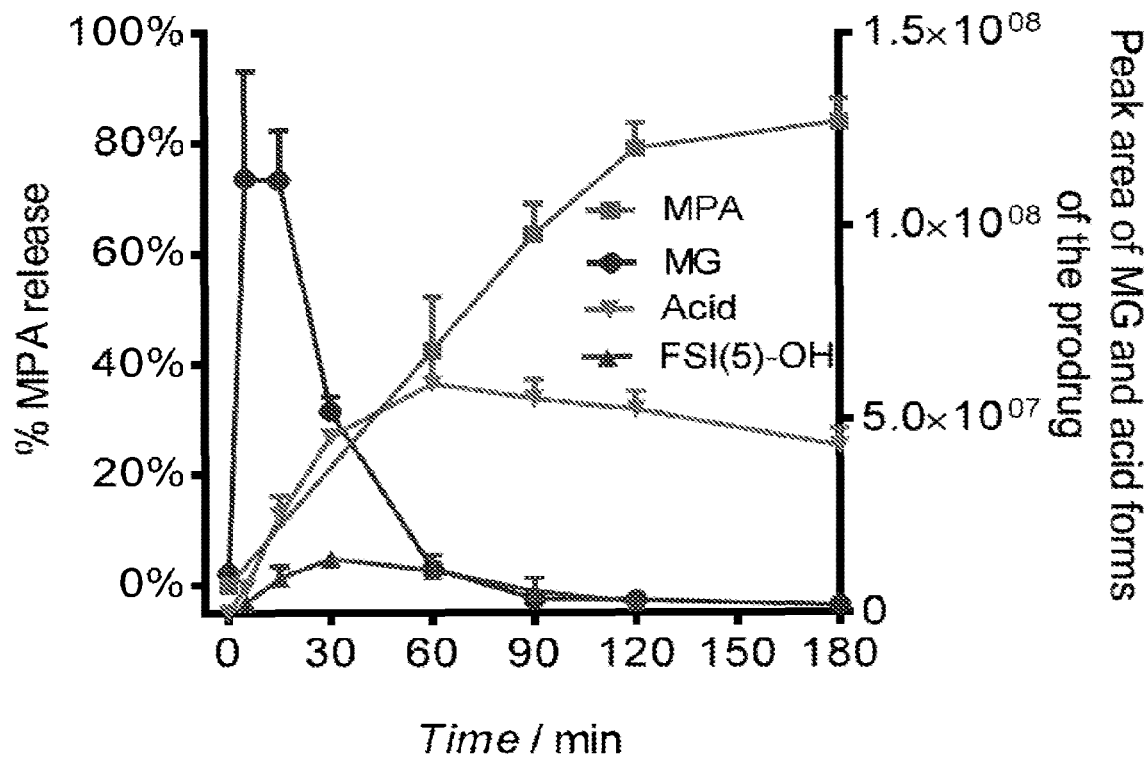
FIG. 10 shows conversion of MPA-I-22 into its monoglyceride form (in which both palmitic acid groups are cleaved) and release of MPA from the monoglyceride followed over time in rat plasma supplemented with LPL.
Figure 11:
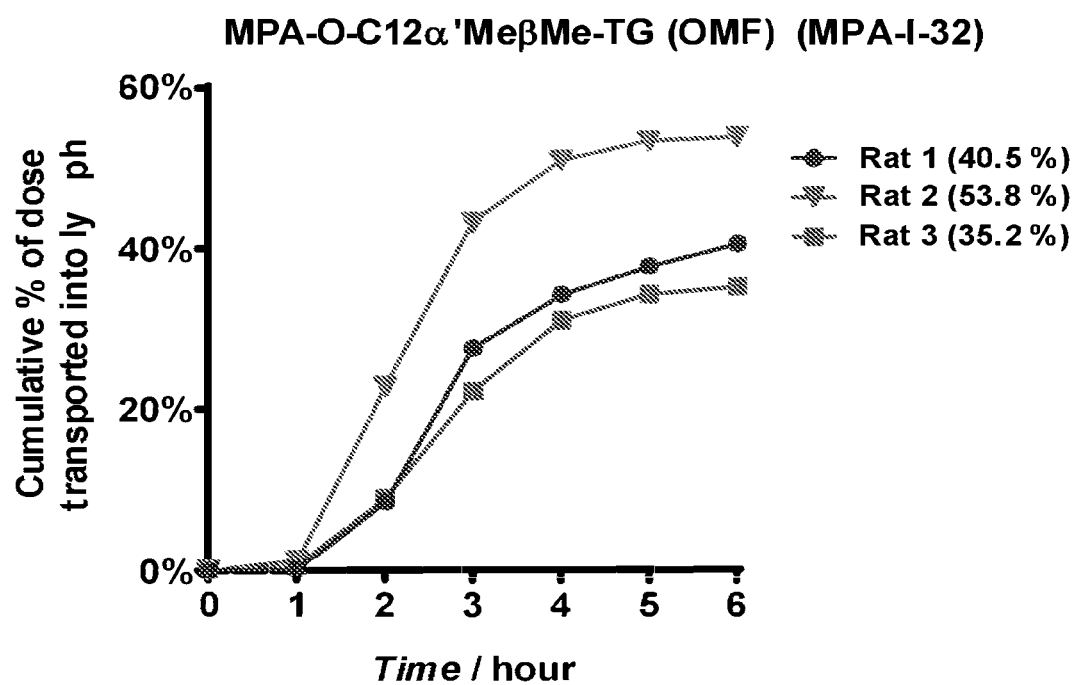
FIG. 11 shows lymphatic transport data for MMF prodrug compound MPA-I-32. The compound was administered as an intraduodenal infusion of 2 mg compound in 5.6 mL of a lipid formulation. Lymphatic transport of approximately 40% was observed.
Figure 12:
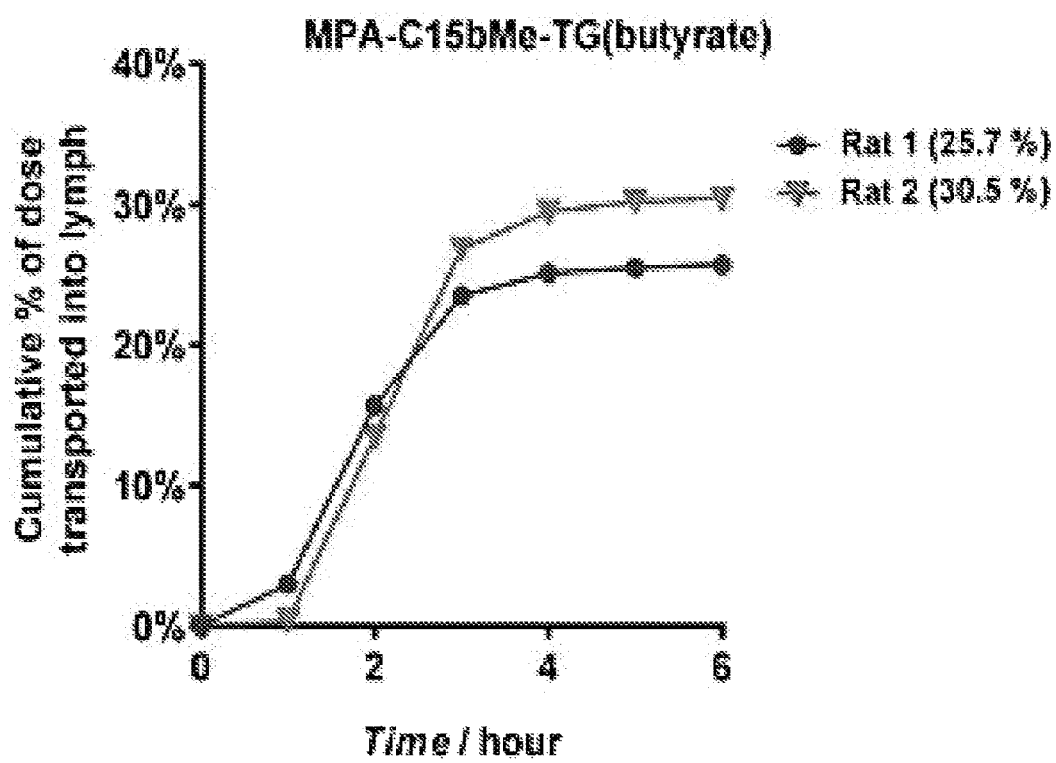
FIG. 12 shows lymphatic transport data for mycophenolic acid prodrug MPA-I-43 in rats (plot of cumulative dose into lymph vs. time for each rat).
Figure 13:
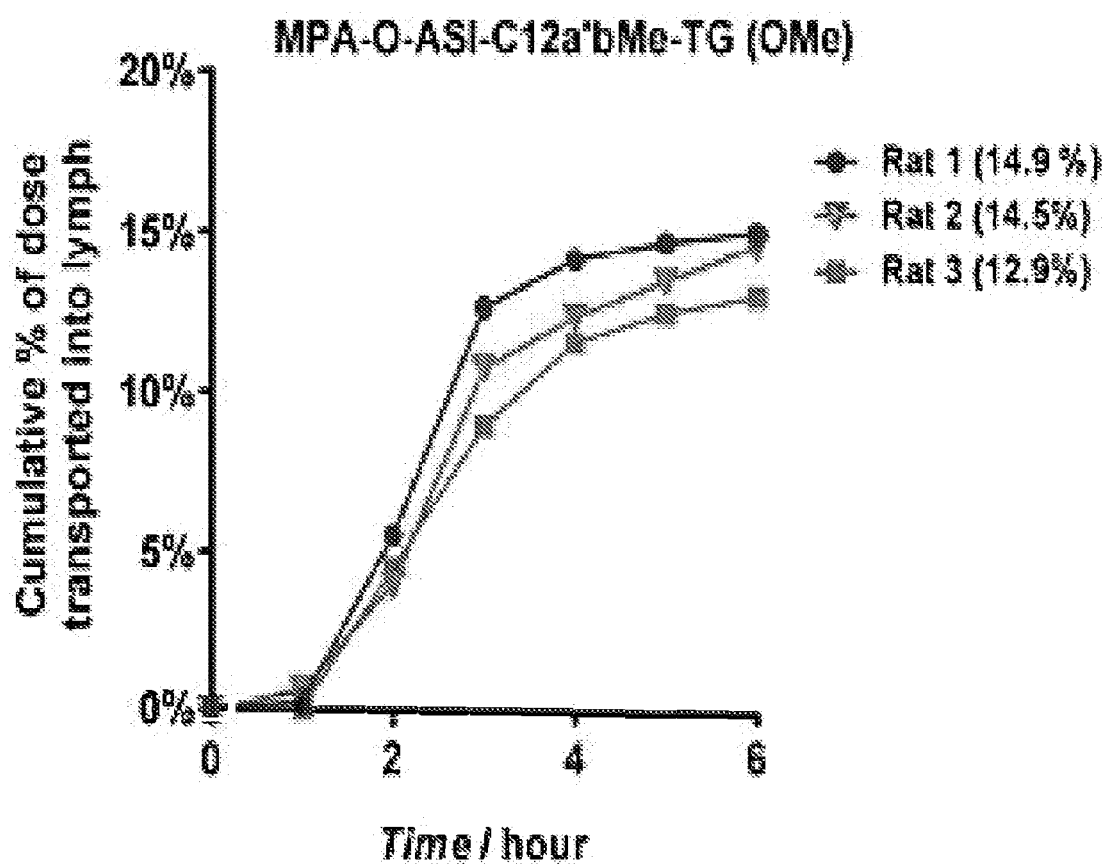
FIG. 13 shows lymphatic transport data for mycophenolic acid prodrug MPA-I-44 in rats.
Figure 14:
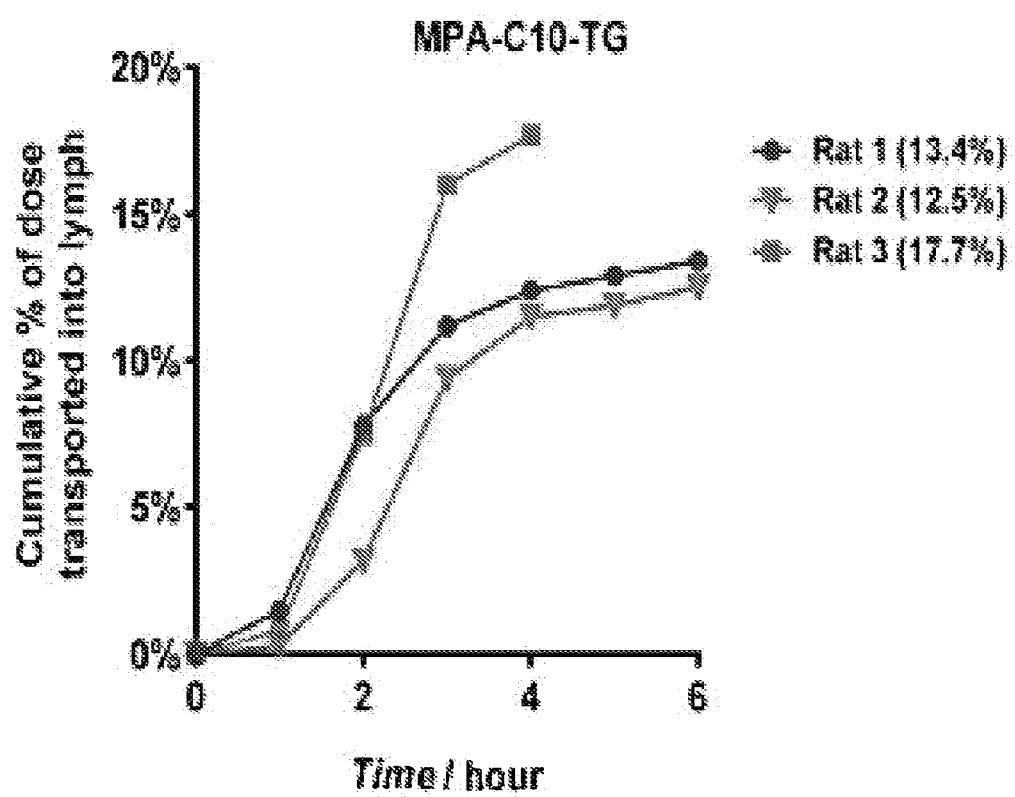
FIG. 14 shows lymphatic transport data for mycophenolic acid prodrug MPA-I-46 in rats.
Figure 15:
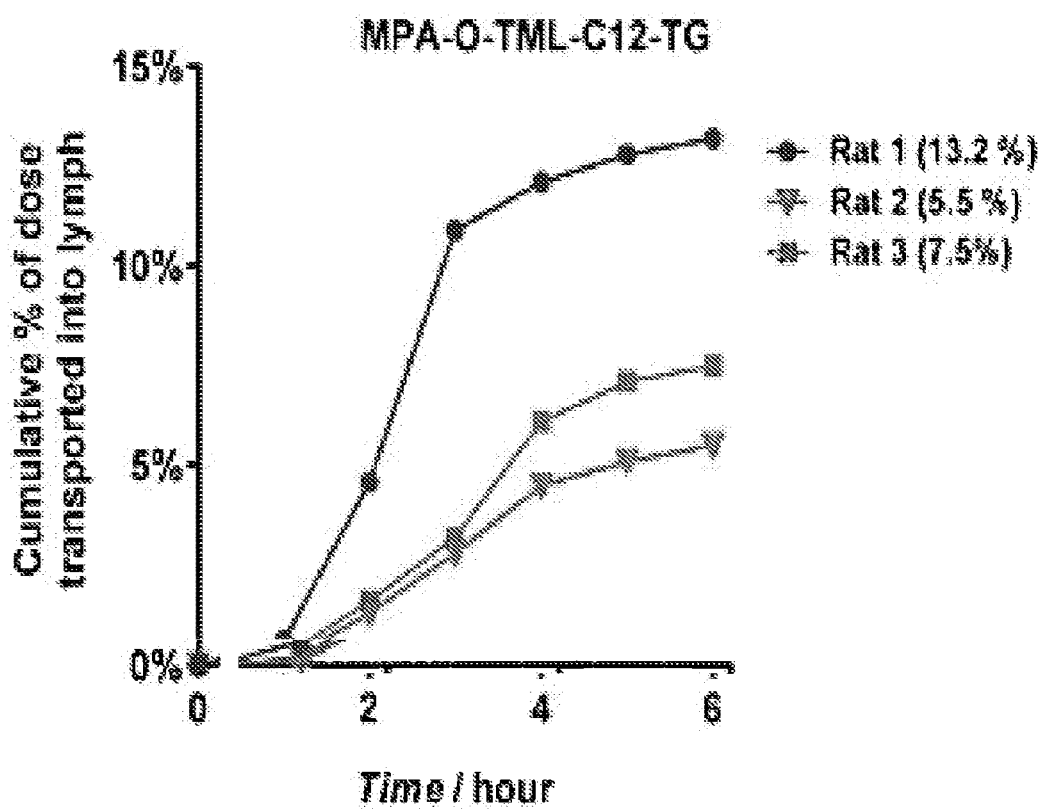
FIG. 15 shows lymphatic transport data for mycophenolic acid prodrug MPA-I-47 in rats.
Figure 16:
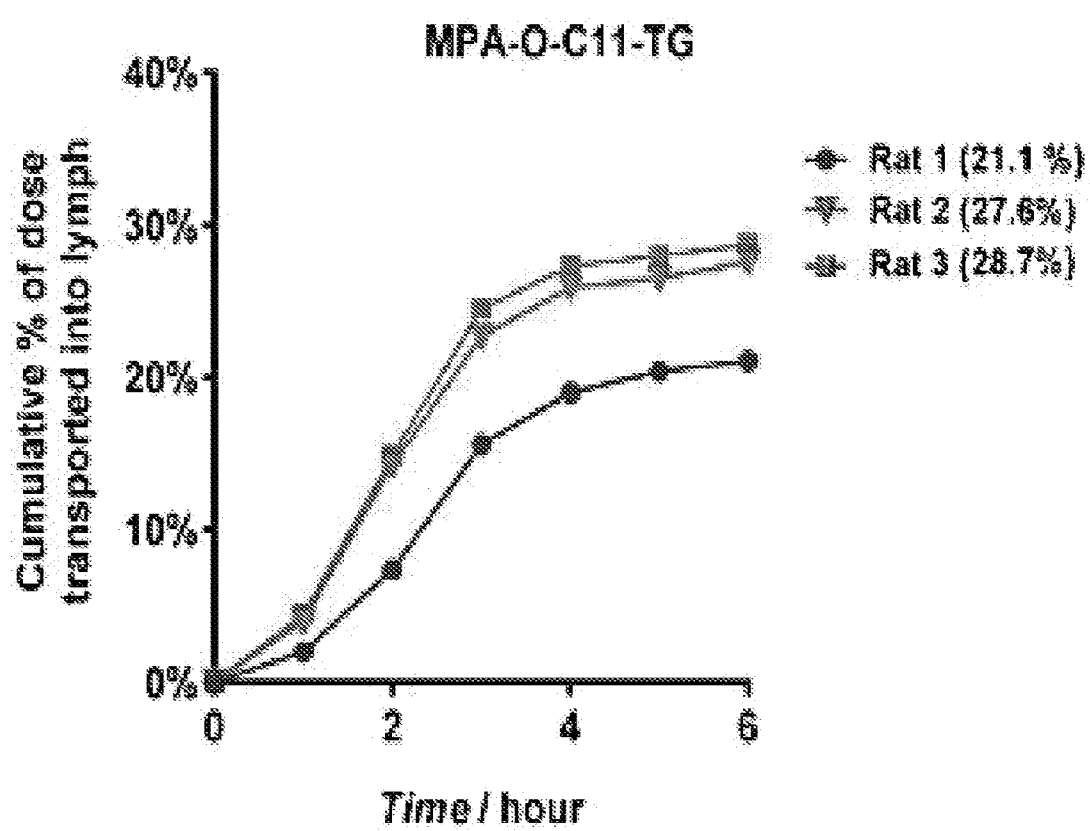
FIG. 16 shows lymphatic transport data for mycophenolic acid prodrug MPA-I-48 in rats.
Figure 17:
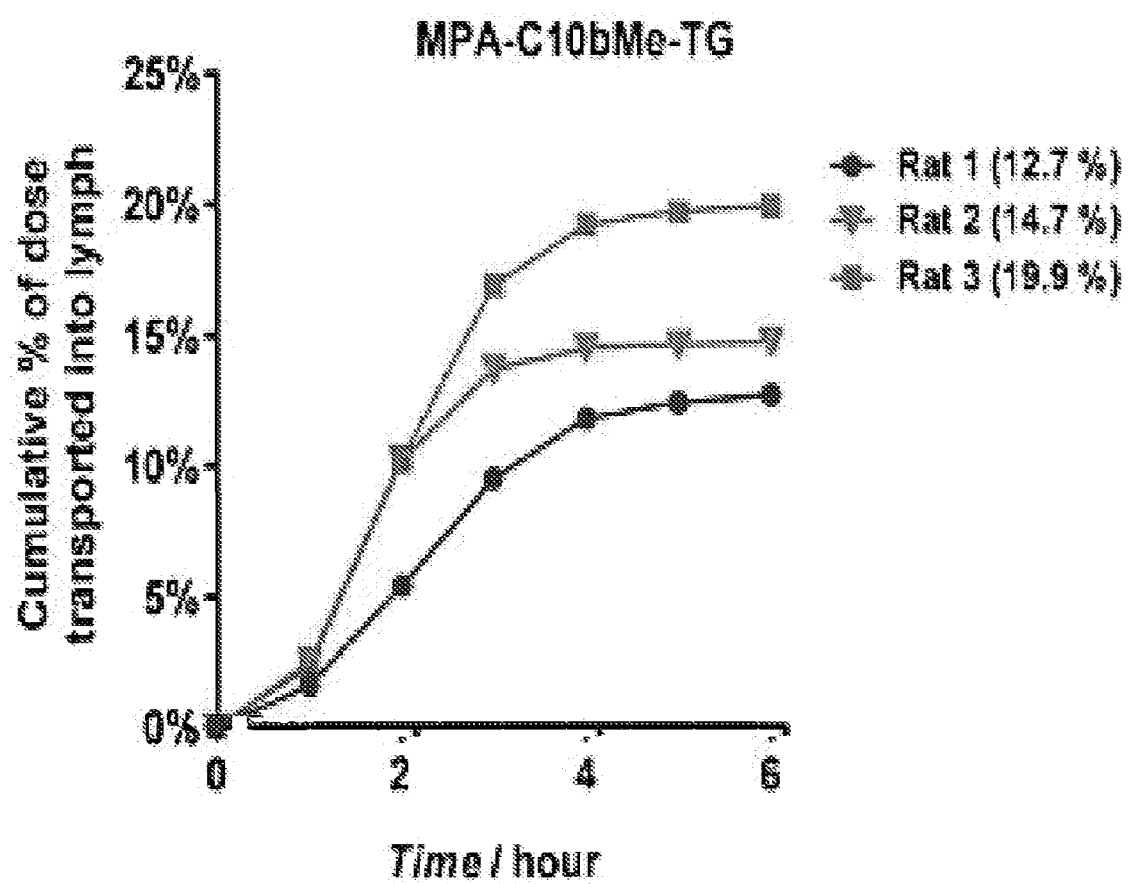
FIG. 17 shows lymphatic transport data for mycophenolic acid prodrug MPA-I-50 in rats.
Figure 18:
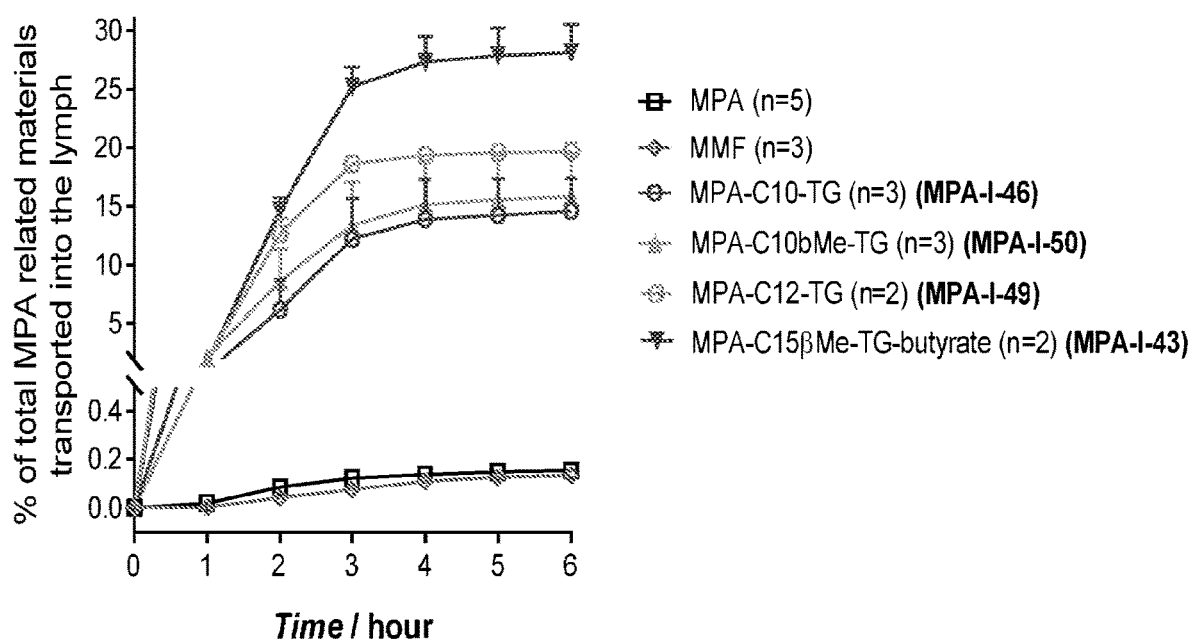
FIG. 18 shows lymphatic transport data for several mycophenolic acid prodrugs (mycophenolic acid (MPA) and mycophenolate mofetil (MMF) shown for comparison).
Figure 19:
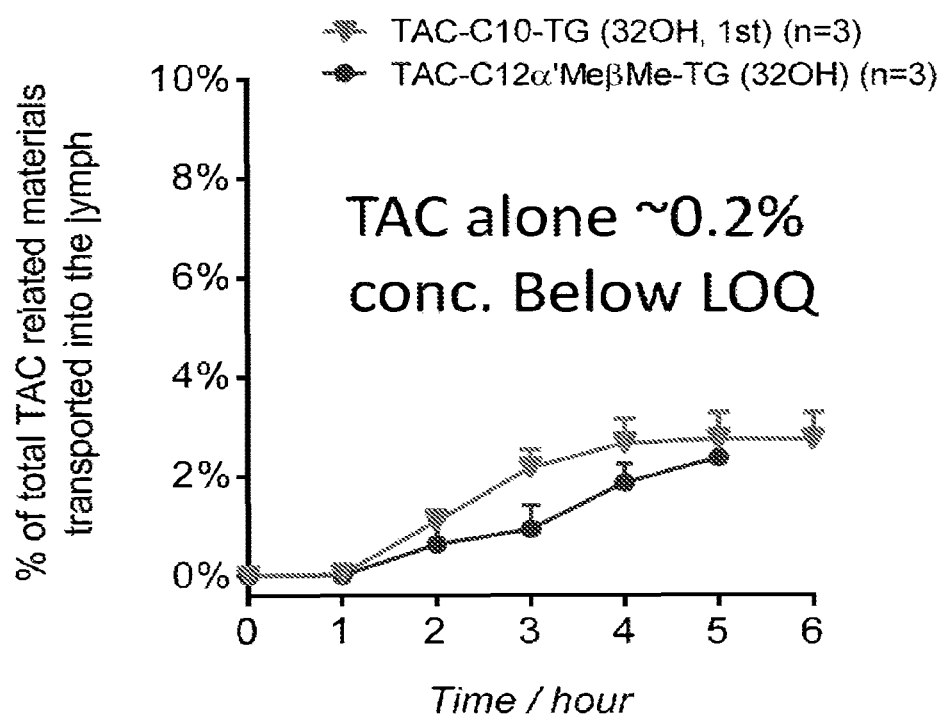
FIG. 19 depicts the lymphatic transport of TAC-I-18 (TAC-C10-TG (320H)) and TAC-I-20 (TAC-C12α′MeβME-TG (320H)) as the concentration of total tacrolimus related compounds detected in the mesenteric lymph following intraduodenal infusion. In comparison, detected total tacrolimus-related compounds following administration of tacrolimus (TAC) alone was about 0.2%, below the limit of quantitation.

As shown in FIG. 9, conversion of MPA-I-20 into its monoglyceride form (in which both palmitic acid groups are cleaved) and release of MPA from the monoglyceride could be followed over time in rat plasma supplemented with LPL. FIG. 10 shows conversion over time after administration of MPA-I-22. For both MPA-I-20 and MPA-I-22, about 80% of the MPA was released after 180 min and the monoglyceride (MG) peak had almost completely disappeared.

In FIG. 10, the "Acid" intermediate is believed to have the following structure:

"FSI(5)-OH" refers to the following intermediate structure:

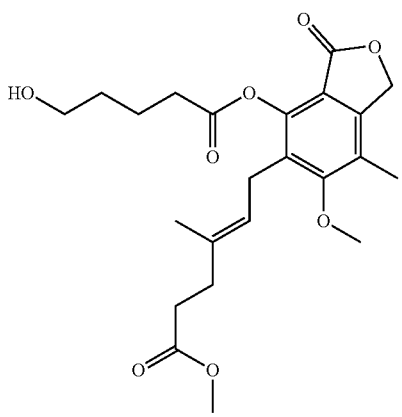

Example 37: Pharmacokinetic (PK) Studies in Rats and Dogs

In order to assess the oral bioavailability of test compounds, pharmacokinetic studies were conducted using the following procedure. The day before drug administration, male Sprague-Dawley rats (240-320 g) were anesthetised and the carotid artery cannulated. The rats were then allowed to regain consciousness and fasted overnight prior to the commencement of experiments with free access to water. The next morning, formulations containing parent compounds or prodrugs were administered via oral gavage and blood samples collected from the carotid artery cannula from −5 min up to 24 h post dosing and centrifuged at 5000 rpm for 5 min to separate plasma. During the blood sample collection period, the rats had free access to water but remained fasted for a further 8 h following drug administration. Plasma samples were stored at −80° C. prior to assay by HPLC-MS-MS. Samples were assayed for free drug (i.e. non-glyceride associated drug) to determine hydrolysis (if any) prior to assay.

For the dog studies, beagle dogs will be held in a large-animal research facility prior to the commencement of studies. The dogs will be fasted for 12 h up to 30 min prior to drug administration. For the fed state studies, dogs will receive ~20 g of high fat dog food (containing ~34% fat),

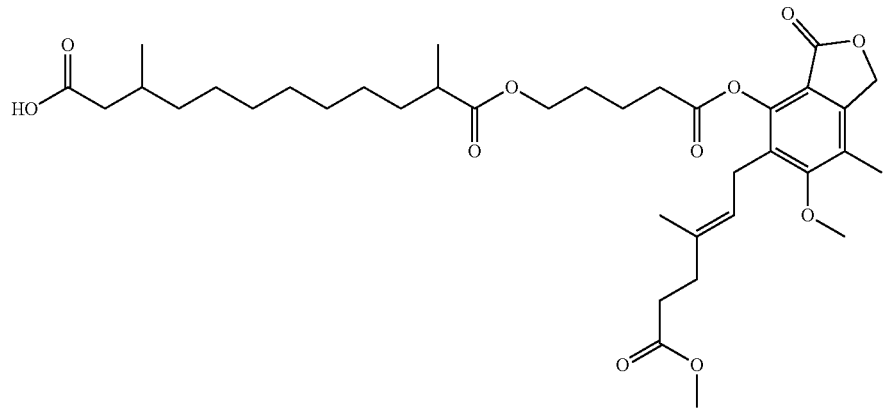 [SMILES: COC(=O)CC/C(C)=C/Cc1c(OC)c(C)c2c(c1OC(=O)CCCCOC(=O)C(C)CCCCCCCC(C)CC(=O)O)C(=O)OC2]

administered by hand, followed by 10 mL water to aid in swallowing, followed by 100 g standard canned dog food (~2.5% fat) 30 min prior to drug administration. Water will be available ad libitum throughout the study for all dogs. Test compounds may be prepared in a suitable formulation such as a long-chain lipid based self-emulsifying drug delivery system (SEDDS) consisting of 30.5% w/w soybean oil, 30.5% w/w Maisine-CC, 31.6% w/w Cremophor EL and 7.4% w/w ethanol. Formulations may be filled into hard gelatin capsules. Compound dissolved in the formulation may be administrated to the fed dog by placing the capsules as far posterior to the pharynx as possible, closing the mouth and rubbing the throat to stimulate swallowing. Subsequently 50 mL of water will be administered orally via a syringe. After oral administration, blood samples (approx. 1.5 mL each) will be taken via venepuncture of the cephalic vein 5 min prior to administration up to 120 hours post-dosing. Plasma will be separated by centrifugation and aliquots of each plasma sample transferred into eppendorf tubes and stored at −80° C. prior to analysis.

For comparison purposes and to allow calculation of bioavailability, the parent drug may be administered intravenously by either infusion (over 5 min) or bolus injection of a suitable dose of drug dissolved in appropriate aqueous formulation (dependent on the nature of the parent drug (for example, for MPA, 95:5 PBS/ethanol may be used, while for other drugs, a 20% hydroxypropyl-β-cyclodextrin solution may be used). The dose also depends on nature of the parent drug. For MPA, about ~2-3 mg per beagle is used, while for others, a higher or lower dose per beagle is used. After IV administration, blood samples (approx. 1.5 mL each) will be taken via venepuncture of the cephalic vein 5 min prior to administration up to 120 hours post-dosing. Plasma will be separated by centrifugation and aliquots of each plasma sample transferred into eppendorf tubes and stored at −80° C. prior to analysis.

Example 38: In Vitro Hydrolysis of Compounds by Rat Digestive Fluid or Porcine Pancreatic Lipase In vitro hydrolysis of test compounds may be performed via incubation with rat digestive fluid. Rat digestive fluid will be collected from anesthetized rats via cannulation of the common bile-pancreatic duct immediately prior to the entry of the duct into the duodenum (i.e. below the point of entry of pancreatic secretions). This allows simultaneous collection of bile and pancreatic fluid. The digestive fluid will be collected continuously for 2 h, during which time a blank lipid formulation (prepared as described in the rat lymphatic transport studies but without the addition of drug) will be infused into the duodenum at a rate of 2.8 mL/h to mimic conditions following drug administration. Bile and pancreatic fluid will be maintained at 37° C. and used within 0.5 h of collection for in vitro prodrug hydrolysis experiments. The hydrolysis experiments will be conducted via incubation (at 37° C.) of ~0.375 mL of rat digestive fluid with ~0.625 ml of the drug-loaded lipid formulations (as described in the rat lymphatic transport studies). The volume ratio of digestive fluid to formulation will mimic the flow rate of bile and pancreatic fluid (~1.5 mL/h) and the infusion rate of the intraduodenal formulations (2.8 mL/h) during the in vivo lymphatic transport studies. Aliquots of 10 μL (samples taken at 0, 2, 5, 10, 15, 30, 60, 90, 120, 180 min) will be added to 990 μL of acetonitrile/water (4:1, v/v) to stop lipolysis, vortexed for 1 min and centrifuged at 4500 g for 5 min to precipitate proteins prior to analysis. The supernatant will be analyzed by HPLC-MS for residual compound concentrations, and the potential products of compound hydrolysis analyzed.

To provide for higher throughput of experiments, unless otherwise stated, in vitro hydrolysis of test compounds will generally be performed via incubation with porcine pancreatic lipase. This provides a more reproducible source of pancreatic enzymes, facilitates enhanced experimental throughput, and is also a greater challenge than collected rat enzymes (since enzyme activity in rat intestinal fluid is low). Briefly, pancreatic lipase solution will be prepared prior to the hydrolysis experiment by dispersion of 1 g porcine pancreatin in 5 ml of lipolysis buffer and 16.9 μL of 0.5 M NaOH. The suspension will be mixed well and centrifuged at 3500 rpm for 15 minutes at 5° C. to provide a supernatant. An amount of 1000 mL of lipolysis buffer will be prepared with 0.474 g of tris-maleate (2 mM), 0.206 g of $CaCl_2·H_2O$ (1.4 mM) and 8.775 g of NaCl (150 mM) adjusted with NaOH to pH 6.5. To assess the potential for prodrug hydrolysis in the intestine, 20 μL of prodrug solution (1 mg/mL dissolved in acetonitrile), 900 μL of simulated intestinal micellar solution [prepared with 0.783 g of NaTDC (3 mM) and 0.291 g of phosphatidyl choline (0.75 mM) in 500 mL lipolysis buffer] and 100 μL of enzyme solution will be incubated at 37° C. 20 μL samples of the incubation solution will be taken at 0, 5, 10, 15, 30, 60, 90, 120 and 180 minutes post incubation and added to 180 μL of MeCN to stop lipolysis. The mixture will be vortexed and centrifuged at 5000 rpm for 5 minutes to precipitate proteins prior to analysis. The supernatant will be analyzed by HPLC-MS for residual compound concentrations, and the potential products of compound hydrolysis analyzed.

On incubation with digestive enzymes, the monoglyceride forms of the prodrugs are formed very rapidly. The stability in simulated intestinal conditions is therefore better assessed by the stability of the monoglyceride form that is generated by the initial digestion process. The monoglyceride form must remain intact to be absorbed and re-esterified in the enterocyte prior to entry into the lymphatics. A comparison of the stability profiles of the monoglyceride forms of test compounds during in vitro incubation with freshly collected rat bile and pancreatic fluid (BPF) or porcine pancreatic lipase will be used to evaluate the influence of linker structure on the stability of the monoglyceride intermediates.

Example 39: In Vitro Release of Therapeutic Agent From Prodrugs in Lymph Supplemented with Lipoprotein Lipase In order to probe the release of free therapeutic agent from lipid prodrugs in the lymphatics, prodrugs will be incubated with rat lymph supplemented with lipoprotein lipase (LPL, 200 unit/mL). LPL is a key enzyme required for the hydrolysis of lipoprotein associated TG in normal physiological conditions and is therefore expected to be a key contributor to lipolysis of the re-esterified drug-TG construct in plasma, largely via liberation of fatty acids in the sn-1 and the sn-3 position of the TG-mimetic, prior to drug release from the 2' positon via esterase hydrolysis. LPL is tethered to lymphocytes or lymphatic/vascular endothelial cells under physiological conditions. In these in vitro studies, rat lymph will therefore be supplemented with LPL to better reflect the in vivo situation. To start hydrolysis, 10 μL of LPL solution (10,000 unit/ml) will be added to a mixture of 10 μL of prodrug solution (1 mg/mL dissolved in acetonitrile) and 500 μL of blank Sprague Dawley rat lymph. The solution will be incubated at 37° C. Samples (20 μL) of the incubation solution will be taken at 0, 5, 10, 15, 30, 60, 90, 120 and 180 minutes post incubation and added to 980 µL of 9:1 (v/v) MeCN/water to stop lipolysis. The mixture will be vortexed and centrifuged at 4500 g for 5 minutes to precipitate proteins prior to analysis. The supernatant will be analyzed by HPLC-MS/MS for concentrations of the released therapeutic agent.

Example 40: Lymphocyte Proliferation Assay

Immune cells from rats (MLN and spleen cells) and PBMCs from human participants will be cultured in flat clear-bottom 96-well microplates (Thermo Scientific Nunc®) at a concentration of 8.4×104 and 5.2×104 cells/well, respectively. Working stock solutions of test and control compounds in RMPI-1640 culture medium-DMSO (99:1, v/v) will be prepared at concentrations of 10, 25, 50, 75, 100, 150, and 200 µg/mL. Working stock solutions of test and control compounds will be incubated with cells at final concentrations of 1, 2.5, 5, 7.5, 10, 15, and g/mL in a humidified atmosphere of 5% $CO_2$ at 37° C. for 30 min. Cells will then be stimulated by the T cell-selective mitogen Phytohaemagglutinin (PHA, 10 µg/mL, Sigma Aldrich; see Janossy, G. et al., Clin. Exp. Immunol. 9, 483-& (1971)) or other stimulant such as Concanavalin A (ConA), and incubated in a humidified atmosphere of 5% $CO_2$ at 37° C. for 2 days. Cell proliferation will be assessed by enzyme-linked immunosorbent assay (ELISA) based on bromo-2'-deoxyuridine (BrdU) incorporation into newly synthesized DNA according to the manufacturer protocol (Roche Applied Science, Roche Diagnostics Ltd, UK). Finally, the absorbance of these wells will be observed at 370 nm, with reference wavelength at 492 nm using plate reader (EnVision® Multilabel Plate Reader, PerkinElmer Inc., USA). Absorbance values will be normalized to the absorbance of culture medium-treated cells.
Reference: Zgair, A. et al., Scientific Reports 2017, 7: 14542, 1-12.

Example 41: Flow Cytometry Analysis

Freshly isolated immune cells of MLN and splenocytes from rats and thawed PBMCs from human participants will be incubated with control or test compound (1-20 µg/mL) for 30 min in FACS tubes. Cells will then be stimulated with phorbol myristate acetate and ionomycin (PMA & I) in the presence of brefeldin A and incubated in a humidified atmosphere of 5% $CO_2$ at 37° C. for 5 hours. After stimulation, cells will be washed with PBS and centrifuged to pellet (290 g, 5 min, 20° C.). Cell pellet will be resuspended and labelled with Zombie UV™ Fixable Viability kit according to the manufacturer's protocol (Biolegend) for the purpose of excluding dead cells during the analysis of data (effect of relevant control compounds on the variability of immune cells isolated from healthy volunteers can be evaluated by methods known in the art). Fixation and permeabilization will be performed using BD Cytofix/Cytoperm™ kit according to the manufacturer's protocol (BD Bioscience). Rat immune cells will be labelled with APC anti-rat CD3, PE anti-mouse/rat TNF-α, and FITC anti-rat IFN-γ antibodies (Biolegend). Human PBMCs will be labelled with BV421 anti-human TNF-α and PerCP/Cy5.5 anti-human IL-2 antibodies (Biolegend), ECD anti-human CD3, FITC anti-human IFN-γ antibodies (Beckman Coulter), and PE anti-human IL-17A, and APC anti-human GM-CSF antibodies (eBioscience). Isotype and fluorescence minus one (FMO) controls will be prepared for all antibodies in each flow cytometry run. Data will be collected on MoFlo® Astrios™ EQ flow cytometer and analyzed using Kaluza analysis software v 1.5 (Beckman Coulter). An appropriate gating strategy may be selected using methods known in the art and the reference below.
Reference: Zgair, A. et al., Scientific Reports 2017, 7: 14542, 1-12.

Example 42: Preparation of Single-Cell Suspension From Mesenteric Lymph Node (MLN) and Spleen of Rats Following 5 days of acclimatization, animals will be euthanized and the ventral abdominal wall incised to expose the intestine. MLN and spleen will be aseptically collected. MLN will be gently dissected from surrounding tissue and spleen will be scored with a clean scalpel before being mashed on cell strainer (70 m Nylon, Corning Falcon™). Red blood cells in the cell suspension of the splenocytes will be lysed by lysing buffer (BD Bioscience). Immune cells from MLN and splenocytes will then be washed twice with PBS. Cell suspension will be centrifuged (400 g, 5 min at room temperature) and resuspended in complete RMPI-1640 culture medium (RMPI-1640 culture medium with L-glutamine supplemented with 10% fetal bovine serum (FBS) and 1% penicillin-streptomycin, all purchased, e.g., from Sigma-Aldrich) at concentration of $1.2×10^6$ cells/mL to be used for proliferation and flow cytometry experiments.
Reference: Zgair, A. et al., Scientific Reports 2017, 7: 14542, 1-12 and Han, S. et al., Journal of Controlled Release 2014, 177, 1-10.

Example 43: In Vitro Release of Therapeutic Agent From Prodrugs in Plasma Supplemented with Lipoprotein Lipase In order to probe the release of free drug from TG prodrugs in the systemic circulation, prodrugs were incubated with plasma (rat, mouse, dog, pig or human) supplemented with lipoprotein lipase (LPL, 200 IU/ml). LPL is a key enzyme required for the hydrolysis of lipoprotein associated TG in the systemic circulation and is therefore expected to be a key contributor to lipolysis of the re-esterified drug-TG construct in plasma, largely via liberation of fatty acids in the sn-1 and the sn-3 position of the TG-mimetic, prior to drug release from the 2' position via esterase hydrolysis. LPL is active in plasma but is tethered to the luminal surface of vascular endothelial cells under physiological conditions. In the current in vitro studies, plasma was therefore supplemented with LPL to better reflect the in vivo situation. To start hydrolysis, 10 µl of LPL solution (10,000 IU/ml) was added to a mixture of 10 µl of prodrug solution (1 mg/ml dissolved in acetonitrile) and 500 µl of blank plasma. The mixture was incubated at 37° C. Samples (20 µl) of the incubation solution were taken at 0, 5, 15, 30, 60, 90, 120 and 180 minutes post-incubation and added to 180 µl of MeCN to stop lipolysis. The mixture was vortexed and centrifuged at 4500×g for 5 minutes to precipitate proteins prior to analysis. The supernatant was analyzed by HPLC-MS/MS for the potential products (MG form, acid form, and free drug) of prodrug hydrolysis.

Figure 20:
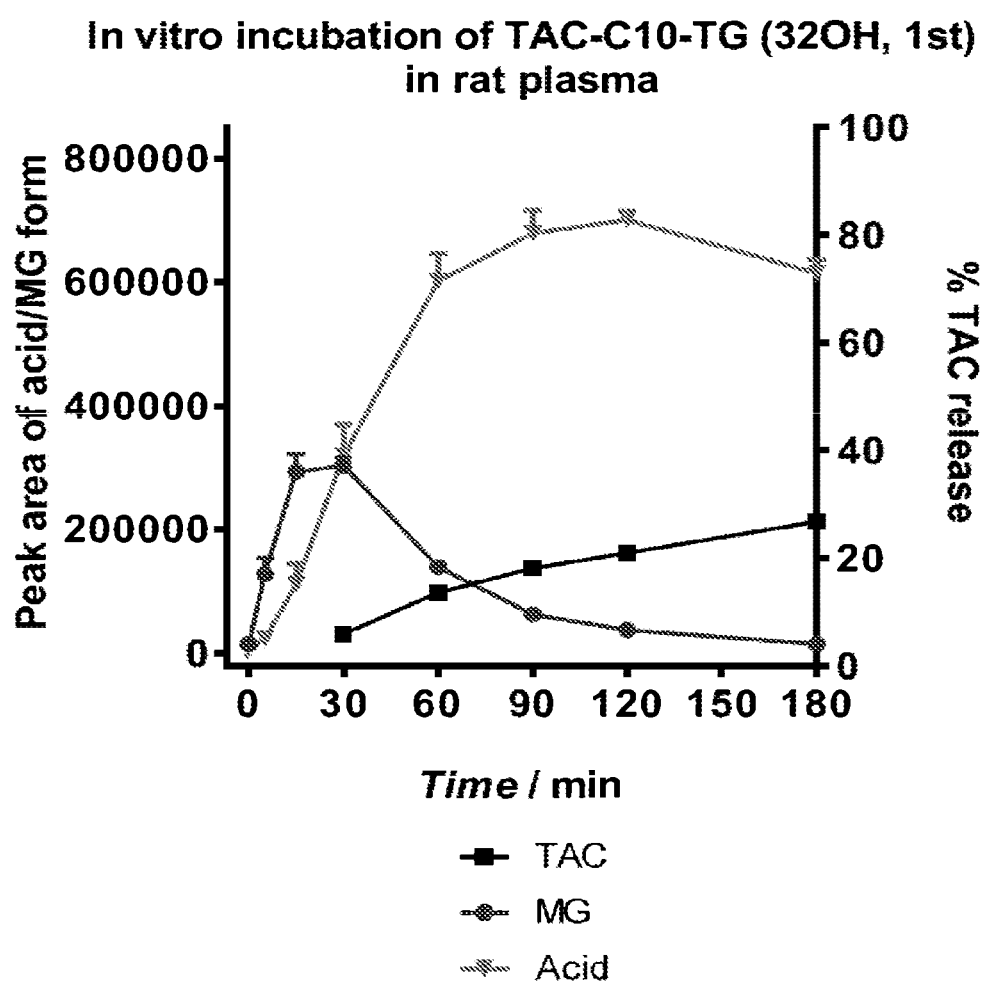
FIG. 20 depicts the results of in vitro release of tacrolimus from TAC-I-18 over time in rate plasma. "TAC" is tacrolimus; "MG" is the monoglyceride form of TAC-I-18; and "acid" is the released lipid prodrug moiety.
Figure 21:
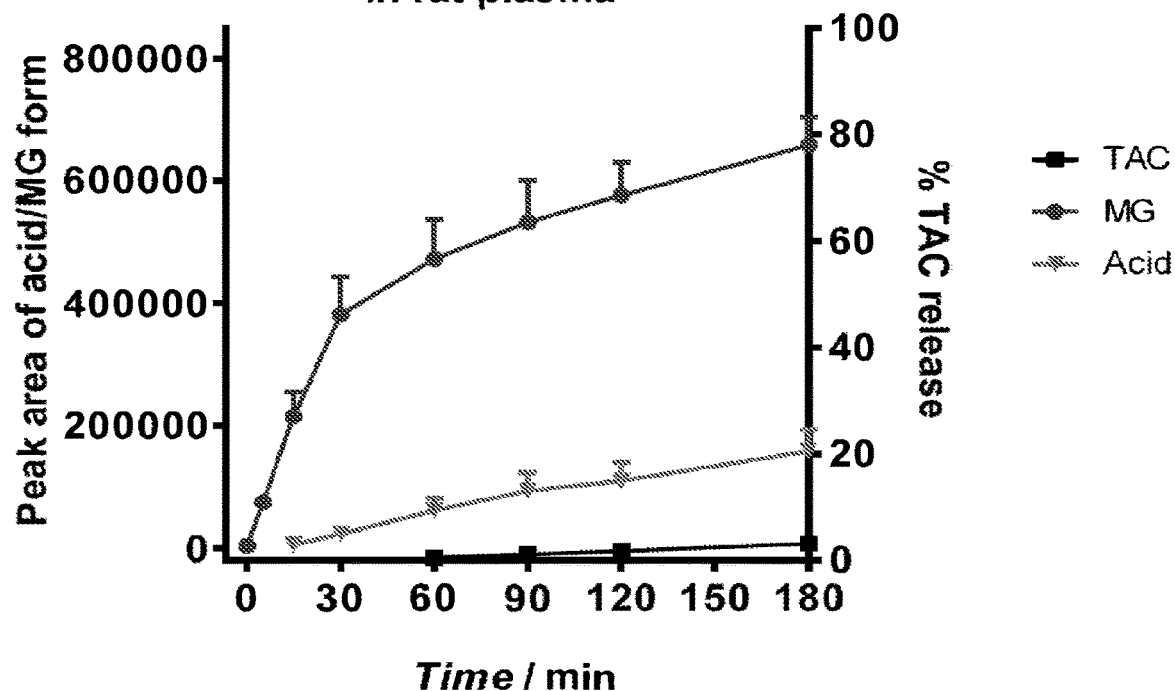
FIG. 21 depicts the in vitro release of tacrolimus from TAC-I-20 over time in rate plasma. "TAC" is tacrolimus; "MG" is the monoglyceride form of TAC-I-20; and "acid" is the released lipid prodrug moiety.

To assess the stability and release profile of compounds of the present invention, compounds TAC-I-18 and TAC-I-20 were incubated with rat plasma and the concentrations of compounds, parent drug tacrolimus, and acid were monitored by LCMS for about three hours. The plasma release profiles for TAC-I-18 are summarized in FIG. 20. The plasma release profiles for TAC-I-20 are summarized in FIG. 21.

Example 44: Oral Ovalbumin Challenge Model

Purification and Labelling of Ovalbumin Specific T Cells

OVA specific CD4$^+$ and CD8$^+$ T cells were purified from the lymph nodes of OT2 and OT1 mice, respectively, and employed in independent experiments to simplify the studies. Lymph nodes collected from OT mice (including MLN, inguinal, brachial, axillary, cervical, iliac) were pressed through a 40 µm sieve using the back of 1 ml syringe plunger, to form a single cell suspension in RPMI 1640 with 2% Fetal Bovine Serum. T cells were then purified using negative selection separation and employing a magnet assisted cell sorting (MACS®) protocol from Miltenyi Biotec. The protocol provided in the kit supplied by Miltenyi Biotec was followed. Briefly, cell suspensions obtained from the lymph node of the OT mice were resuspended in MACS buffer (PBS with 2 mM EDTA and 0.2% Bovine Serum Albumin (BSA)) and labelled with antibodies against all other surface markers, except for the marker for the cells of interest (i.e. CD4+ T cells are isolated by depletion of non CD4+ T cells using a cocktail of biotin-conjugated antibodies against CD8a, CD11b, CD11c, CD19, CD45R (B220), CD49b (DX5), CD105, Anti-MHC-class II, Ter-119 and TCR γ/δ as primary labelling reagent). The cells were then incubated with Anti-biotin labelled magnetic microbeads and passed through the MACS LS column along with MACS buffer within the magnetic field of the Vario MACS separator. The labelled cells are retained within the column while the unlabelled cells flow through the column. The quantity of reagents used was as described in the kit. The purity of the isolated cells was confirmed by flow cytometry of a small sample. These cells were stained with antibodies to CD4 (OT2) or CD8 (OT1) and for Ly 5.1 (surface protein present in lymphocytes of OT mice). The purified CD4 or CD8 T cells were subsequently labelled with CellTrace violet (CTV) dye to allow downstream quantification of cell proliferation. CTV labelling was performed in two steps. First the CTV dye was diluted 100 fold (from 5 mM to 50 µM) with 0.1% BSA in PBS in an eppendorf tube. This solution was then further diluted 10 fold (to 5 µm) at the same time as adding to the cell suspension (≤50×10$^6$ cells/ml) in a 10 mL Falcon tube. The tube was sealed and vortexed immediately to allow even distribution of the dye to the cells. The number of OT cells purified and thus labelled were counted using a haemocytometer under the microscope. The cells were then pelleted and resuspended in PBS, pH 7.4 (10$^7$ cells/ml), for administration to the recipient mice.

Oral Ovalbumin Challenge Model (Late Dosing Protocol)

Recipient female C57Bl/6 mice (20-22 g) were administered 50 mg ovalbumin in 0.2 mL of PBS as a single dose, by oral gavage on Day 1. A negative control group received only PBS (the saline "treatment" group). Each mouse was then administered ~0.2 ml of the appropriate cell suspension containing 2×10$^6$ donor cells, by the tail vein (from above; purified and labelled CD4 or CD8 T cells, obtained from donor OT mice), within 0.5-3 hours of ovalbumin administration. The ovalbumin dosed mice were then divided into four treatment groups and administered different treatments via oral gavage. One group received no additional treatment (OVA treated group), a second received 50 mg/kg parent drug (MPA) as a suspension in 0.2 ml of 0.5% CMC (MPA treatment group), a third received the MPA-2-TG prodrug at a dose equivalent to 50 mg/kg of MPA formulated in a lipid emulsion (MPA-2-TG treatment group) and the fourth received the blank lipid emulsion (blank lipid treatment group) in which the prodrug was administered. The treatments were administered on days 2, 3 and 4, twice a day in the morning and evening. The mice were killed on day 5 and mesenteric lymph nodes (MLN) and peripheral lymph nodes (PLN, including inguinal, brachial, axillary, cervical, iliac) were collected and analyzed by flow cytometry (as below) to assess the proliferation of ovalbumin specific T cells.

Flow Cytometry Analysis

For flow cytometry analysis, cells were isolated from the MLN and PLN and formed into a single cell suspension as described above in PBS buffer containing 2% Foetal Bovine Serum. The cells were then incubated for 20 mins at 4° C. with FITC anti-mouse CD45.1 antibody or FITC anti-mouse TCR Vα2 antibody to label lymphocytes derived from the OT mice (for transgenic mice obtained from WEHI, TCR Vα2 antibody was used, for mice from Bio21 CD45.1 antibody was employed). APC anti-mouse CD8a antibody was used to label CD8 cells and PE anti-mouse CD4 antibody to label CD4 cells. Cells were then washed with buffer. All antibodies were used as per the dilution suggested by the commercial (Biolegend) labelling procedure. Propidium iodide, 10 ng/ml, was added to the cells just prior to flow cytometry analysis to stain for dead cells. Cells that were double positive for CD4/CD8 and CD45.1 (i.e. CD4 or CD8 lymphocytes derived from OT mice) were selected to detect the CTV fluorescence, using the Pacific blue filter (450/50). One million total events were acquired by the flow cytometer (BD Biosciences FACSCanto II analyser, Becton, Dickinson and Company, NJ, USA) and data were analysed using FlowJo software, by Tree Star Inc., Ashland, OR, USA.

Example 45: Lymph Transport Study in Beagle Dogs

A modified version of protocols described in Han, S. et al., "Lymphatic Transport and Lymphocyte Targeting of a Triglyceride Mimetic Prodrug Is Enhanced in a Large Animal Model: Studies in Greyhound Dogs," Mol. Pharm. 2016, 13 (10), 3351-3361, may be used to perform lymph transport assays of test compounds in beagle dogs. The assay will be performed as follows.

The thoracic lymph duct will be cannulated under surgical anesthesia as previously described (Edwards, et al. Adv. Drug Delivery Rev. 2001, 50 (1-2), 45-60.). Following surgery, dogs will be allowed to recover unrestrained in a closed run overnight (12-16 h) and returned to normal ambulatory movement before commencement of the study. In the initial recovery period fluids will be administered IV to ensure adequate hydration and to prevent hypoproteinemia. Water will be also available ad libitum throughout the experiment period. Prior to drug administration, a 20 G intravenous catheter will be inserted into the cephalic vein to enable serial blood sampling and the catheter kept patent by periodic flushing with heparinized saline (1 IU/mL). To limit possible dehydration due to the continuous collection of thoracic lymph, 25 mL of normal saline will be also administered hourly by IV bolus during the sampling period. The dogs will be fasted for 12 h up to 30 min prior to drug administration. For fed state studies, dogs will receive ~20 g of high fat dog food (containing ~34% fat), administered by hand, followed by 10 mL water to aid in swallowing, followed by 100 g standard canned dog food (~2.5% fat) 30 min prior to drug administration. Water will be available ad libitum throughout the study for all dogs. Test compounds may be prepared in a suitable formulation such as a long-chain lipid based self-emulsifying drug delivery system (SEDDS) consisting of 30.5% w/w soybean oil, 30.5% w/w Maisine-CC, 31.6% w/w Cremophor EL and 7.4% w/w ethanol. Formulations may be filled into hard gelatin capsules. Compound dissolved in the formulation may be administrated to the fed dog by placing the capsules as far posterior to the pharynx as possible, closing the mouth and rubbing the throat to stimulate swallowing. Subsequently 50 mL of water will be administered orally via a syringe. Lymph will be collected continuously into preweighed 50 mL collection tubes containing 75 mg of disodium EDTA for the duration of the 10 h postdosing period. Individual lymph samples for each half hourly or hourly collection period will be combined, and the mass of lymph collected will be determined gravimetrically. Several 20 and 200 µL aliquots of each lymph sample will be transferred into individual 1.5 mL Eppendorf tubes and stored at −80° C. until analysis of drug concentrations. The remaining lymph from each collection period (half hourly or hourly) will be transferred into 10 mL tubes, which will be centrifuged at 2000 g for 10 min to obtain lymphocyte pellets, which will be stored at −80° C. until analysis of drug concentrations. Systemic blood samples (3 mL) will be taken via the indwelling cephalic vein catheter and placed in individual heparinized tubes (13×75 mm BD Vacutainer, 68 IU). Blood samples will be collected at predose (−5 min) and at 0.5, 1, 1.5, 2, 2.5, 3, 3.5, 4, 5, 6, 8, and 10 h following drug administration. Plasma will be separated by centrifugation and stored at −80° C. prior to analysis.

We claim:

1. A compound of Formula X-b:

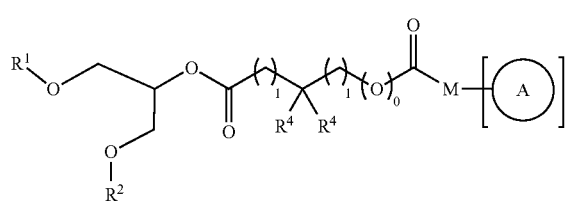

(X-b)

wherein $R^1$ and $R^2$ are each independently a fatty acid having a $C_4$-$C_{18}$ chain;

one instance of $R^4$ is hydrogen and one instance of $R^4$ is methyl;

-M- is

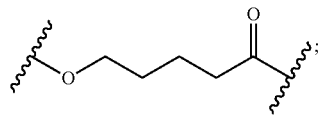 [SMILES: *OCCCCC(*)=O]

and

A is cannabidiol.

2. A pharmaceutical composition comprising the compound according to claim 1, and a pharmaceutically acceptable carrier, adjuvant, or vehicle.

3. The pharmaceutical composition according to claim 2, wherein the pharmaceutical composition is formulated for oral administration.

4. An oral dosage form comprising the compound according to claim 1.

5. The oral dosage form of claim 4, further comprising a lipid-based vehicle.

6. The oral dosage form of claim 4, wherein the oral dosage form comprises a self-emulsifying drug delivery system (SEDDS).

7. The oral dosage form of claim 4, wherein the oral dosage form is a capsule.

8. The compound according to claim 1, wherein $R^1$ and $R^2$ are each independently a fatty acid having a $C_6$-$C_{16}$ chain.

9. The compound according to claim 8, wherein each fatty acid is a saturated fatty acid.

10. The compound according to claim 9, wherein each saturated fatty acid is a straight-chain fatty acid.

11. The compound according to claim 1, wherein the compound is:

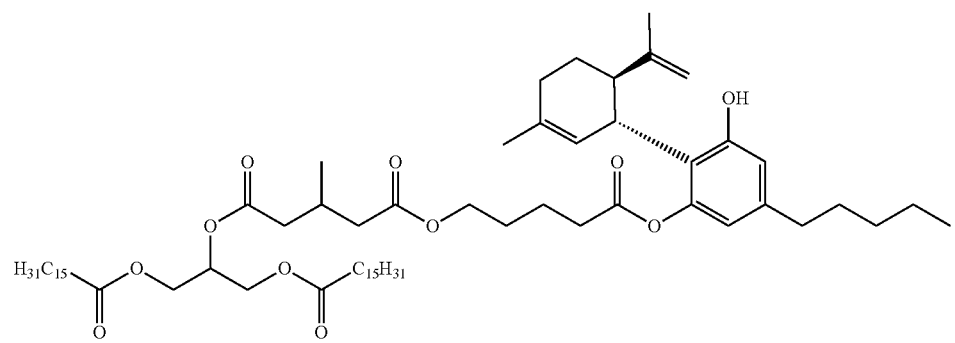

* * * * *